US011800797B2

(12) United States Patent
Kwon et al.

(10) Patent No.: US 11,800,797 B2
(45) Date of Patent: Oct. 24, 2023

(54) HETEROCYCLIC COMPOUND AND ORGANIC LIGHT-EMITTING DEVICE INCLUDING THE SAME

(71) Applicants: Samsung Electronics Co., Ltd., Suwon-si (KR); Samsung SDI Co., Ltd., Yongin-si (KR)

(72) Inventors: Eunsuk Kwon, Suwon-si (KR); Youngmin Nam, Seoul (KR); Sangho Park, Anyang-si (KR); Hyejin Bae, Suwon-si (KR); Jhunmo Son, Yongin-si (KR); Wonseok Oh, Suwon-si (KR); Yongsik Jung, Seoul (KR); Dmitry Kravchuk, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 657 days.

(21) Appl. No.: 16/800,104

(22) Filed: Feb. 25, 2020

(65) Prior Publication Data

US 2020/0274074 A1 Aug. 27, 2020

(30) Foreign Application Priority Data

Feb. 26, 2019 (KR) ........................ 10-2019-0022734

(51) Int. Cl.
| | | |
|---|---|---|
| H10K 85/60 | (2023.01) | |
| C07D 209/86 | (2006.01) | |
| C07D 401/14 | (2006.01) | |
| H10K 50/11 | (2023.01) | |
| H10K 101/30 | (2023.01) | |
| H10K 101/40 | (2023.01) | |

(52) U.S. Cl.
CPC ....... *H10K 85/6572* (2023.02); *C07D 209/86* (2013.01); *C07D 401/14* (2013.01); *H10K 85/654* (2023.02); *H10K 50/11* (2023.02); *H10K 2101/30* (2023.02); *H10K 2101/40* (2023.02)

(58) Field of Classification Search
CPC ............. H01L 51/0072; H01L 51/0067; H01L 51/5004; H01L 2251/552; H01L 51/0085; H01L 51/5016; H01L 51/50; C07D 209/86; C07D 401/14; C07D 209/88; C07D 471/04; C07D 209/82; C09K 11/06; H05B 33/14; H10K 85/6572; H10K 85/654; H10K 50/11; H10K 2101/30; H10K 2101/40; H10K 85/342; H10K 2101/10; H10K 50/00
USPC ....................................................... 428/690
See application file for complete search history.

(56) References Cited

U.S. PATENT DOCUMENTS

| | | | |
|---|---|---|---|
| 8,859,109 B2 | 10/2014 | Sawada et al. | |
| 9,530,969 B2 | 12/2016 | Mizuki et al. | |
| 10,243,149 B2 | 3/2019 | Kang et al. | |
| 10,263,196 B2 | 4/2019 | Danz et al. | |
| 10,340,460 B2 | 7/2019 | Fukumatsu et al. | |
| 2012/0126692 A1 | 5/2012 | Ise et al. | |
| 2012/0161617 A1 | 6/2012 | Fukuzaki | |
| 2016/0013423 A1 | 1/2016 | Huh et al. | |
| 2017/0194570 A1* | 7/2017 | Kang | .................... H01L 51/008 |
| 2017/0358756 A1* | 12/2017 | Chung | ................ H01L 51/0071 |
| 2018/0198075 A1 | 7/2018 | Danz et al. | |
| 2019/0177303 A1 | 6/2019 | Danz et al. | |
| 2019/0296247 A1 | 9/2019 | Sakamoto | |

FOREIGN PATENT DOCUMENTS

| | | | | |
|---|---|---|---|---|
| CN | 101333438 B | 11/2011 | | |
| CN | 107074765 A | 8/2017 | | |
| CN | 108285452 A | 7/2018 | | |
| CN | 109942551 A | 6/2019 | | |
| CN | 110294743 A | 10/2019 | | |
| EP | 1829871 A1 | 9/2007 | | |
| EP | 2272828 A1 | 1/2011 | | |
| EP | 3543230 A1 * | 9/2019 | ........... | C07D 401/14 |
| JP | 2009035524 A | 2/2009 | | |
| JP | 2011054696 A | 3/2011 | | |
| JP | 2019096876 A * | 6/2019 | ............. | C09K 11/06 |
| KR | 1020100135815 A | 12/2010 | | |
| KR | 1020120018231 A | 2/2012 | | |
| KR | 1020150003223 A | 1/2015 | | |
| KR | 1020150116337 A | 10/2015 | | |
| KR | 1020160006629 A | 1/2016 | | |

(Continued)

OTHER PUBLICATIONS

English translation of JP 2019096876, Jun. 20, 2019. (Year: 2019).*
CAS reg. No. 2478470-57-2, Sep. 11, 2020. (Year: 2020).*
Extended European search report issued by the European Patent Office dated May 12, 2020 in the examination of the European Patent Application No. 20158448.9, which corresponds to the U.S. Application above.

(Continued)

*Primary Examiner* — Douglas J McGinty
(74) *Attorney, Agent, or Firm* — CANTOR COLBURN LLP

(57) ABSTRACT

A heterocyclic compound represented by Formula 1:

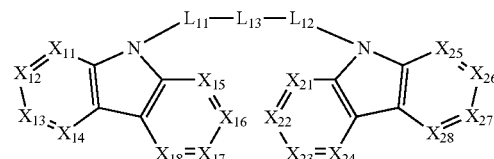

Formula 1 and an organic light-emitting device including the same are provided.

17 Claims, 1 Drawing Sheet

(56) References Cited

FOREIGN PATENT DOCUMENTS

| KR | 1020170082126 A | 7/2017 |
|----|-----------------|--------|
| KR | 1020170088822 A | 8/2017 |
| WO | 2013084885      | 6/2013 |

OTHER PUBLICATIONS

Youtian Tao, et al., Tuning the Optoelectronic Properties of Carbazole/Oxadiazole Hybrids through Linkage Modes: Hosts for Highly Efficient Green Electrophosphprescence, 2010, Adv. Funct. Mater. 20, 304-311, XP001551600.
Wei Li, J. Bipolar host materials for high-efficiency blue phosphorescent and delayed-fluorescence OLEDs, Mater. Chem. C, 2015.
English Translation of Office Action dated Aug. 8, 2023, issued in corresponding CN Patent Application No. 202010130909.4, 10 pp.
Office Action dated Aug. 8, 2023, issued in corresponding CN Patent Application No. 202010130909.4, 8 pp.

\* cited by examiner

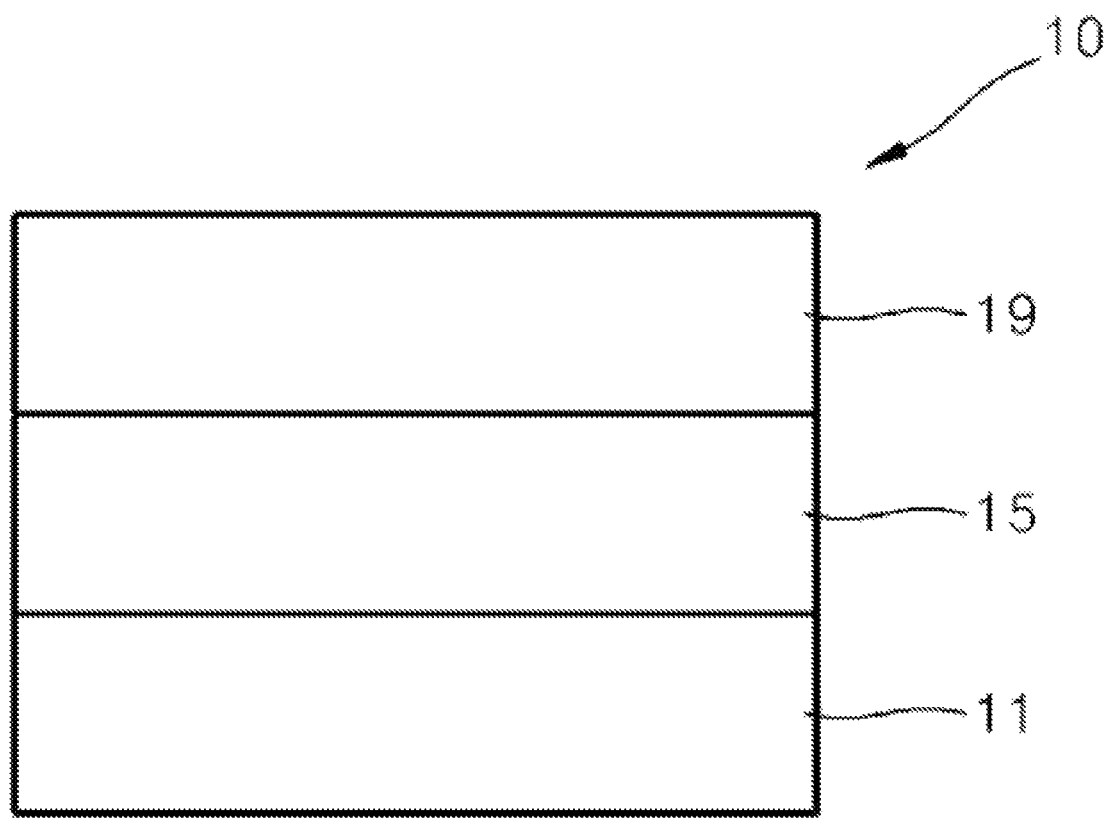

HETEROCYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2019-0022734, filed on Feb. 26, 2019, in the Korean Intellectual Property Office, and all the benefits accruing therefrom under 35 U.S.C. § 119, the content of which is incorporated herein in its entirety by reference.

BACKGROUND

1. Field

The present disclosure relates to a heterocyclic compound and an organic light-emitting device including the same.

2. Description of the Related Art

Organic light-emitting devices (OLEDs) are self-emission devices which have wide viewing angles, high contrast ratios, short response times, and excellent brightness, driving voltage, and response speed characteristics, and produce full-color images.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state to thereby generate light.

SUMMARY

Provided are a heterocyclic compound and an organic light-emitting device including the same.

Additional aspects will be set forth in part in the description which follows and, in part, will be apparent from the description, or may be learned by practice of the presented embodiments.

According to an aspect of an embodiment, a heterocyclic compound may be represented by Formula 1:

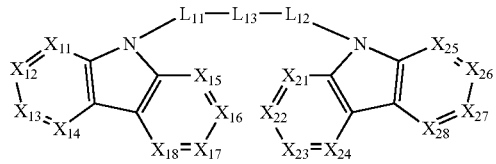

Formula 1

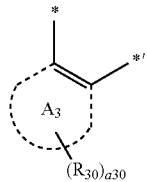

Formula 2

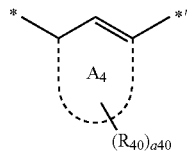

Formula 3

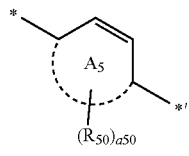

Formula 4 wherein, in Formula 1, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, $X_{17}$ may be N or $C(R_{17})$, $X_{18}$ may be N or $C(R_{18})$, $X_{21}$ may be N or $C(R_{21})$, $X_{22}$ may be N or $C(R_{22})$, $X_{23}$ may be N or $C(R_{23})$, $X_{24}$ may be N or $C(R_{24})$, $X_{25}$ may be N or $C(R_{25})$, $X_{26}$ may be N or $C(R_{26})$, $X_{27}$ may be N or $C(R_{27})$, $X_{28}$ may be N or $C(R_{28})$, $L_{11}$ may be a group represented by Formula 2, $L_{12}$ may be a group represented by one of Formulae 3 and 4, $L_{13}$ may be a group represented by one of Formulae 2 to 4, wherein in Formulae 2 to 4, ring $A_3$ to ring $A_5$ may each independently be a $C_5$-$C_{60}$ carbocyclic group or a $C_2$-$C_{60}$ heterocyclic group, $R_{11}$ to $R_{18}$, $R_{21}$ to $R_{28}$, $R_{30}$, $R_{40}$, and $R_{50}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, or —$B(Q_6)(Q_7)$, at least one of $R_{30}$, $R_{40}$, or $R_{50}$ may be a cyano group, a30, a40, and a50 may each independently be an integer from 1 to 10,

* and *' each indicate a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), or —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_{3-10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), or —B($Q_{26}$)($Q_{27}$); or —Si($Q_{31}$)($Q_{32}$)($Q_{33}$), —N($Q_{34}$)($Q_{35}$) or —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

According to an aspect of another embodiment, an organic light-emitting device may include: a first electrode; a second electrode; and an organic layer between the first electrode and the second electrode, the organic layer including an emission layer and at least one of the heterocyclic compound represented by Formula 1.

BRIEF DESCRIPTION OF THE DRAWINGS

These and/or other aspects will become apparent and more readily appreciated from the following description of the embodiments, taken in conjunction with the accompanying drawings.

The FIGURE is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A heterocyclic compound may be represented by Formula 1:

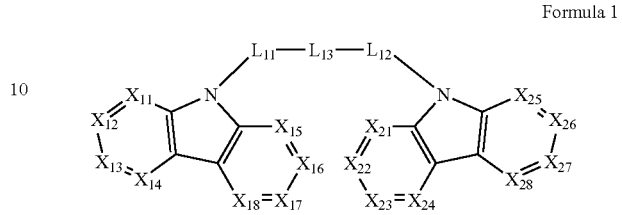

Formula 1 wherein, in Formula 1, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, $X_{17}$ may be N or $C(R_{17})$, $X_{18}$ may be N or $C(R_{18})$, and $X_{21}$ may be N or $C(R_{21})$, $X_{22}$ may be N or $C(R_{22})$, $X_{23}$ may be N or $C(R_{23})$, $X_{24}$ may be N or $C(R_{24})$, $X_{25}$ may be N or $C(R_{25})$, $X_{26}$ may be N or $C(R_{26})$, $X_{27}$ may be N or $C(R_{27})$, $X_{28}$ may be N or $C(R_{28})$.

In some embodiments, $X_{11}$ to $X_{18}$ and $X_{21}$ to $X_{28}$ may not each be N, and one or two of $X_{11}$ to $X_{18}$ and $X_{21}$ to $X_{28}$ may each be N.

In Formula 1, $L_{11}$ may be a group represented by Formula 2, $L_{12}$ may be a group represented by one of Formulae 3 and 4, and $L_{13}$ may be a group represented by one of Formulae 2 to 4:


Formula 2


Formula 3

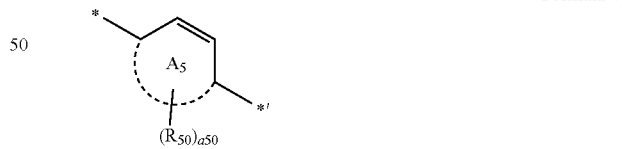

Formula 4

The heterocyclic compound represented by Formula 1 may be asymmetric with respect to $L_{13}$. Since the heterocyclic compound has an asymmetric structure, characteristics of a relatively excellent amorphous thin film may be secured.

In contrast, since a compound having a symmetric structure has a high crystallinity, device characteristics may be deteriorated due to crystal formation of materials in a thin film during a process such as panel preparation.

In Formulae 2 to 4, ring $A_3$ to ring $A_5$ may each independently be a $C_5$-$C_{60}$ carbocyclic group or a $C_2$-$C_{60}$ heterocyclic group.

In some embodiments, ring $A_3$ to ring $A_5$ may each independently be a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group.

In some embodiments, ring $A_3$ to ring $A_5$ may each independently be a benzene group, a pyridine group, a pyrazine group, a pyrimidine group, a pyridazine group, or a triazine group.

In some embodiments, $L_{11}$ may be one of Formulae O-1 to O-6.

In some embodiments, $L_{12}$ may be one of Formulae M-1 to M-9 and P-1 to P-5.

In addition, in some embodiments, $L_{13}$ may be one of Formulae O-1 to O-6, M-1 to M-9, and P-1 to P-5:

O-1

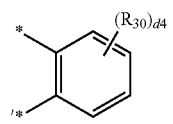

O-2

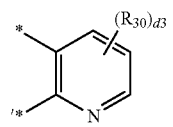

O-3

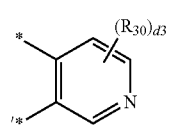

O-4

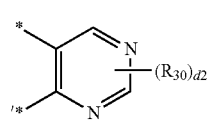

O-5

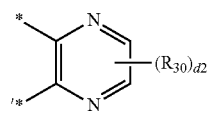

O-6

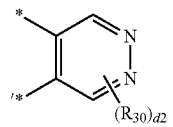

M-1

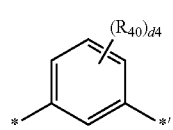

-continued

M-2

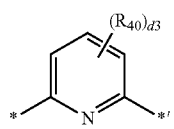

M-3

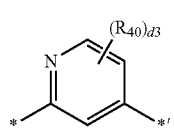

M-4

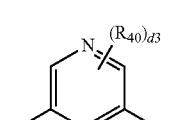

M-5

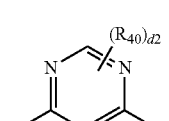

M-6

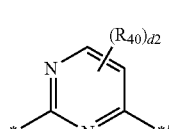

M-7

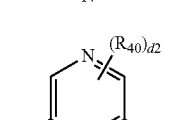

M-8

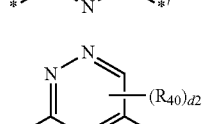

M-9

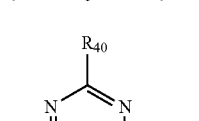

P-1

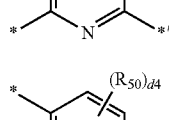

P-2

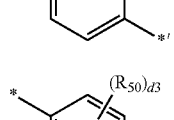

P-3

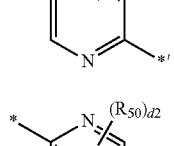

P-4

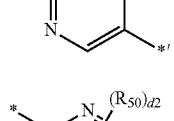

-continued

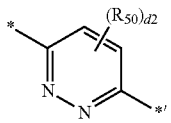

P-5 wherein, in Formulae O-1 to O-6, M-1 to M-9, and P-1 to P-5,
$R_{30}$, $R_{40}$, and $R_{50}$ may respectively be understood by referring to the descriptions therefor provided herein,
d2 may be an integer from 0 to 2,
d3 may be an integer from 0 to 3,
d4 may be an integer from 0 to 4, and
* and *' each indicate a binding site to an adjacent atom.

In some embodiments, in Formula O-1, $R_{30}$ may be hydrogen or a cyano group, and $R_{30}$ in Formulae O-2 to O-6 may be hydrogen.

In some embodiments, $R_{40}$ in Formula M-1 may be hydrogen or a cyano group, and $R_{40}$ in Formula M-2 to M-9 may be hydrogen.

In some embodiments, $R_{50}$ in Formula P-1 may be hydrogen or a cyano group, and $R_{50}$ in Formula P-2 to P-5 may be hydrogen.

In Formulae 1 to 4, $R_{11}$ to $R_{18}$, $R_{21}$ to $R_{28}$, $R_{30}$, $R_{40}$, and $R_{50}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), and
at least one of $R_{30}$, $R_{40}$, or $R_{50}$ may be a cyano group.

In some embodiments, $R_{11}$ to $R_{18}$, $R_{21}$ to $R_{28}$, $R_{30}$, $R_{40}$, and $R_{50}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group and a $C_1$-$C_{20}$ alkoxy group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, or a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, or an imidazopyridinyl group; or a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, or an imidazopyridinyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, or a quinazolinyl group, and
at least one of $R_{30}$, $R_{40}$, or $R_{50}$ may be a cyano group.

In some embodiments, $R_{11}$ to $R_{18}$, $R_{21}$ to $R_{28}$, $R_{30}$, $R_{40}$, and $R_{50}$ may each independently be hydrogen, deuterium, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, a cyano group, a phenyl group, a biphenyl group, a terphenyl group, or a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, or a dibenzothiophenyl group; or a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, or a dibenzothiophenyl group, each substituted with at least one deuterium, a cyano group, a $C_1$-$C_{20}$ alkyl group, a $C_1$-$C_{20}$ alkoxy group, a phenyl group, a biphenyl group, a terphenyl group, or a naphthyl group, and at least one of $R_{30}$, $R_{40}$, or $R_{50}$ may be a cyano group.

In some embodiments, $R_{30}$, $R_{40}$, and $R_{50}$ may each independently be hydrogen or a cyano group, and at least one of $R_{30}$, $R_{40}$, or $R_{50}$ may be a cyano group.

In some embodiments, $R_{11}$ to $R_{18}$, $R_{21}$ to $R_{28}$, $R_{30}$, $R_{40}$, and $R_{50}$ may each independently be hydrogen or a cyano group, and at least one of $R_{30}$, $R_{40}$, or $R_{50}$ may be a cyano group.

In Formulae 1 to 4, a30, a40, and a50 may each independently be an integer from 1 to 10.

a30 indicates the number of $R_{30}(s)$; and when a30 is 2 or greater, at least two $R_{30}(s)$ may be identical to or different from each other. a40 indicates the number of $R_{40}(s)$; and when a40 is 2 or greater, at least two $R_{40}(s)$ may be identical to or different from each other. a50 indicates the number of $R_{50}(s)$; and when a50 is 2 or greater, at least two $R_{50}(s)$ may be identical to or different from each other.

In some embodiments, the number of cyano groups included in the heterocyclic compound represented by Formula 1 may be 1 to 4.

In some embodiments, $R_{11}$ to $R_{18}$ and $R_{21}$ to $R_{28}$ may not each be a cyano group, or one or two of $R_{11}$ to $R_{18}$ and $R_{21}$ to $R_{28}$ may each be a cyano group; one, two, or three of $R_{30}$, $R_{40}$, and $R_{50}$ may each be a cyano group; and the number of cyano groups included in the heterocyclic compound represented by Formula 1 may be 1 to 4.

In Formulae 1 to 4, * and *' each indicate a binding site to an adjacent atom.

In some embodiments, the heterocyclic compound represented by Formula 1 may be represented by one of Formulae 10-1 to 10-6:

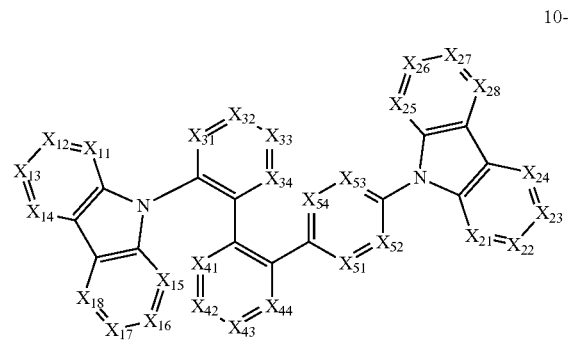

10-1

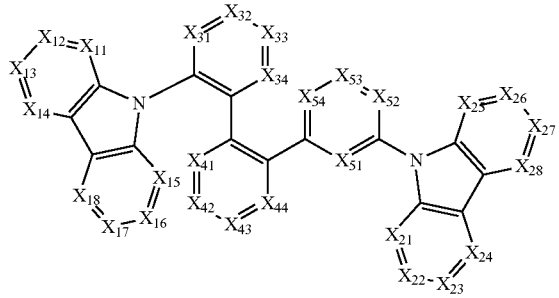

10-2

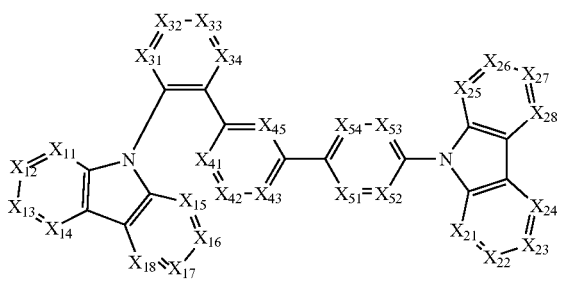

10-3

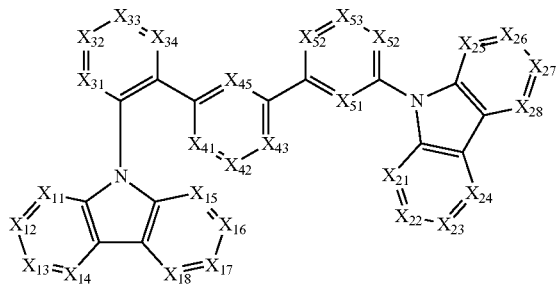

10-4

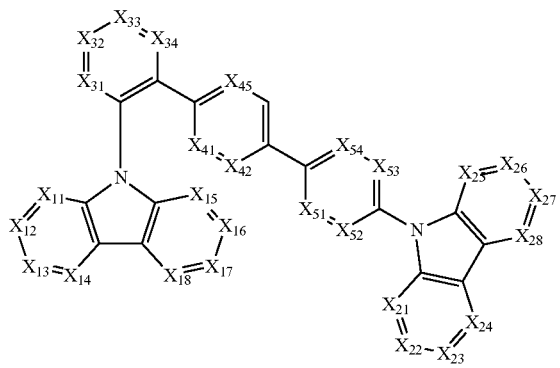

10-5

-continued

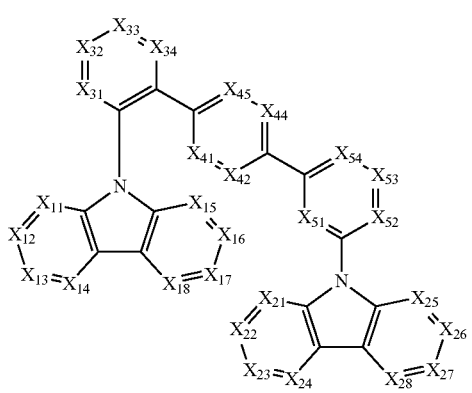

10-6 wherein, in Formulae 10-1 to 10-6, $X_{11}$ to $X_{18}$ and $X_{21}$ to $X_{28}$ may each be understood by referring to the descriptions therefor provided herein, $X_{31}$ may be N or $C(R_{31})$, $X_{32}$ may be N or $C(R_{32})$, $X_{33}$ may be N or $C(R_{33})$, $X_{34}$ may be N or $C(R_{34})$, $X_{41}$ may be N or $C(R_{41})$, $X_{42}$ may be N or $C(R_{42})$, $X_{43}$ may be N or $C(R_{43})$, $X_{44}$ may be N or $C(R_{44})$, $X_{45}$ may be N or $C(R_{45})$, $X_{51}$ may be N or $C(R_{51})$, $X_{52}$ may be N or $C(R_{52})$, $X_{53}$ may be N or $C(R_{53})$, $X_{54}$ may be N or $C(R_{54})$, $R_{31}$ to $R_{34}$ may each be understood by referring to the descriptions for $R_{30}$ provided herein, $R_{41}$ to $R_{45}$ may each be understood by referring to the descriptions for Rao provided herein, $R_{51}$ to $R_{54}$ may each be understood by referring to the descriptions for $R_{50}$ provided herein, and at least one of $R_{31}$ to $R_{34}$, $R_{41}$ to $R_{45}$, or $R_{51}$ to $R_{54}$ may be a cyano group.

In some embodiments, $X_{31}$ to $X_{34}$, $X_{41}$ to $X_{45}$, and $X_{51}$ to $X_{54}$ may not each be N, and one or two of $X_{31}$ to $X_{34}$, $X_{41}$ to $X_{45}$, and $X_{51}$ to $X_{54}$ may each be N.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, or —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_{3-10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, or —$B(Q_{26})(Q_{27})$; or —$Si(Q_{31})(Q_{32})(Q_{33})$, —$N(Q_{34})(Q_{35})$ or —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

In an embodiment, the heterocyclic compound may be of Compounds 1 to 665, 667 to 2317, and 2320 to 2461:
1
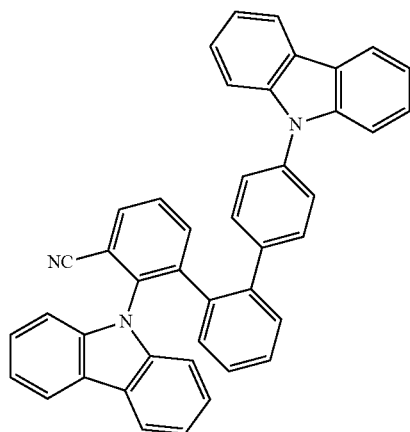
2
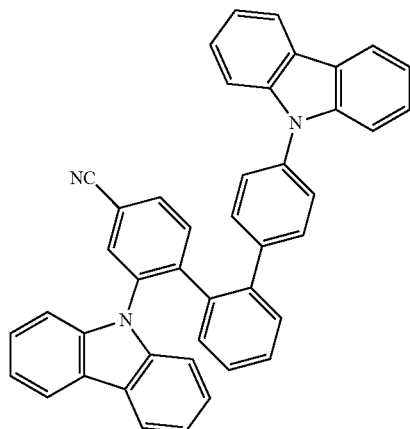
3
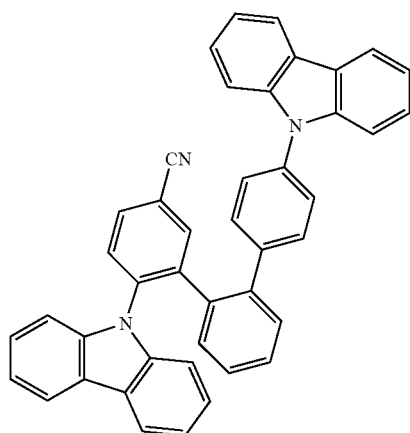
4
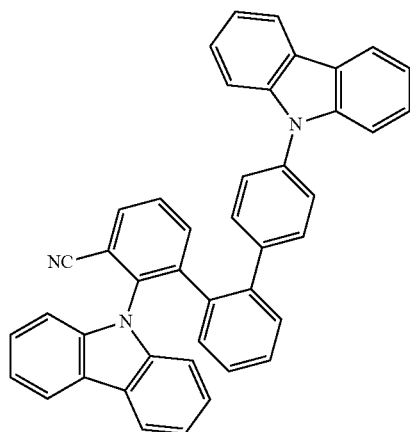
5
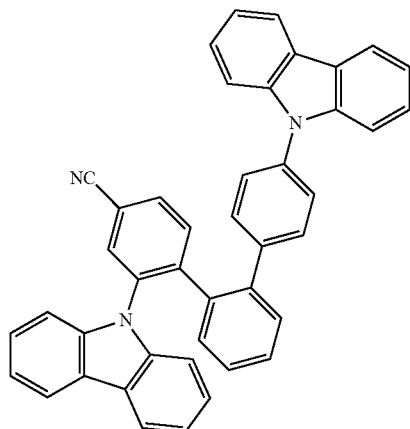
6
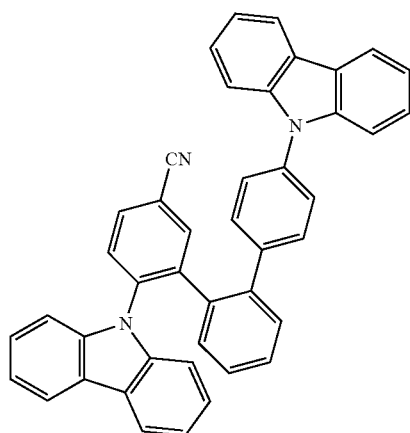

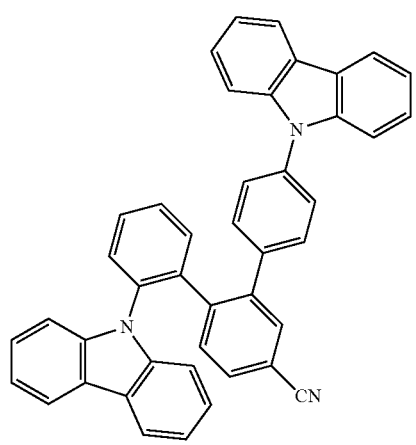
7
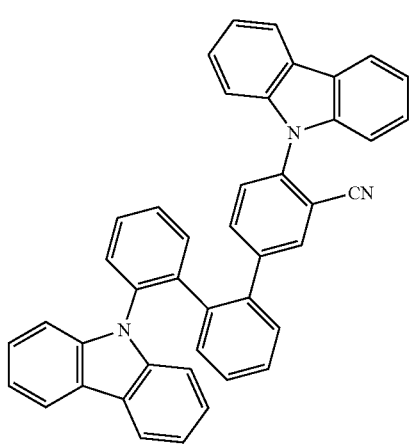
10
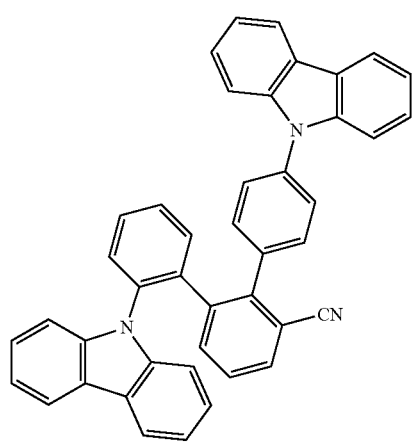
8
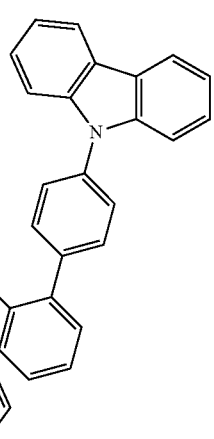
11
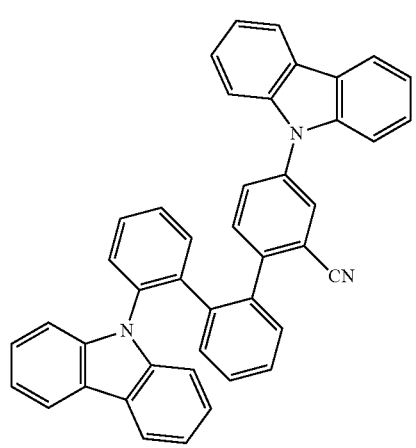
9
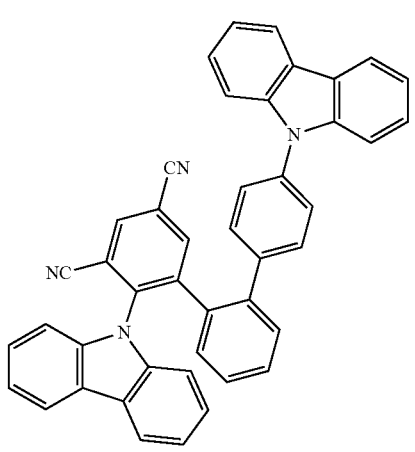
12

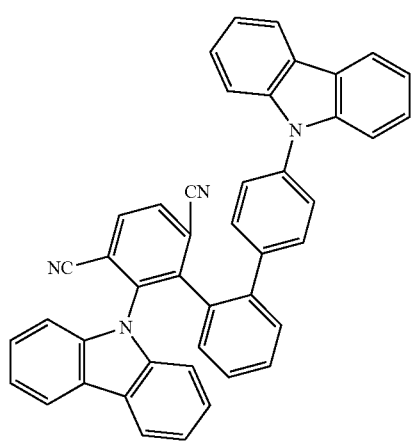
13
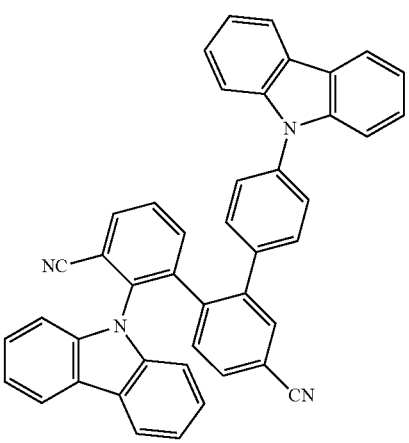
16
14
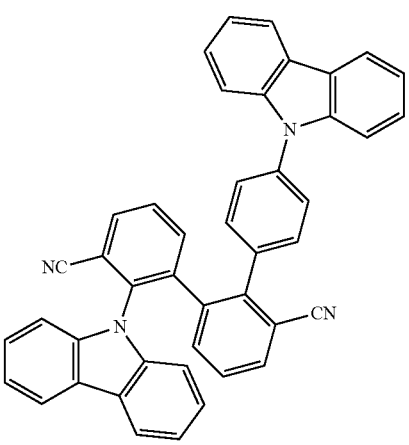
17
15
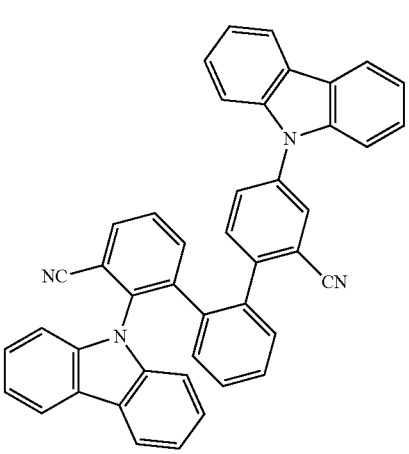
18

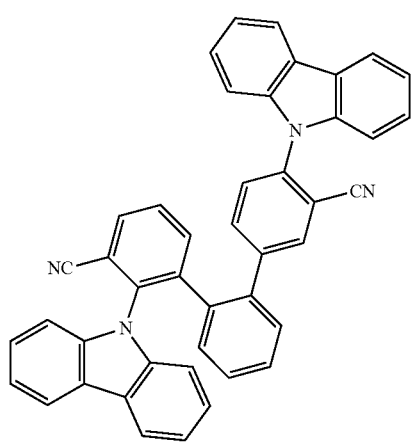
19
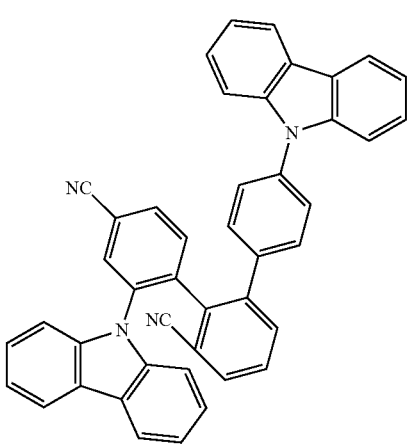
22
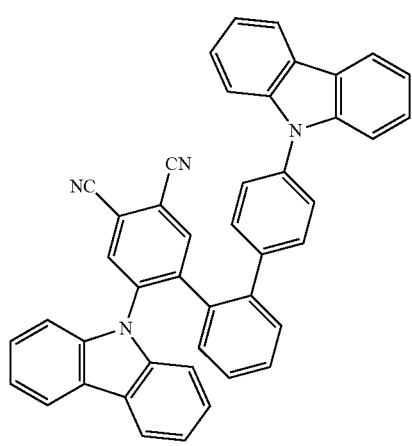
20
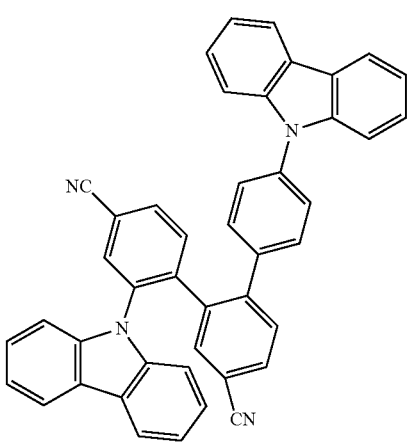
23
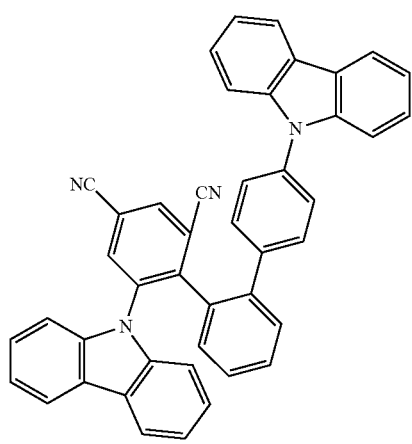
21
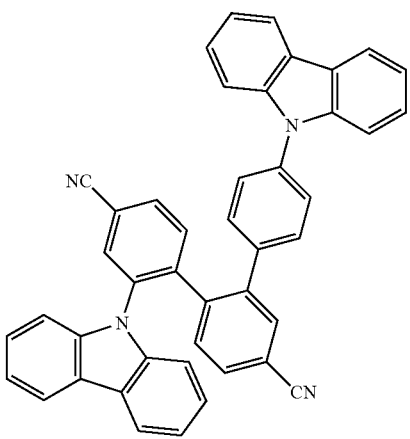
24

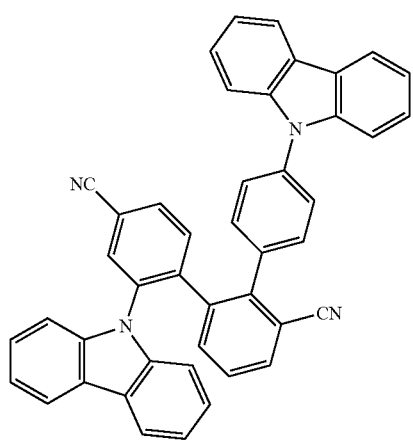
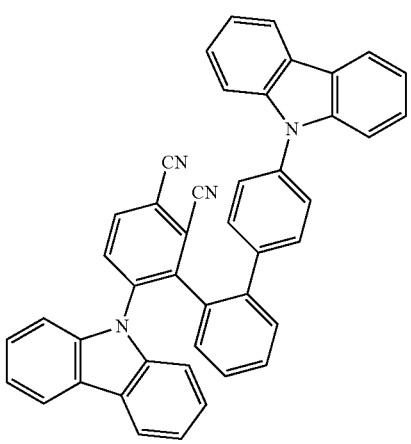

31
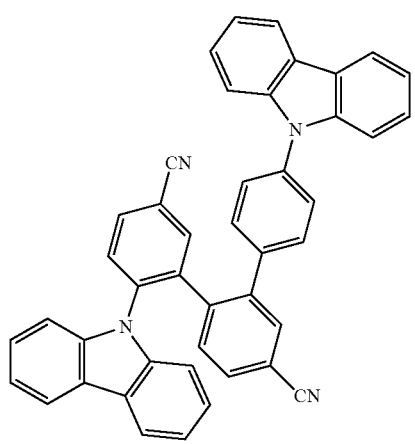
32
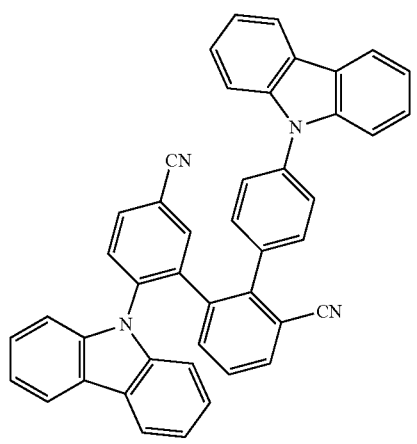
33
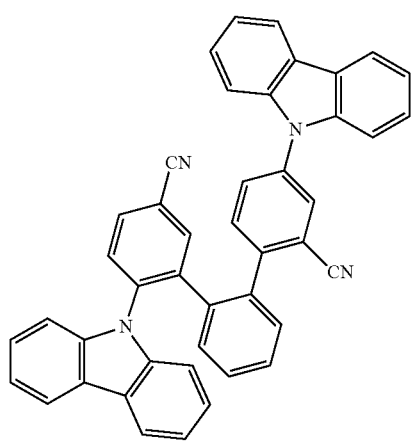
34
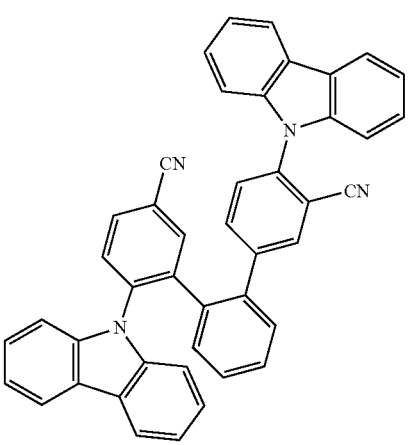
35
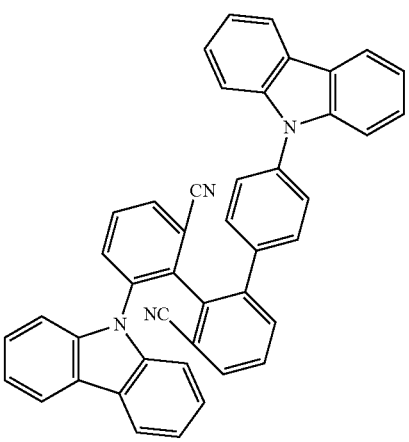
36
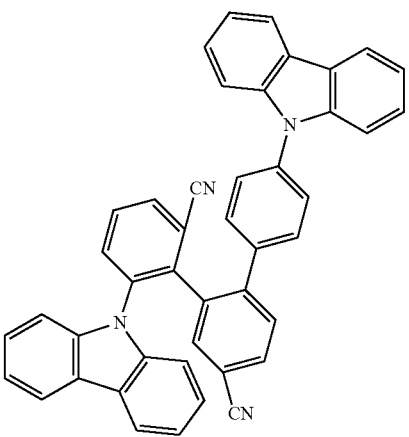

37
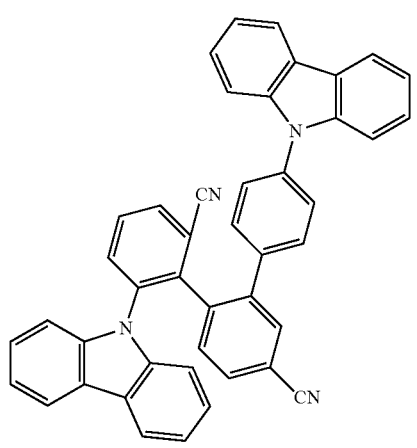
38
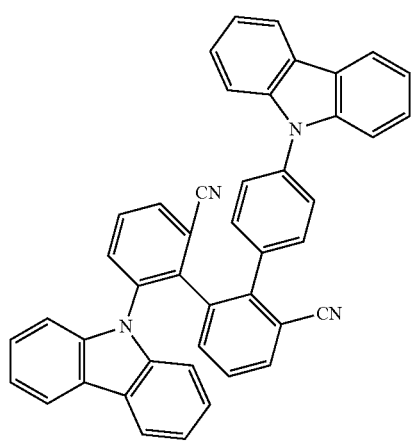
39
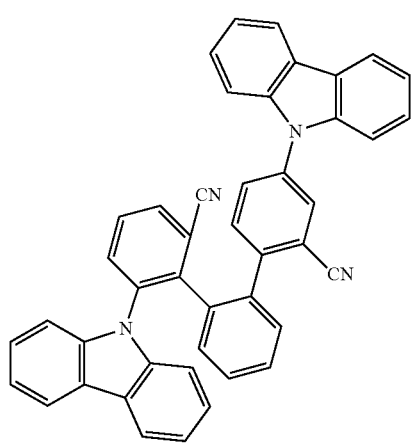
40
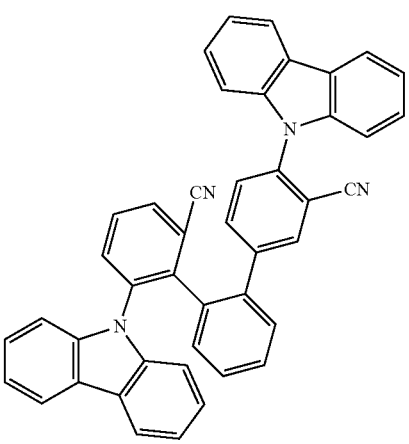
41
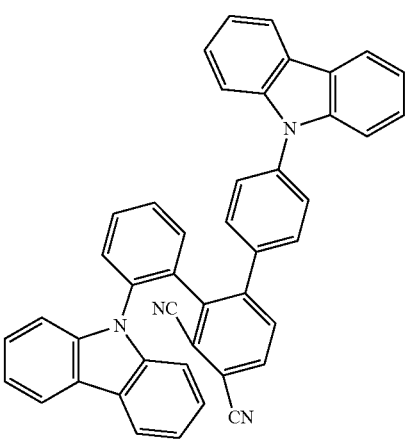
42
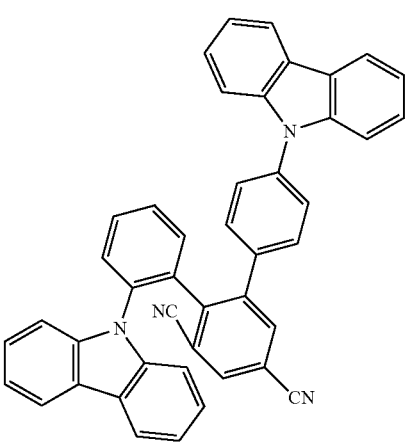

43
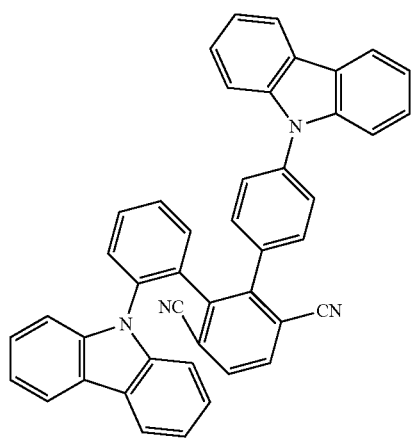
44
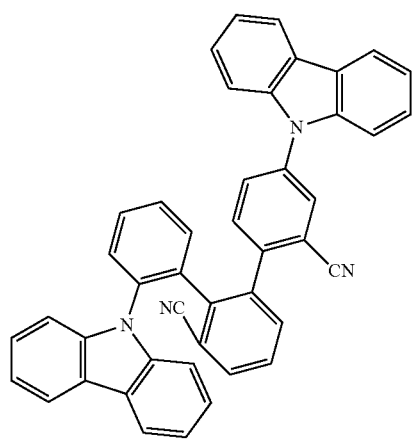
45
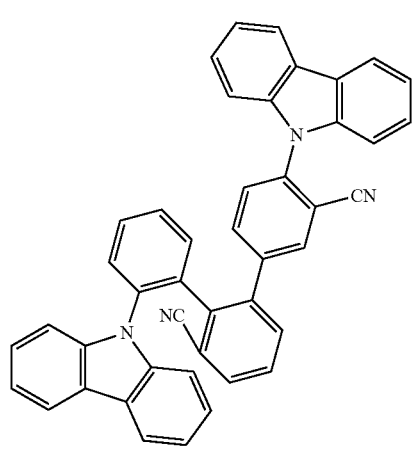
46
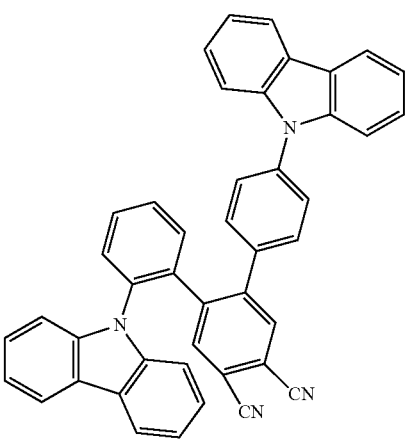
47
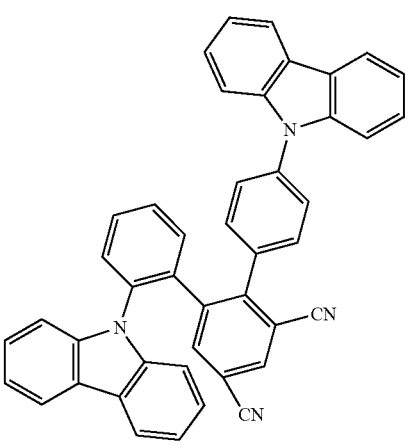
48
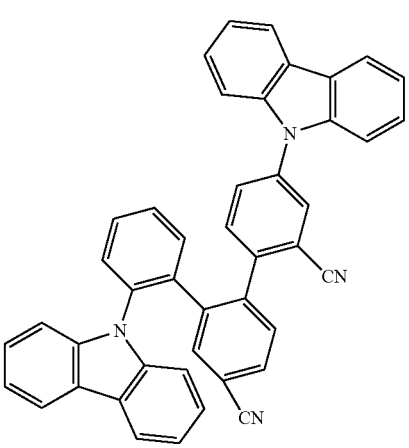

49
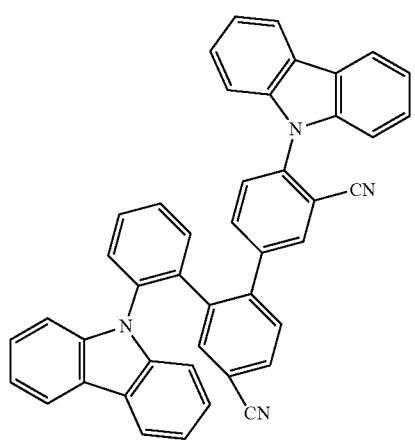
50
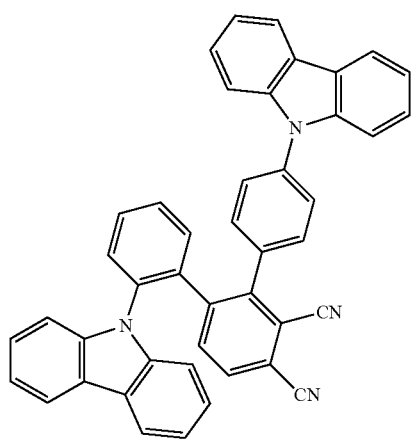
51
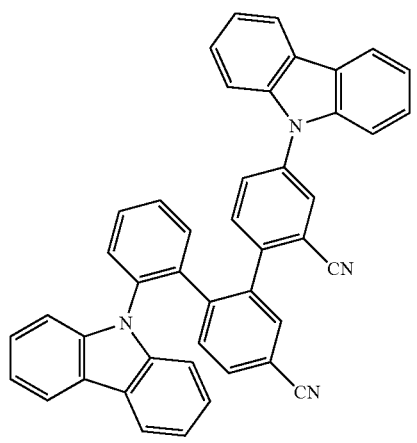
52
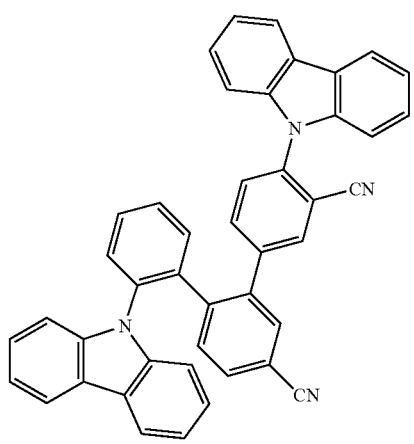
53
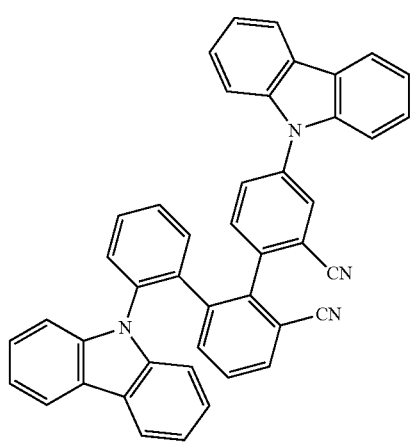
54
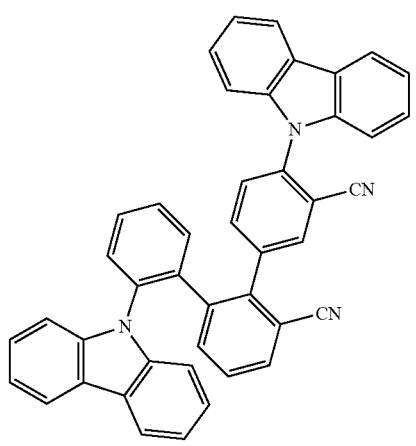

55
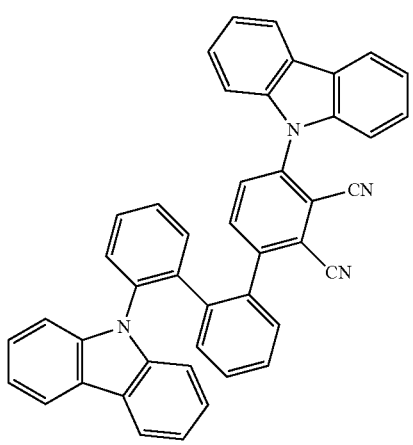
56
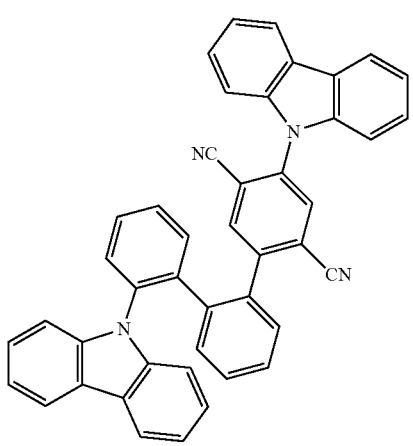
57
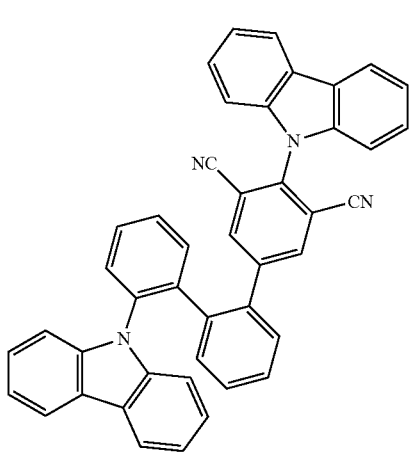
58
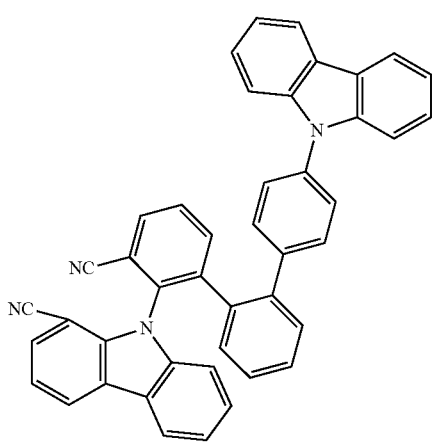
59
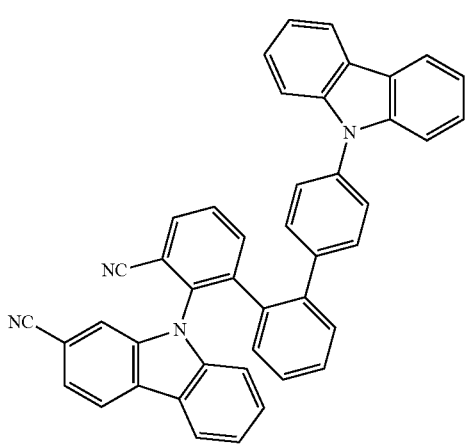
60
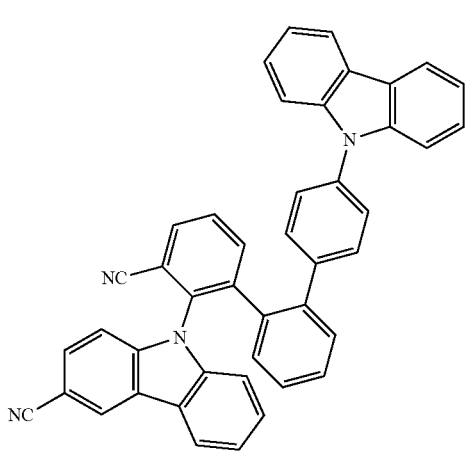

61
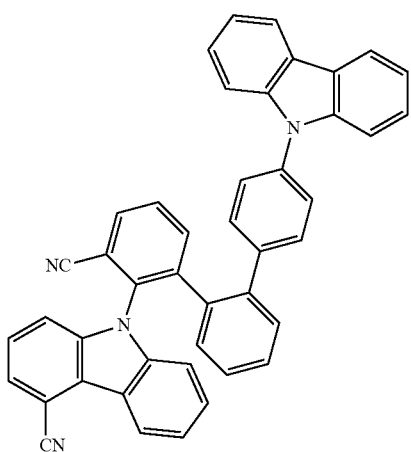
62
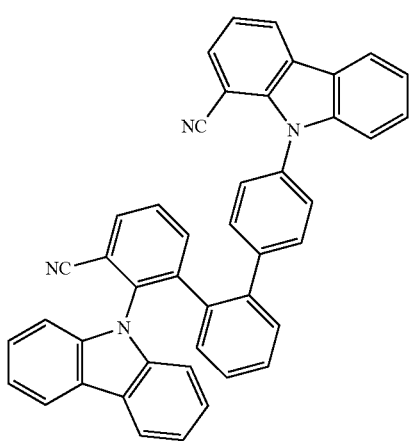
63
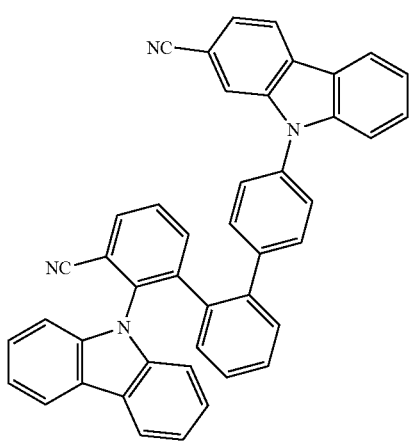
64
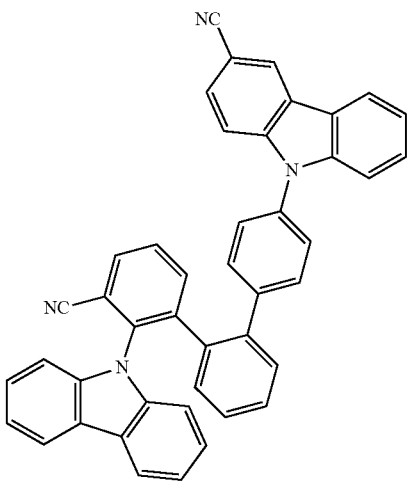
65
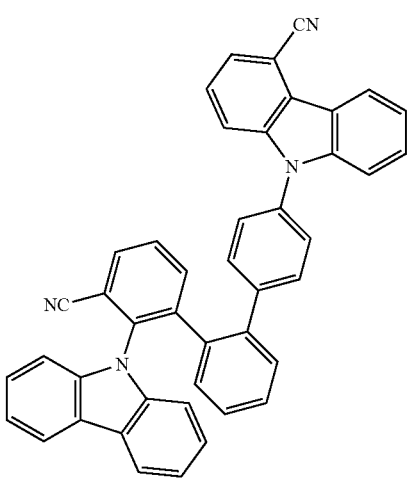
66
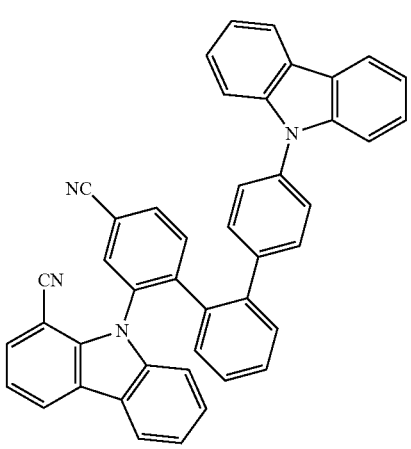

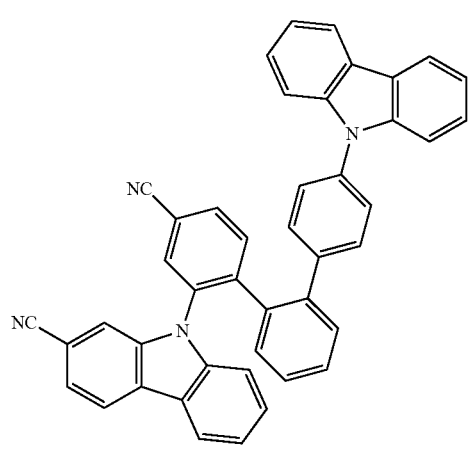
67
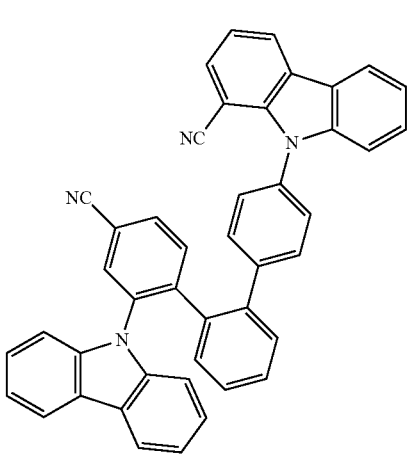
70
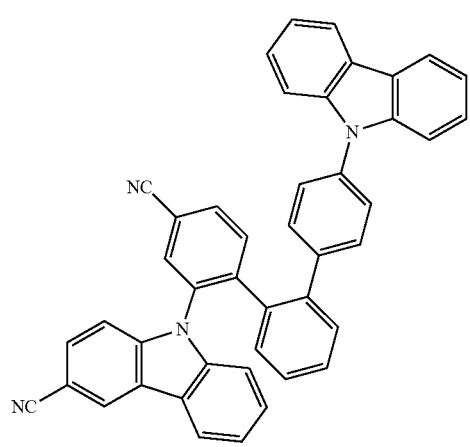
68
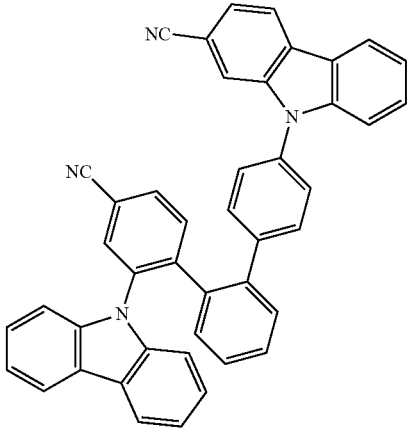
71
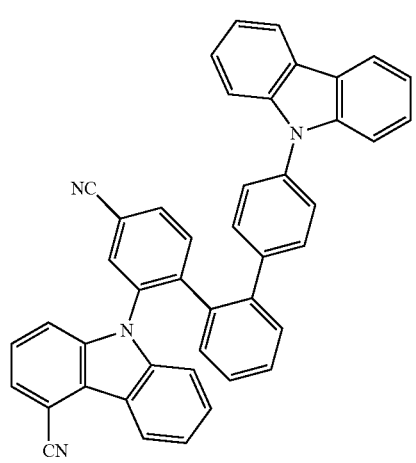
69
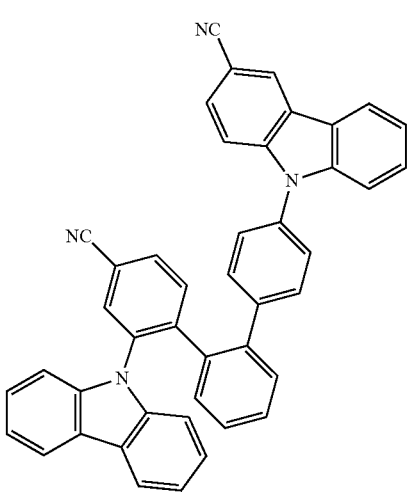
72

73
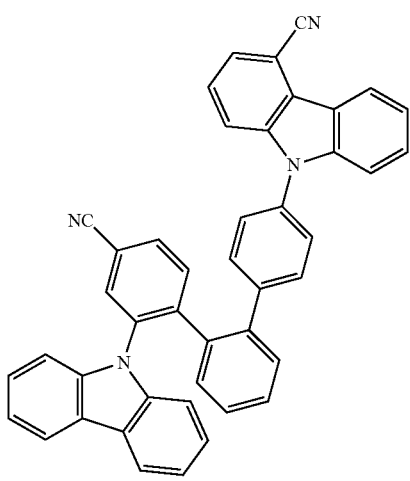
74
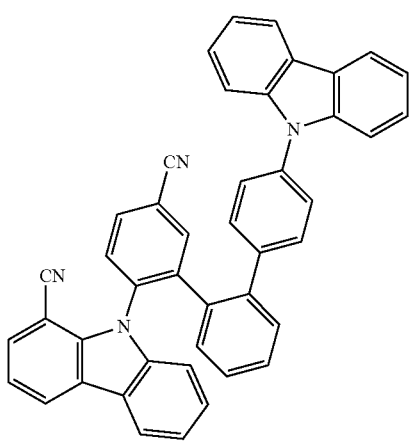
75
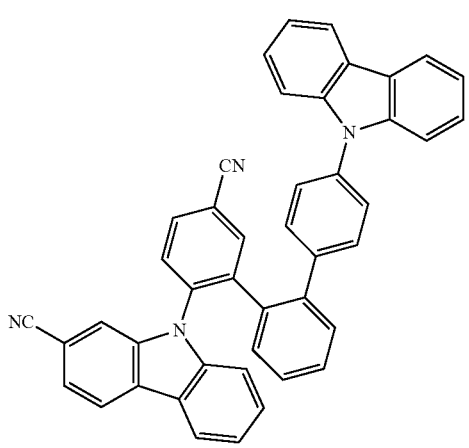
76
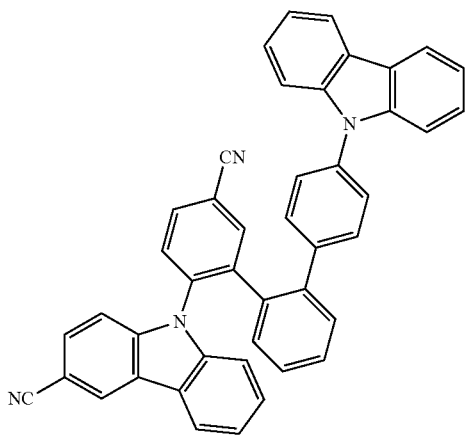
77
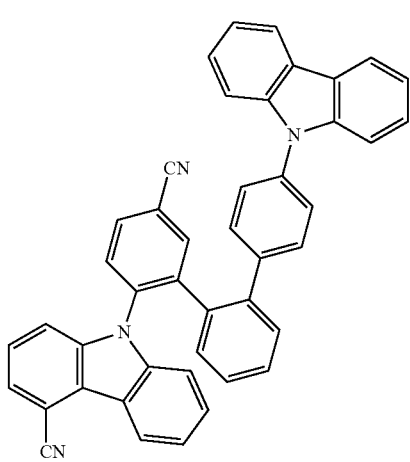
78
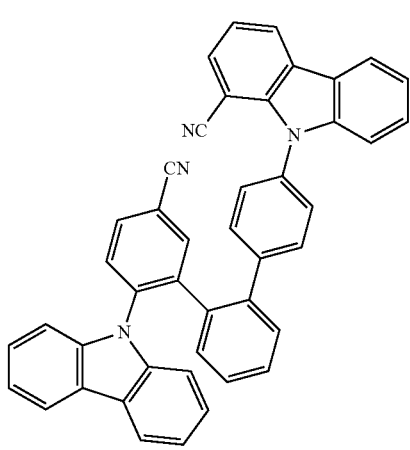

-continued
79
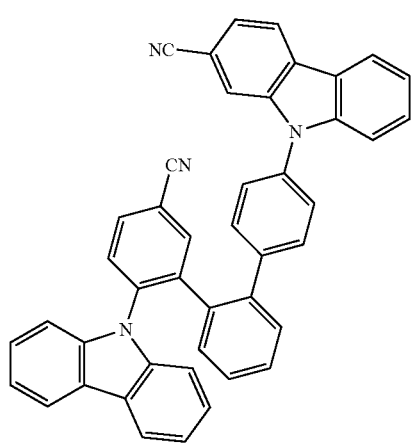
82
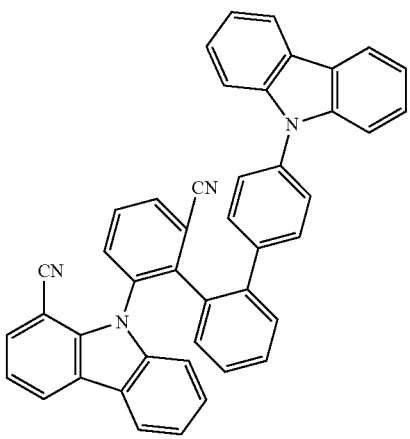
80
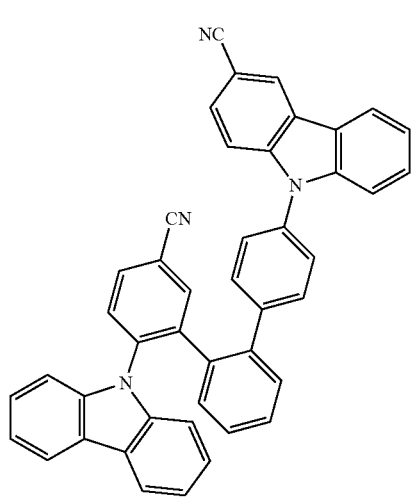
83
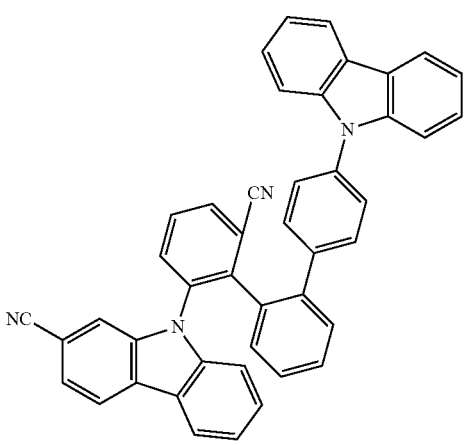
81
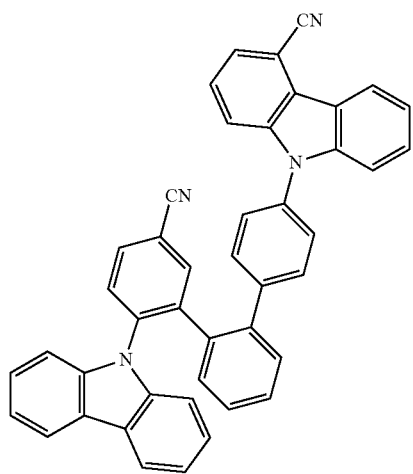
84
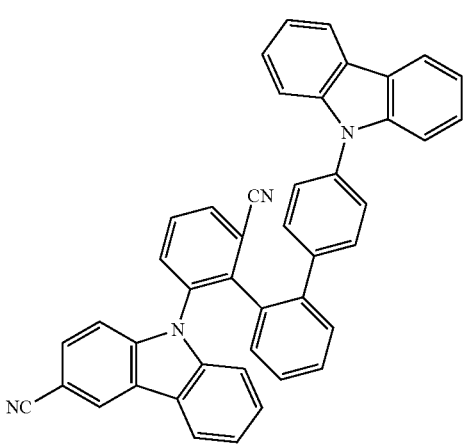

85
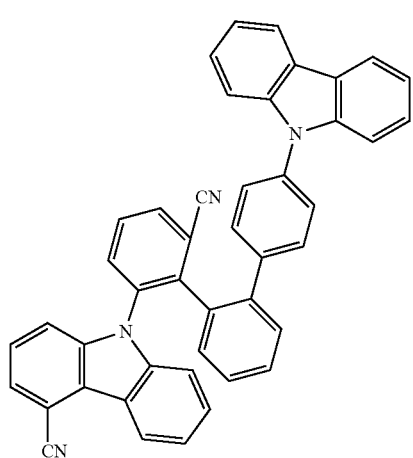
86
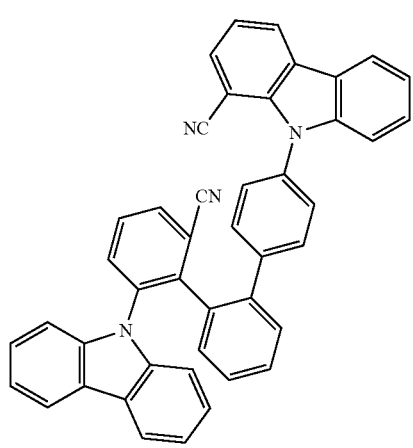
87
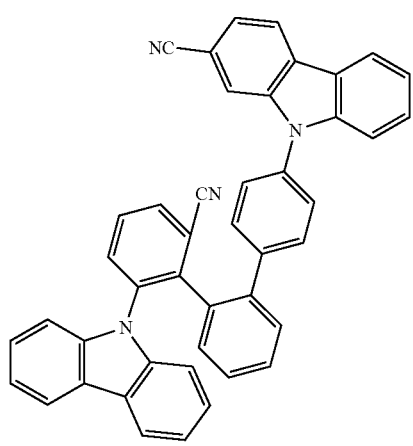
88
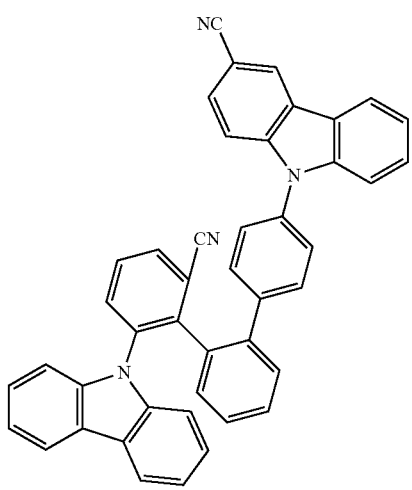
89
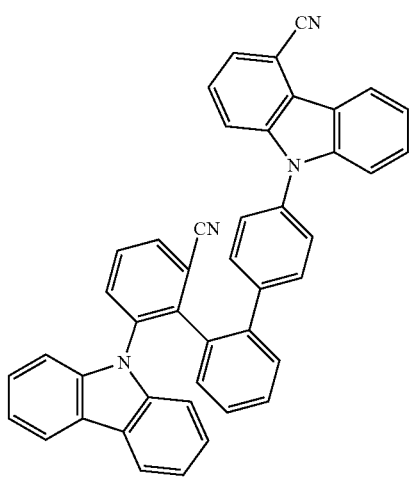
90
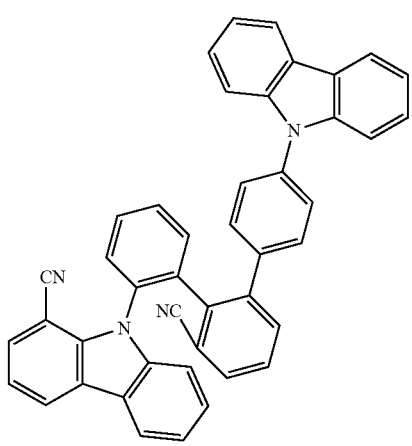

91
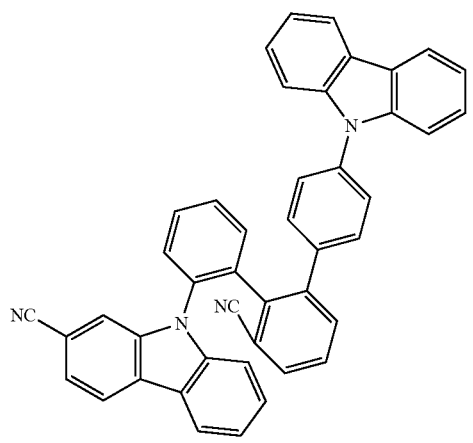
92
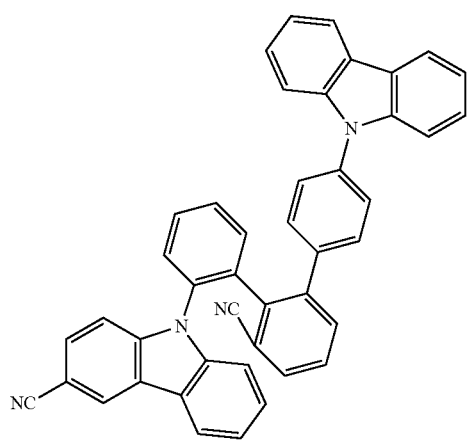
93
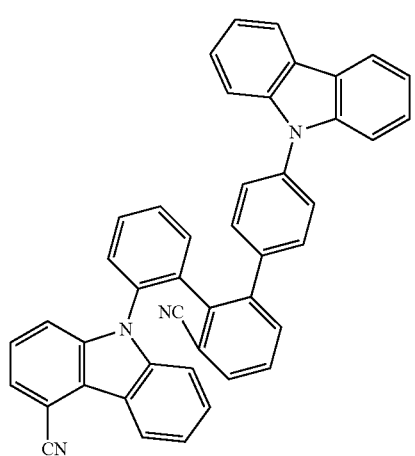
94
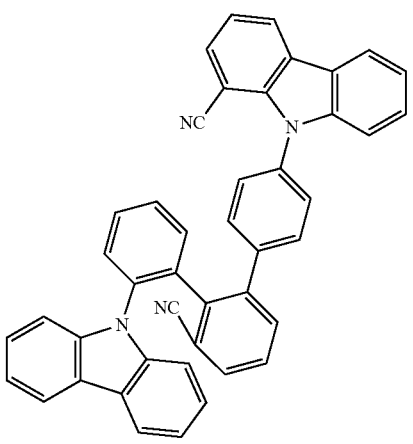
95
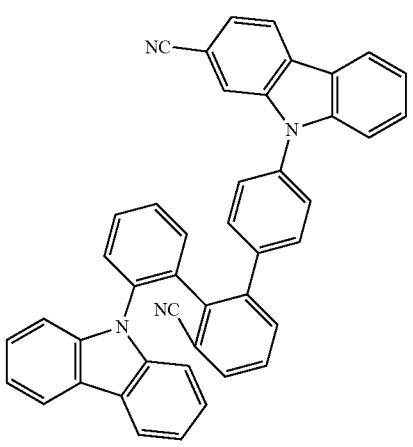
96
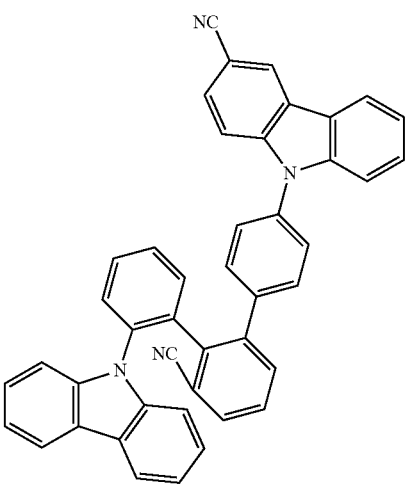

97
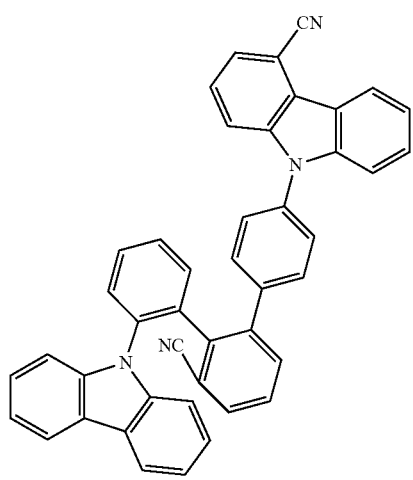
98
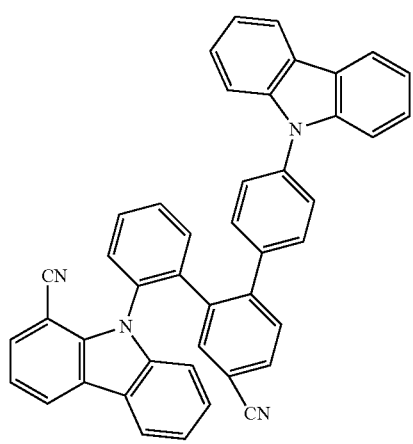
99
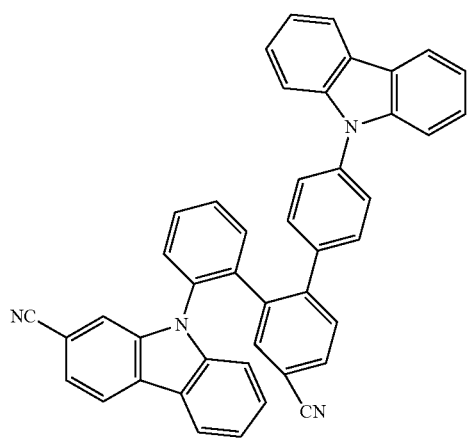
100
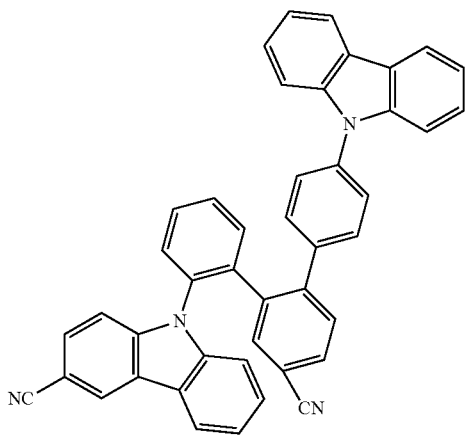
101
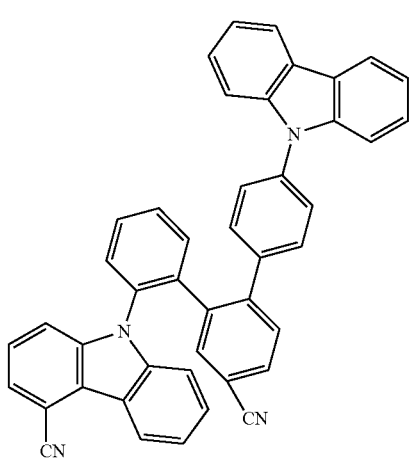
102
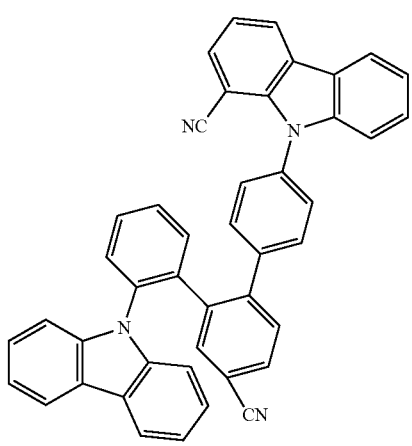

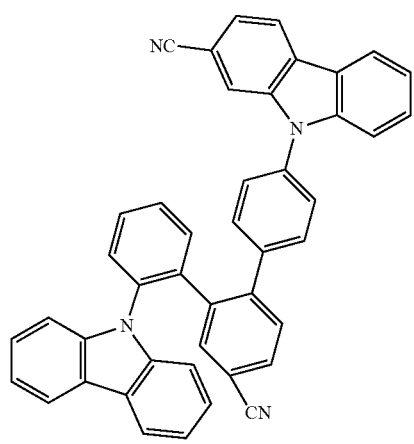
103
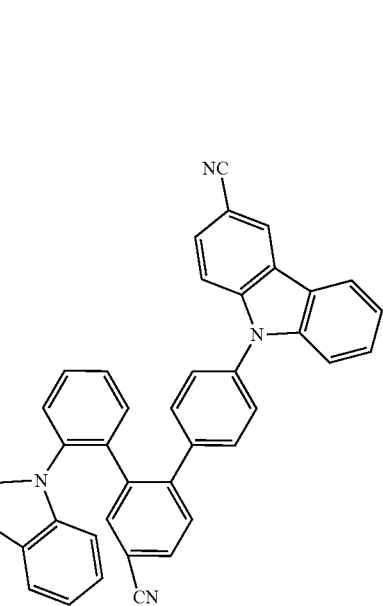
104
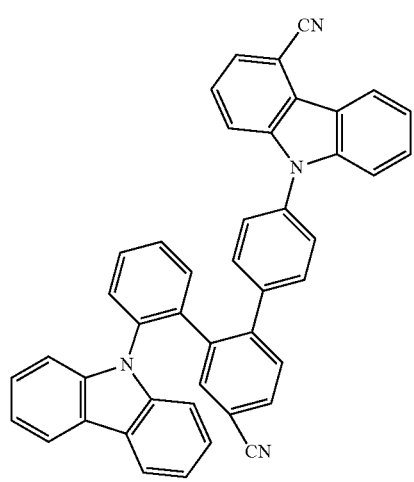
105
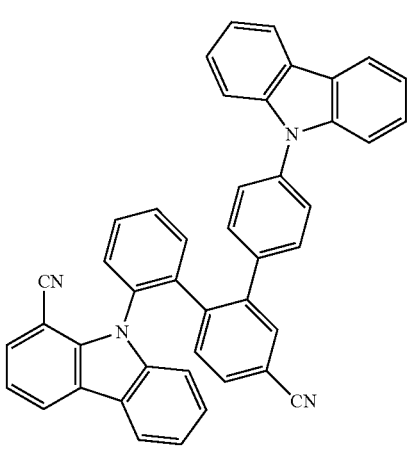
106
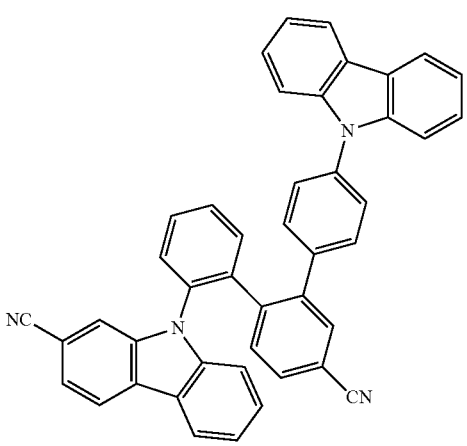
107
108

109
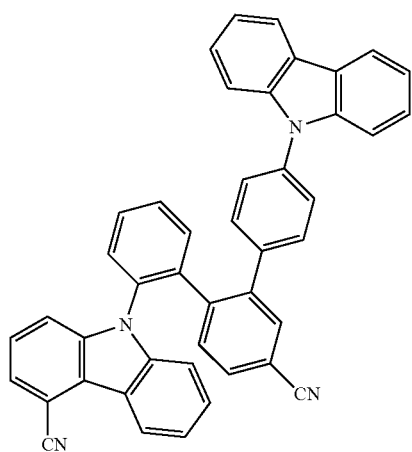
110
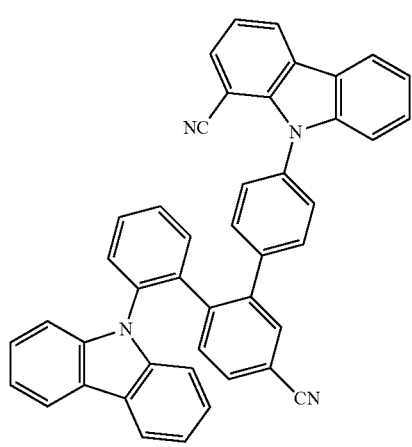
111
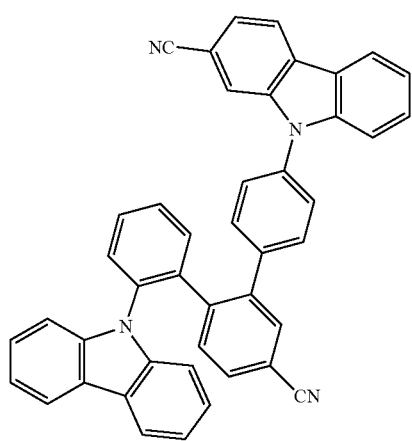
112
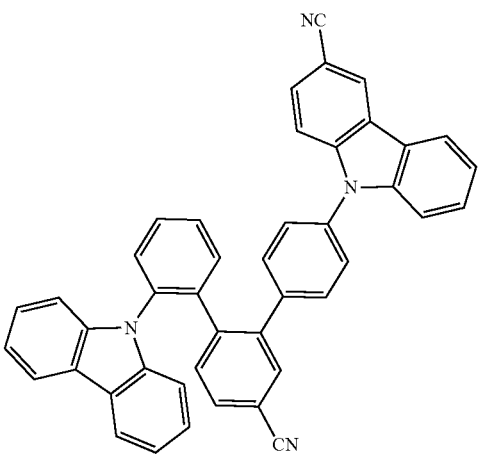
113
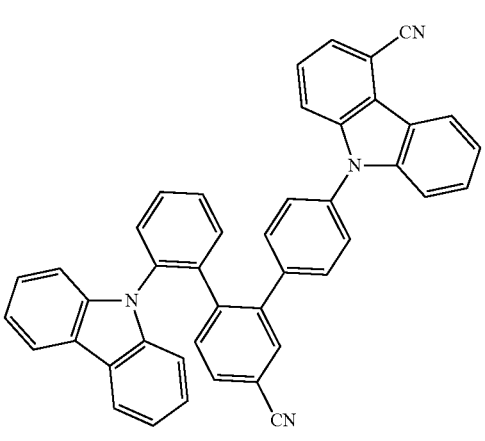
114
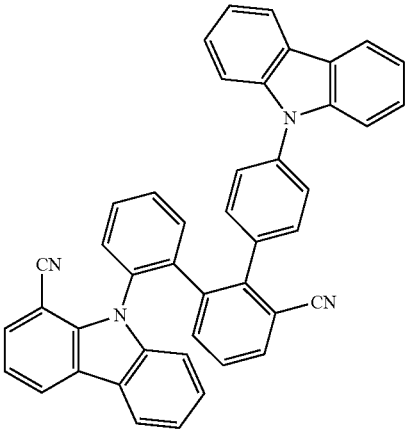

115 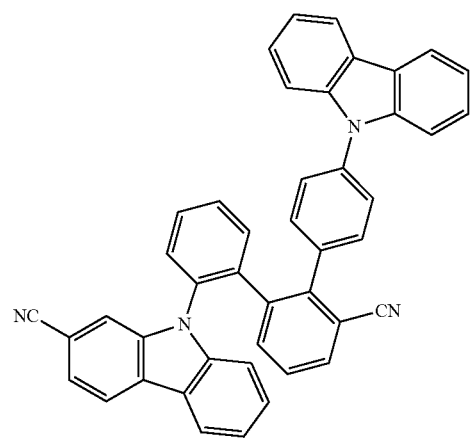
116 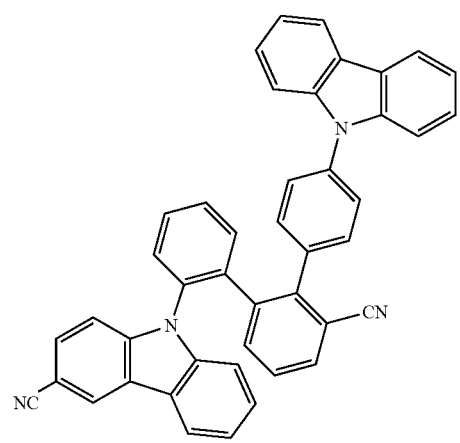
117 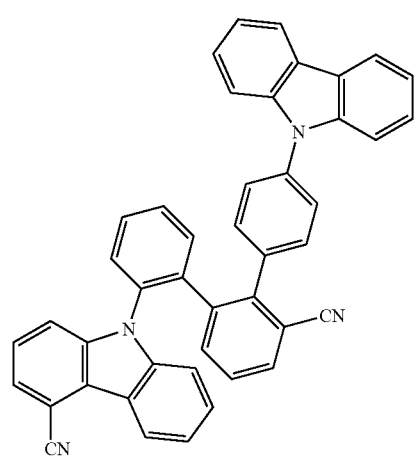
118 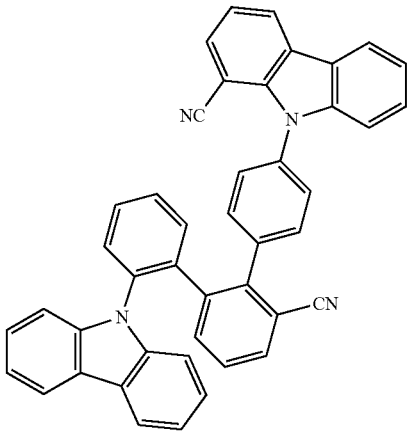
119 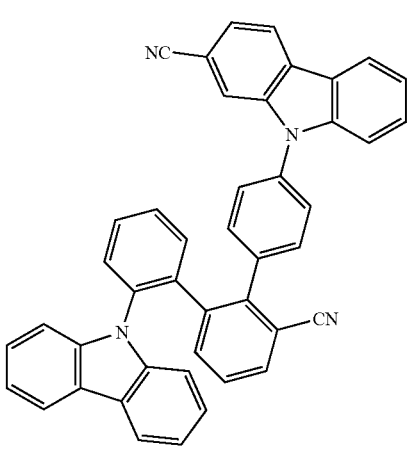
120 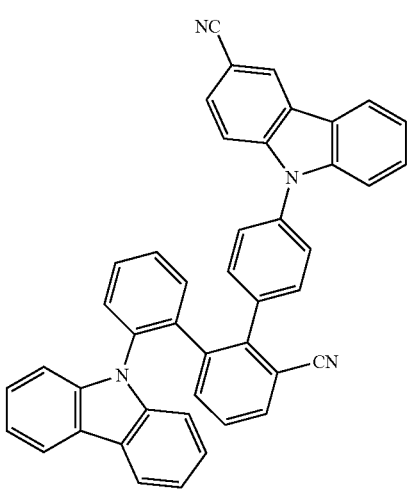

121
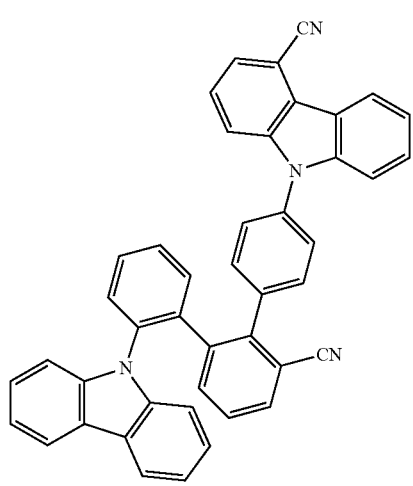
122
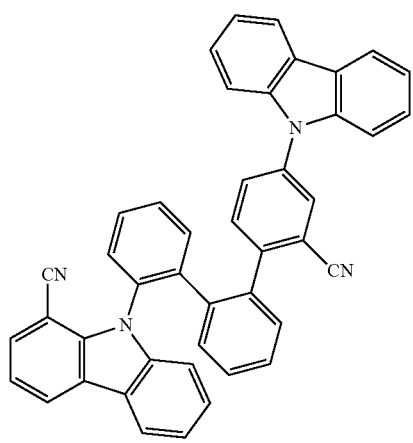
123
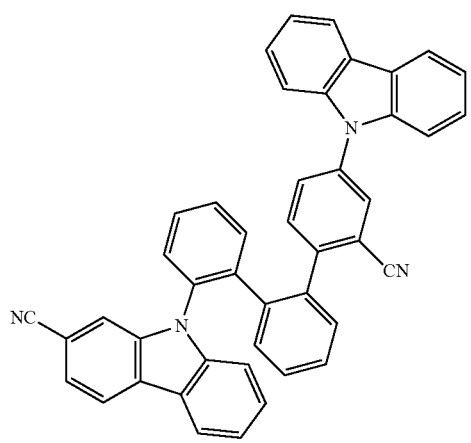
124
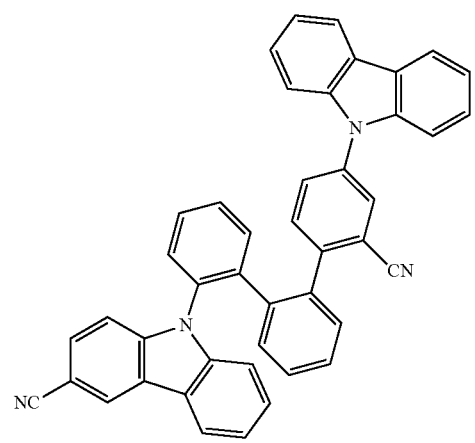
125
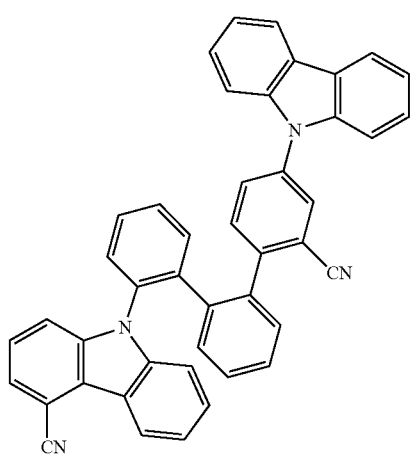
126
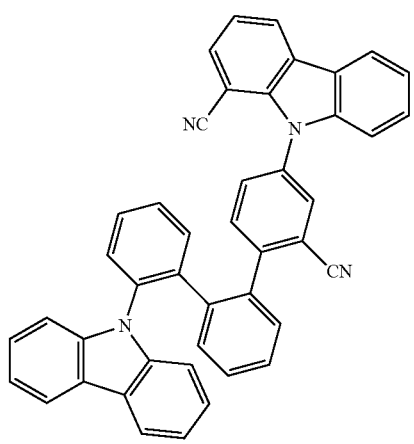

127
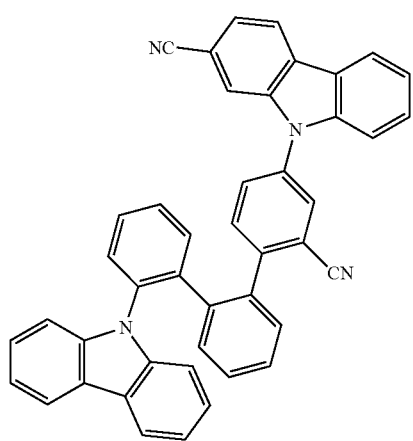
128
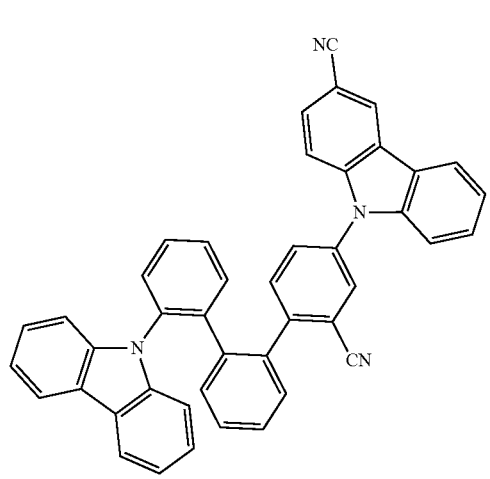
129
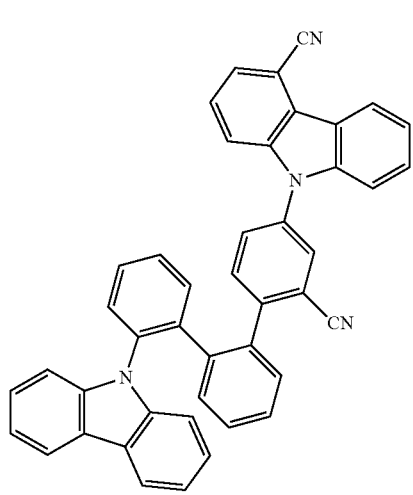
130
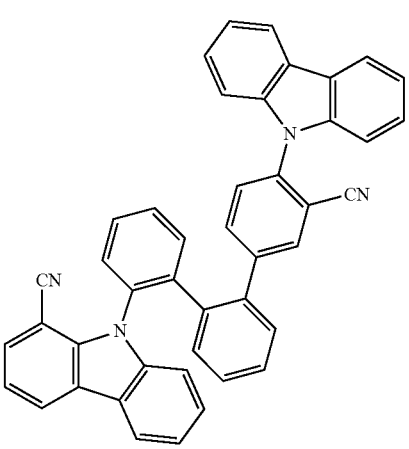
131
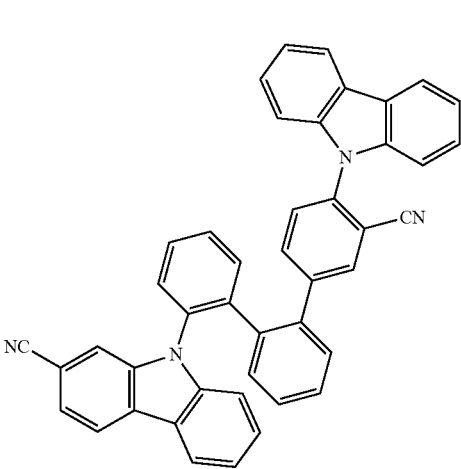
132
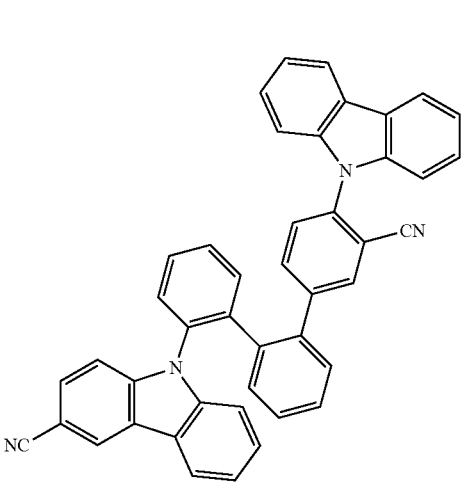

133
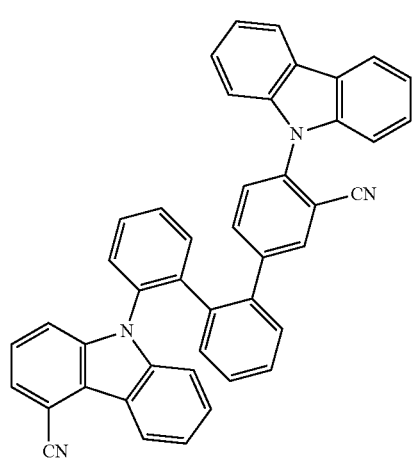
134
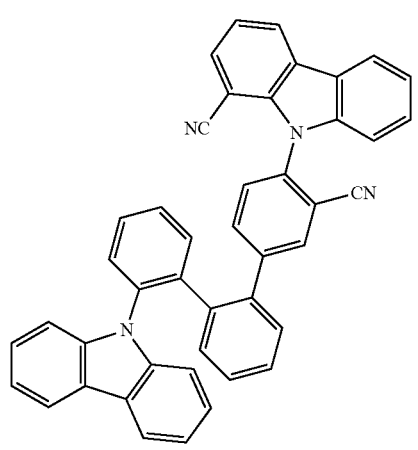
135
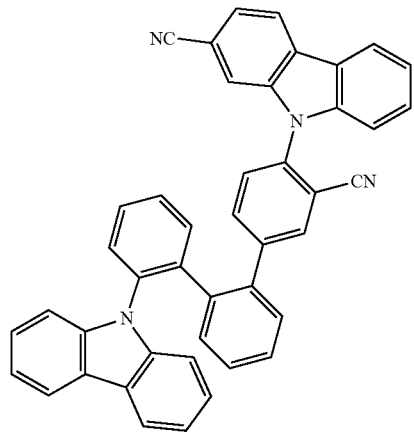
136
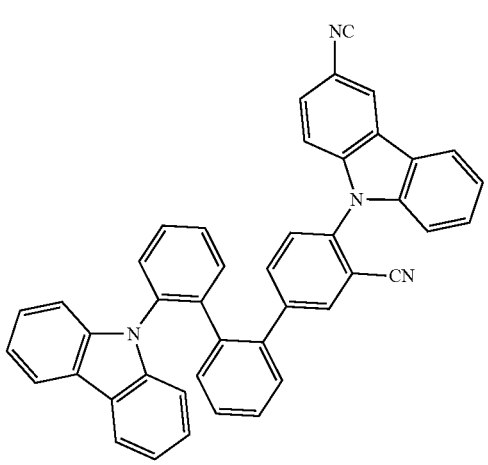
137
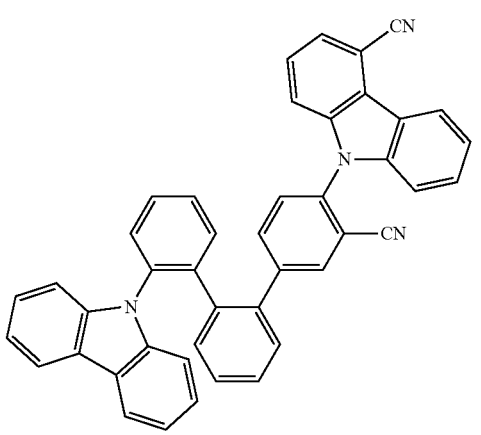
138
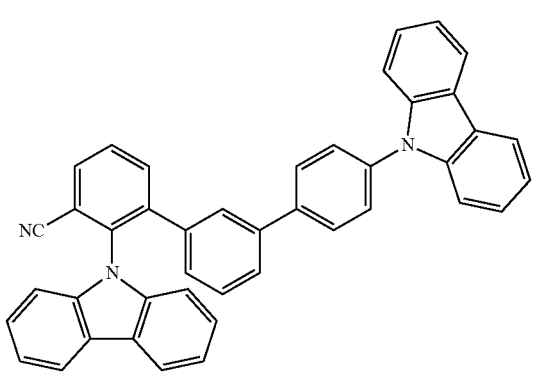
139
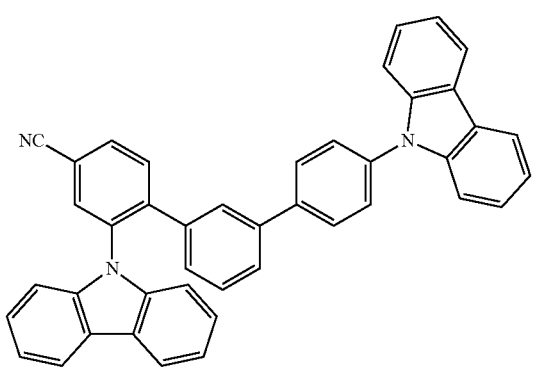

140
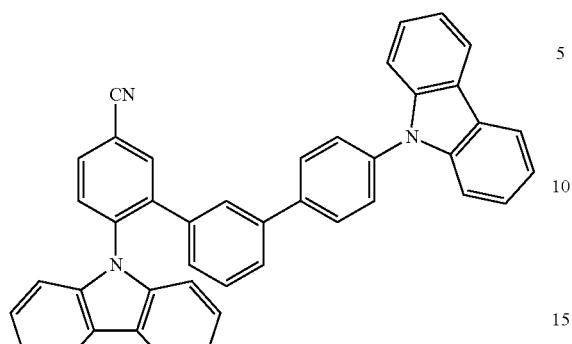
141
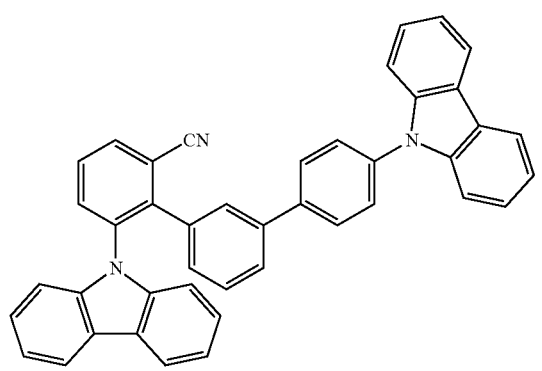
142
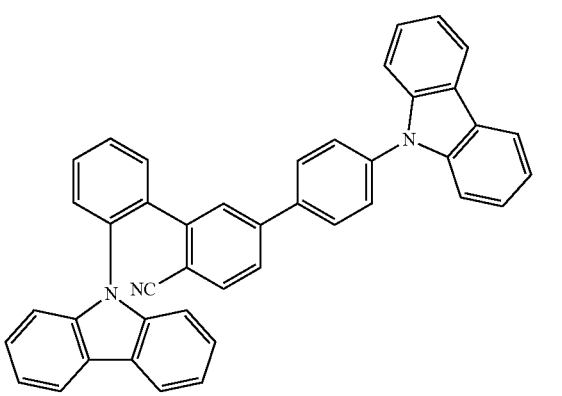
143
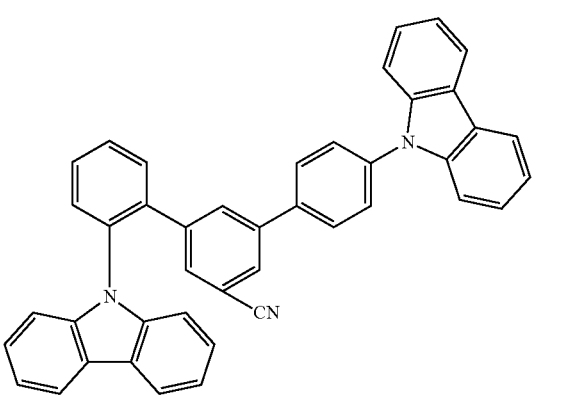
144
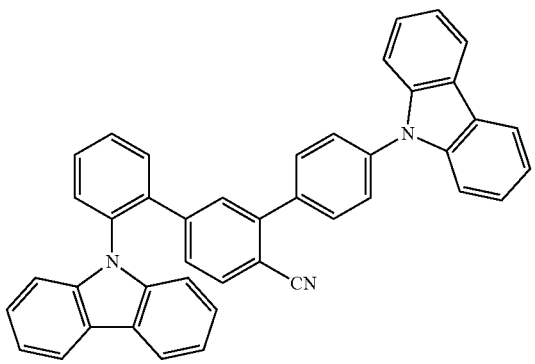
145
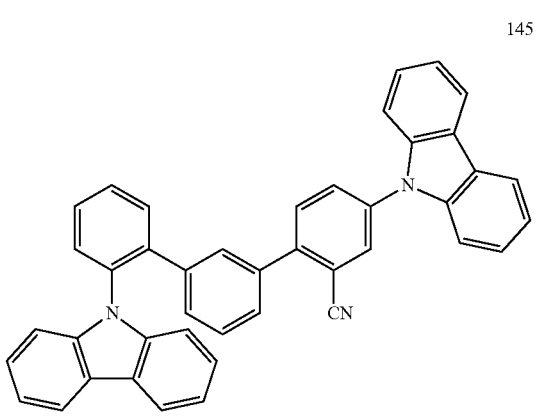
146
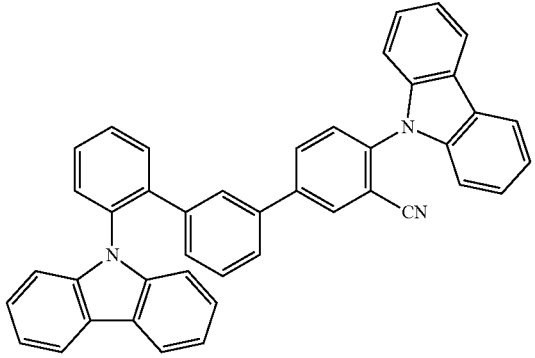
147
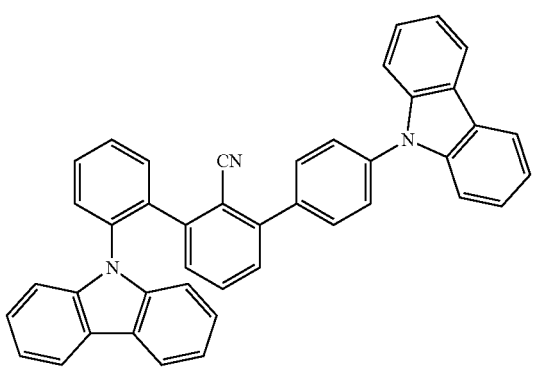

148
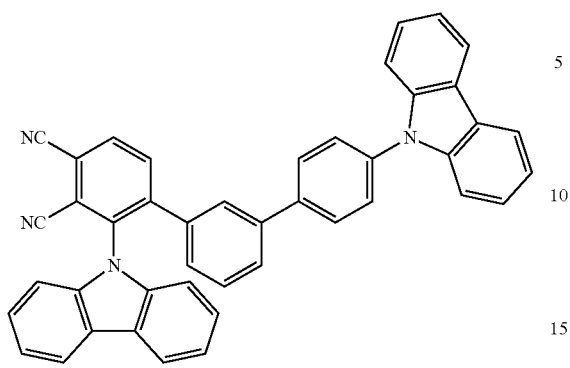
149
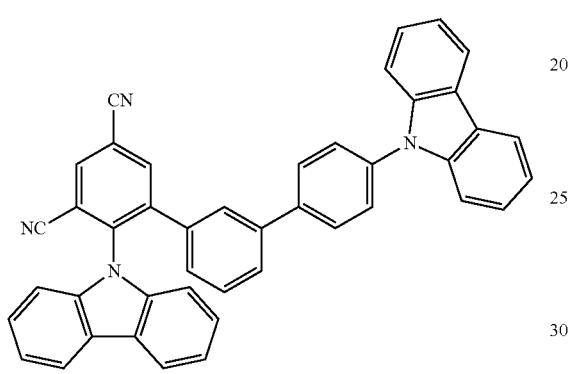
150
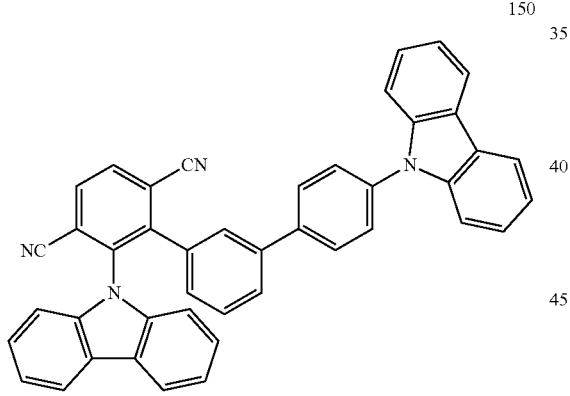
151
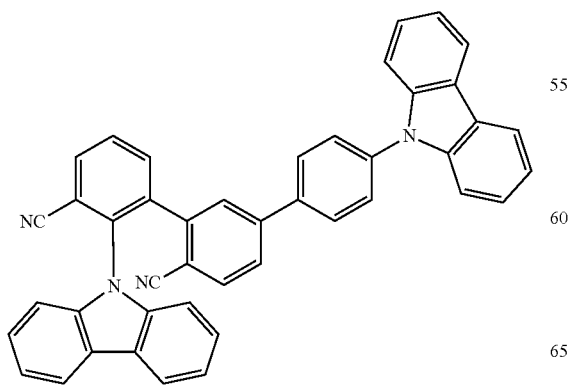
152
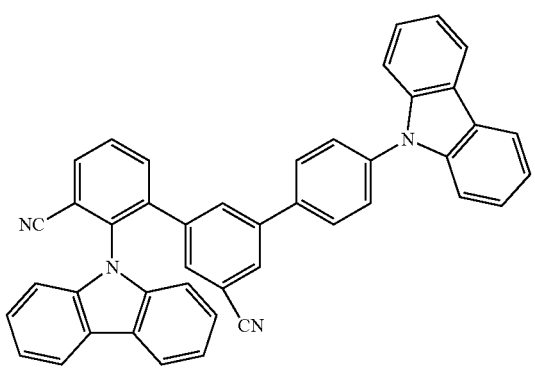
153
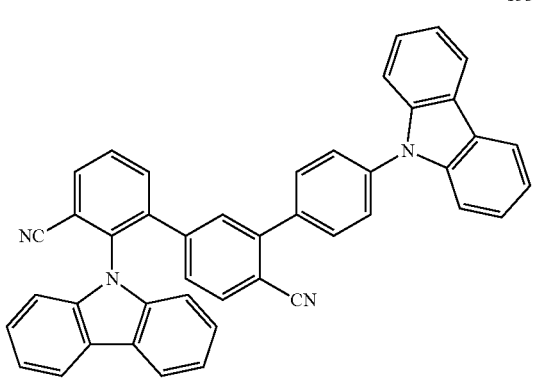
154
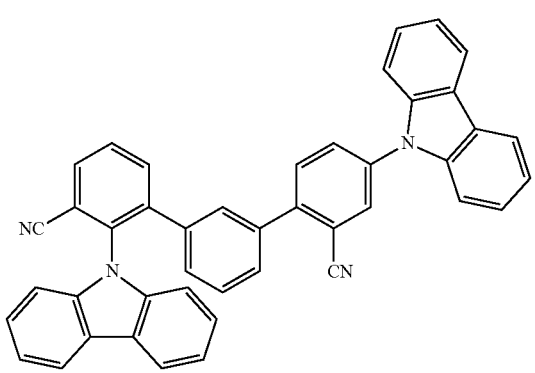
155
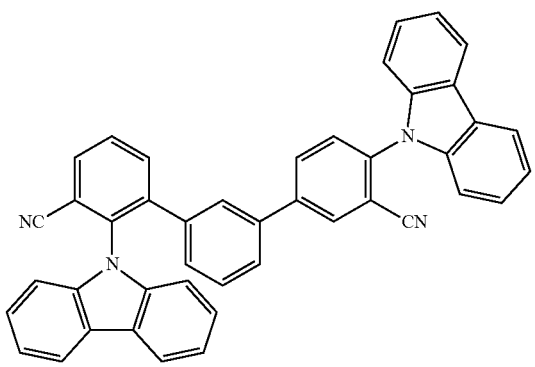

156

157

158
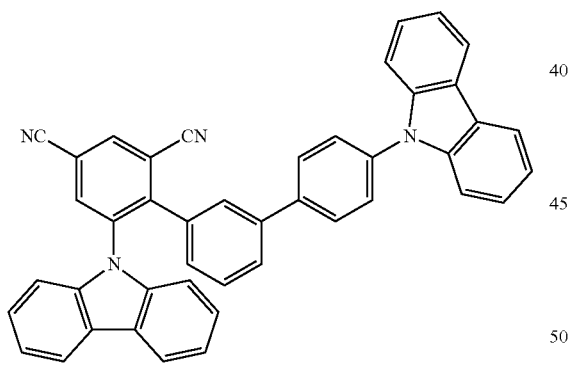
159

160
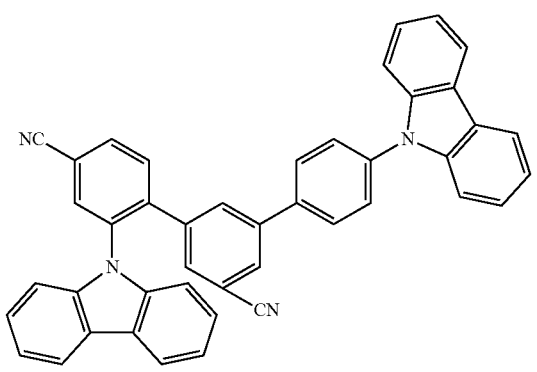
161
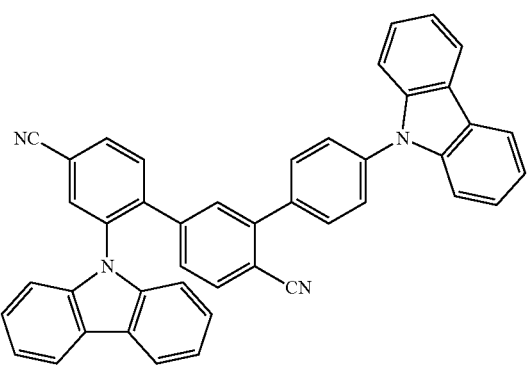
162
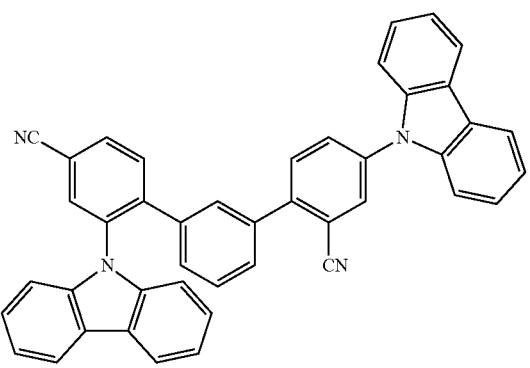
163
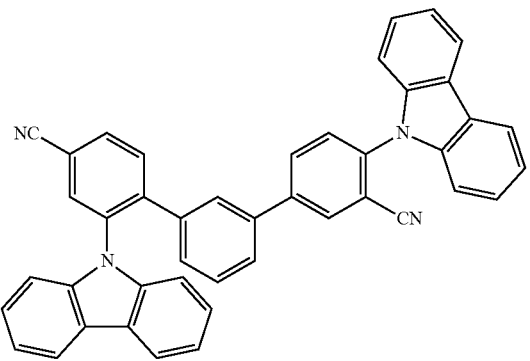

-continued
164
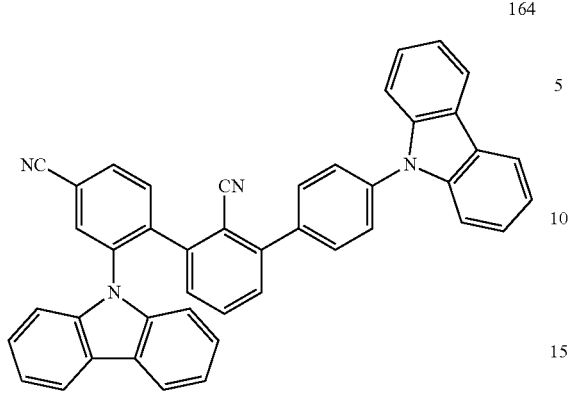
165
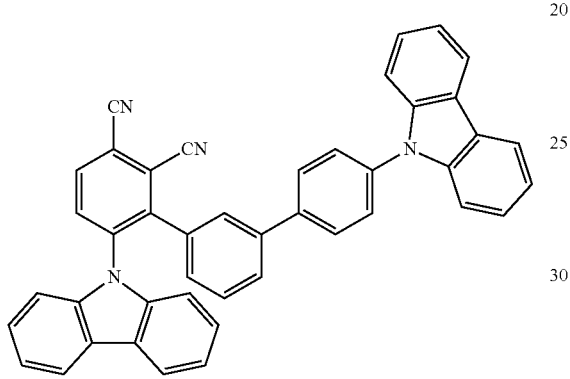
166
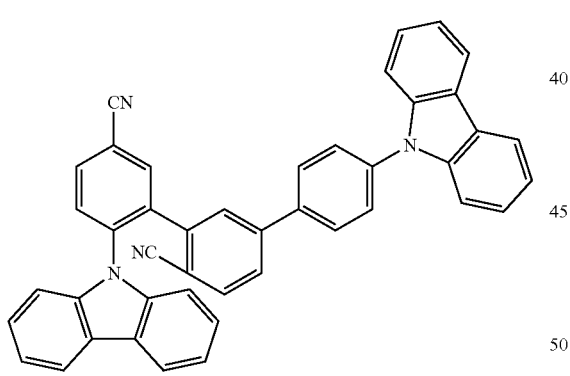
167
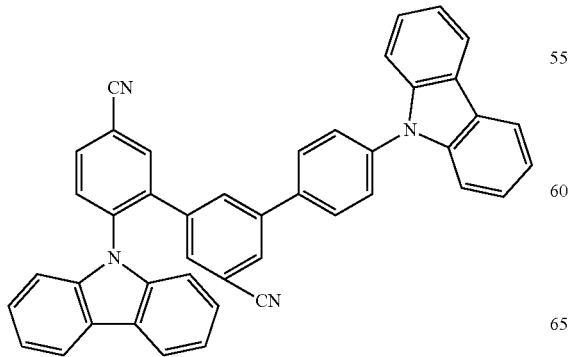
-continued
168
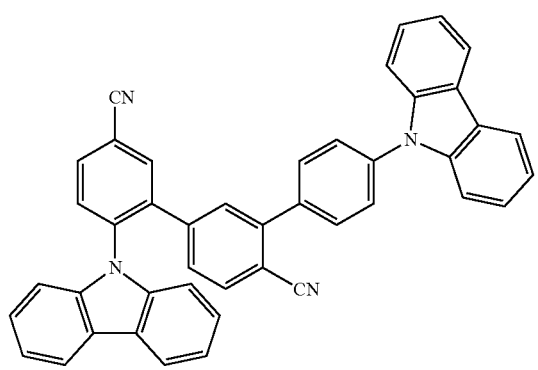
169
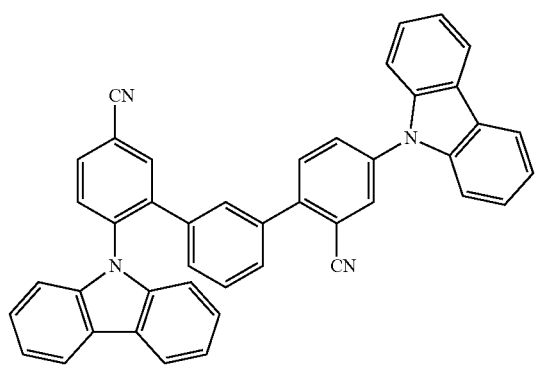
170
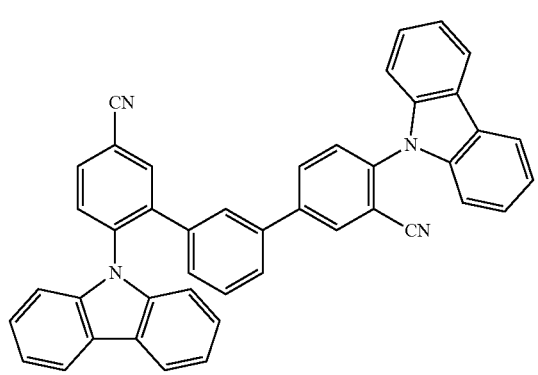
171
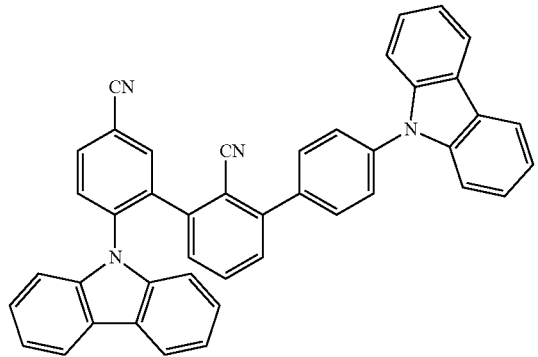

172
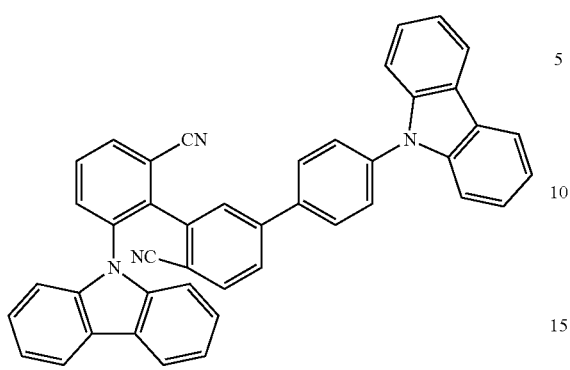
173
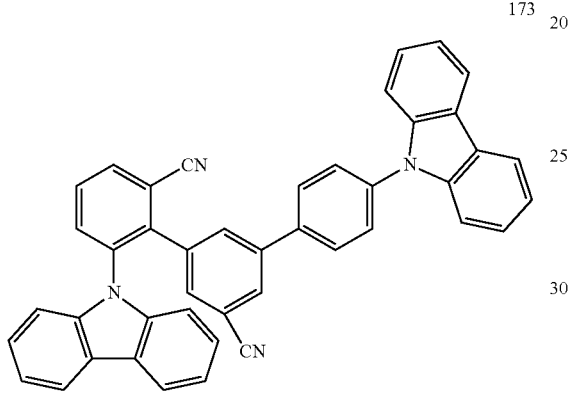
174
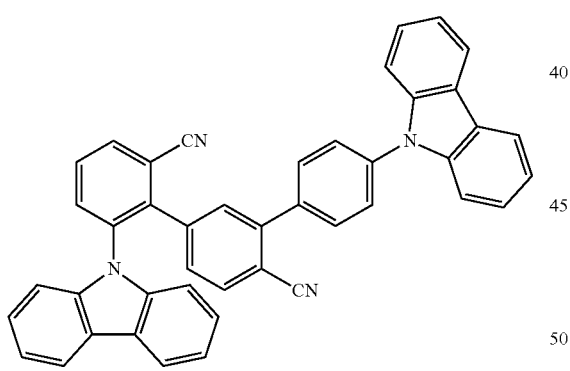
175
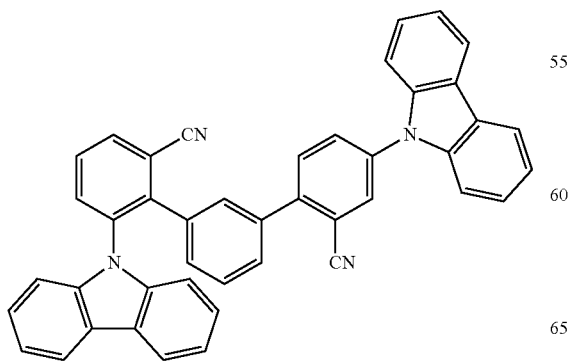
176
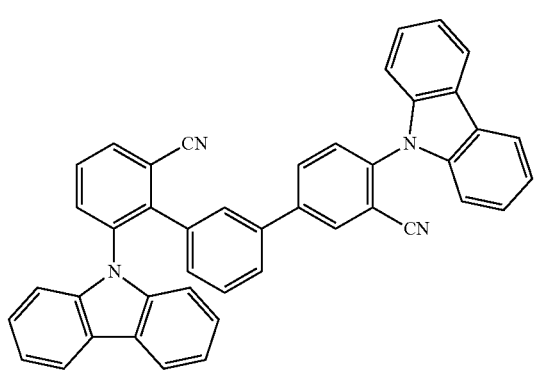
177
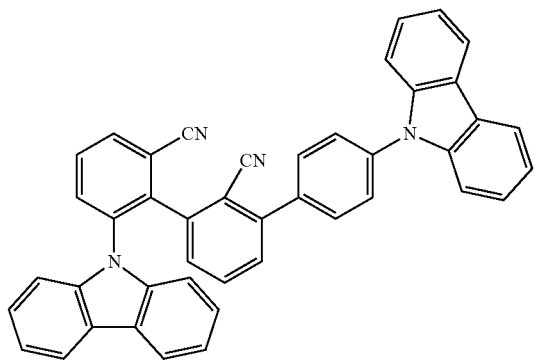
178
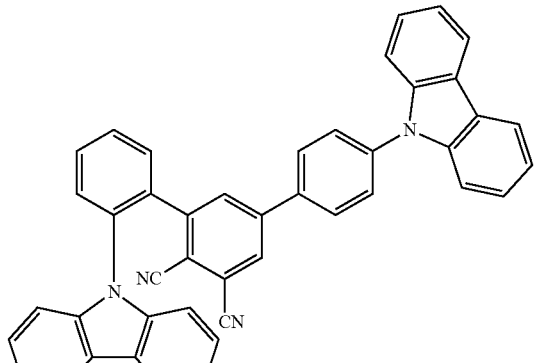
179
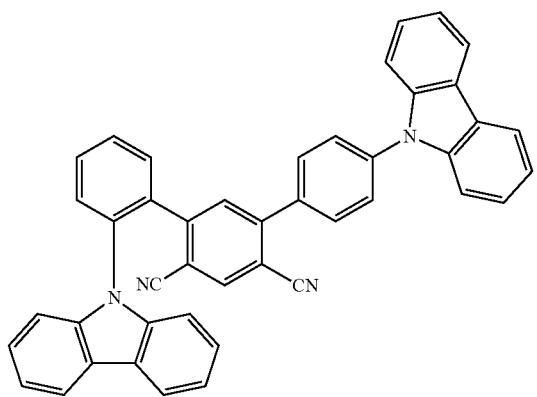

-continued
180
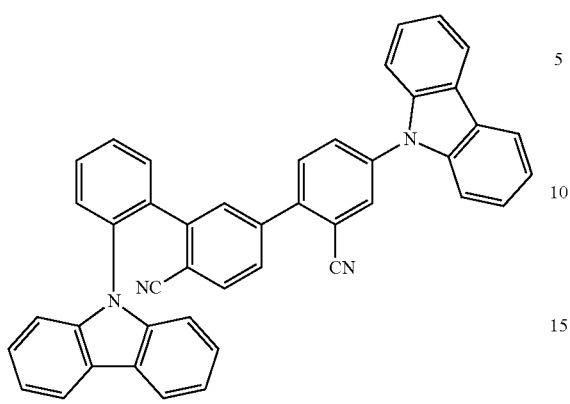
181
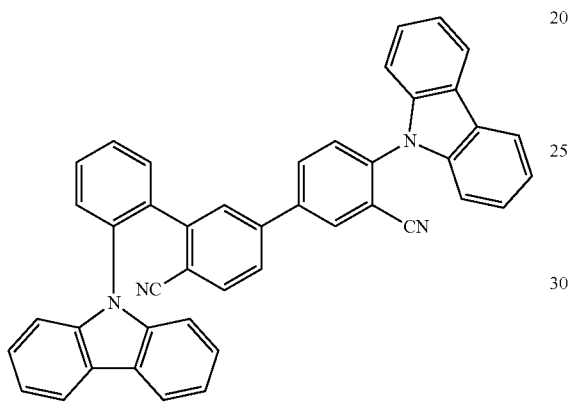
182
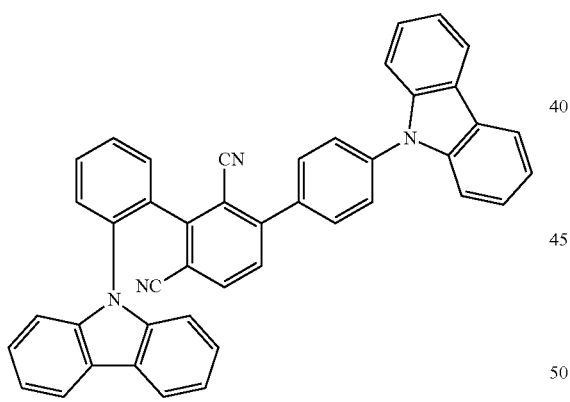
183
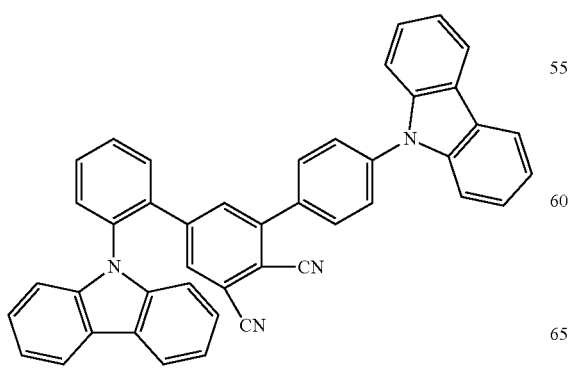
-continued
184
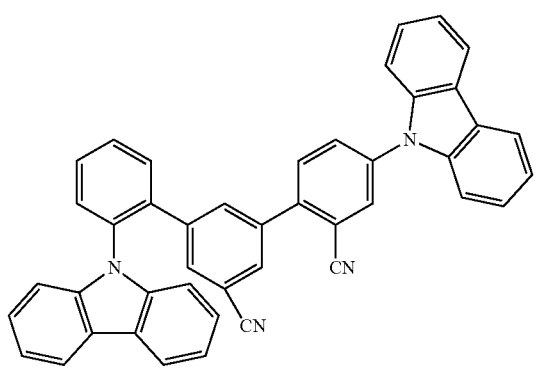
185
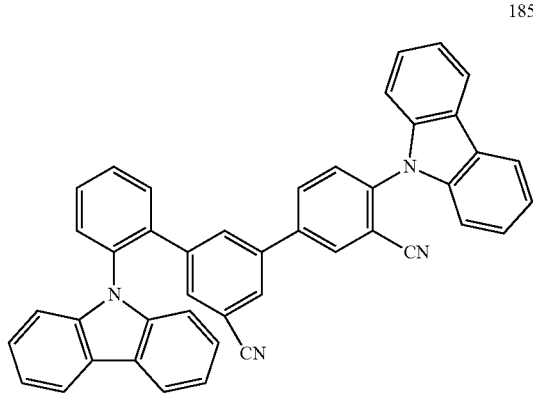
186
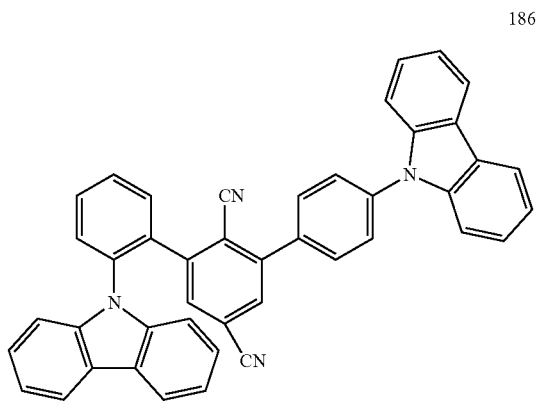
187
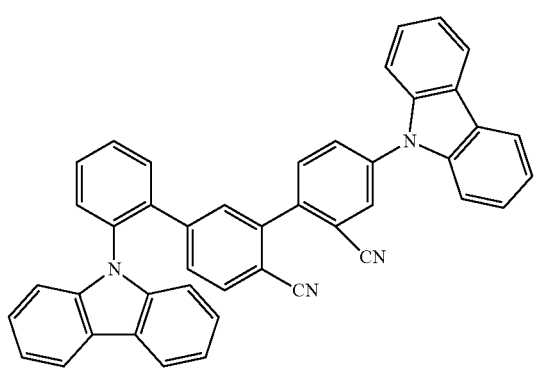

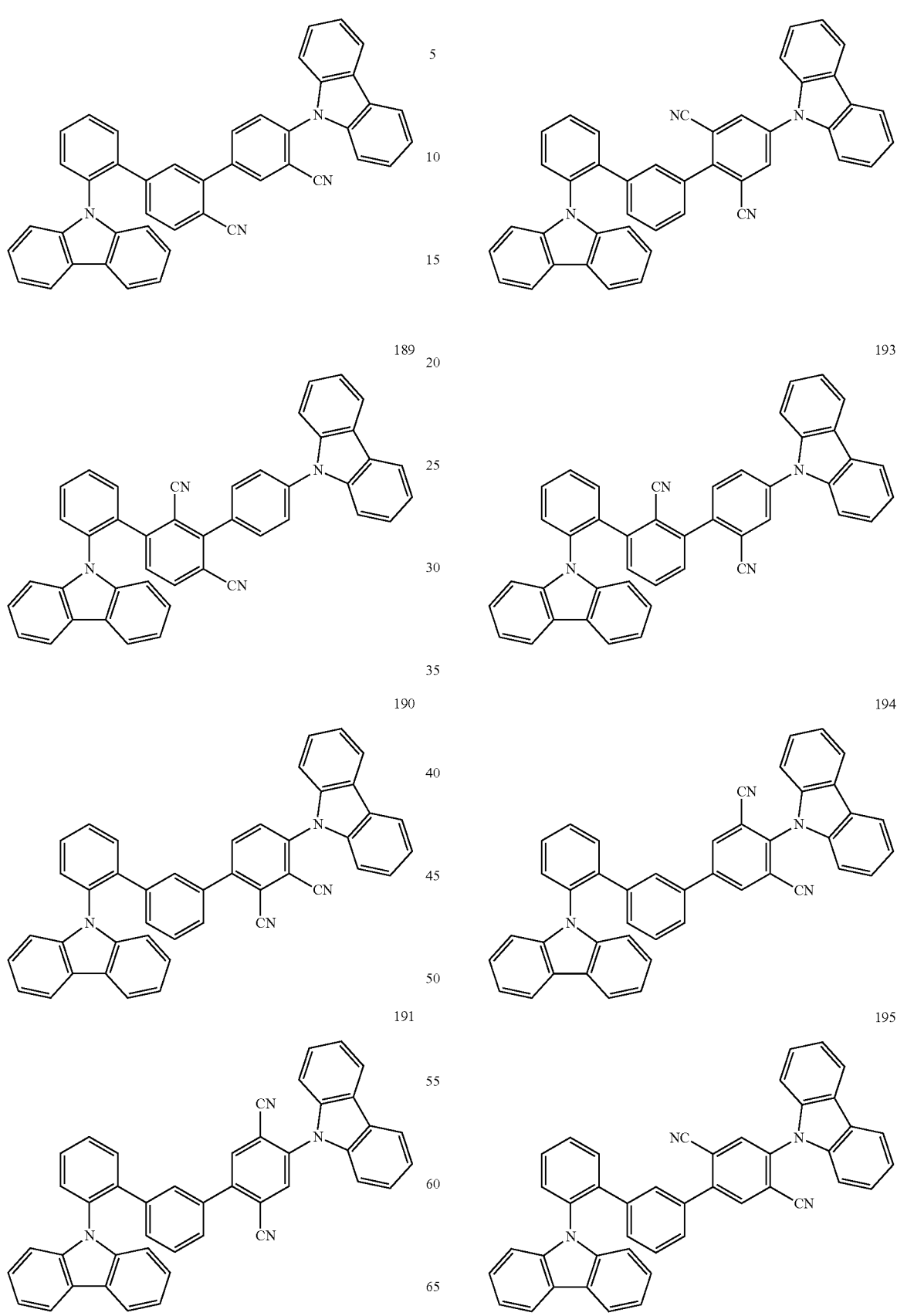

196
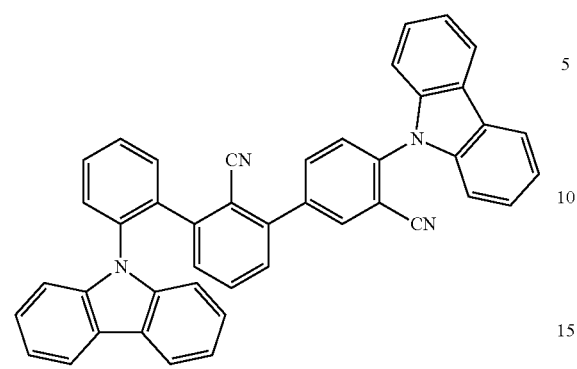
197
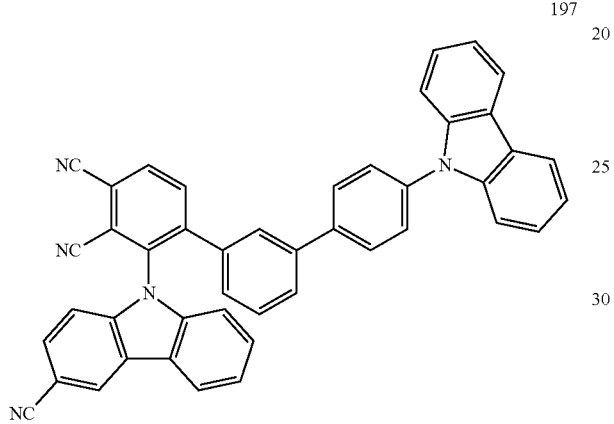
200
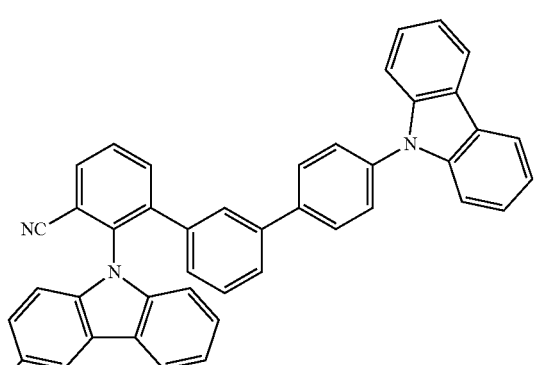
201
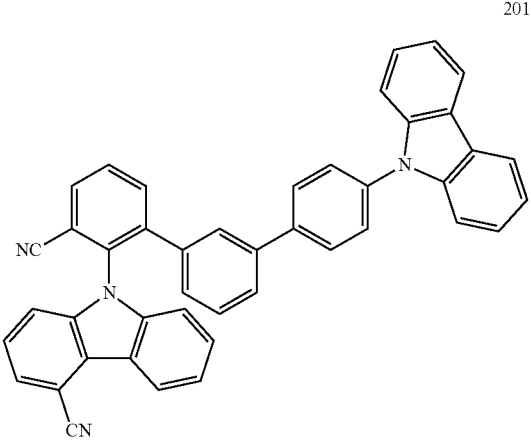
202
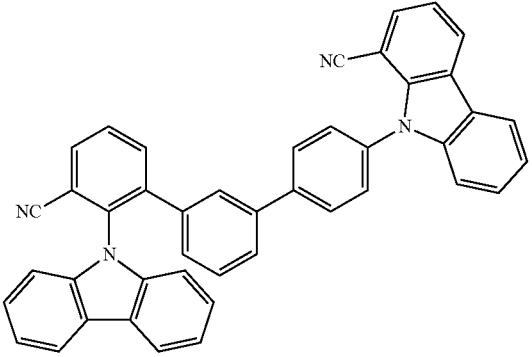
203
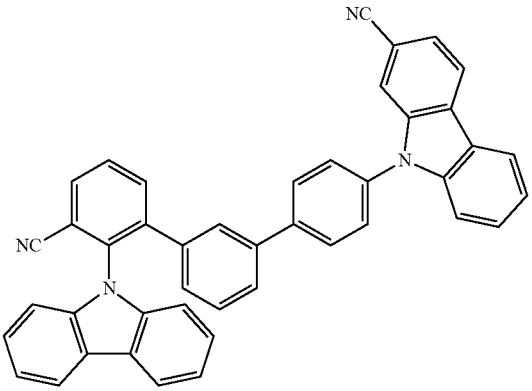

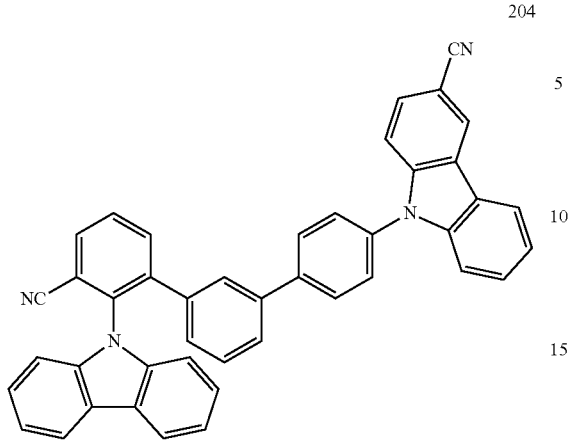
204
205
206
207
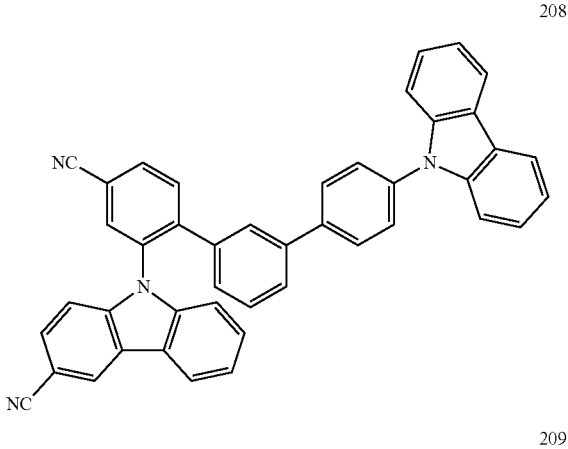
208
209
210
211

212
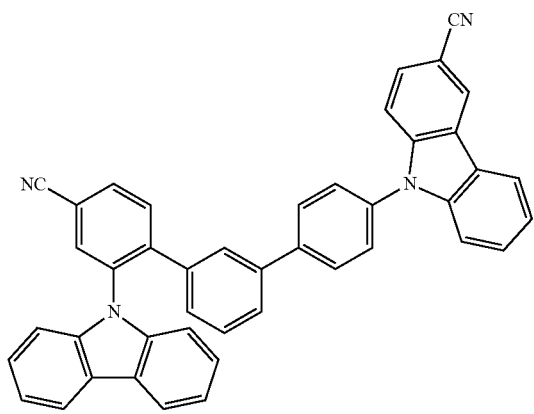
213
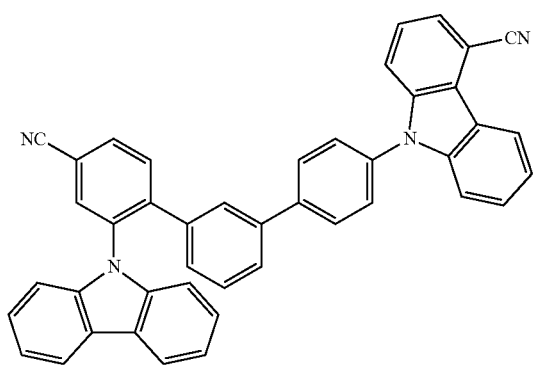
214
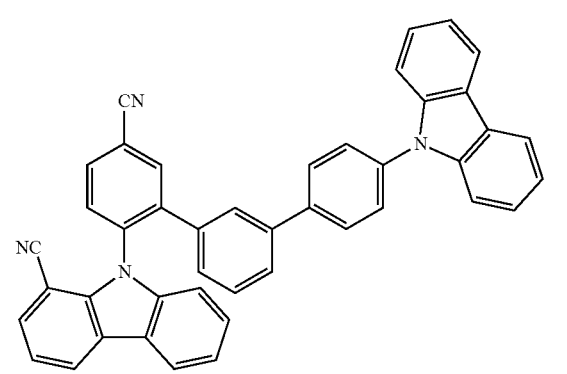
215
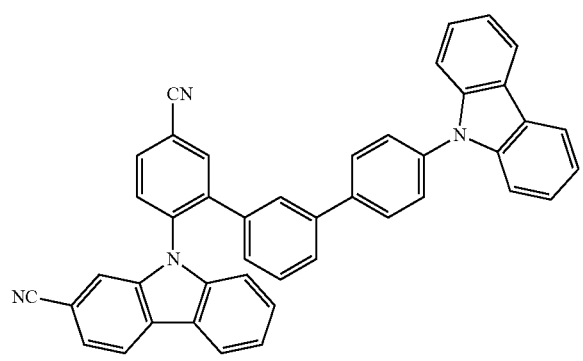
216
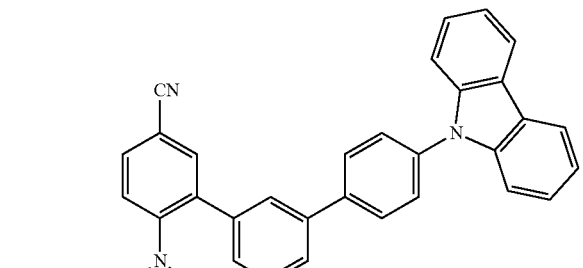
217
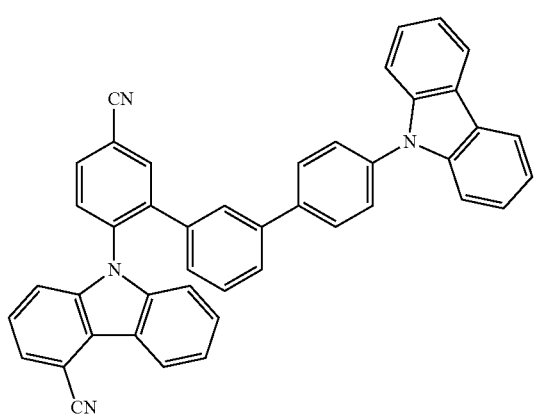
218
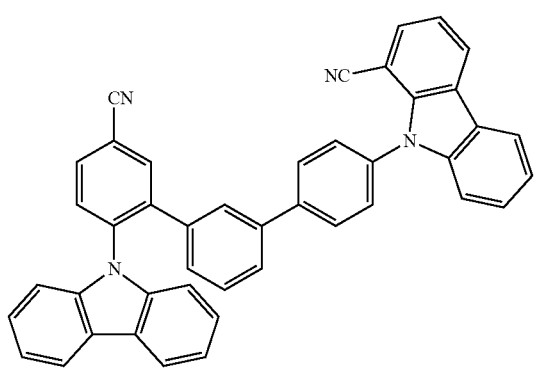
219
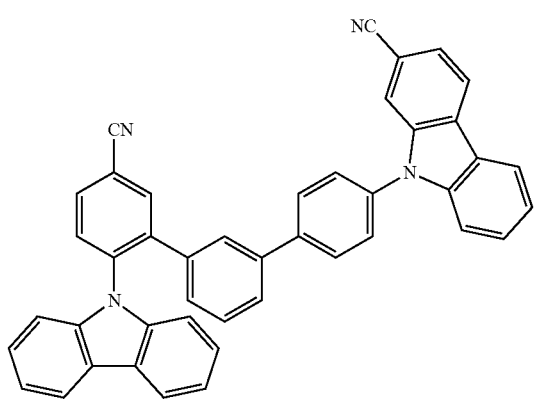

220
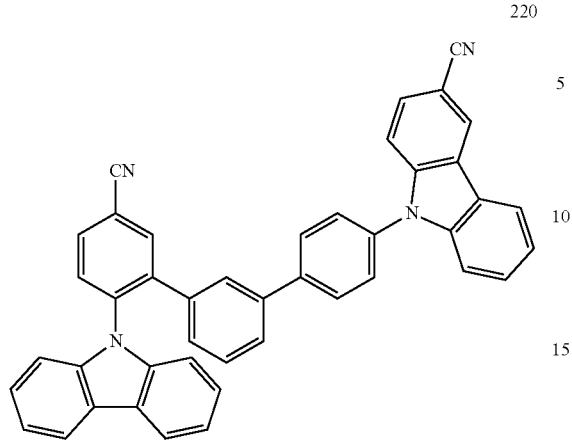
224
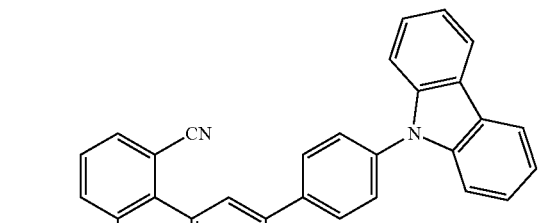
221
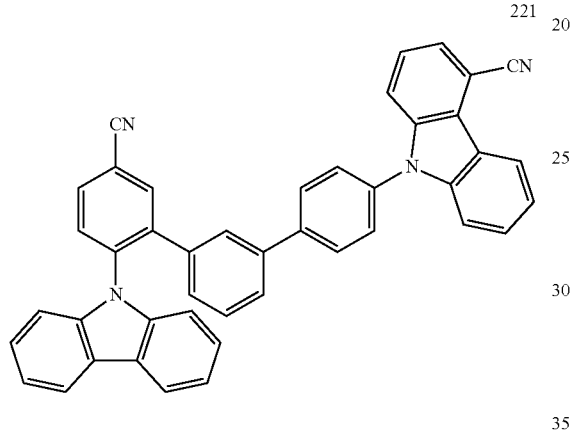
225
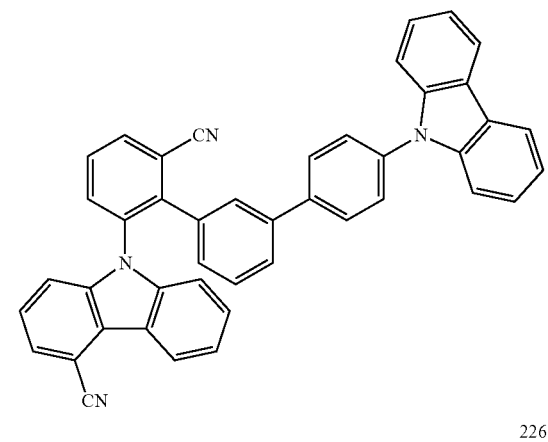
222
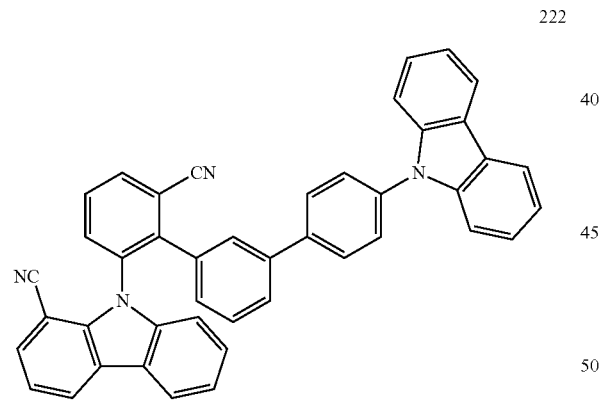
226
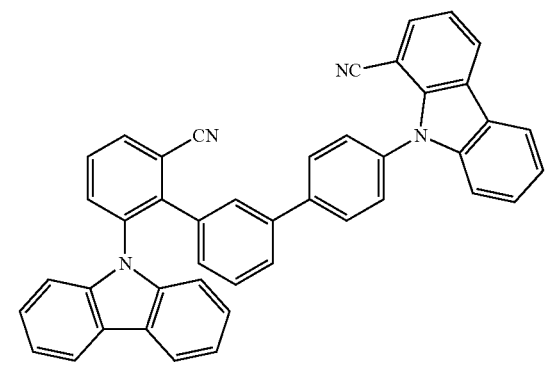
223
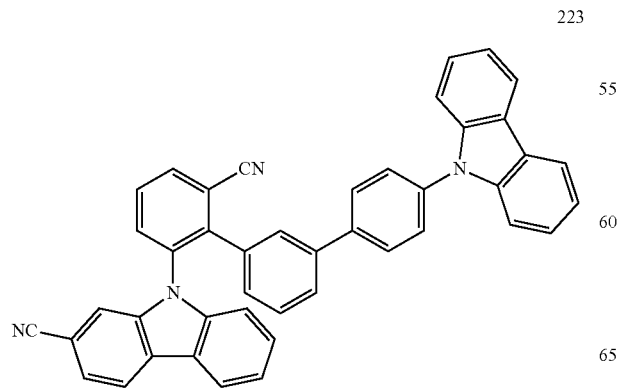
227
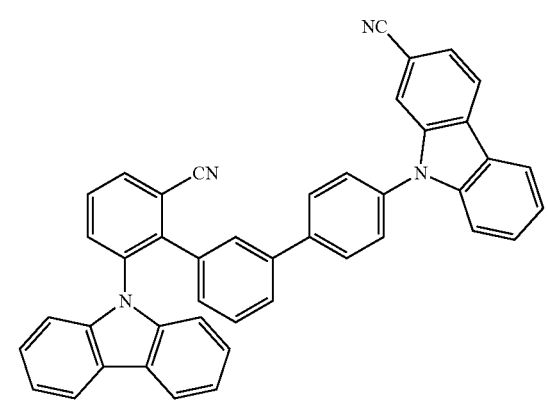

228
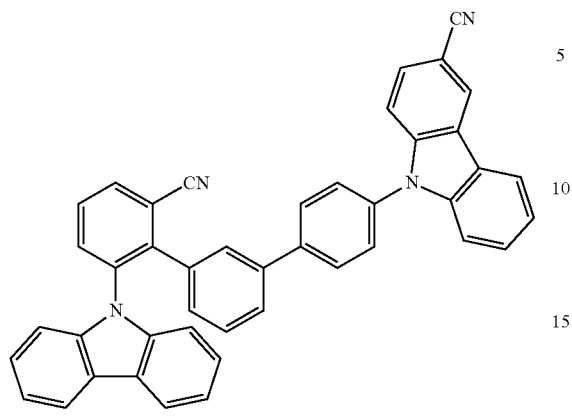
232
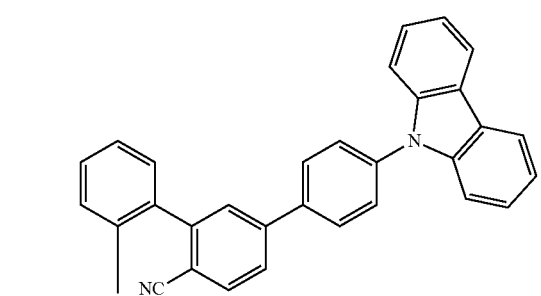
229
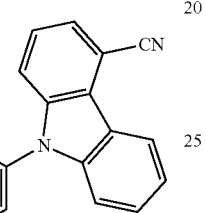
233
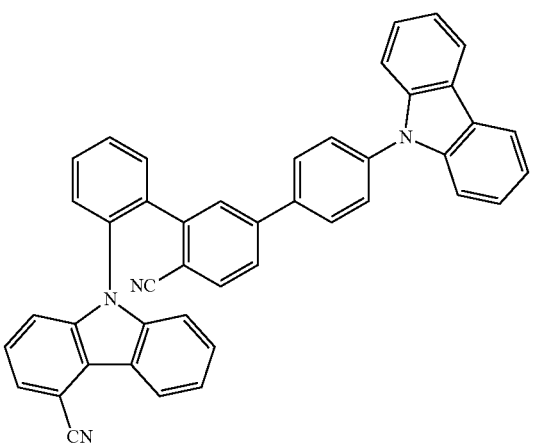
230
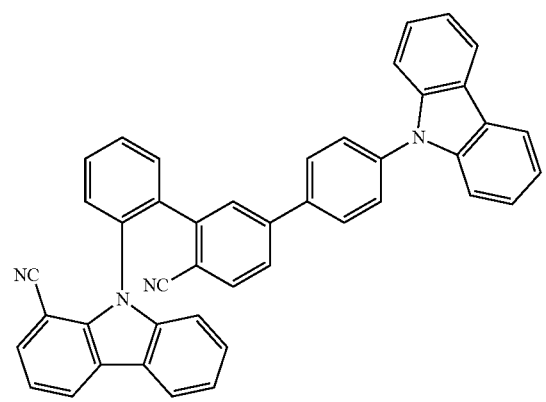
231
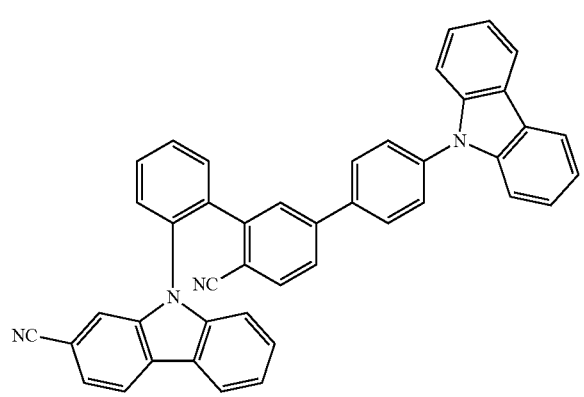
234
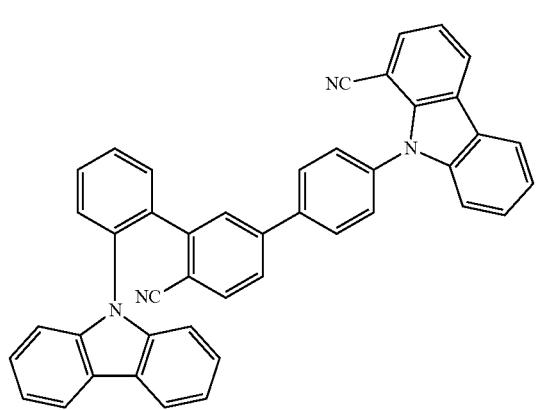

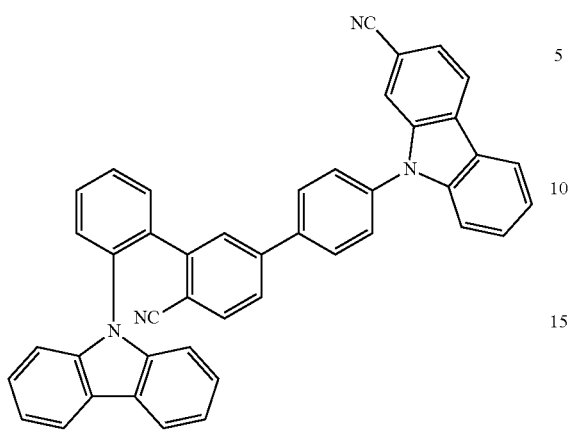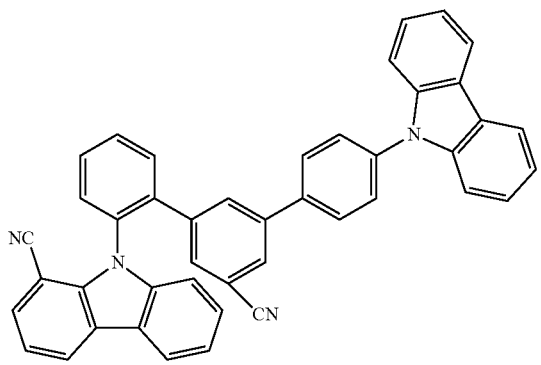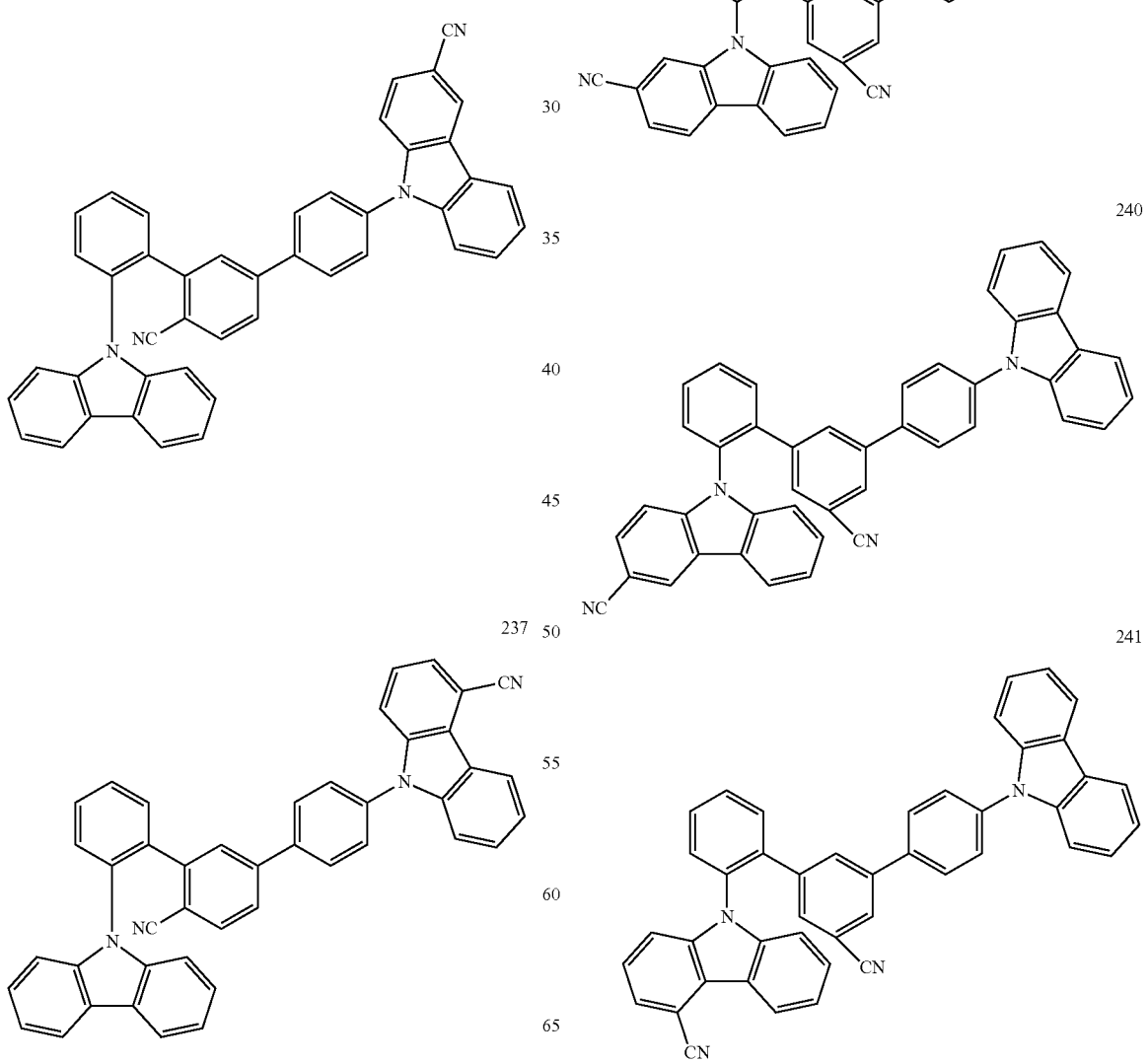

242
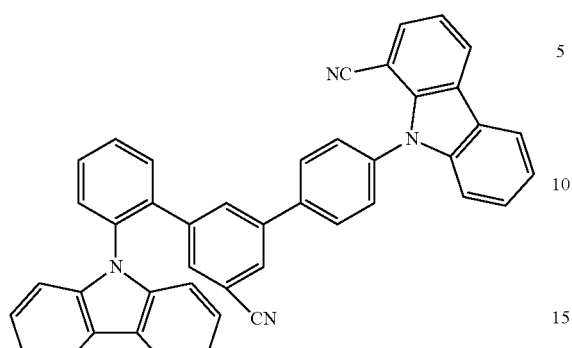
243
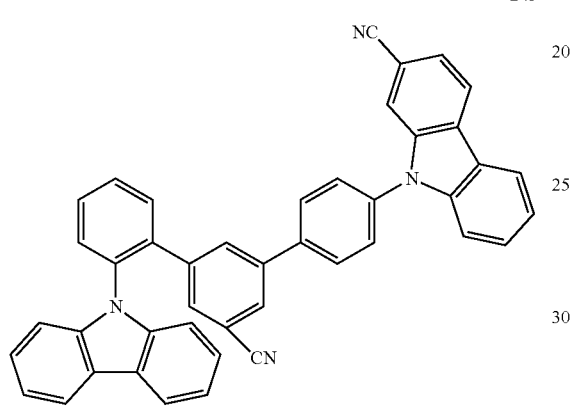
244
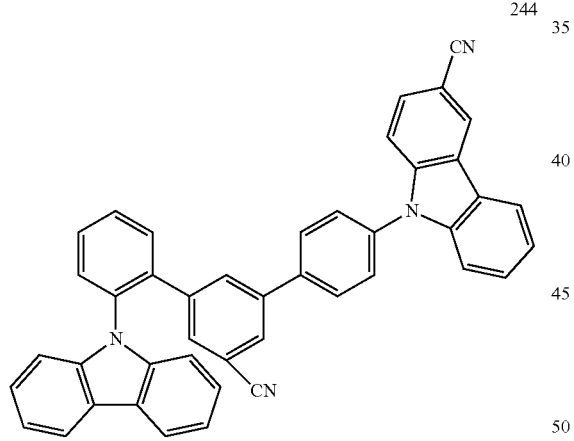
245
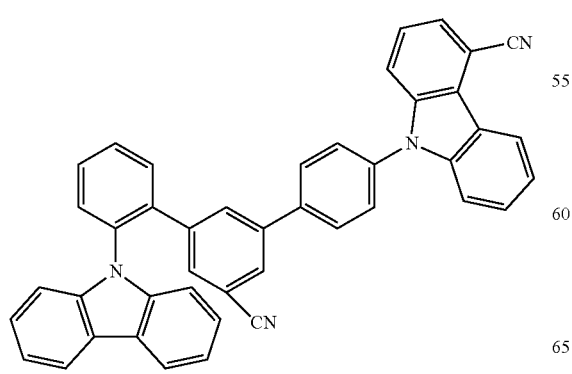
246
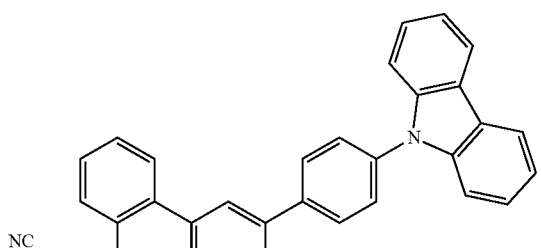
247
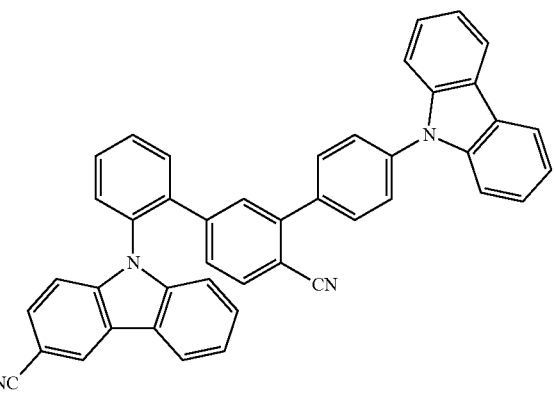
248
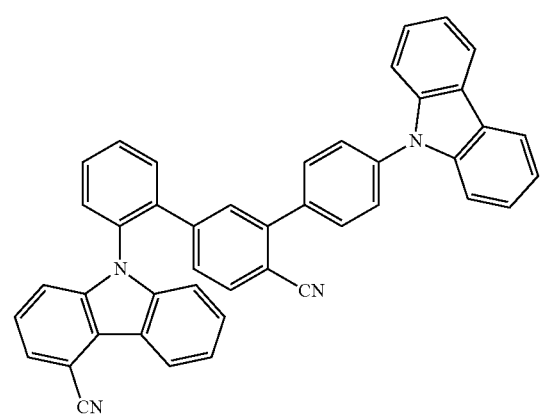
249

-continued
250
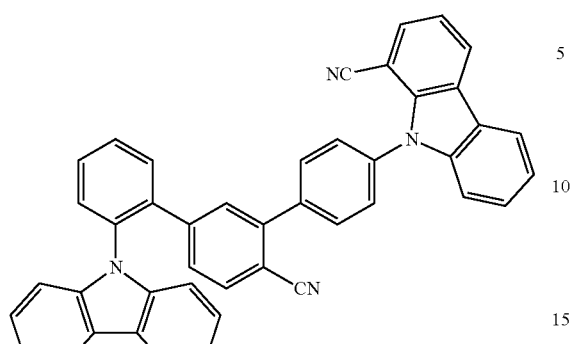
251
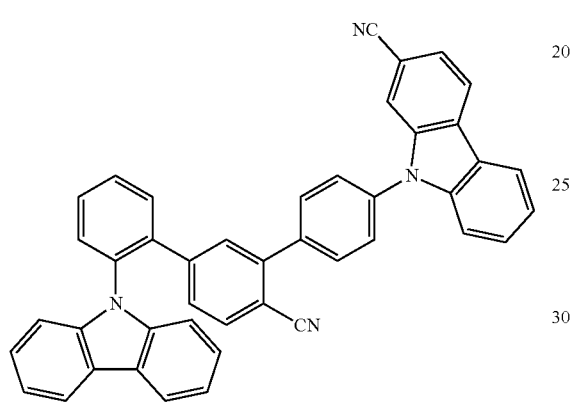
252
253
-continued
254
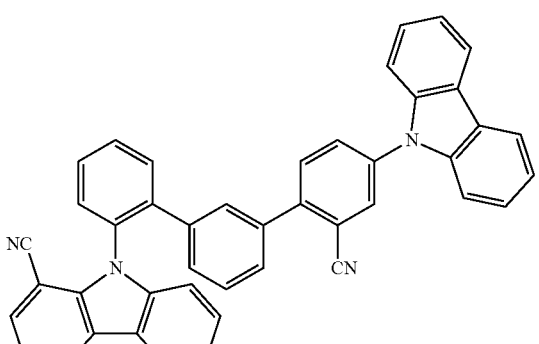
255
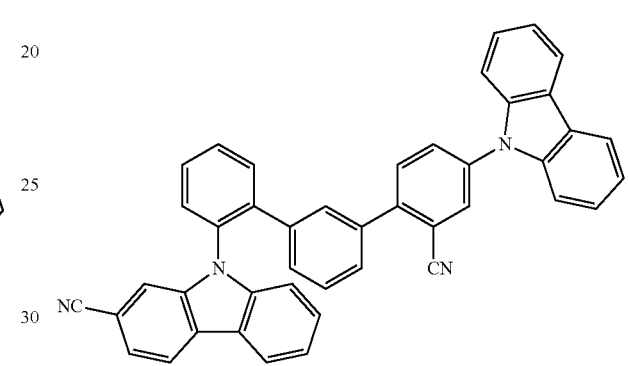
256
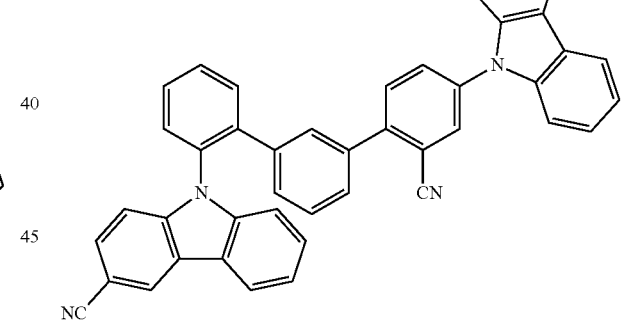
257
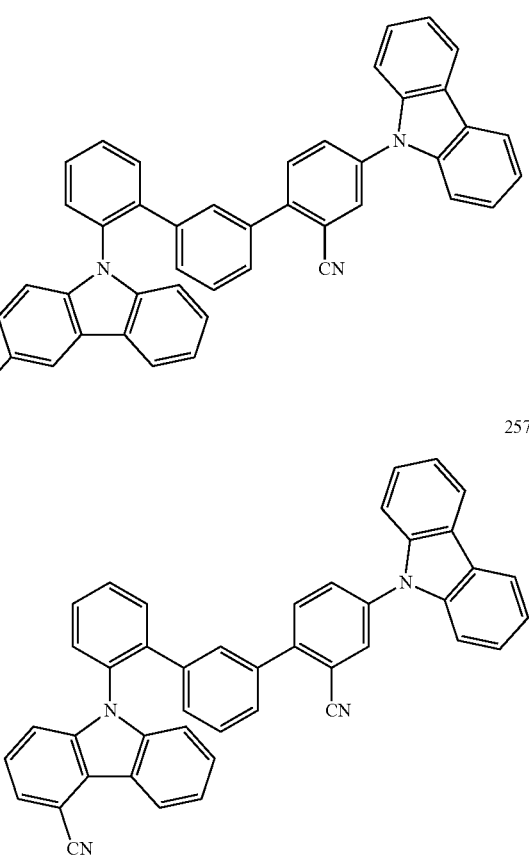

258
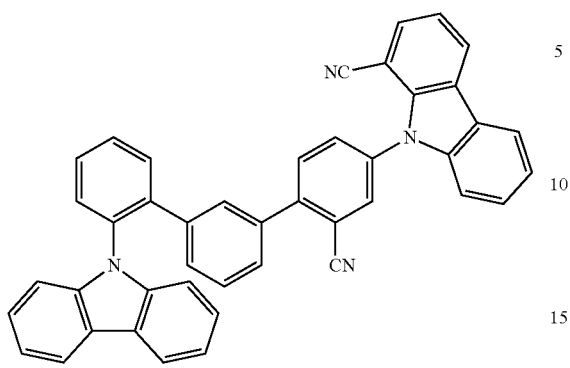
259
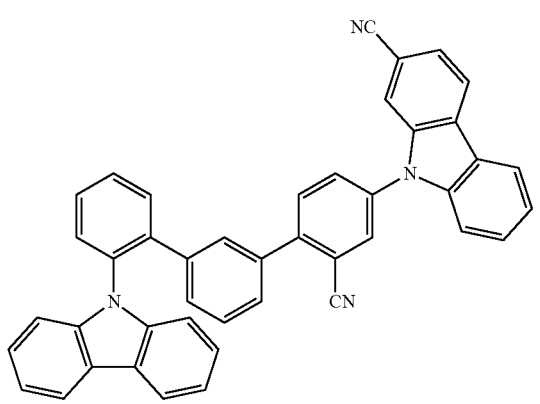
260
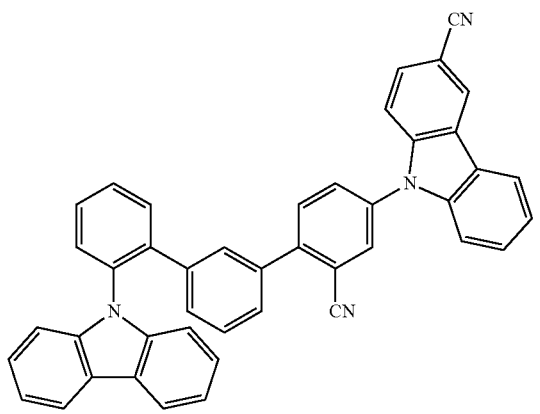
261
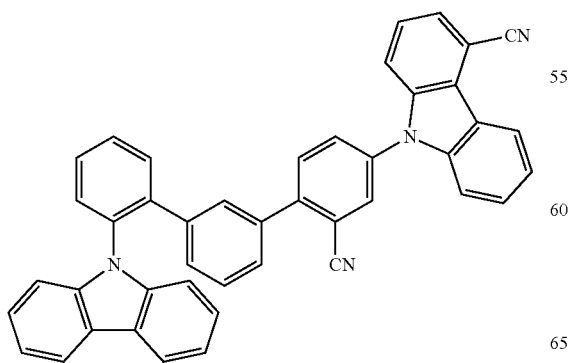
262
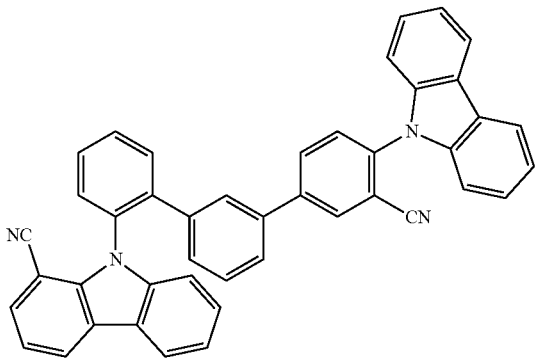
263
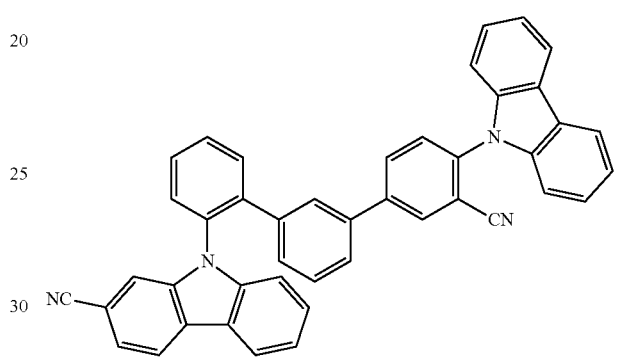
264
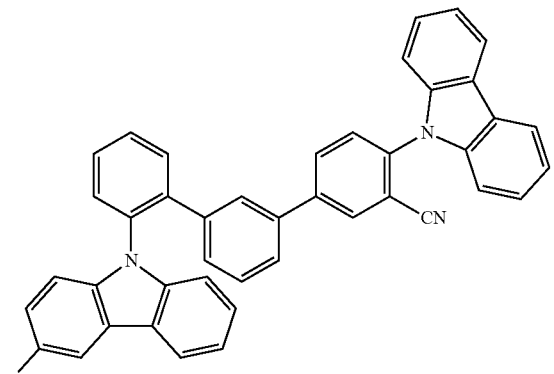
265
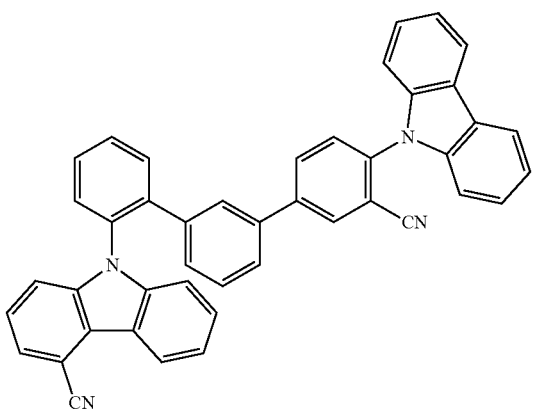

-continued
266
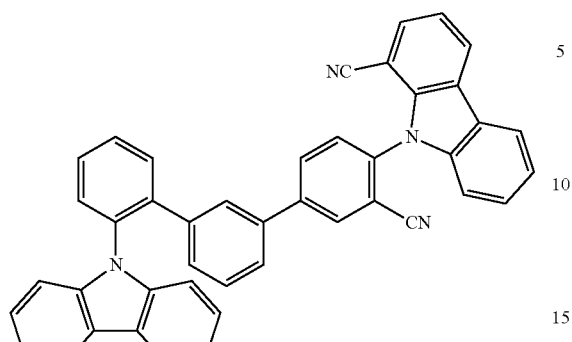
267
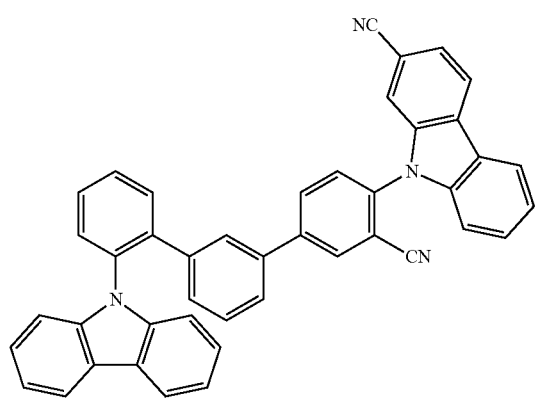
268
269
270
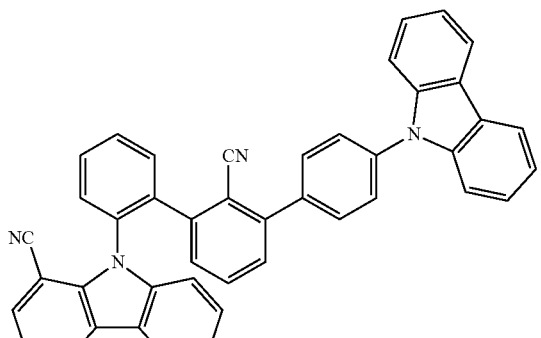
271
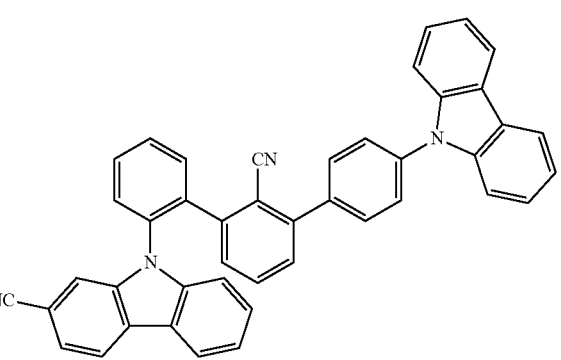
272
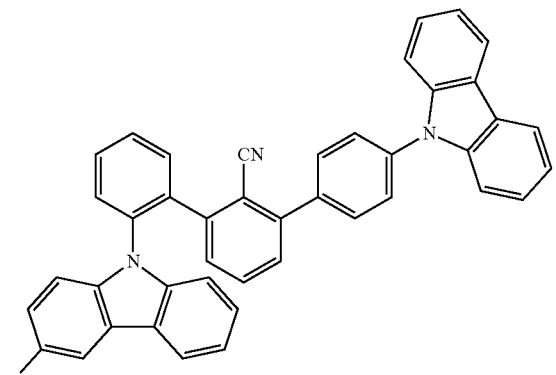
273
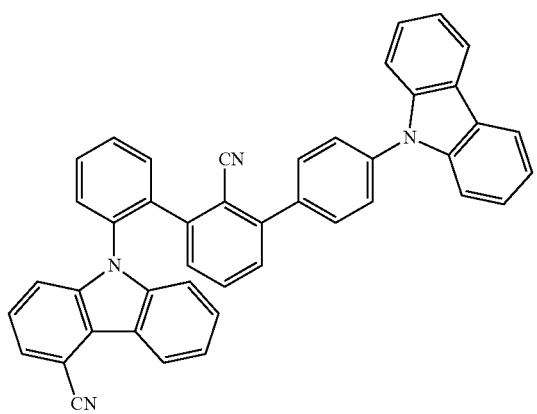

95
-continued
274
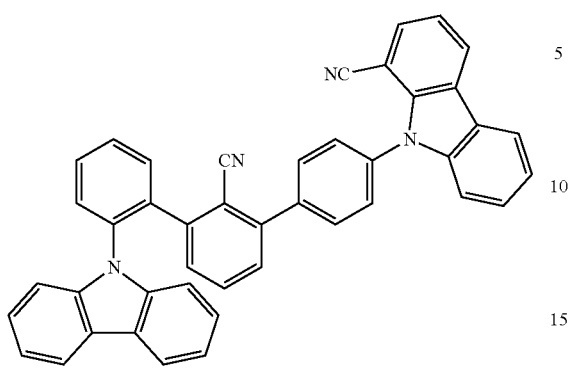
275

276

277
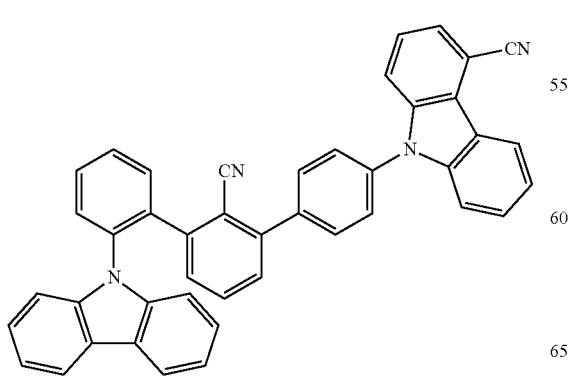
96
-continued
278
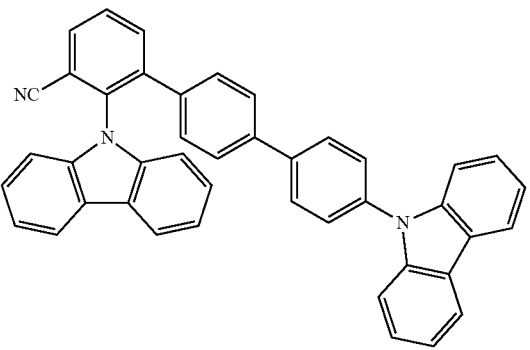
279
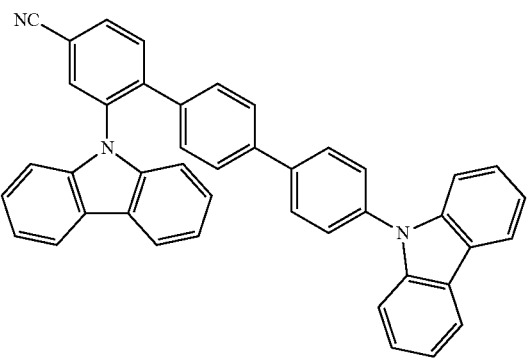
280
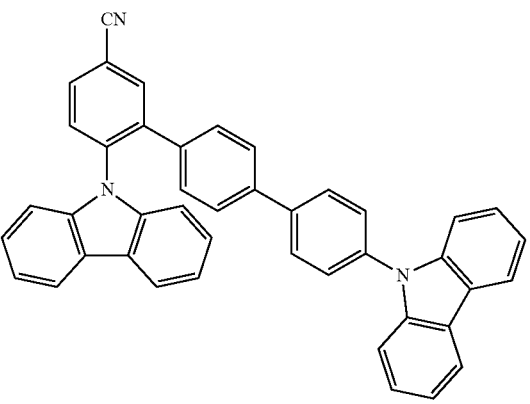
281
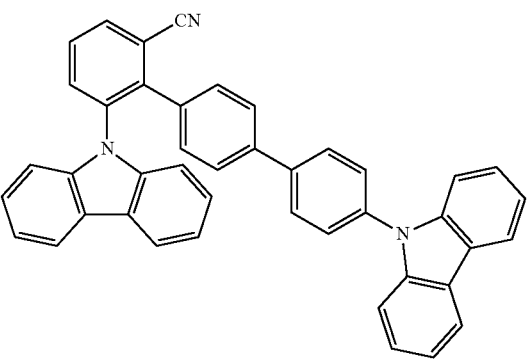

-continued
282
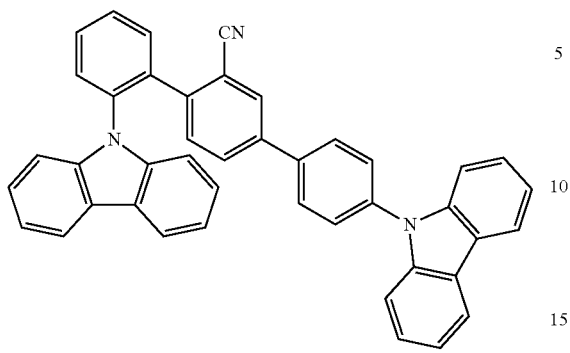
283
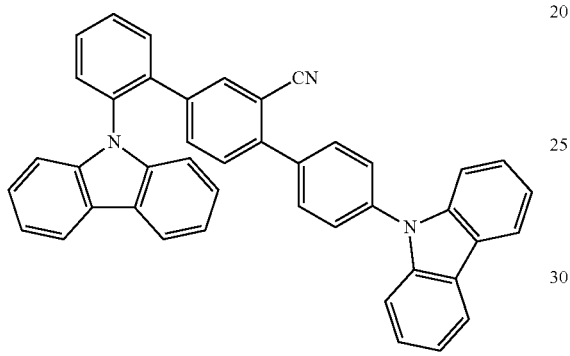
284
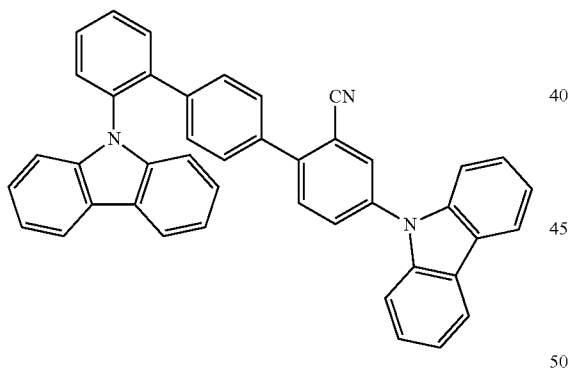
285
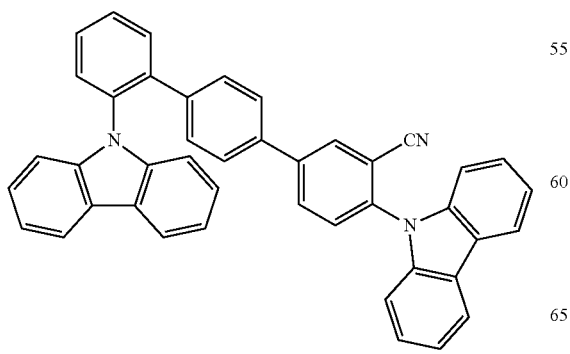
-continued
286
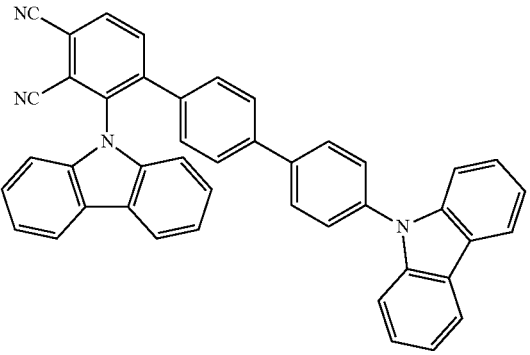
287
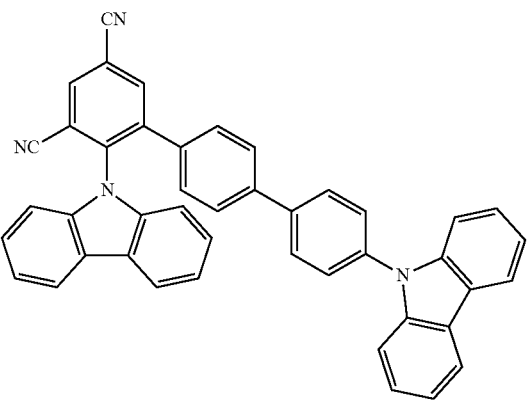
288
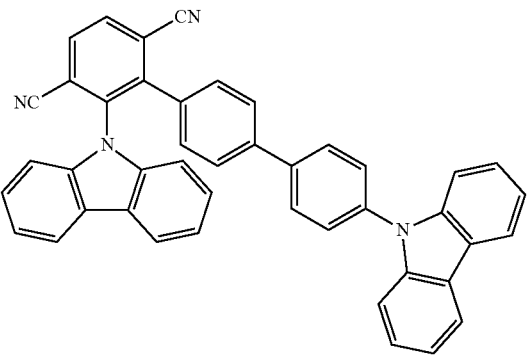
289
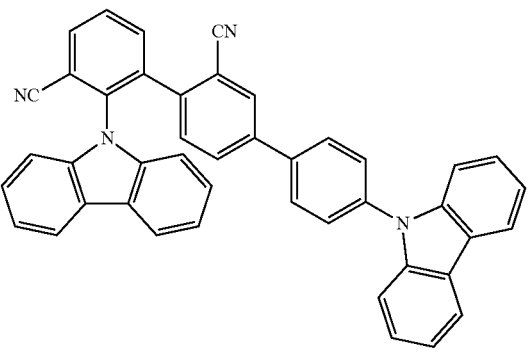

290
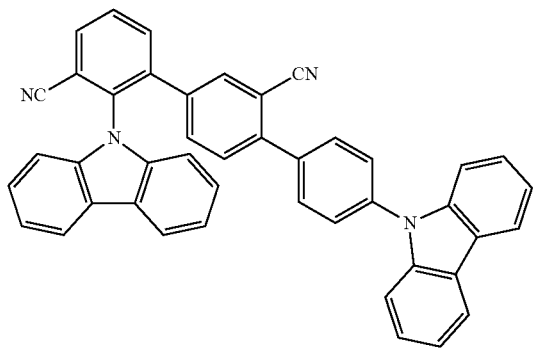
291
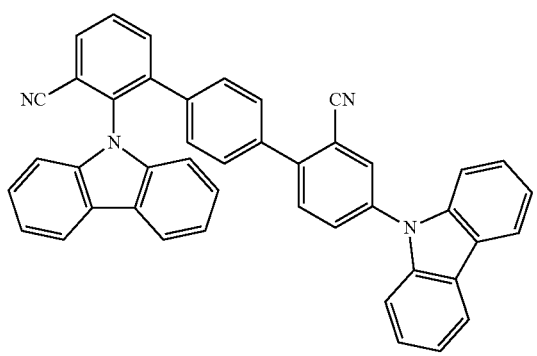
292
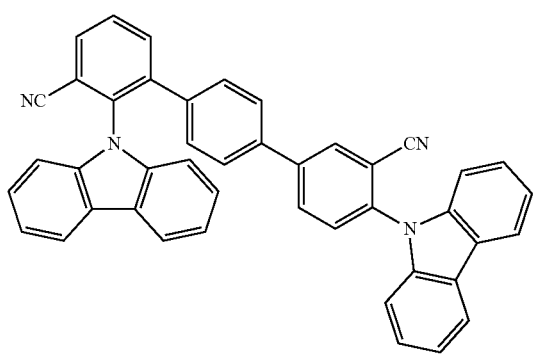
293
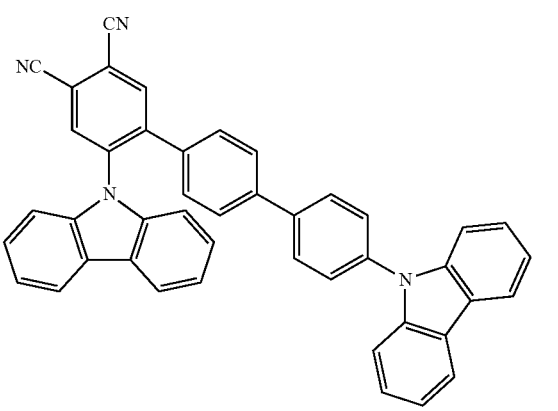
294
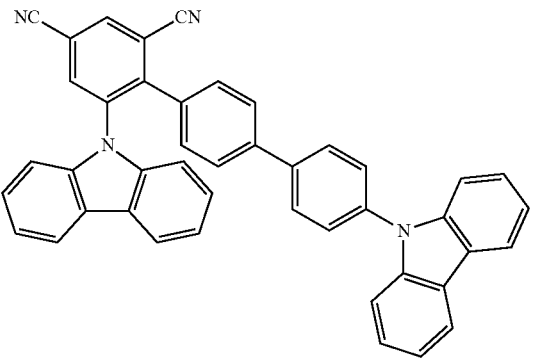
295
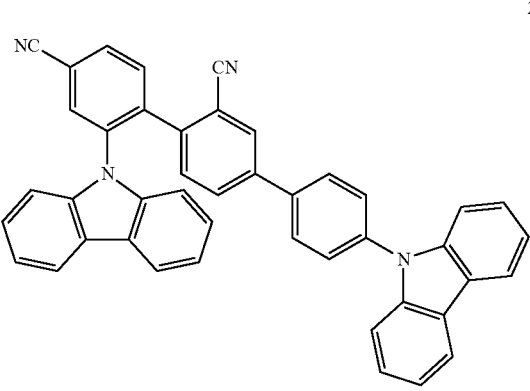
296
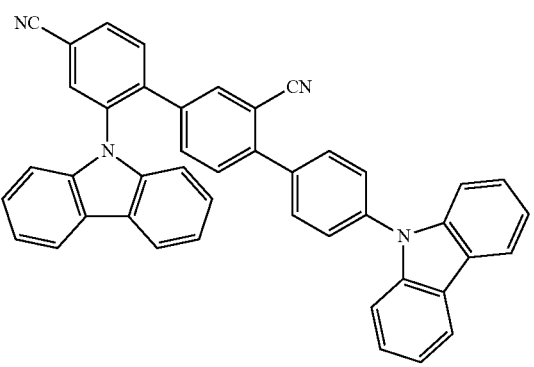
297
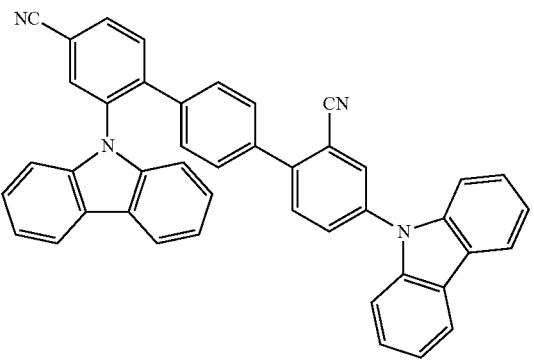

-continued
298
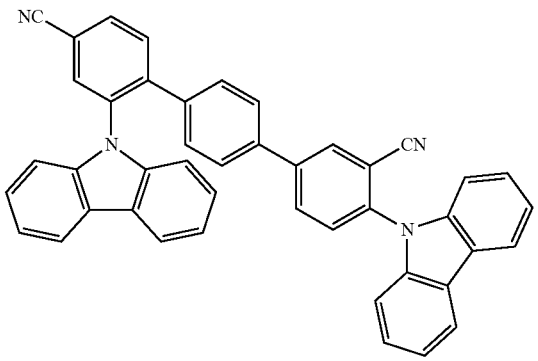
299
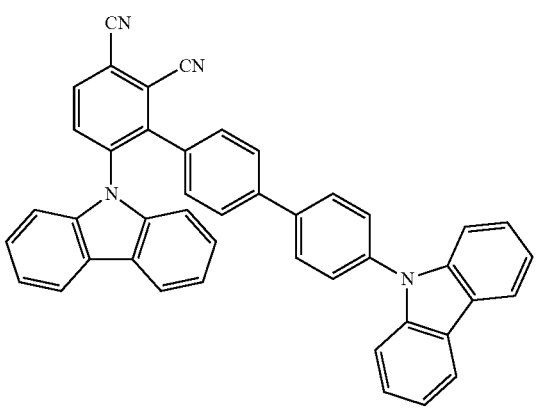
300
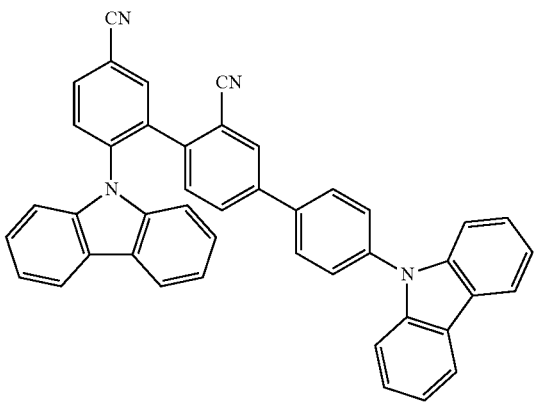
301
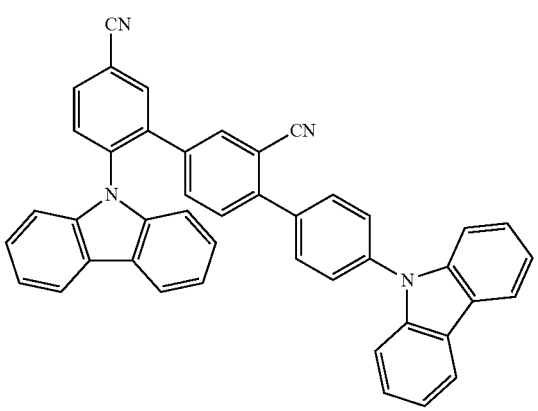
-continued
302
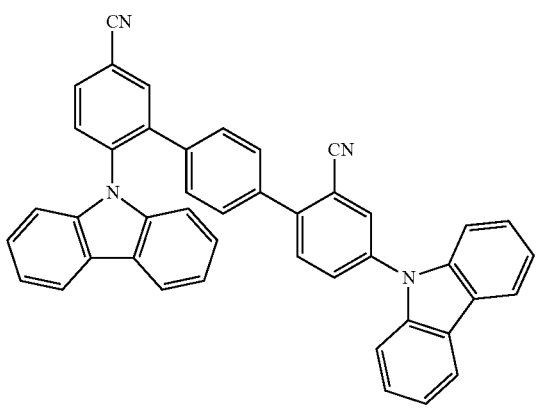
303
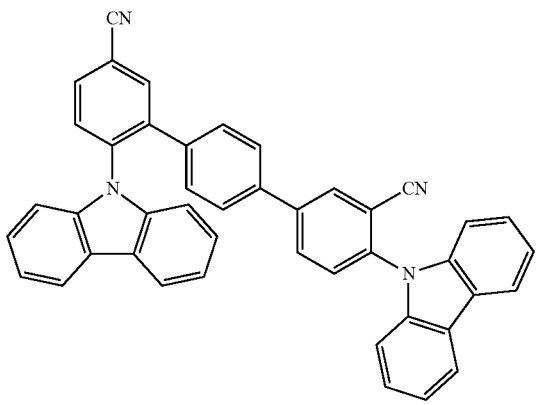
304
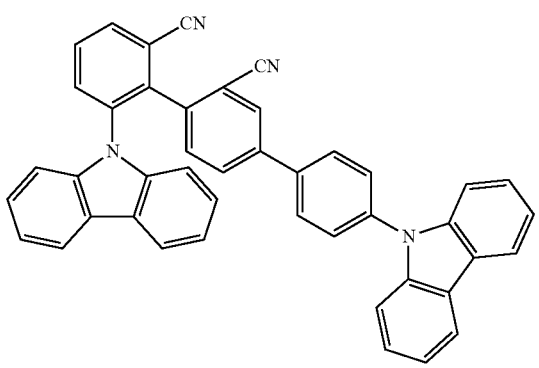
305
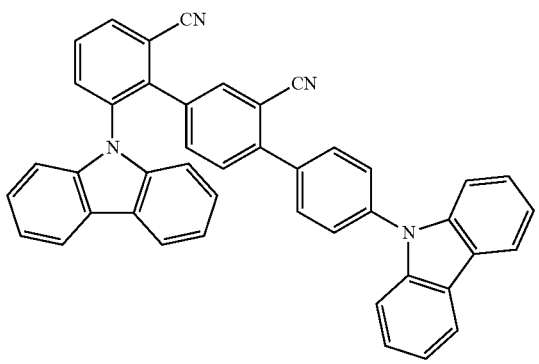

306
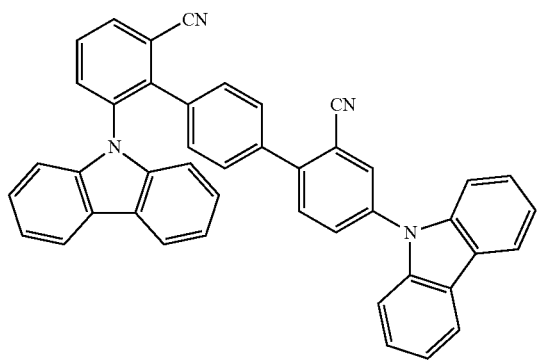
307
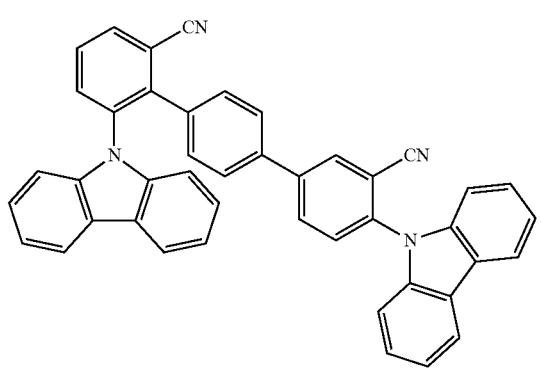
308
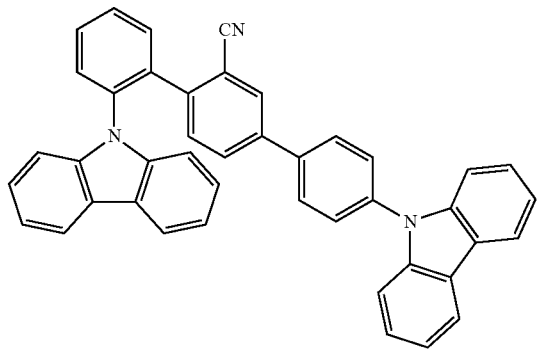
309
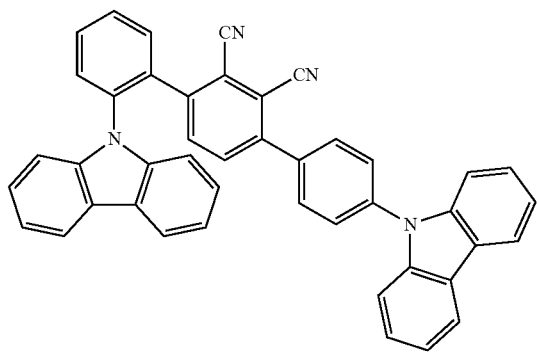
310
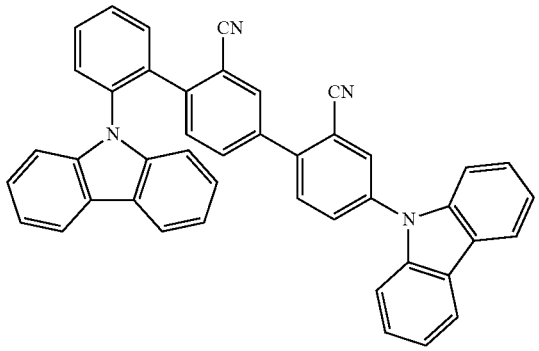
311
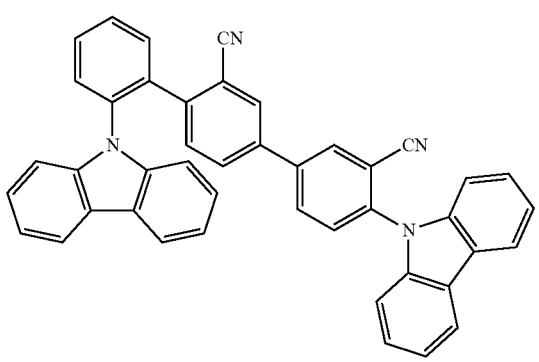
312
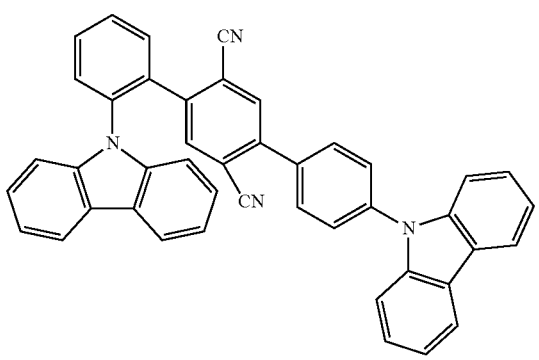
313
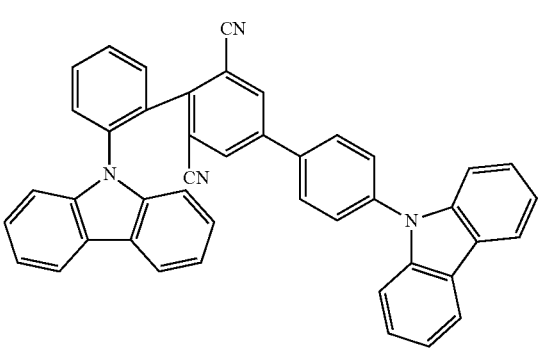

314
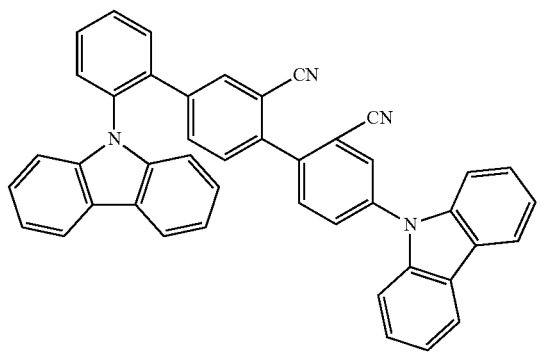
315
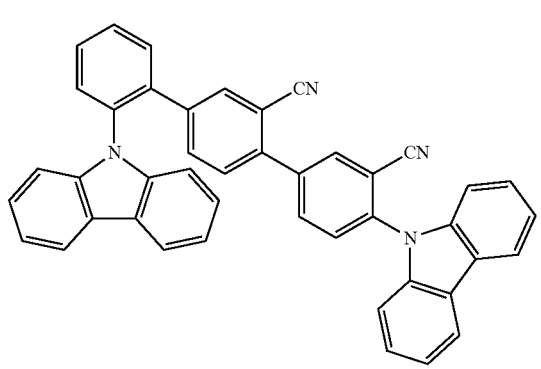
316
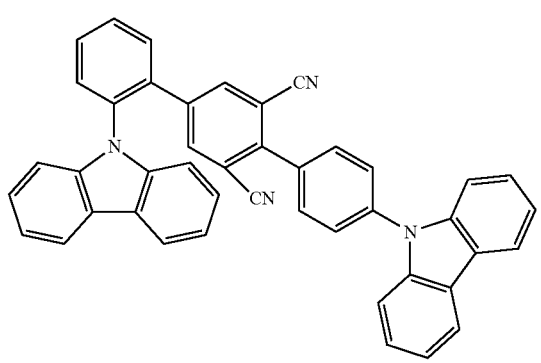
317
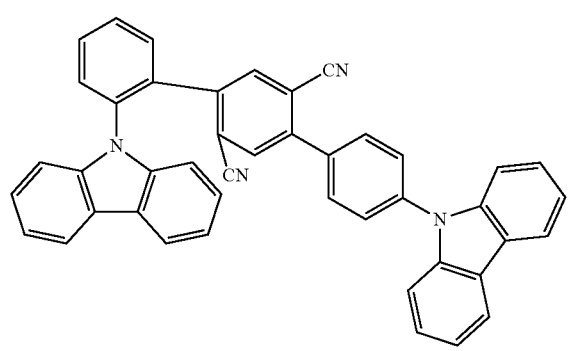
318
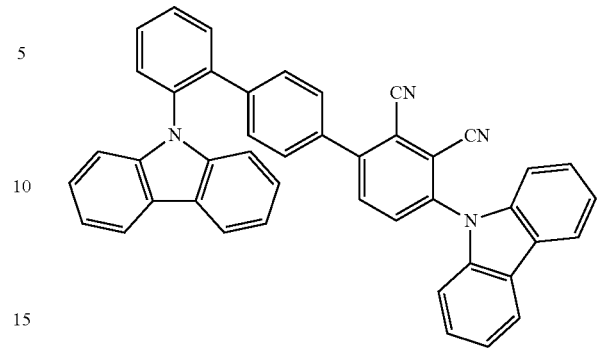
319
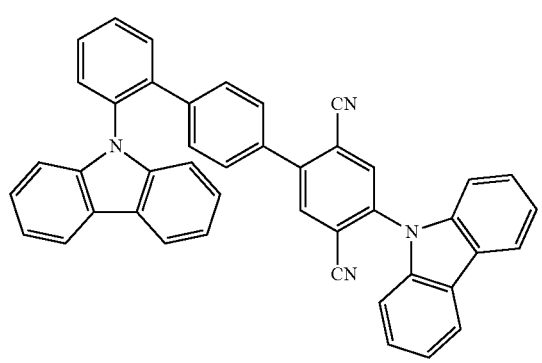
320
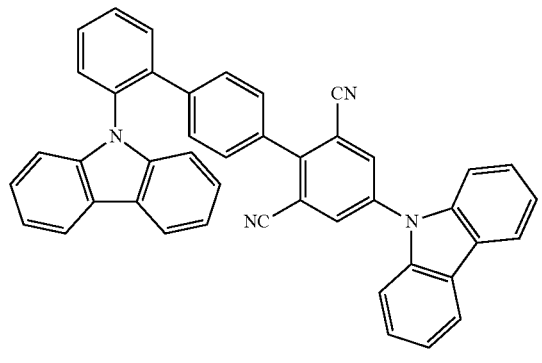
321
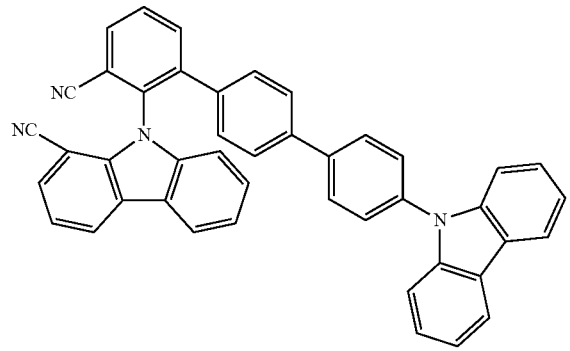

322
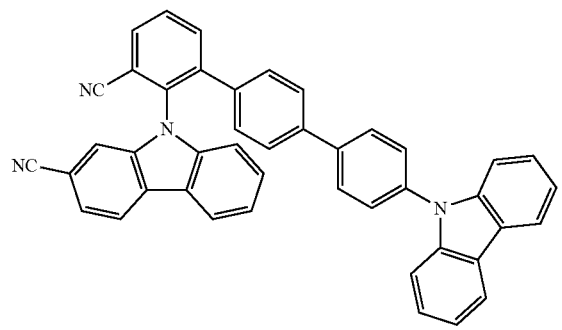
323
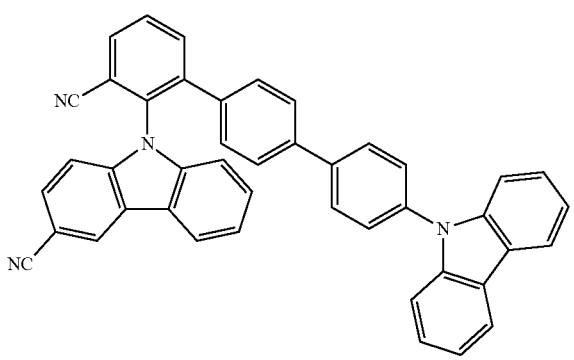
324
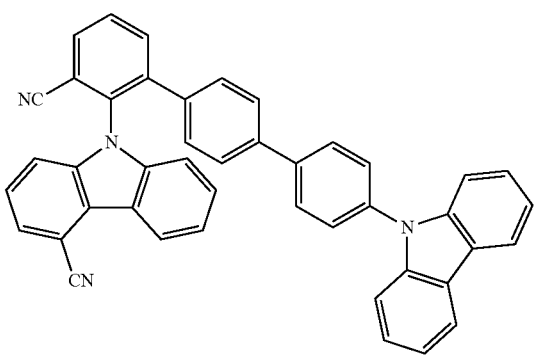
325
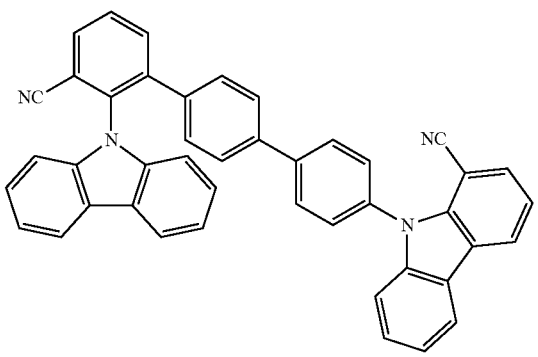
326
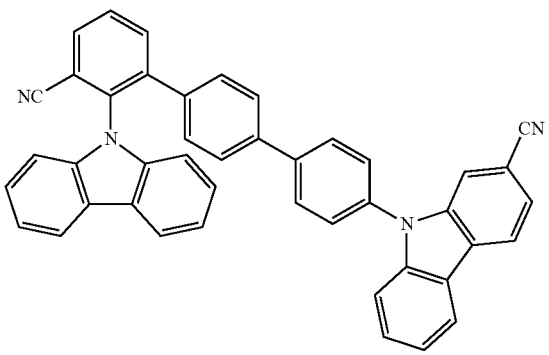
327
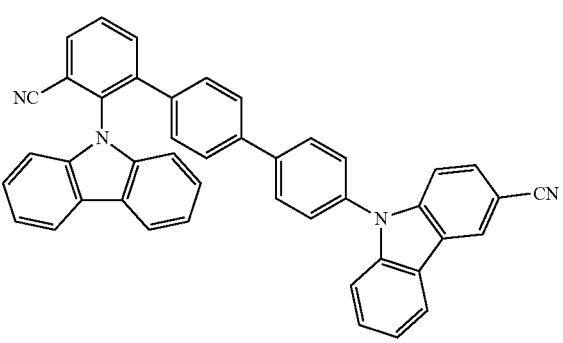
328
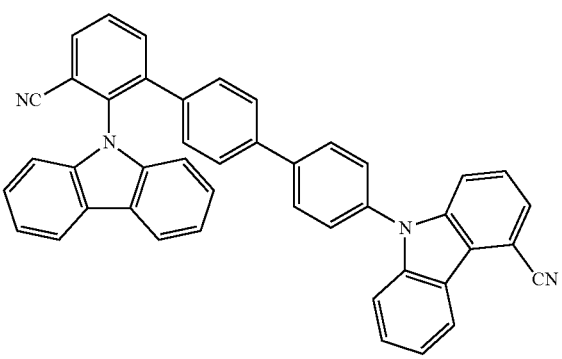
329
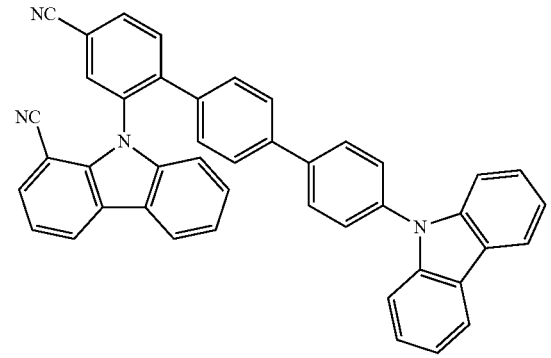

330
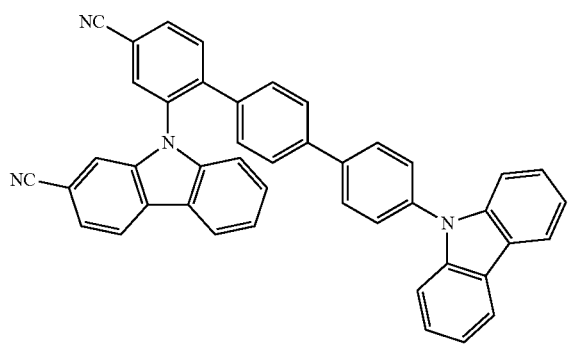
334
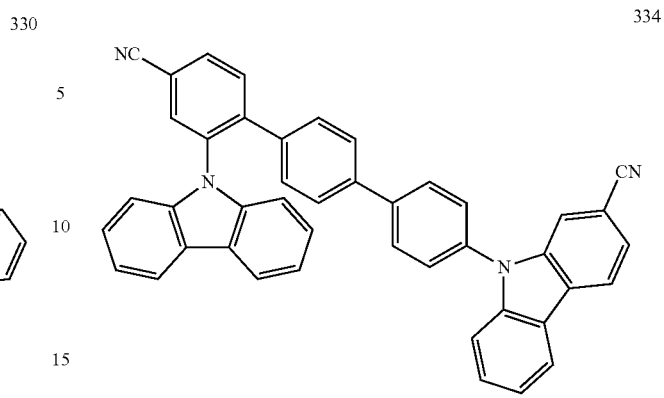
331
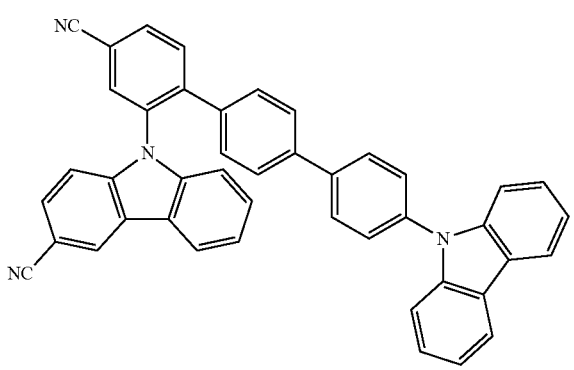
335
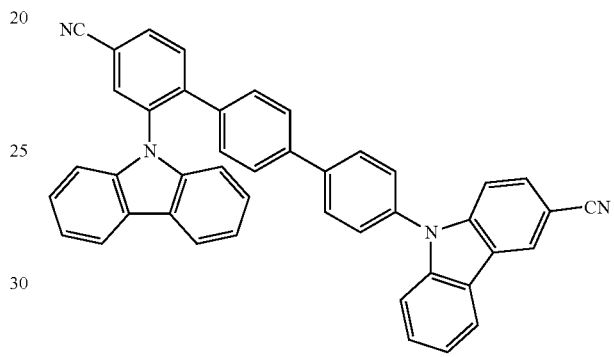
332
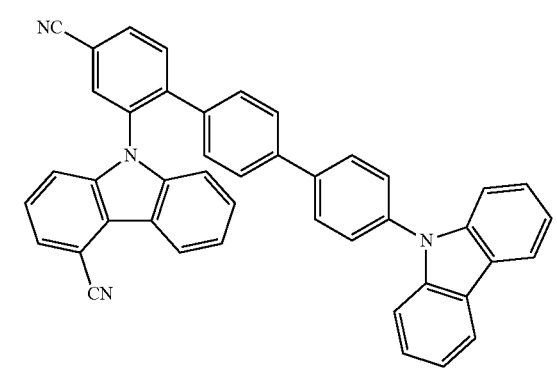
336
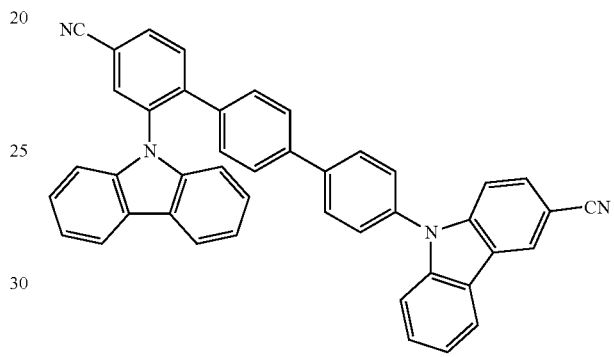
333
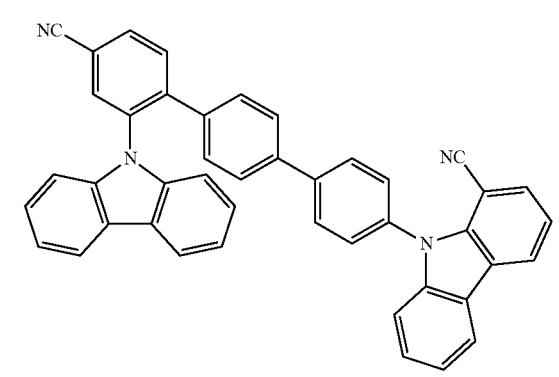
337
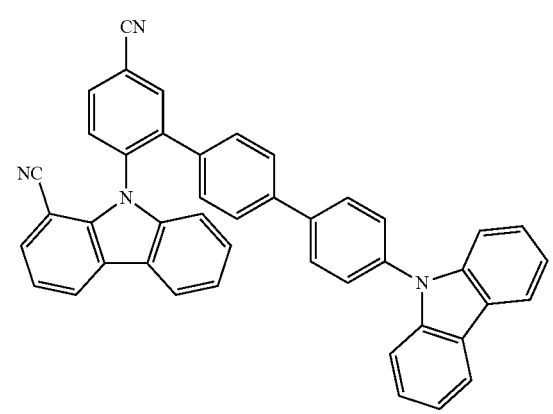

338
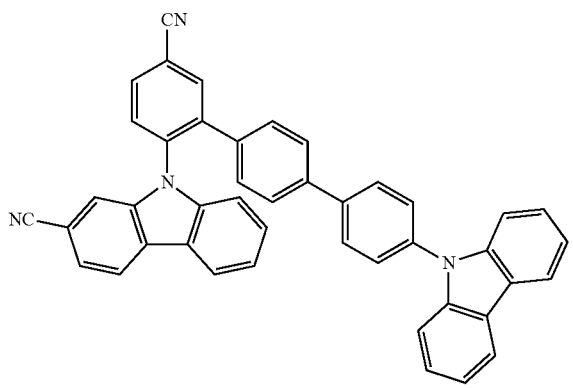
341
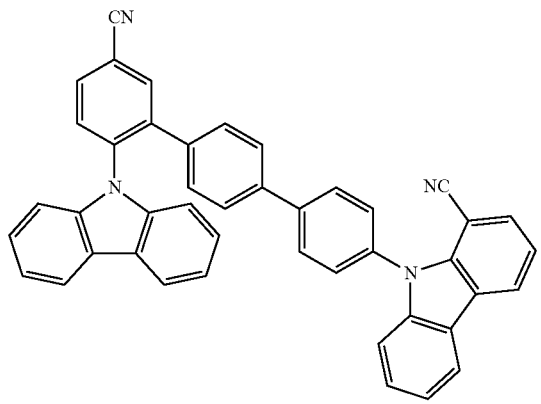
339
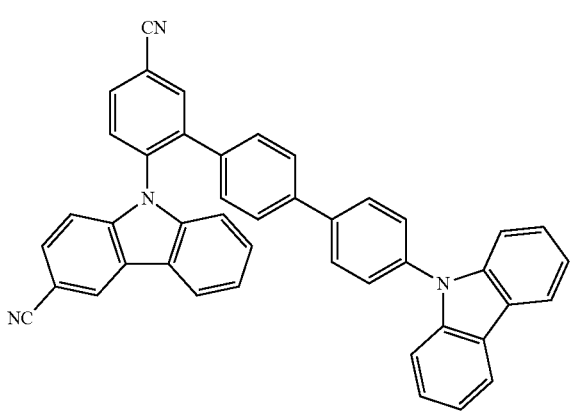
342
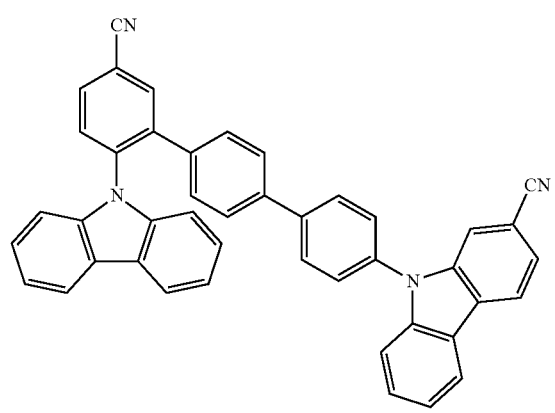
340
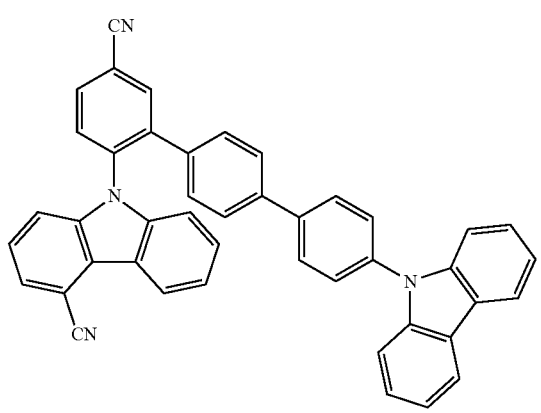
343
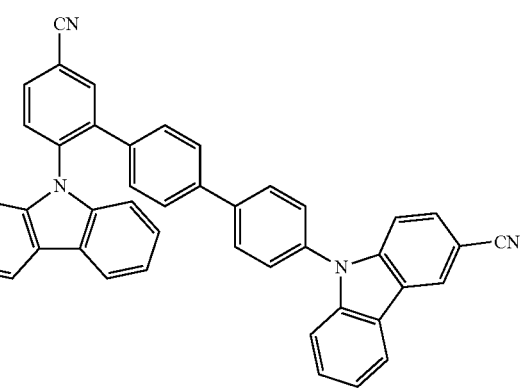

345
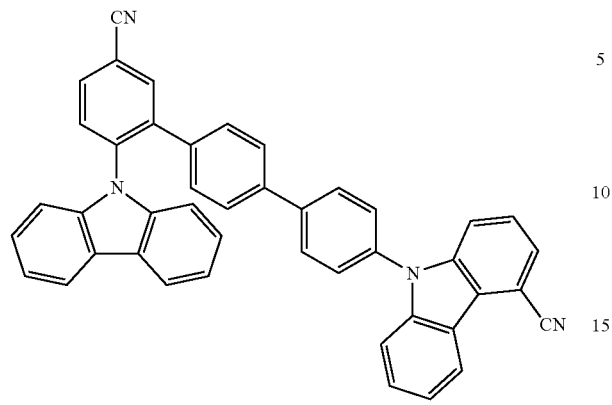
346
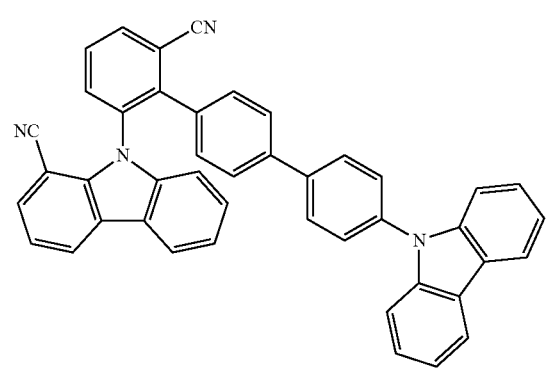
347
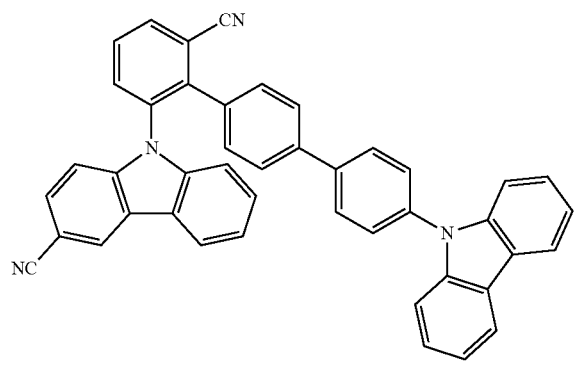
348
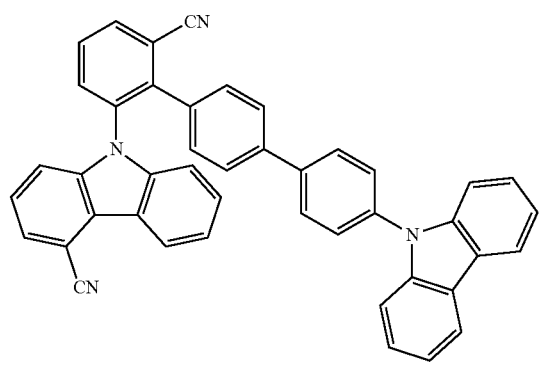
349
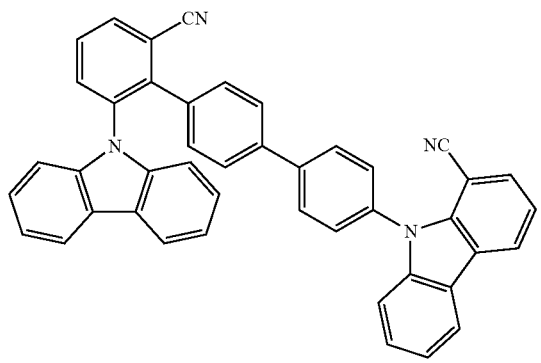
350
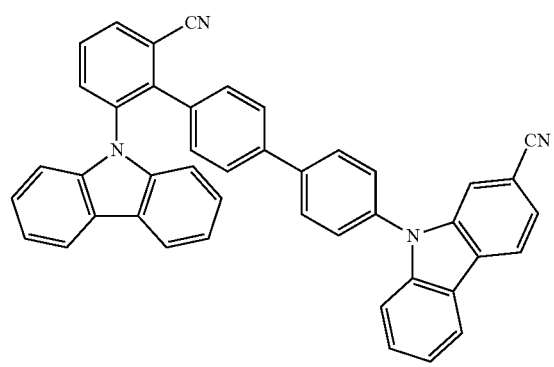
351
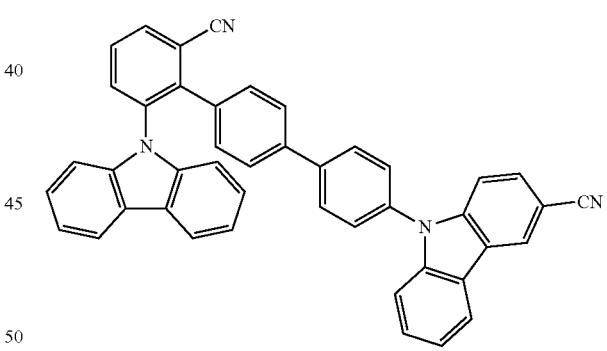
352
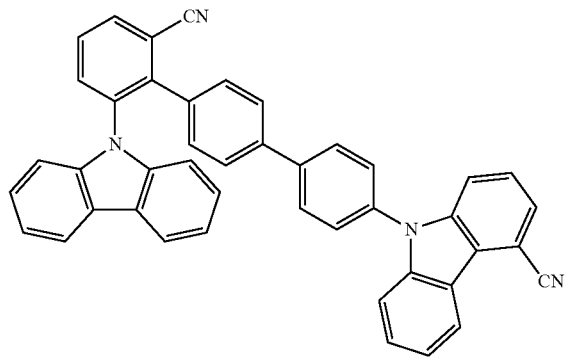

353
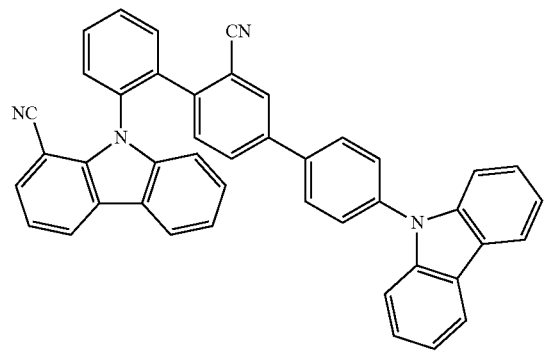
354
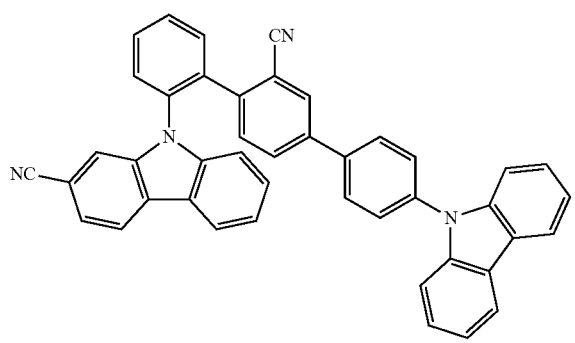
355
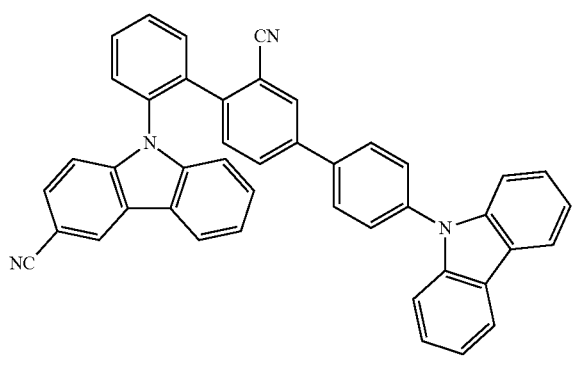
356
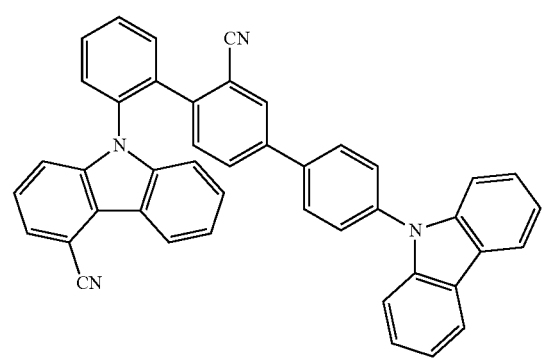
357
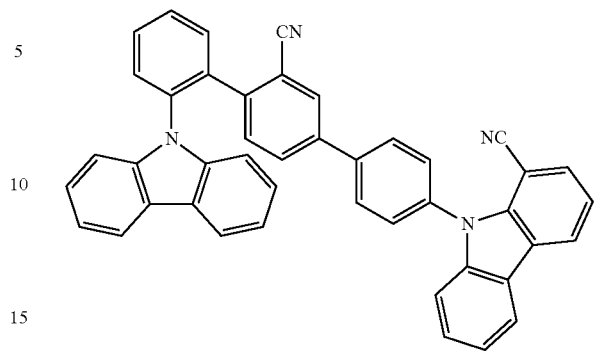
358
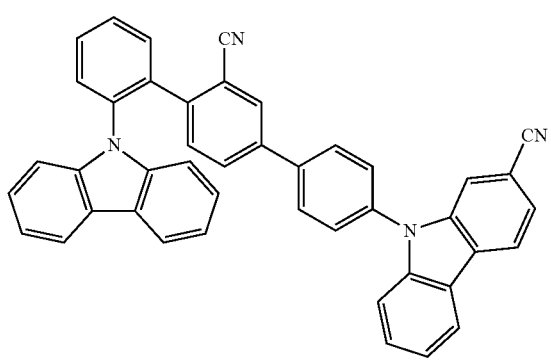
359
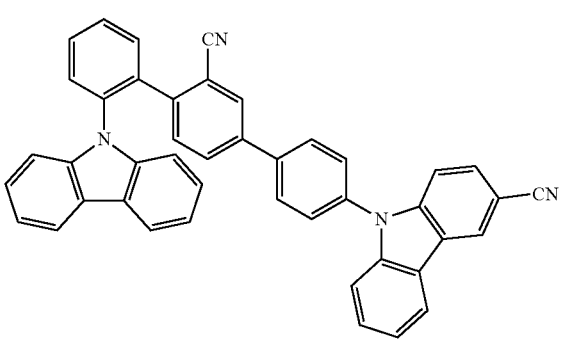
360
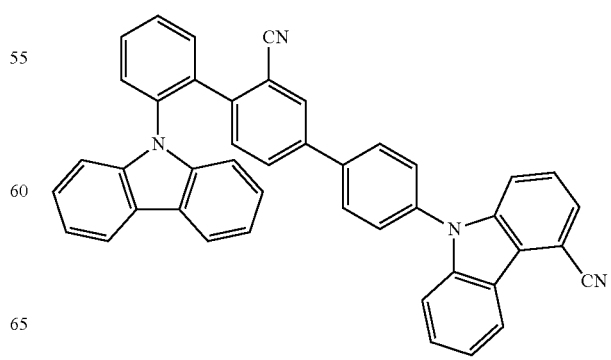

361
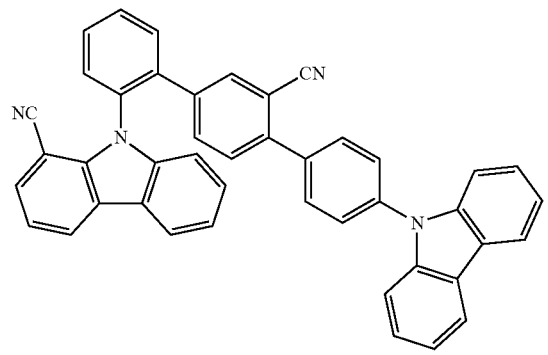
365
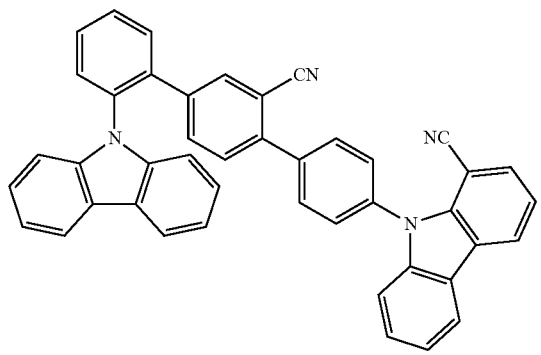
362
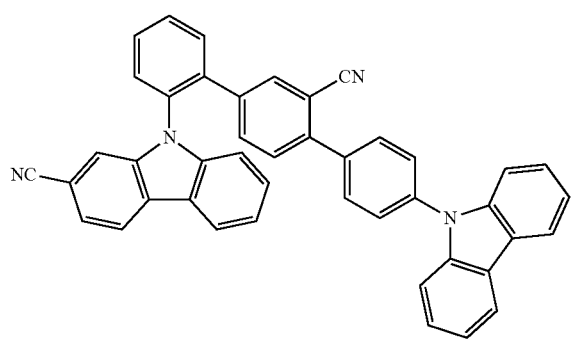
366
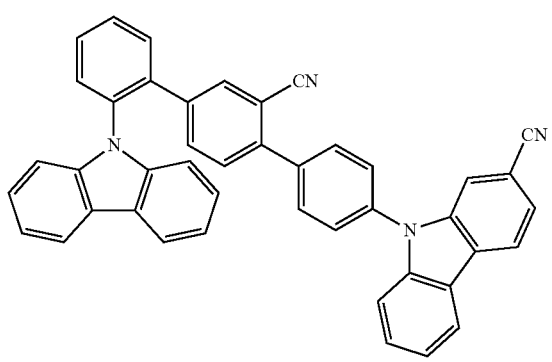
363
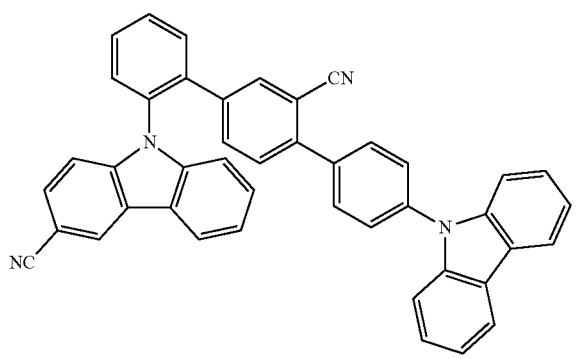
367
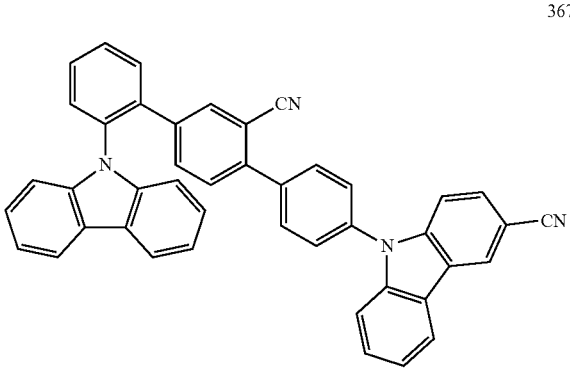
364
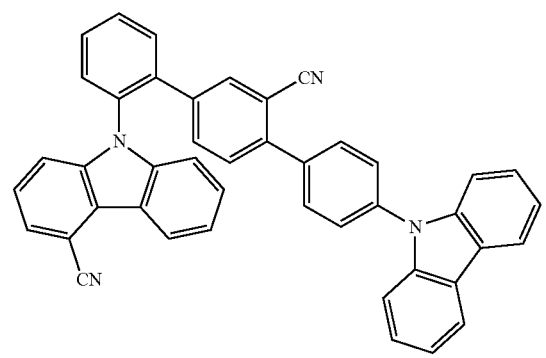
368
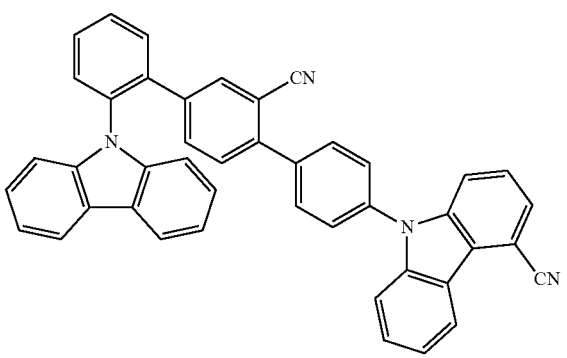

369
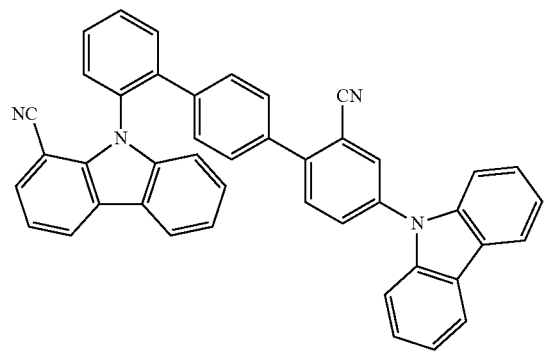
370
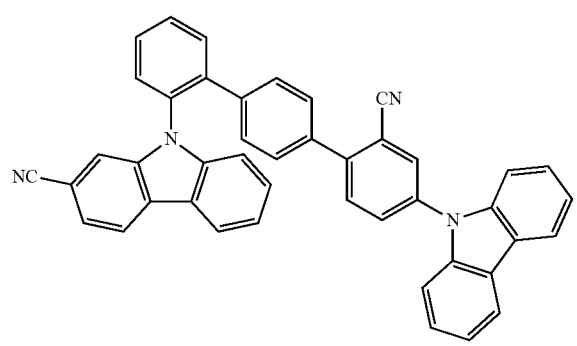
371
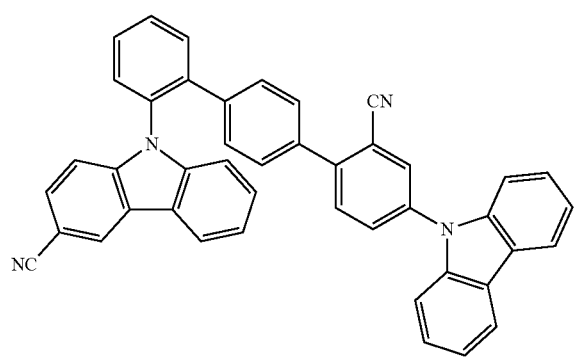
372
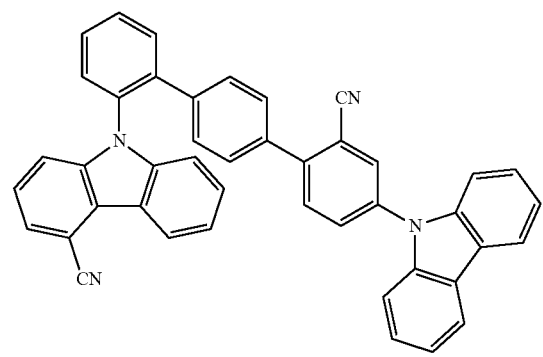
373
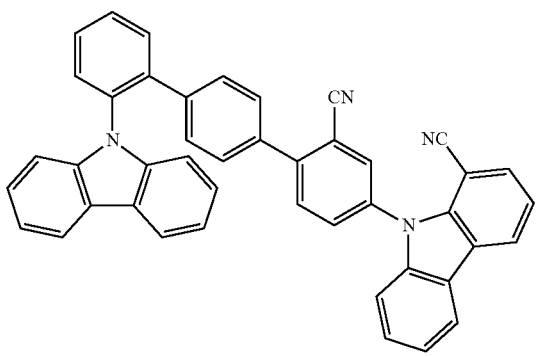
374
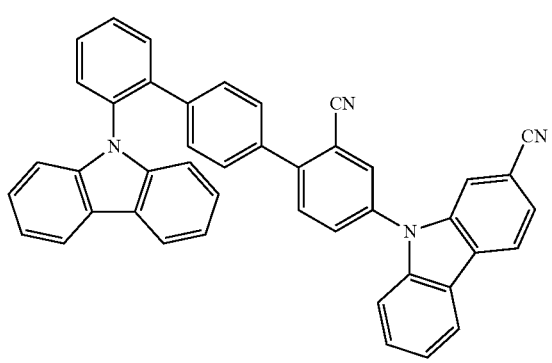
375
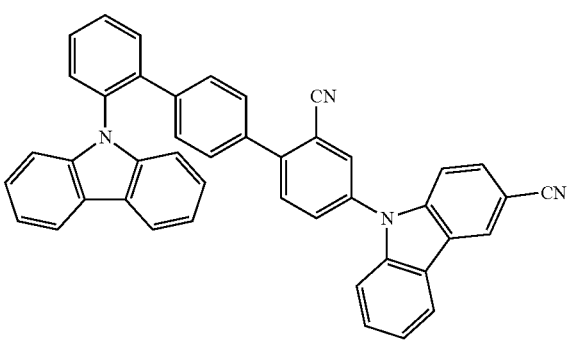
376
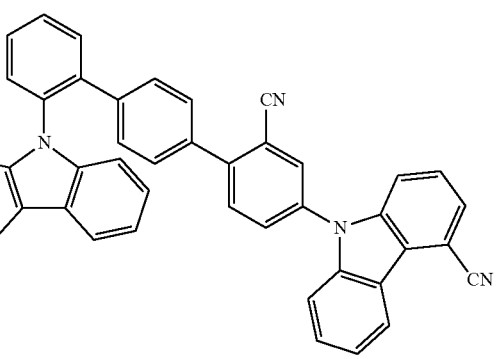

-continued
377
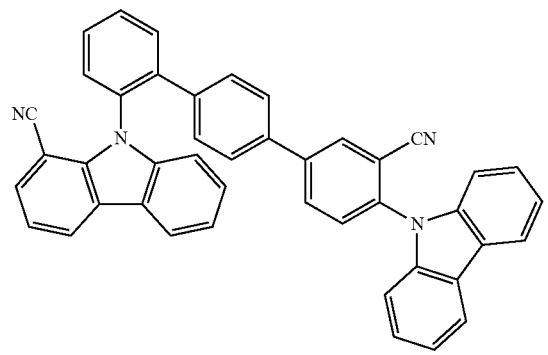
378
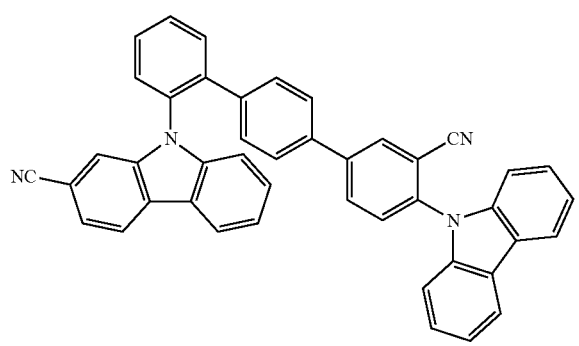
379
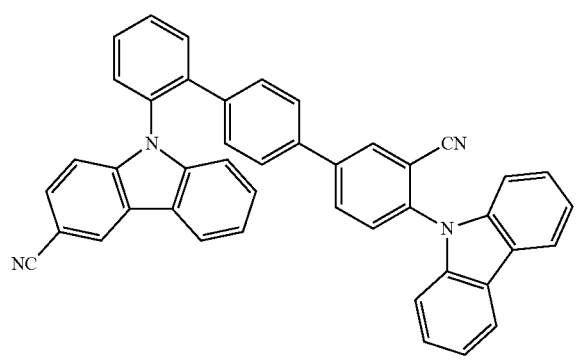
380
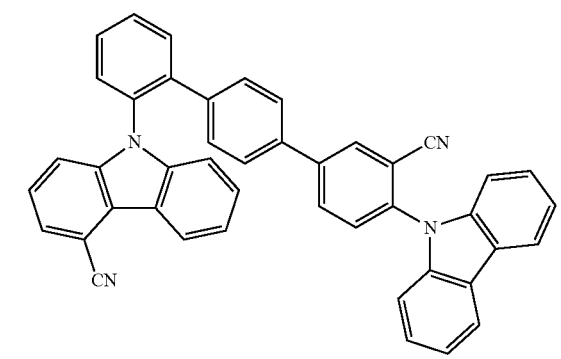
-continued
381
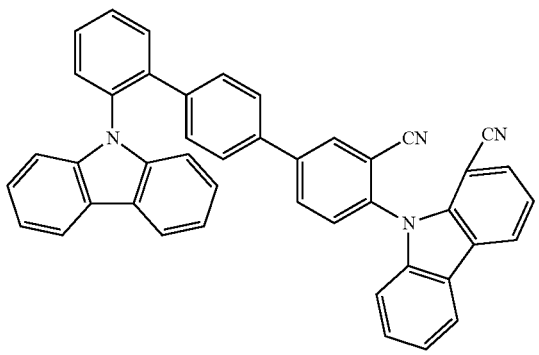
382
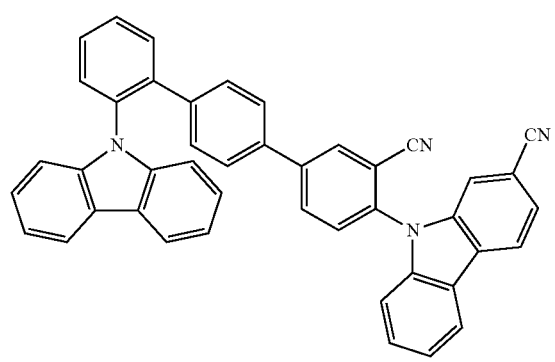
383
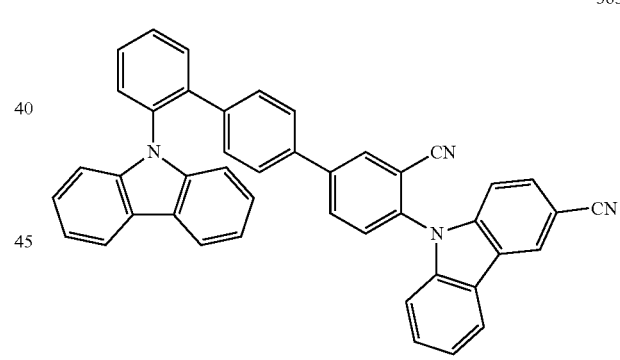
384
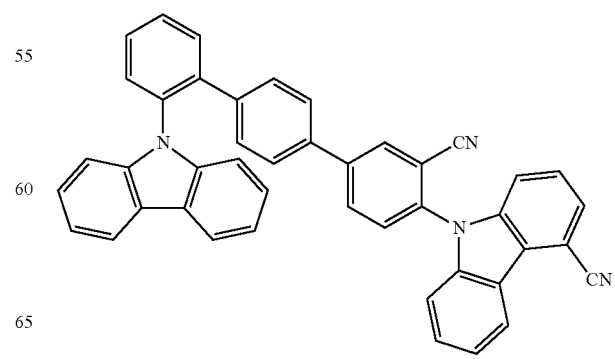

385
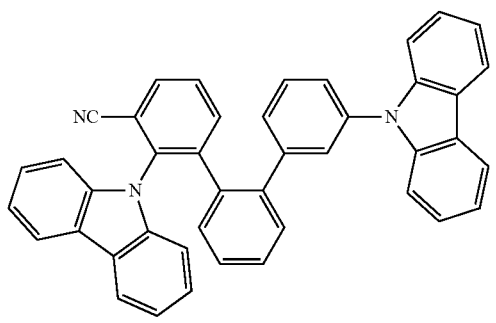
386
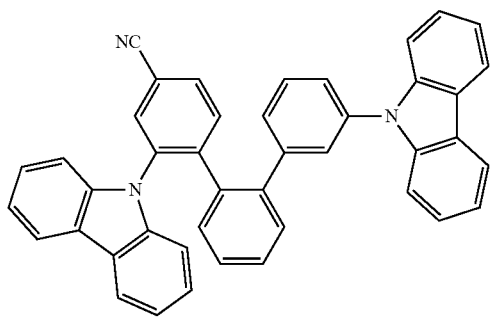
387
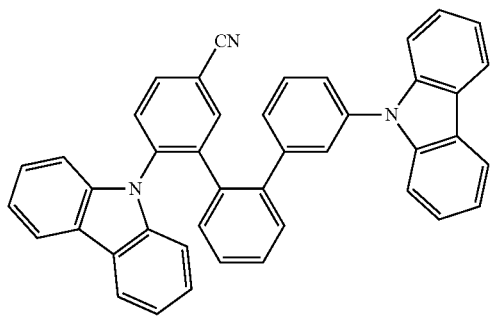
388
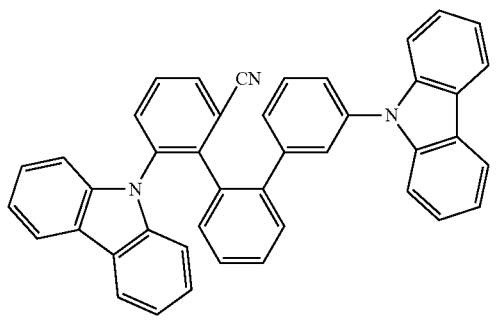
389
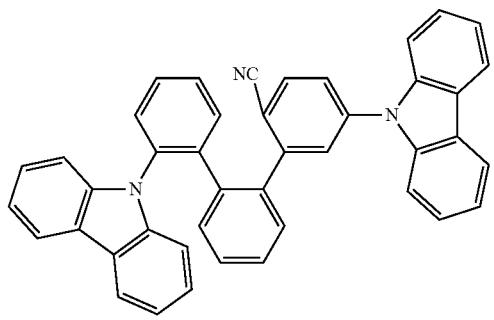
390
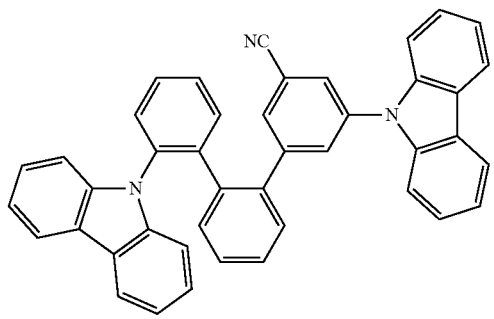
391
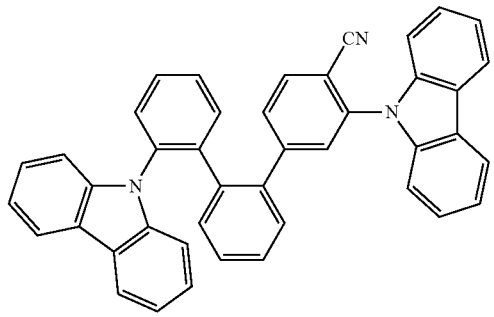
392
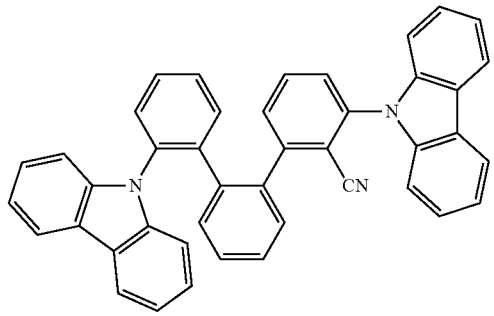

125
-continued
393
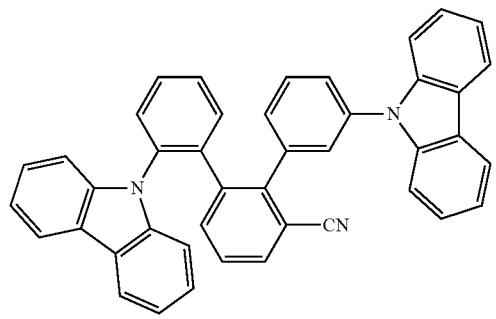
394
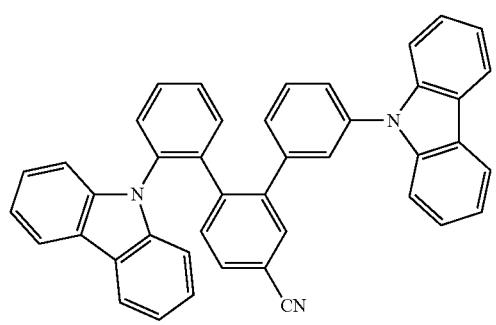
395
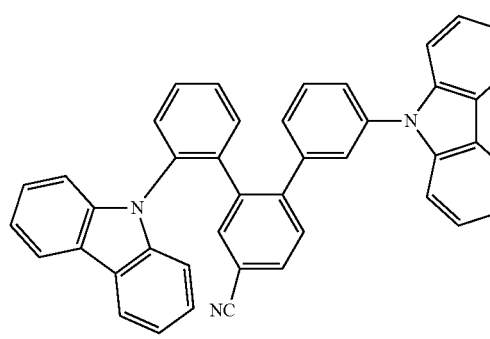
396
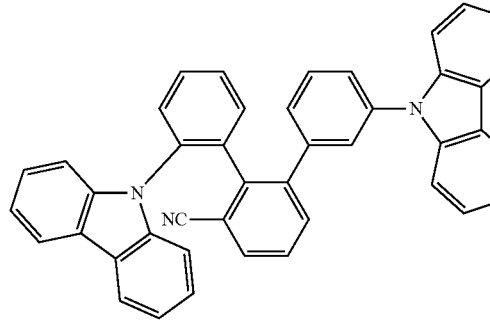
126
-continued
397
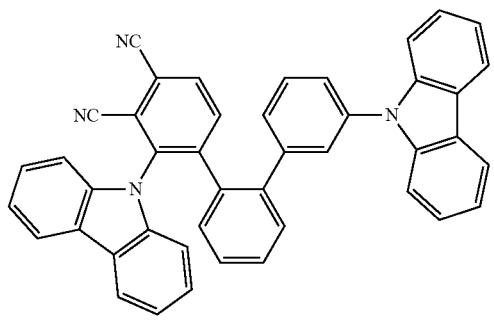
398
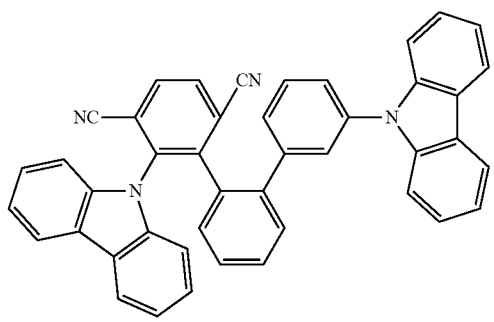
399
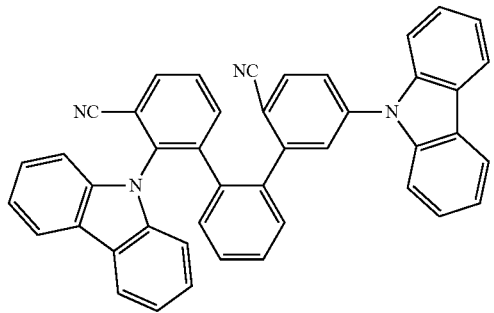
400

401
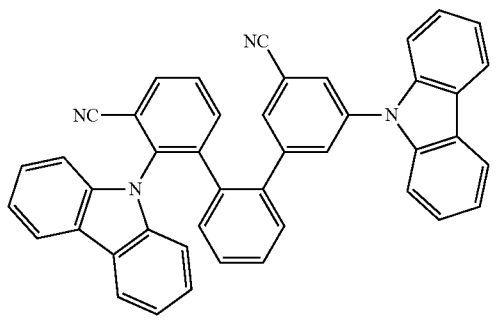
402
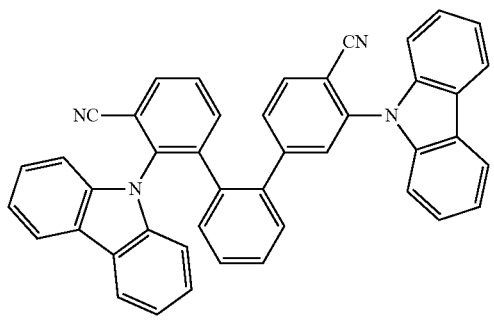
403
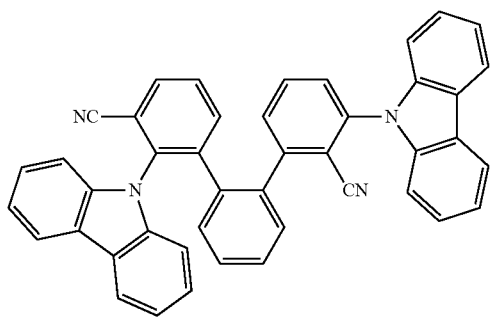
404
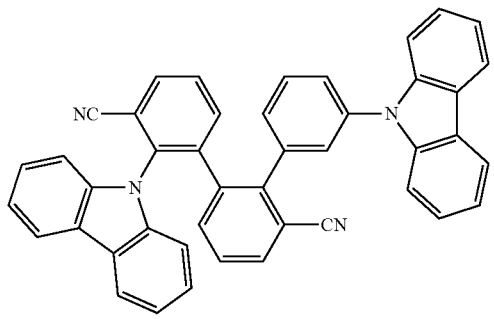
405
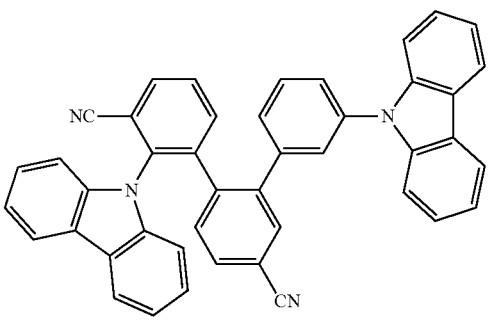
406
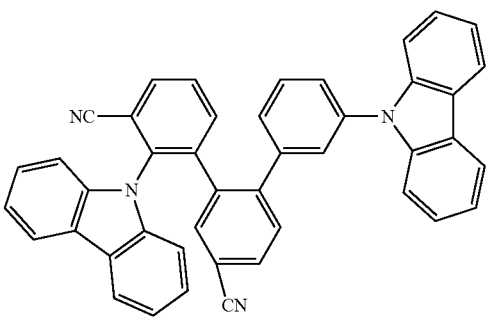
407
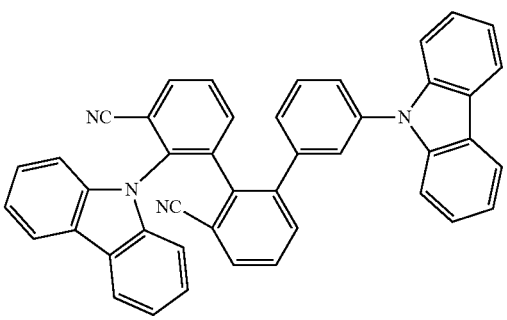
408
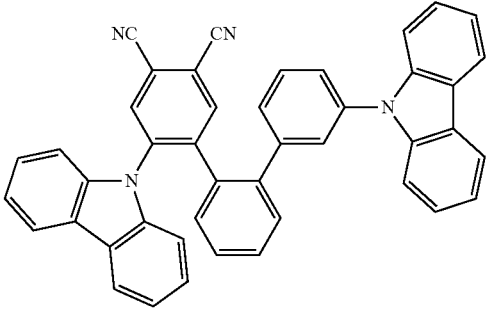

409
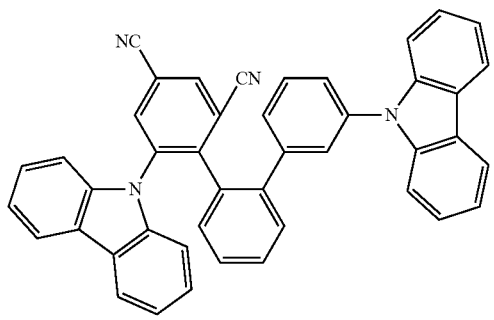
410
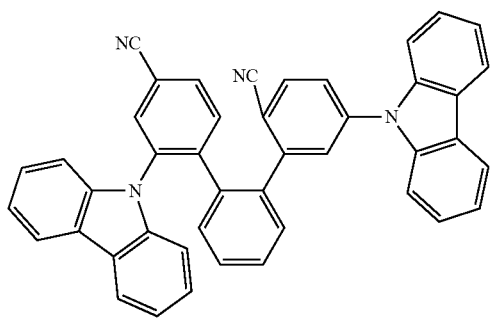
411
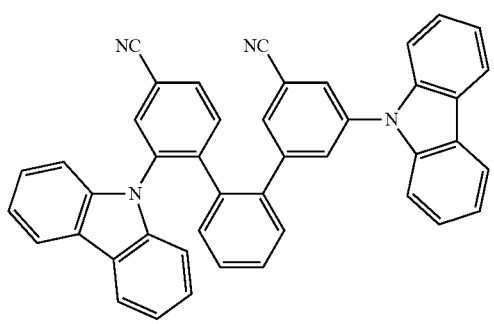
412
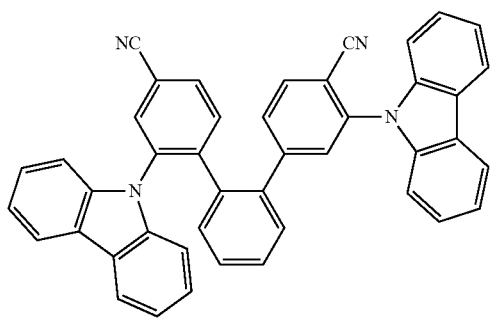
413
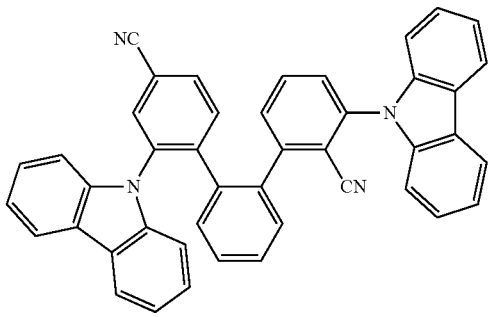
414
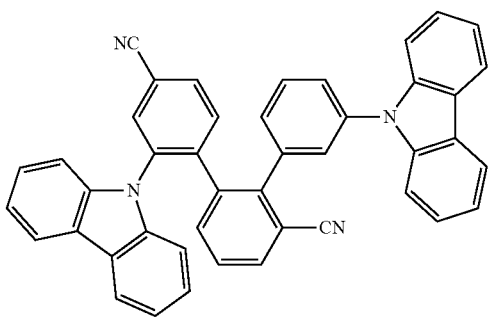
415
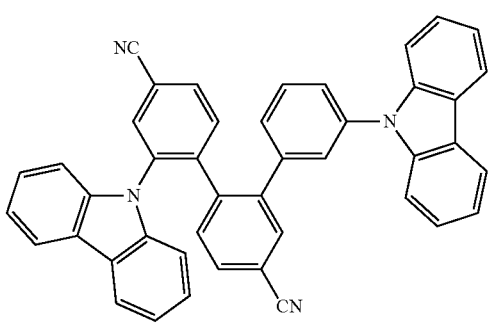
416
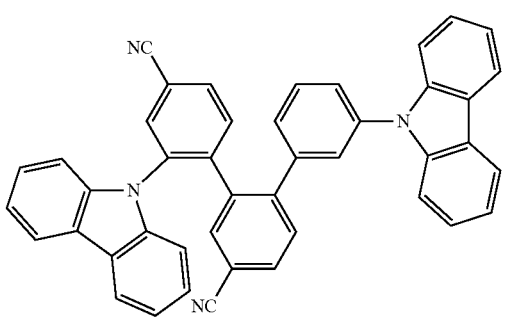

-continued
417
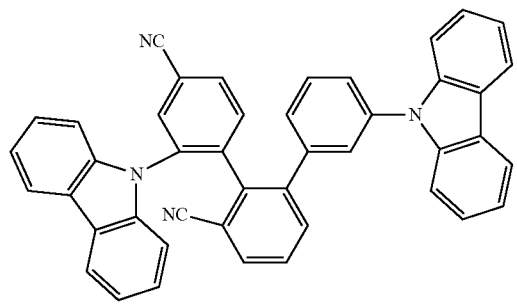
418
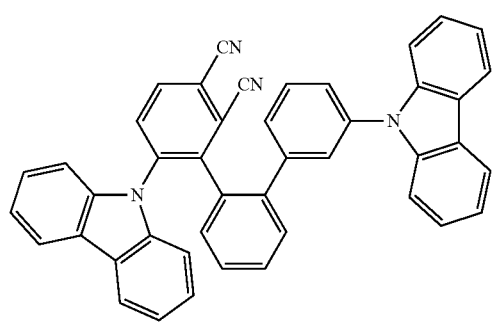
419
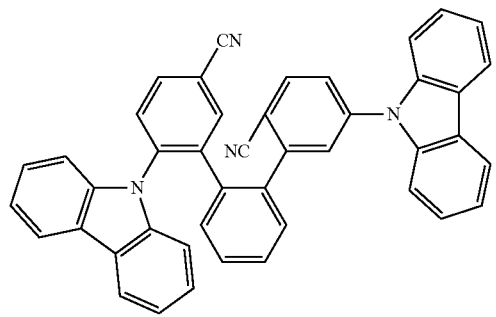
420
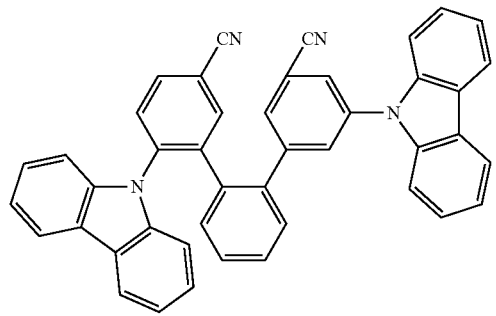
-continued
421
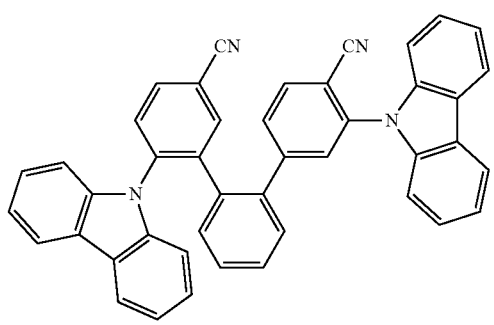
422
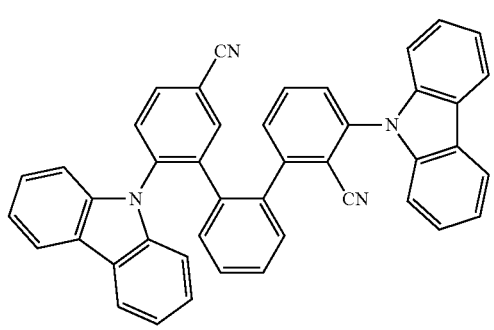
423
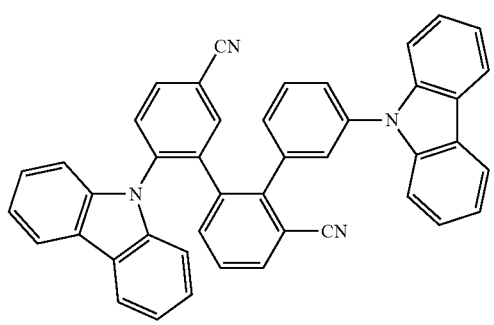
424
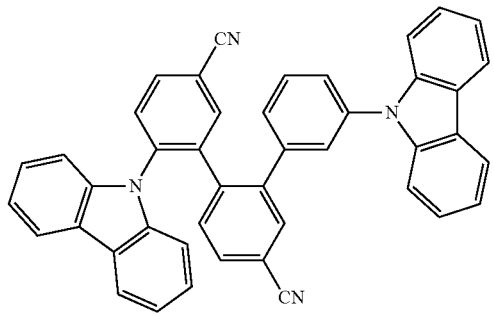

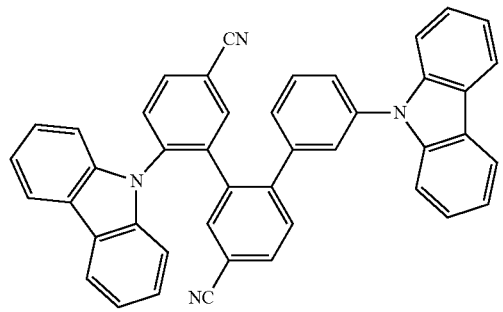
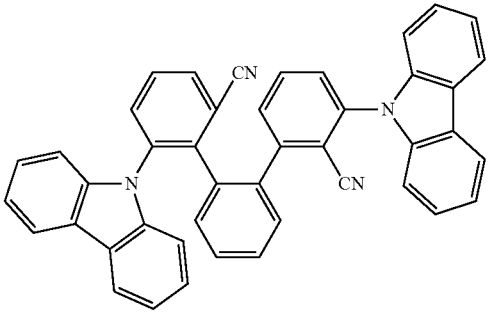
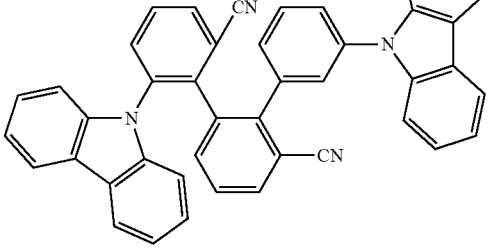
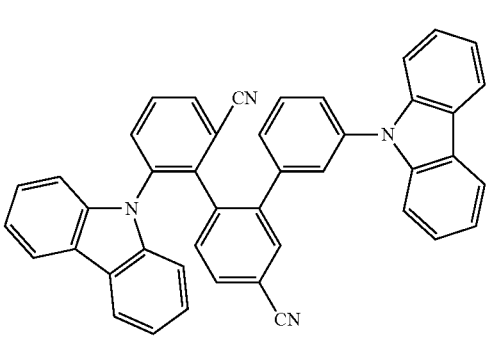
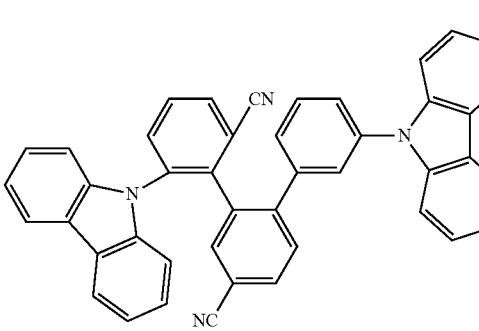
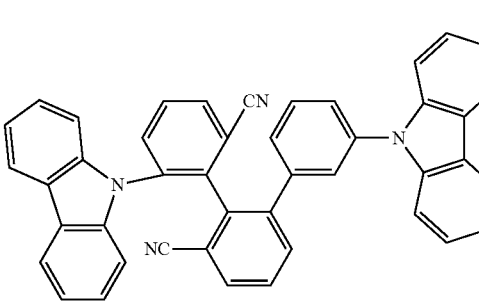

435 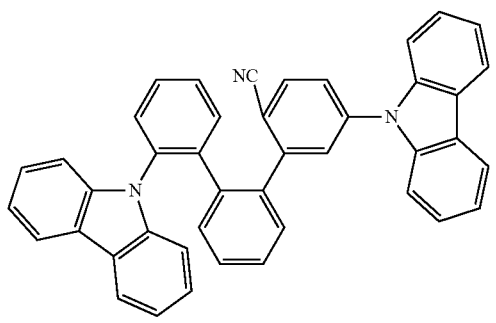
436 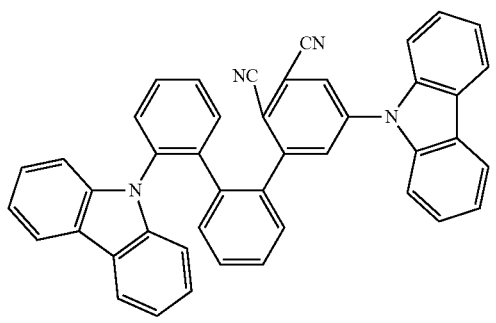
437 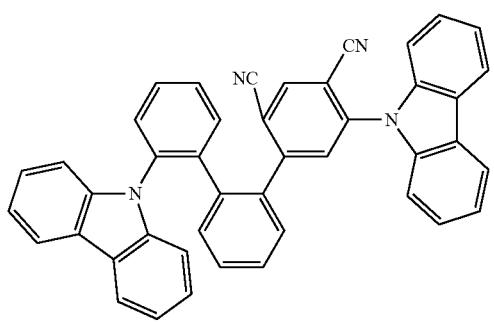
438 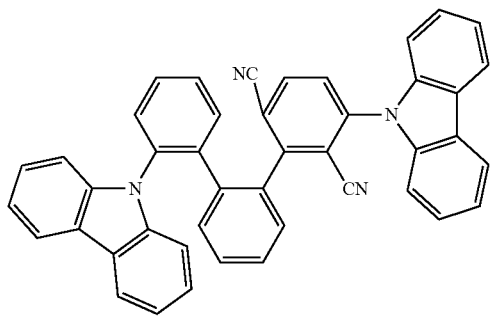
439 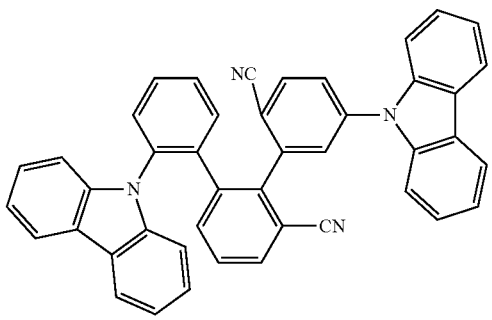
440 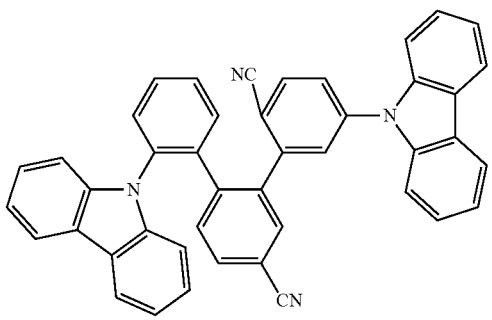
441 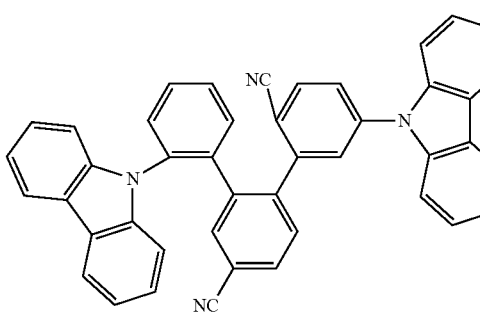
442 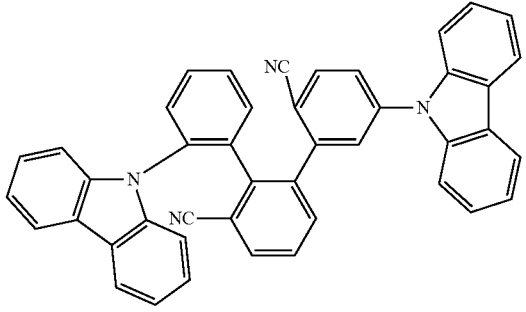

443
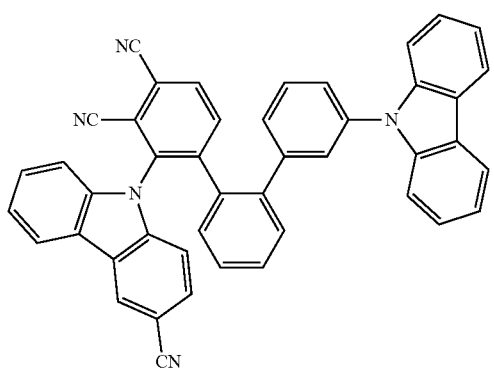
444
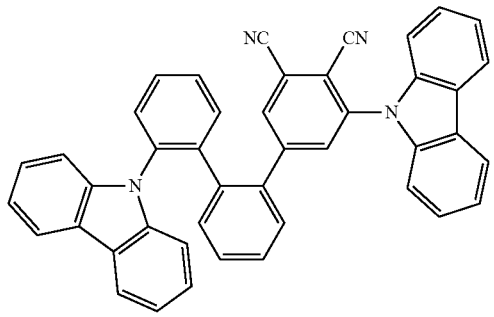
445
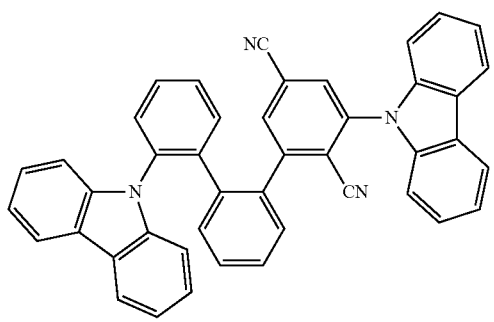
446
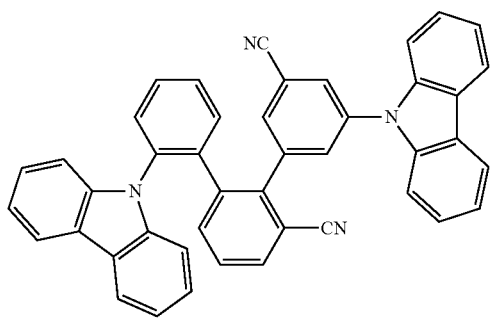
447
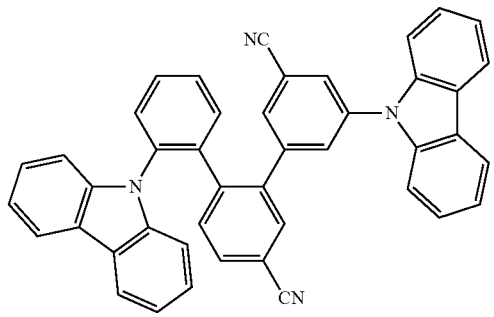
448
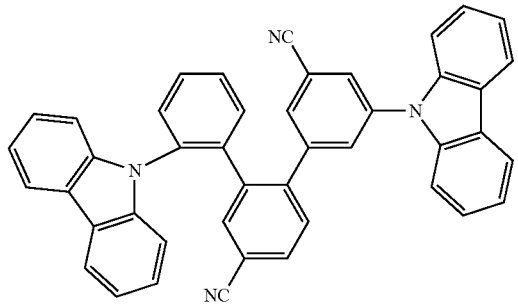
449
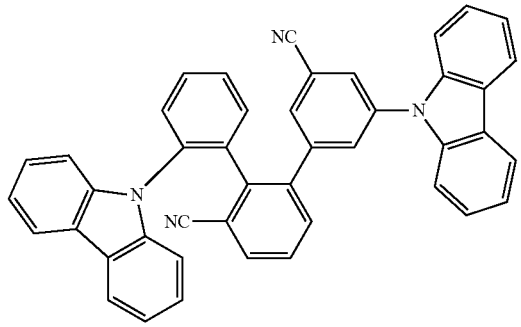
450
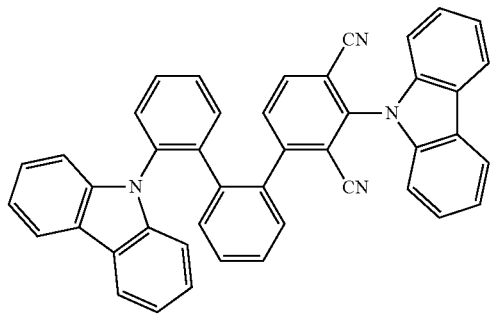

-continued
451
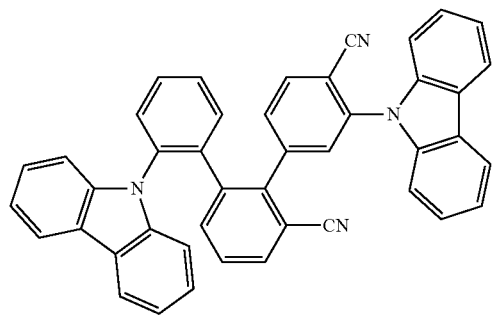
452
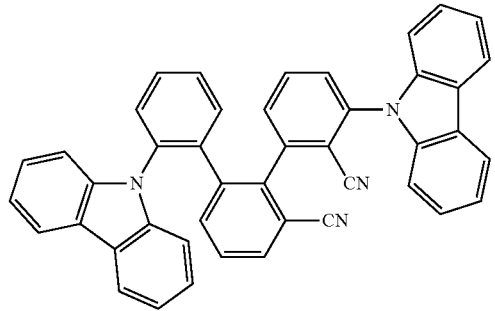
453
454
455
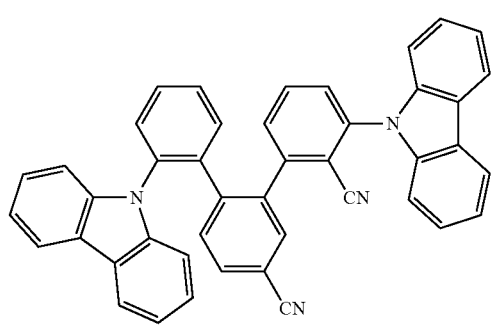
456
457
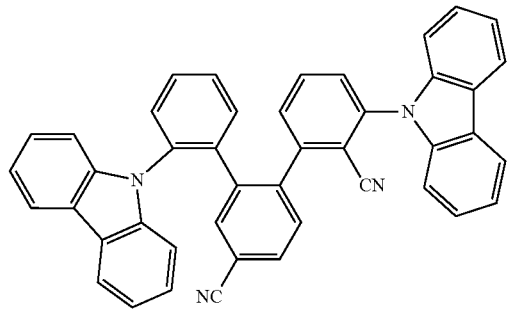
458
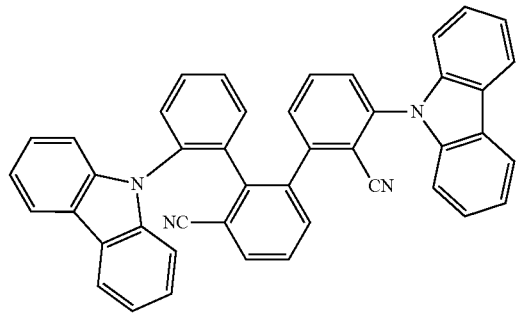

459
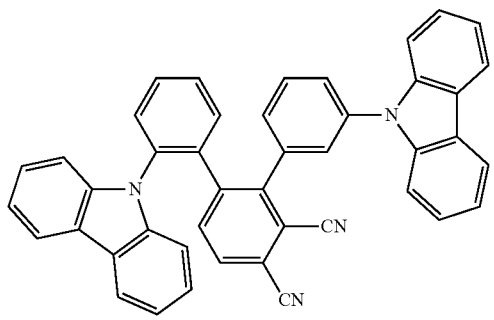
463
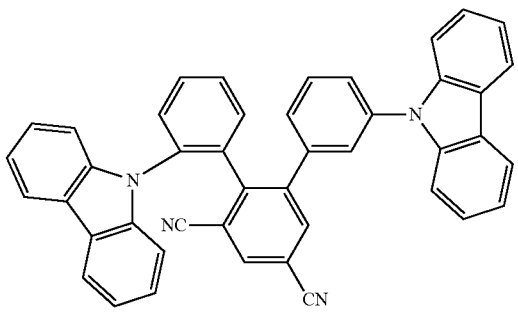
460
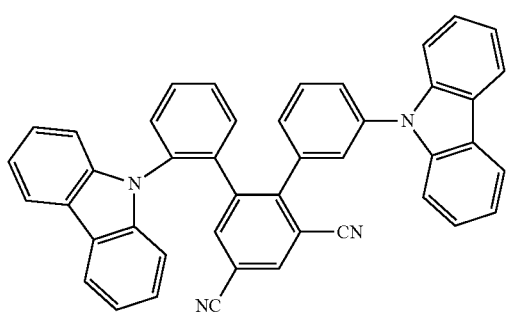
464
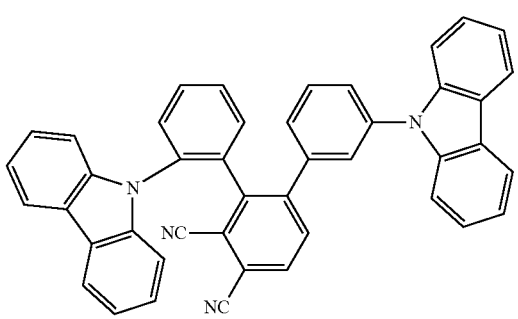
461
465
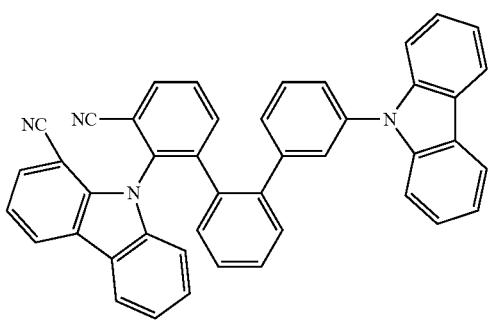
462
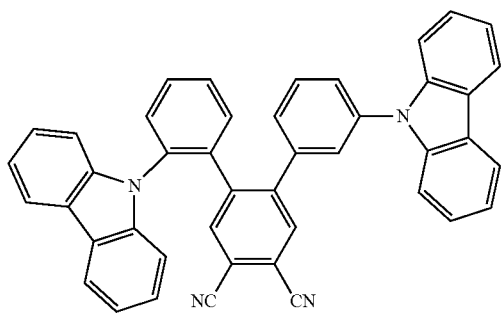
466
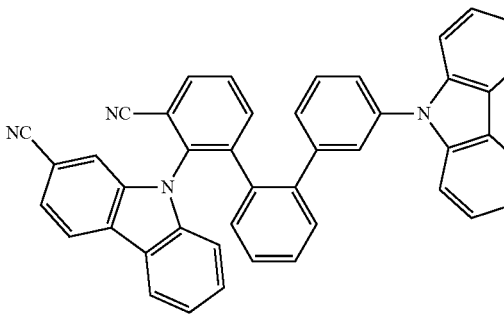

467
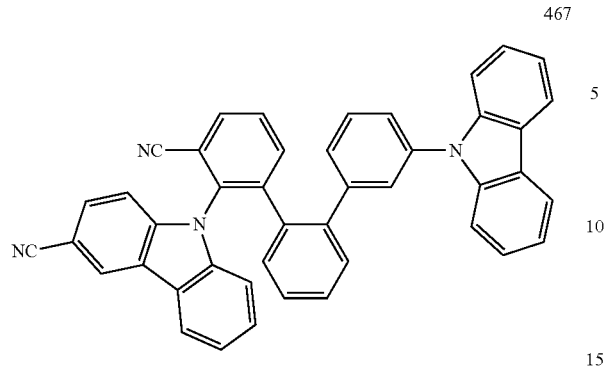
471
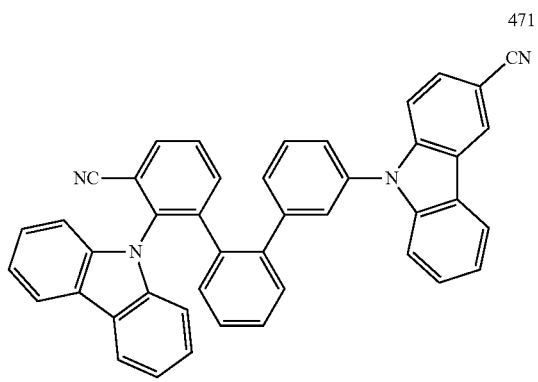
468
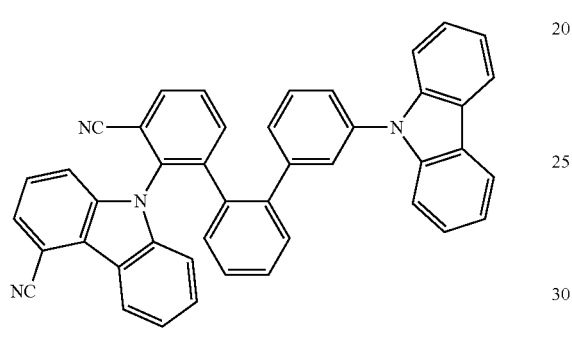
472
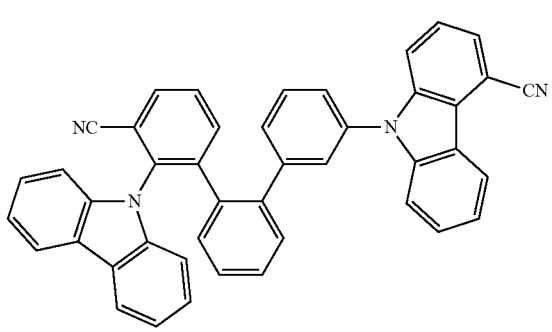
469
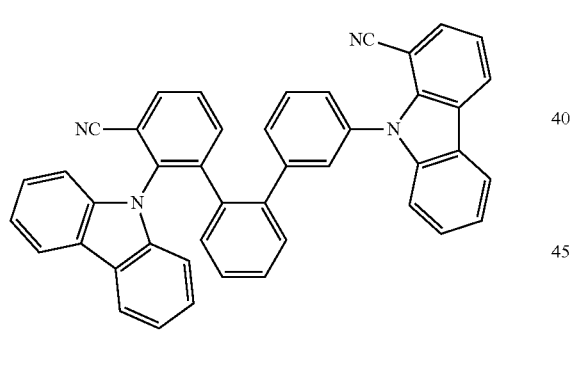
473
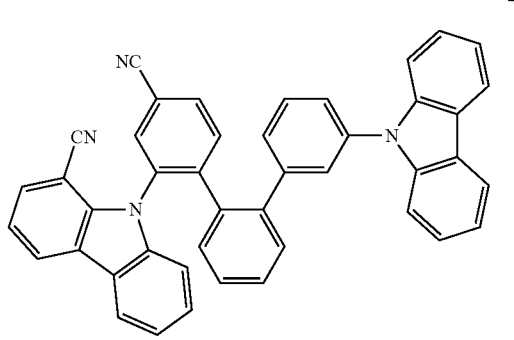
470
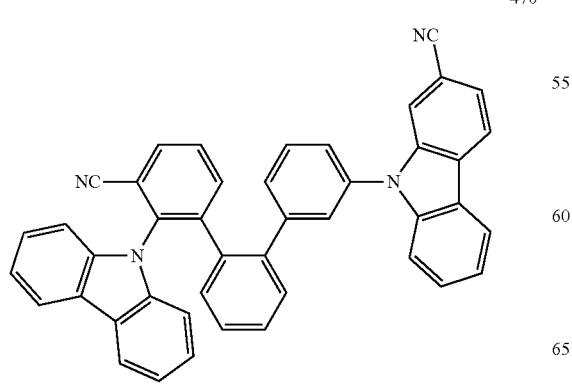
474
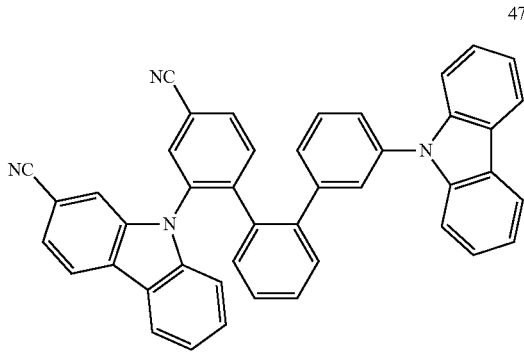

475
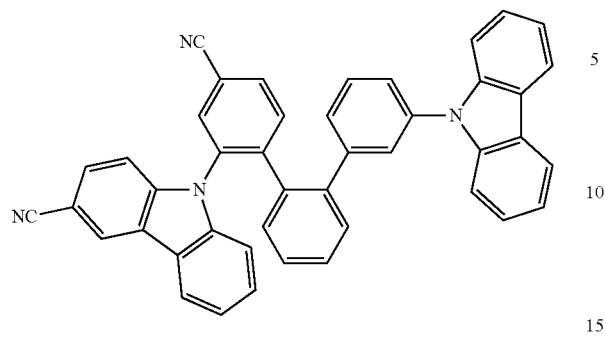
479
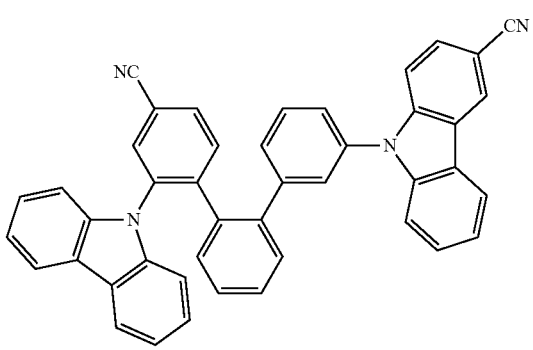
476
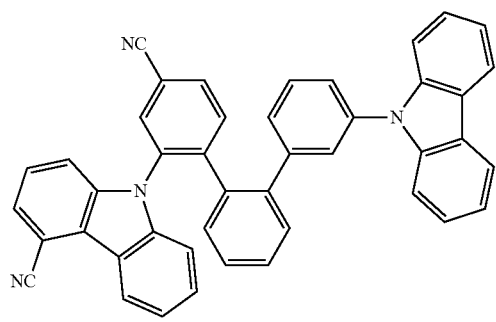
480
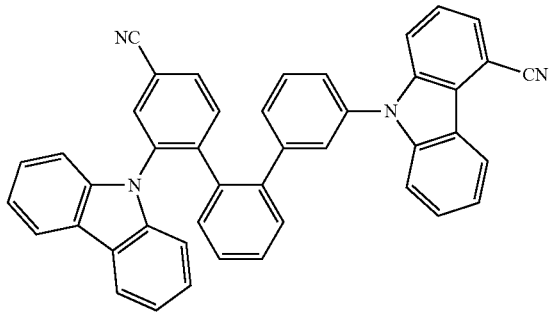
477
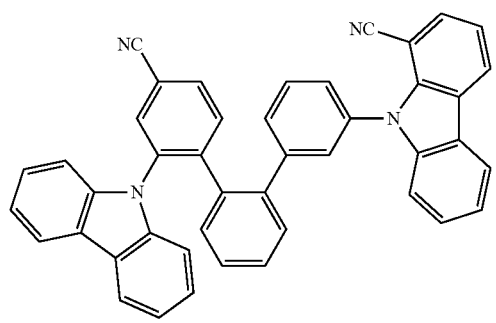
481
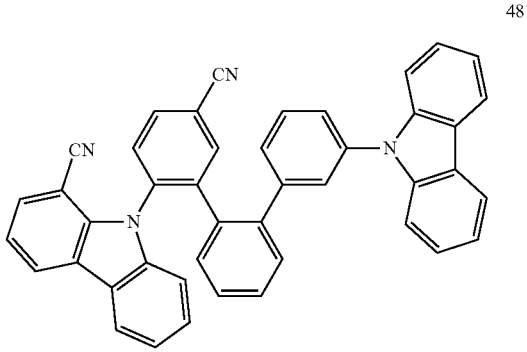
478
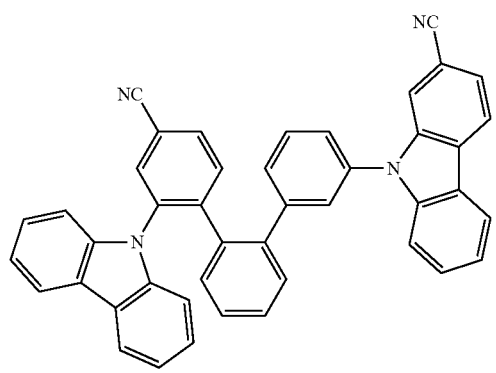
482
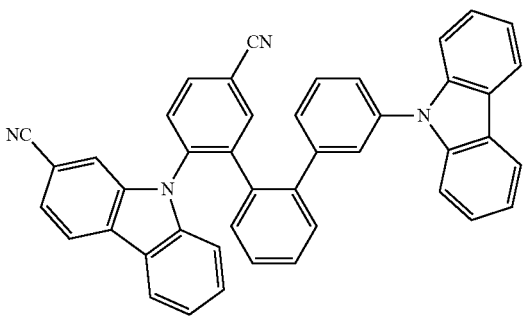

-continued
483
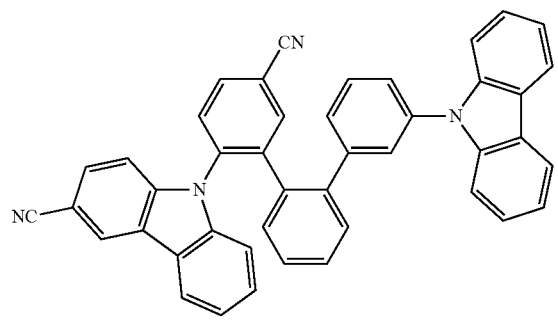
484
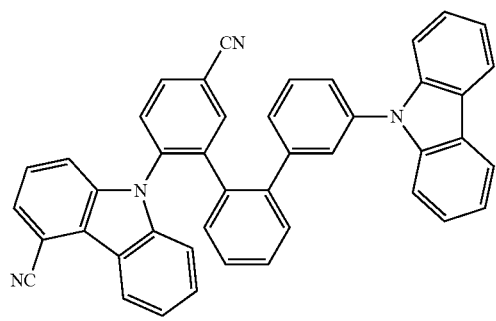
485
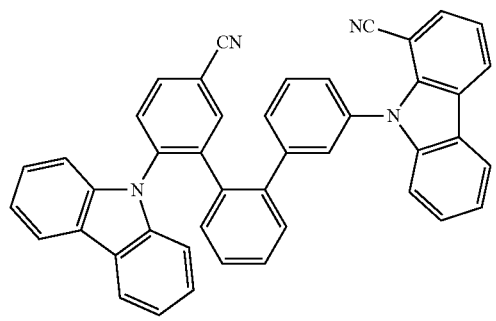
486
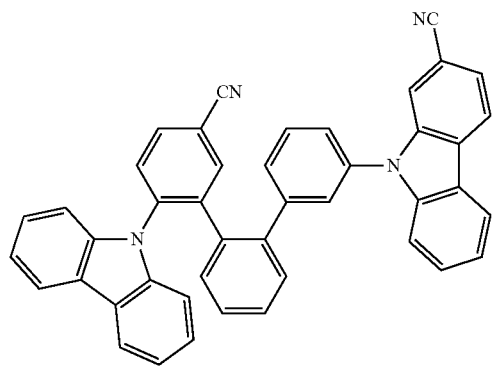
-continued
487
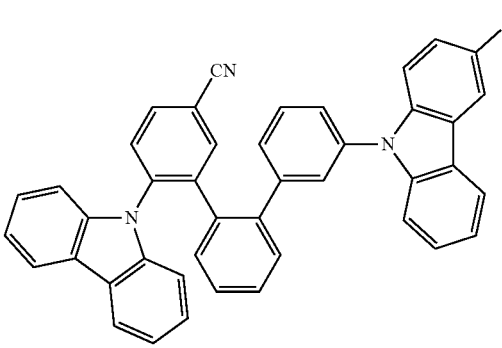
488
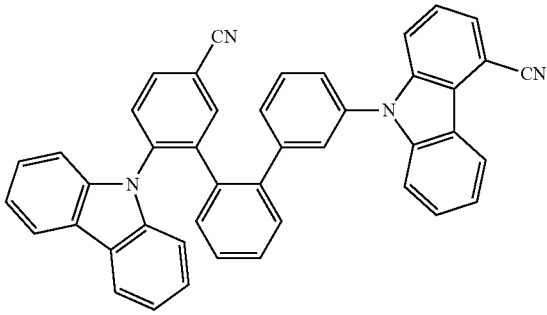
489
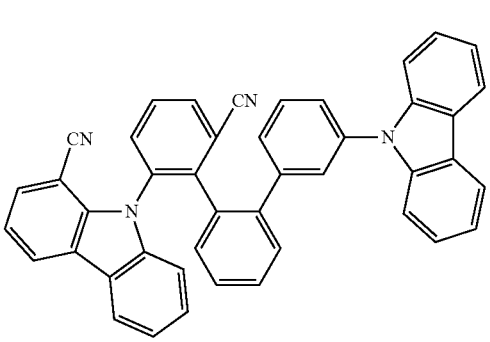
490
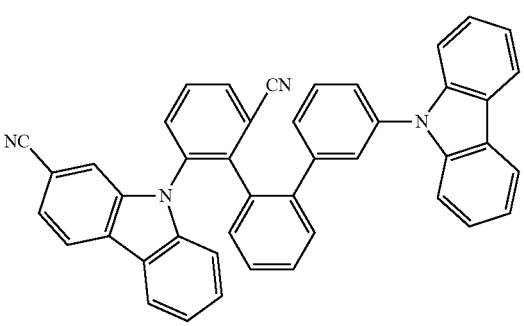

491
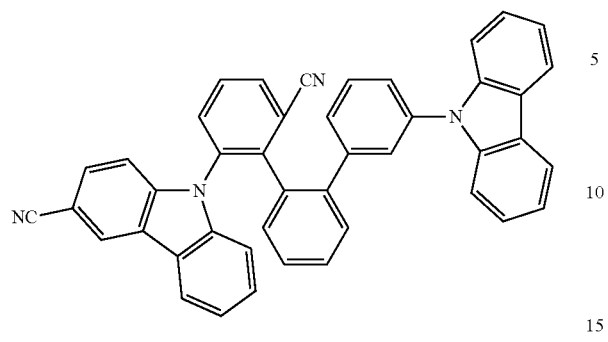
492
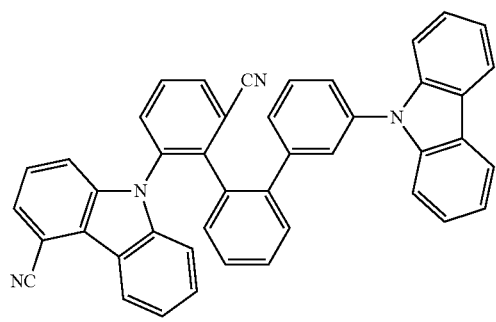
493
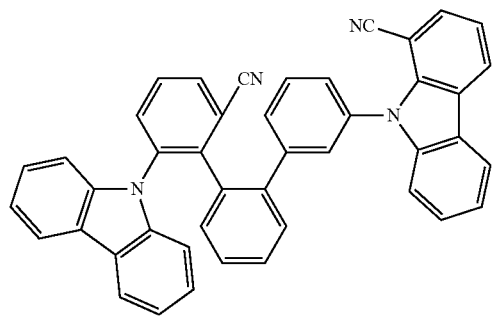
494
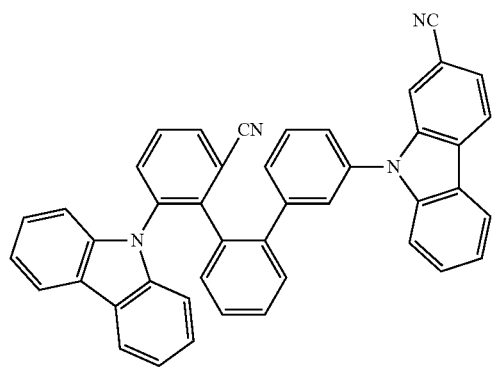
495
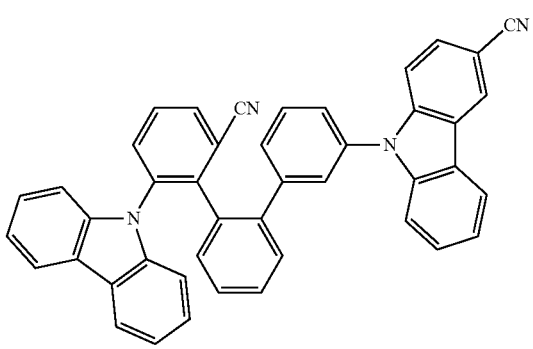
496
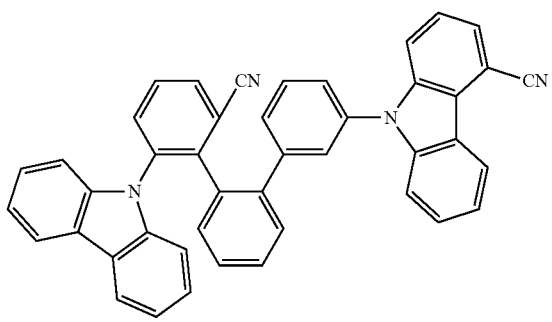
497
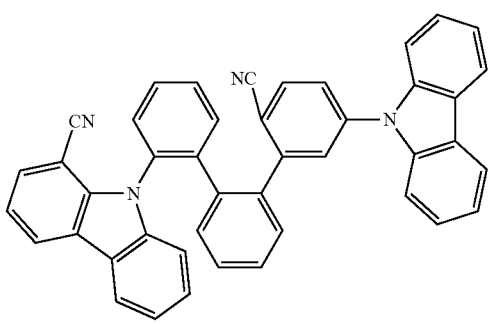
498
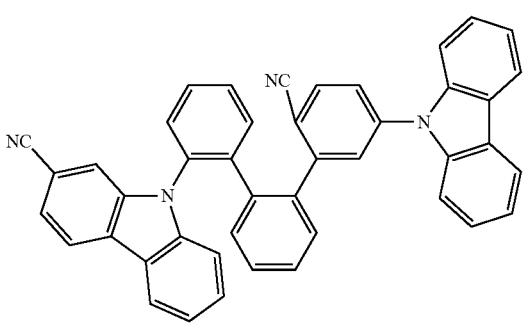

-continued
499
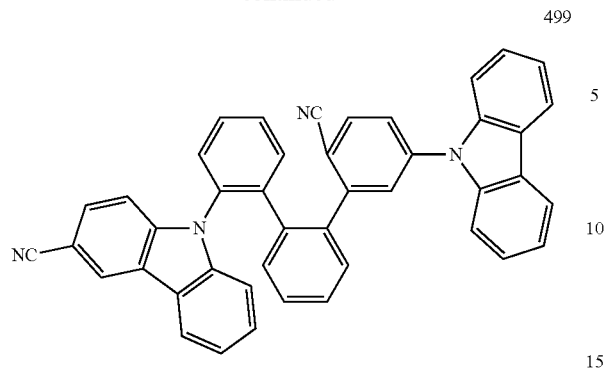
500
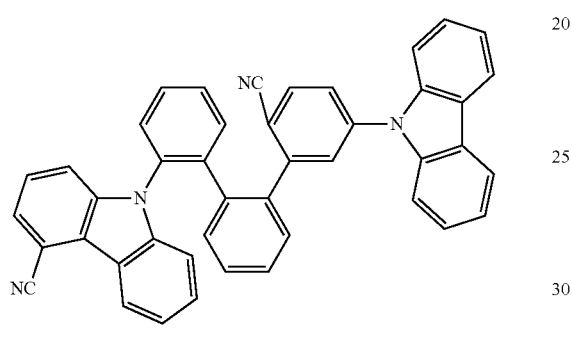
501
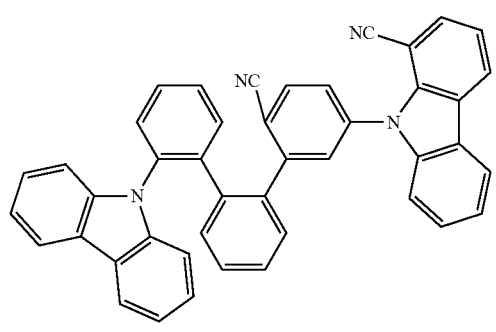
502
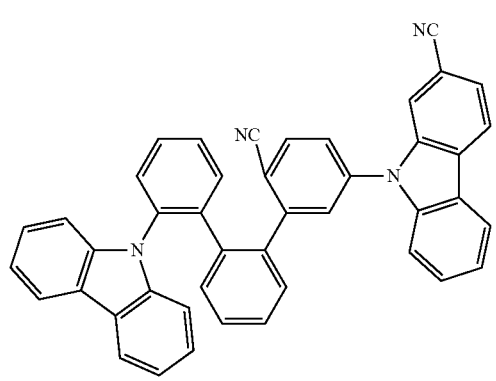
-continued
503
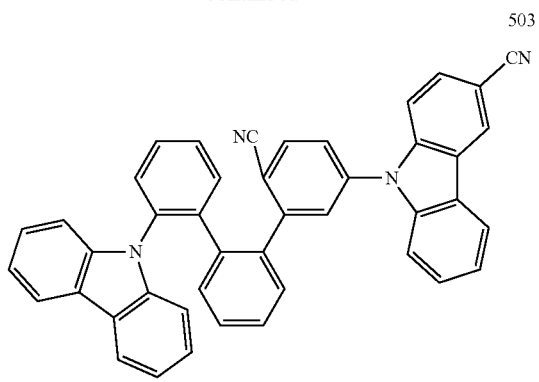
504
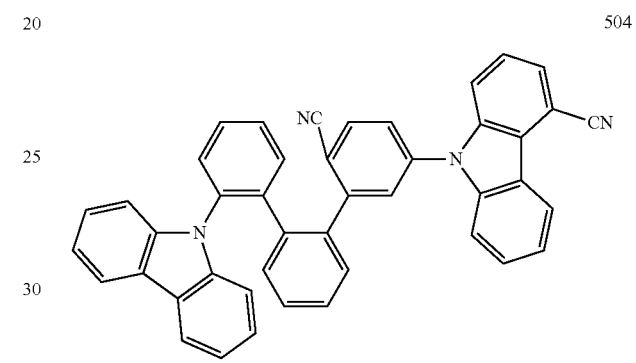
505
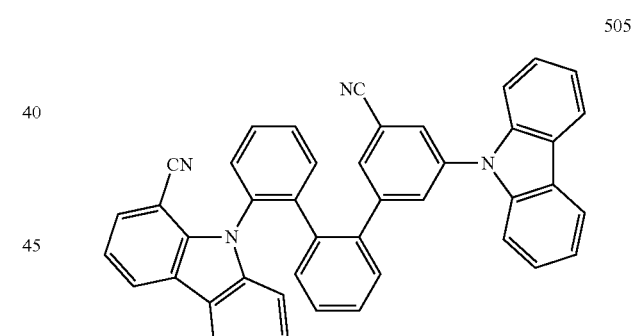
506
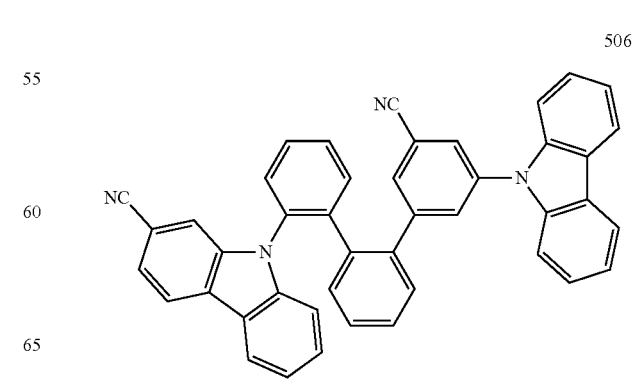

-continued
507
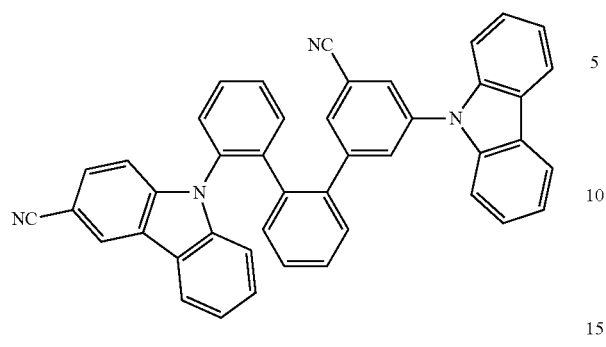
511
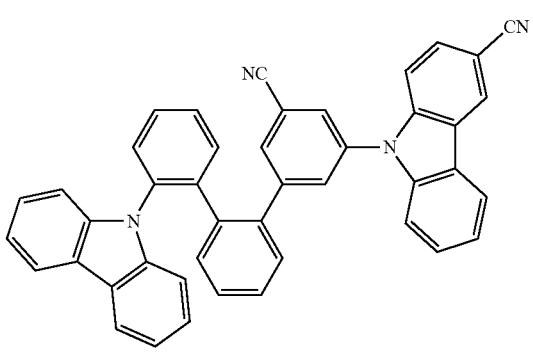
508
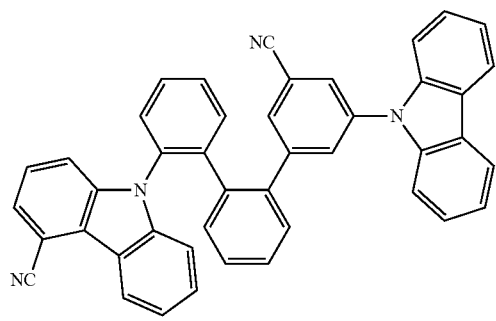
512
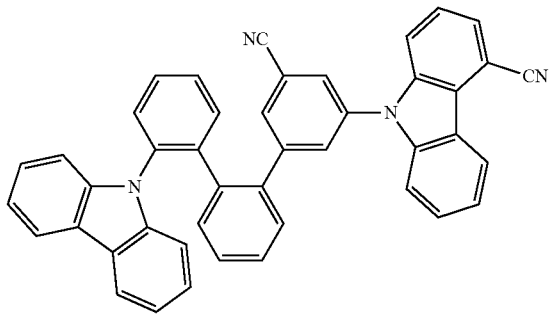
509
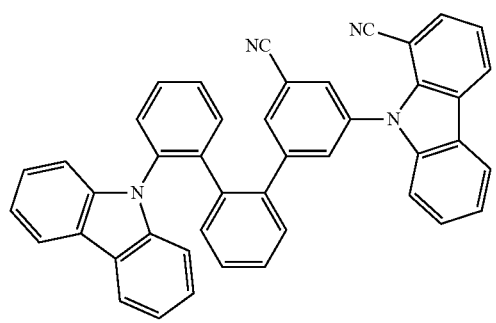
513
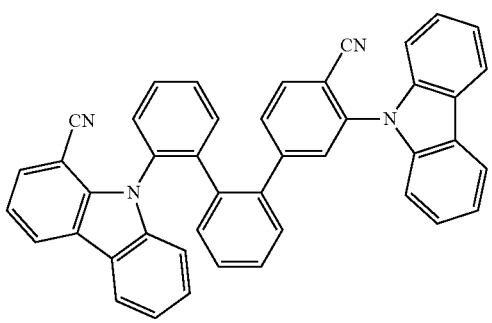
510
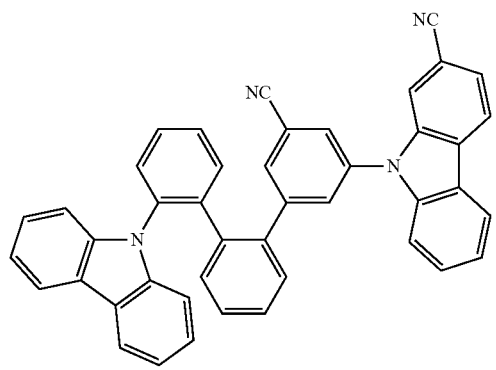
514
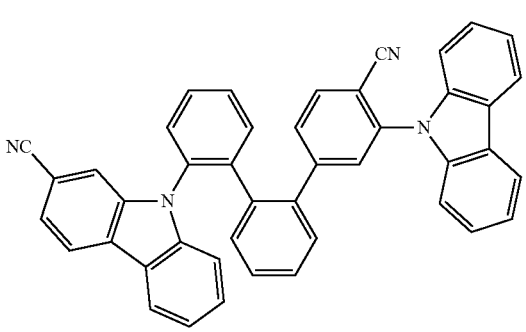

-continued
515
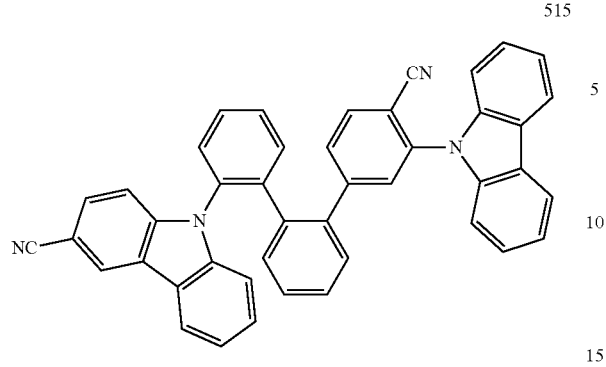
516
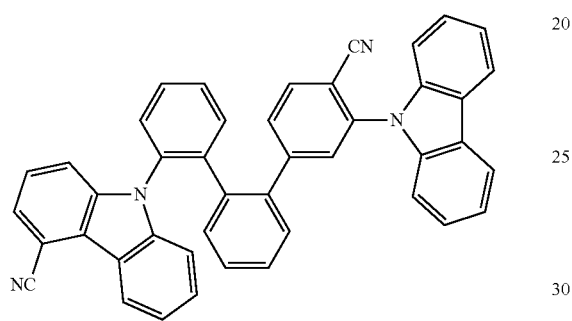
517
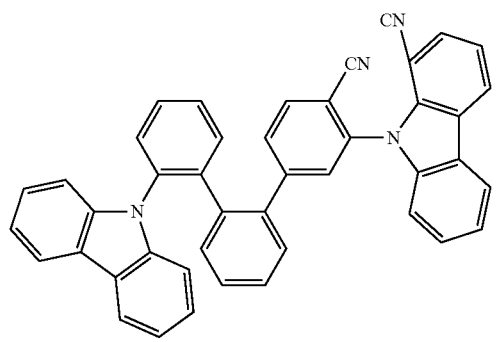
518
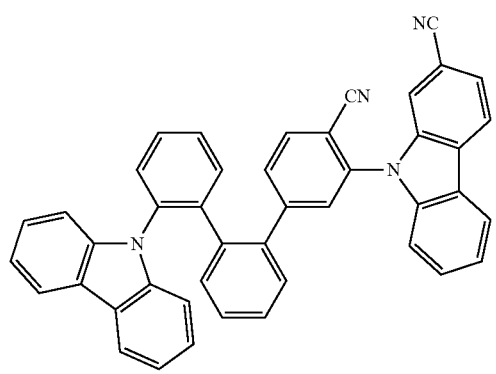
-continued
519
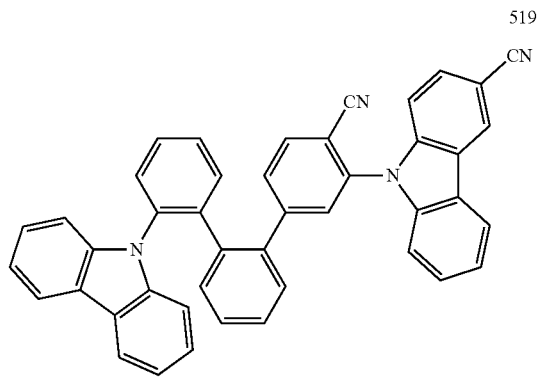
520
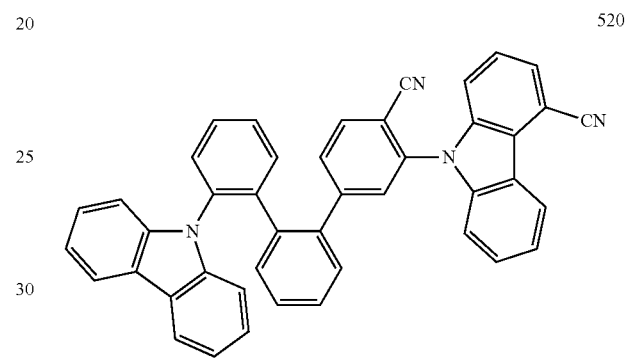
521
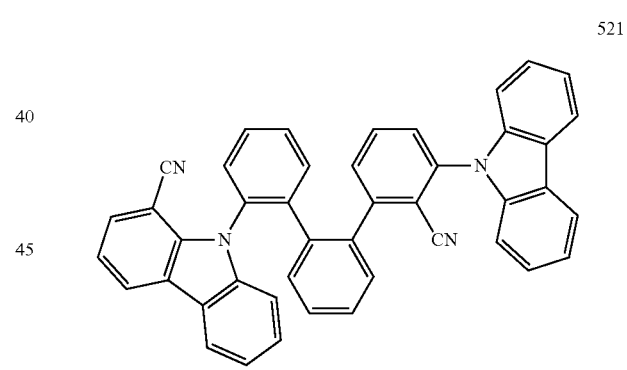
522
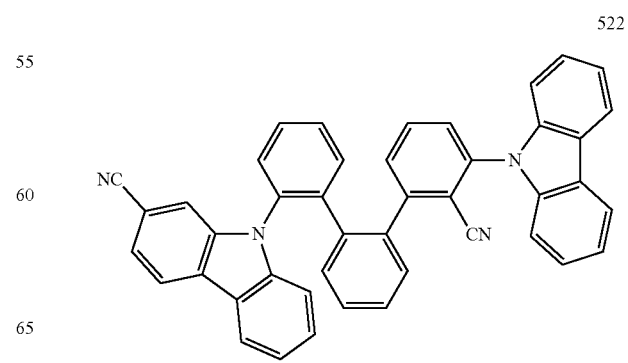

-continued
523
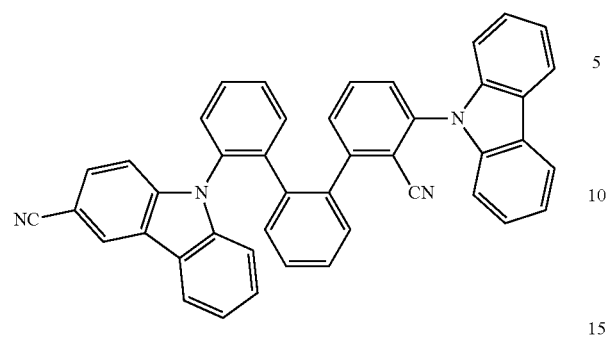
524
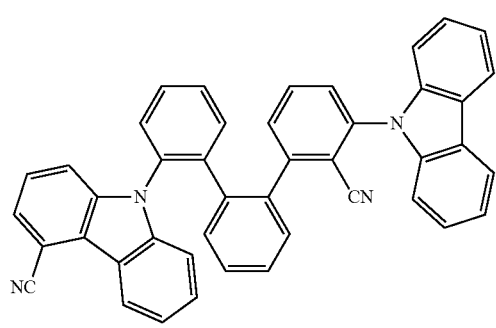
525
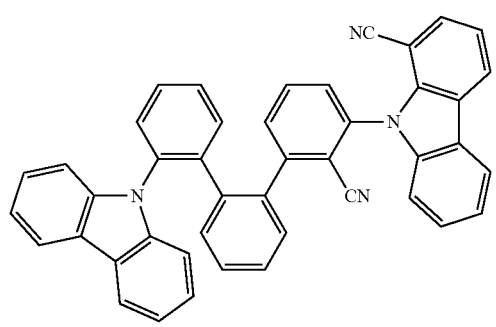
526
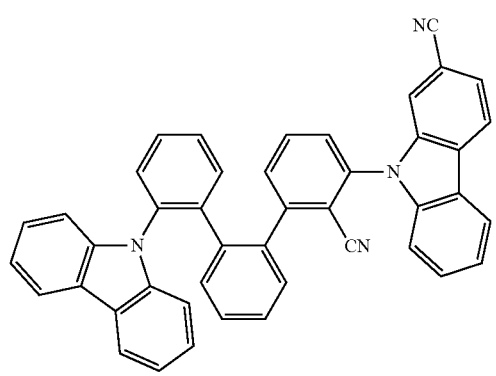
-continued
527
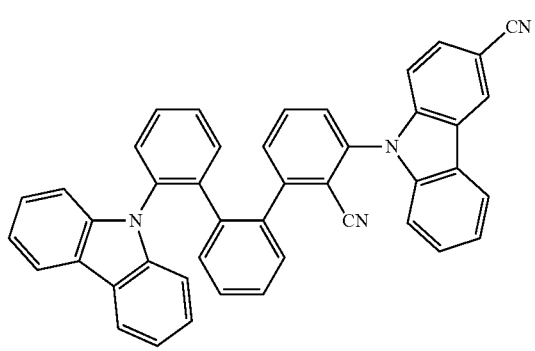
528
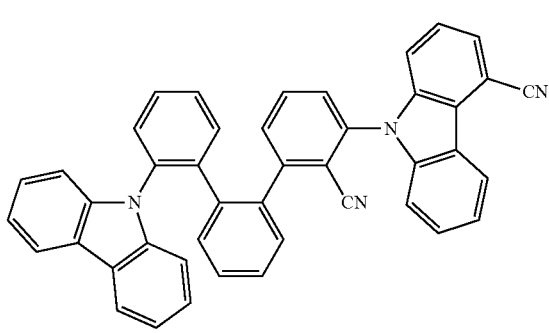
529
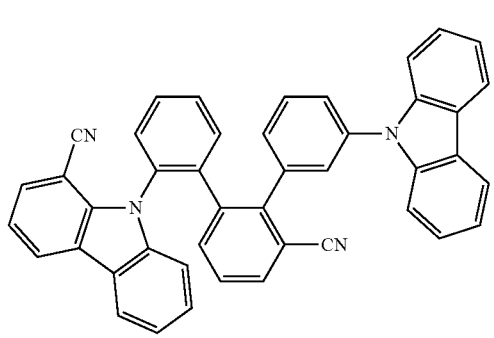
530
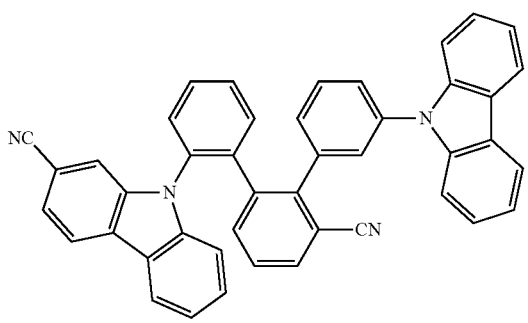

-continued
531
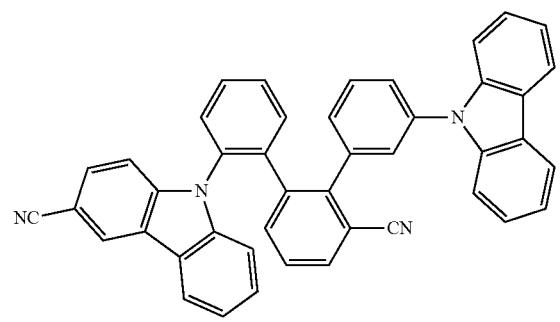
532
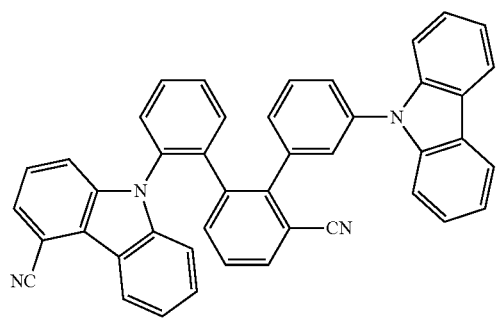
533
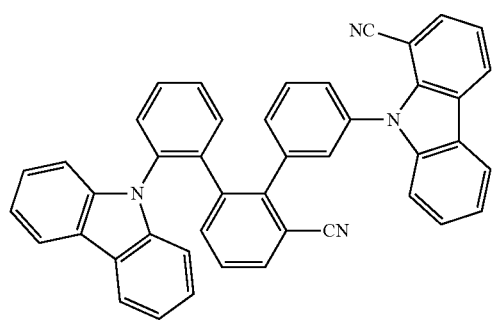
534
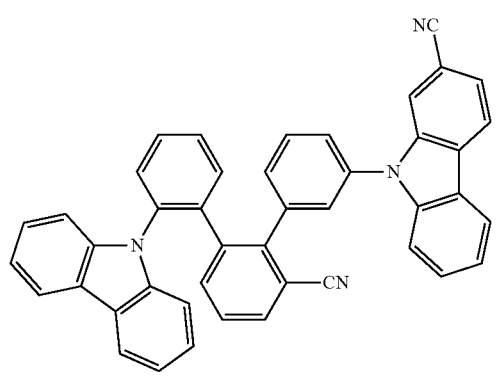
-continued
535
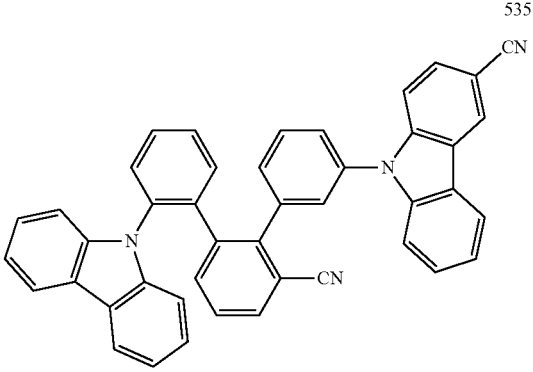
536
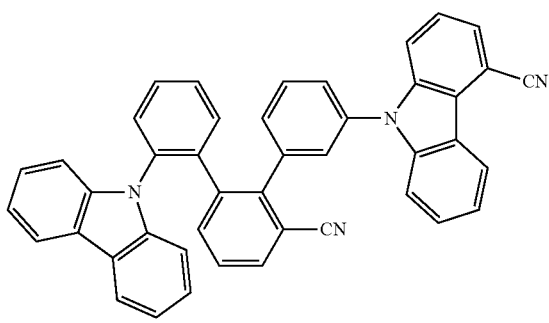
537
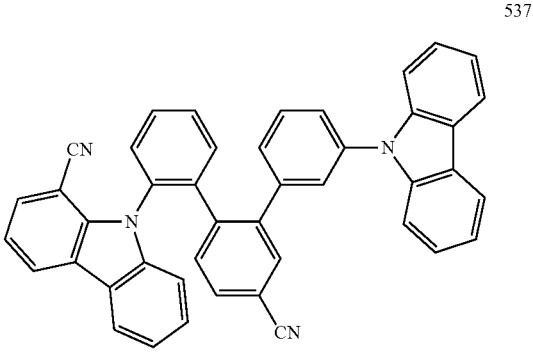
538
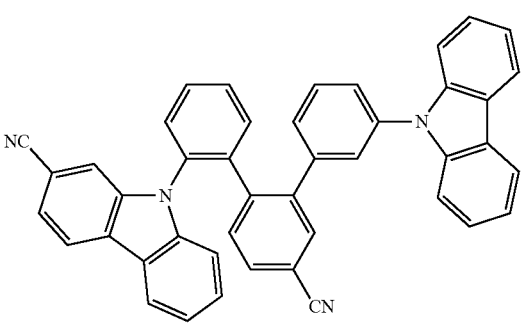

539
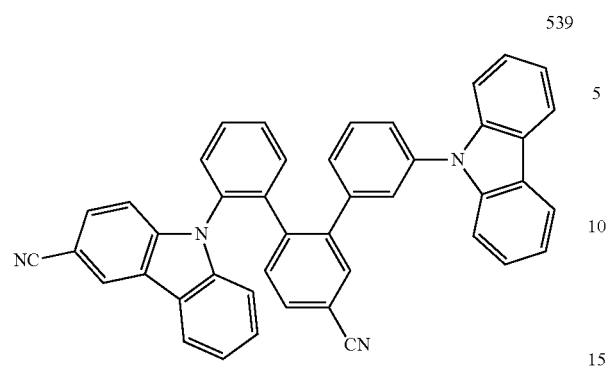
543
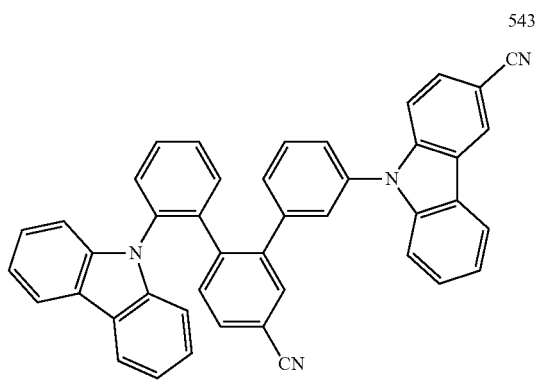
540
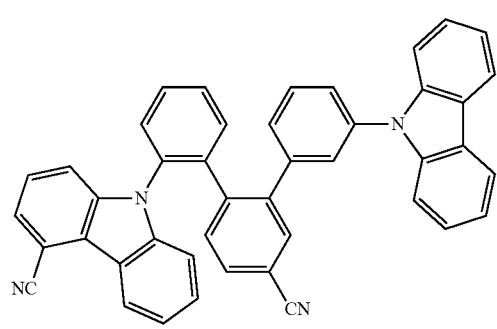
544
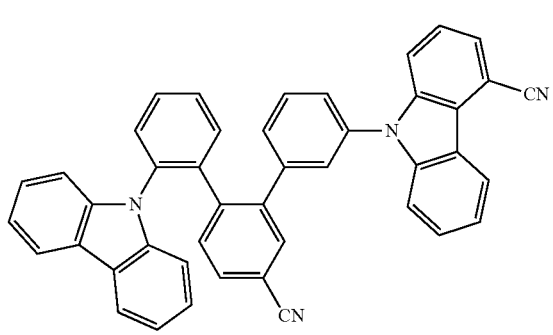
541
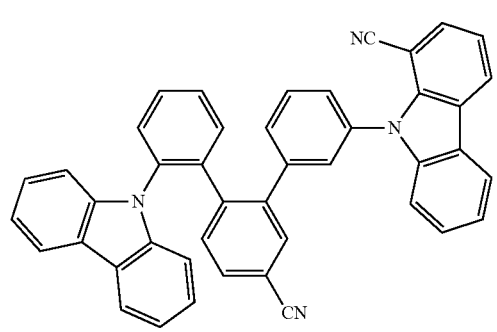
545
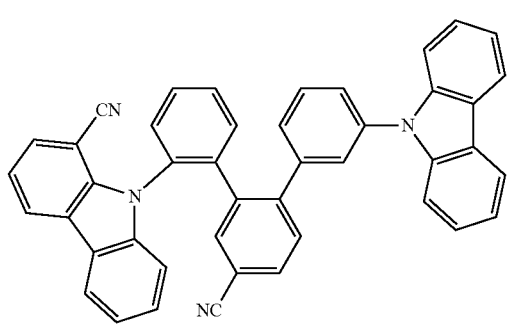
542
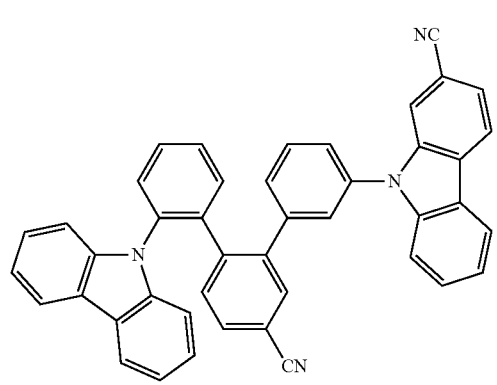
546
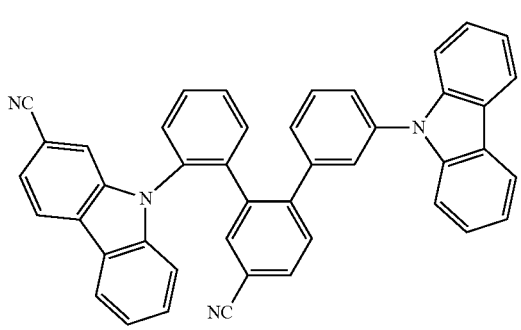

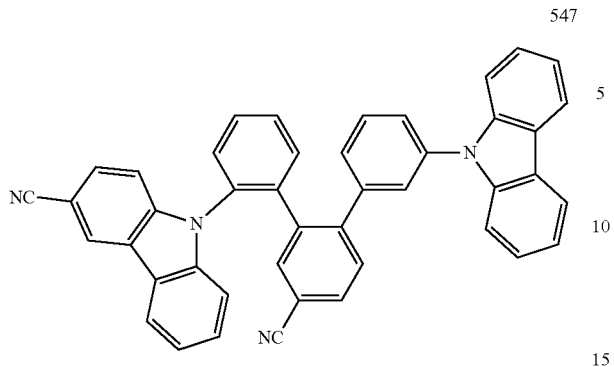
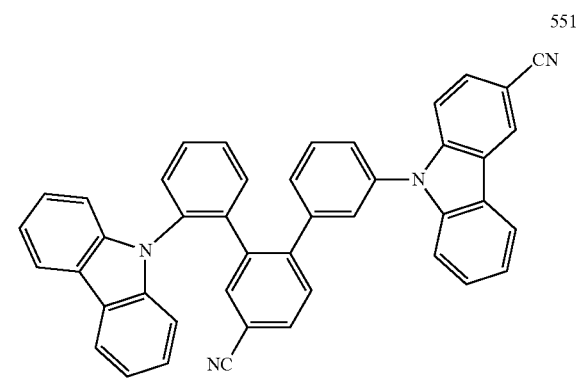
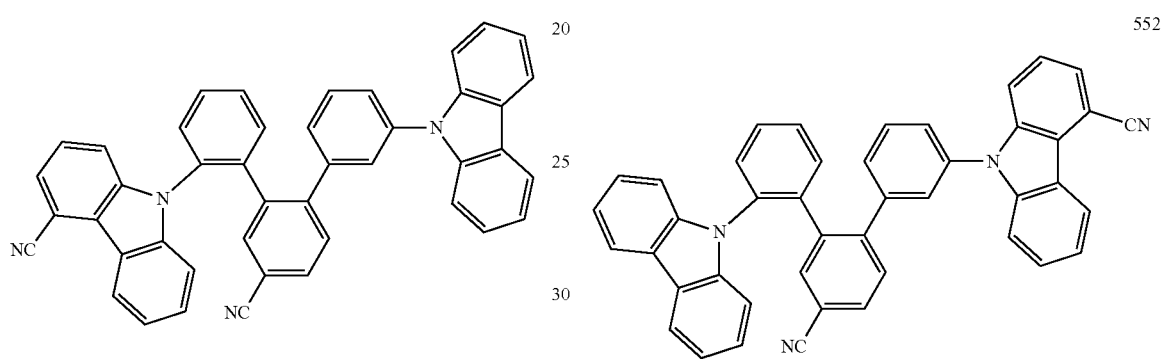
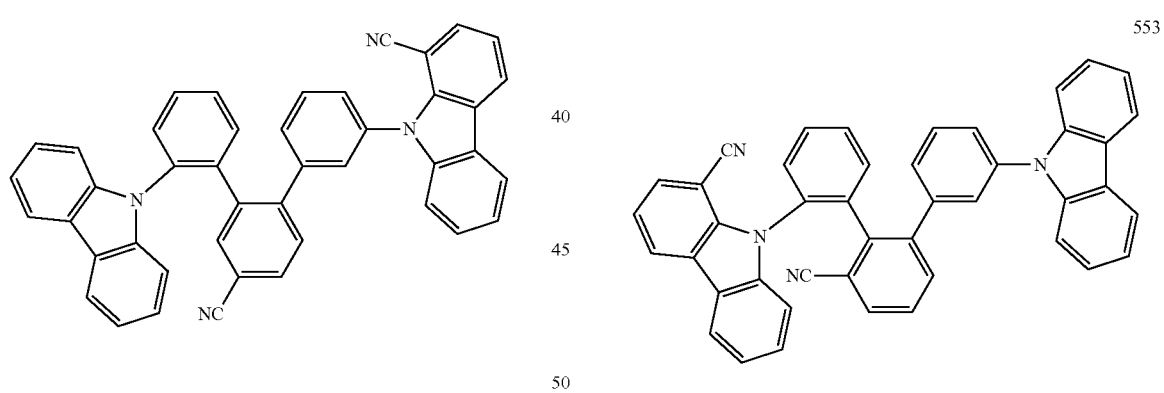
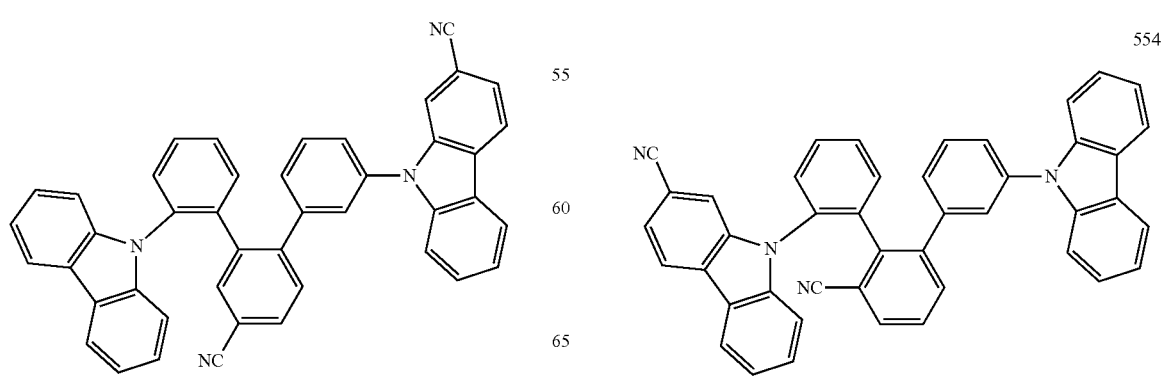

555
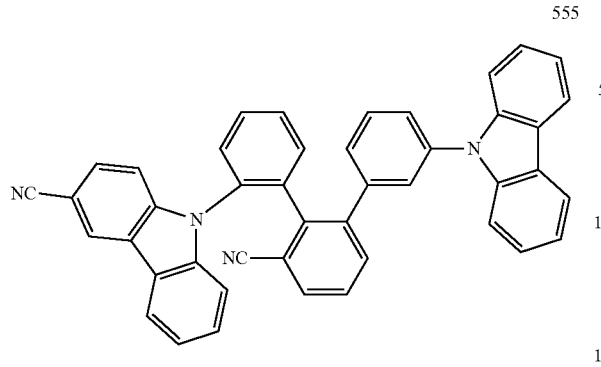
556
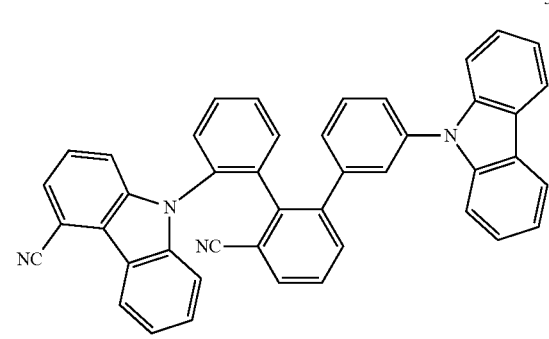
557
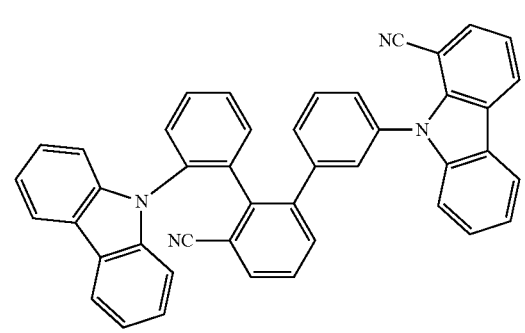
558
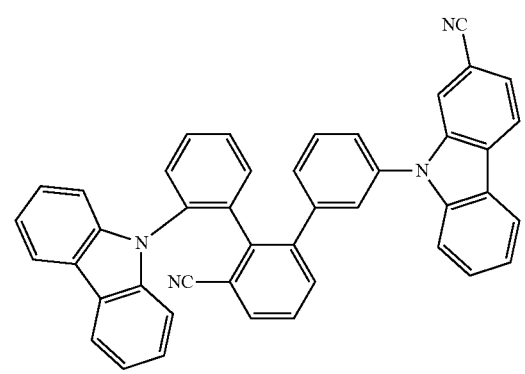
559
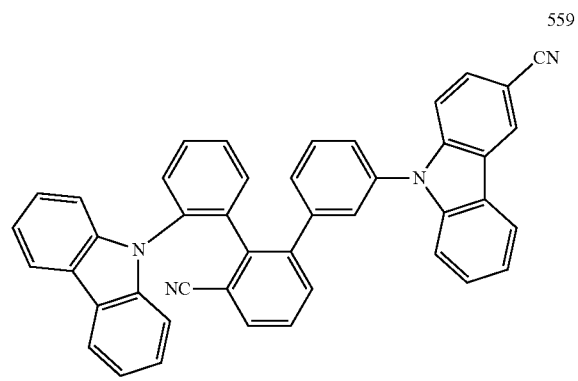
560
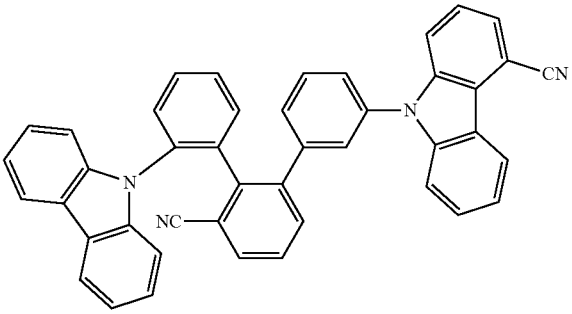
561
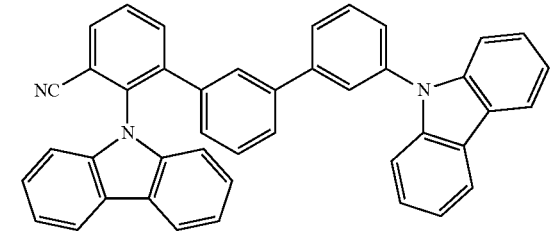
562
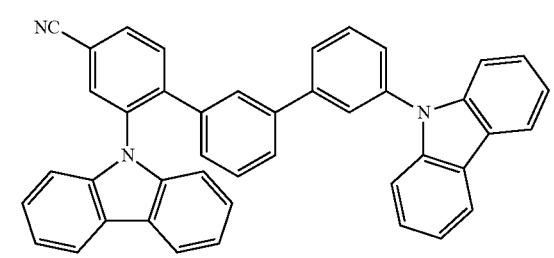
563
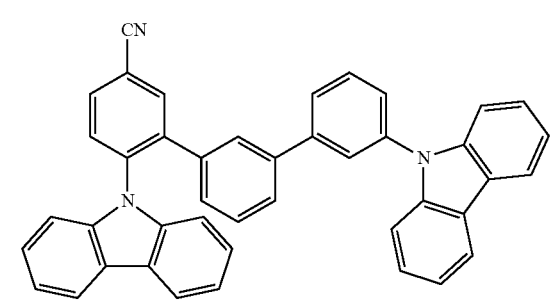

-continued
564
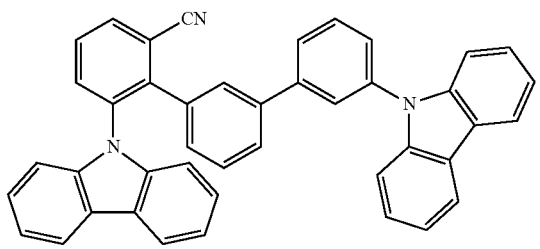
565
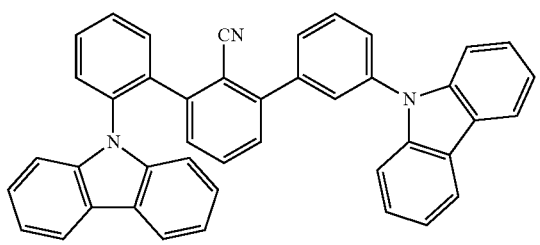
566
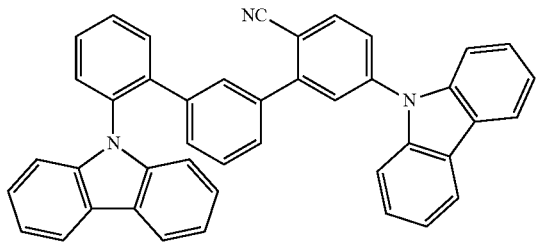
567
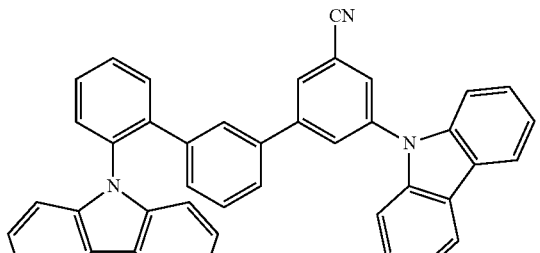
568
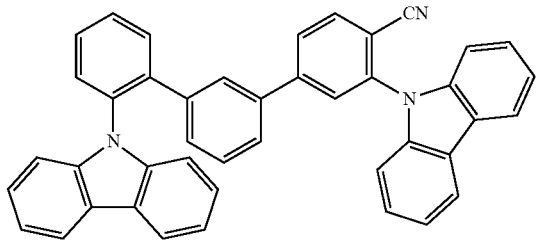
569
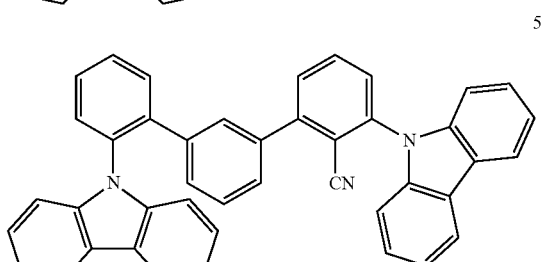
-continued
570
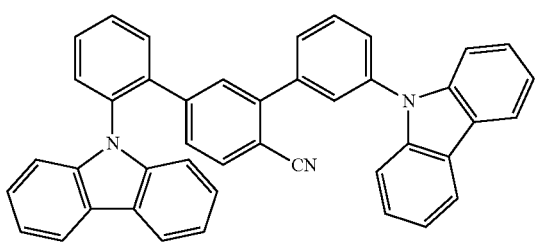
571
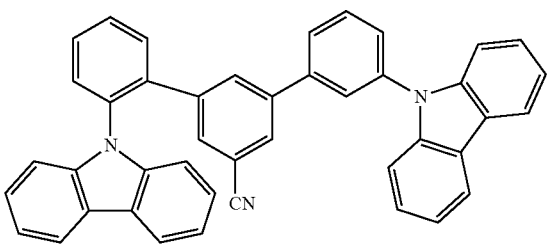
572
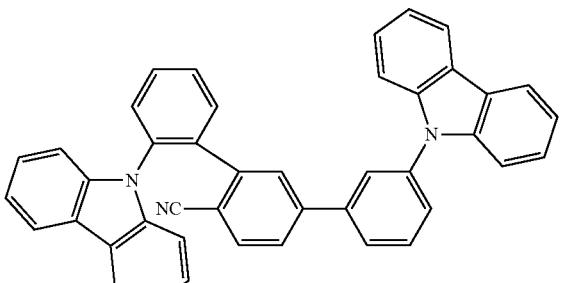
573
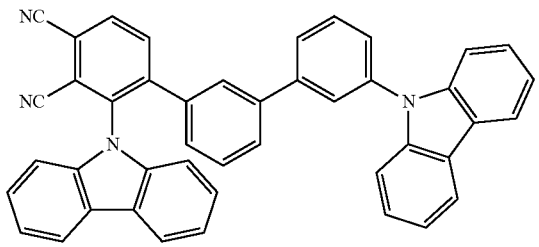
574
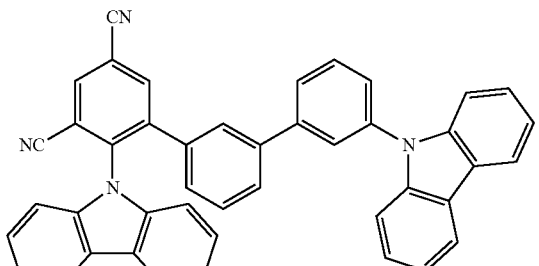

575
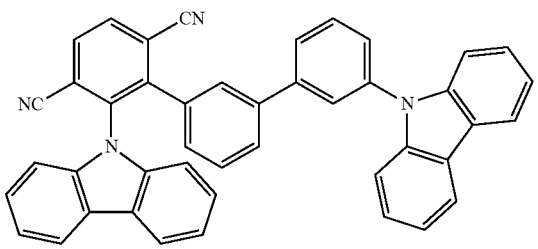
576
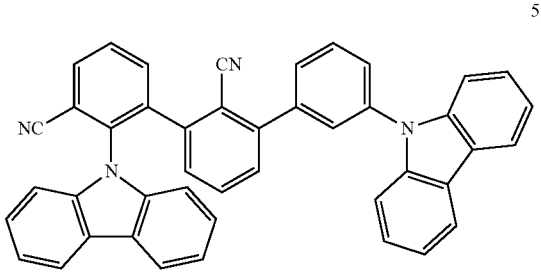
577
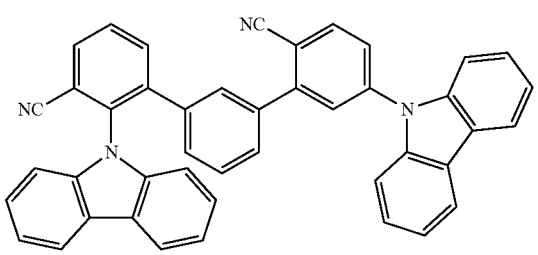
578
579
580
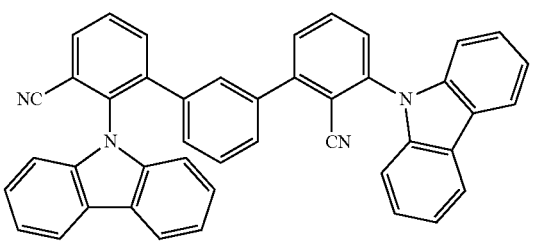
581
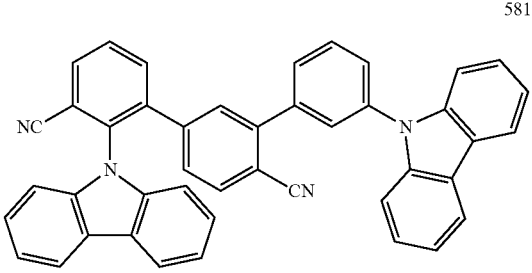
582
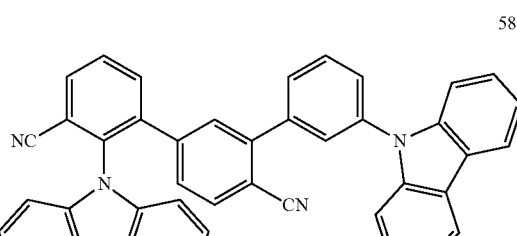
583

584

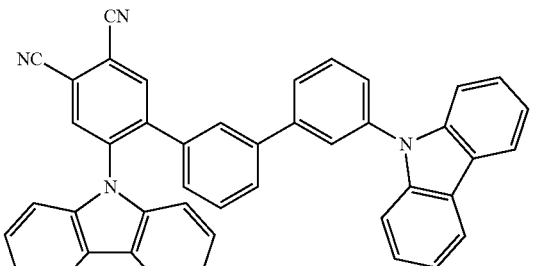

585
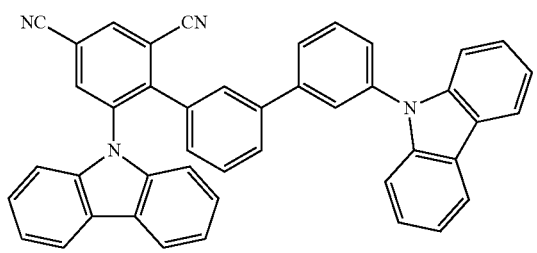
586
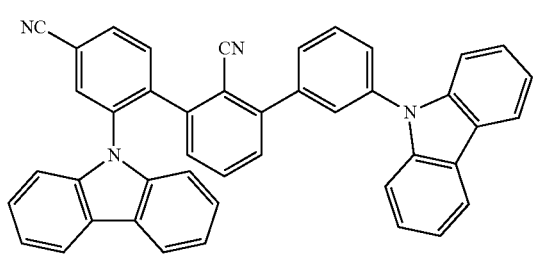
587
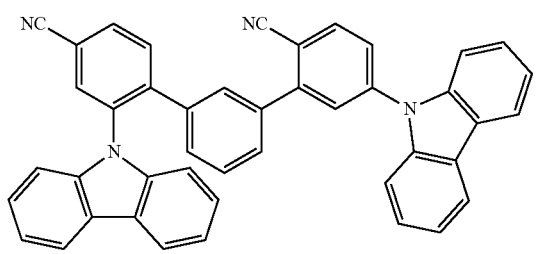
588
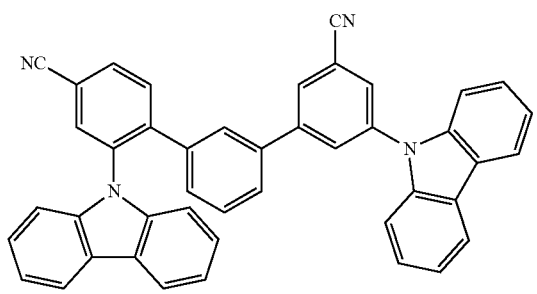
589
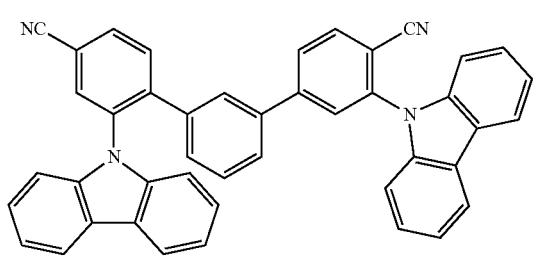
590
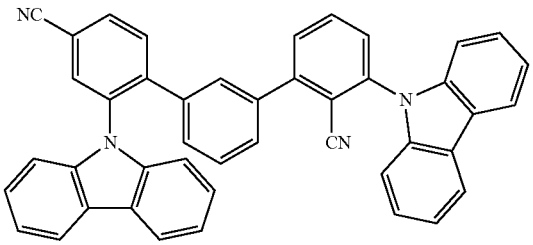
591
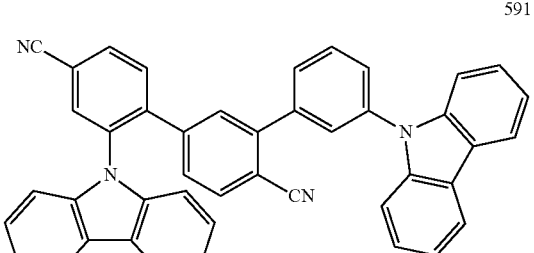
592
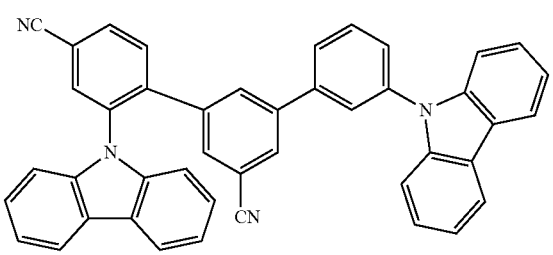
593
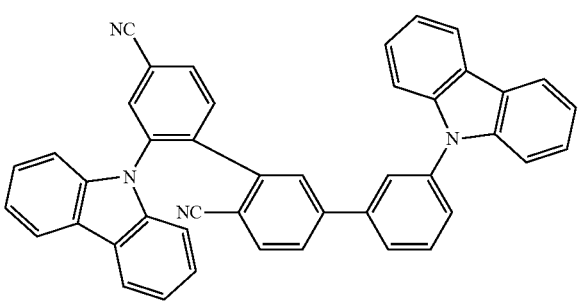
594
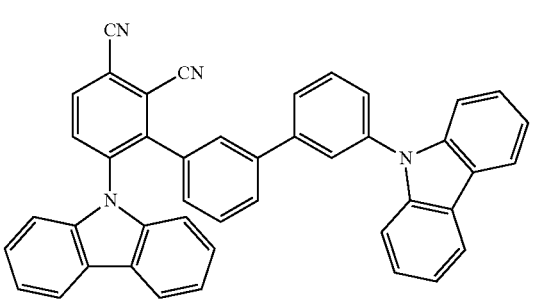

595
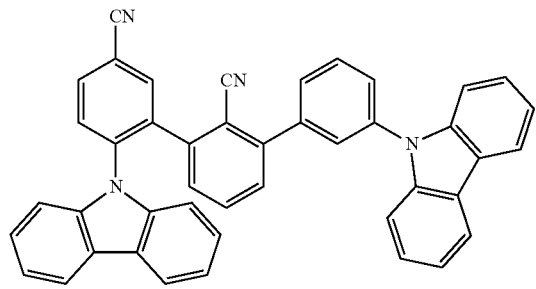
596
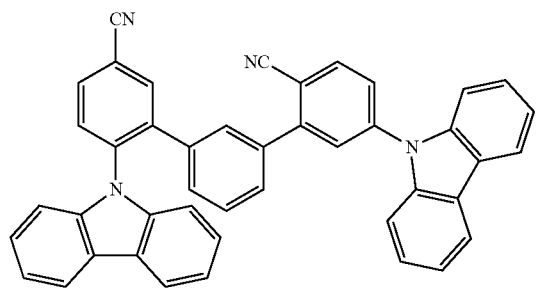
597
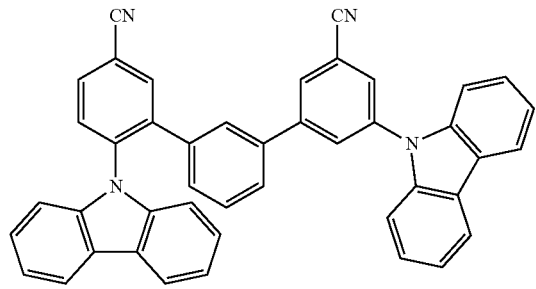
598
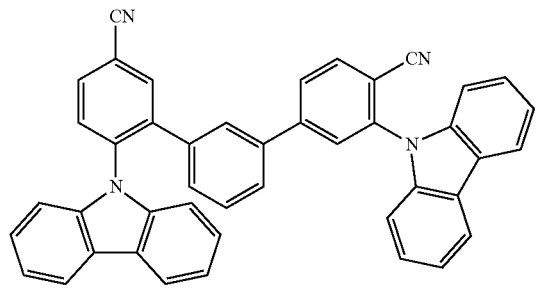
599
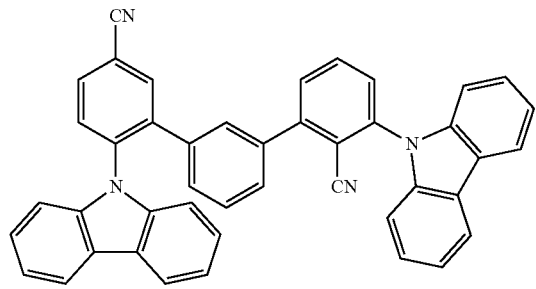
600
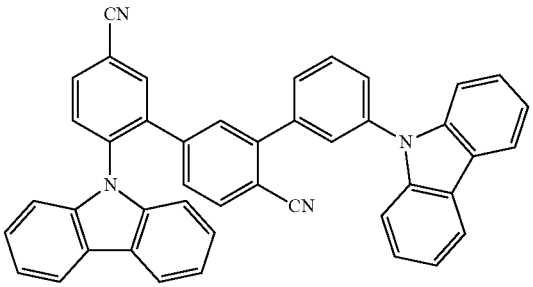
601
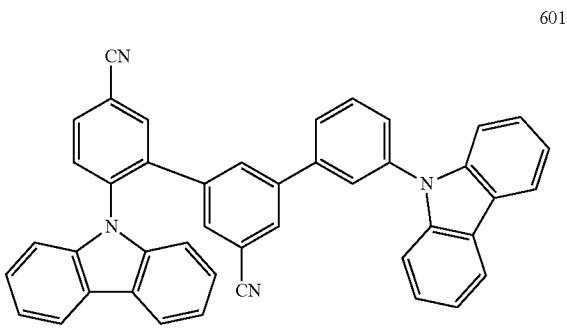
602
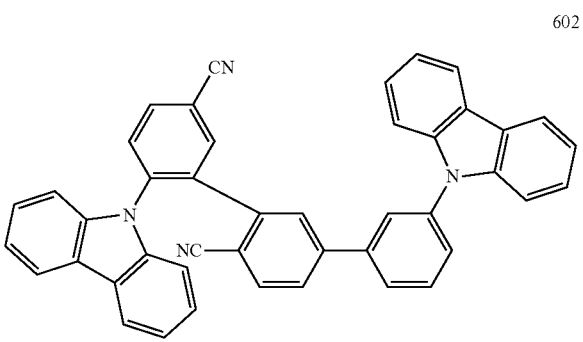
603
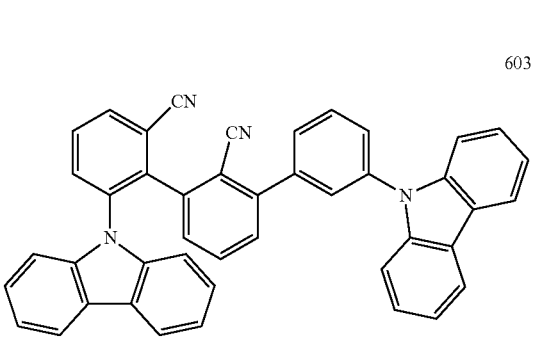
604
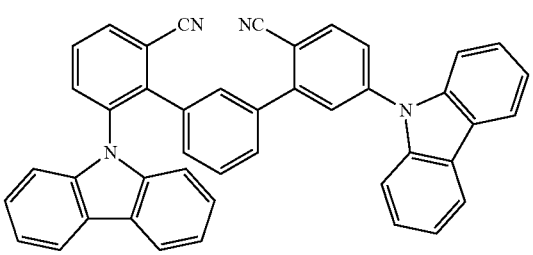

605
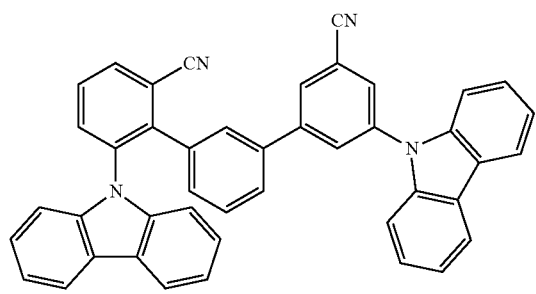
606
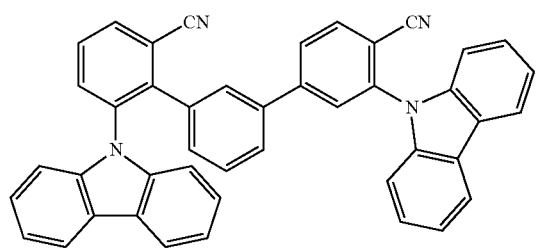
607
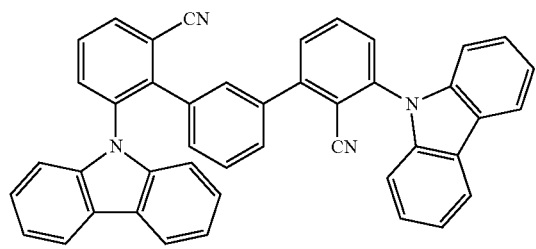
608
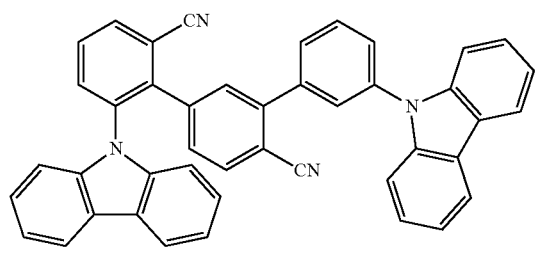
609
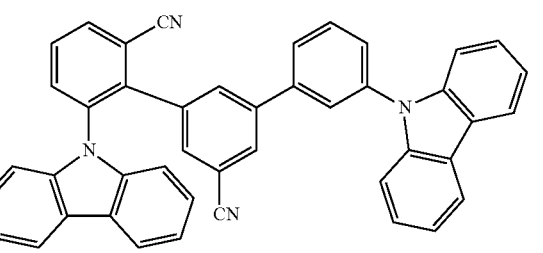
610
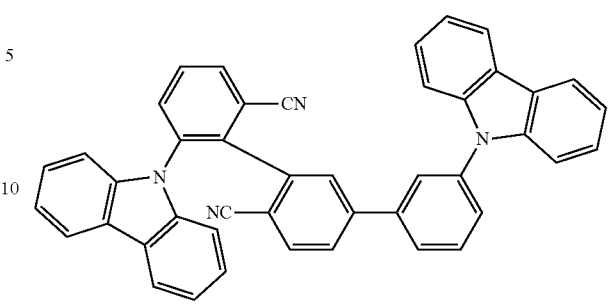
611
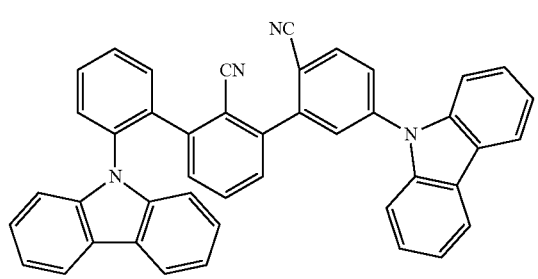
612
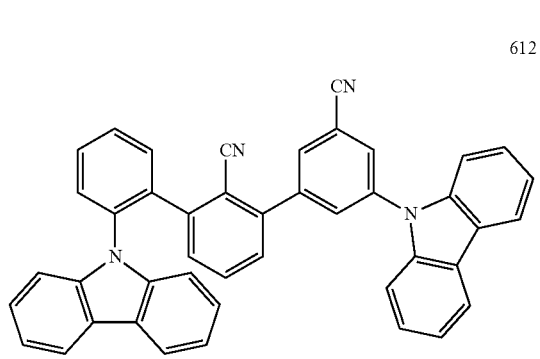
613
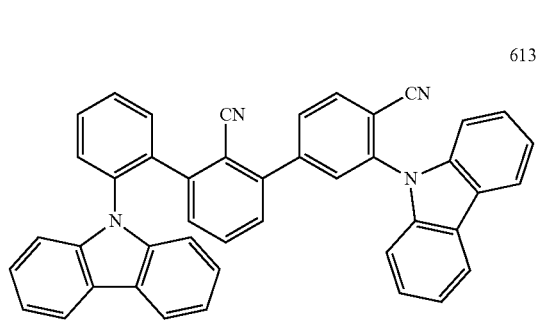
614
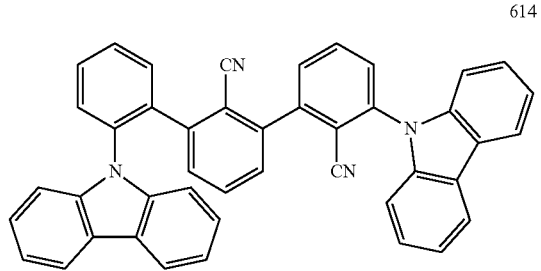

-continued
615
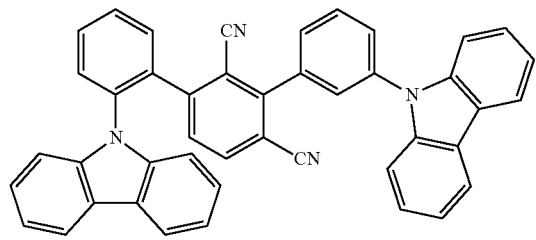
616
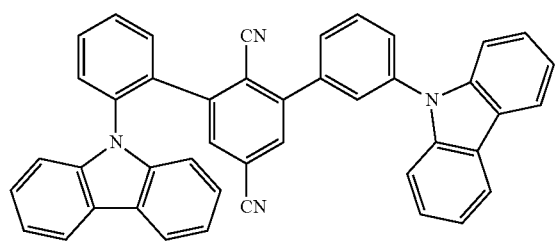
617
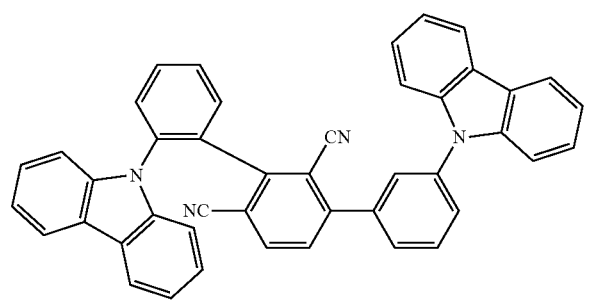
618
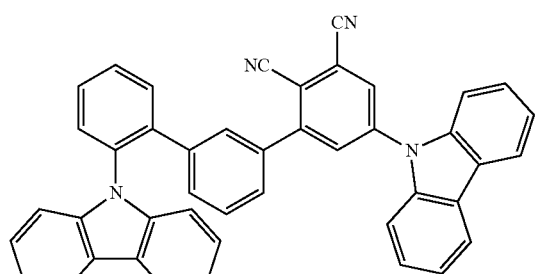
619
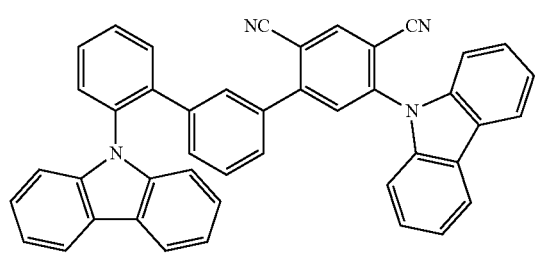
-continued
620
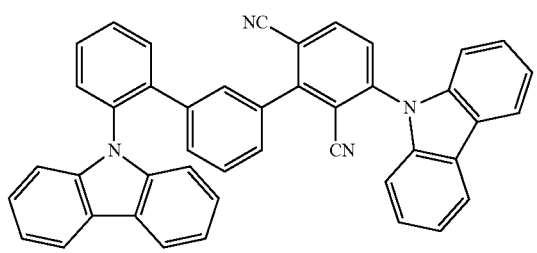
621
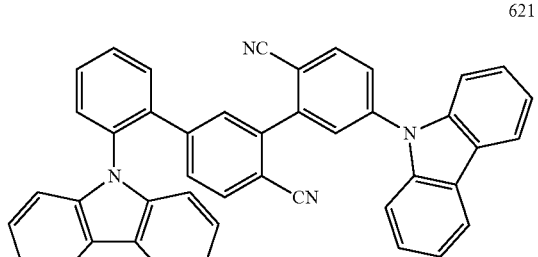
622
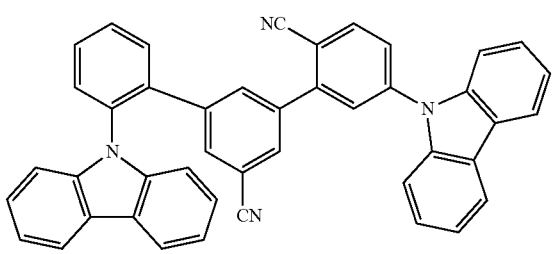
623
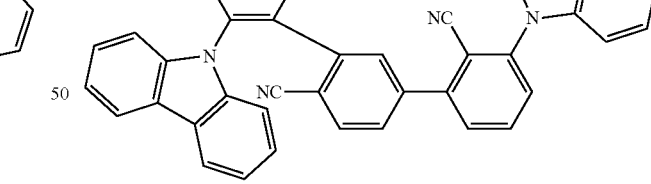
624
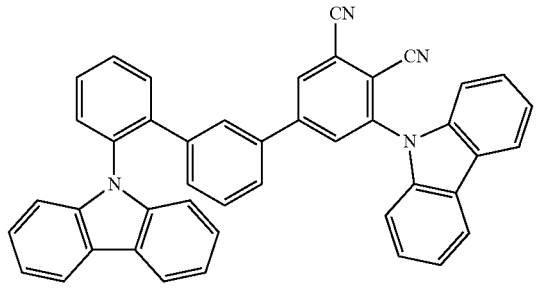

-continued
625
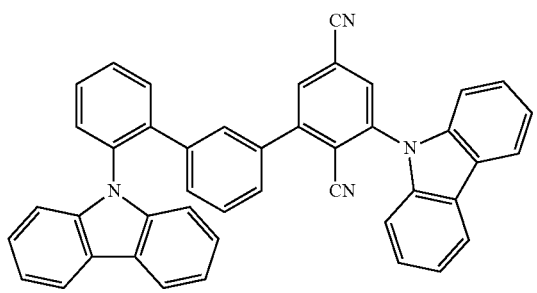
626
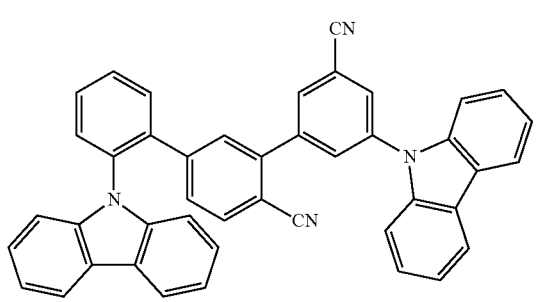
627
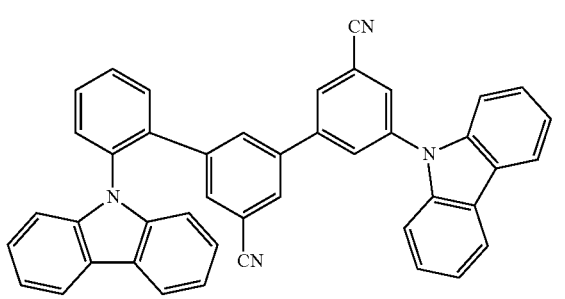
628
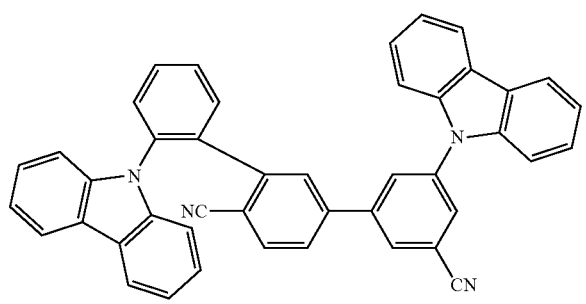
629
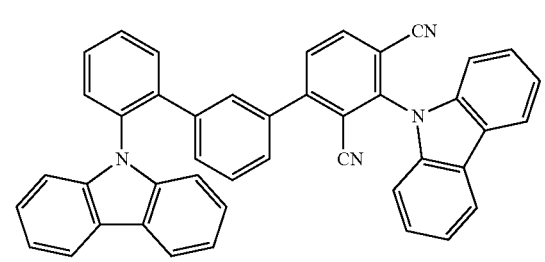
-continued
630
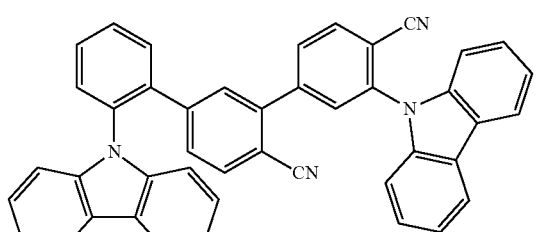
631
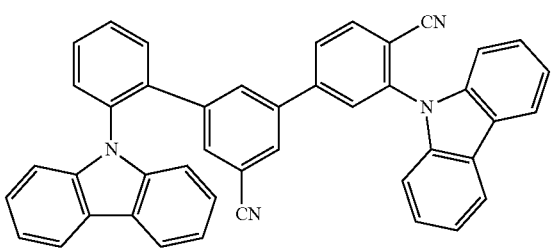
632
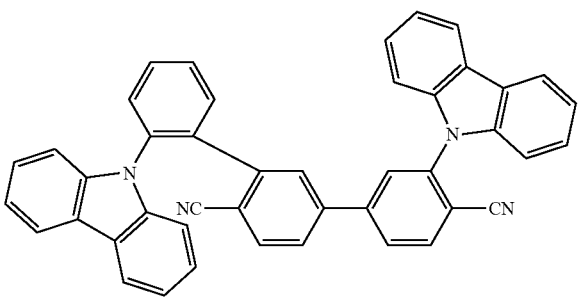
633
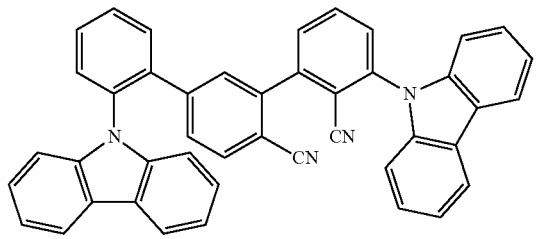
634
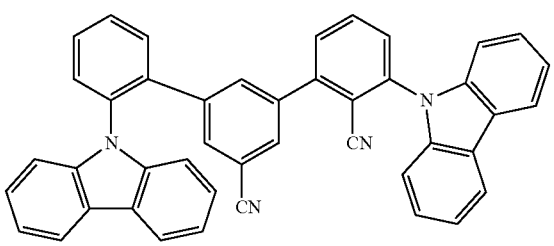

-continued
635
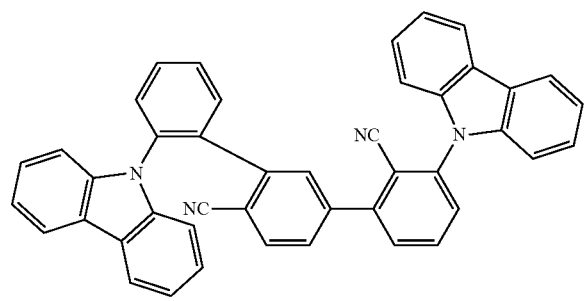
636
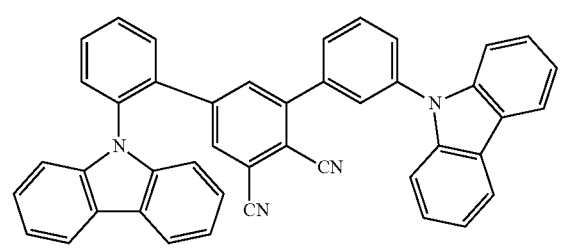
637
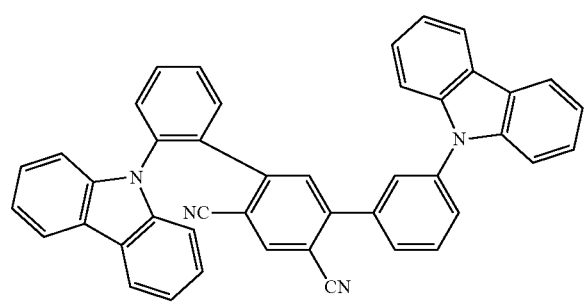
638
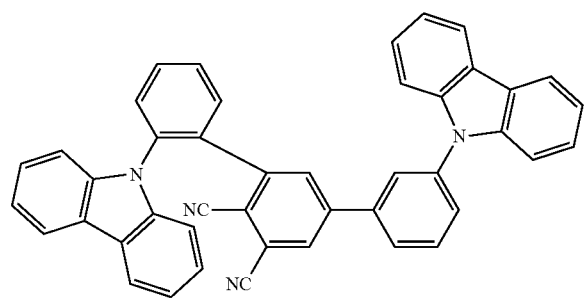
639
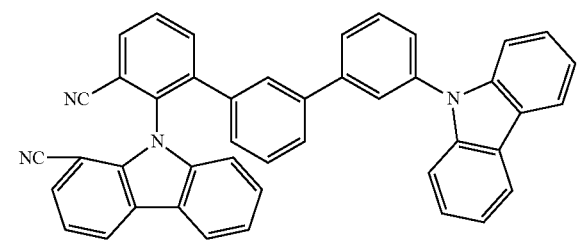
-continued
640
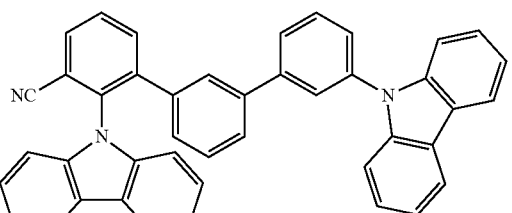
641
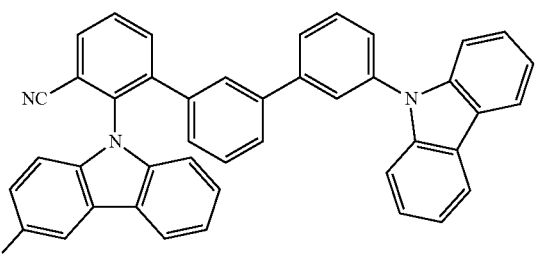
642
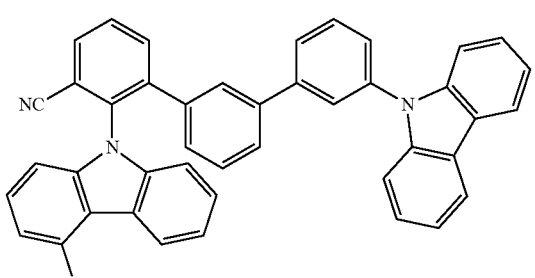
643
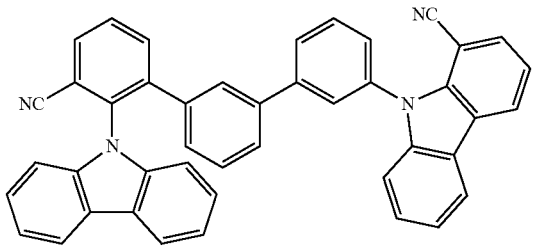
644
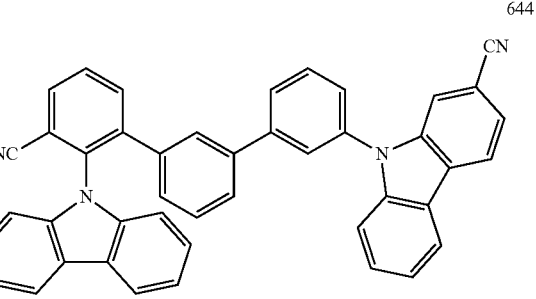

-continued
645
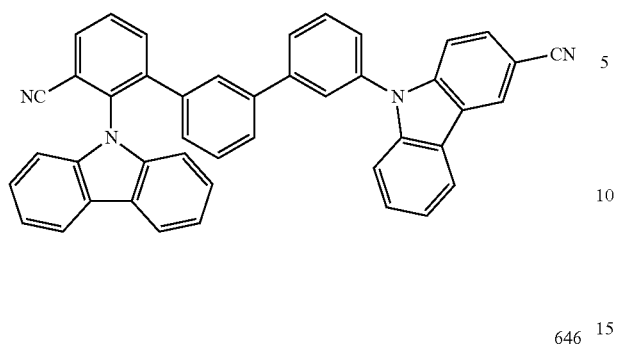
646
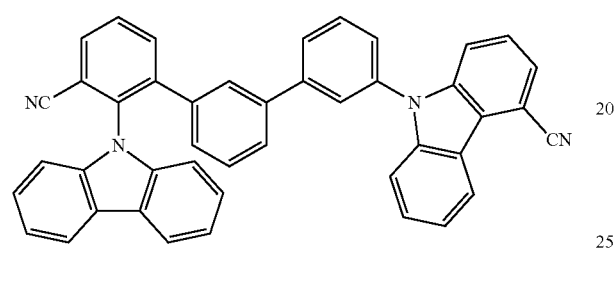
647
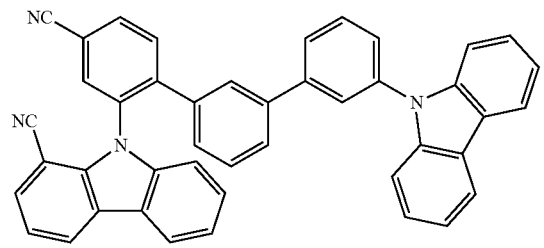
648
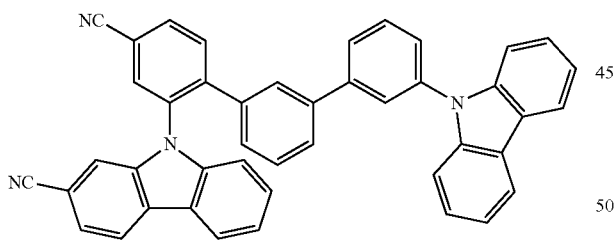
649
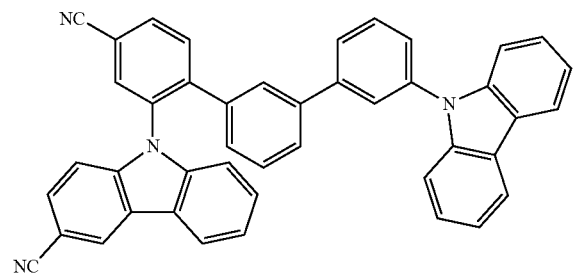
-continued
650
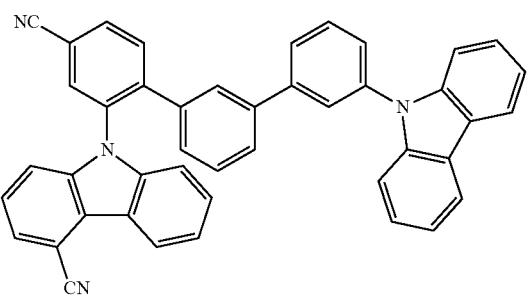
651
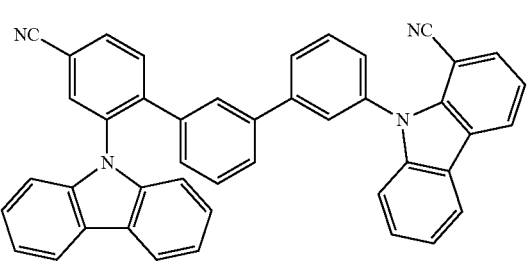
652
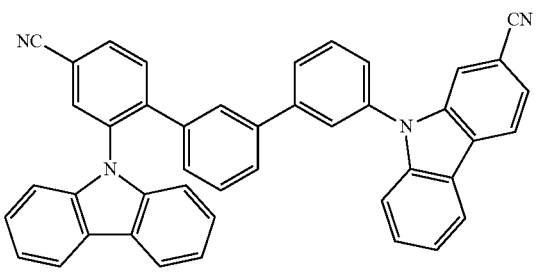
653
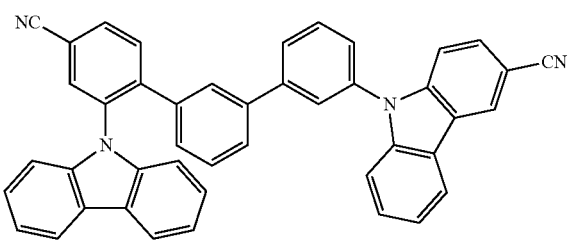
654
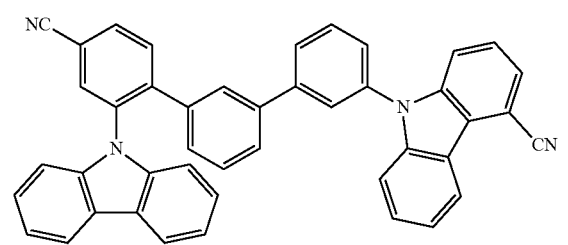

655
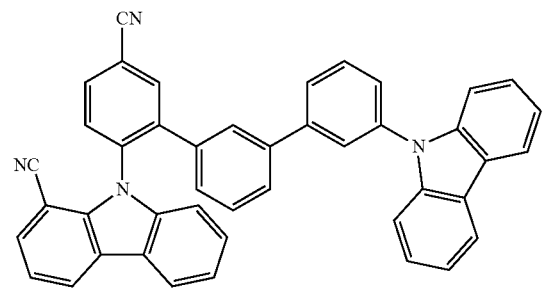
656
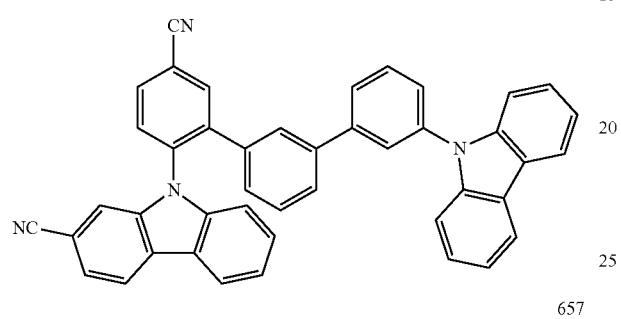
657
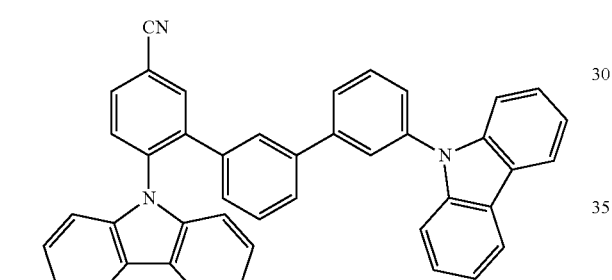
658
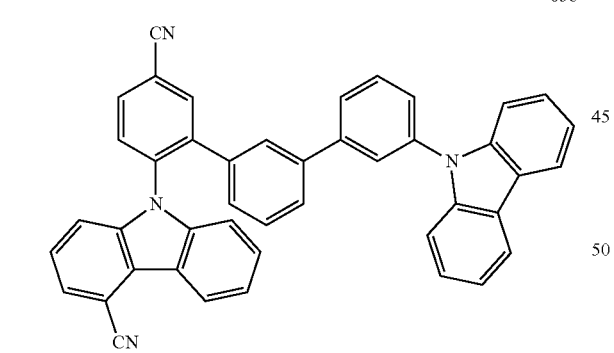
659
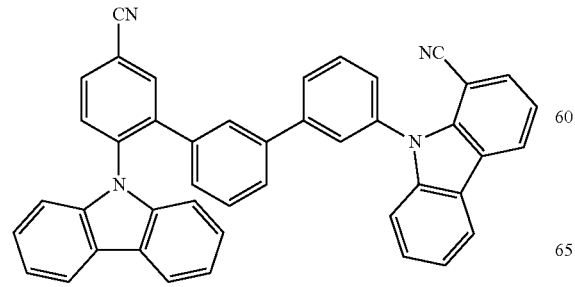
660
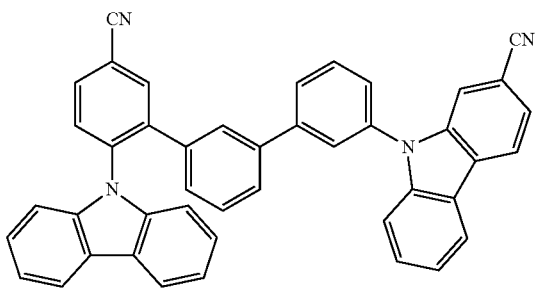
661
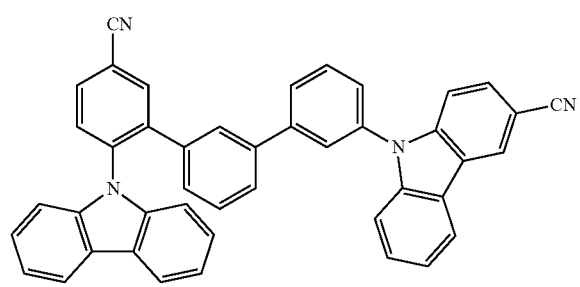
662
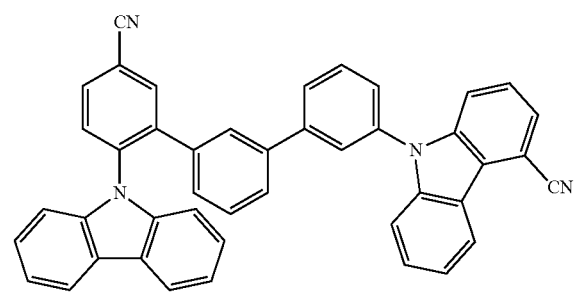
663
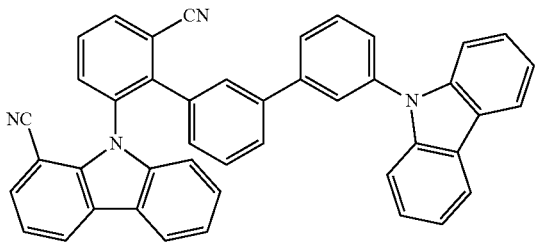
664
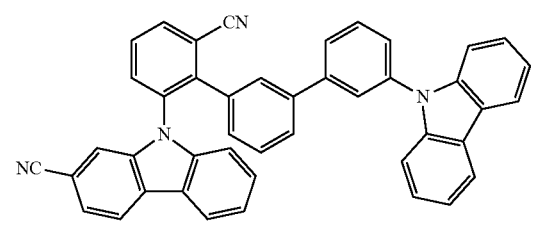

-continued
665
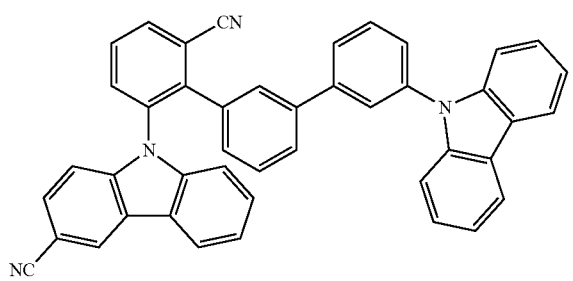
667
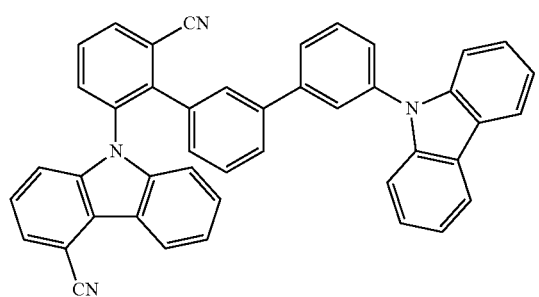
668
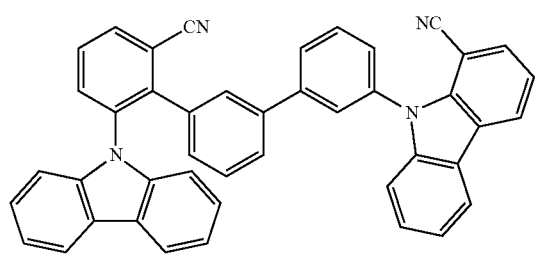
669
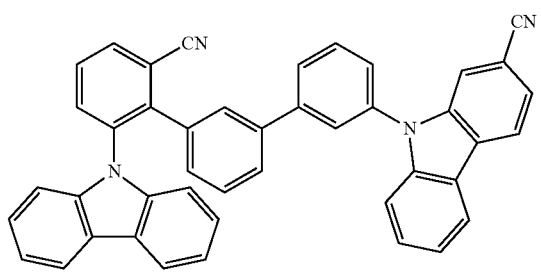
670
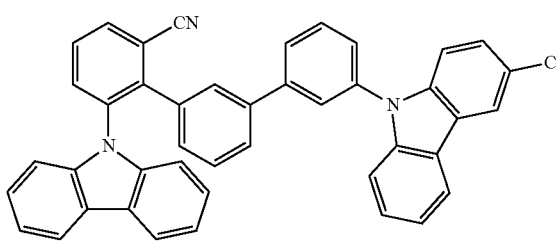
-continued
671
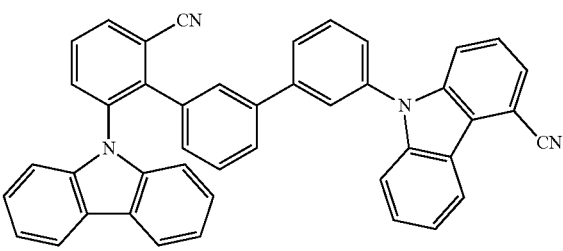
672
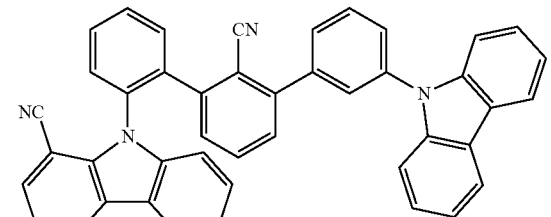
673
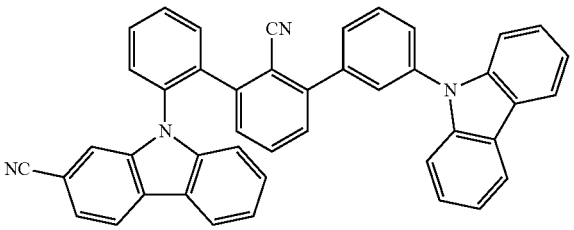
674
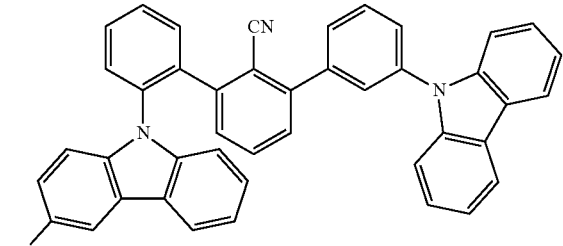
675
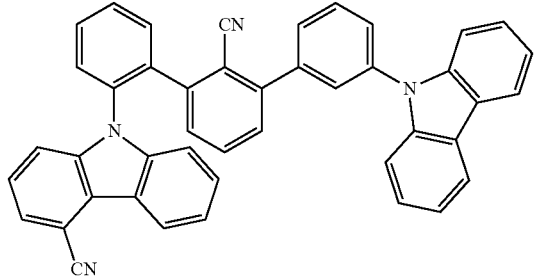

676
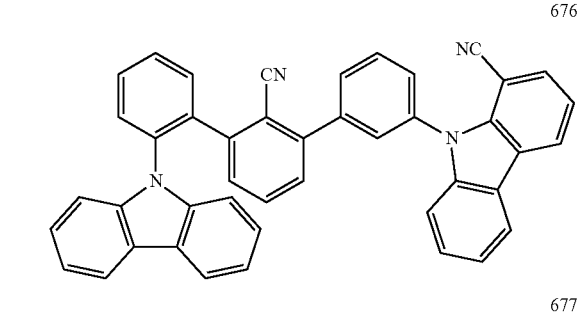
677
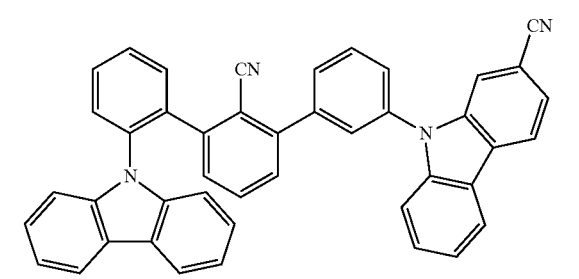
678
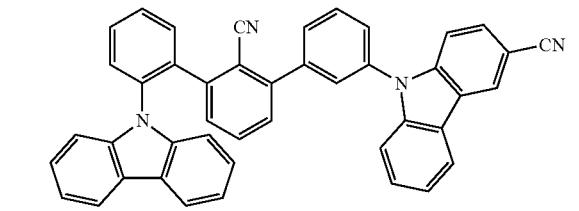
679
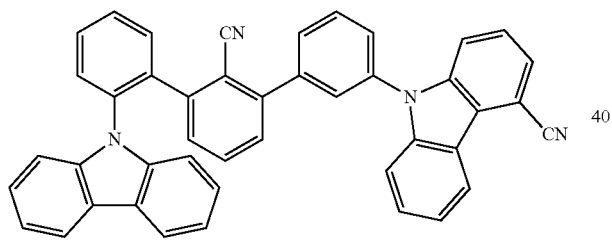
680
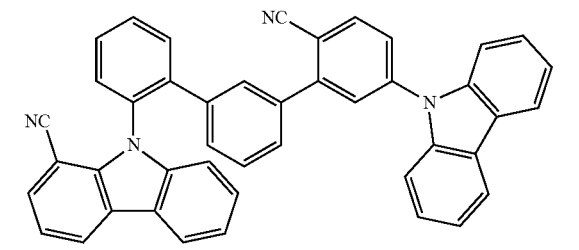
681
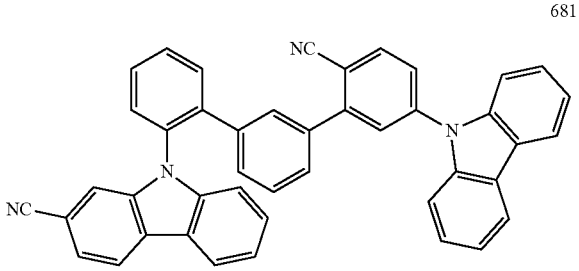
682
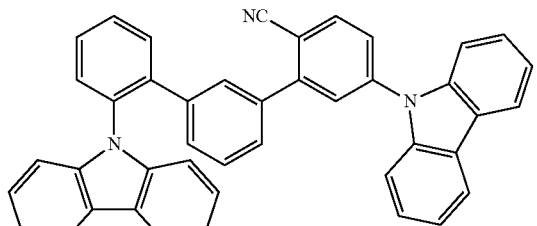
683
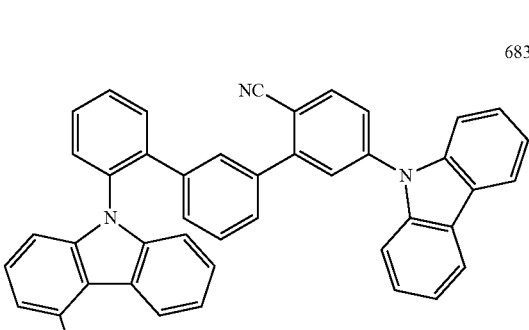
684
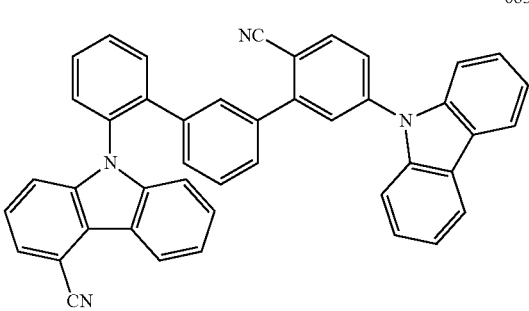
685
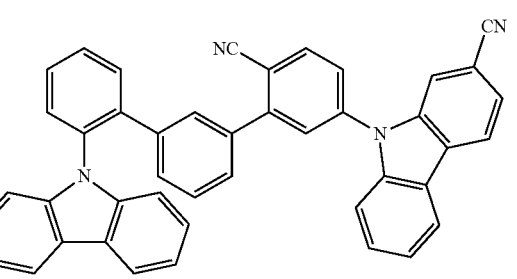
686
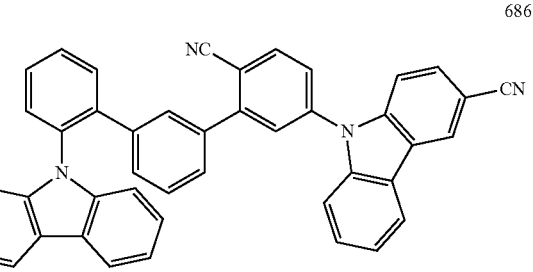

-continued
687
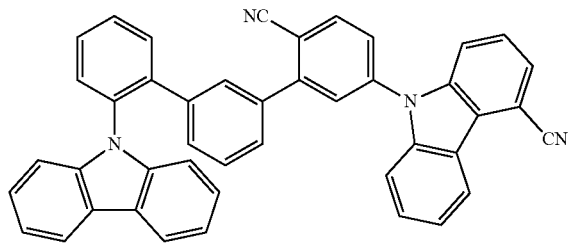
688
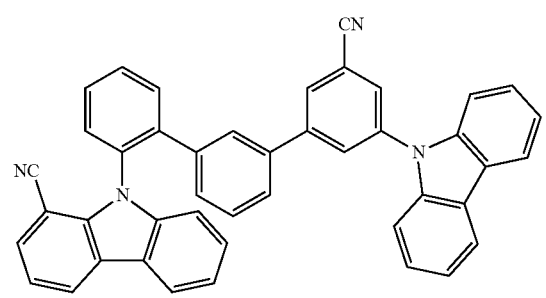
689
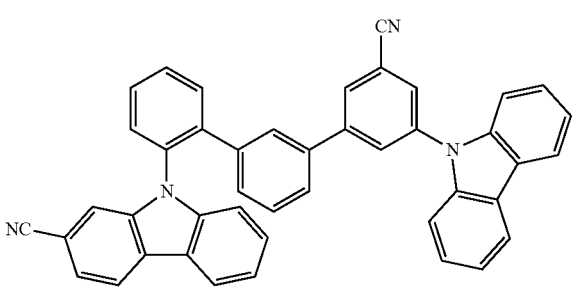
690
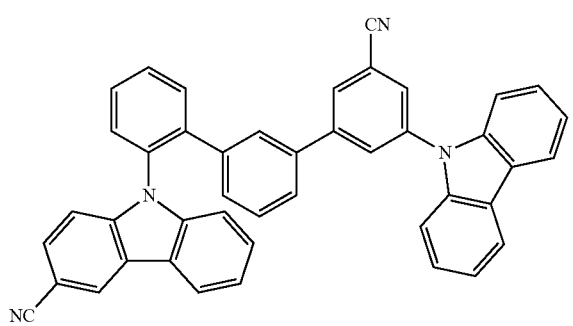
691
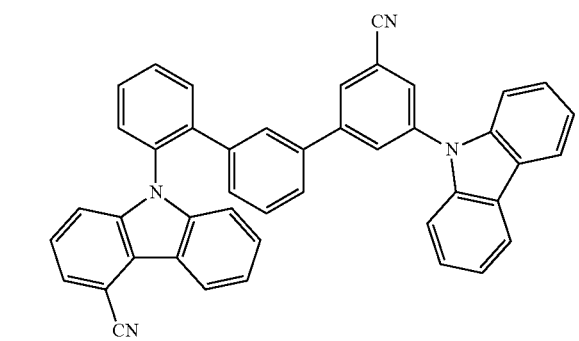
-continued
692
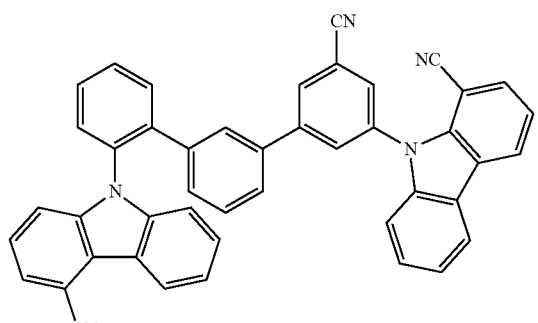
693
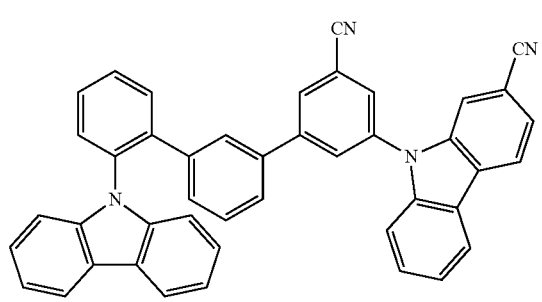
694
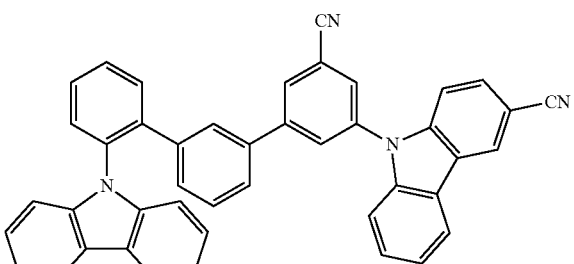
695
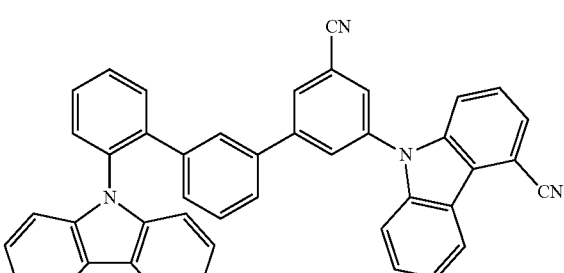
696
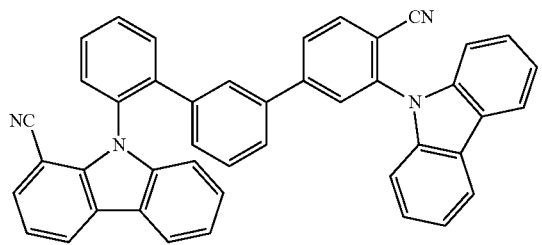

697
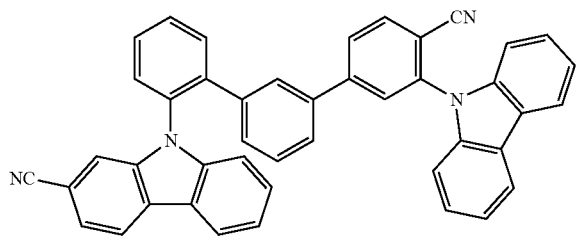
698
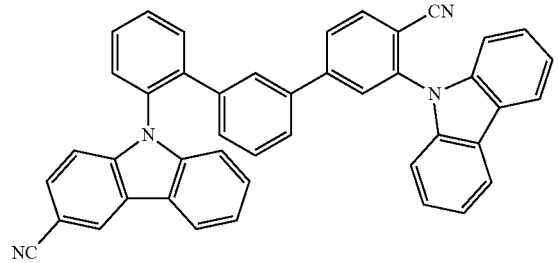
699
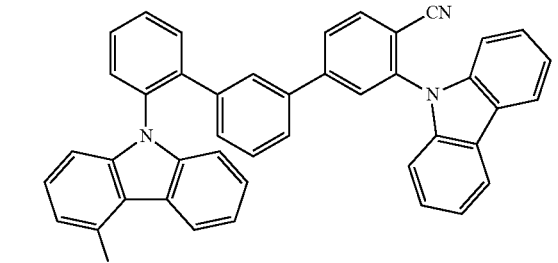
700
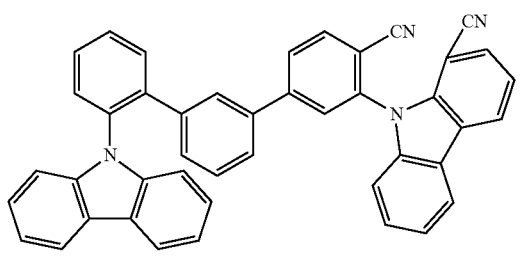
701
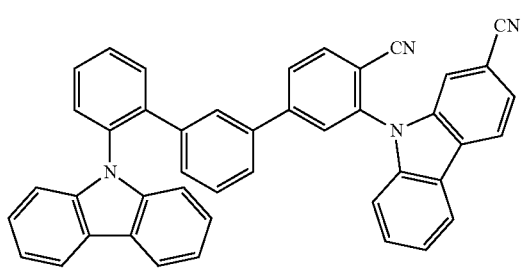
702
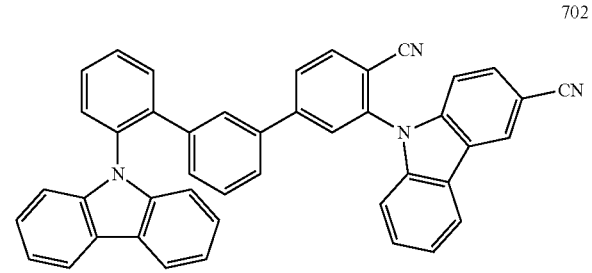
703
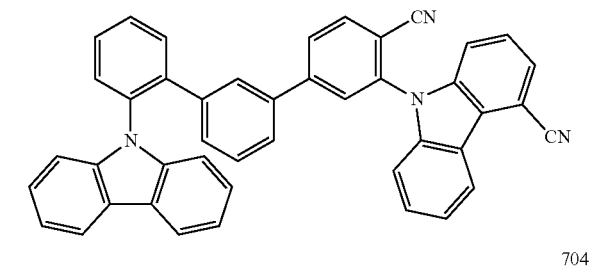
704
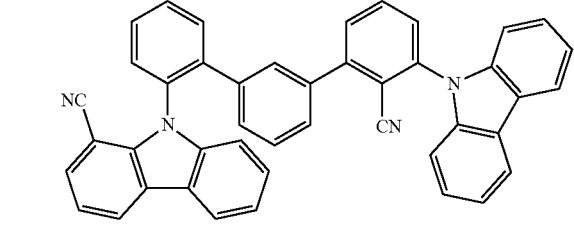
705
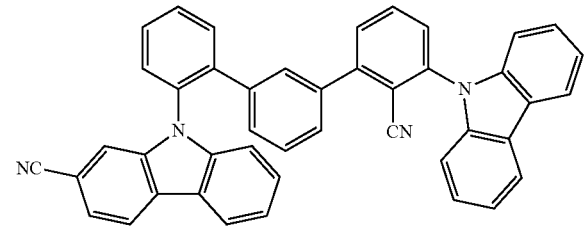
706
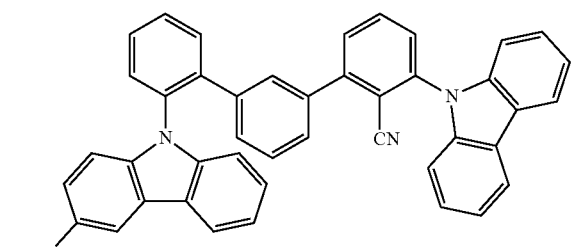
707
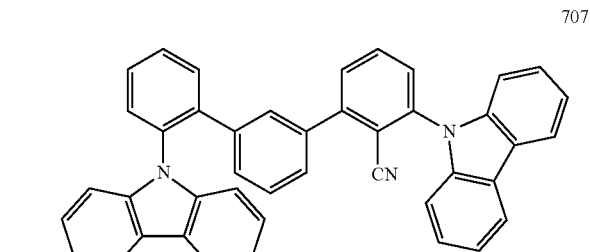

708
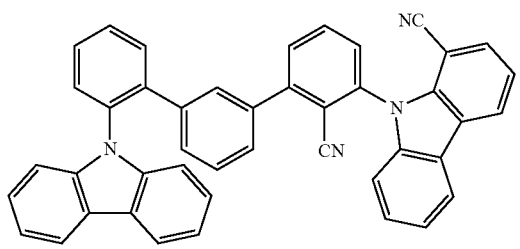
709
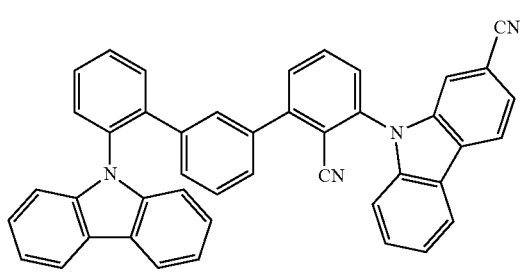
710
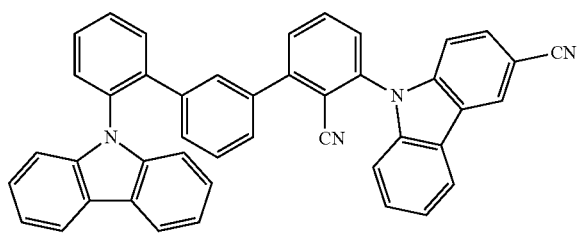
711
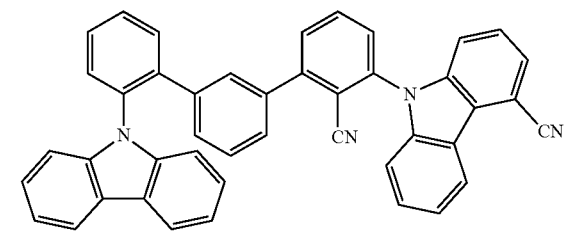
712
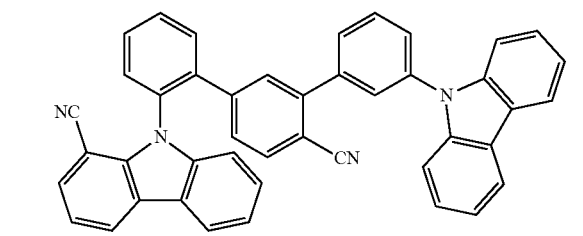
713
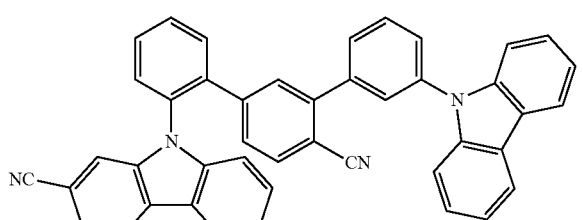
714
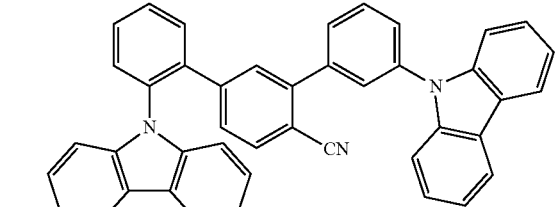
715
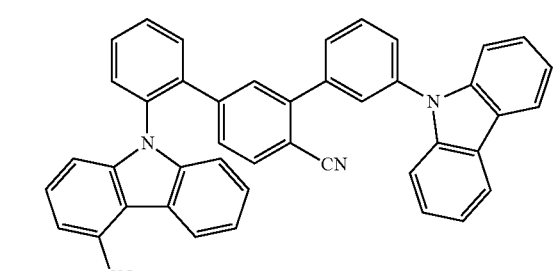
716
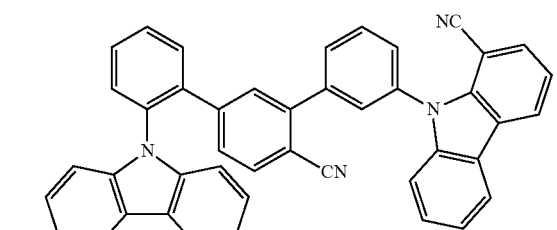
717
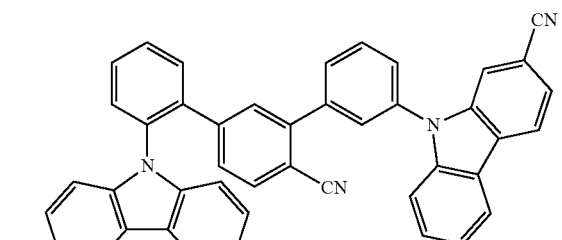
718
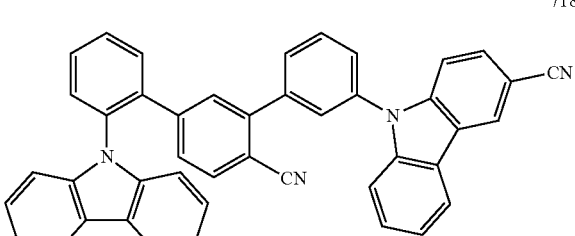
719
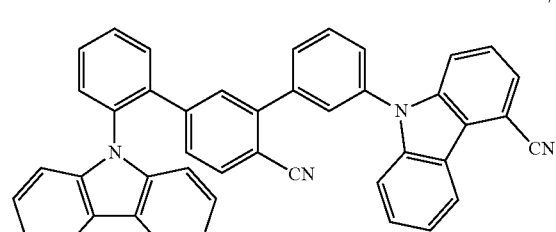

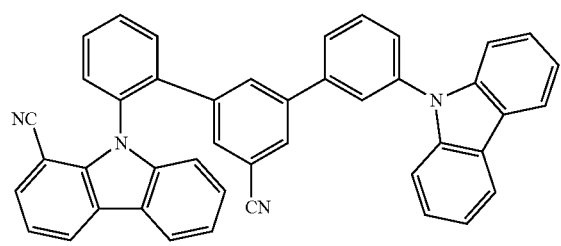
720
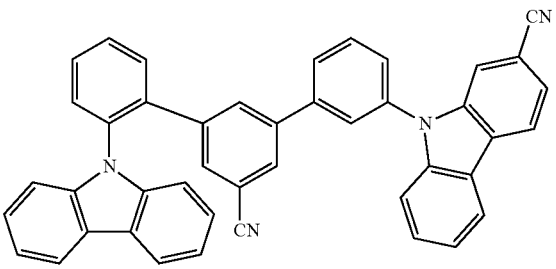
725
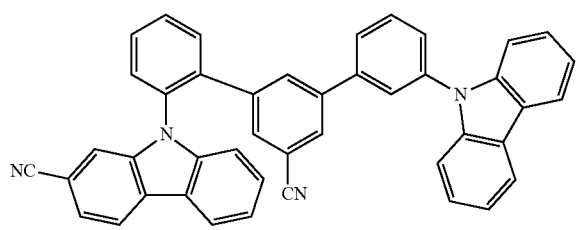
721
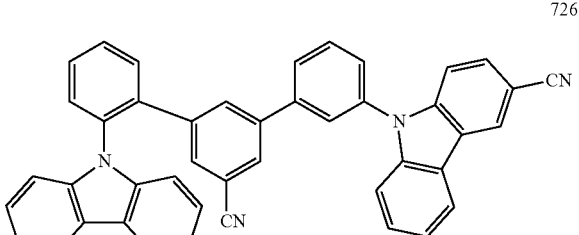
726
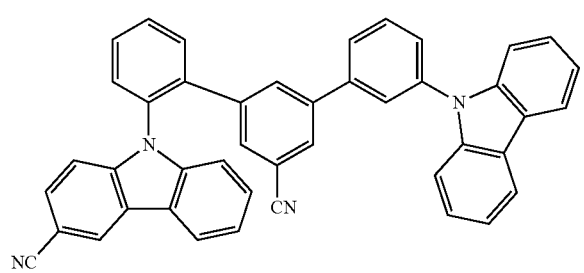
722
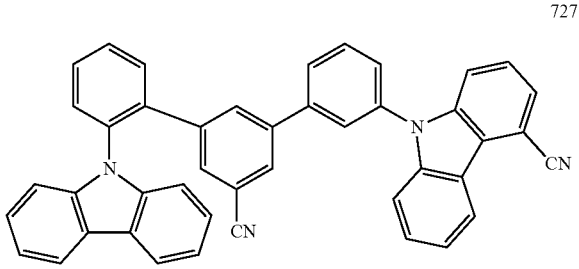
727
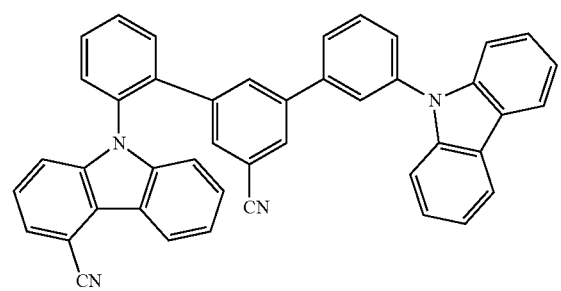
723
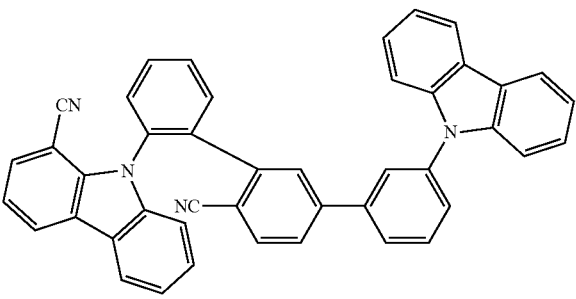
728
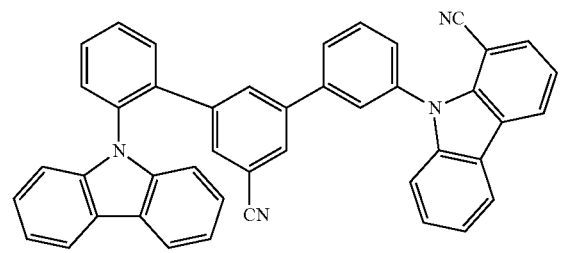
724
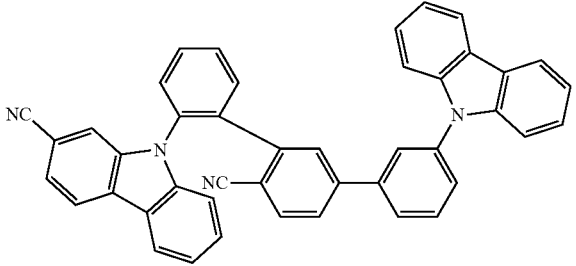
729

730
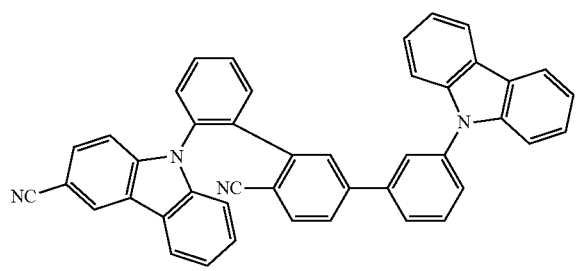
731
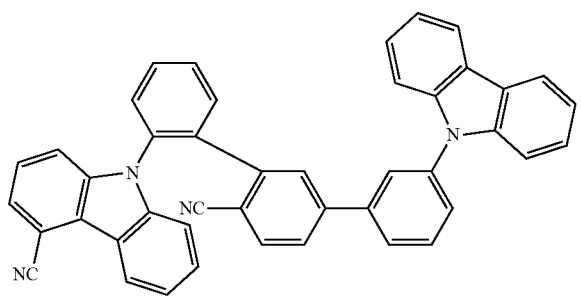
732
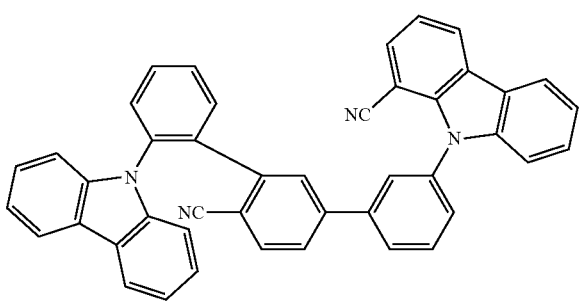
733
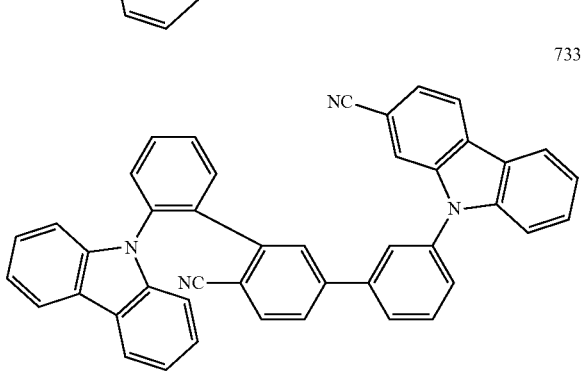
734
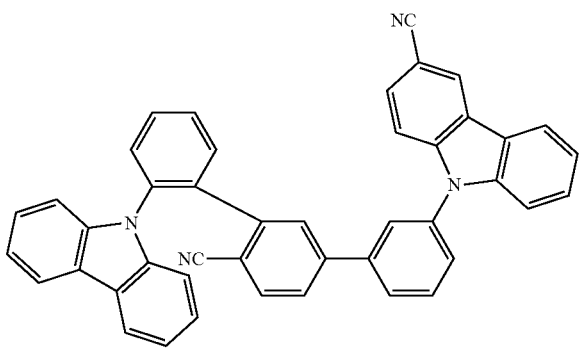
735
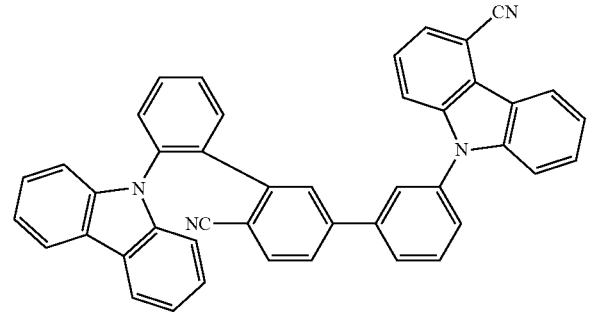
736
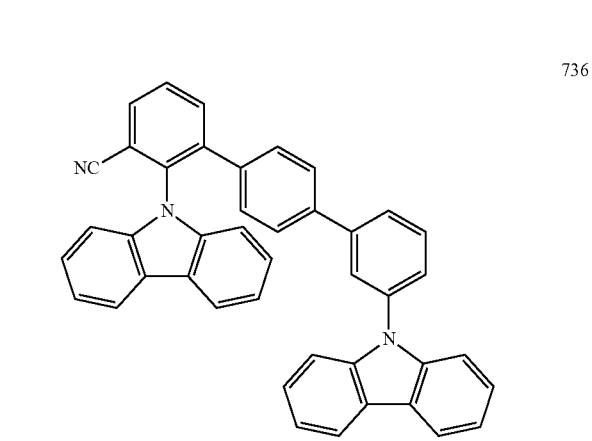
737
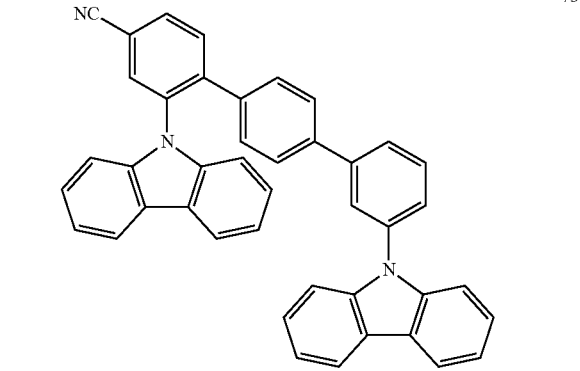
738
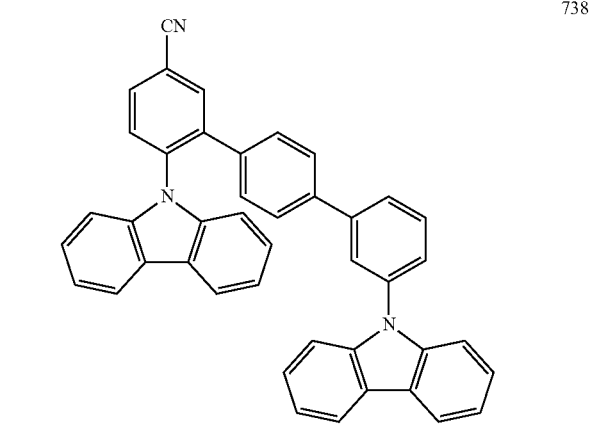

| 201 -continued | 202 -continued |
|---|---|
| 739 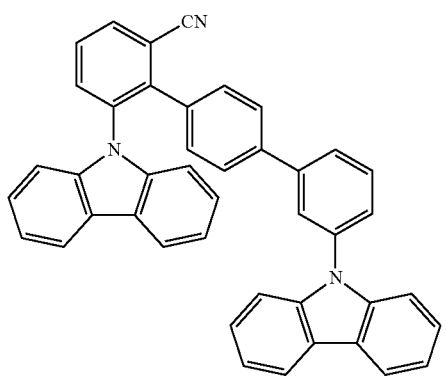 | 743 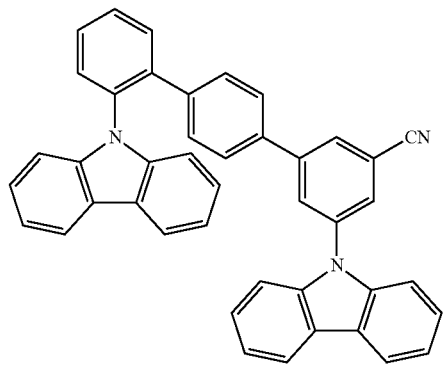 |
| 740 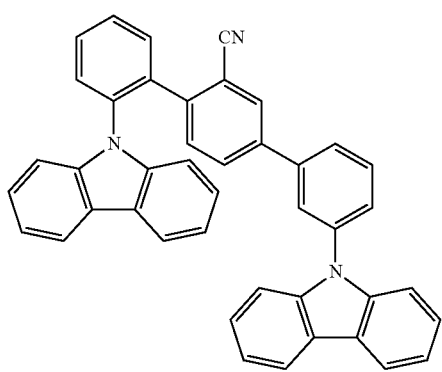 | 744 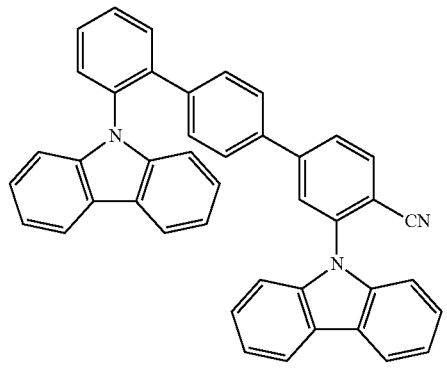 |
| 741 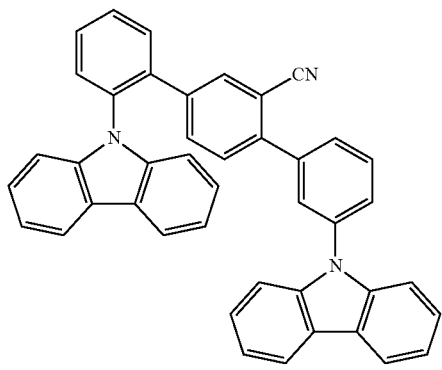 | 745 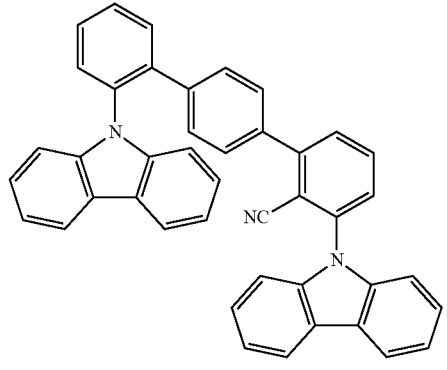 |
| 742 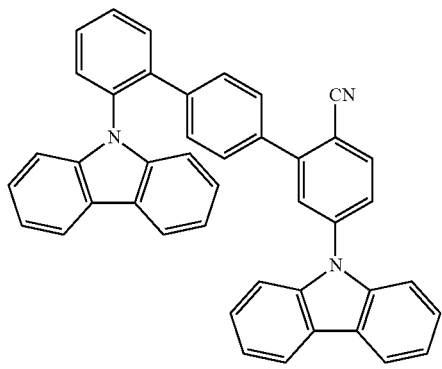 | 746 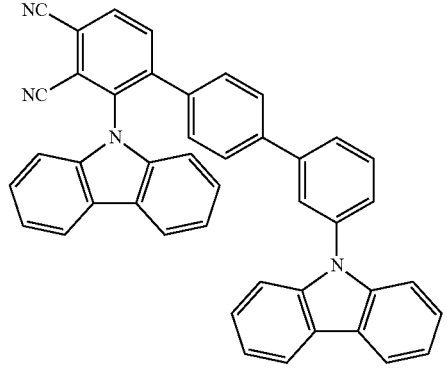 |

747
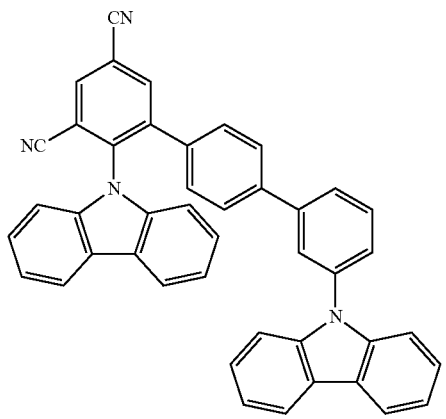
748
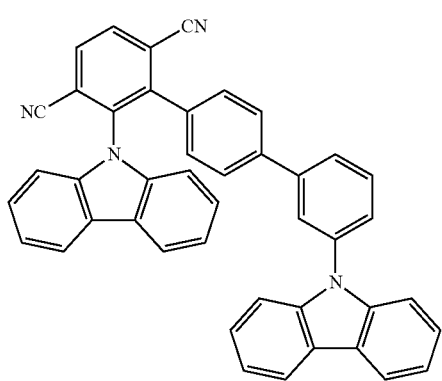
749
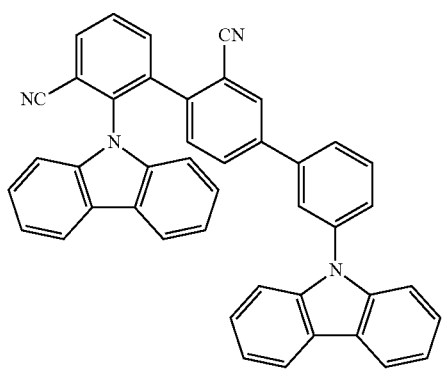
750
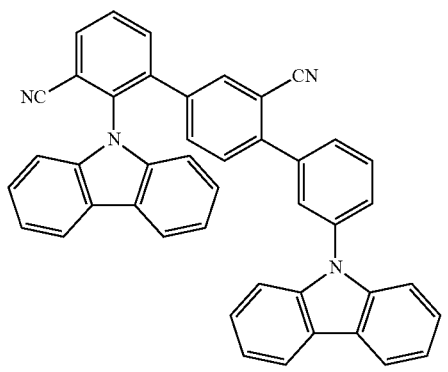
751
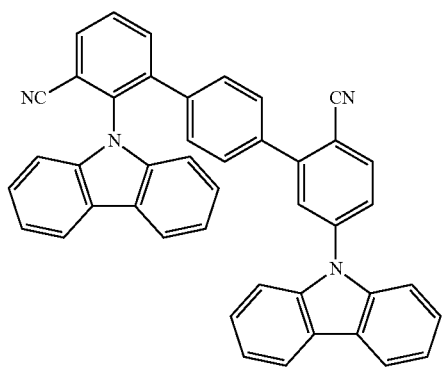
752
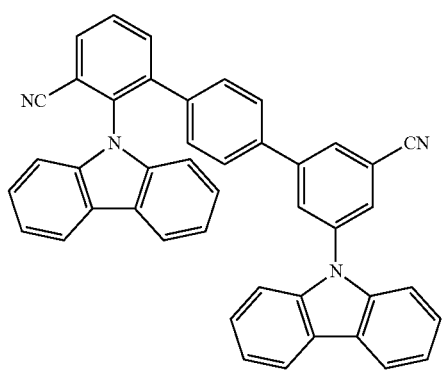
753
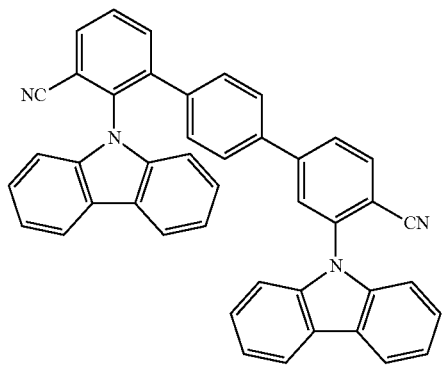
754
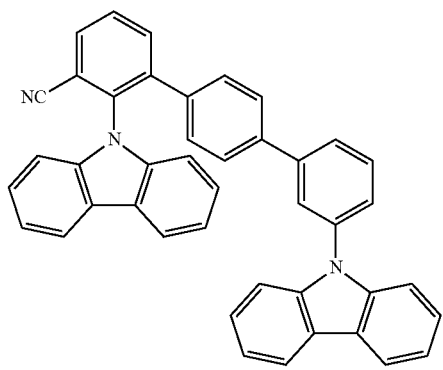

755
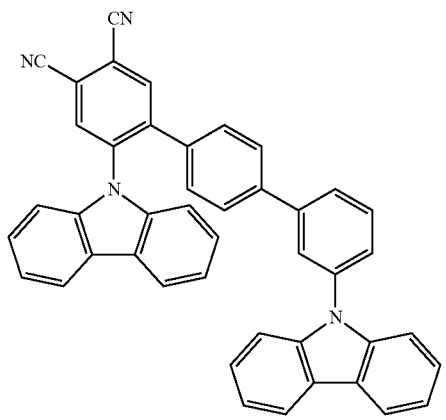
756
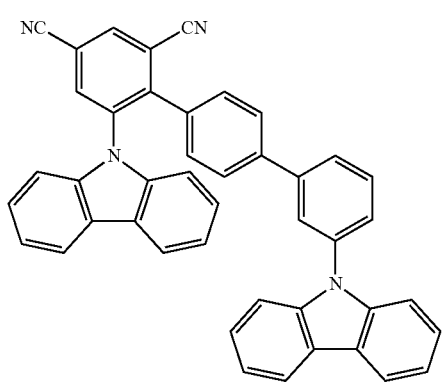
757
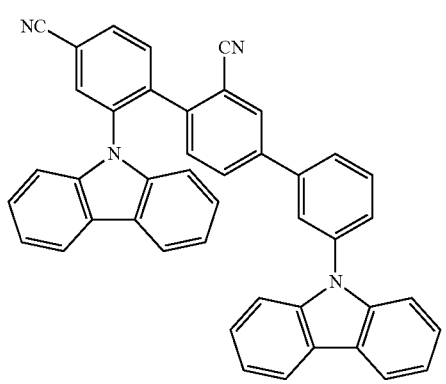
758
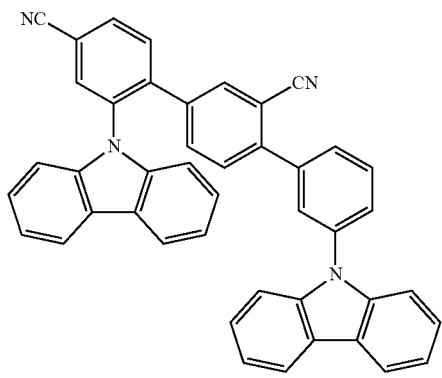
759
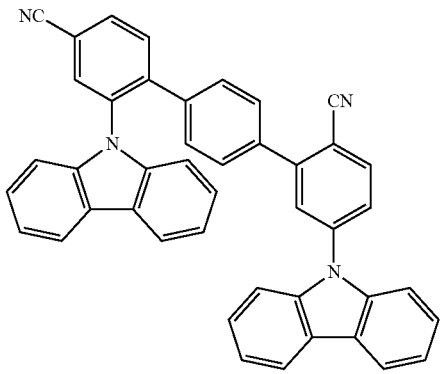
760
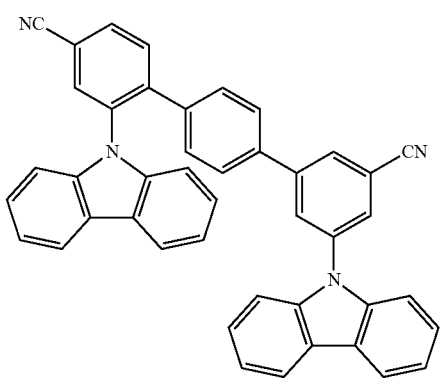
761
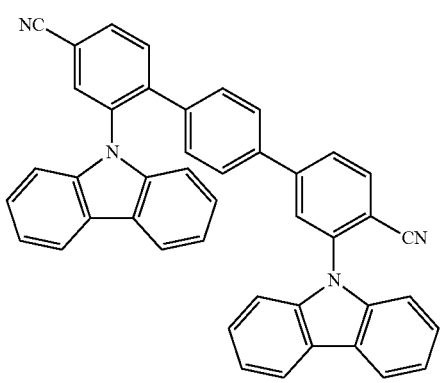
762
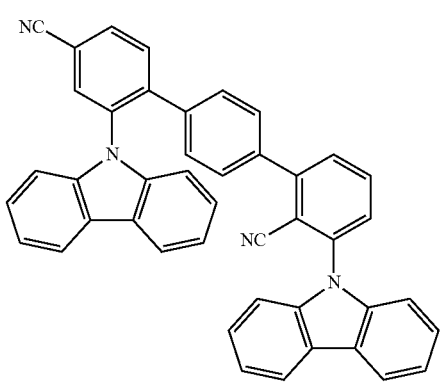

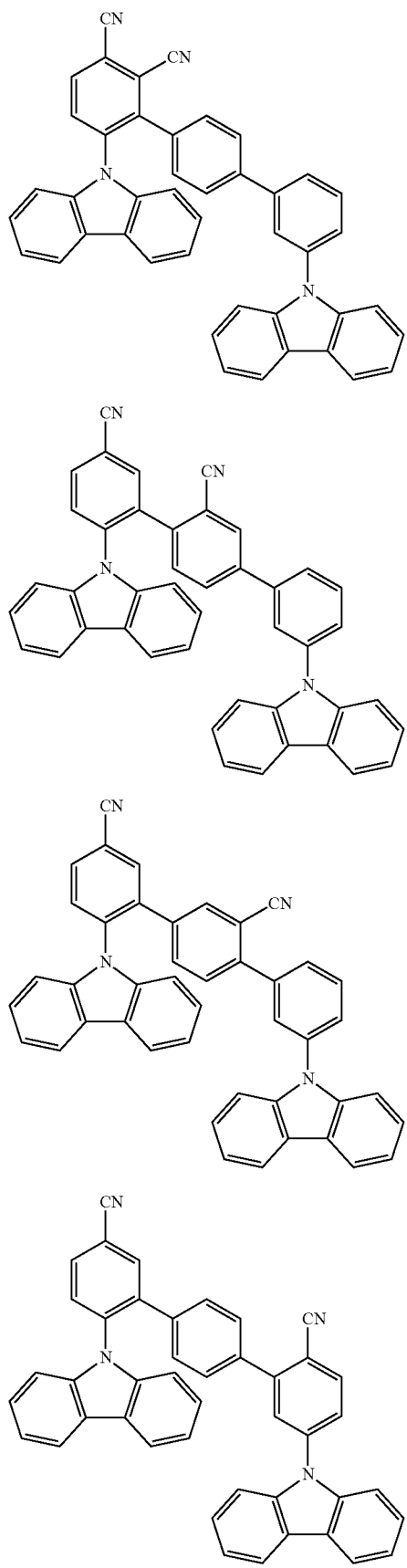
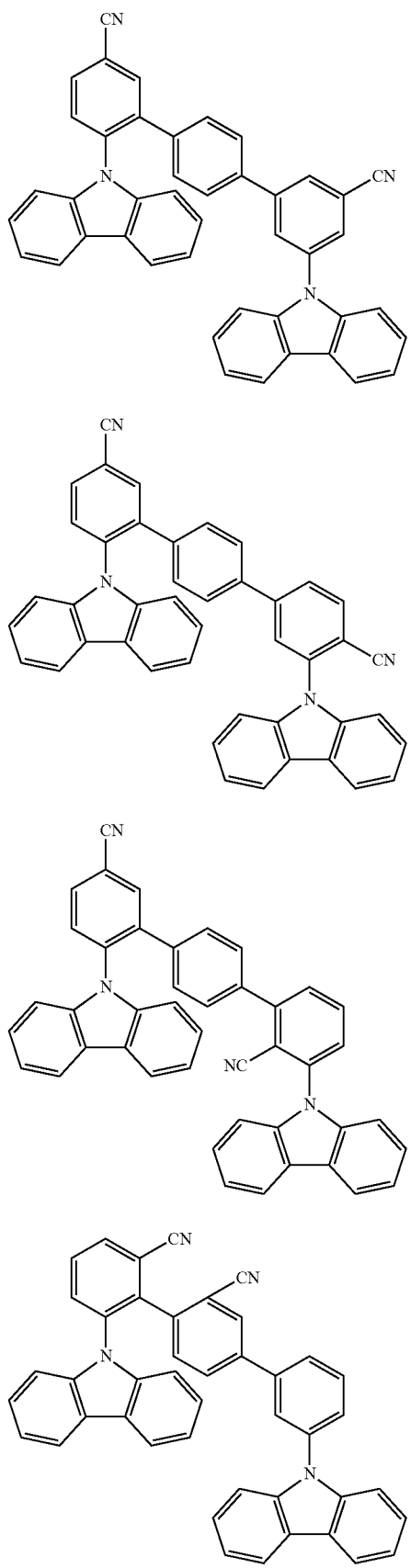

771
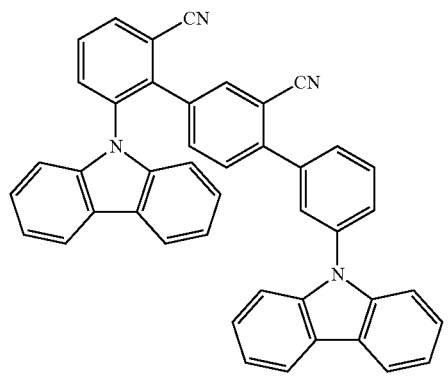
772
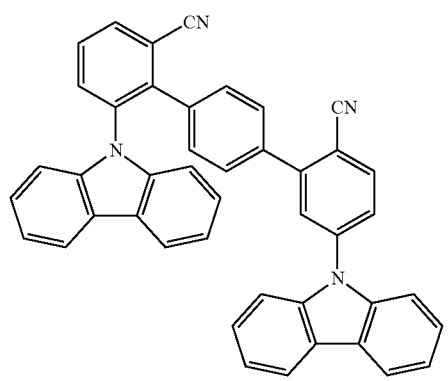
773
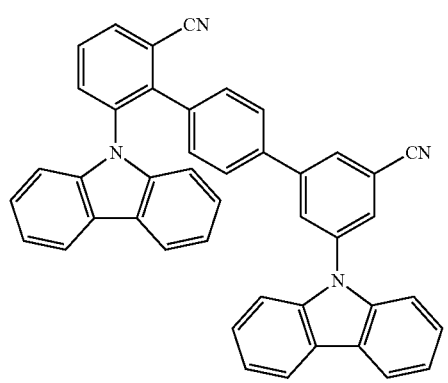
774
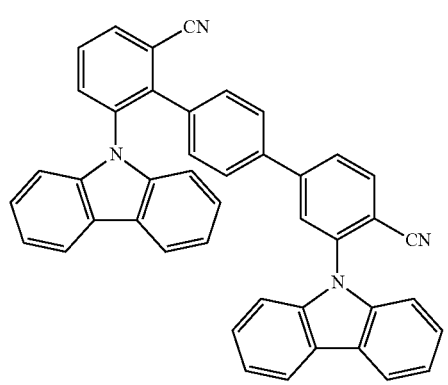
775
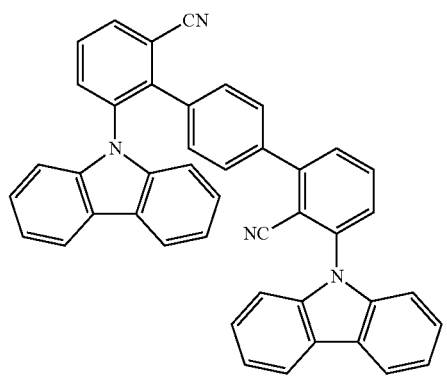
776
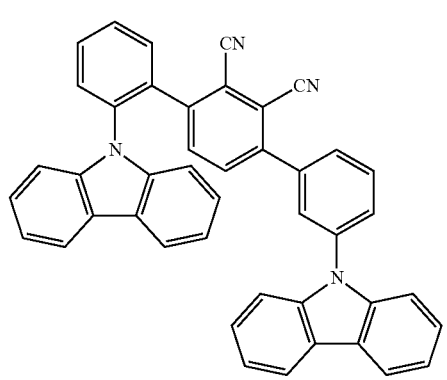
777
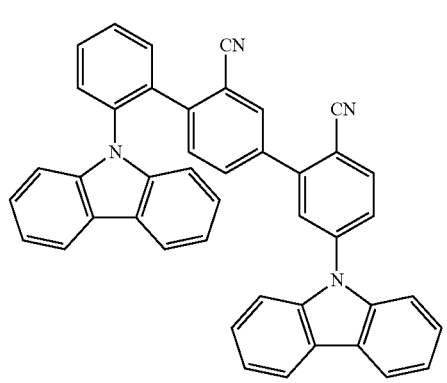
778
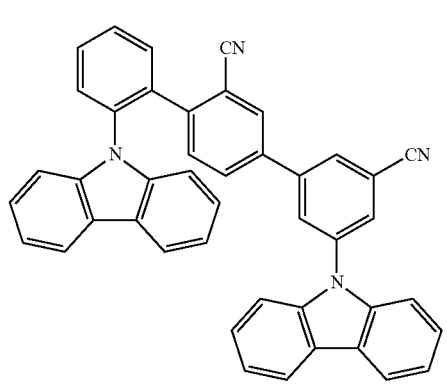

| 211 -continued | 212 -continued |
|---|---|
| 779 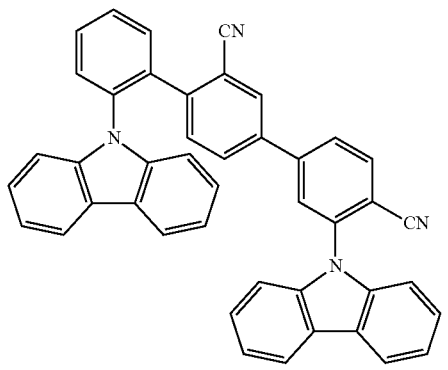 | 783 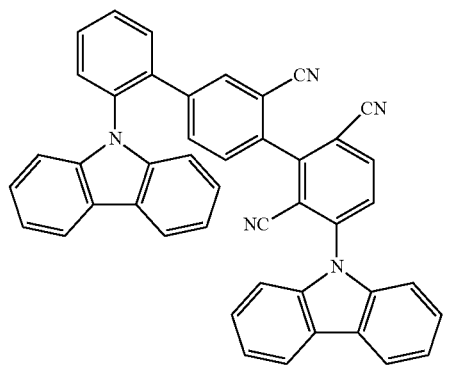 |
| 780 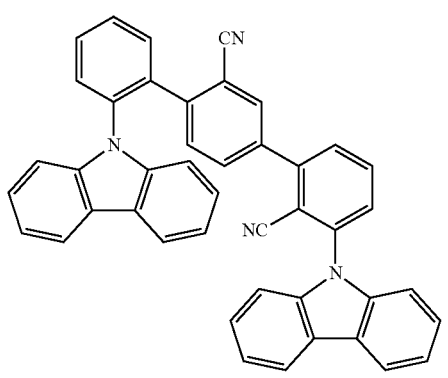 | 784 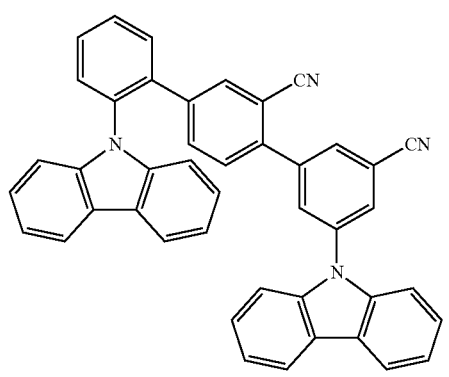 |
| 781 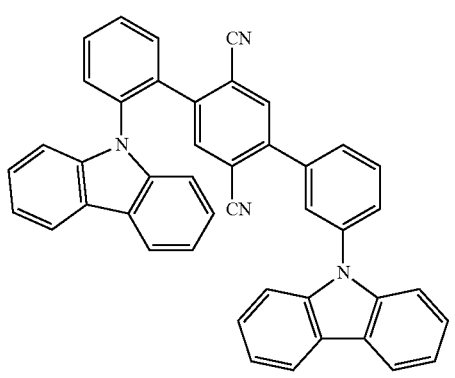 | 785 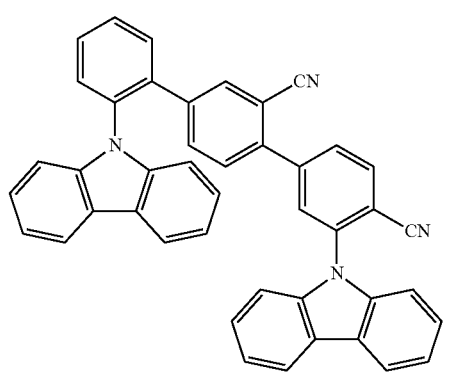 |
| 782 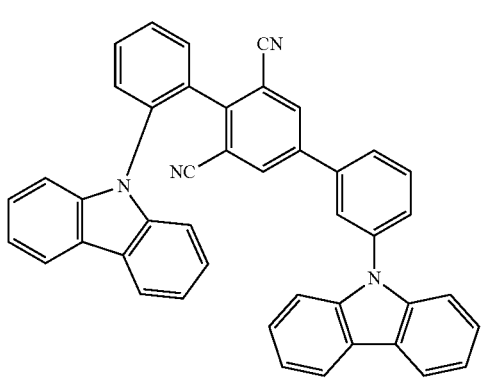 | 786 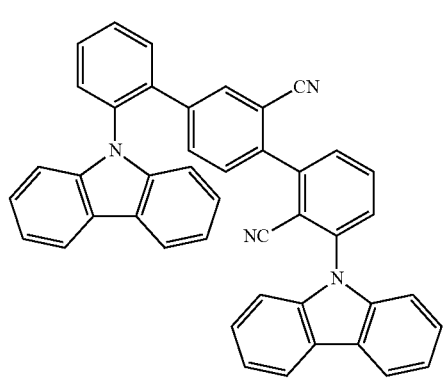 |

787
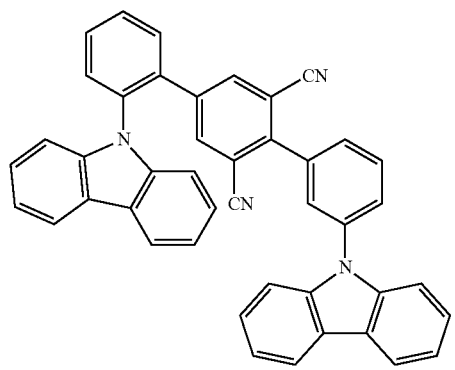
788
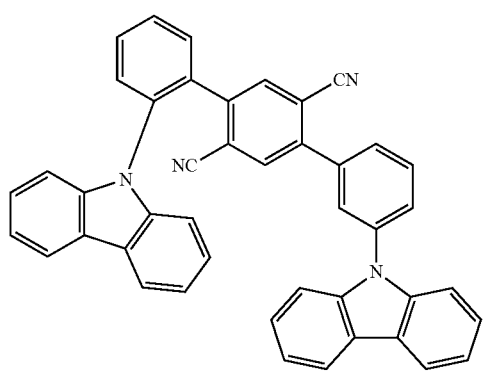
789
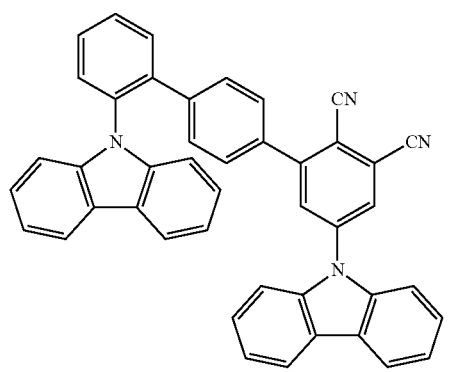
790
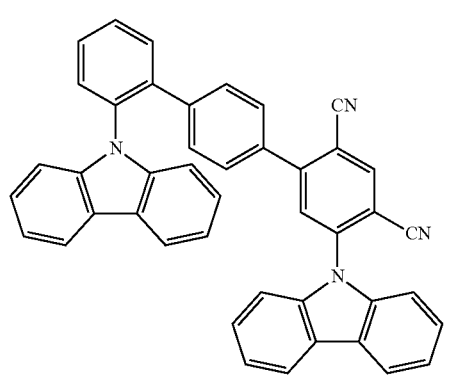
791
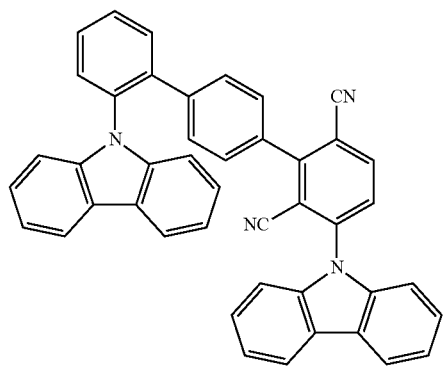
792
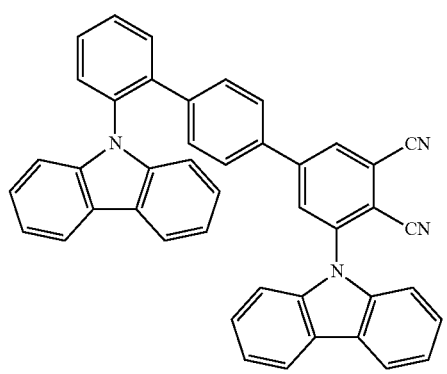
793
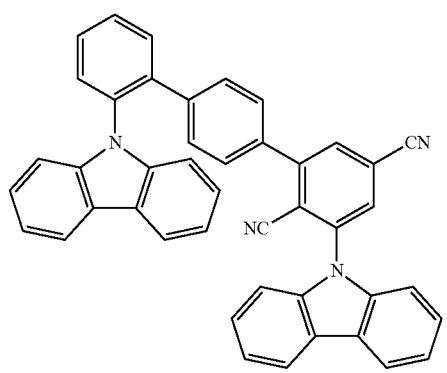
794
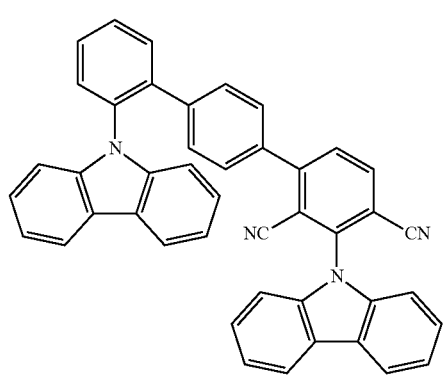

215
-continued
795
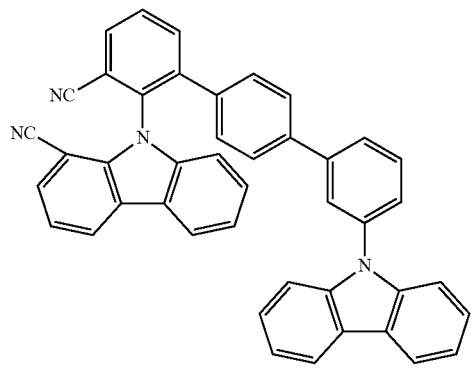
796
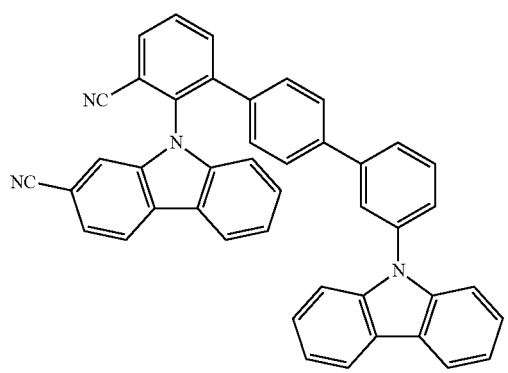
797
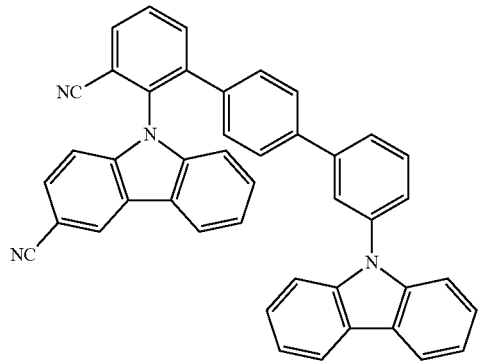
798
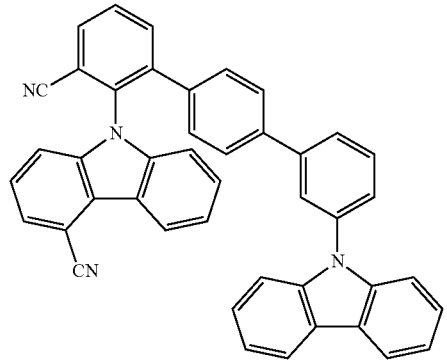
216
-continued
799
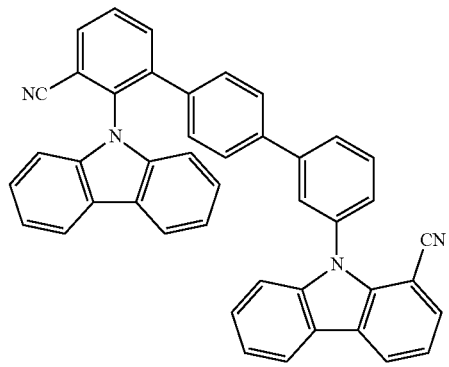
800
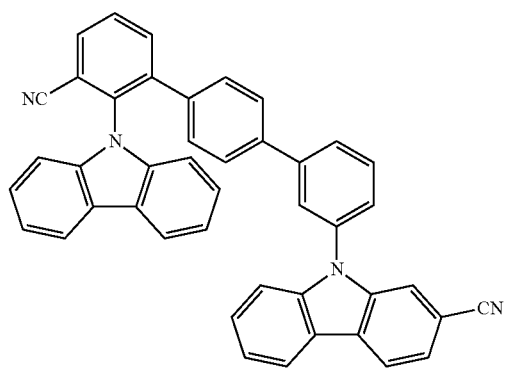
801
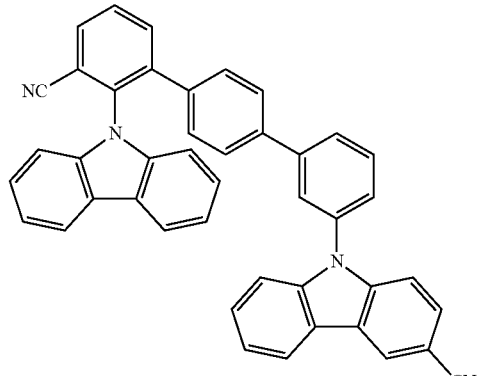
802
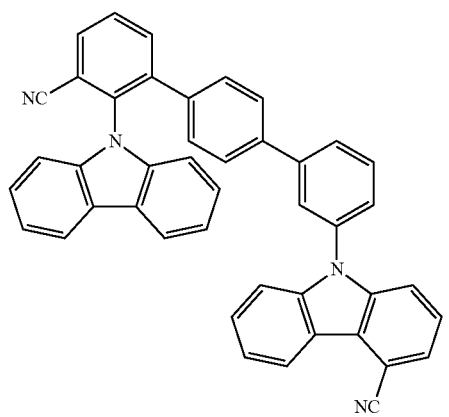

803 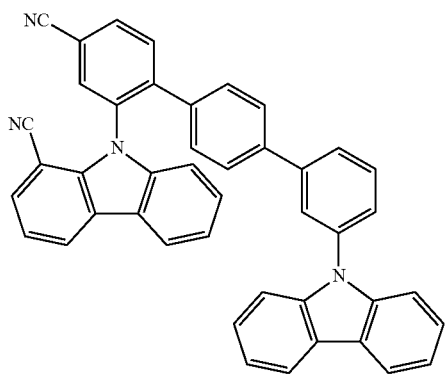
804 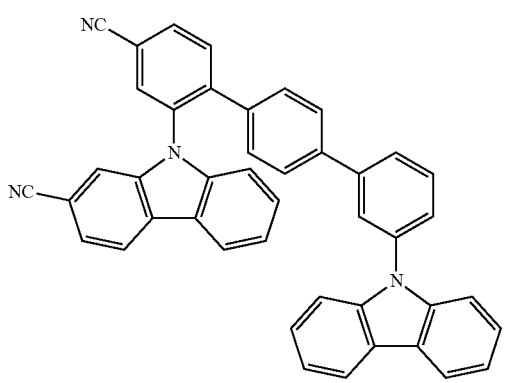
805 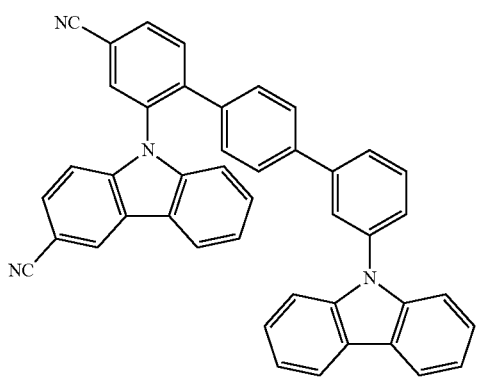
806 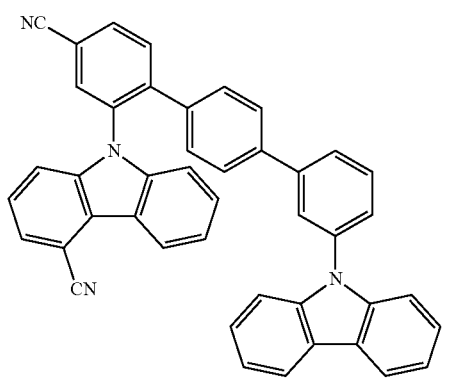
807 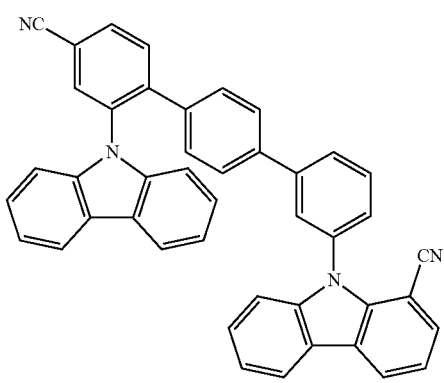
808 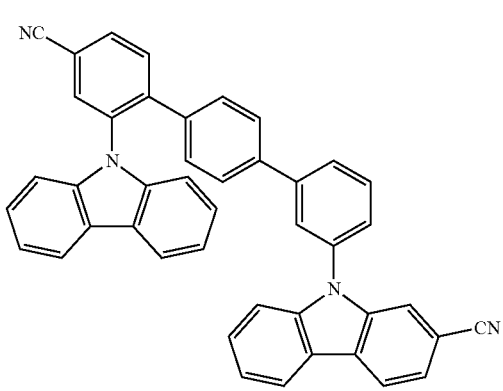
809 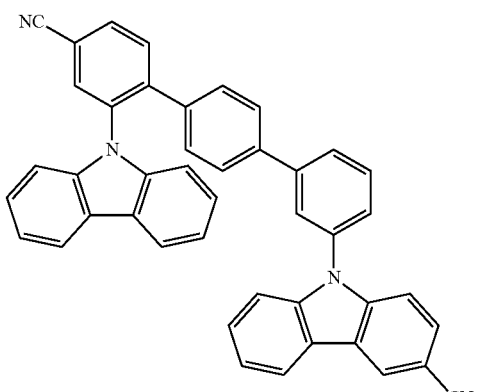
810 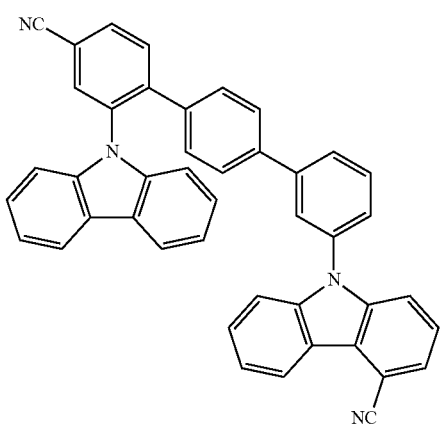

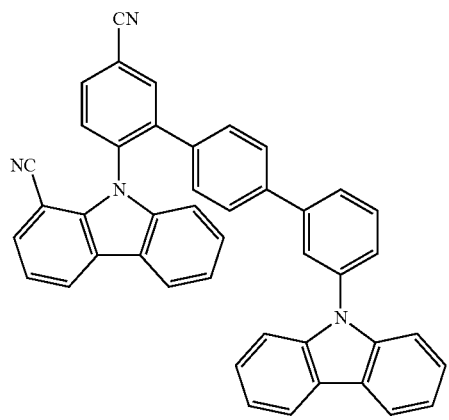
811
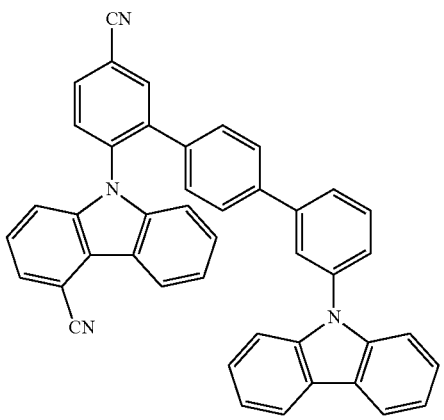
814
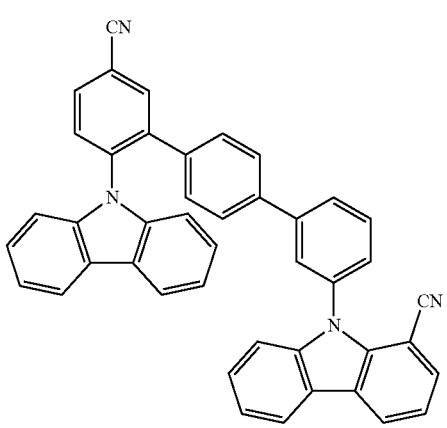
815
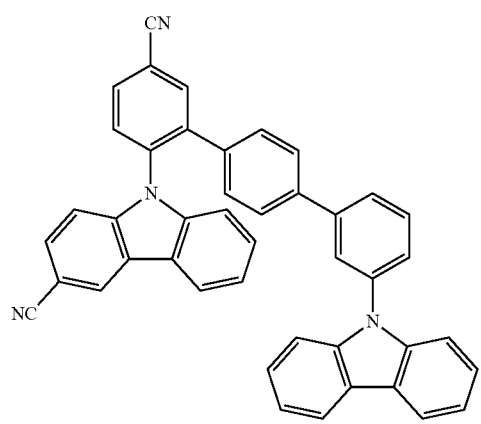
812
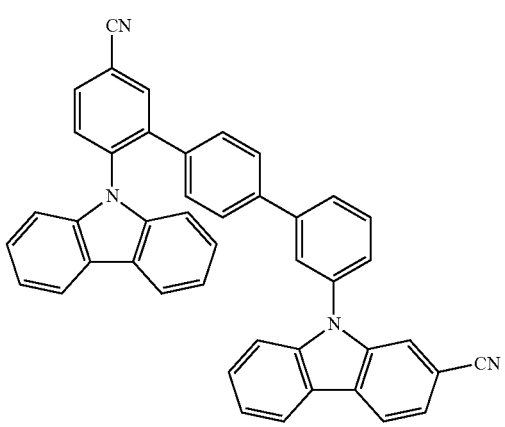
816

-continued
817
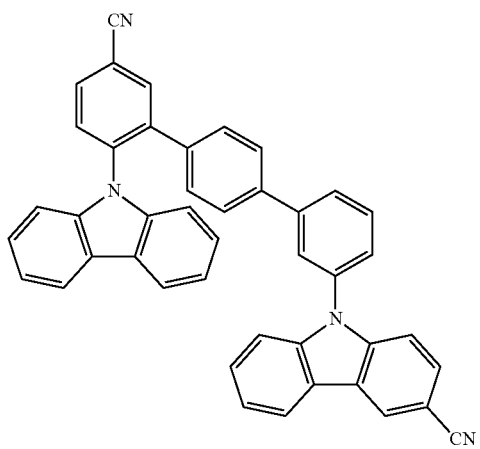
818
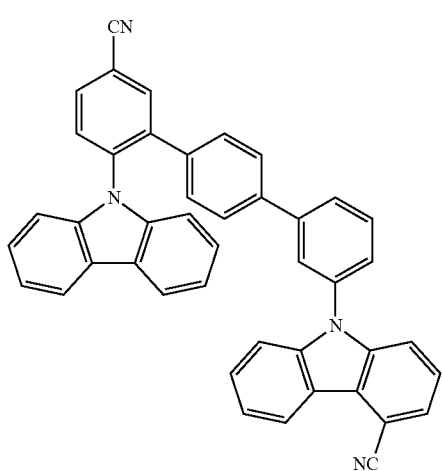
819
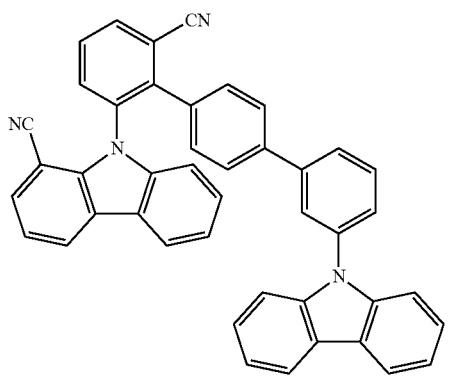
-continued
820
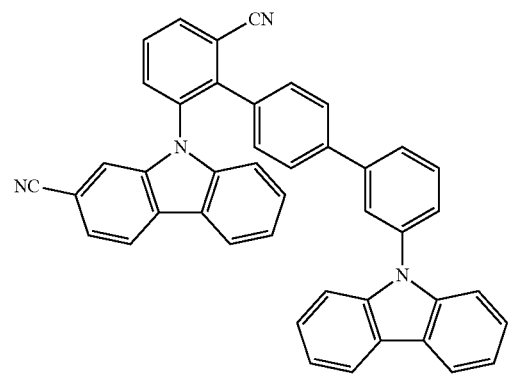
821
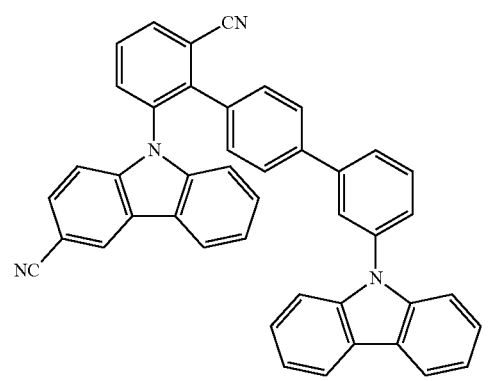
822
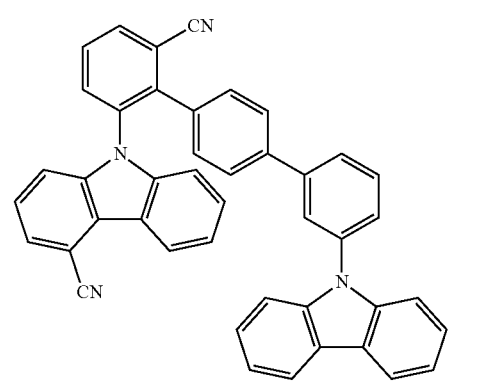
823
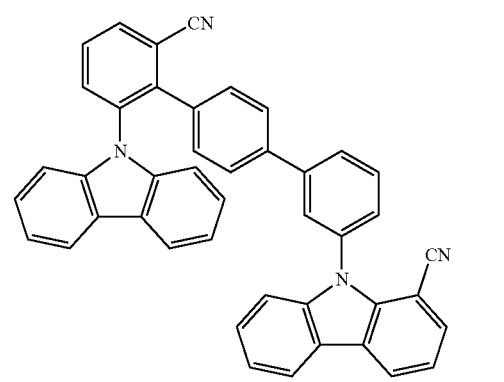

-continued
824
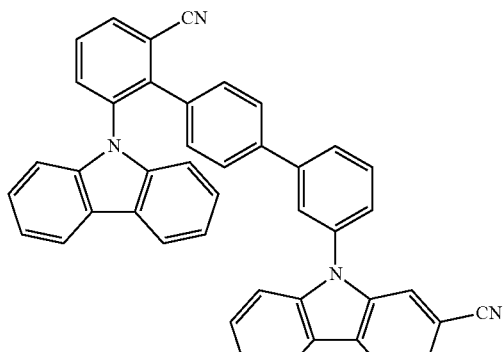
825
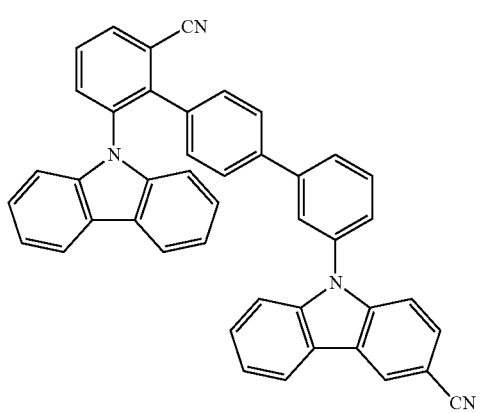
826
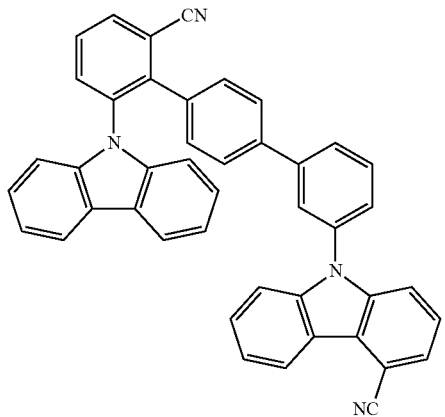
827
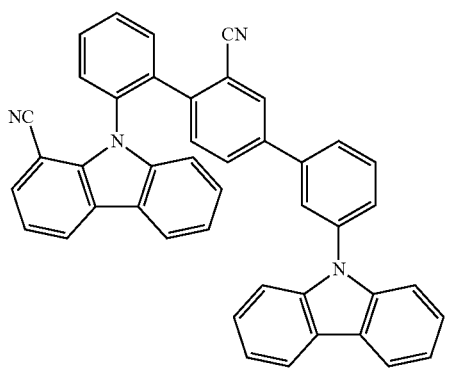
-continued
828
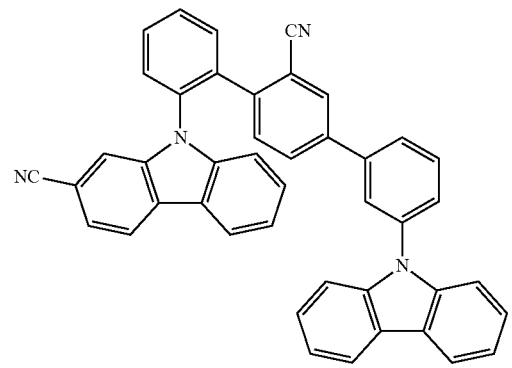
829
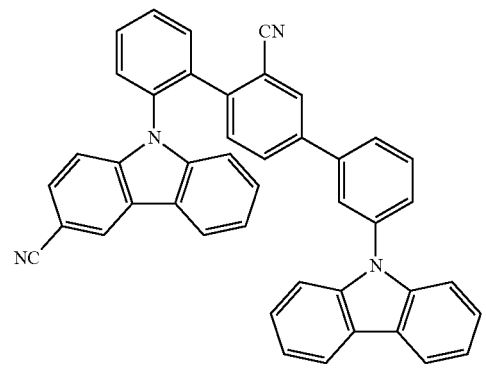
830
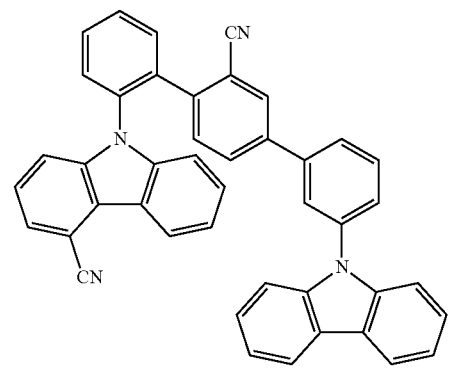
831
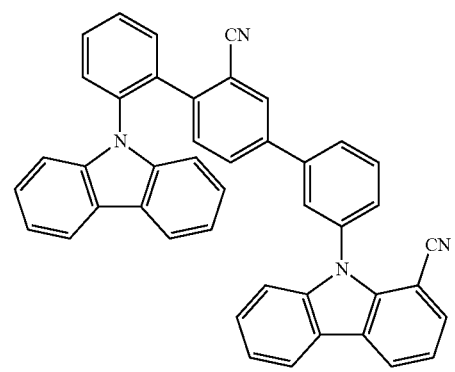

-continued
832
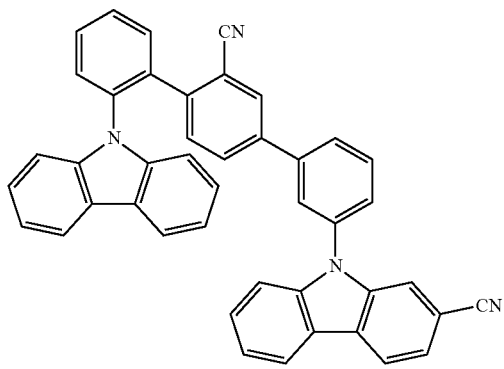
833
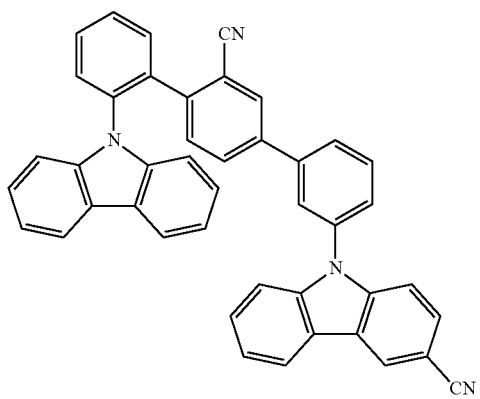
834
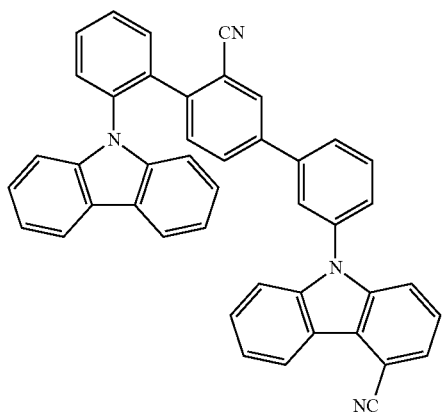
835
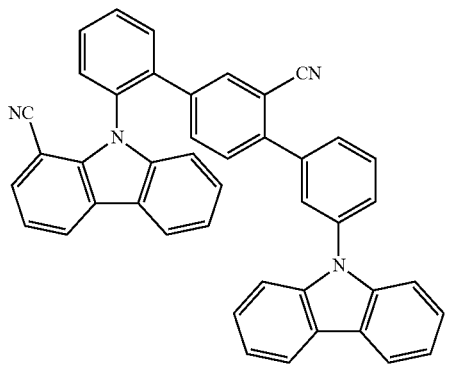
-continued
836
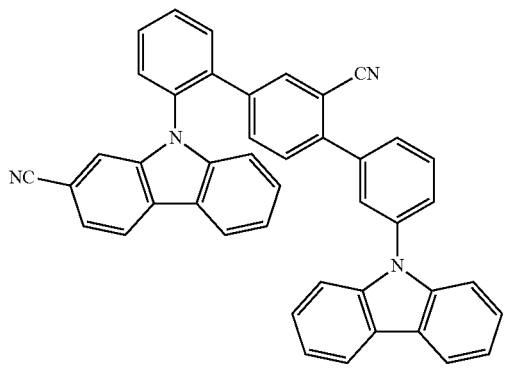
837
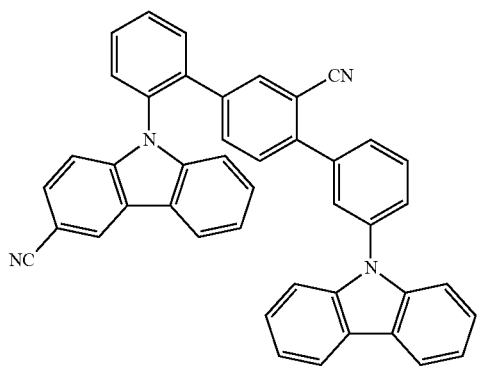
838
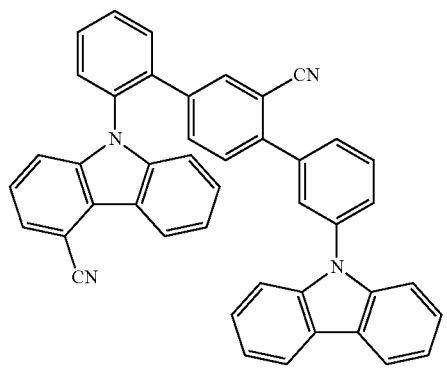
839
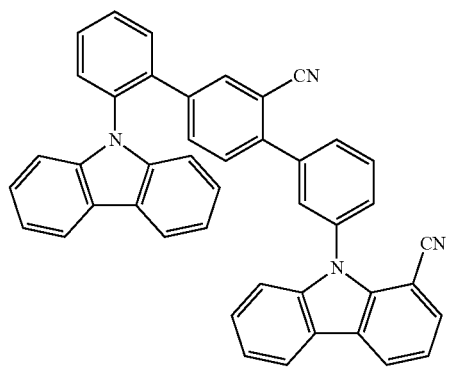

227
-continued
840
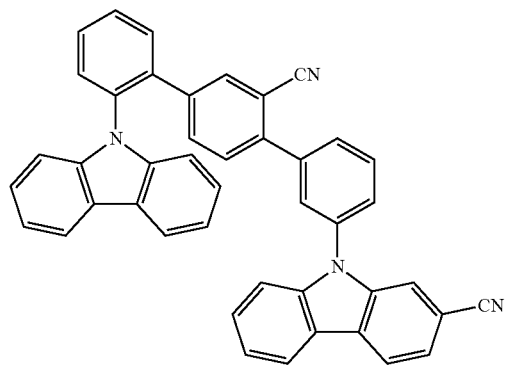
841
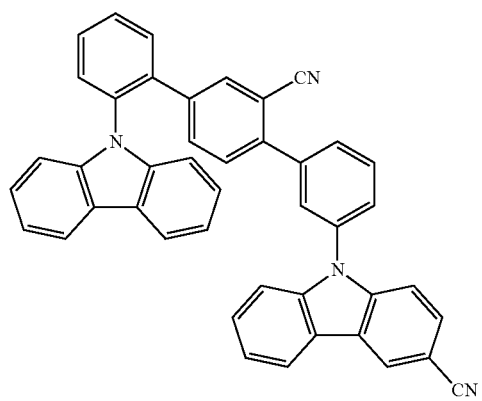
842
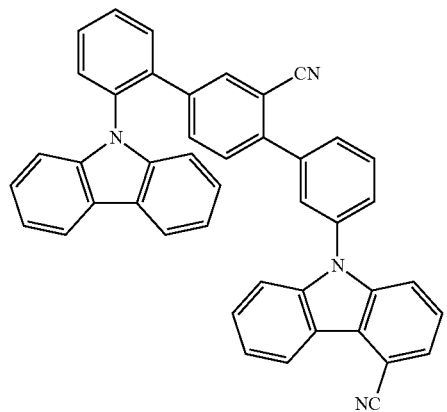
843
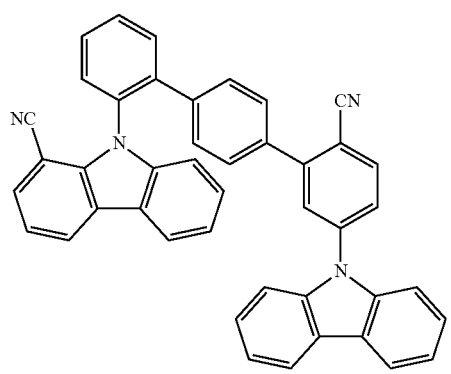
228
-continued
844
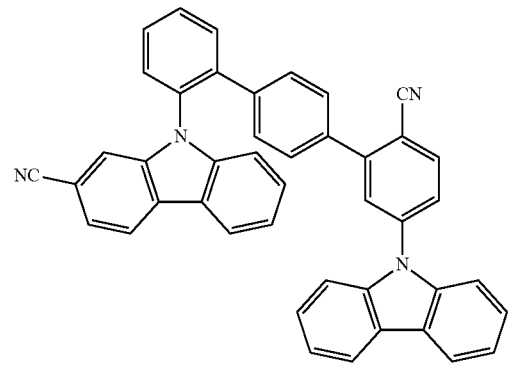
845
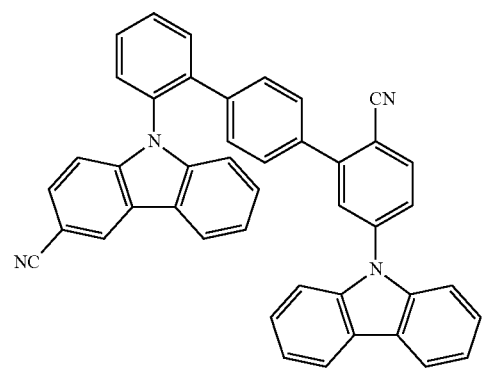
846
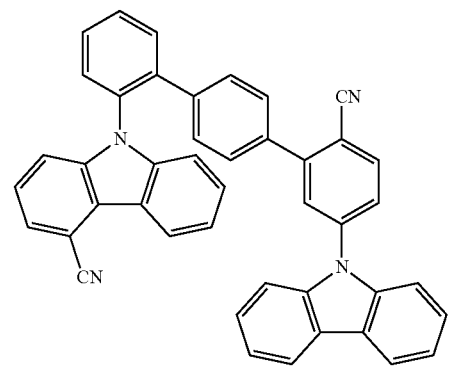
847
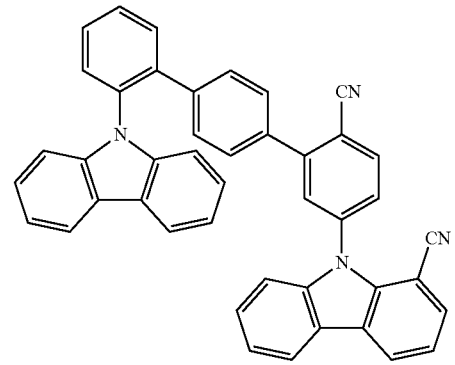

229
-continued
848
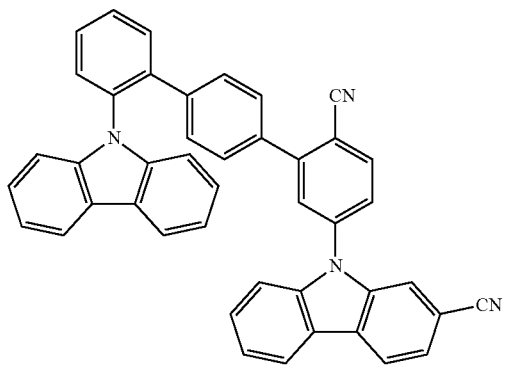
849
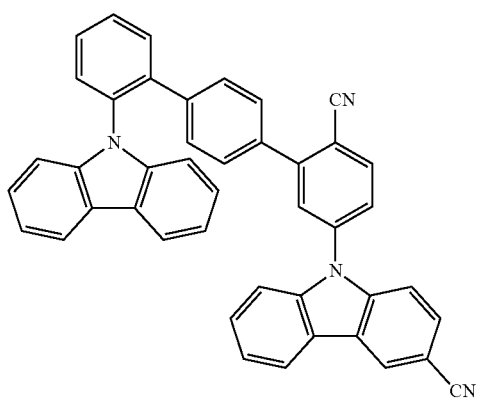
850
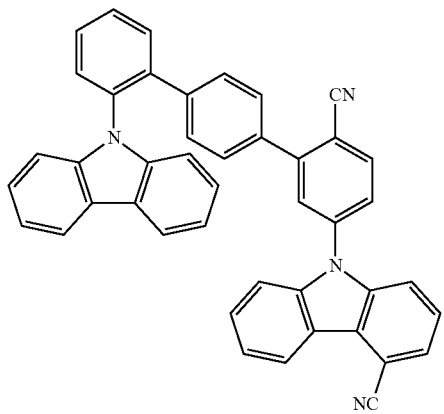
851
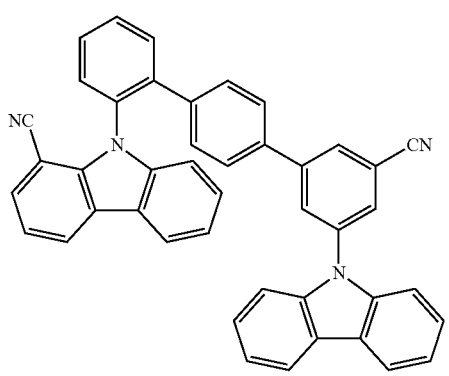
230
-continued
852
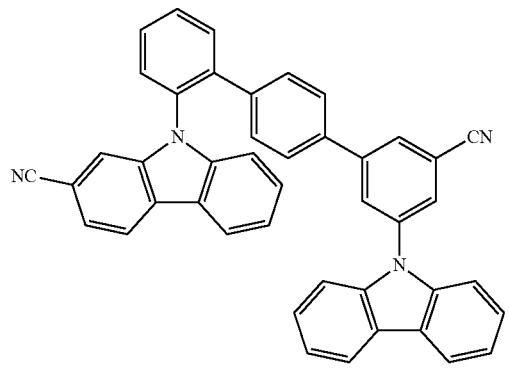
853
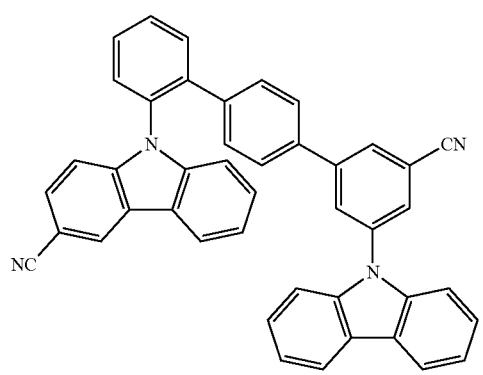
854
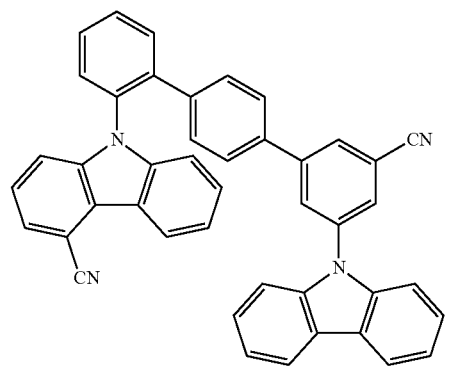
855
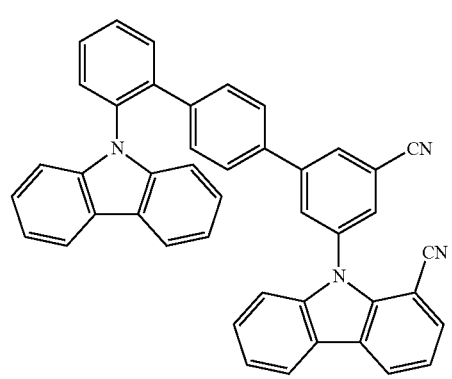

-continued
856
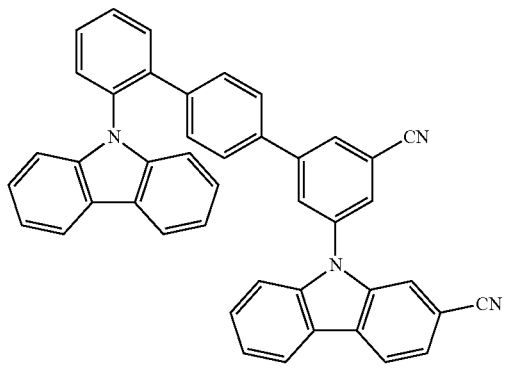
857
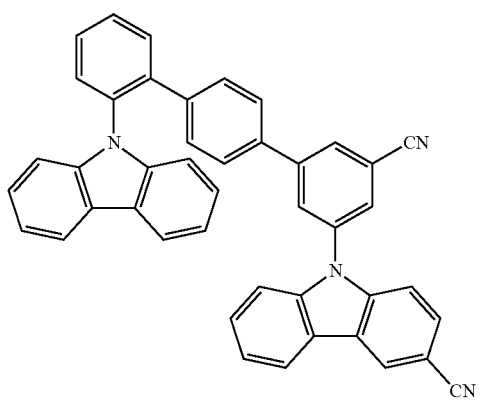
858
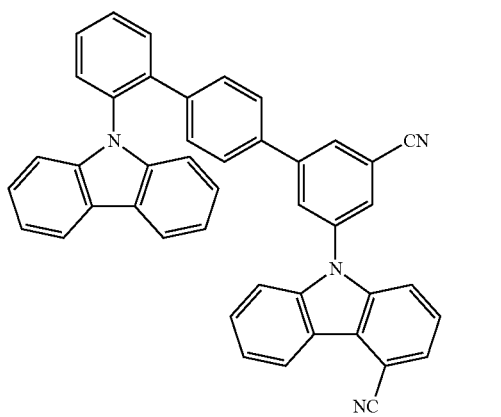
859
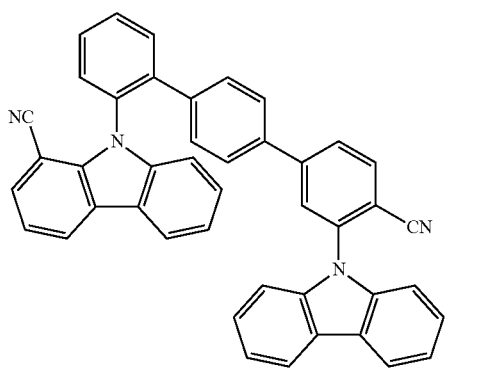
-continued
860
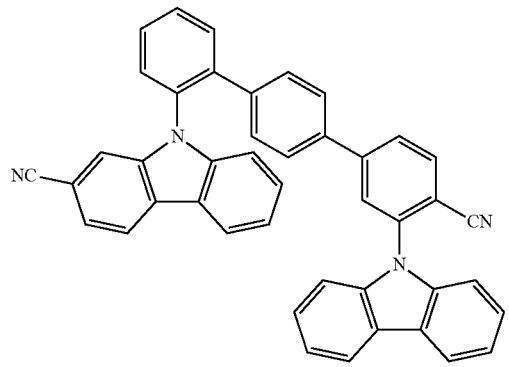
861
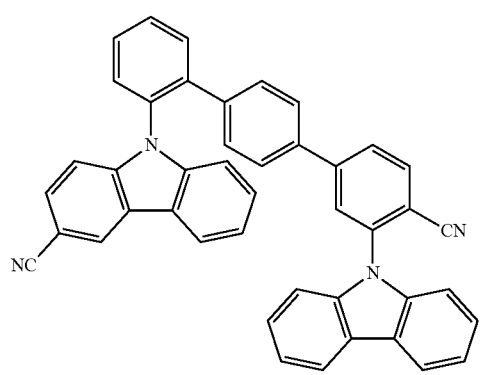
862
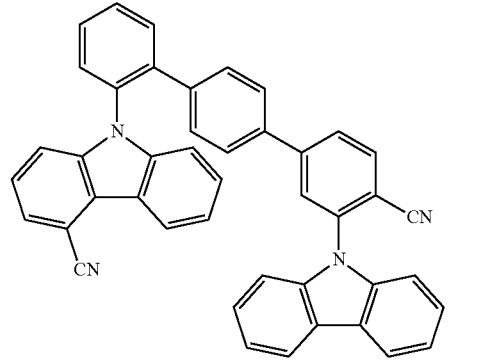
863
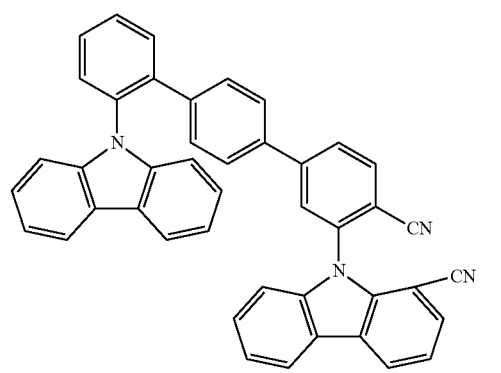

864 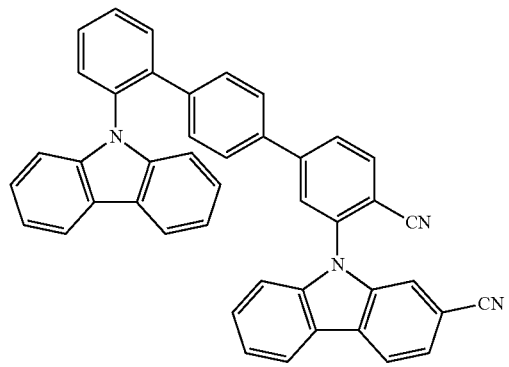
865 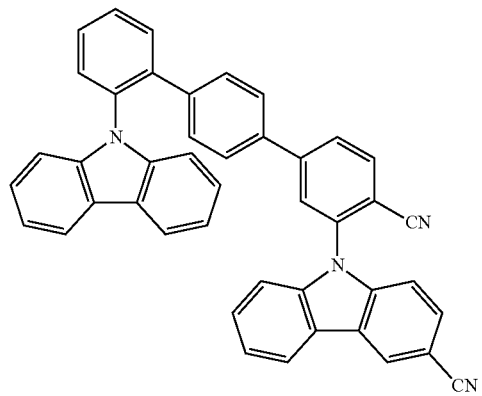
866 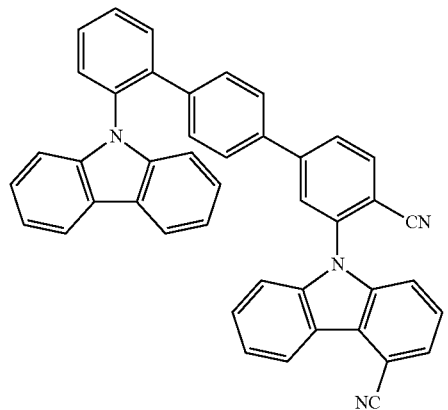
867 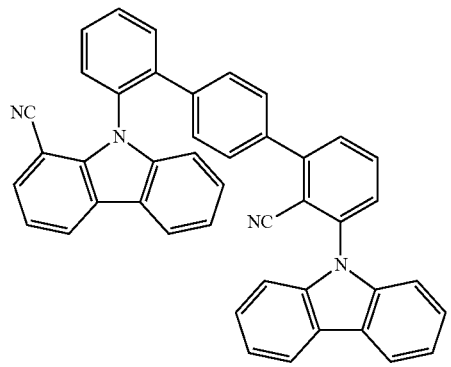
868 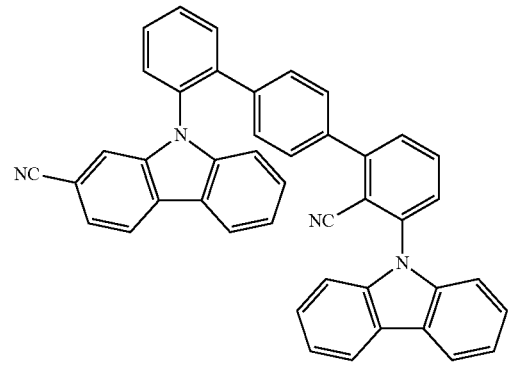
869 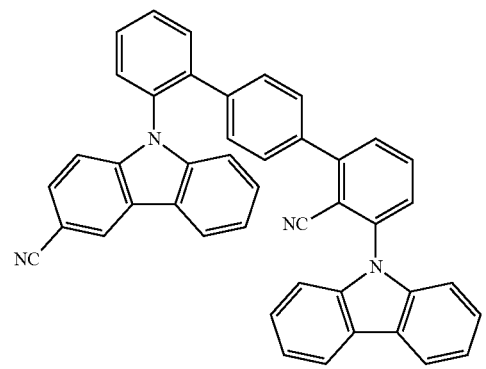
870 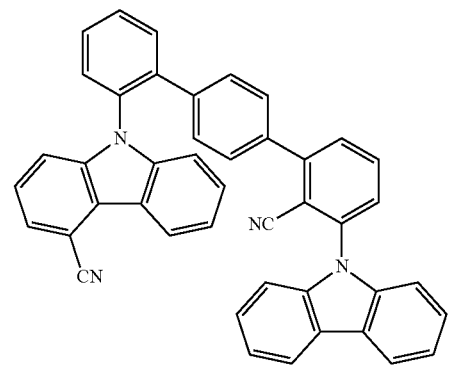
871 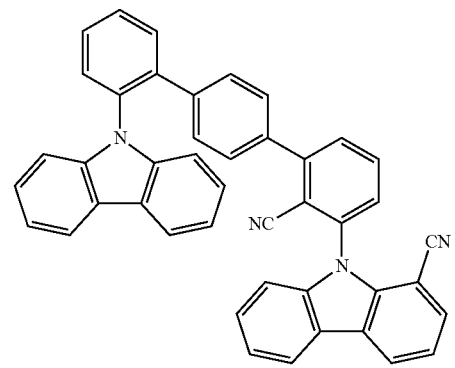

-continued
872
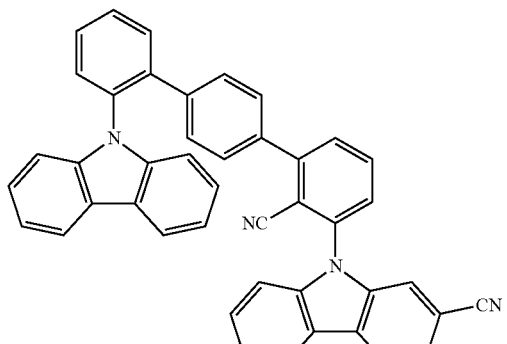
873
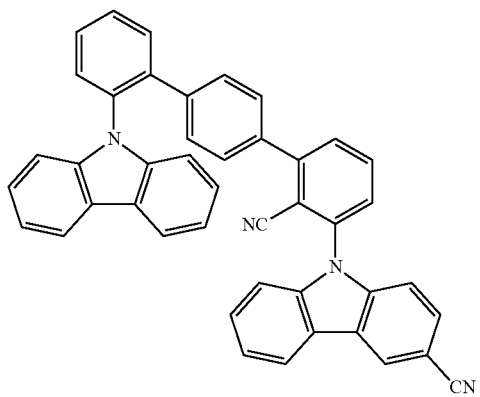
874
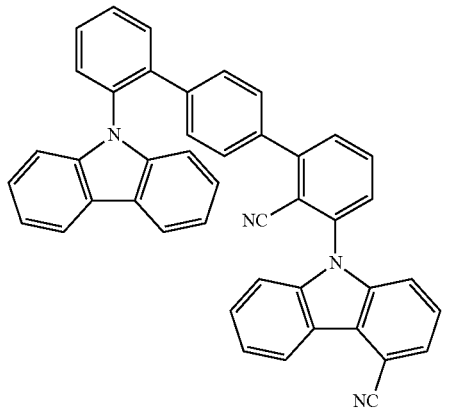
875
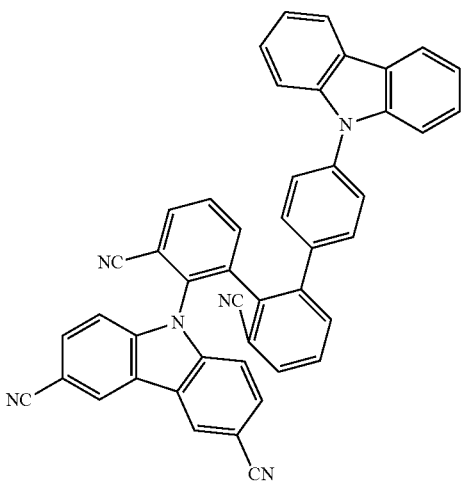
-continued
876
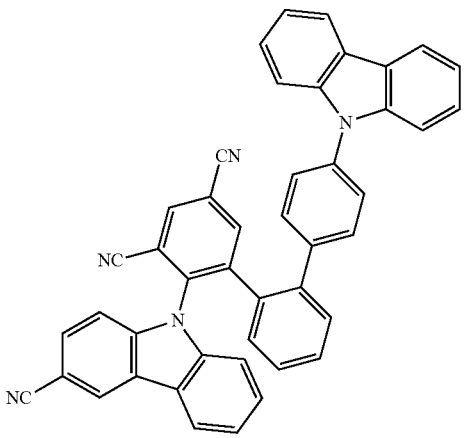
877
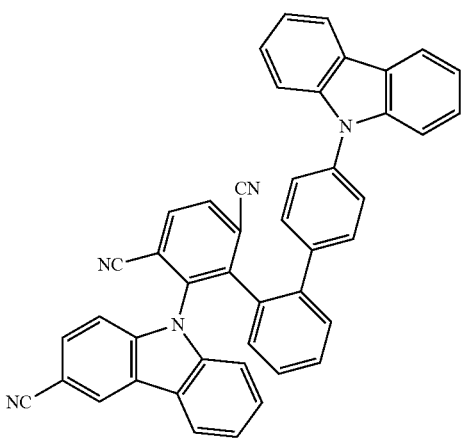
878

237
-continued
879
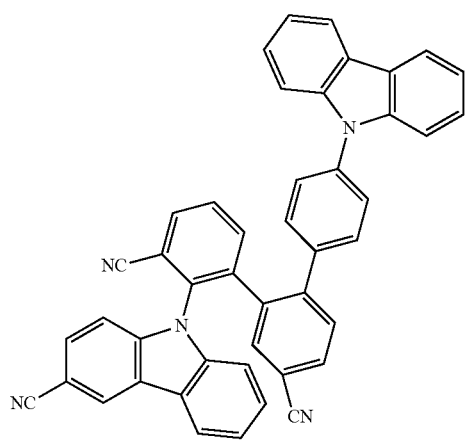
880
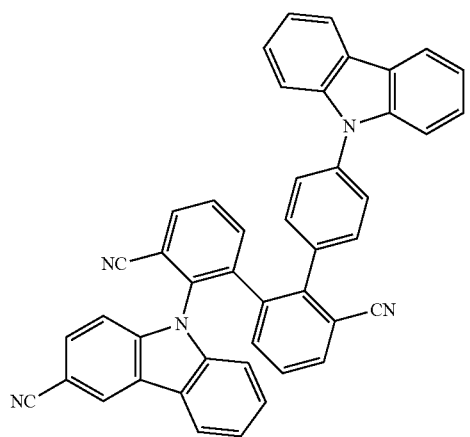
881
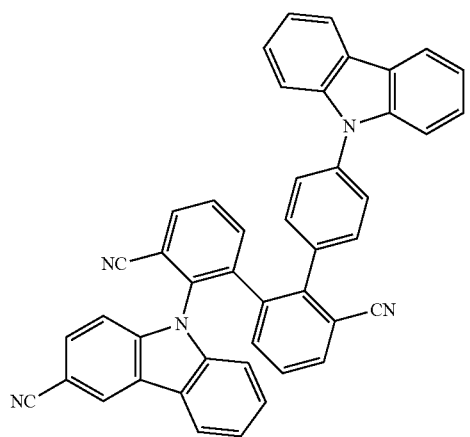
238
-continued
882
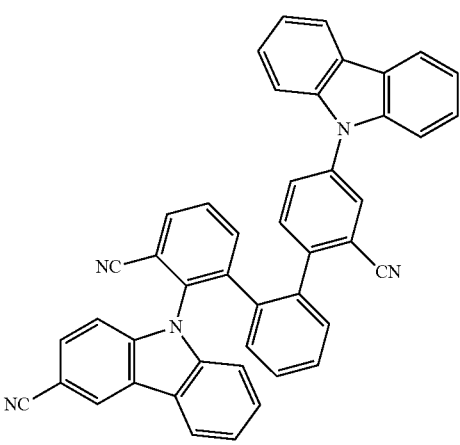
883
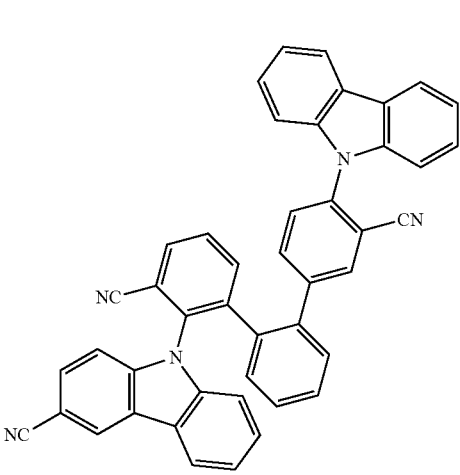
884
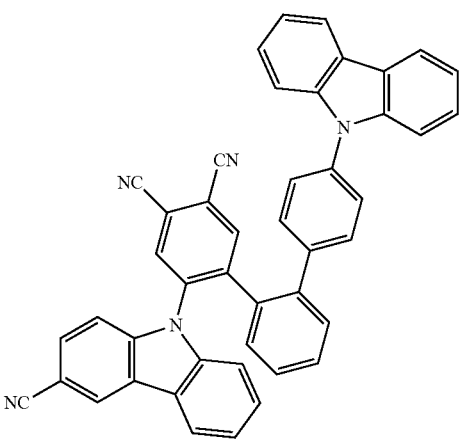

885
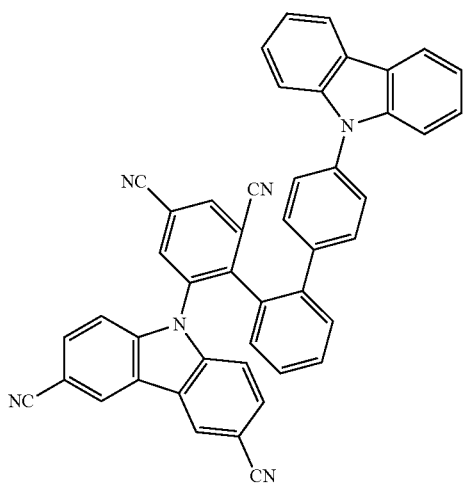
886
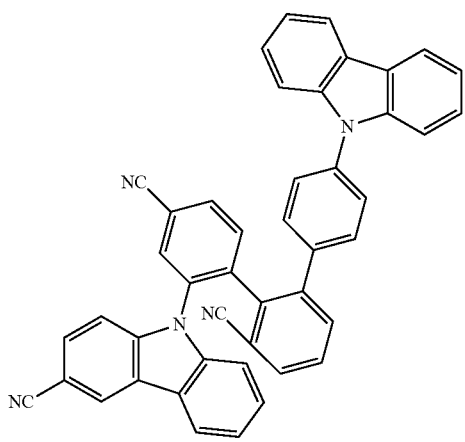
887
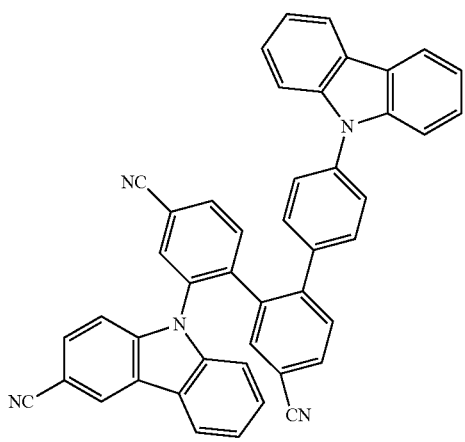
888
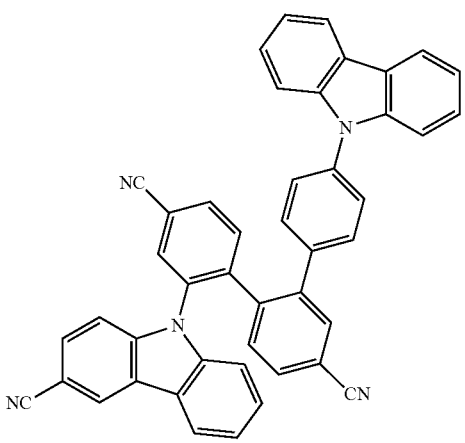
889
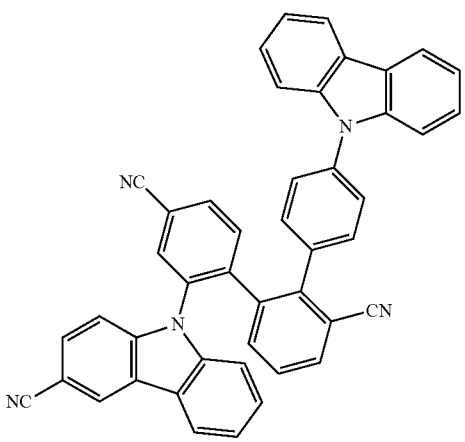
890
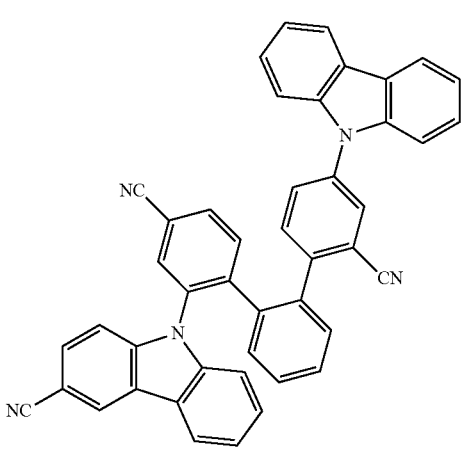

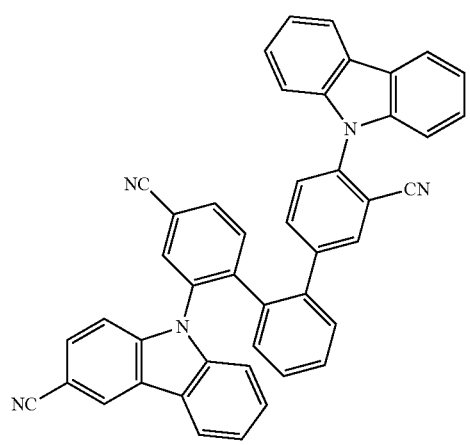
891
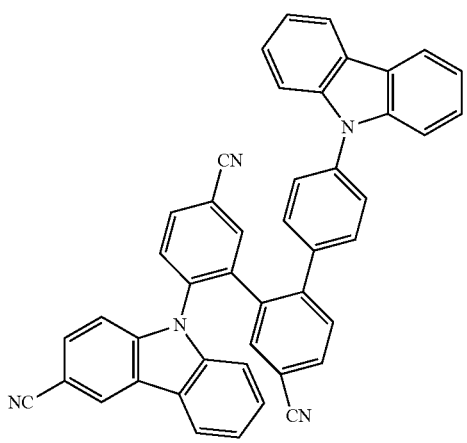
894
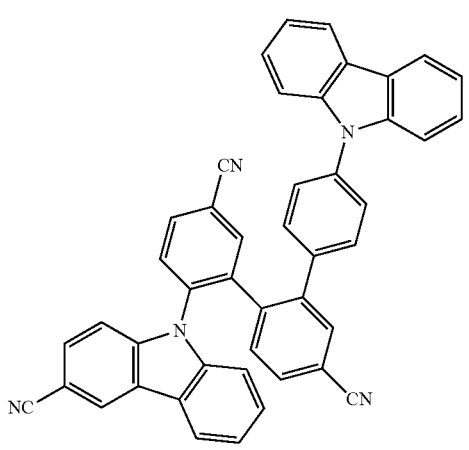
895
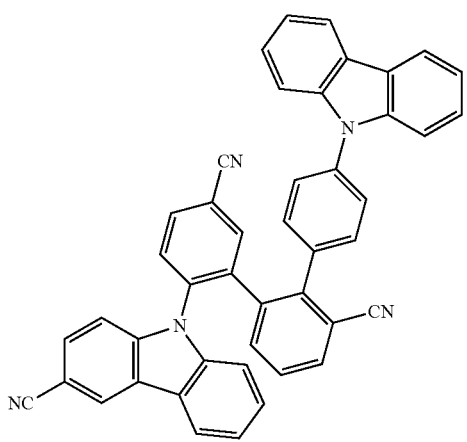
896

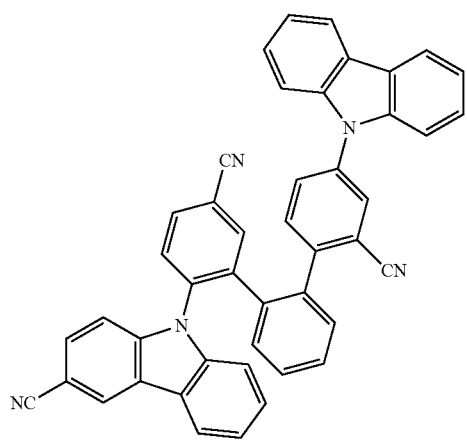
897
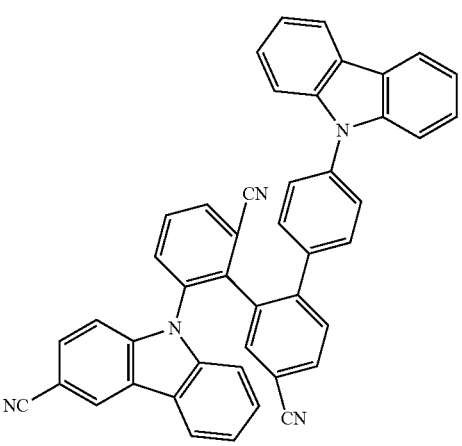
900
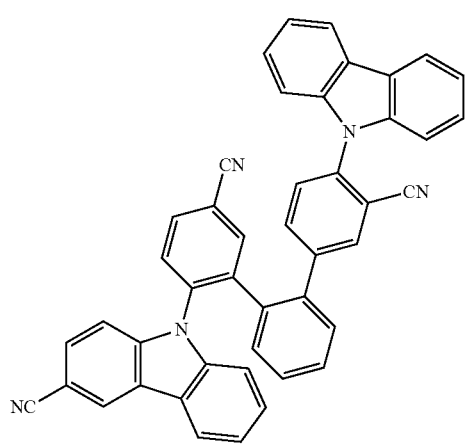
898
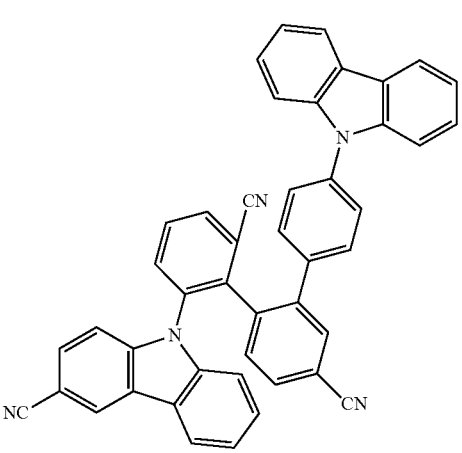
901
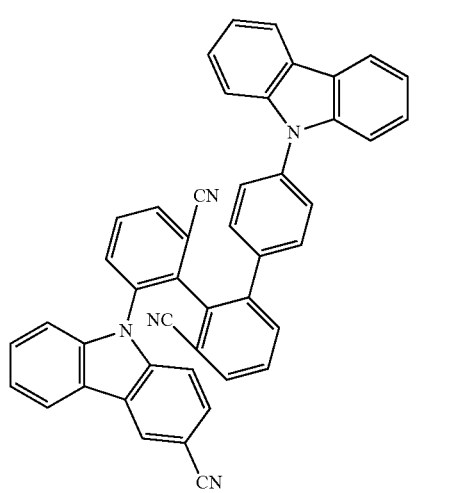
899
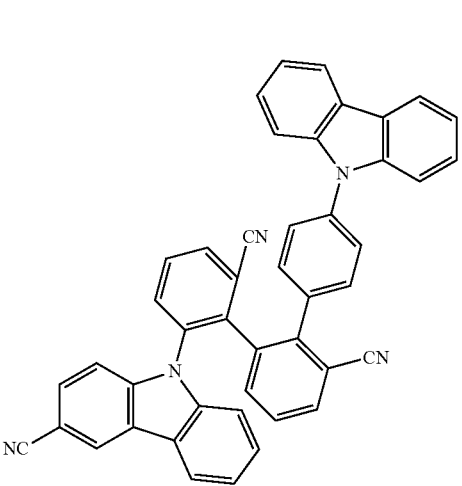
902

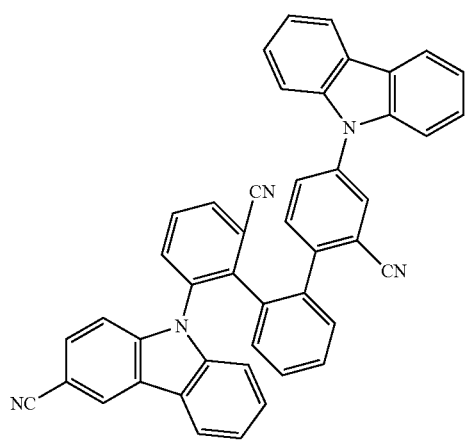
903
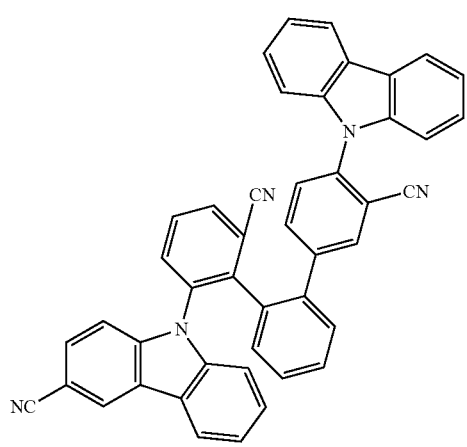
904
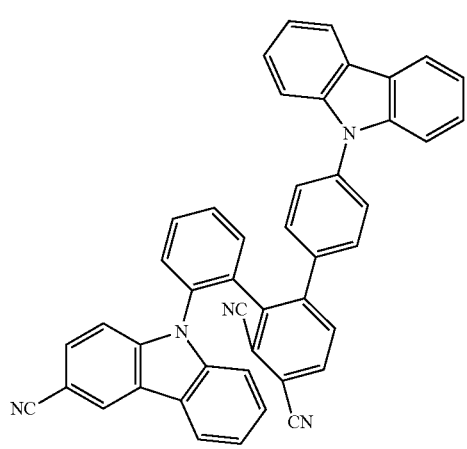
905
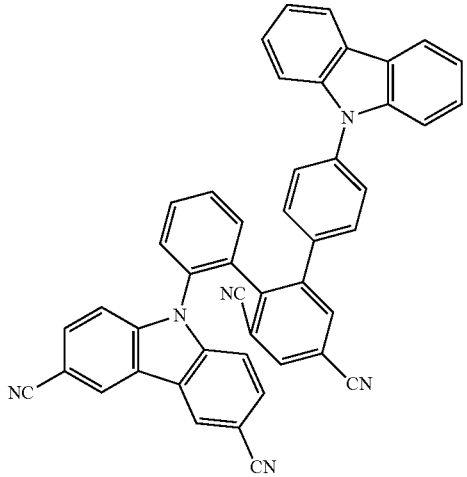
906
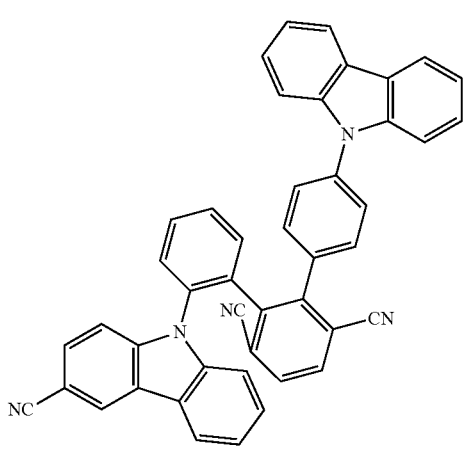
907
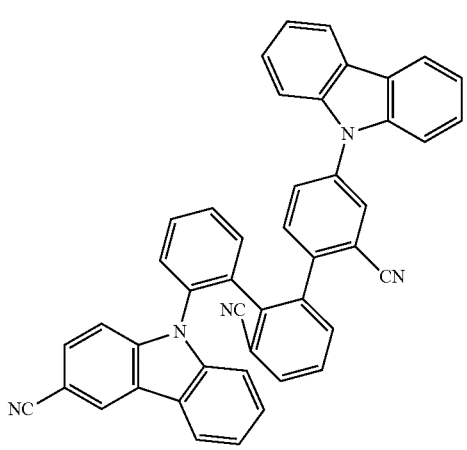
908

-continued
909
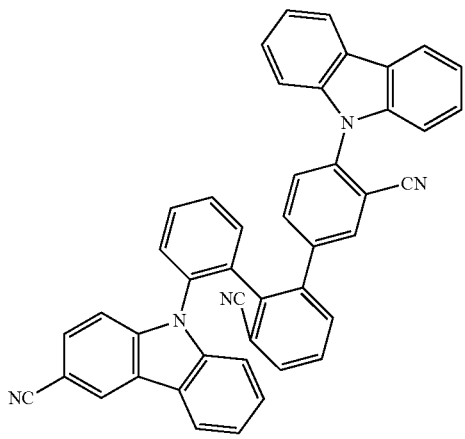
910
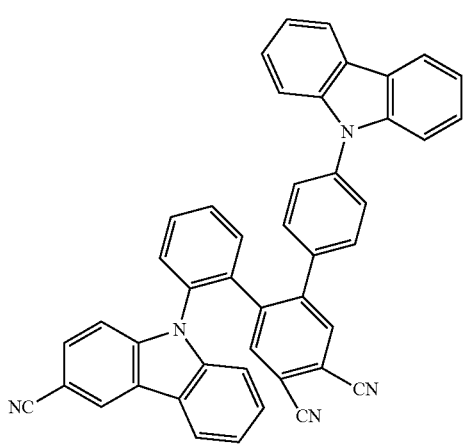
911
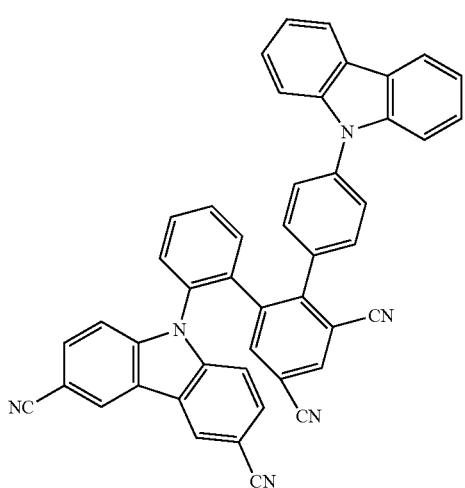
-continued
912
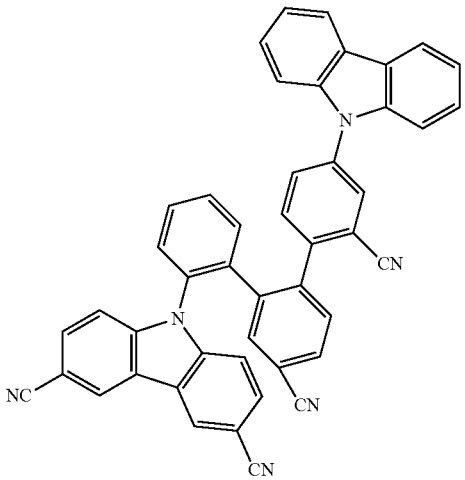
913
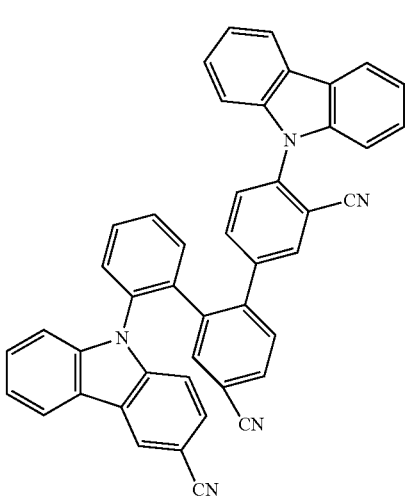
914
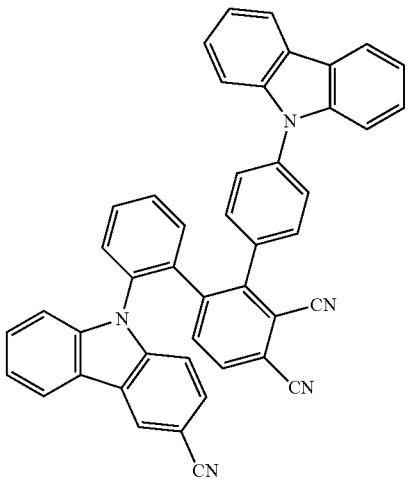

249
-continued
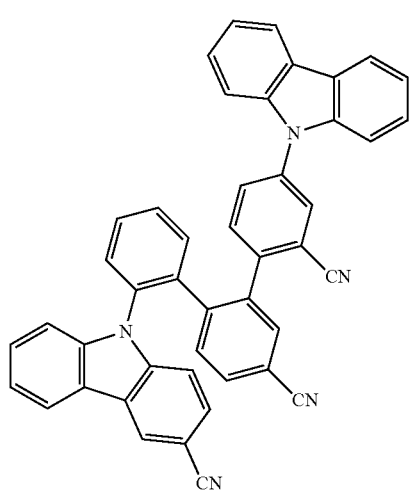
915
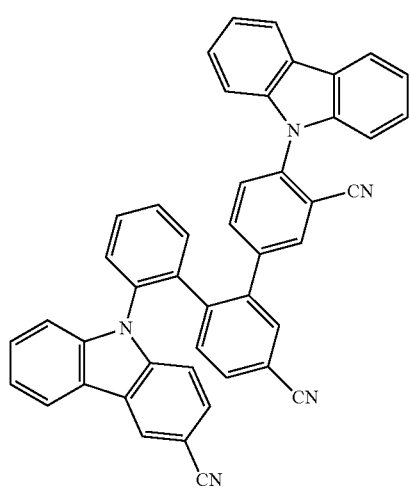
916
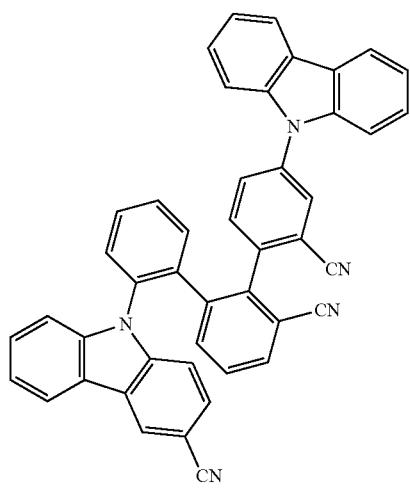
917
250
-continued
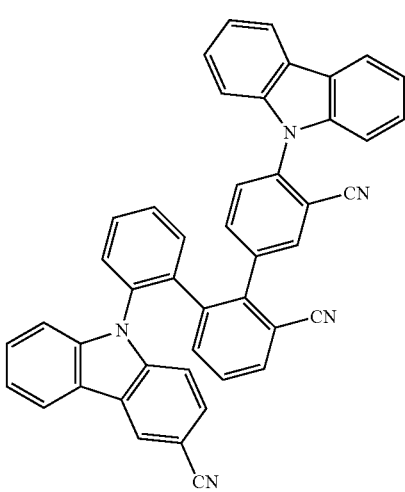
918
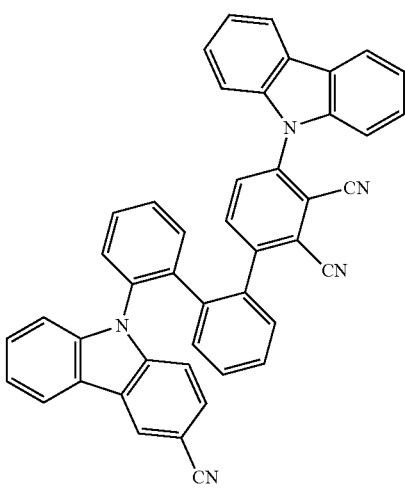
919
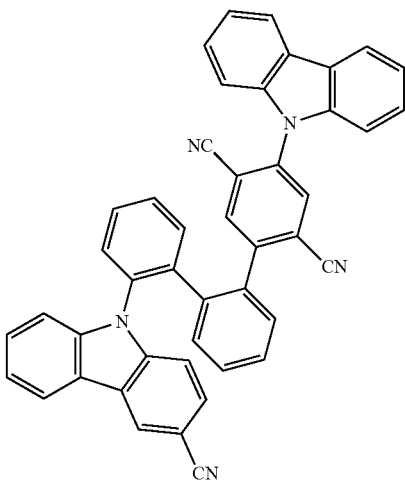
920

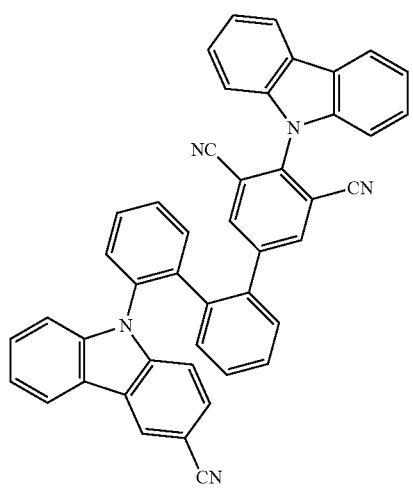
921
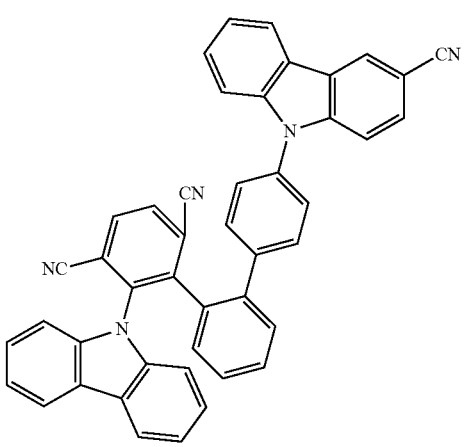
924
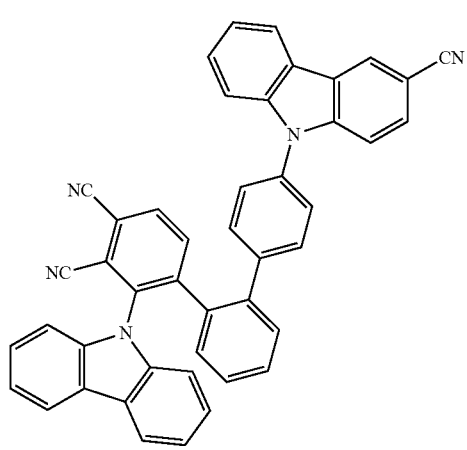
922
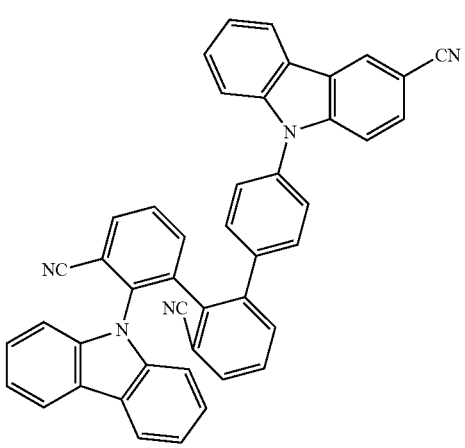
925
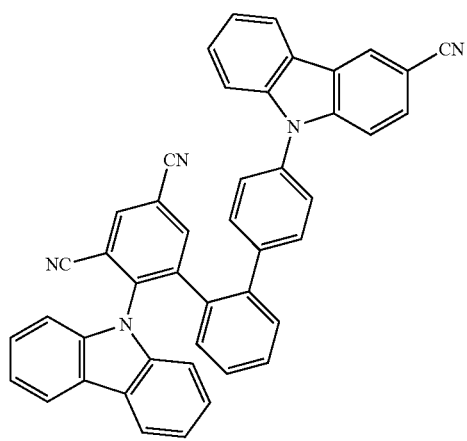
923
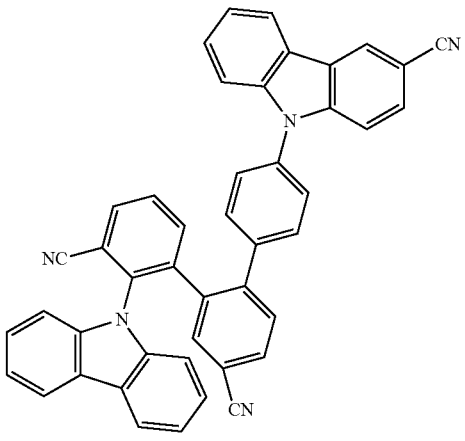
926

253
-continued
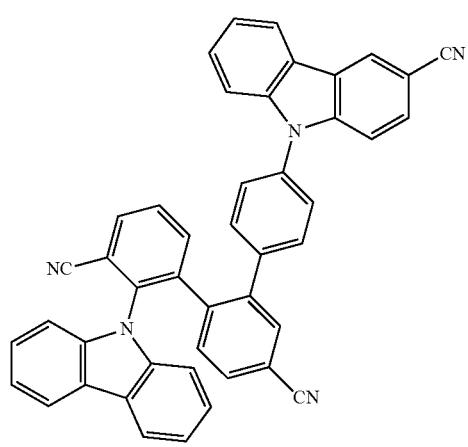
927
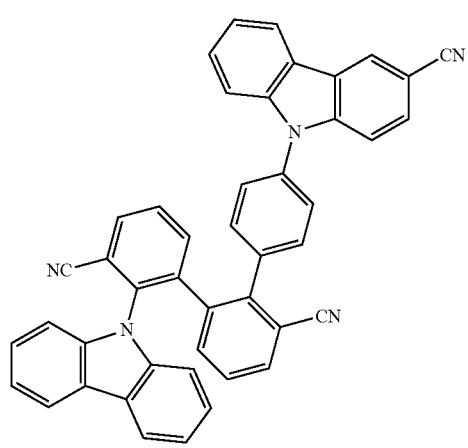
928
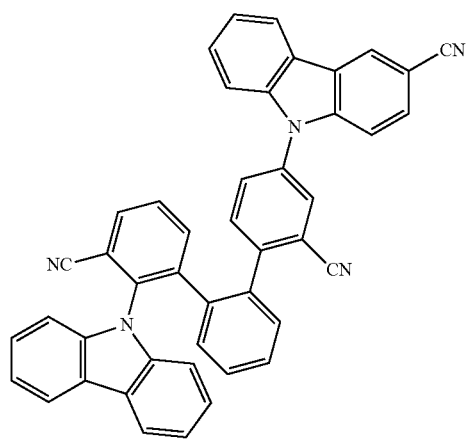
929
254
-continued
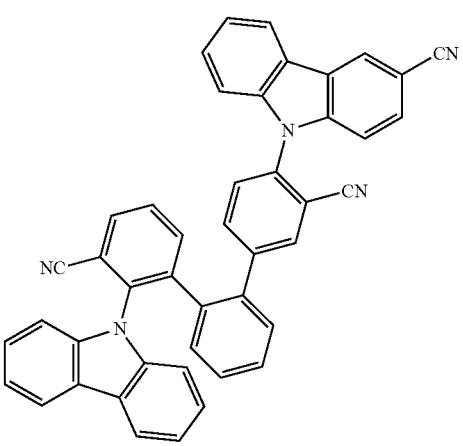
930
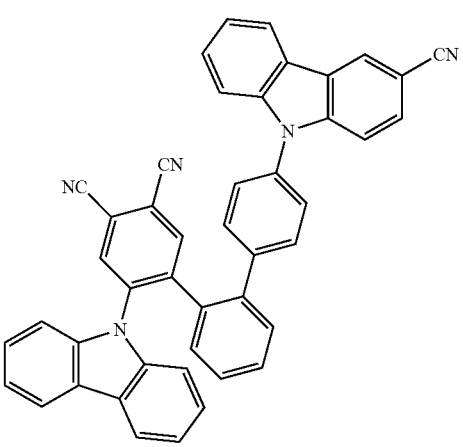
931
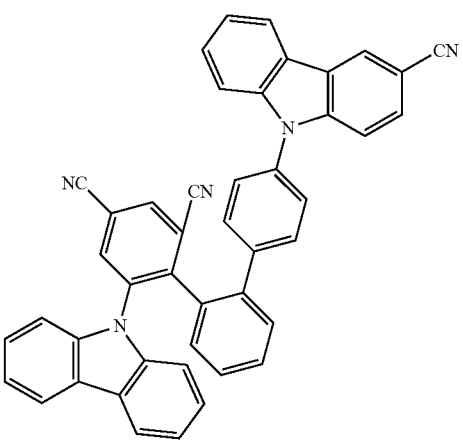
932

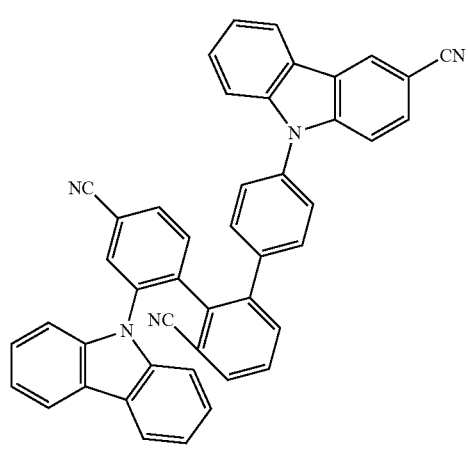
933
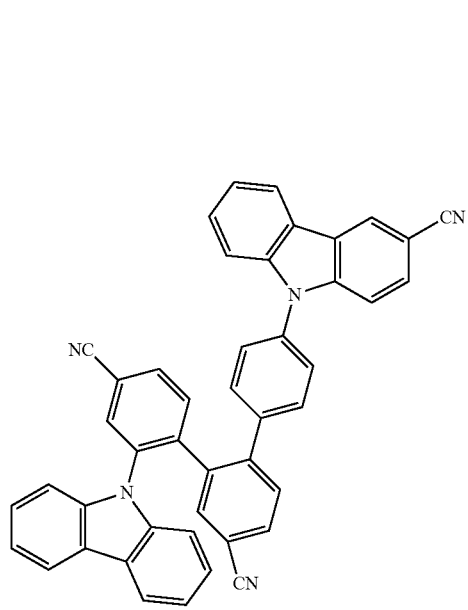
934
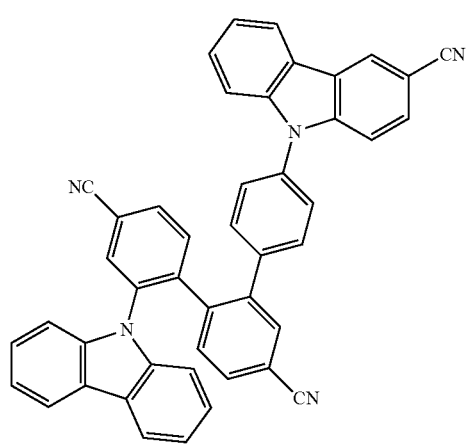
935
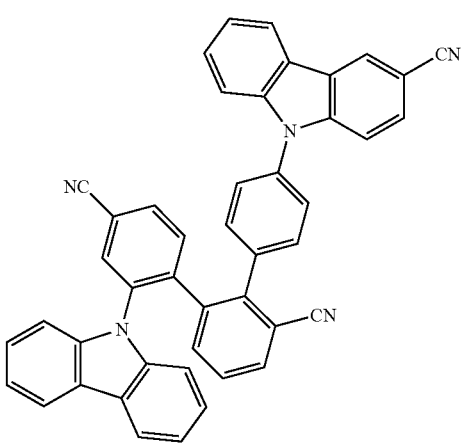
936
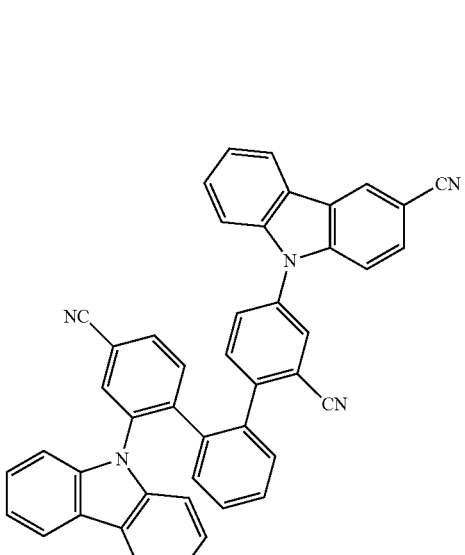
937
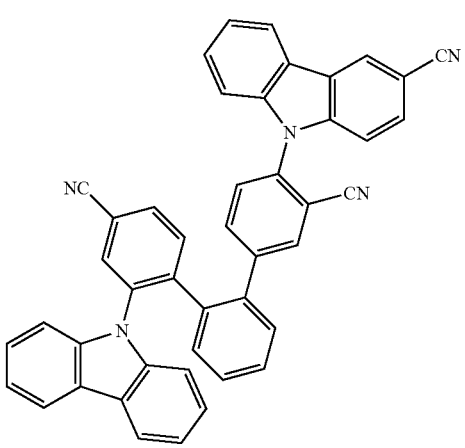
938

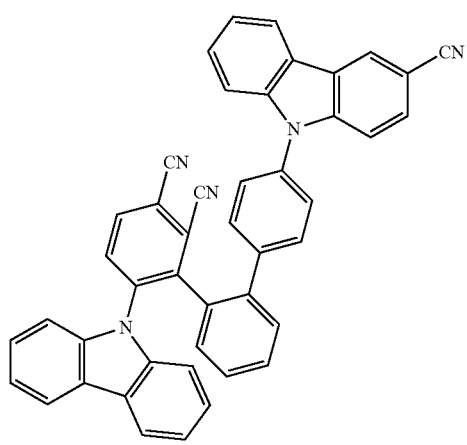
939
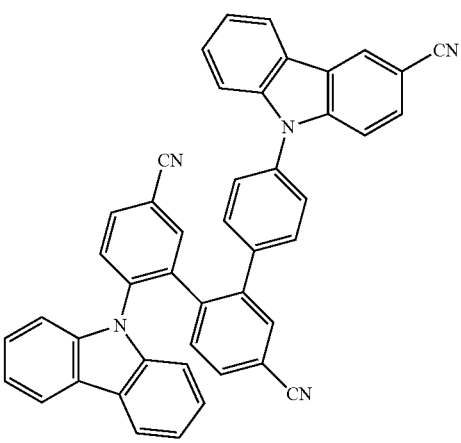
942
940
943
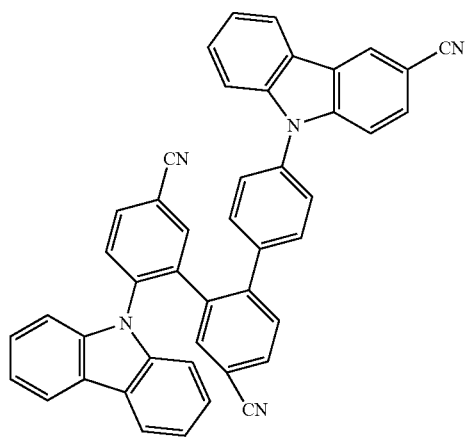
941
944

945
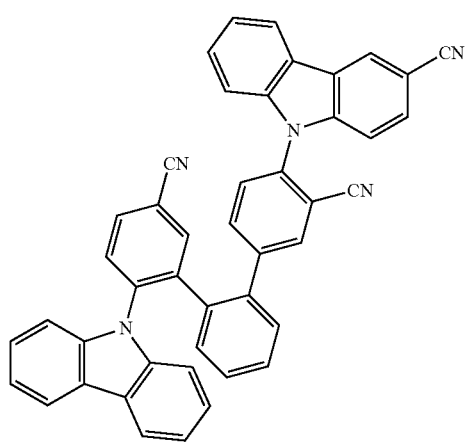
946
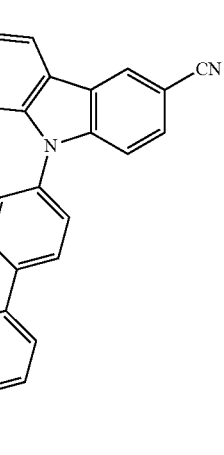
947
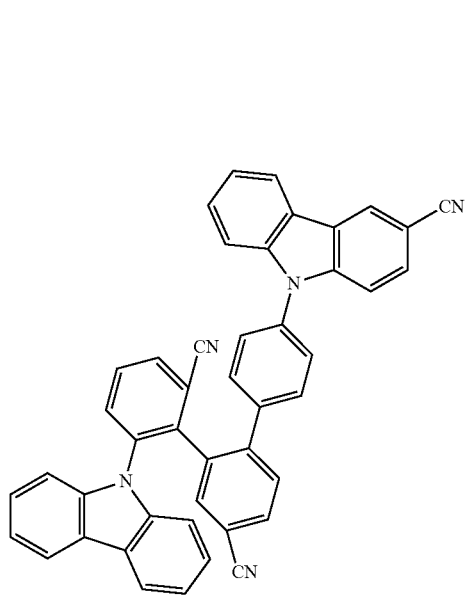
948
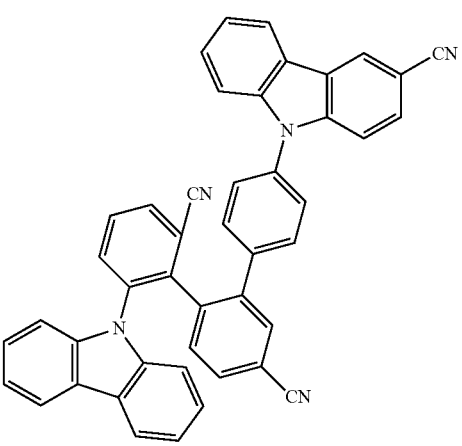
949
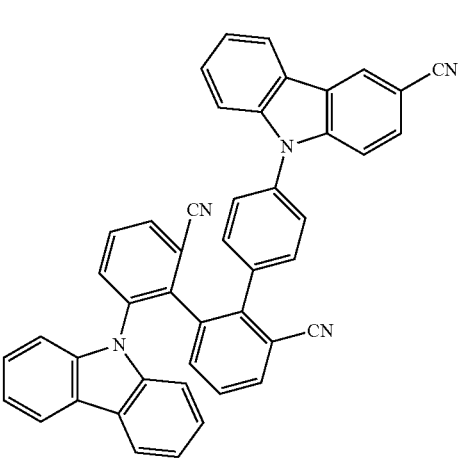
950
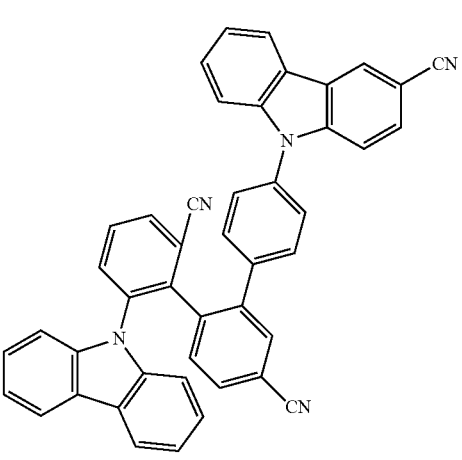

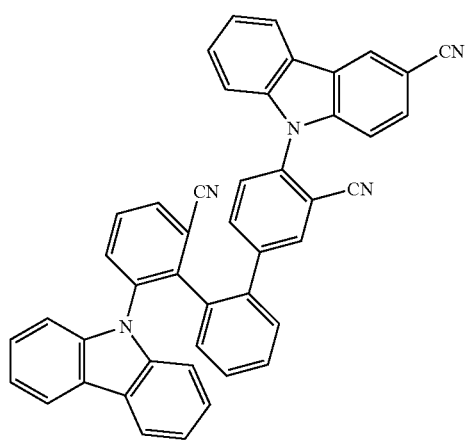
951
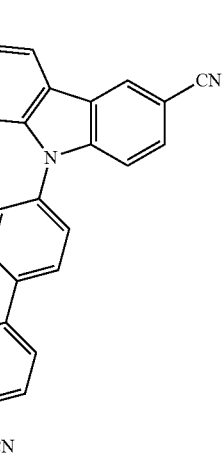
952
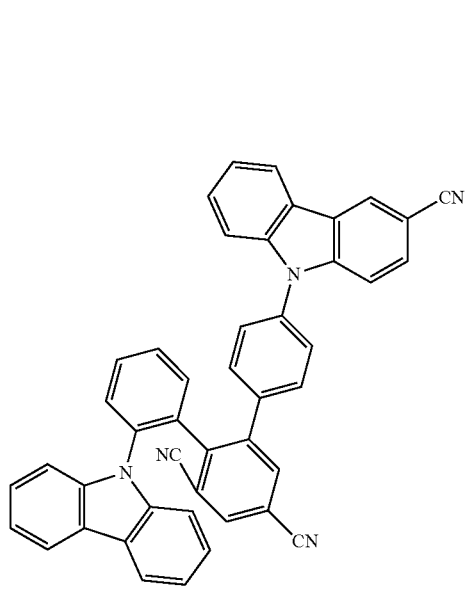
953
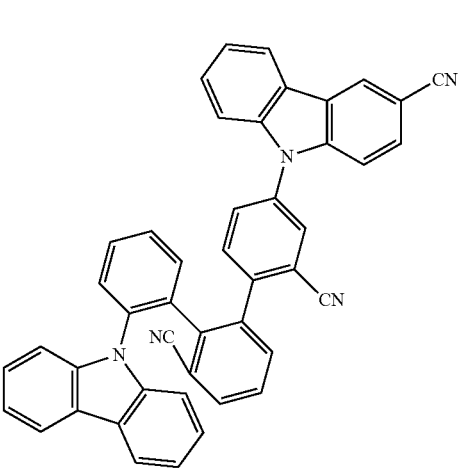
954
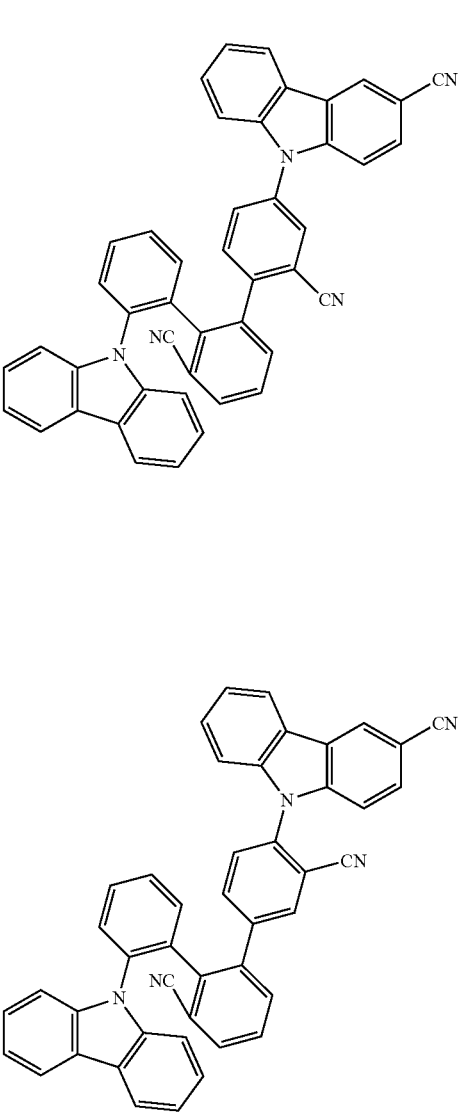
955
956

263
-continued
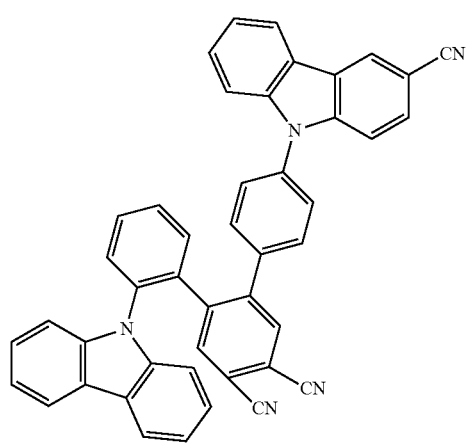
957
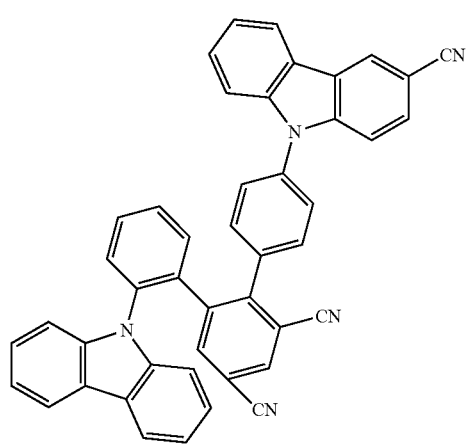
958
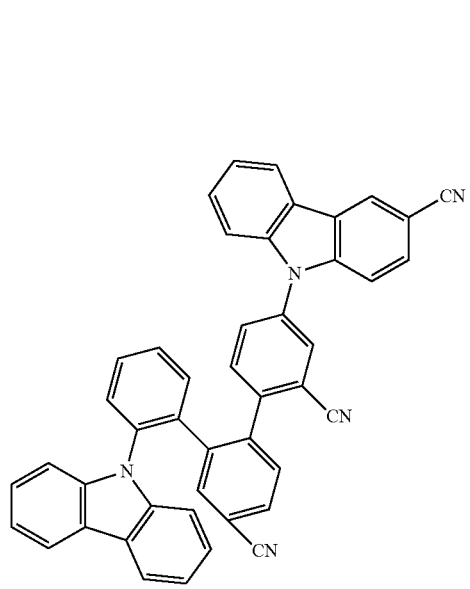
959
264
-continued
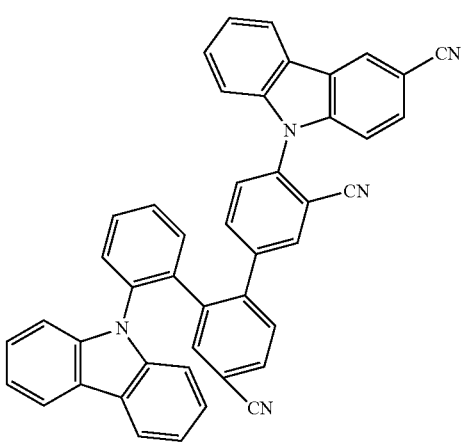
960
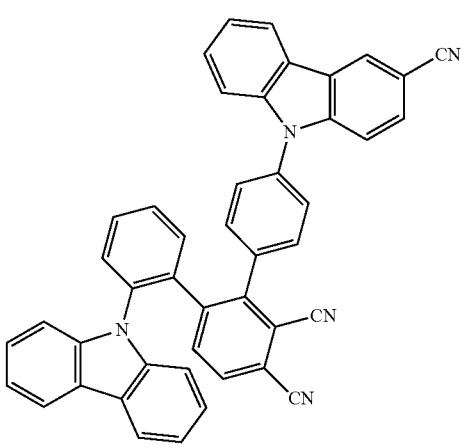
961
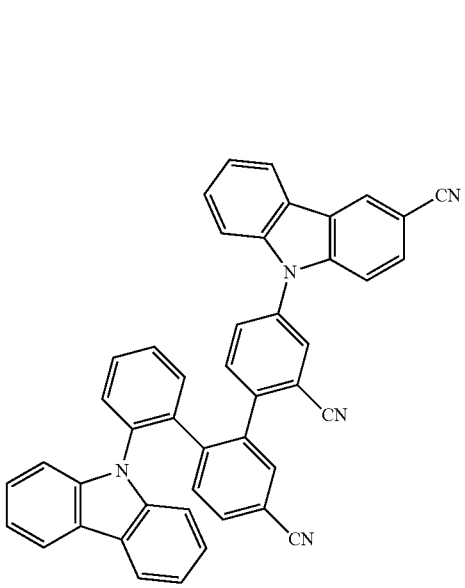
962

265
-continued
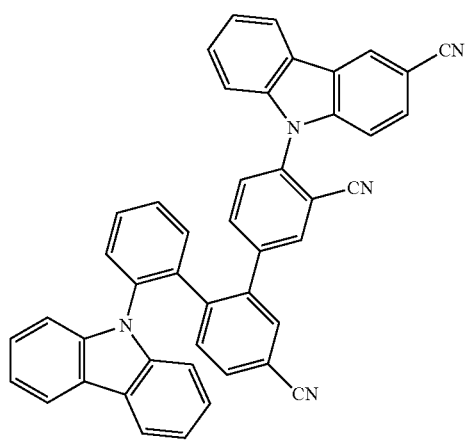
963
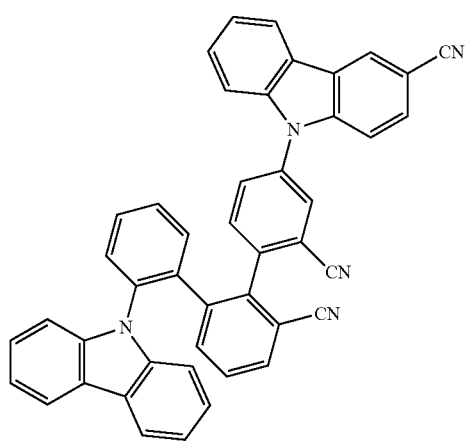
964
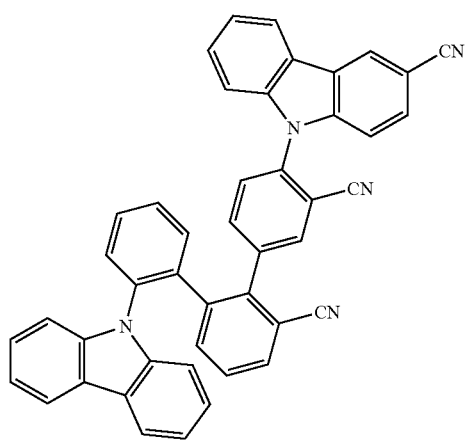
965
266
-continued
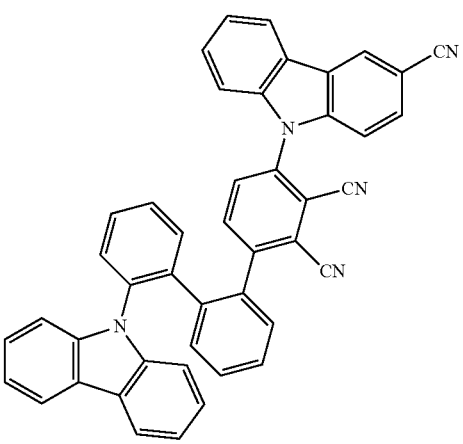
966
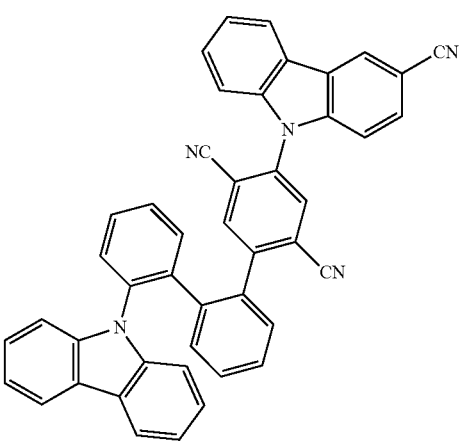
967
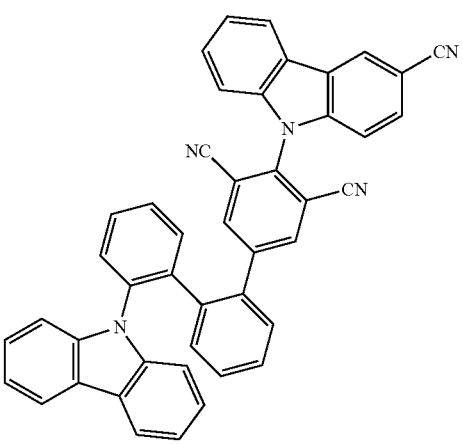
968

-continued
969
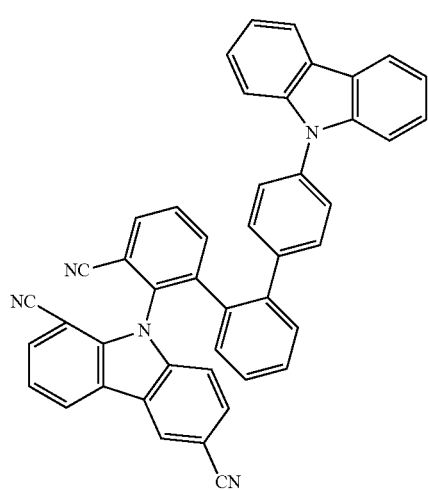
970
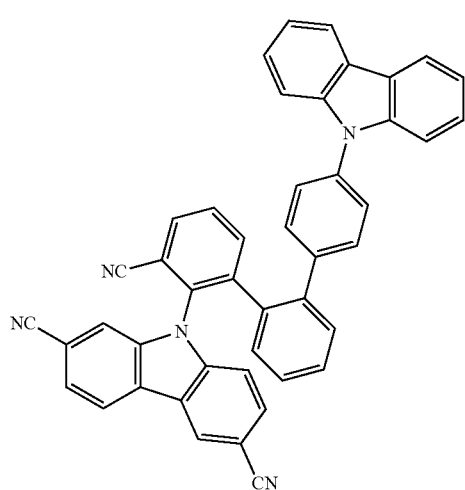
971
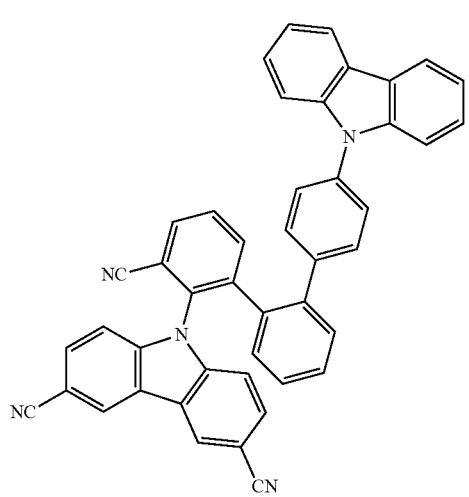
-continued
972
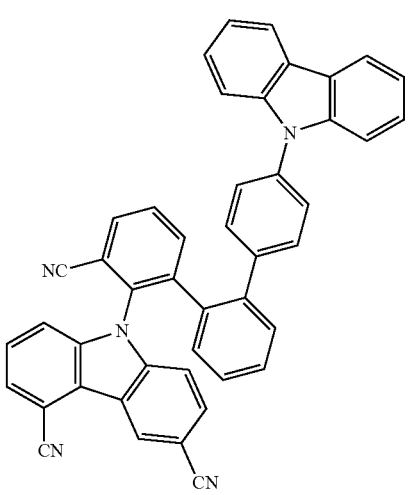
973
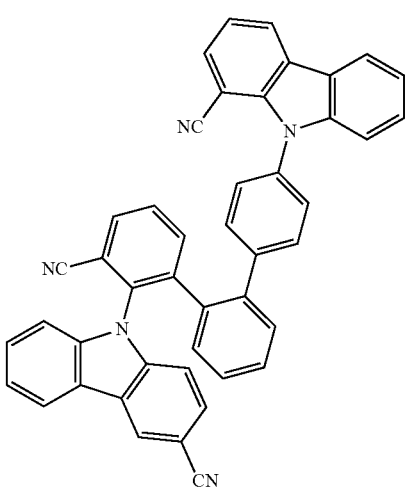
974
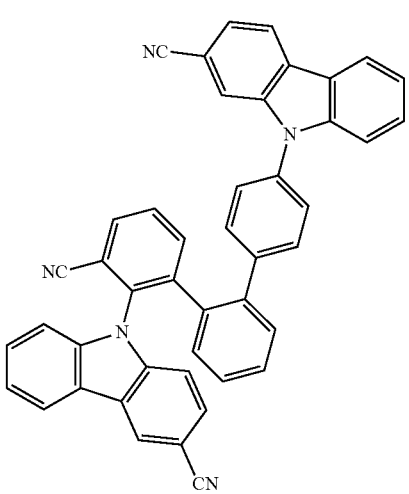

-continued
975
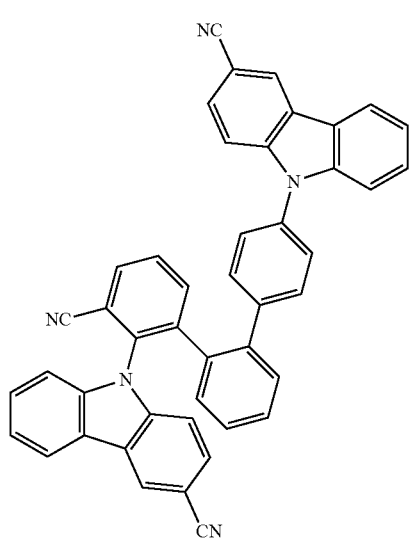
976
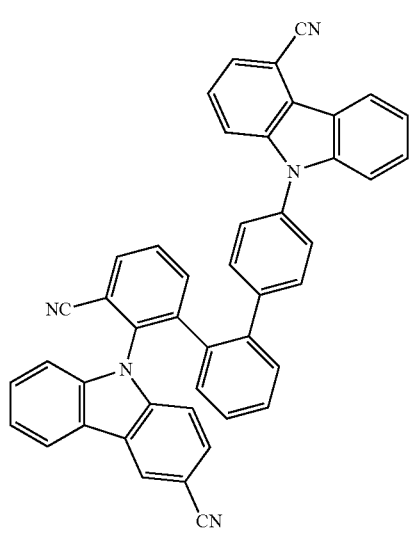
977
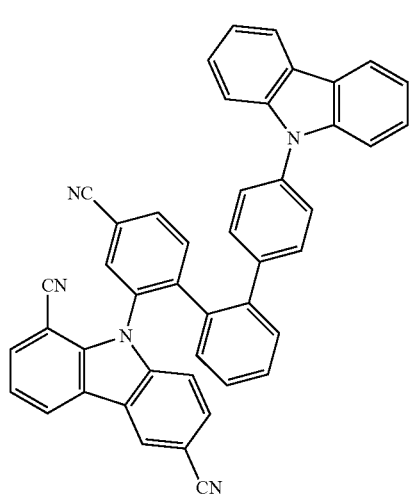
978
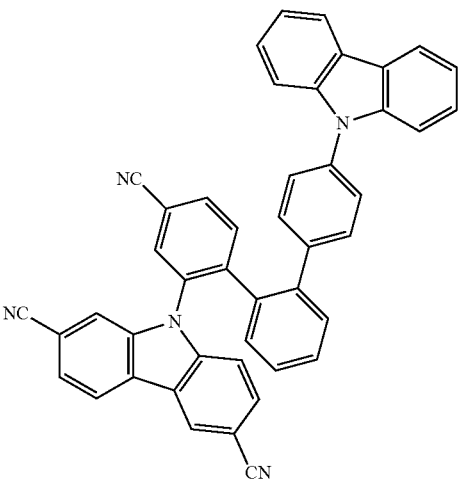
979
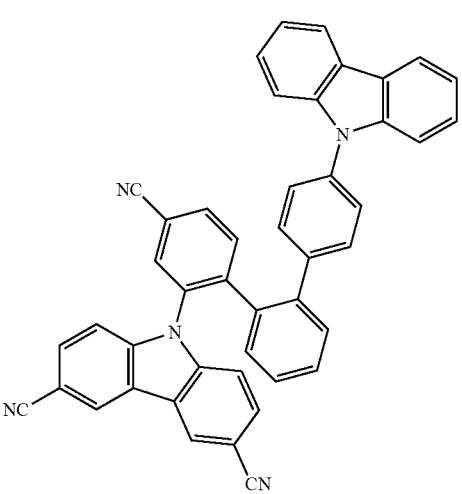
980
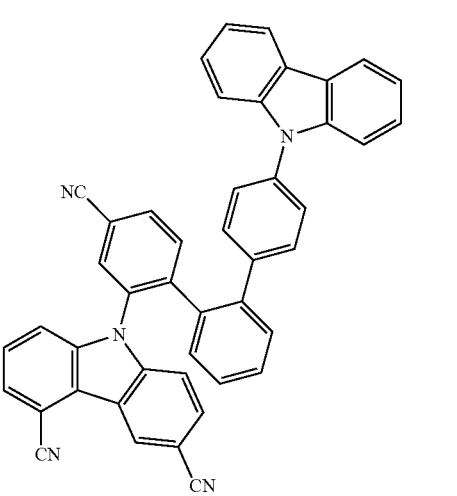

-continued
981
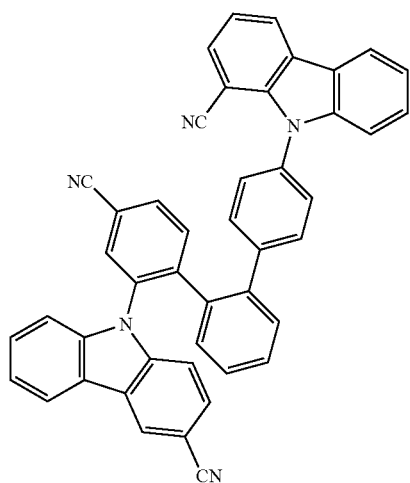
982
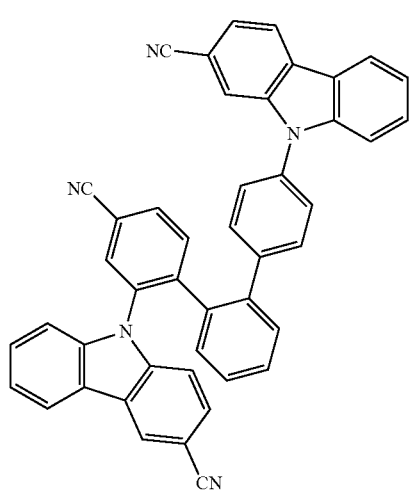
983
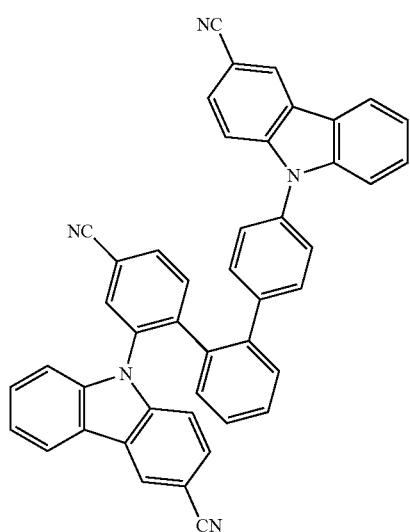
-continued
984
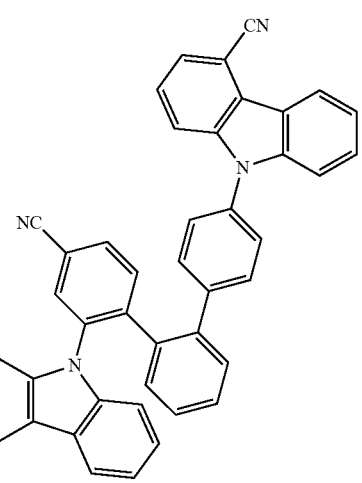
985
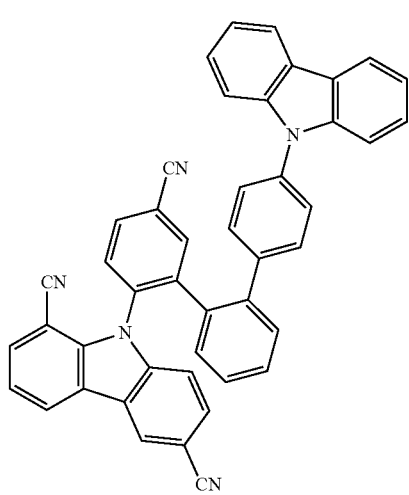
986
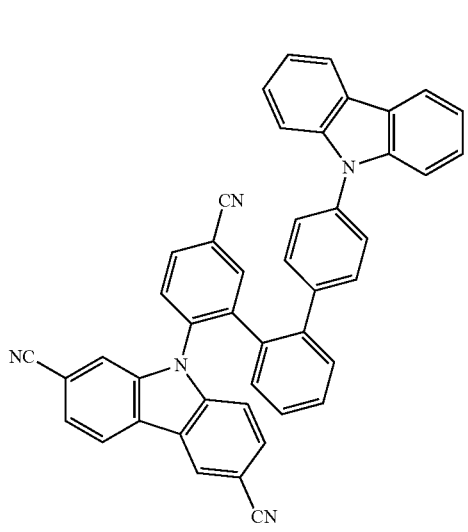

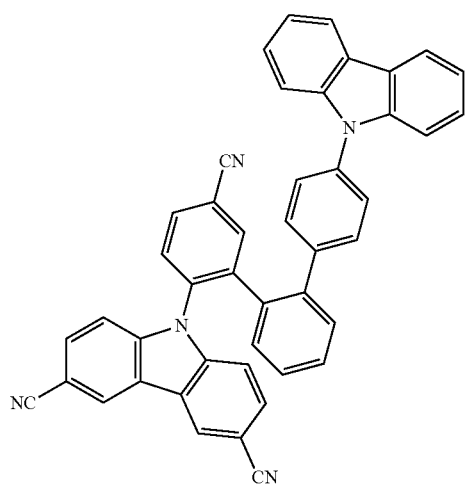
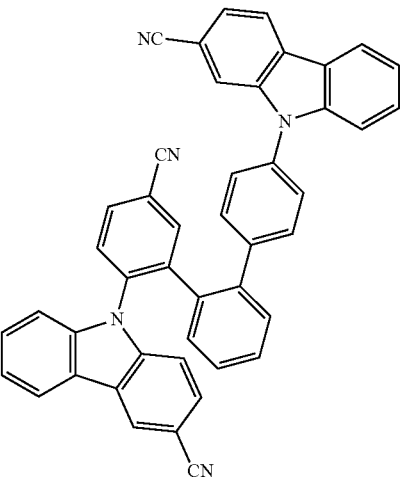

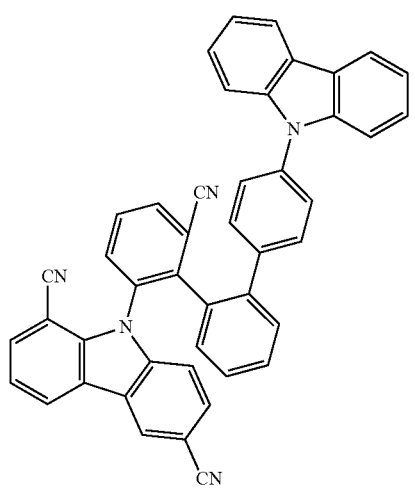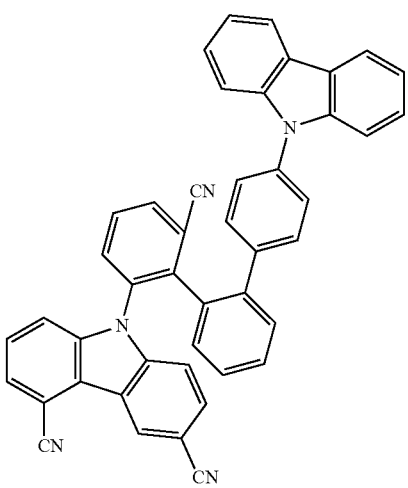

-continued
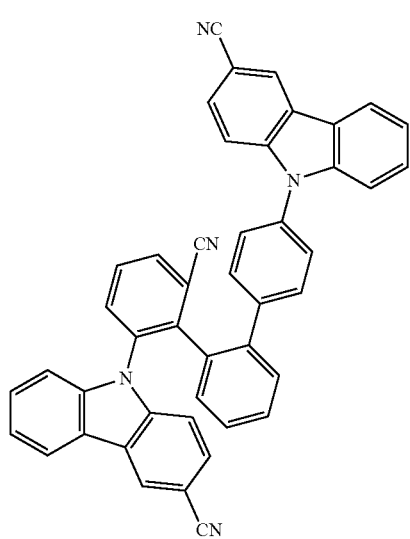
999
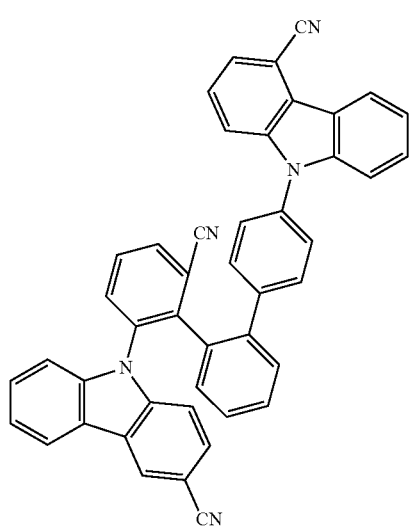
1000
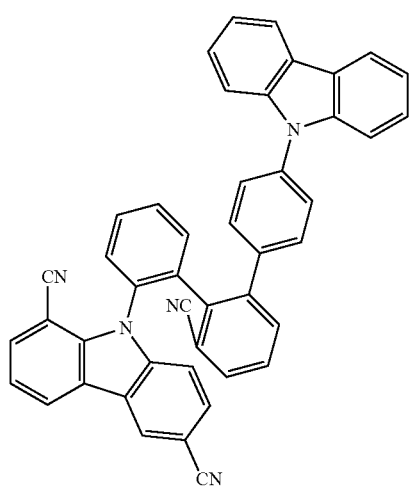
1001
-continued
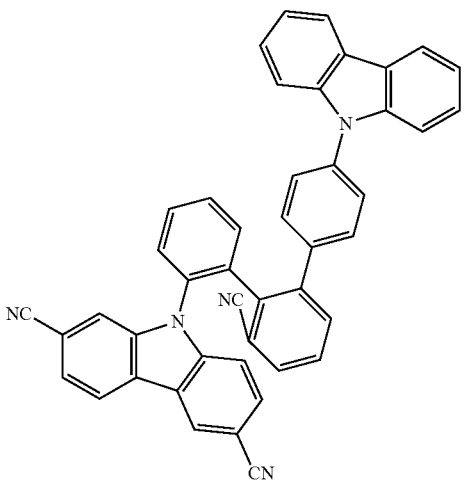
1002
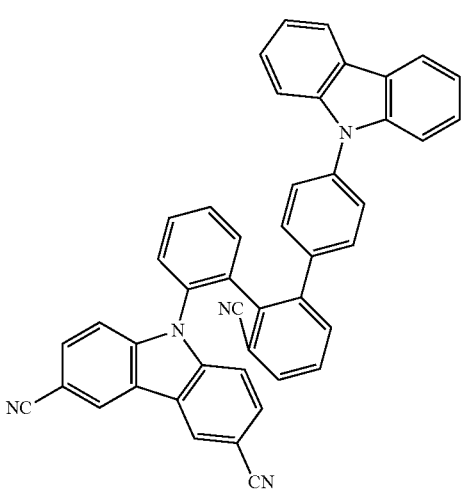
1003
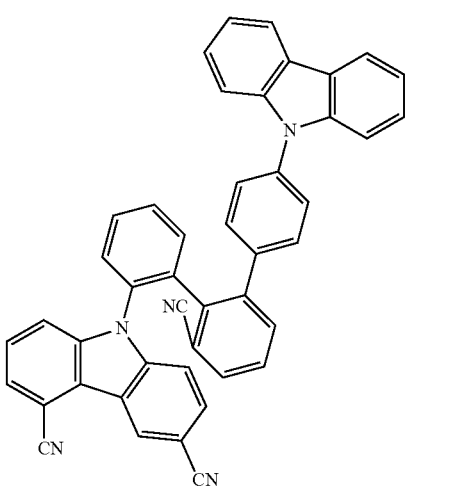
1004

-continued
1005
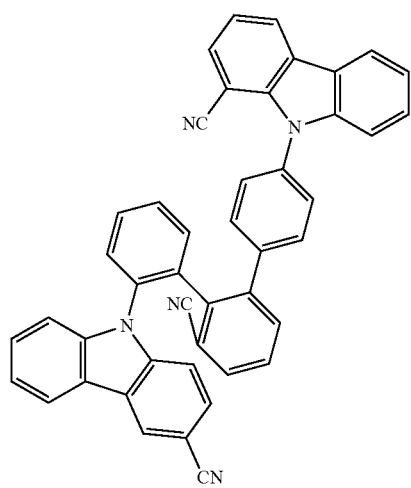
1006
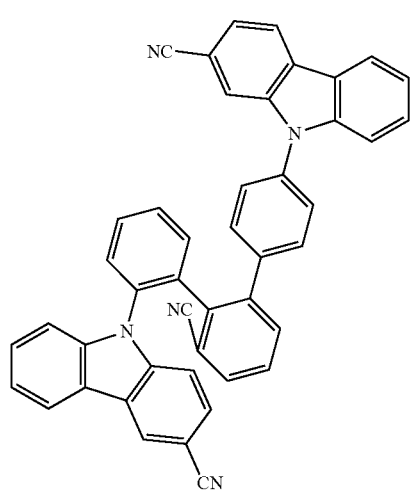
1007
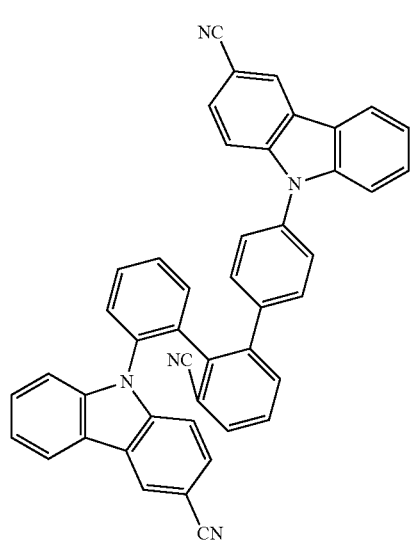
-continued
1008
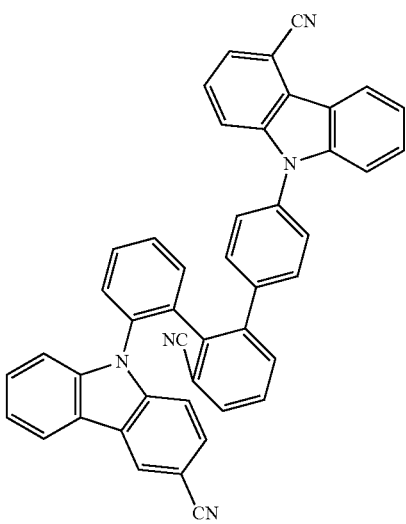
1009
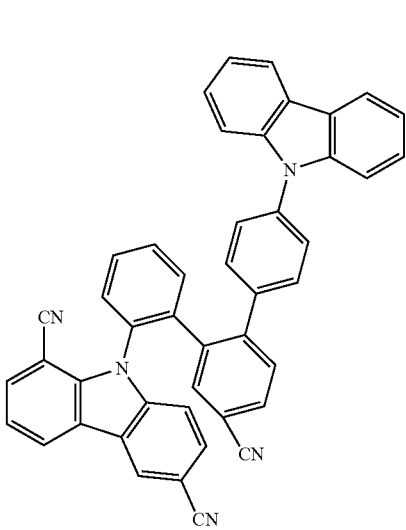
1010
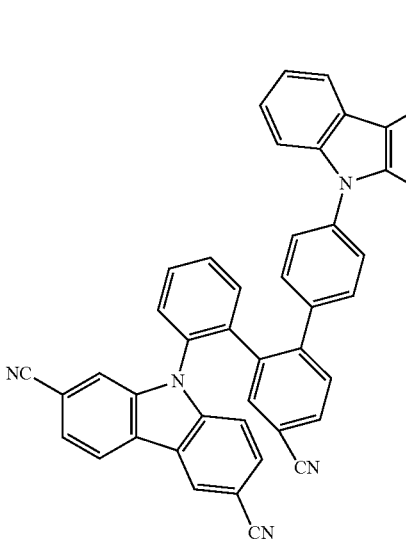

-continued
1011
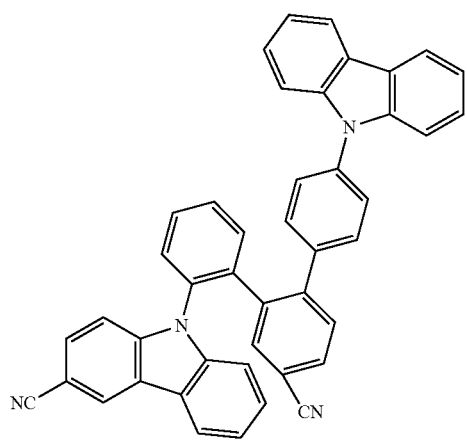
1012
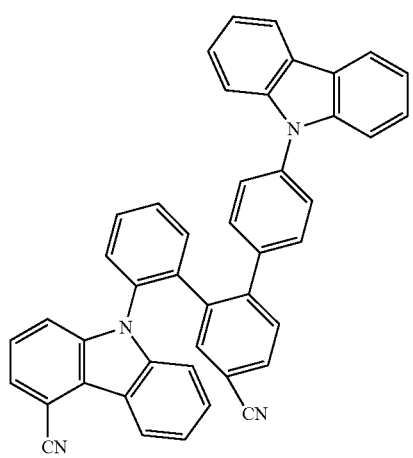
1013
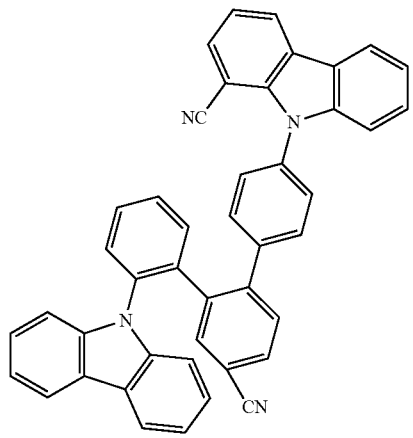
-continued
1014
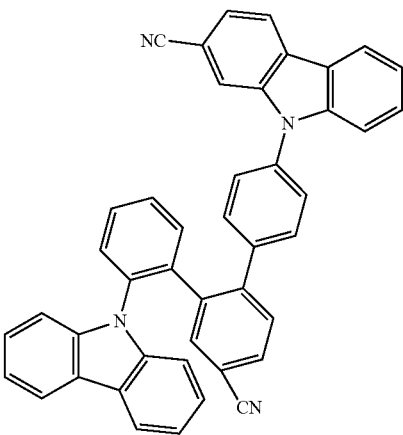
1015
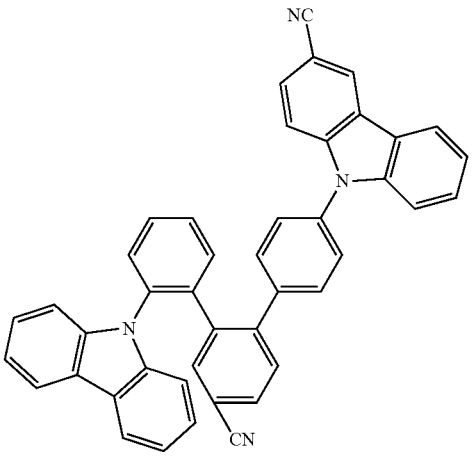
1016
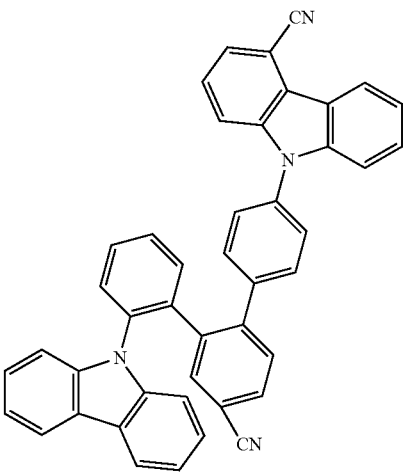

283
-continued
1017
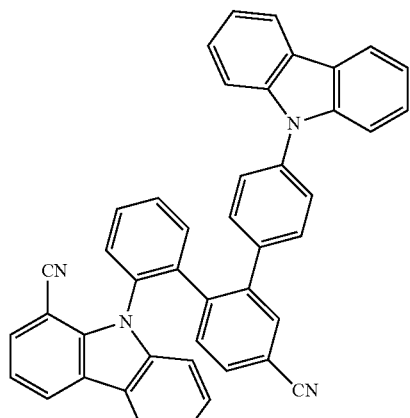
1018
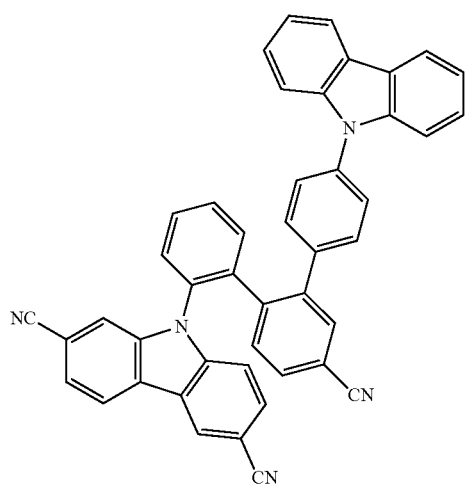
1019
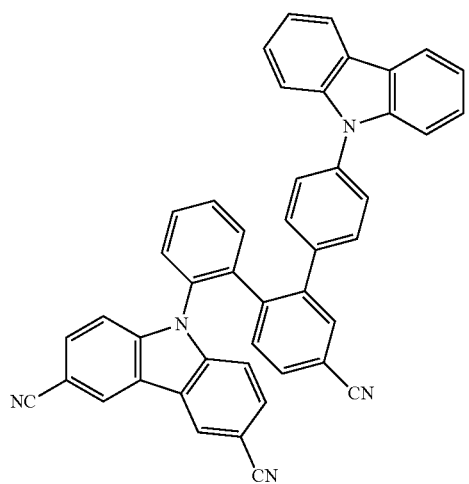
284
-continued
1020
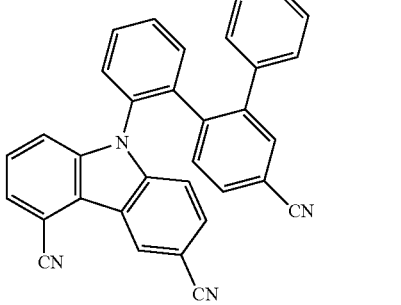
1021
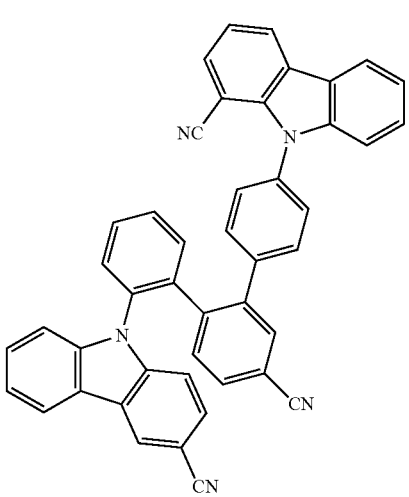
1022
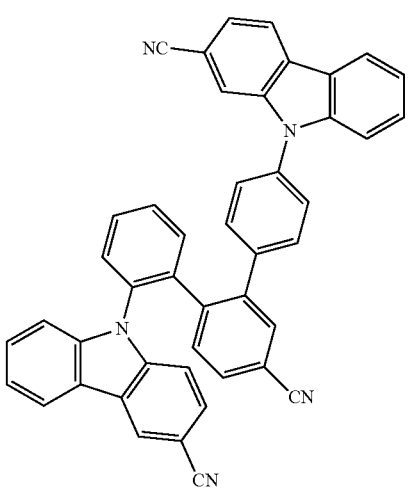

285
-continued
1023
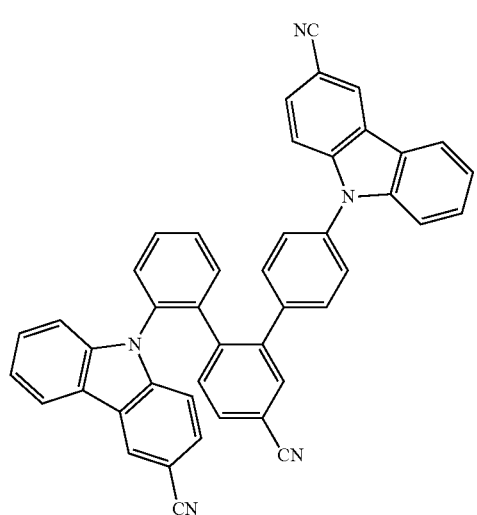
1024
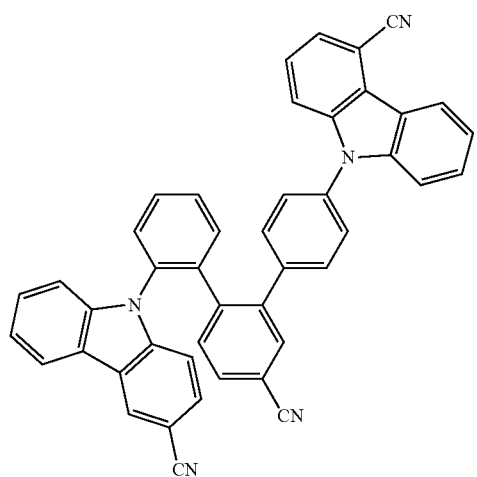
1025
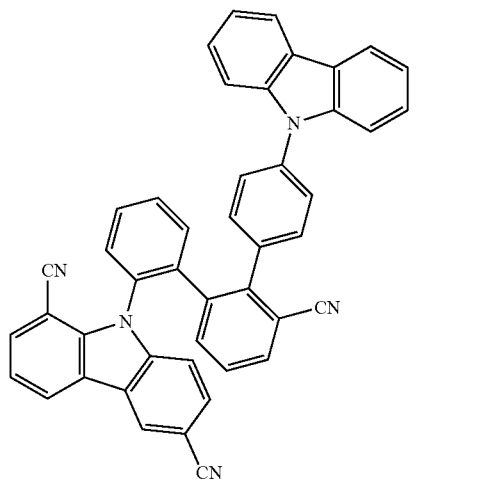
286
-continued
1026
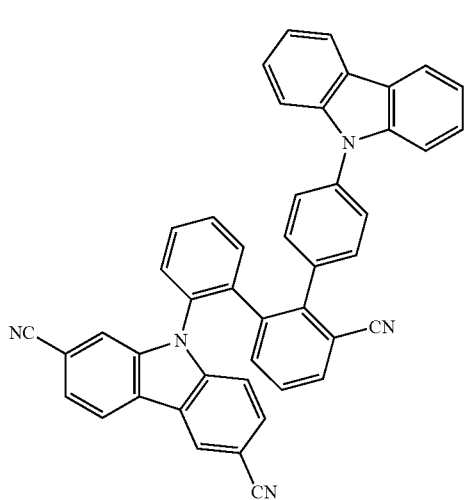
1027
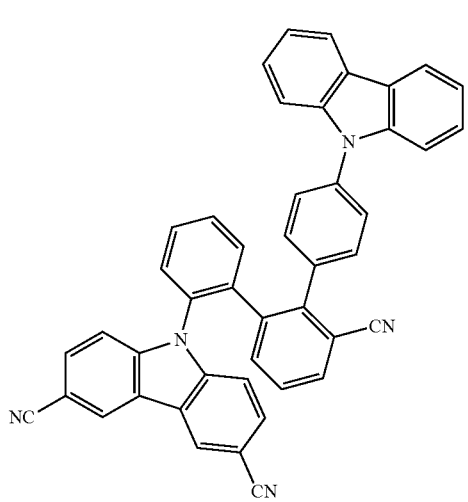
1028
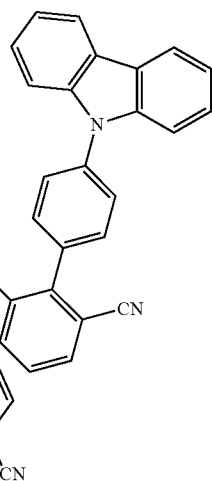

1029
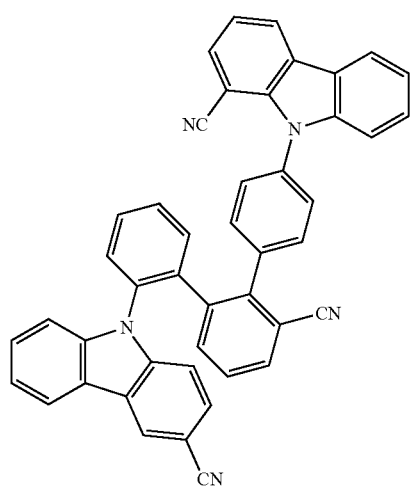
1030
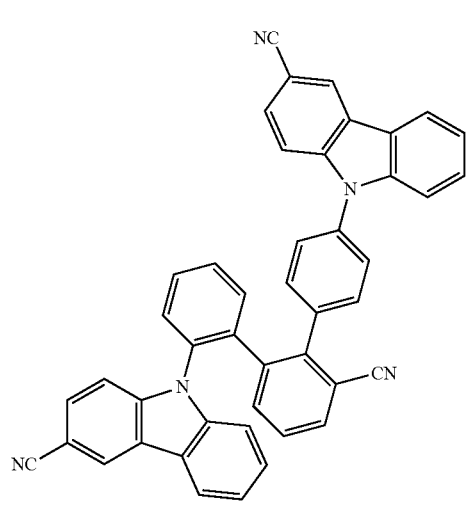
1031
1032
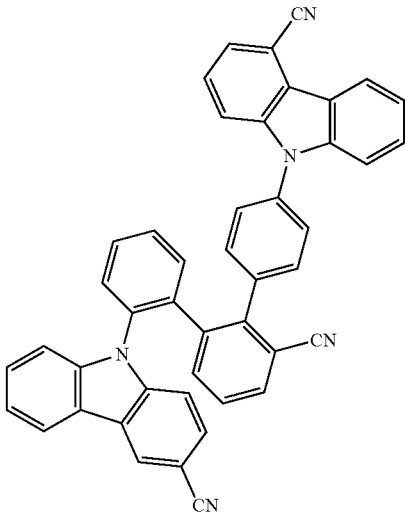
1033
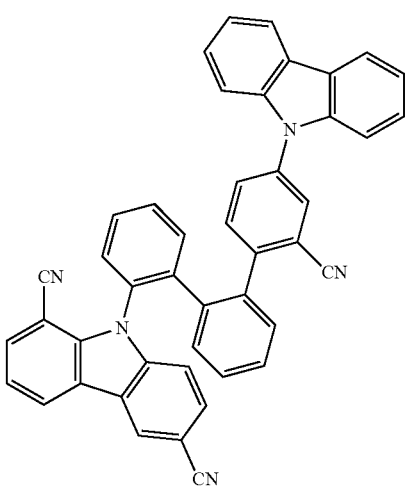
1034
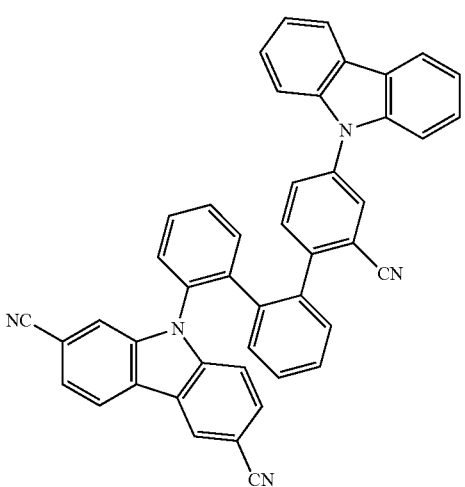

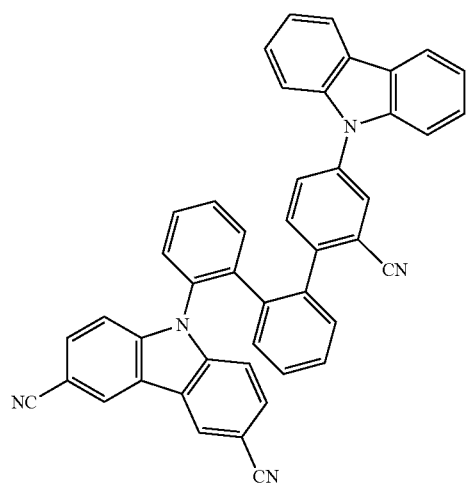
1035
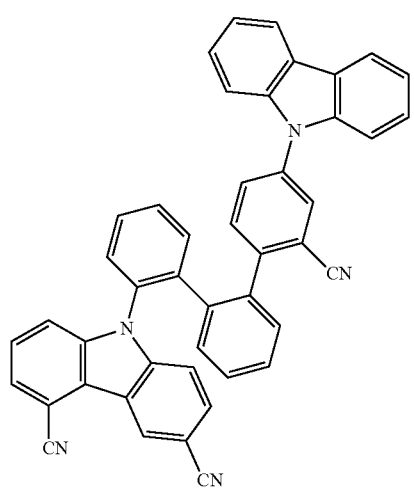
1036
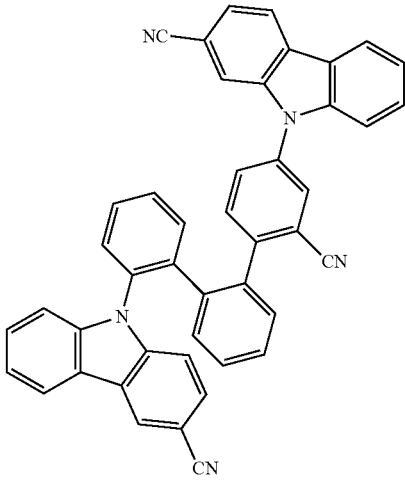
1038
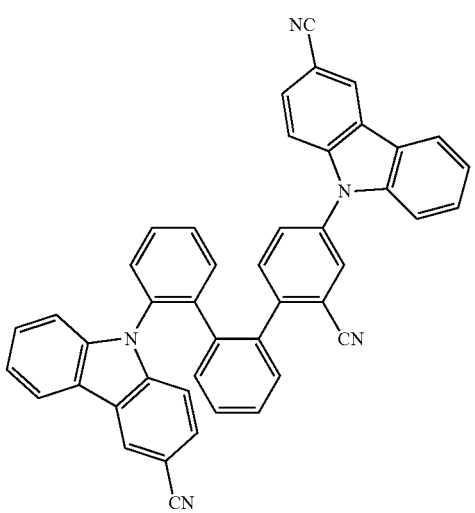
1039
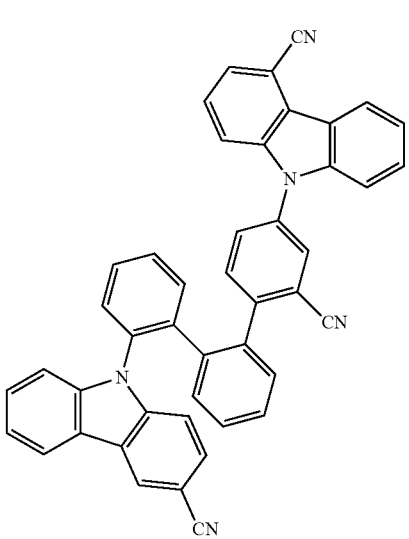
1040

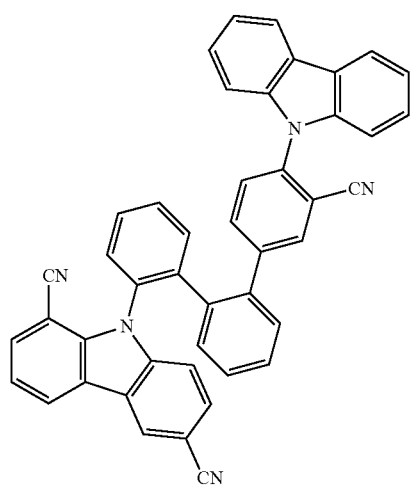
1041
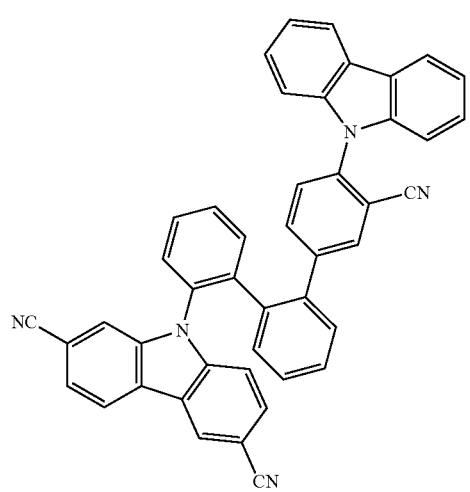
1042
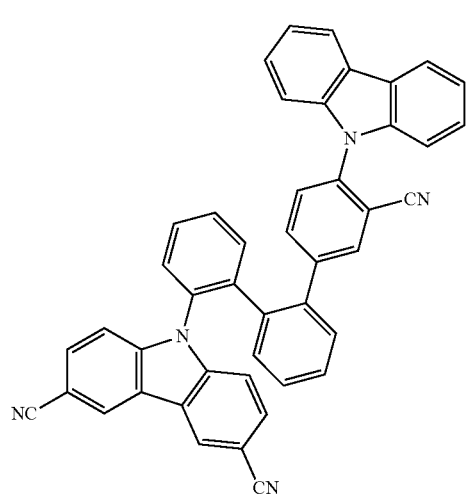
1043
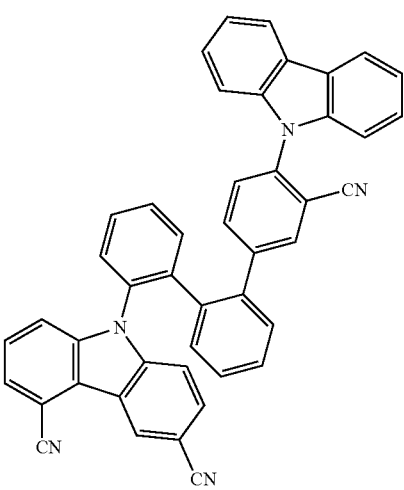
1044
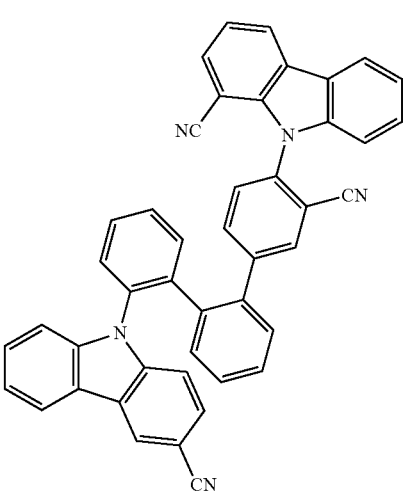
1045
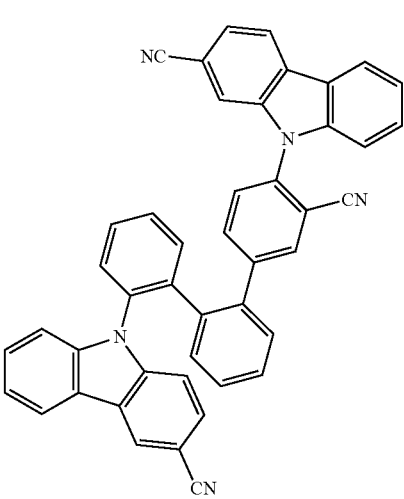
1046

-continued
1047
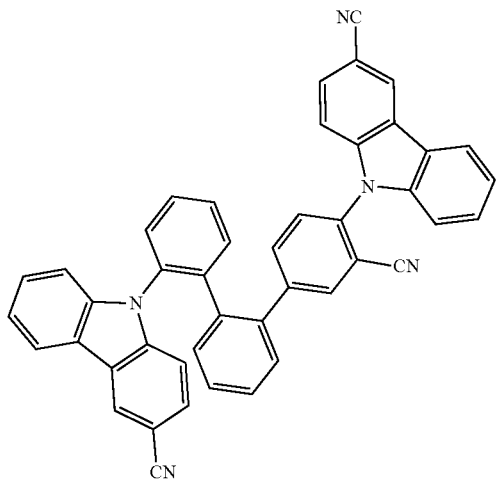
1048
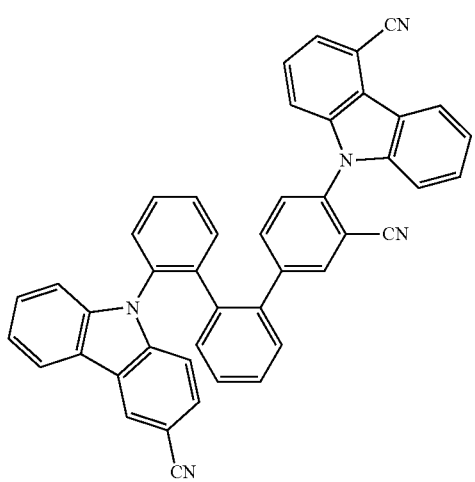
1049
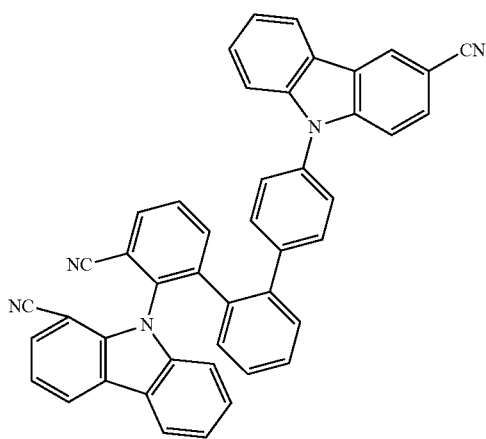
-continued
1050
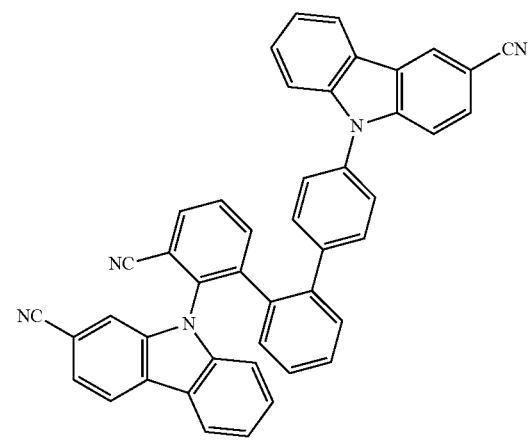
1051
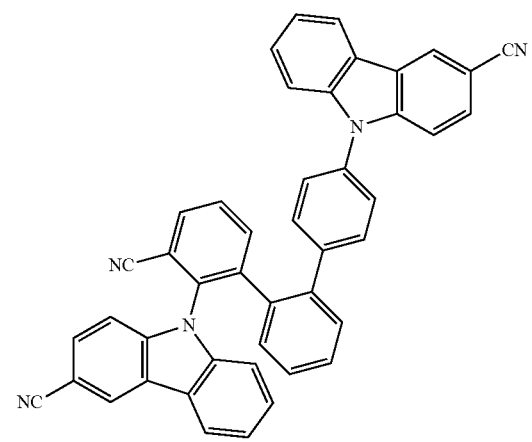
1052
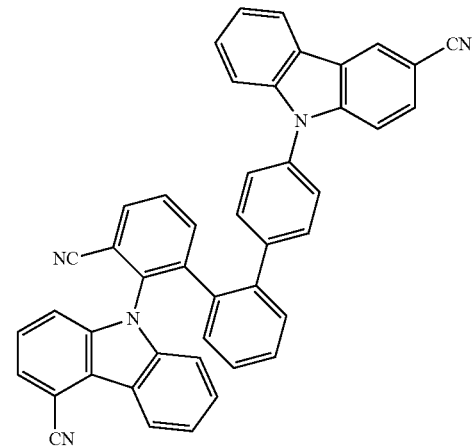

-continued
1053
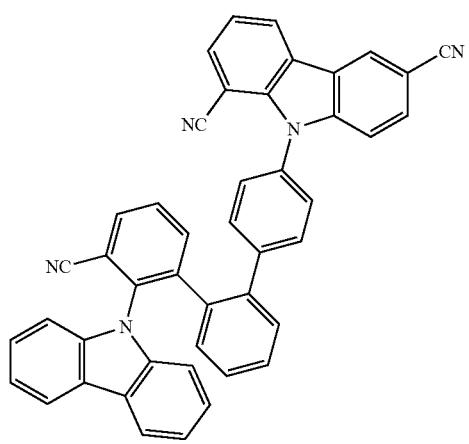
1054
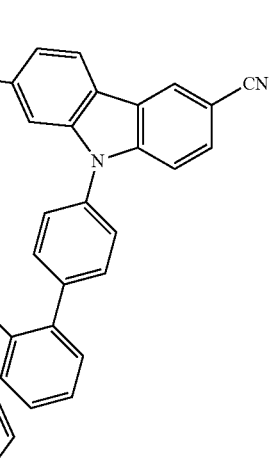
1055
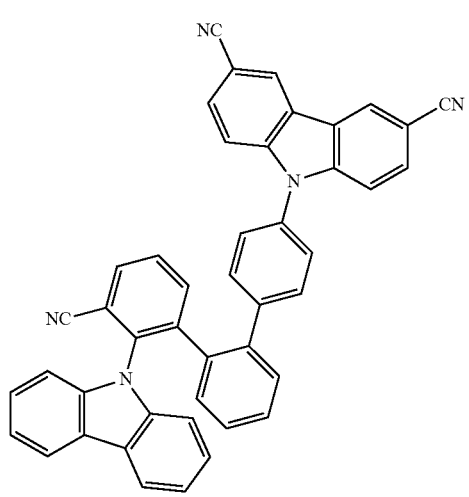
-continued
1056
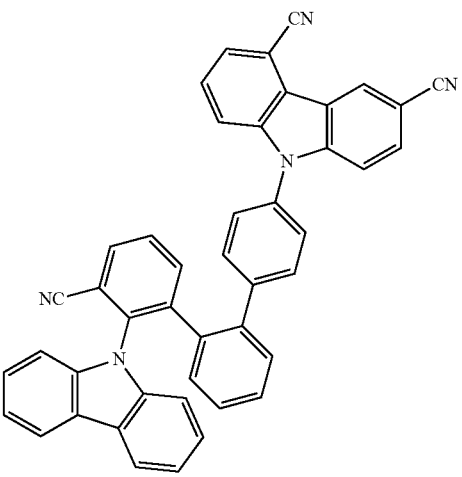
1057
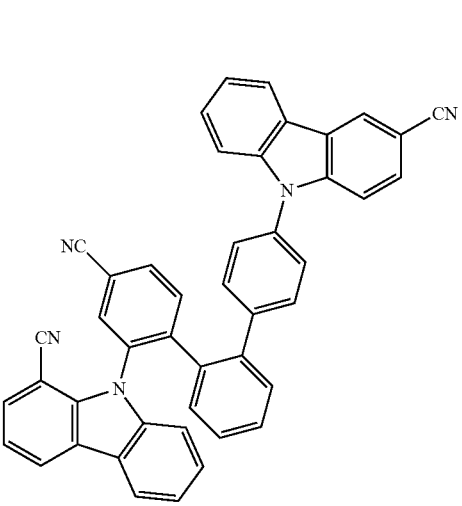
1058
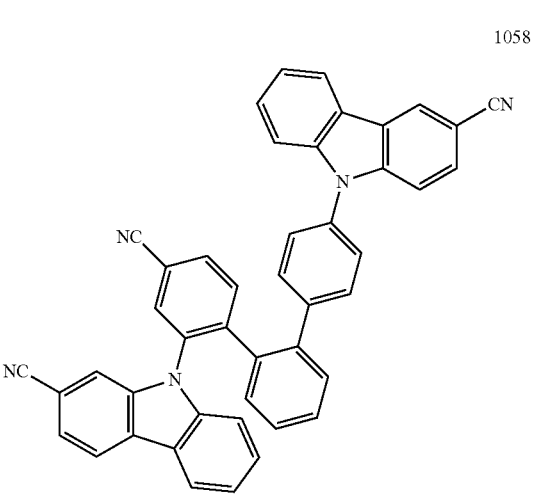

-continued
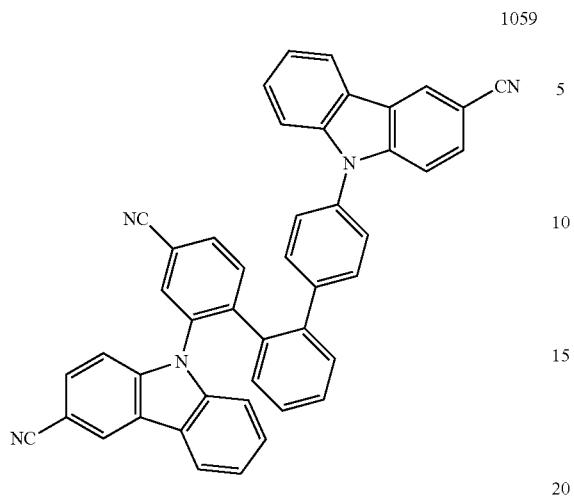
1059
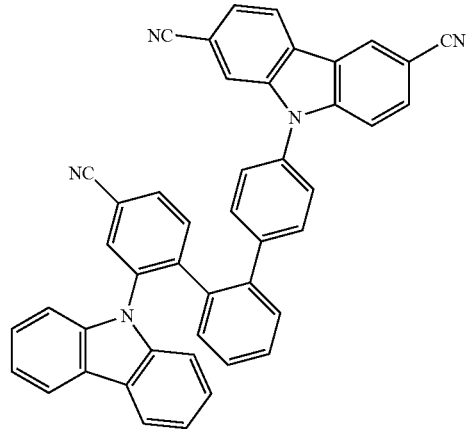
1062
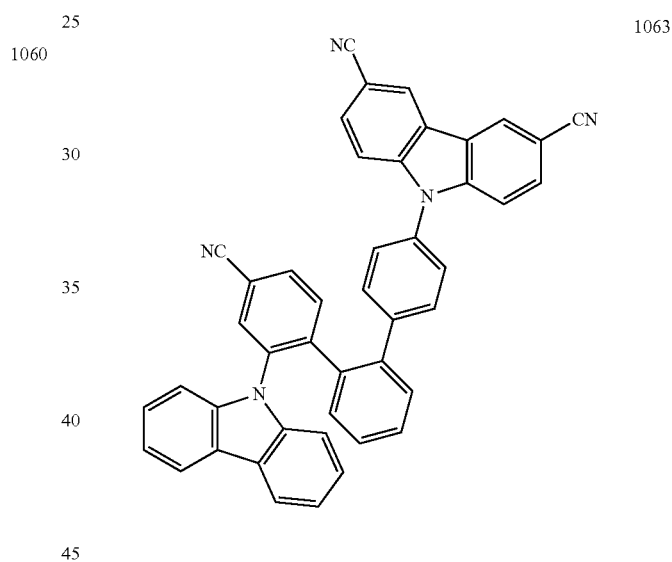
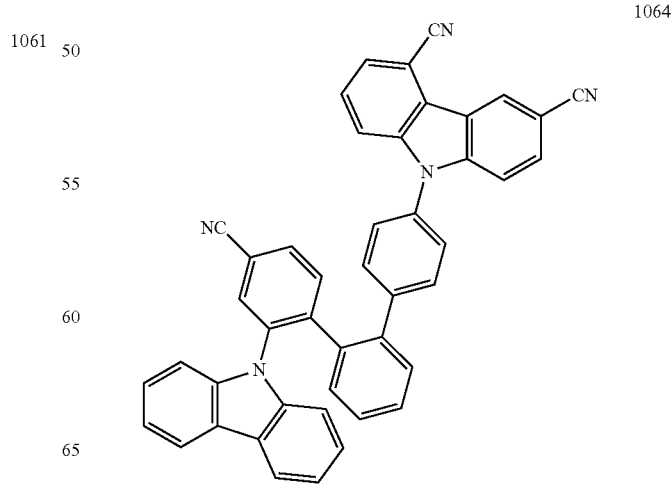

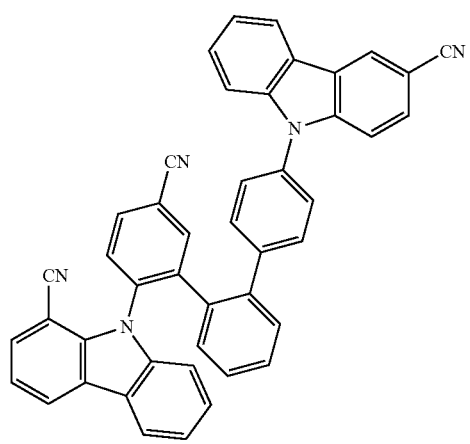
1065
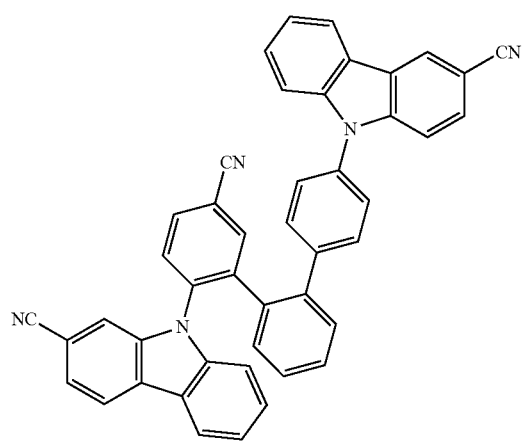
1066
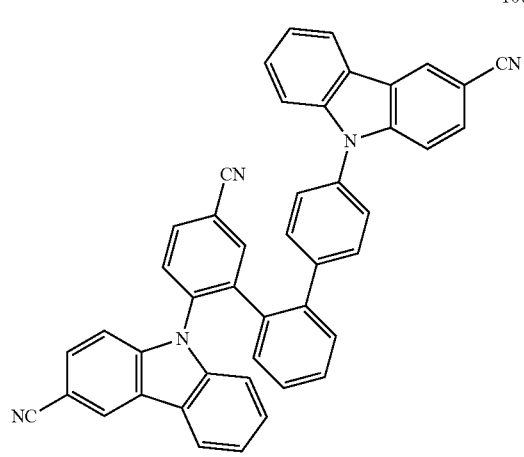
1067
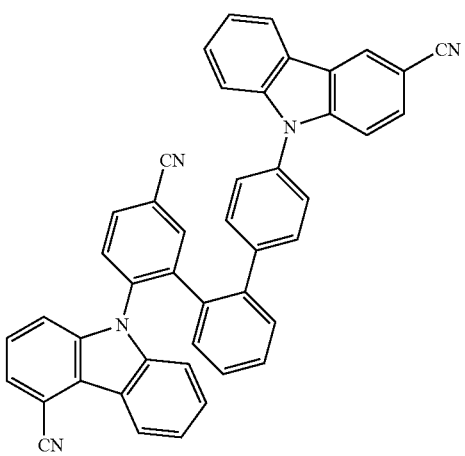
1068
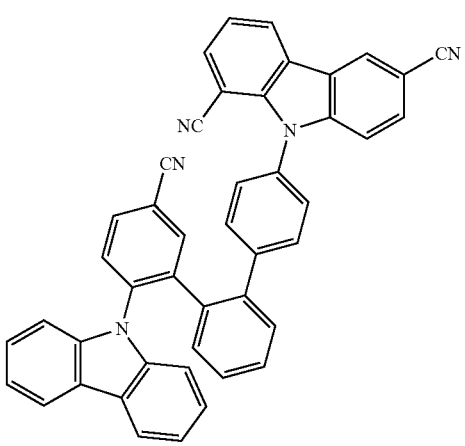
1069
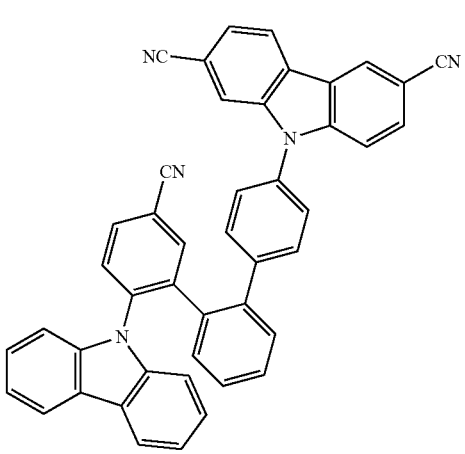
1070

301
-continued
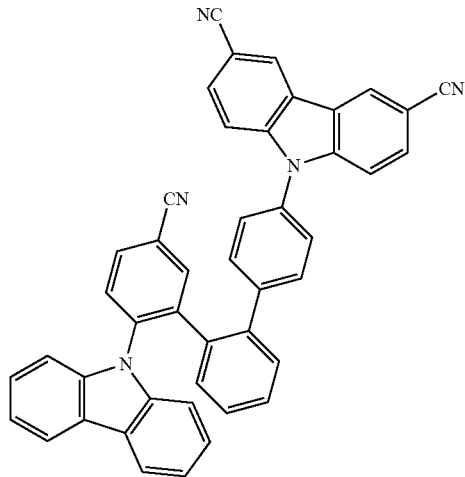
1071
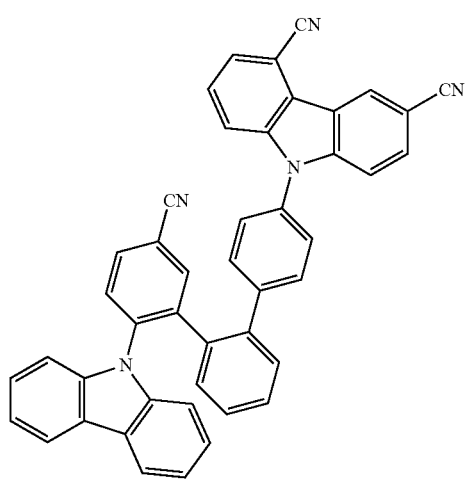
1072
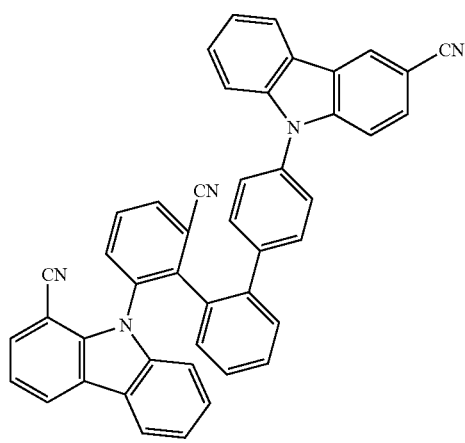
1073
302
-continued
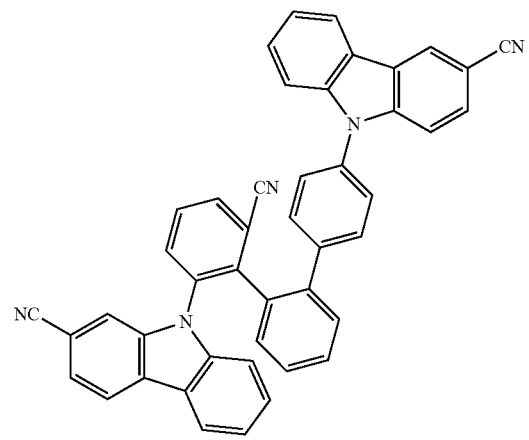
1074
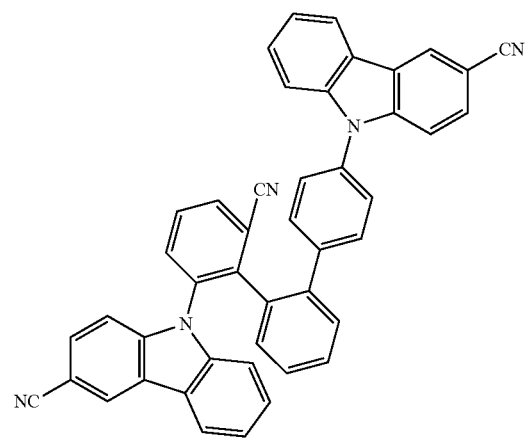
1075
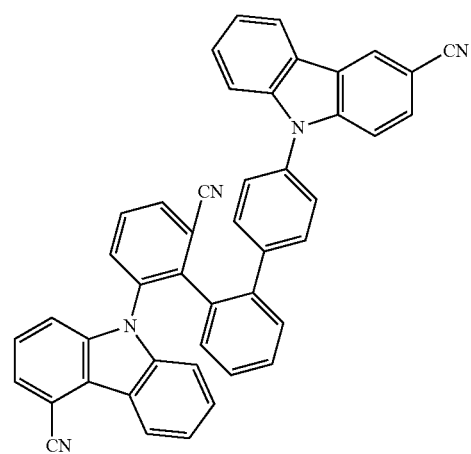
1076

| 303 -continued | 304 -continued |
|---|---|
| 1077 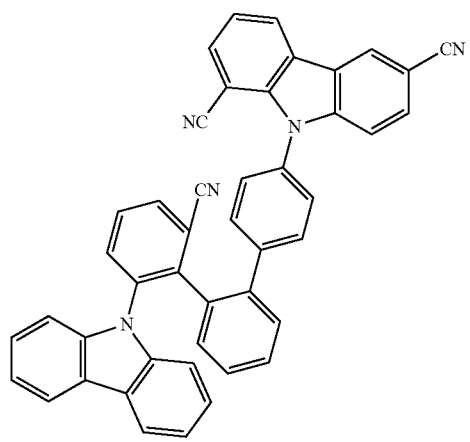 | 1080 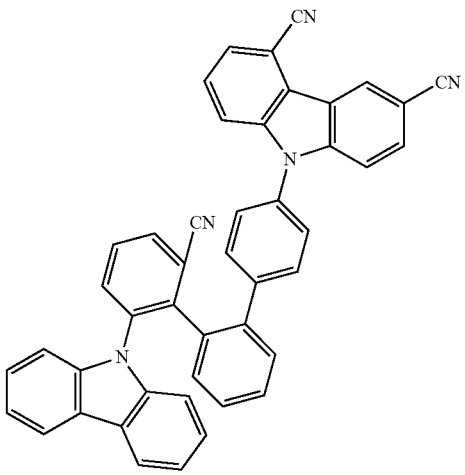 |
| 1078 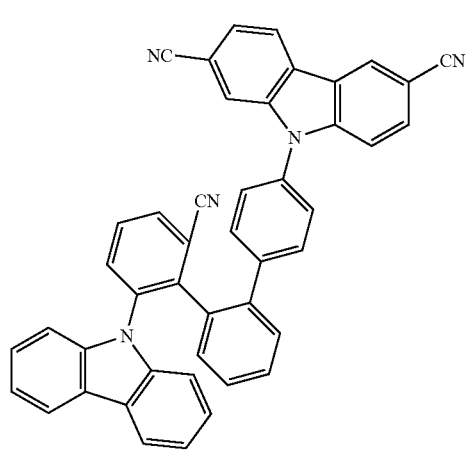 | 1081 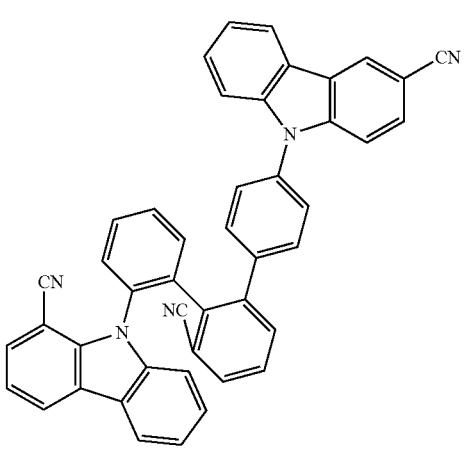 |
| 1079 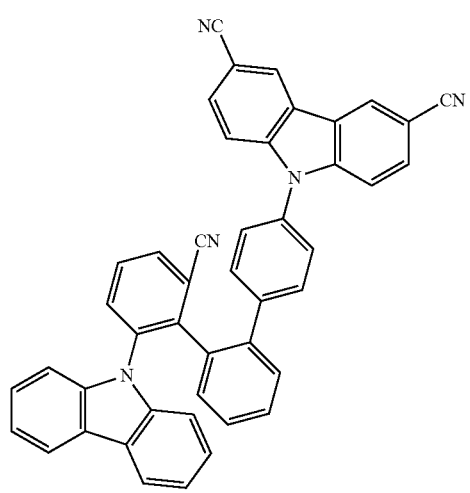 | 1082 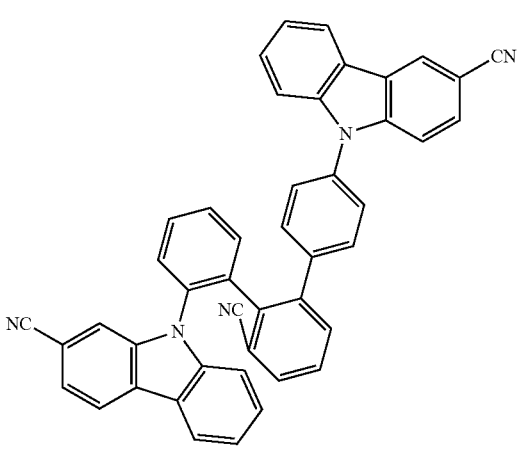 |

305
-continued
1083
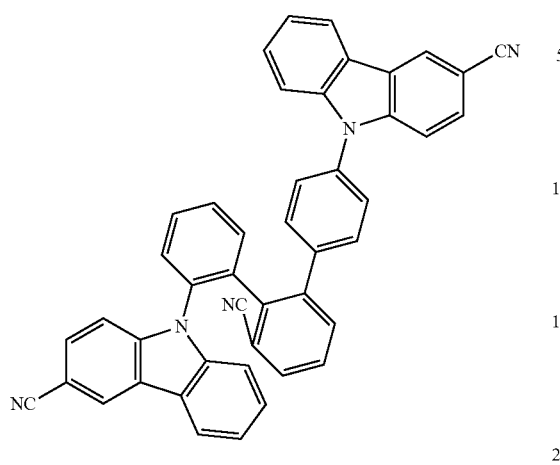
1084
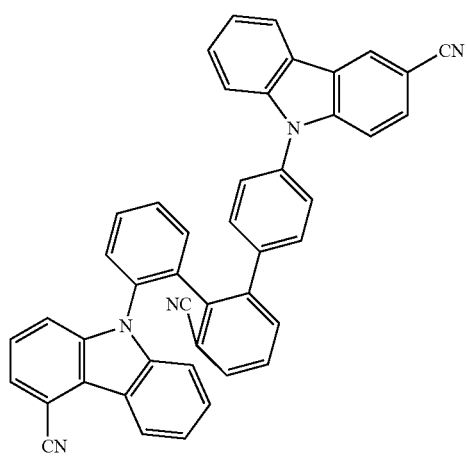
1085
306
-continued
1086
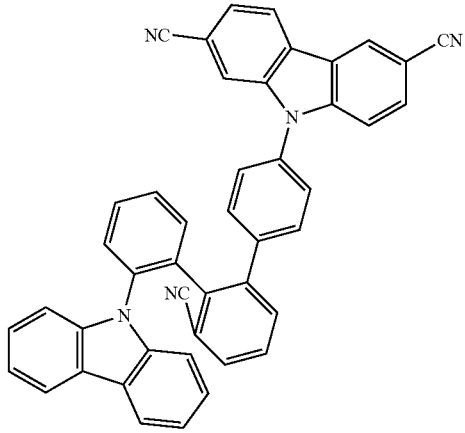
1087
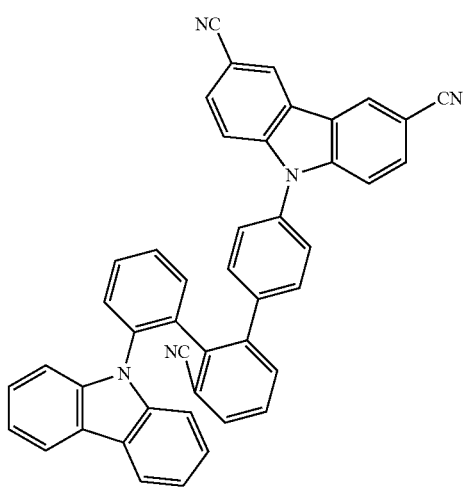
1088
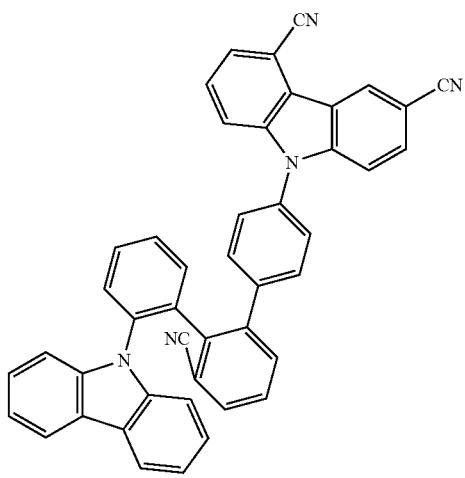

1089 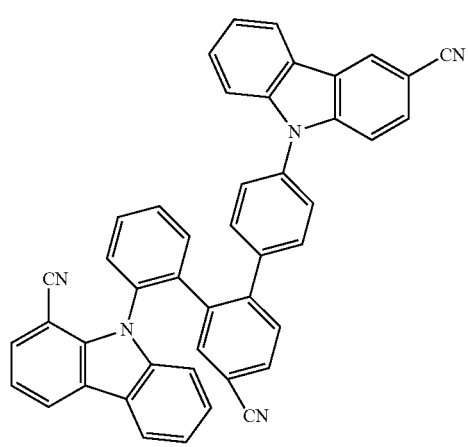
1090 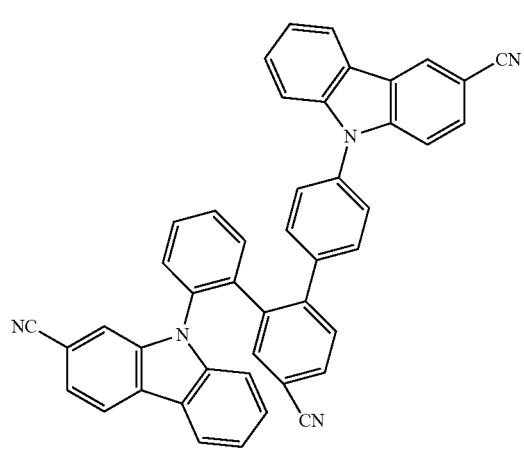
1091 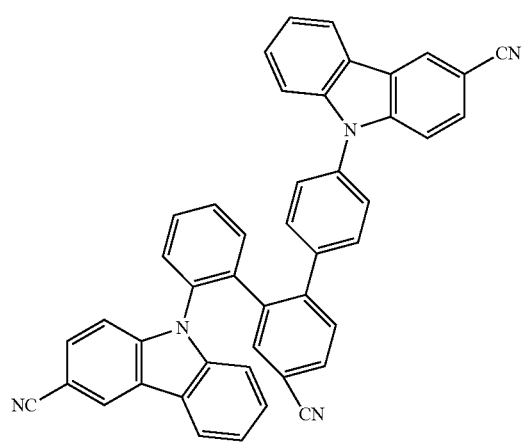
1092 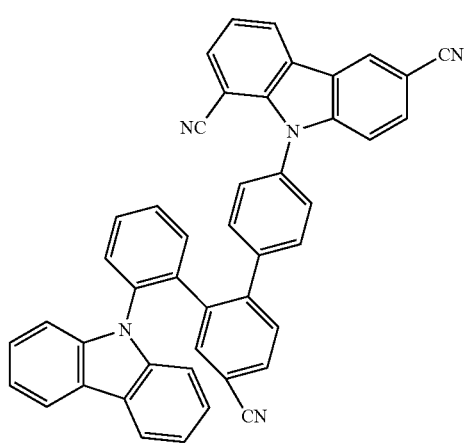
1093 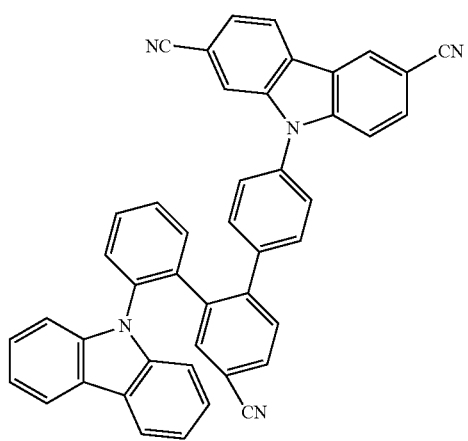
1094

309
-continued
1095
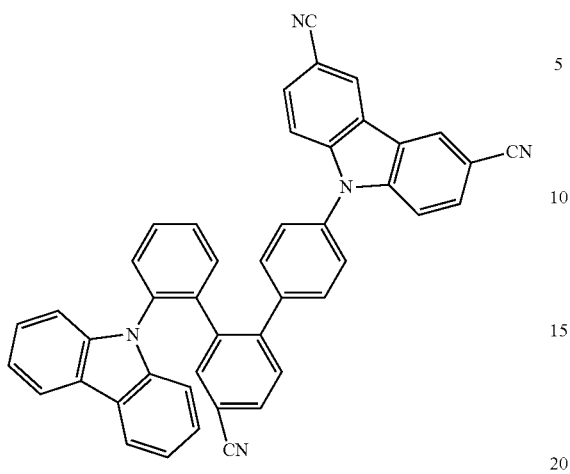
1096
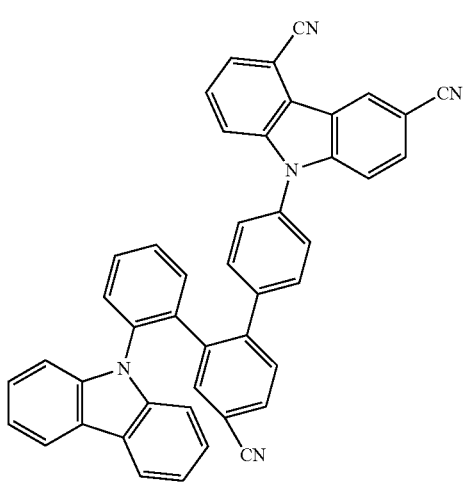
1097
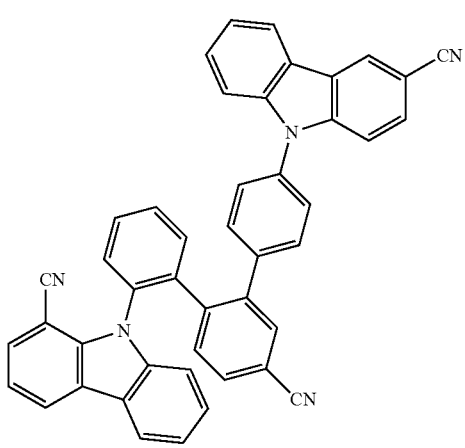
310
-continued
1098
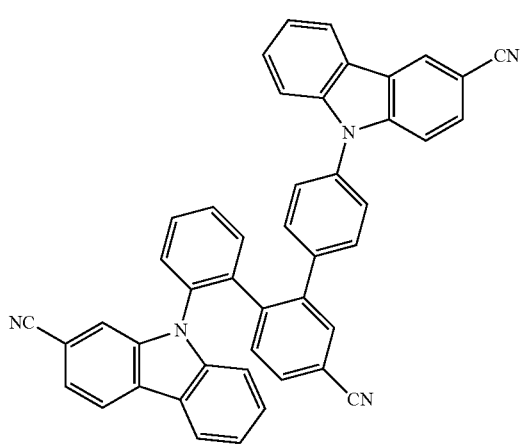
1099
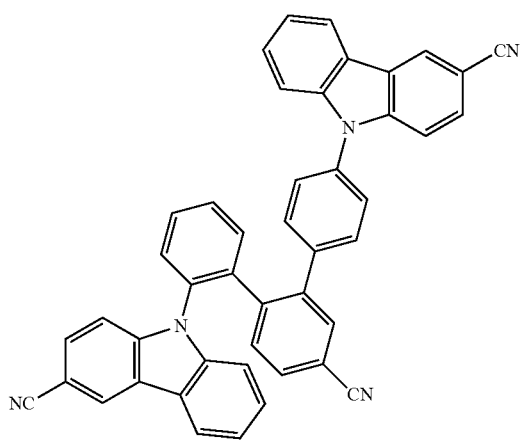
1100
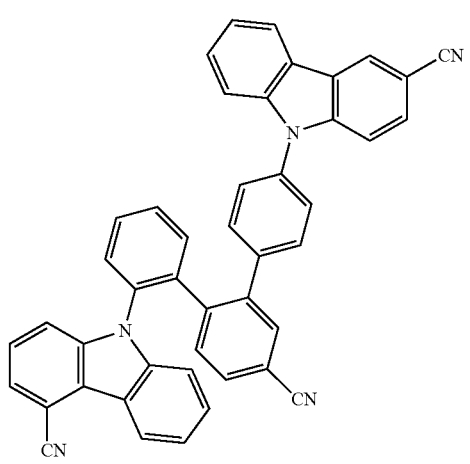

-continued
1101
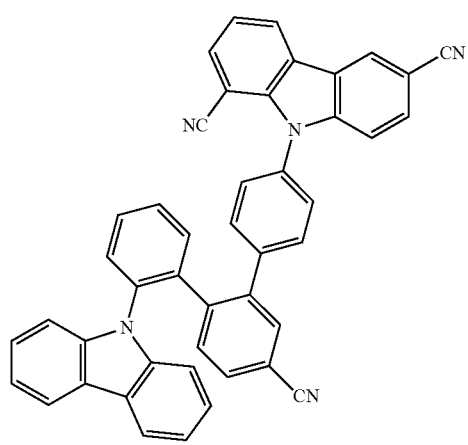
1102
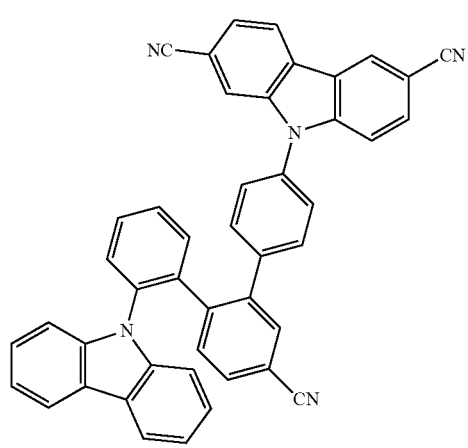
1103
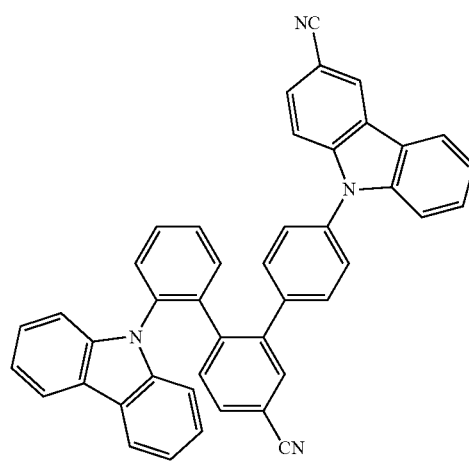
-continued
1104
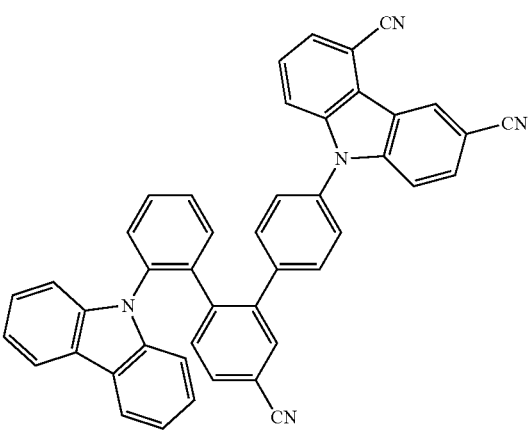
1105
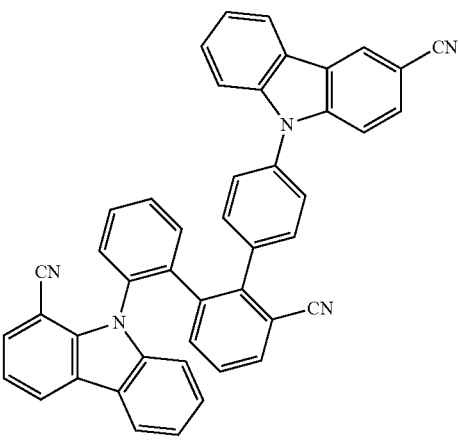
1106
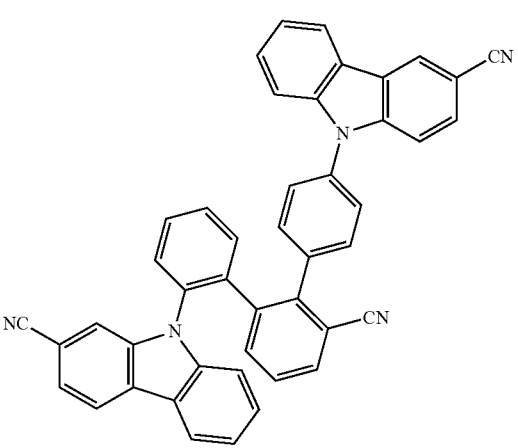

-continued
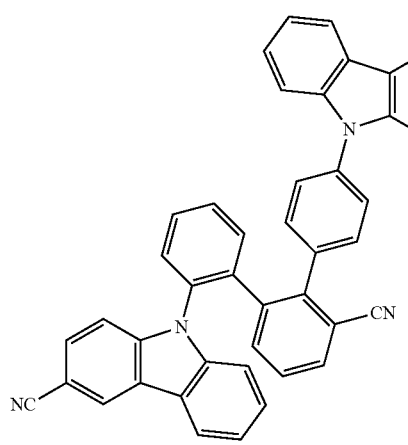
1107
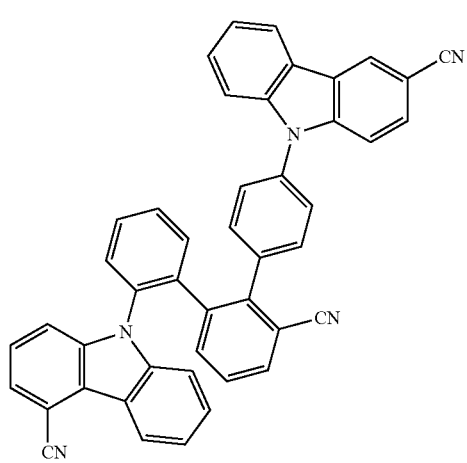
1108
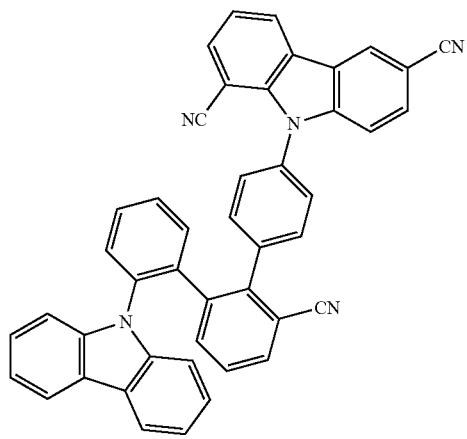
1109
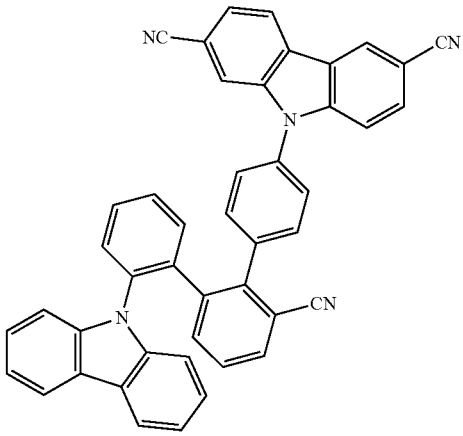
1110
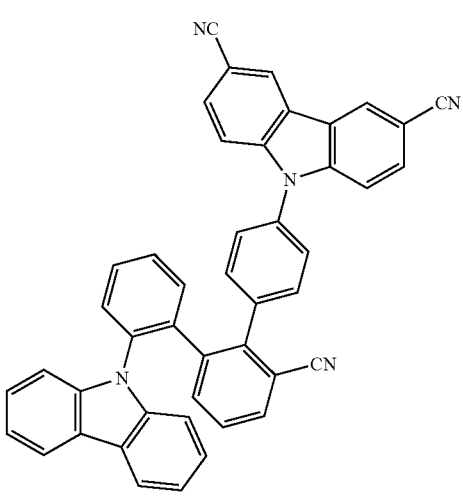
1111
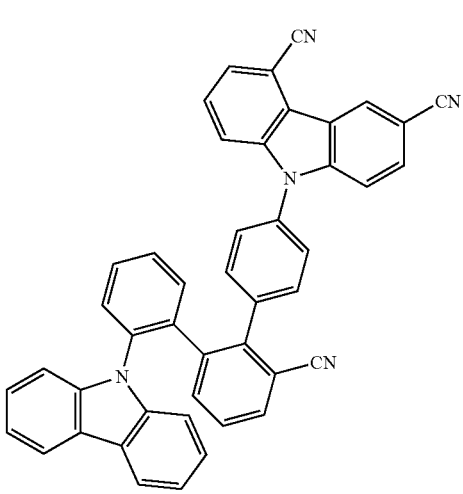
1112

315
-continued
1113
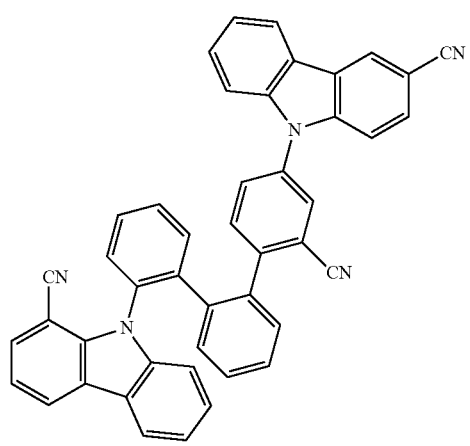
1114
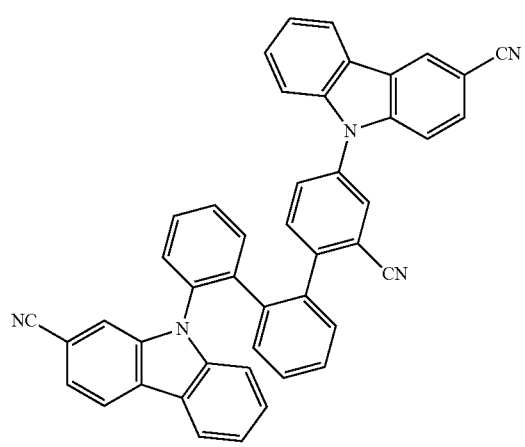
1115
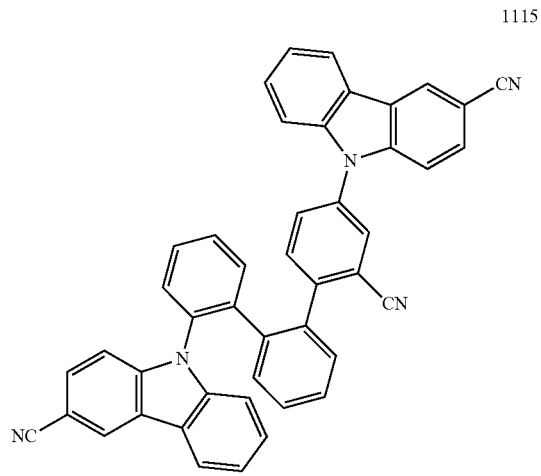
316
-continued
1116
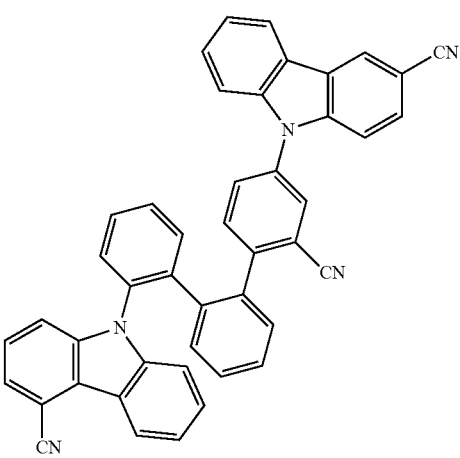
1117
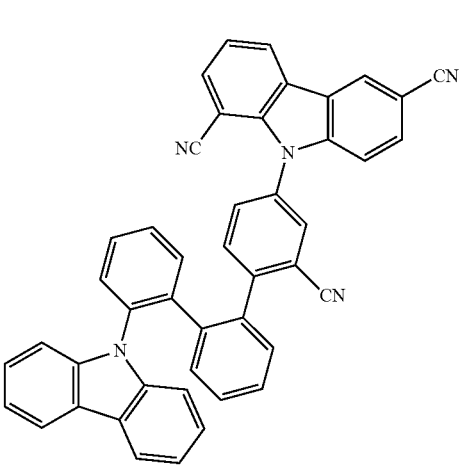
1118
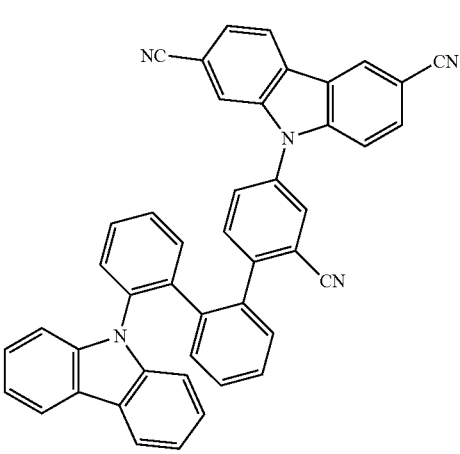

-continued
1119
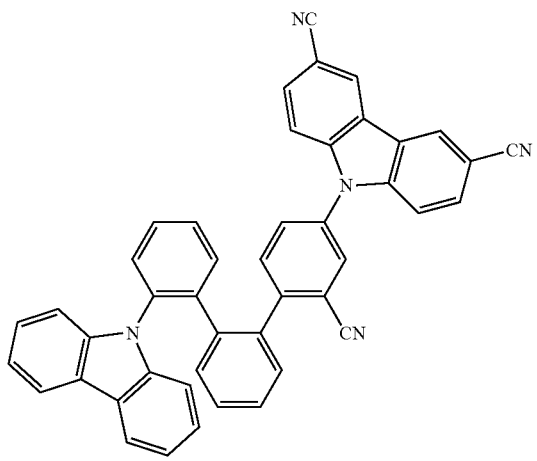
1120
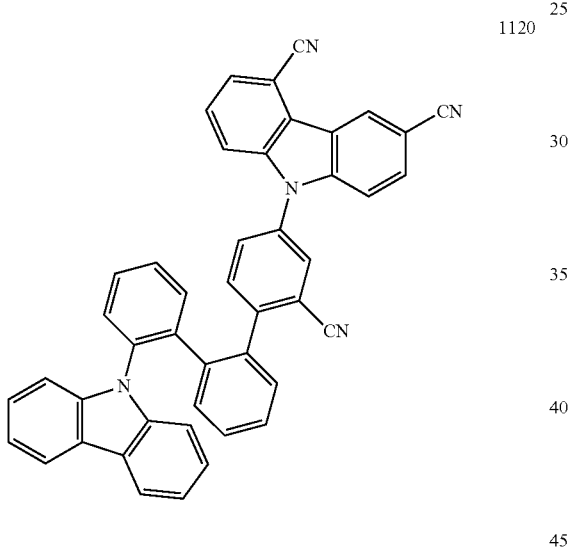
1121
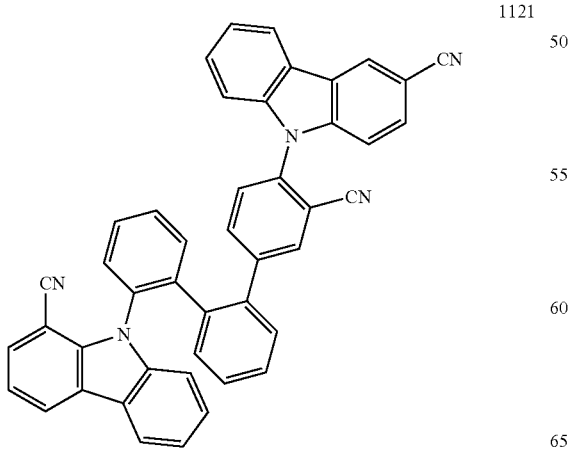
-continued
1122
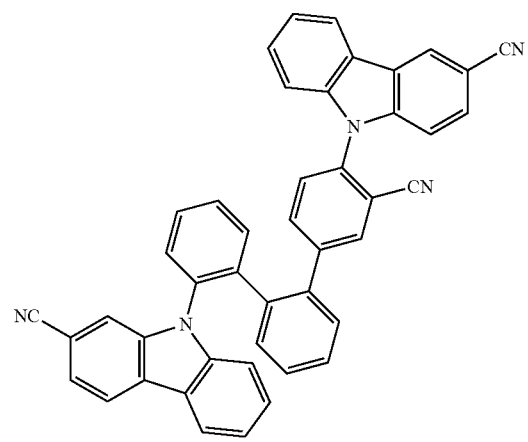
1123
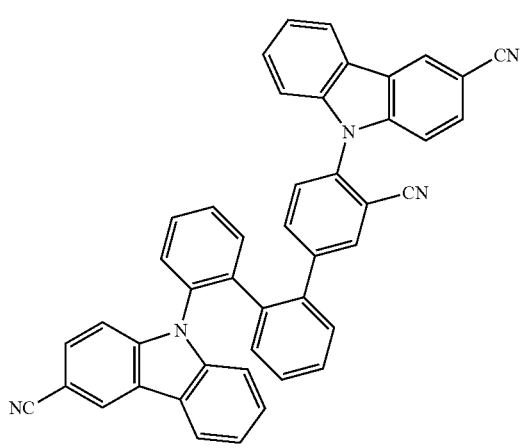
1124
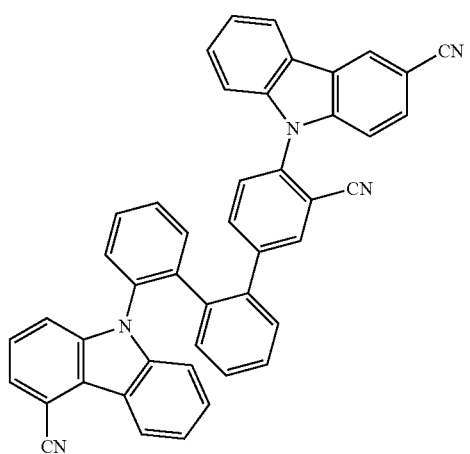

-continued
1125
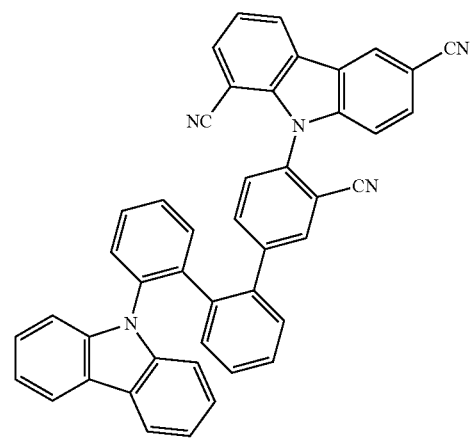
1126
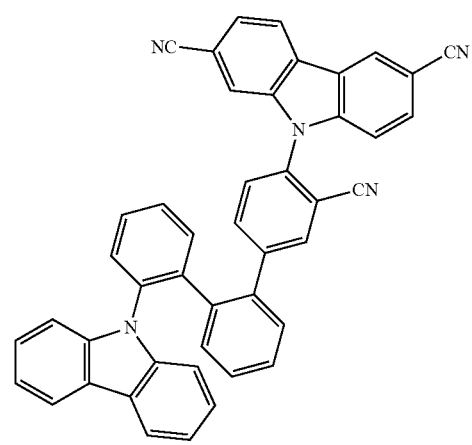
1127
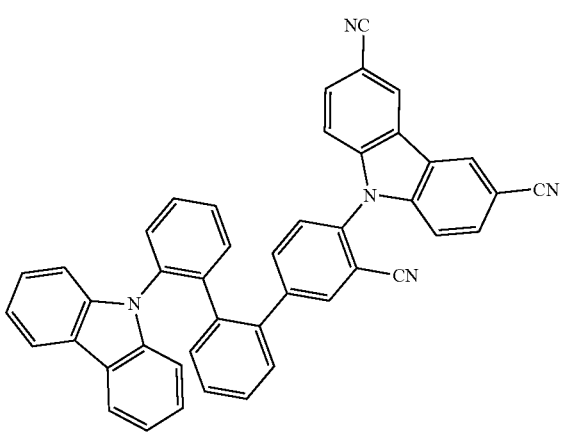
-continued
1128
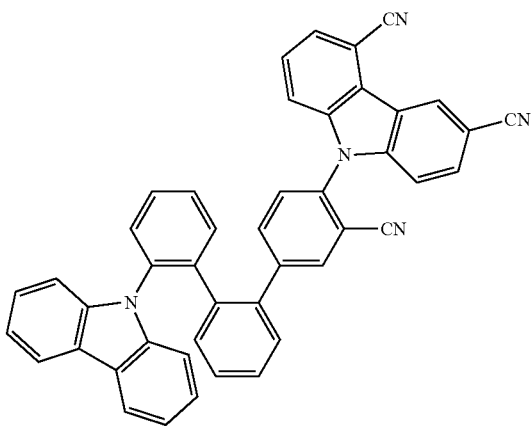
1129
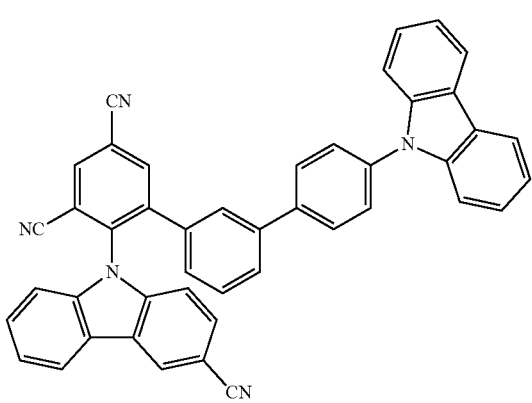
1130
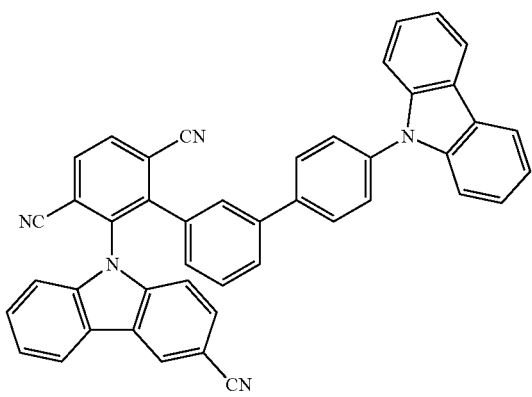
1131
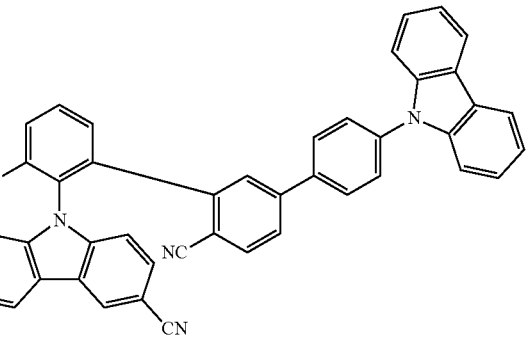

-continued
1132
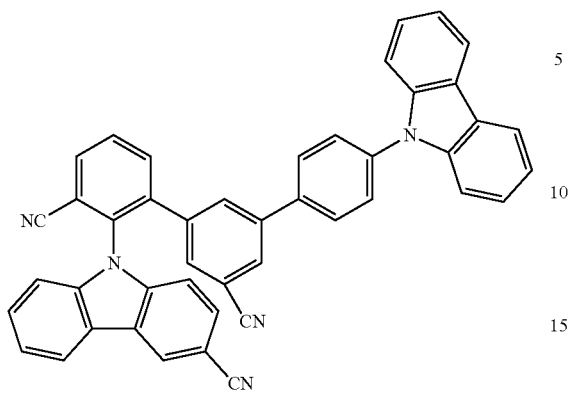
1133
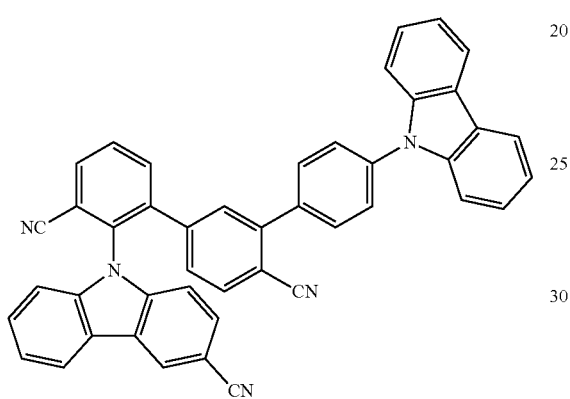
1134
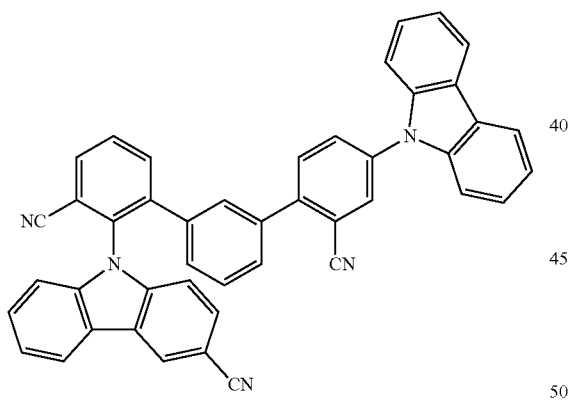
1135
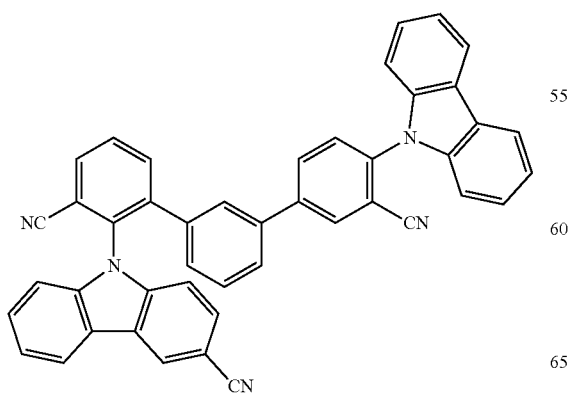
-continued
1136
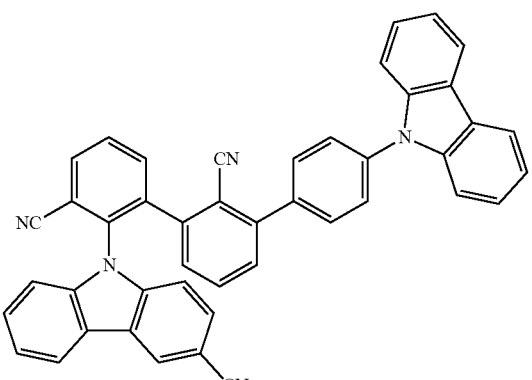
1137
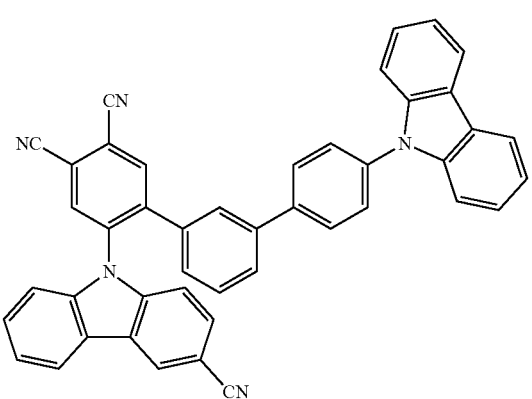
1138
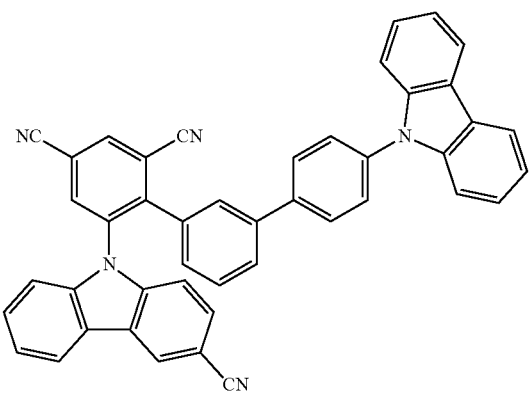
1139
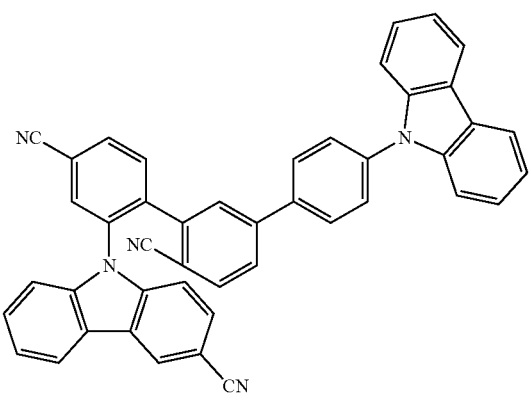

-continued
1140
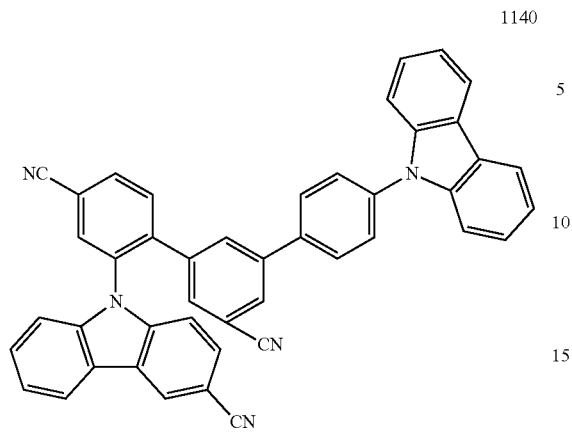
1141
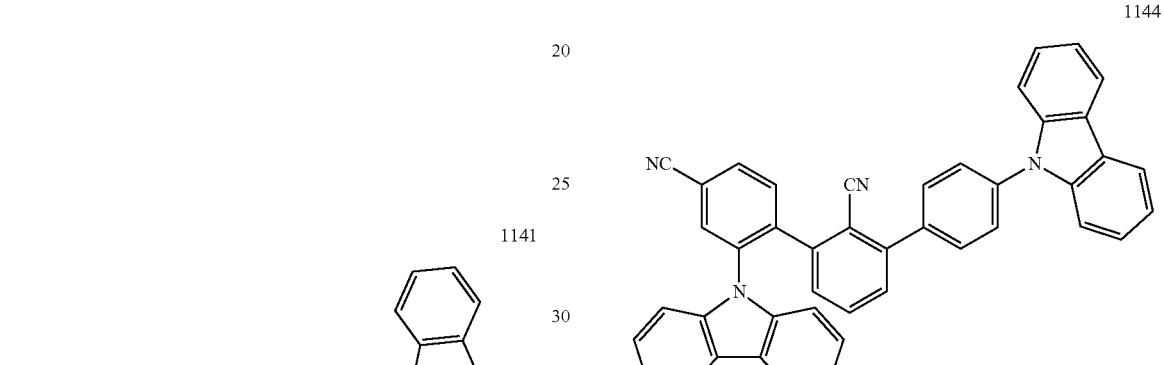
1142
-continued
1143
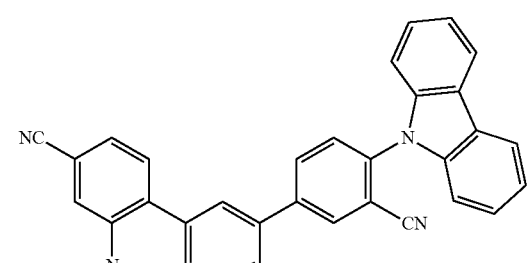
1144
1145
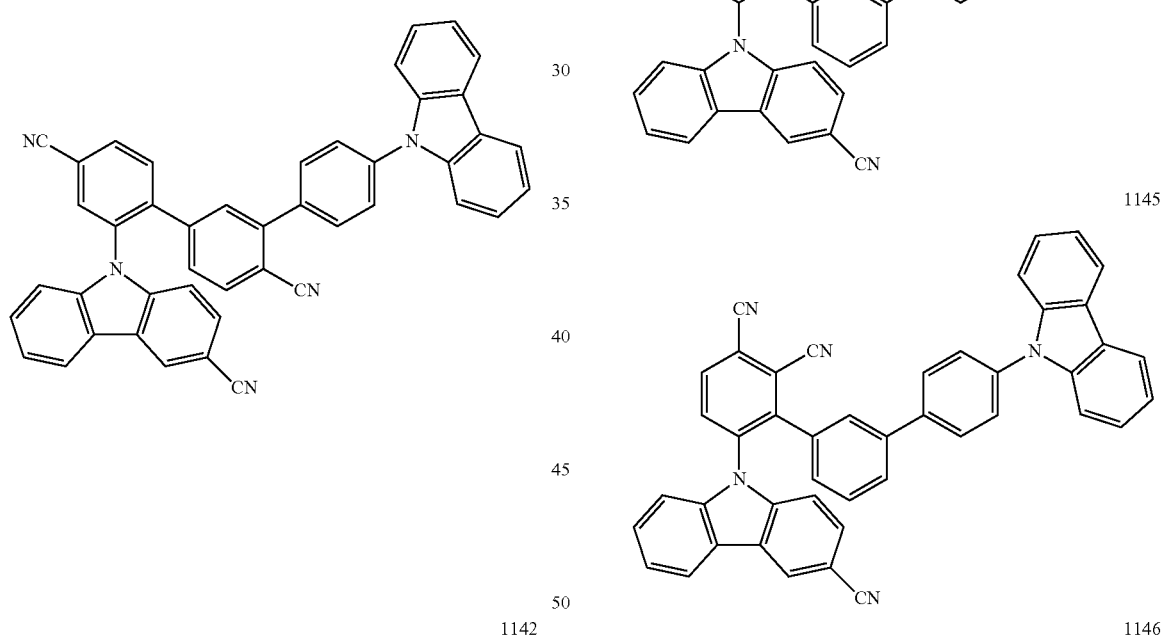
1146
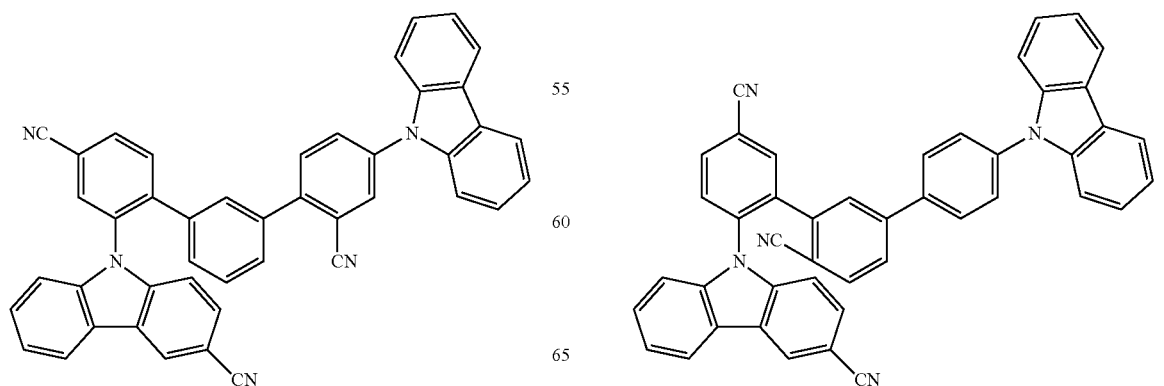

325
-continued
1147
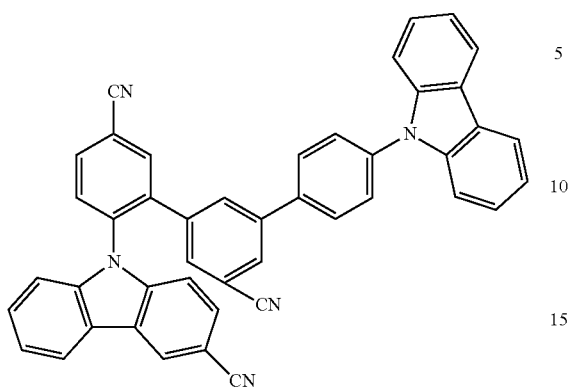
1148
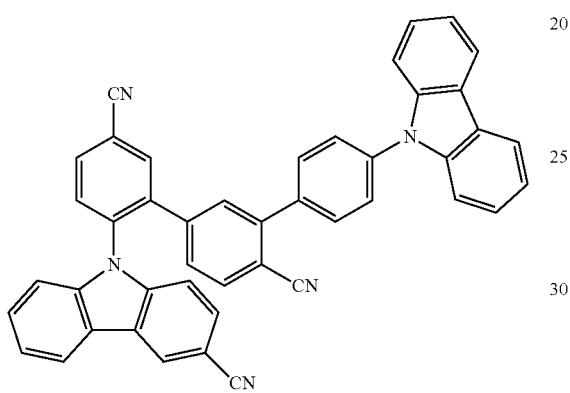
1149
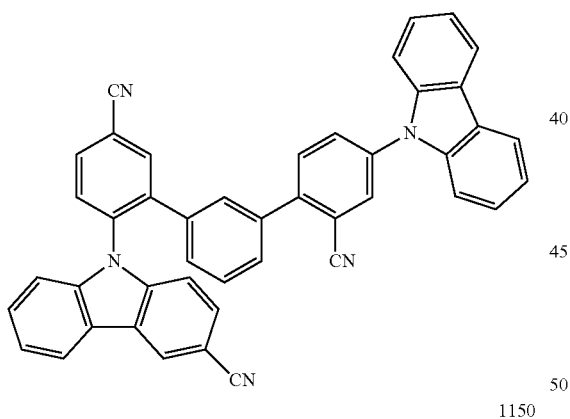
1150

326
-continued
1151
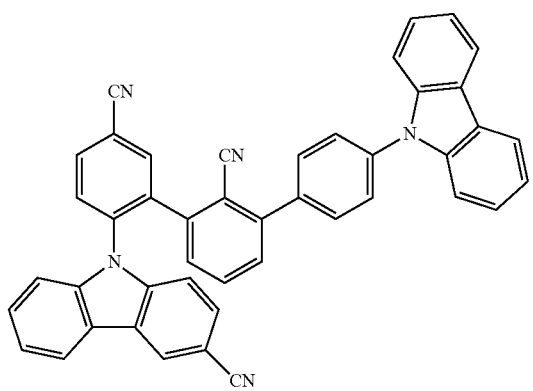
1152
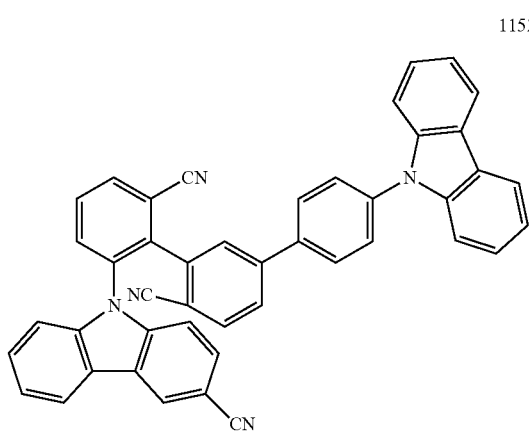
1153
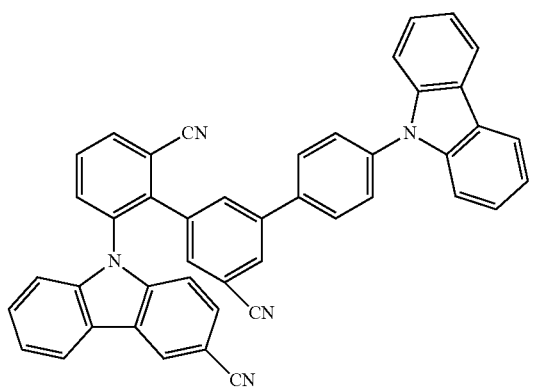
1154
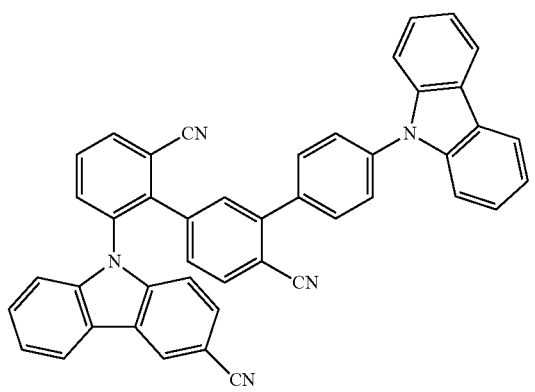

327
-continued
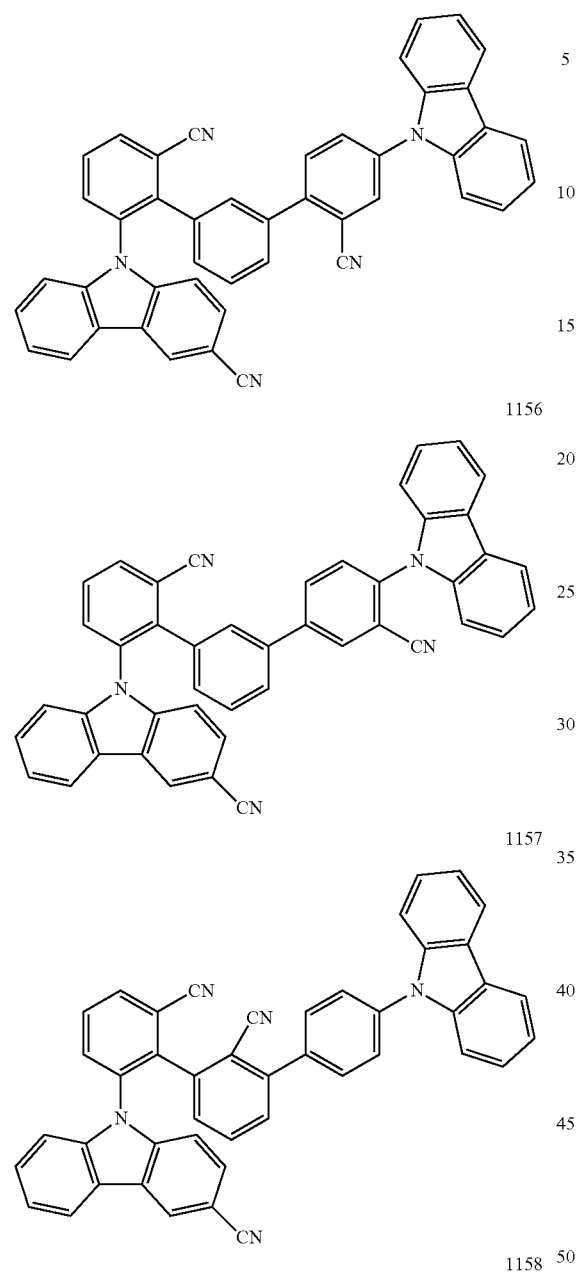
328
-continued
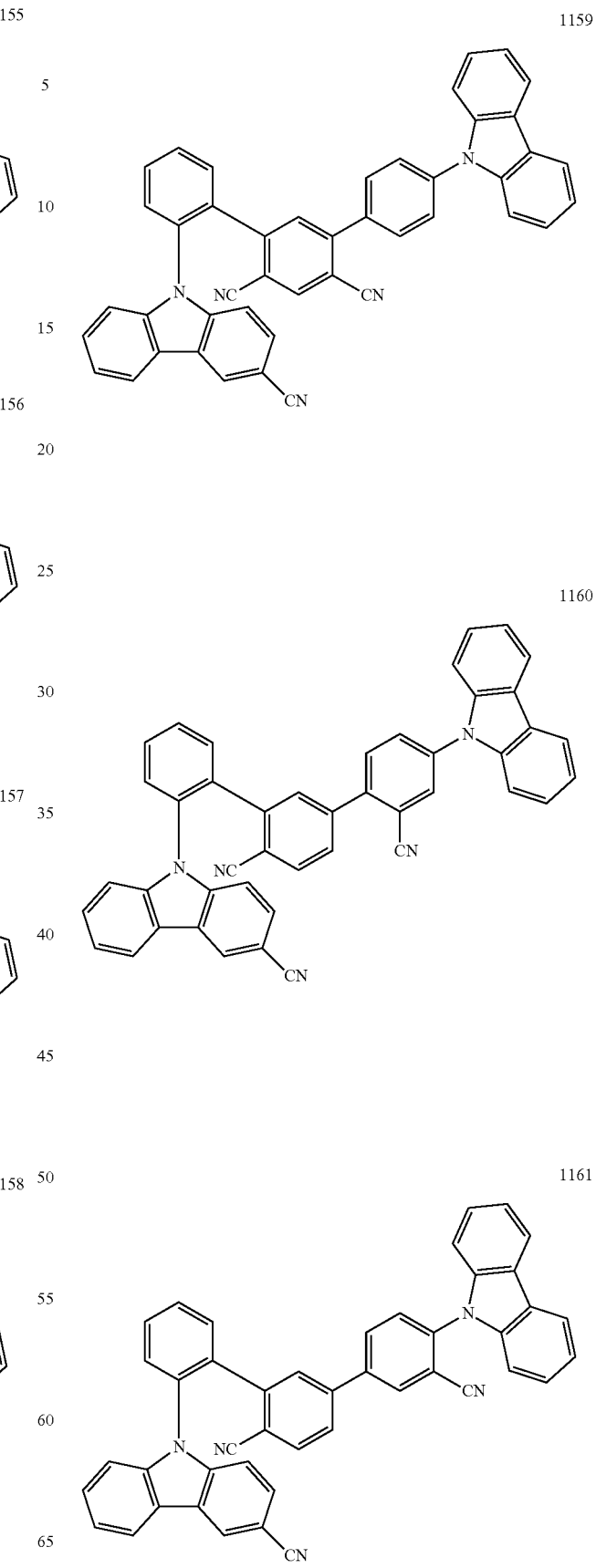

1162
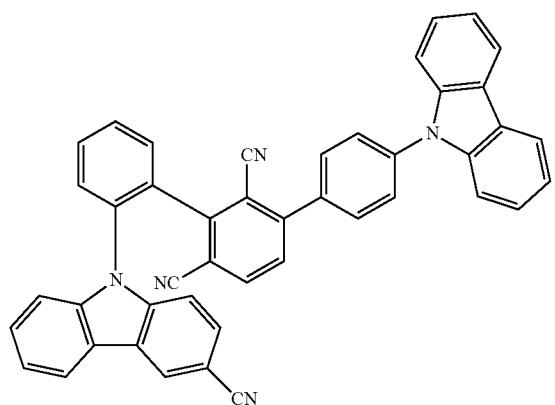
1163
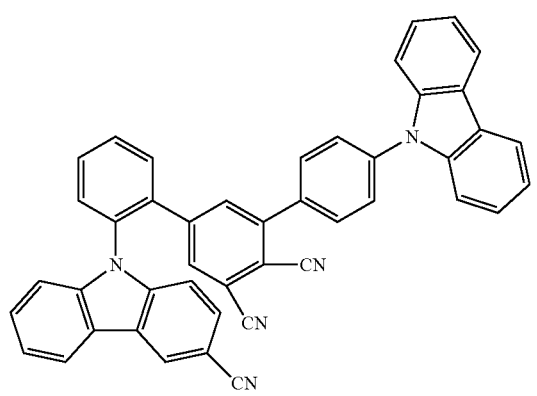
1164
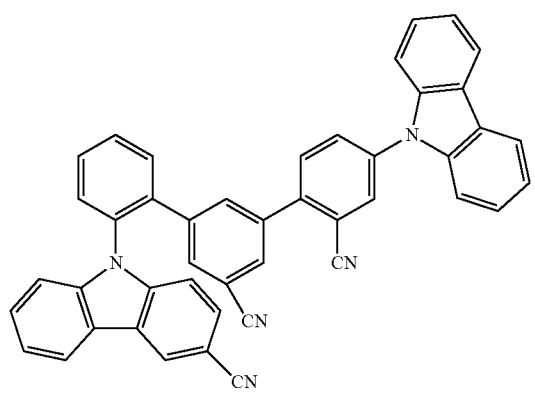
1165
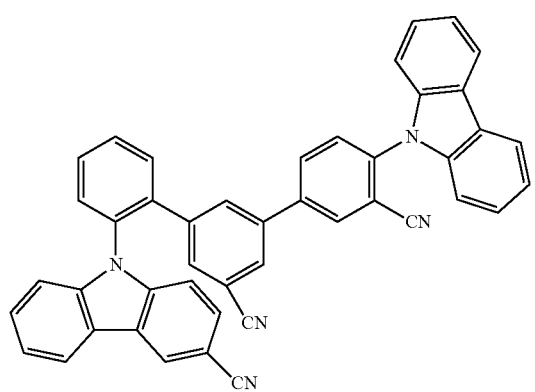
1166
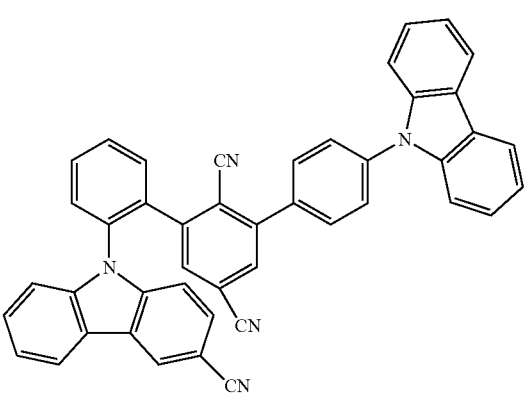
1167
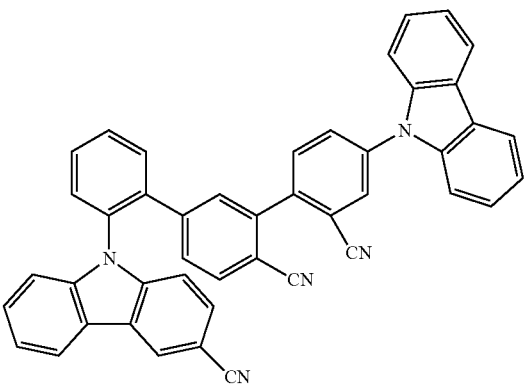
1168
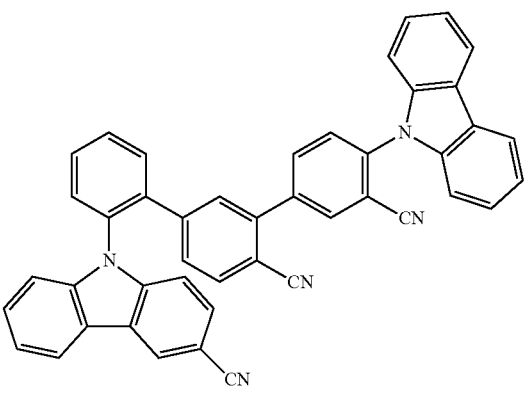
1169
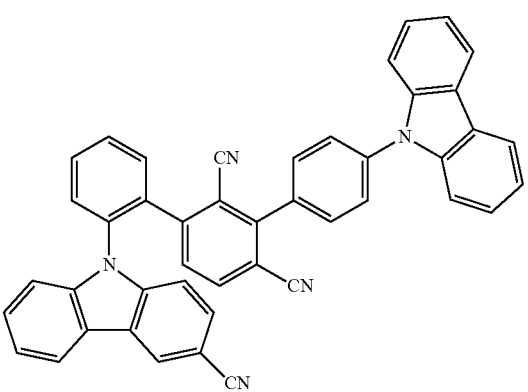

-continued
1170
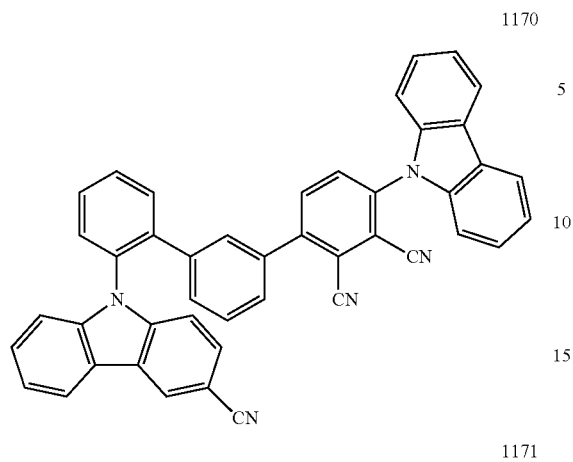
1171
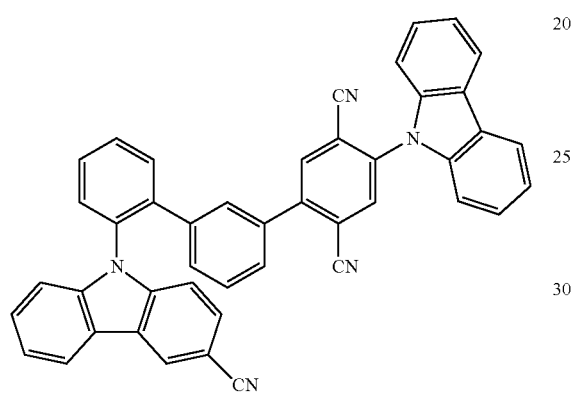
1172
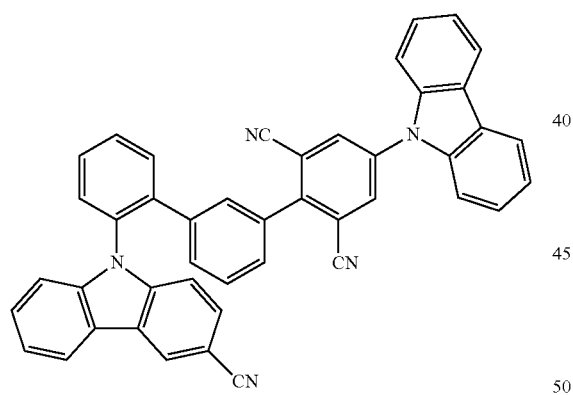
1173
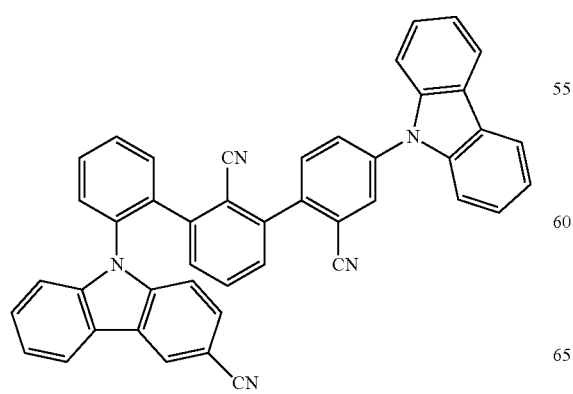
-continued
1174
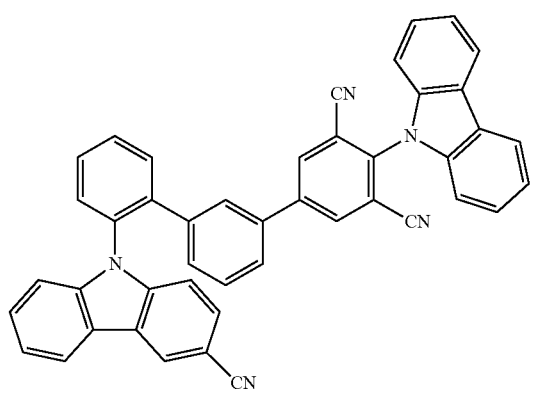
1175
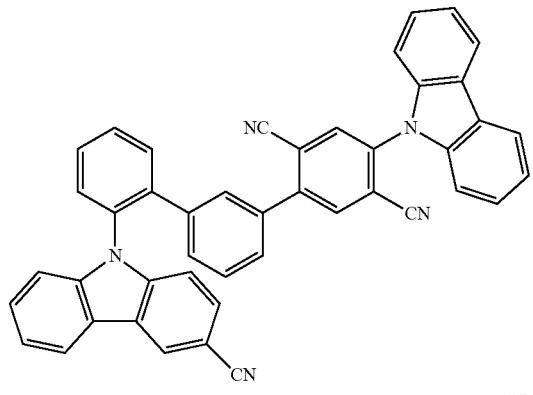
1176
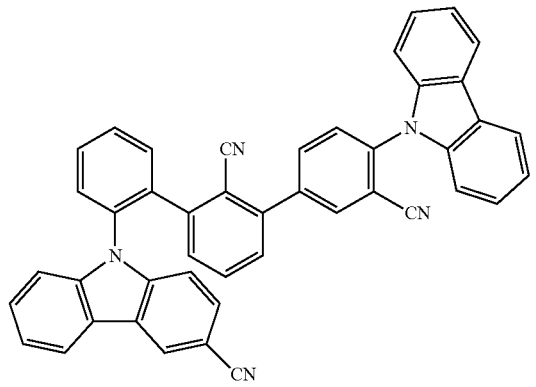
1177
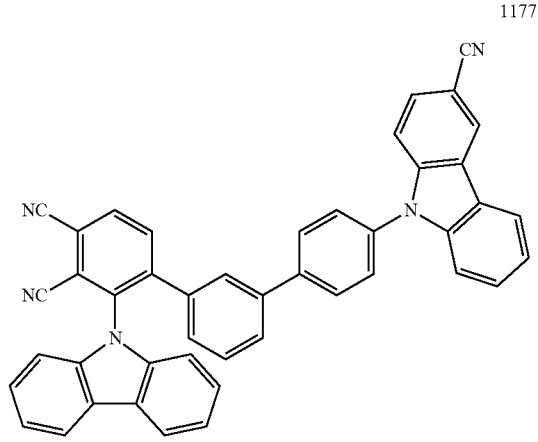

1178
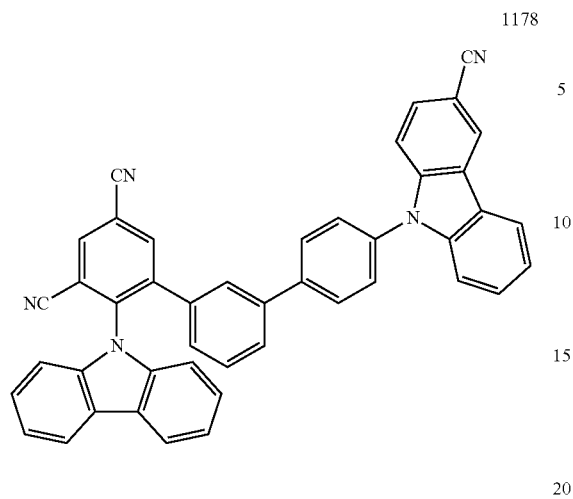
1179
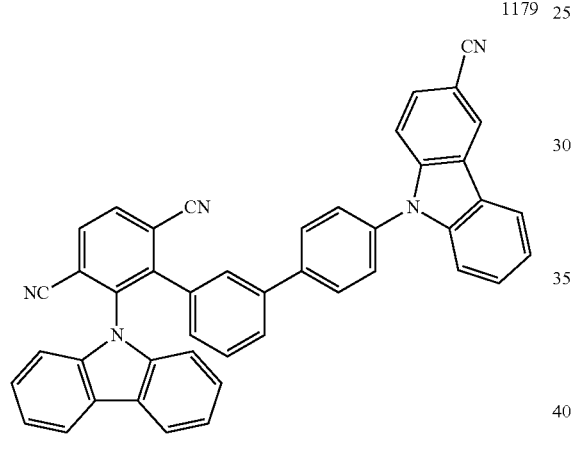
1180
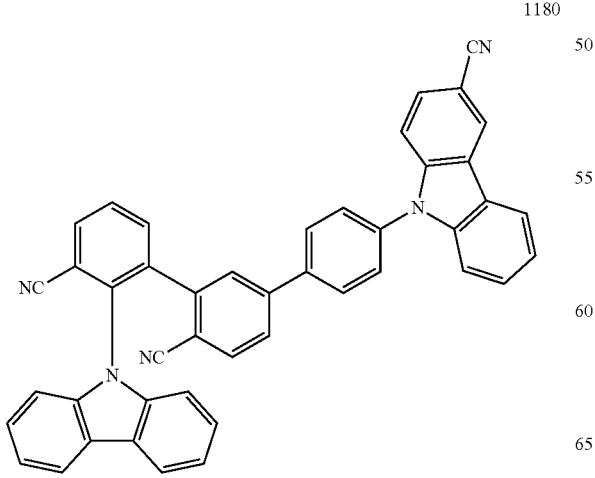
1181
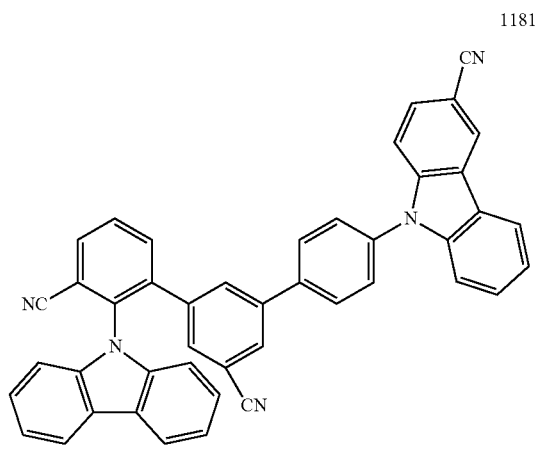
1182
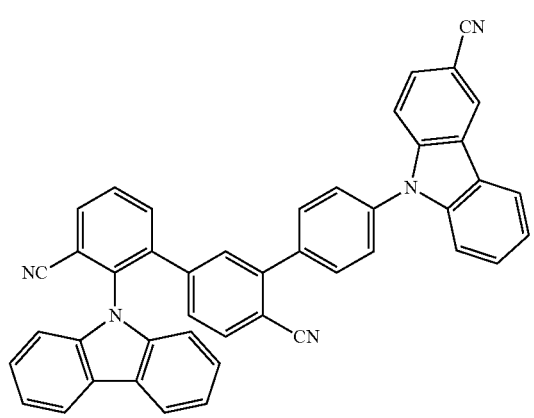
1183
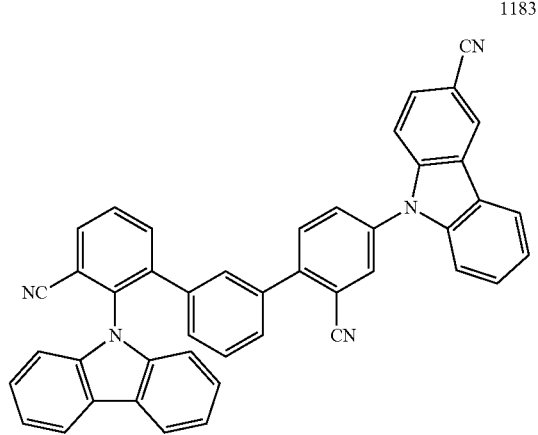

-continued
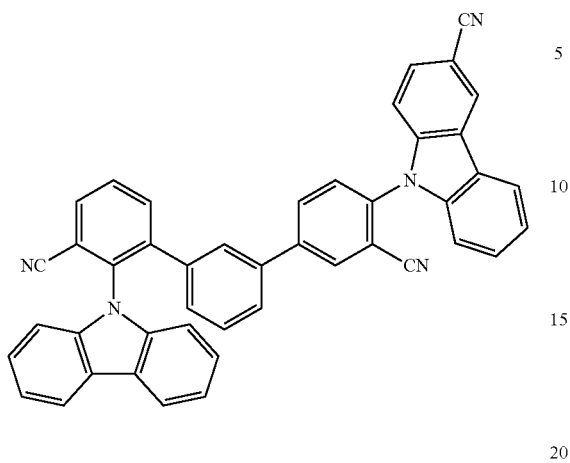
1184
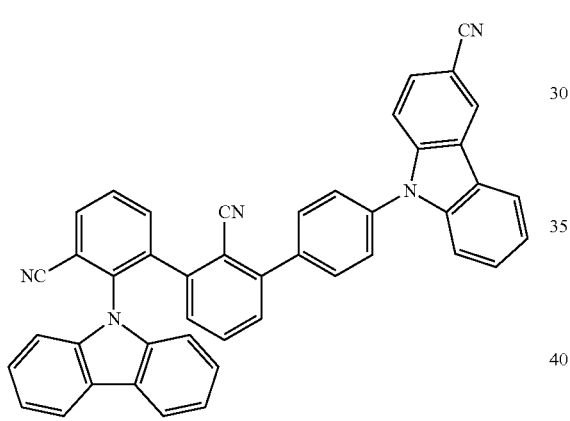
1185
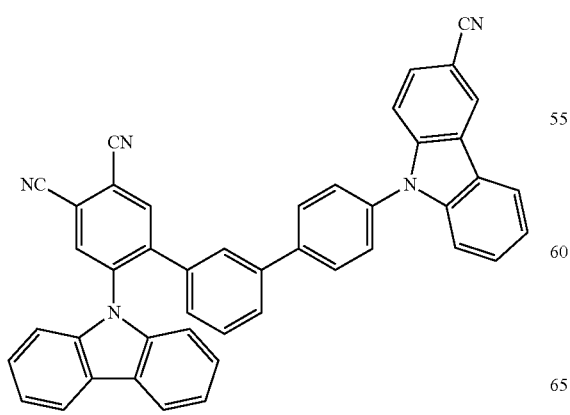
1186
-continued
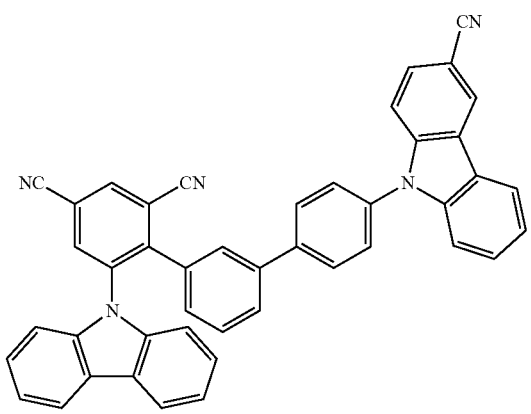
1187
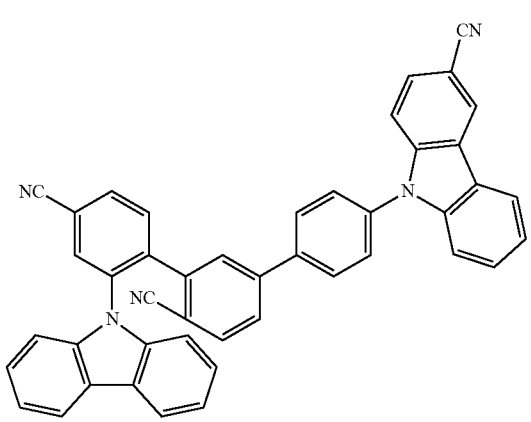
1188
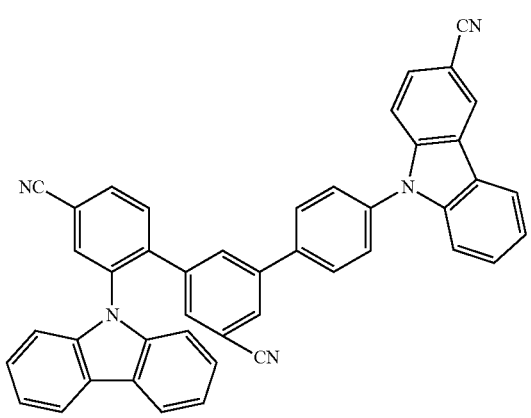
1189

1190
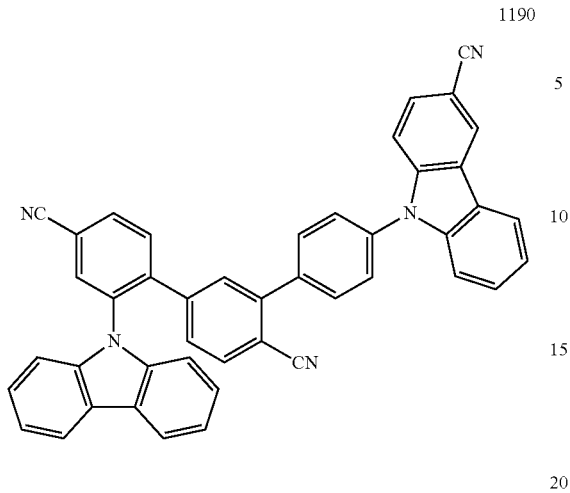
1191
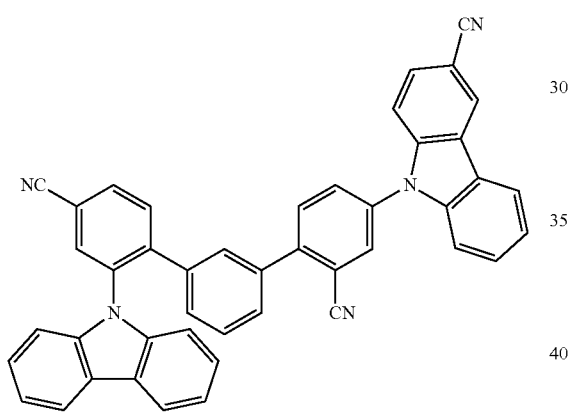
1192
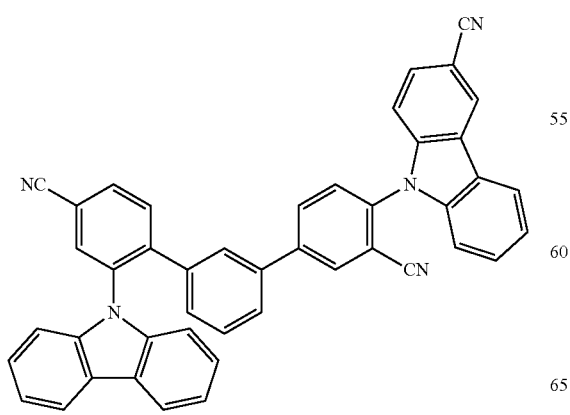
1193
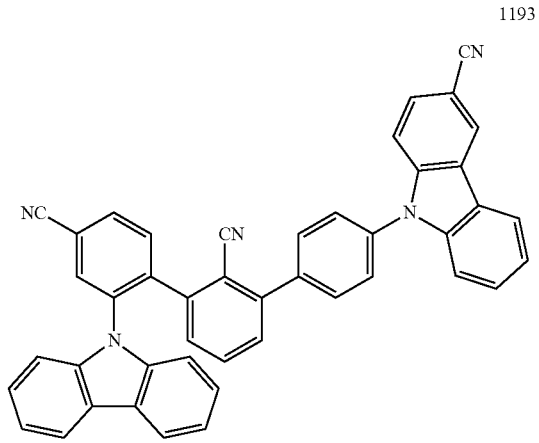
1194
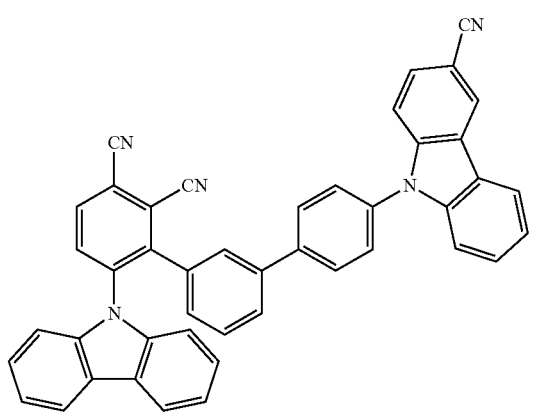
1195
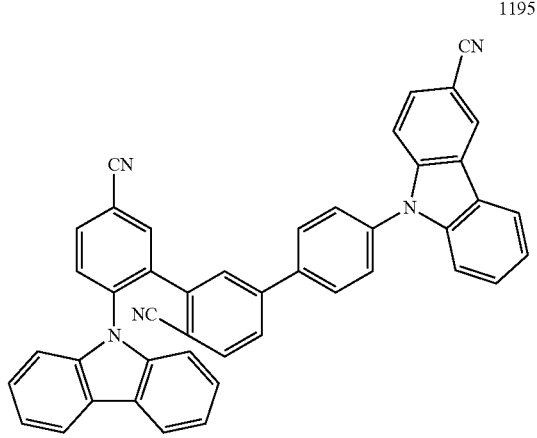

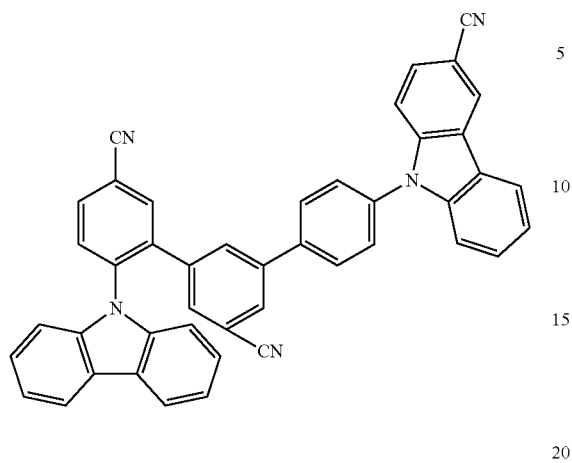
1196
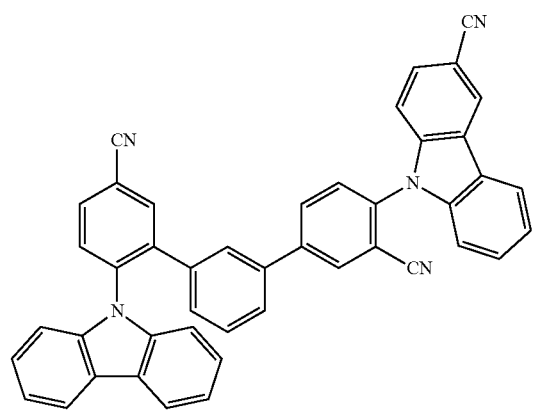
1199
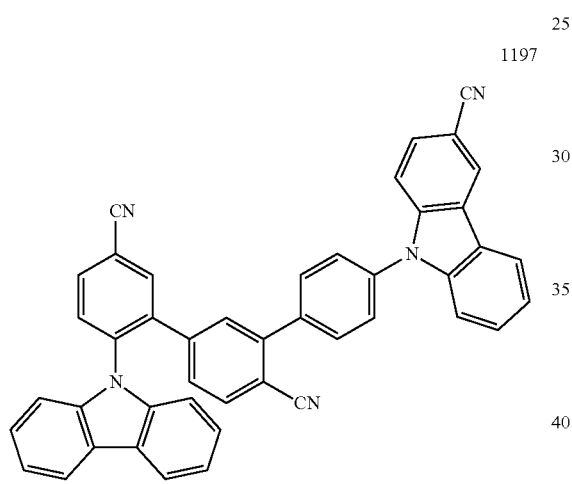
1197
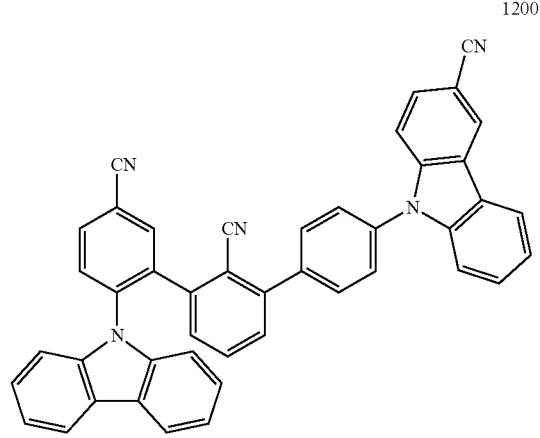
1200
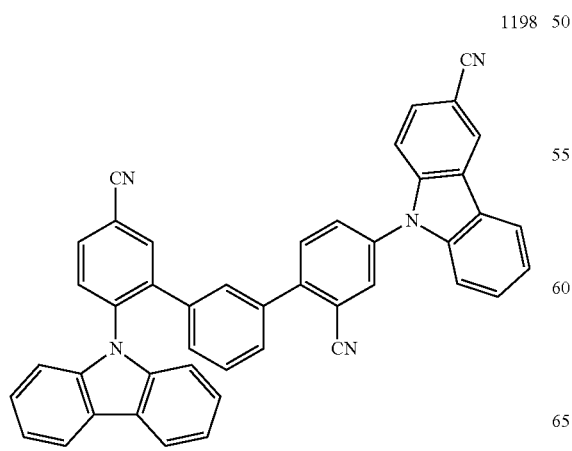
1198
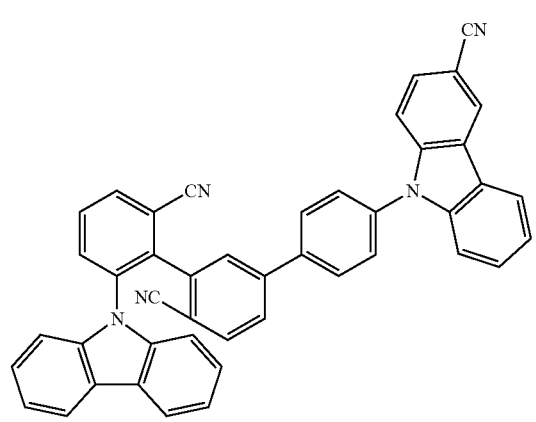
1201

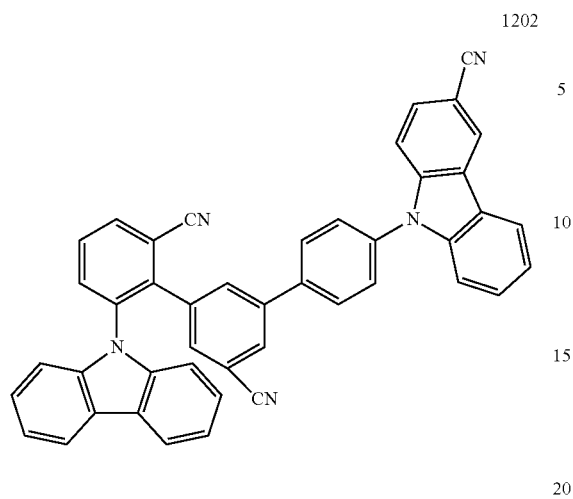
1202
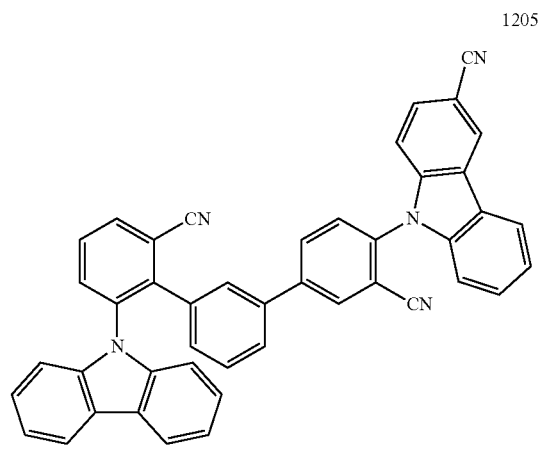
1205
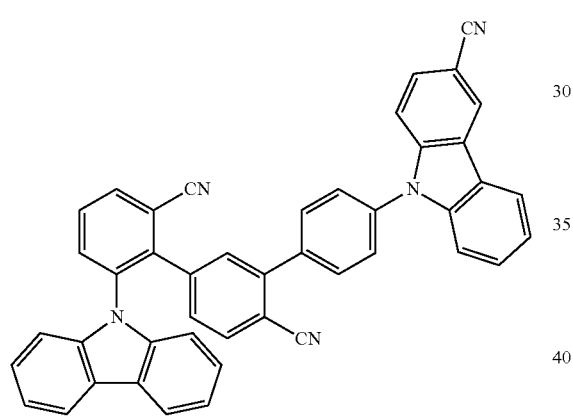
1203
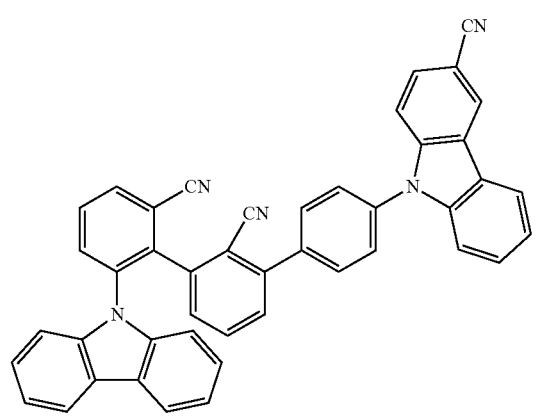
1206
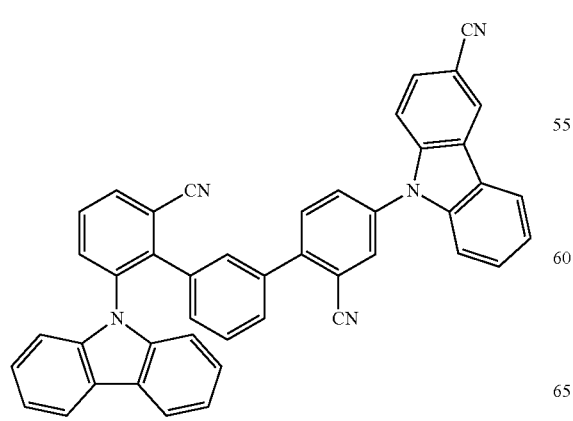
1204
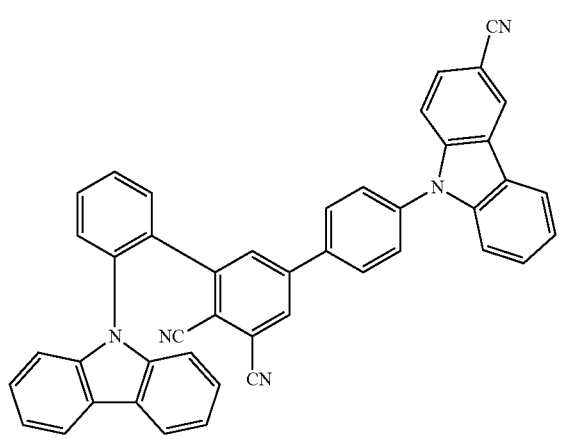
1207

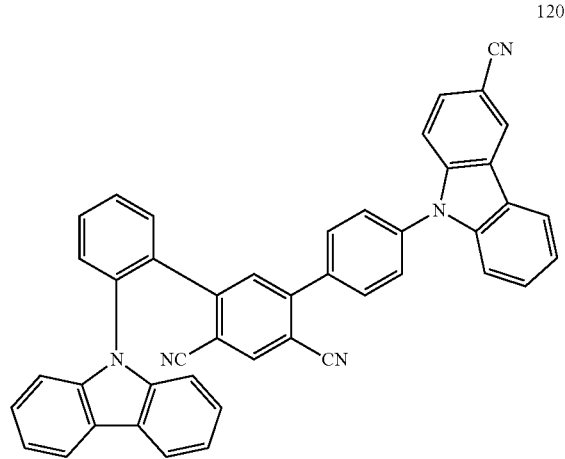
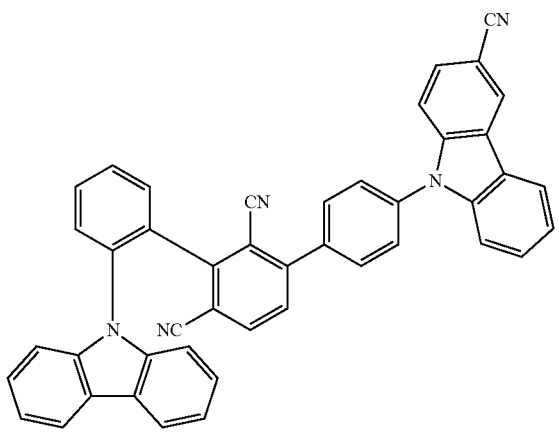
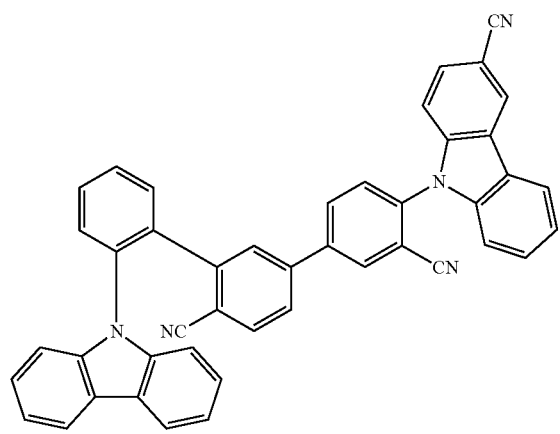

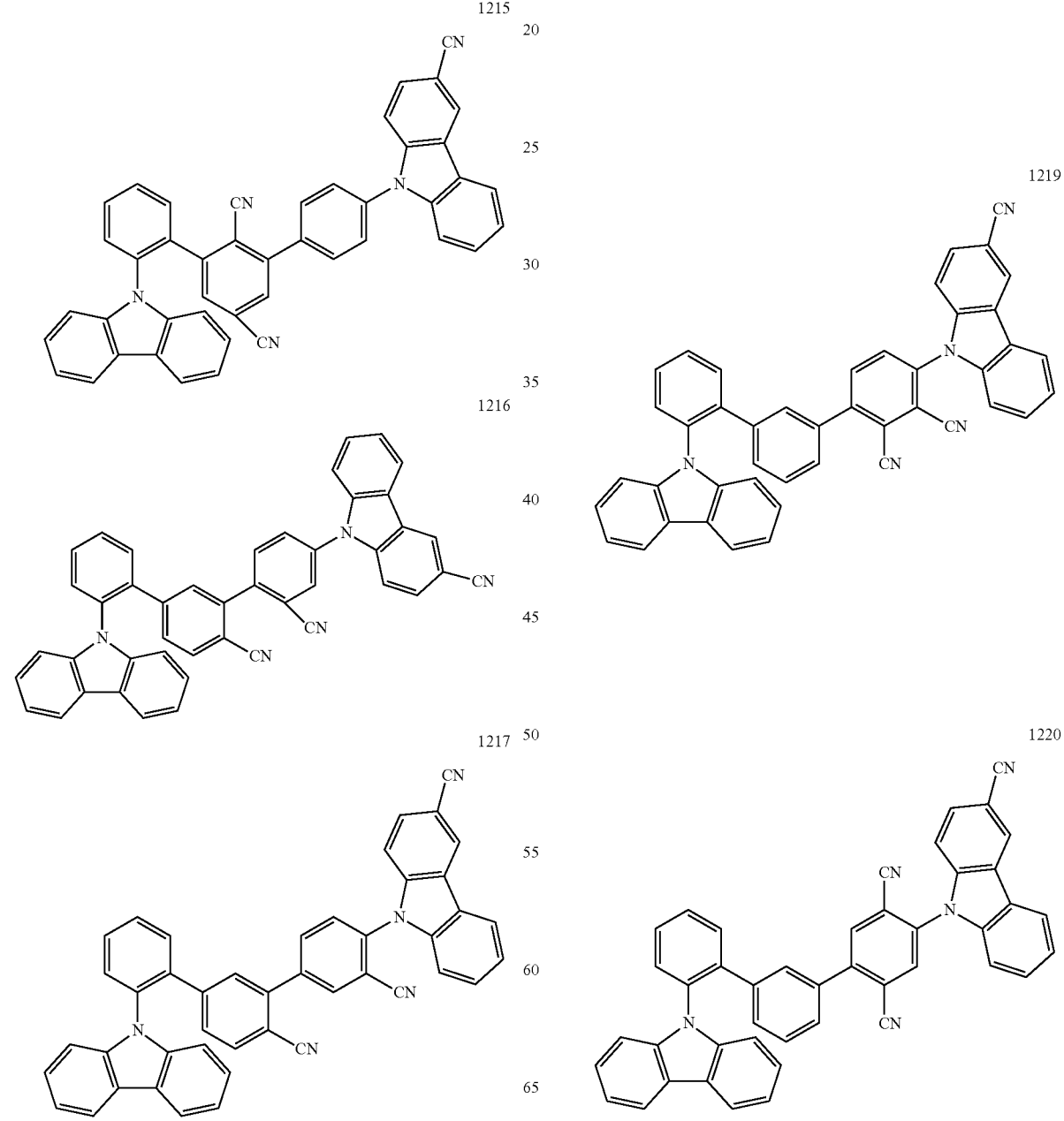

1221
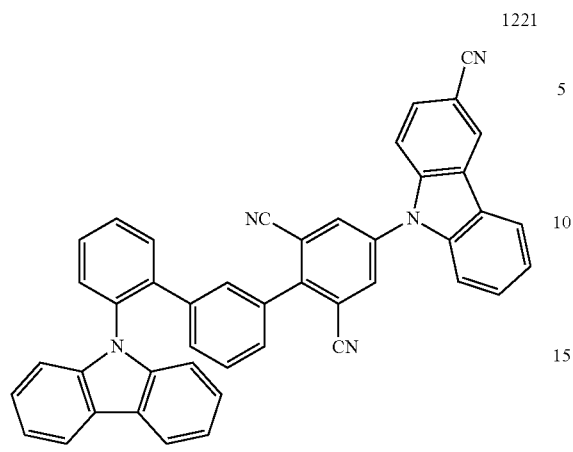
1224
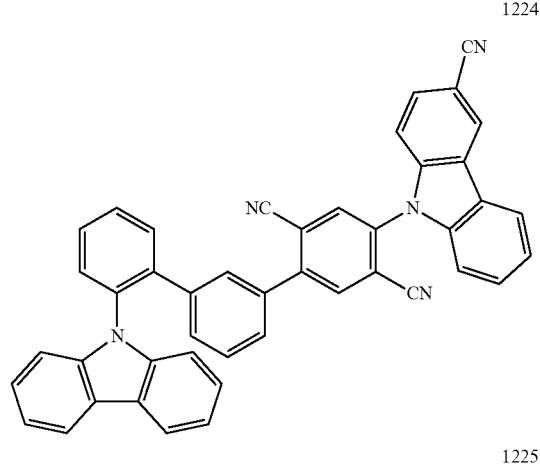
1222
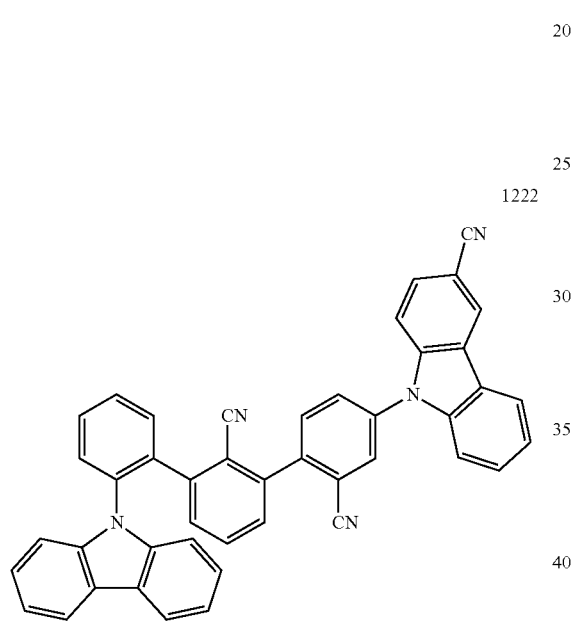
1225
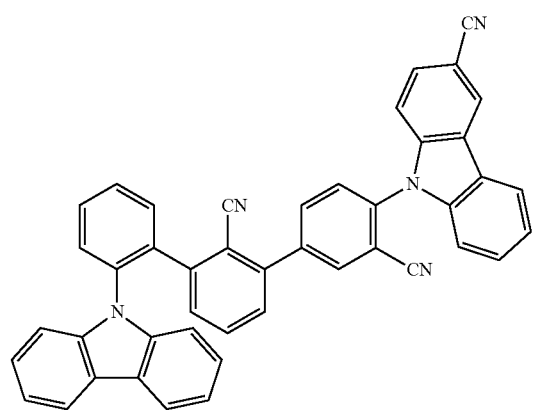
1226
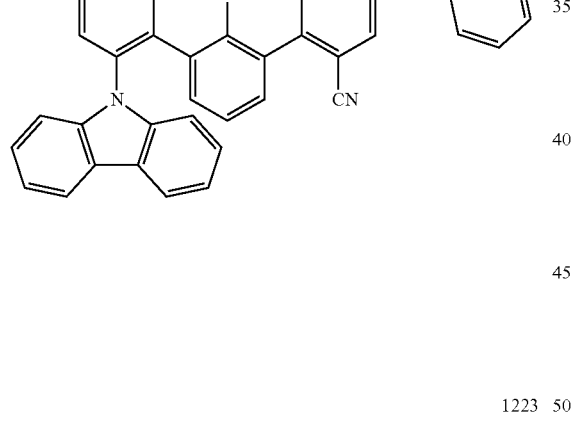
1223
1227
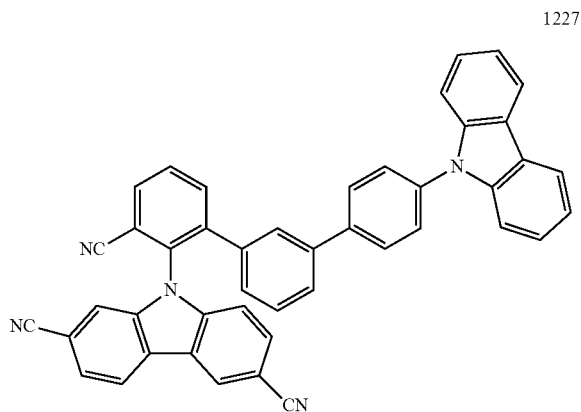

-continued
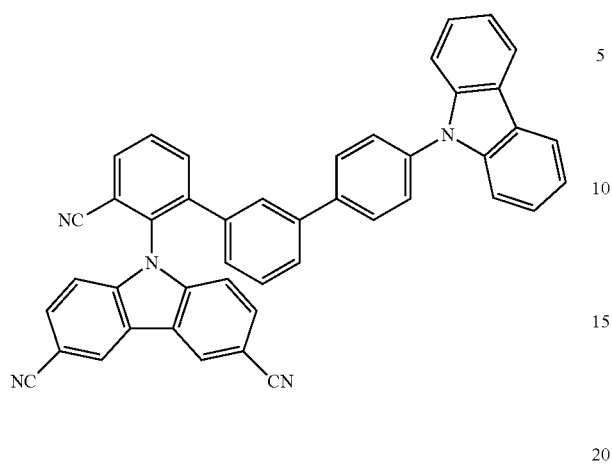
1228
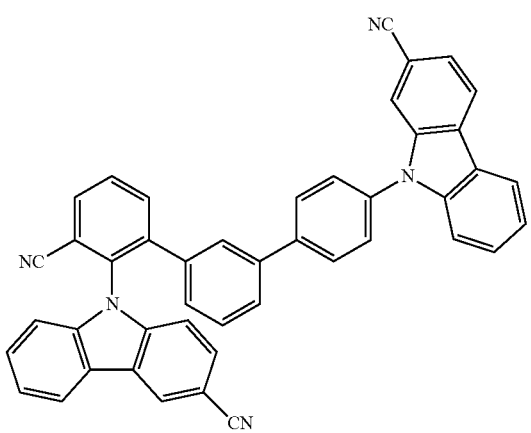
1231
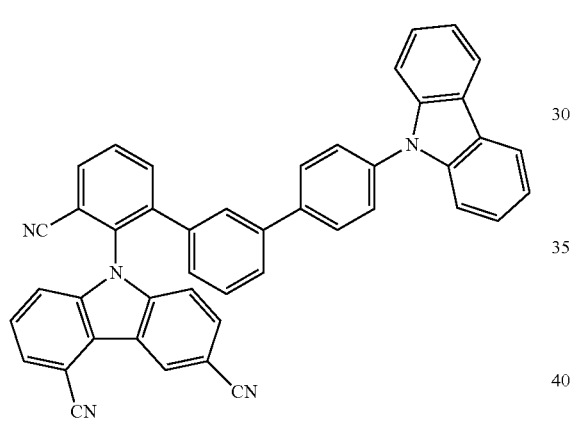
1229
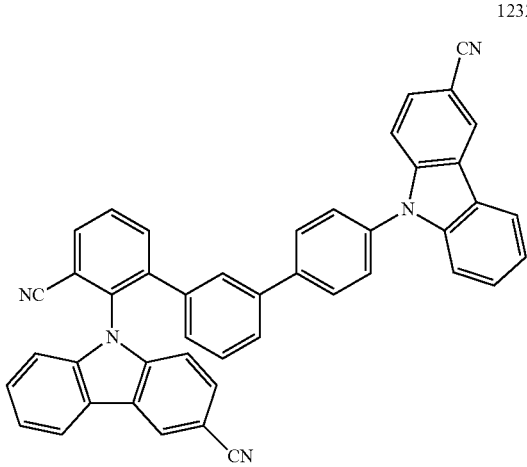
1232
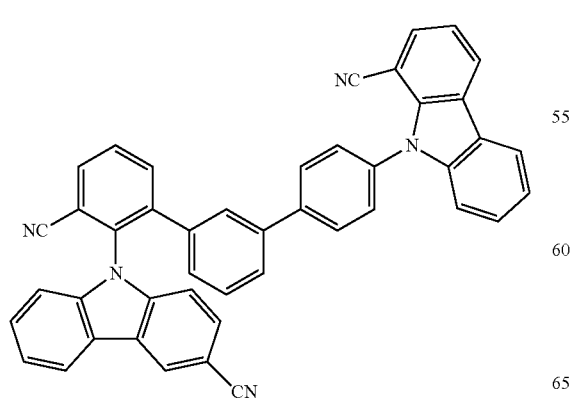
1230
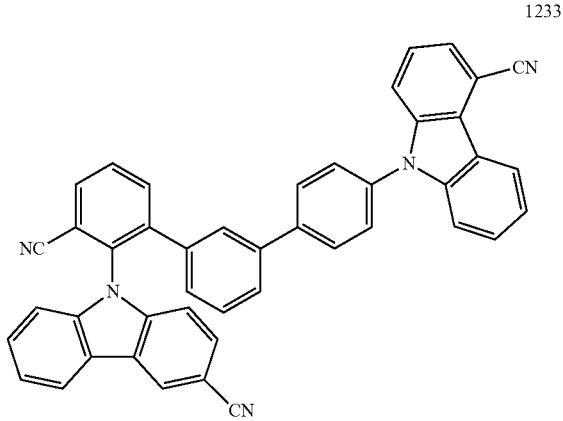
1233

1234
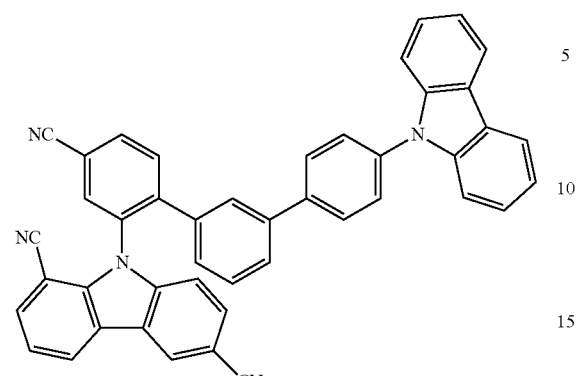
1235
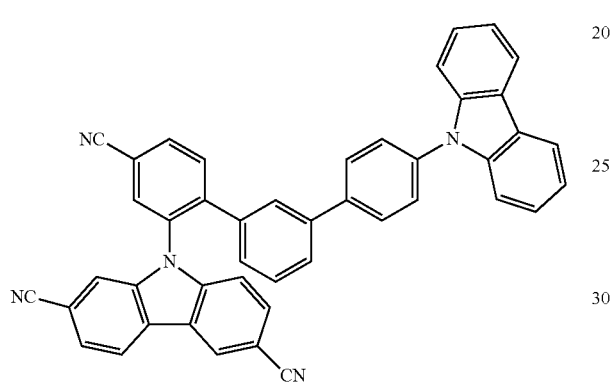
1236
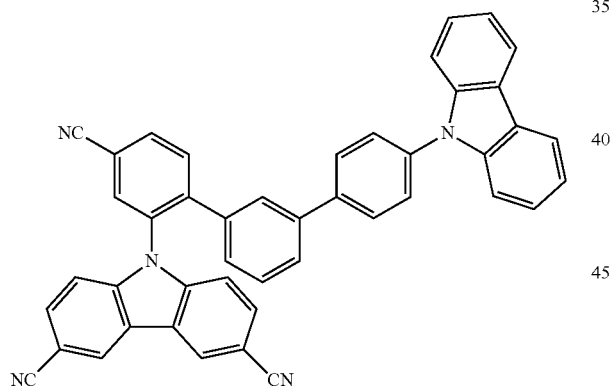
1237
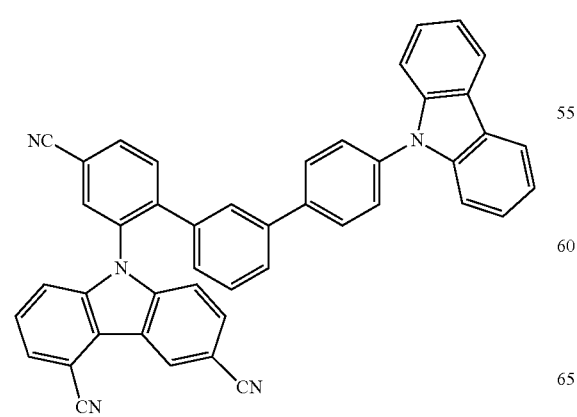
1238
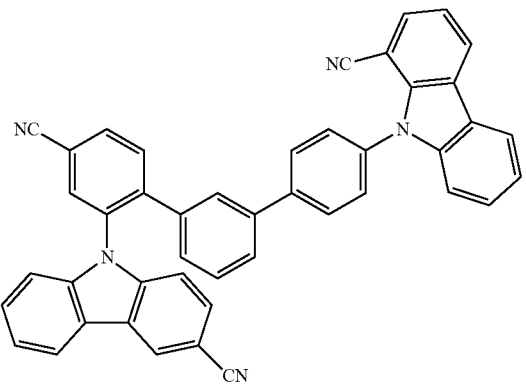
1239
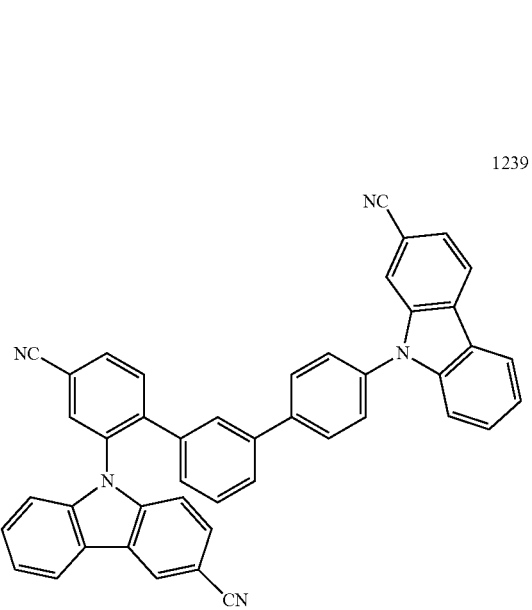
1240
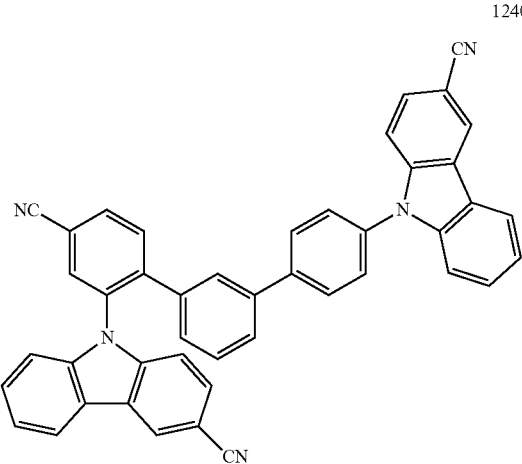

-continued
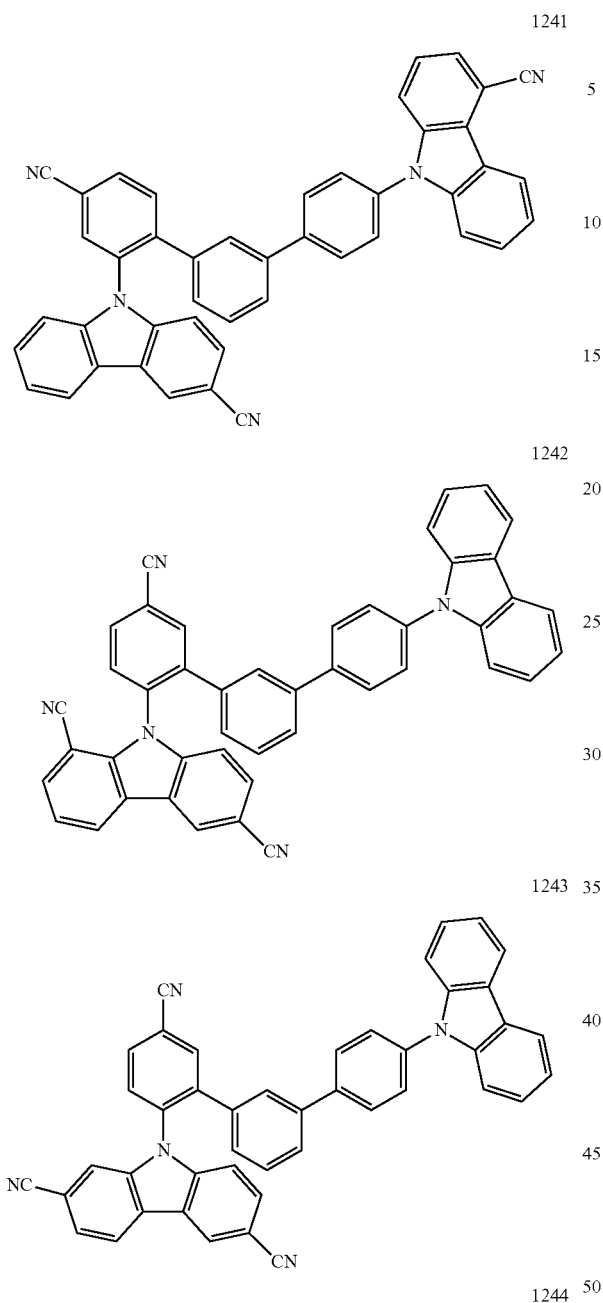
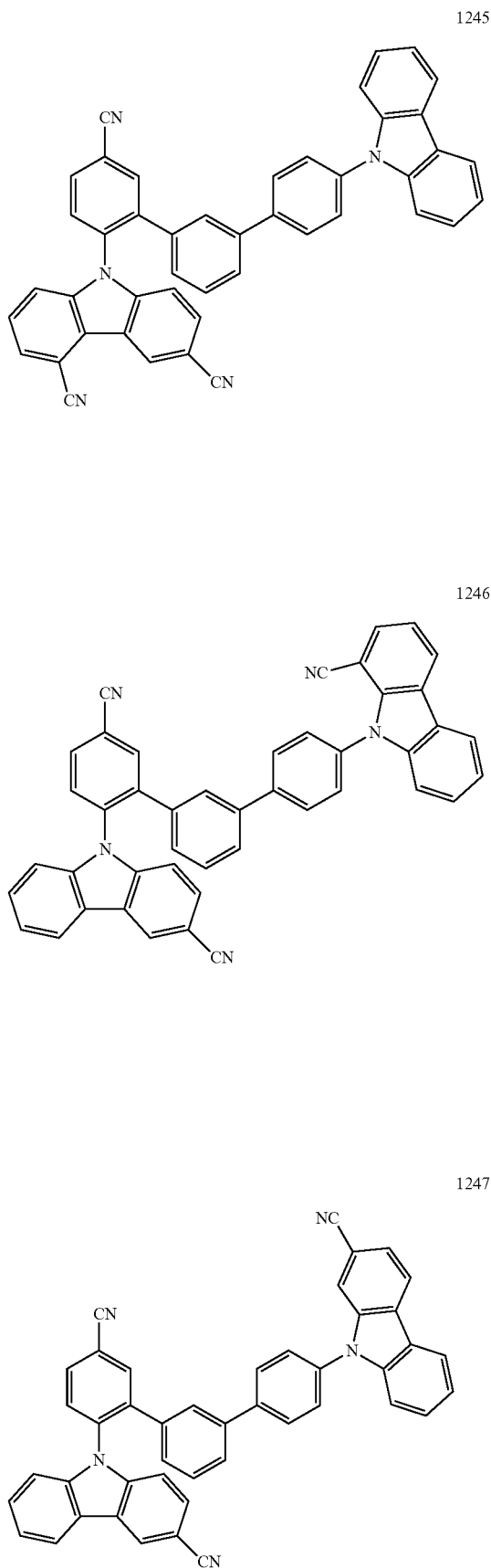

1248
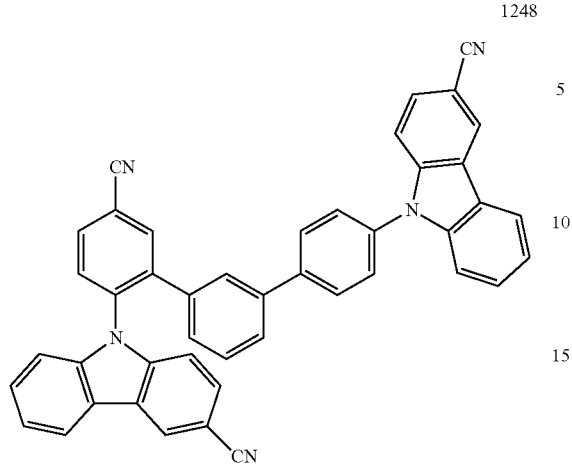
1249
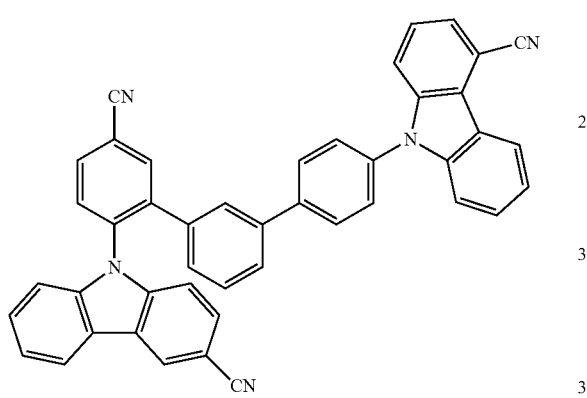
1250
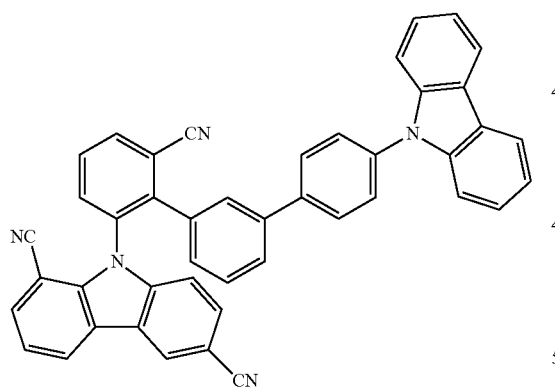
1251
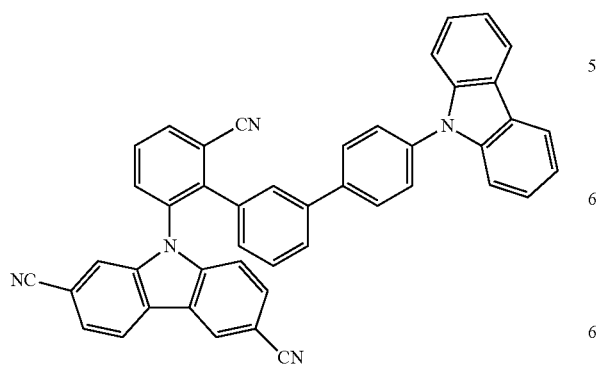
1252
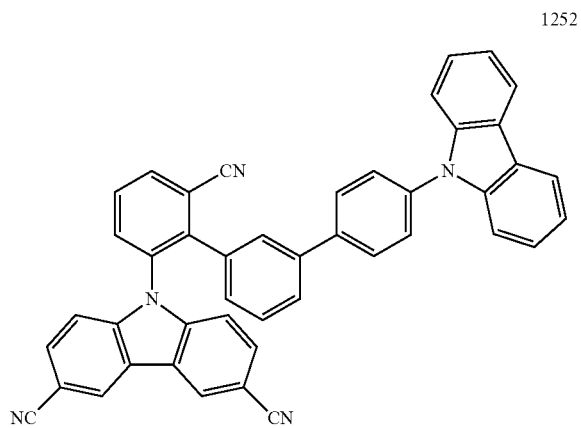
1253
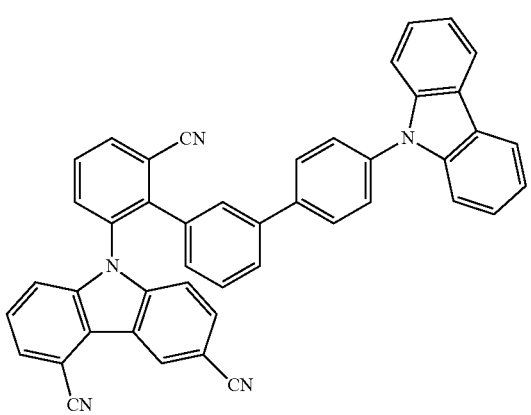
1254
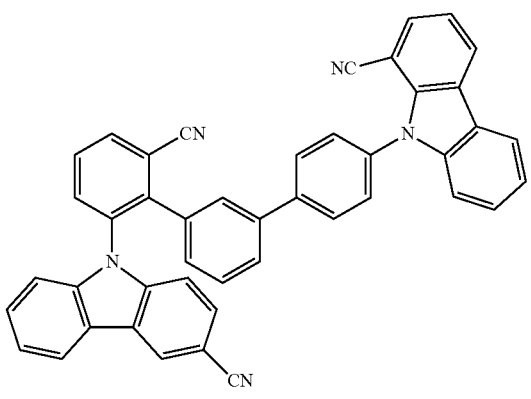

1255
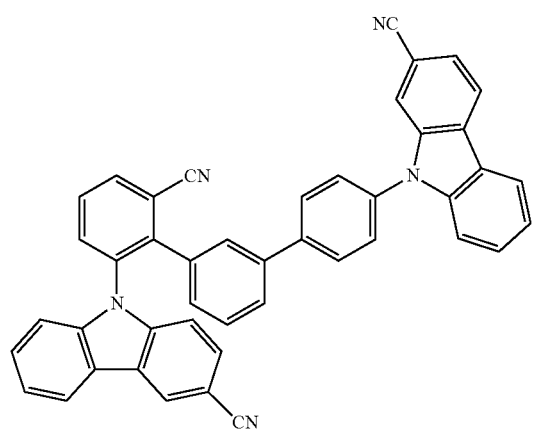
1258
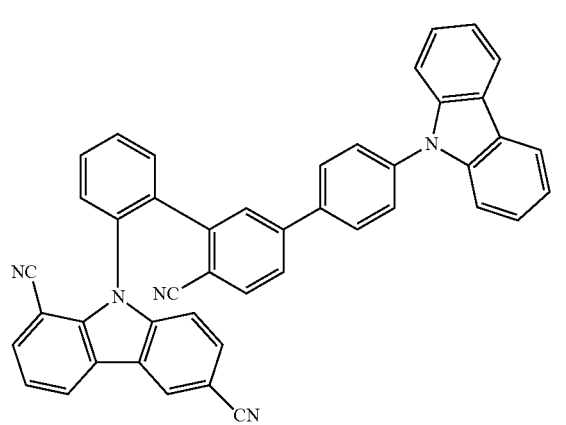
1256
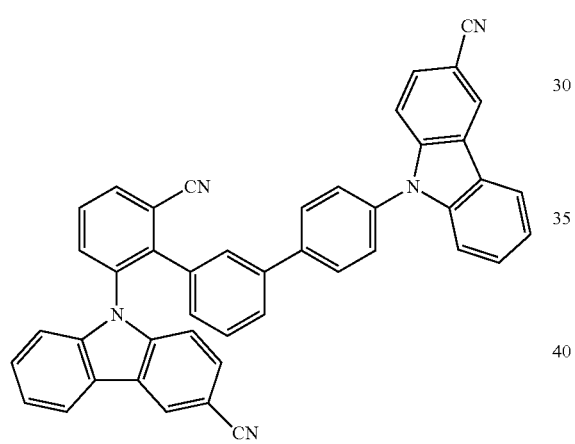
1259
1257
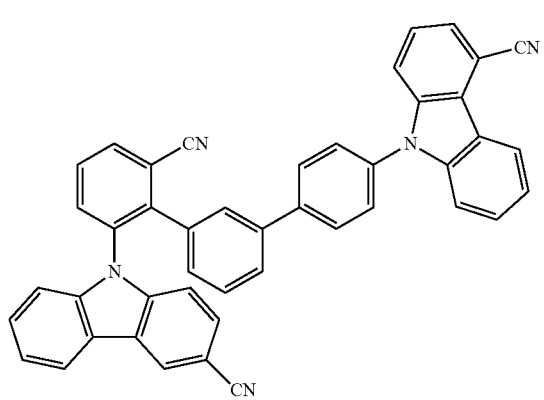
1260
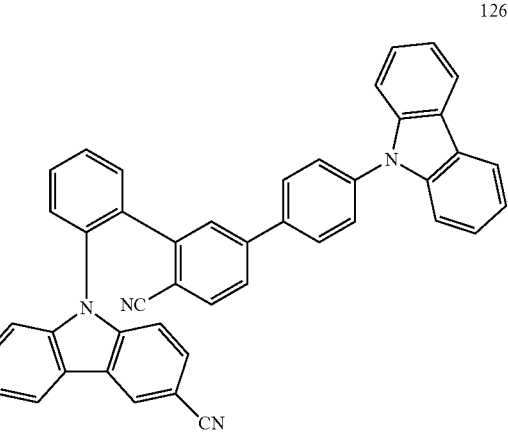

359
-continued
1261
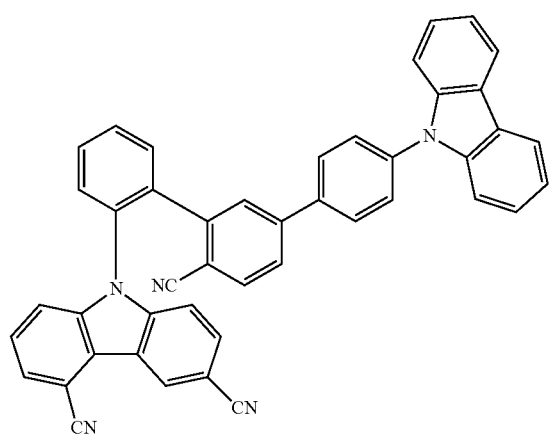
1262
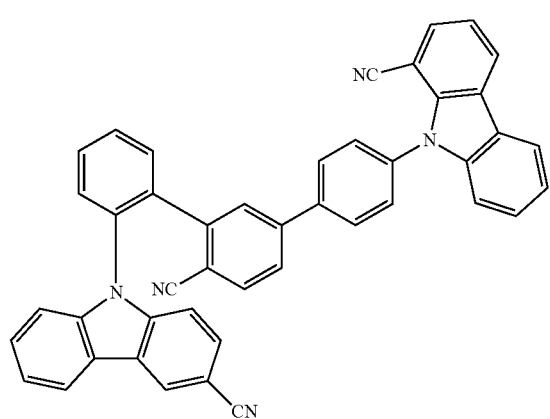
1263
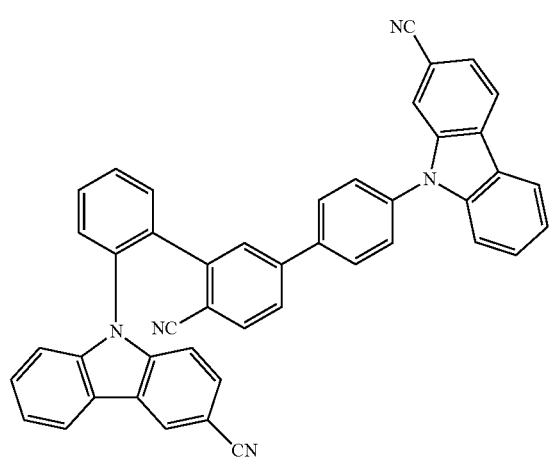
360
-continued
1264
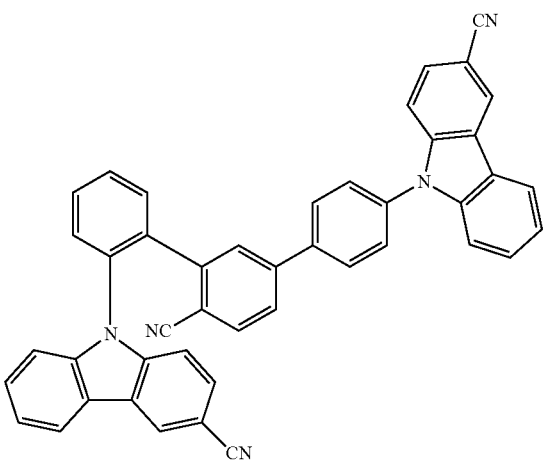
1265
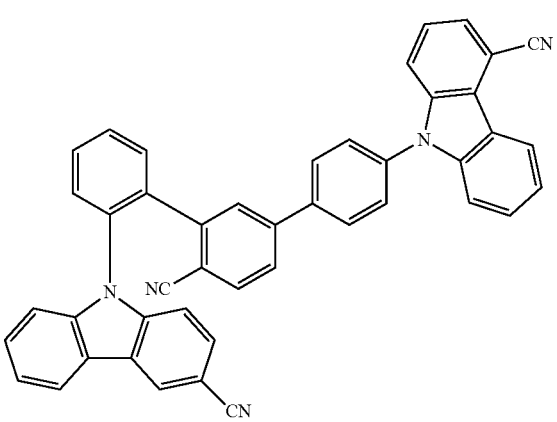
1266
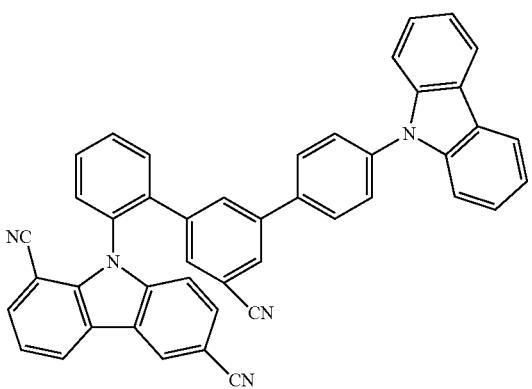

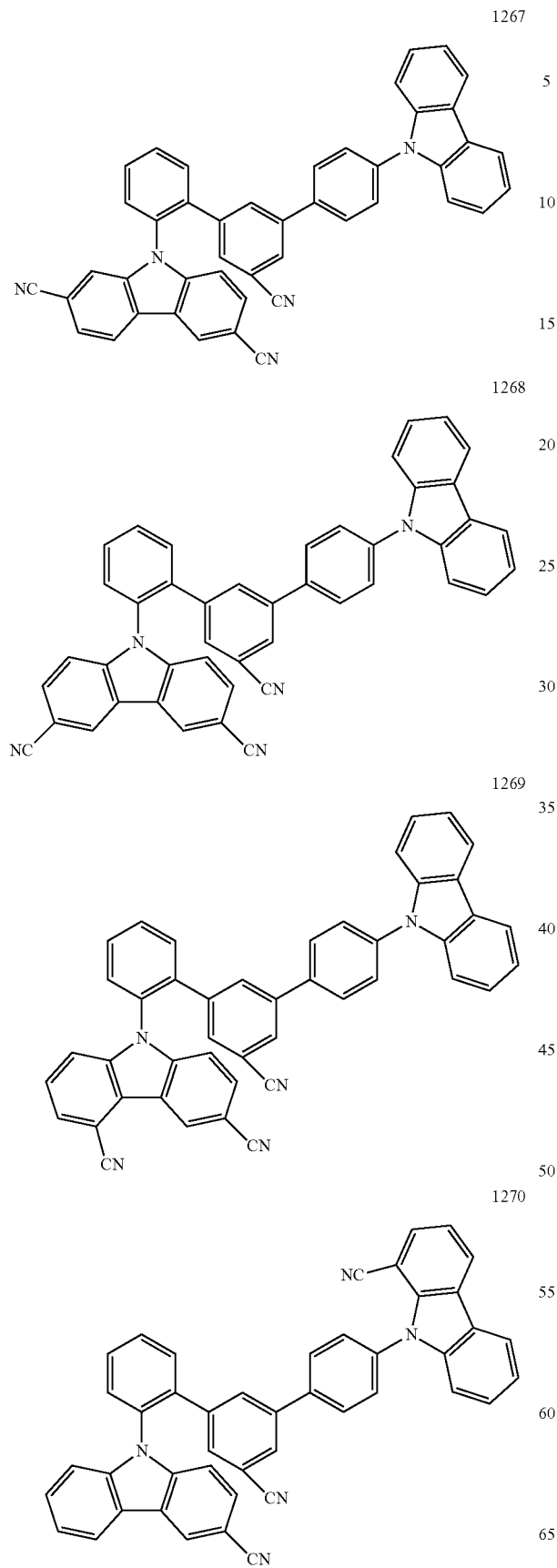
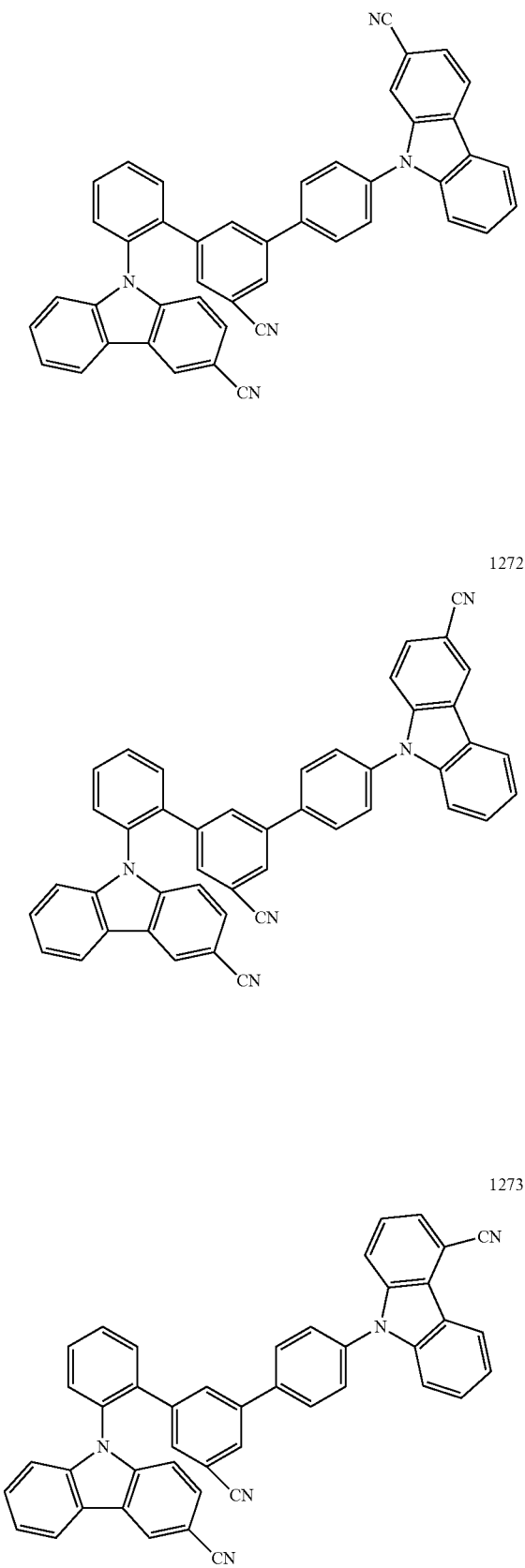

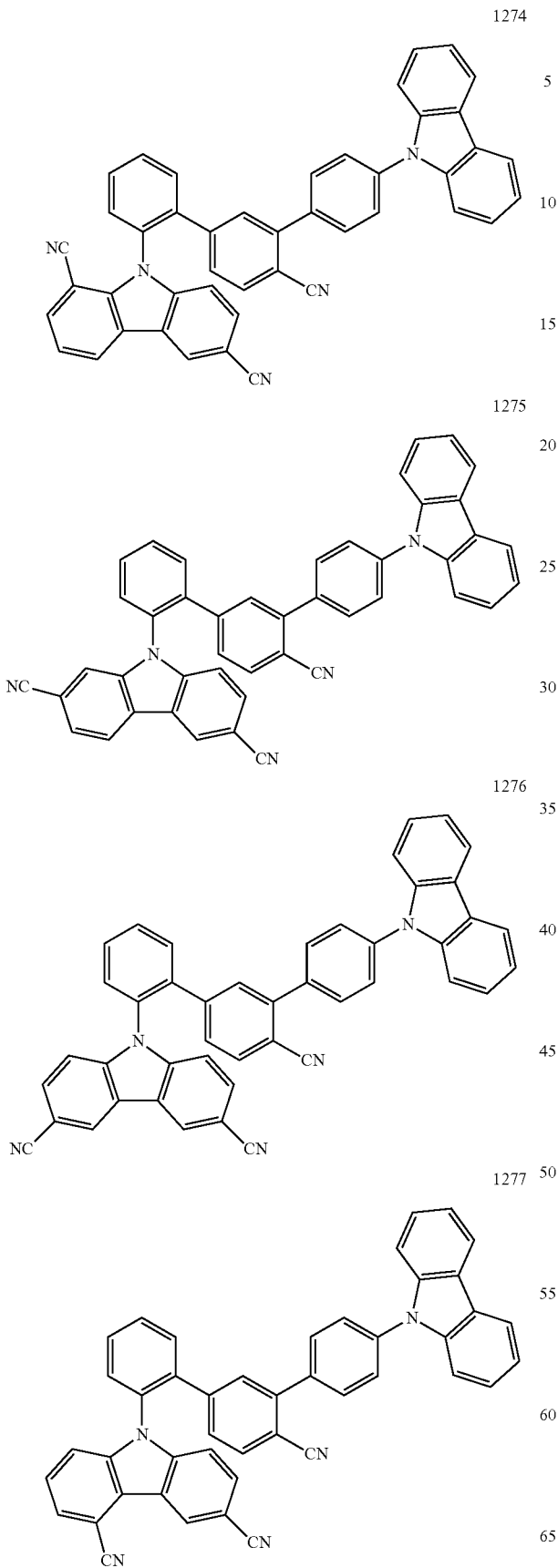
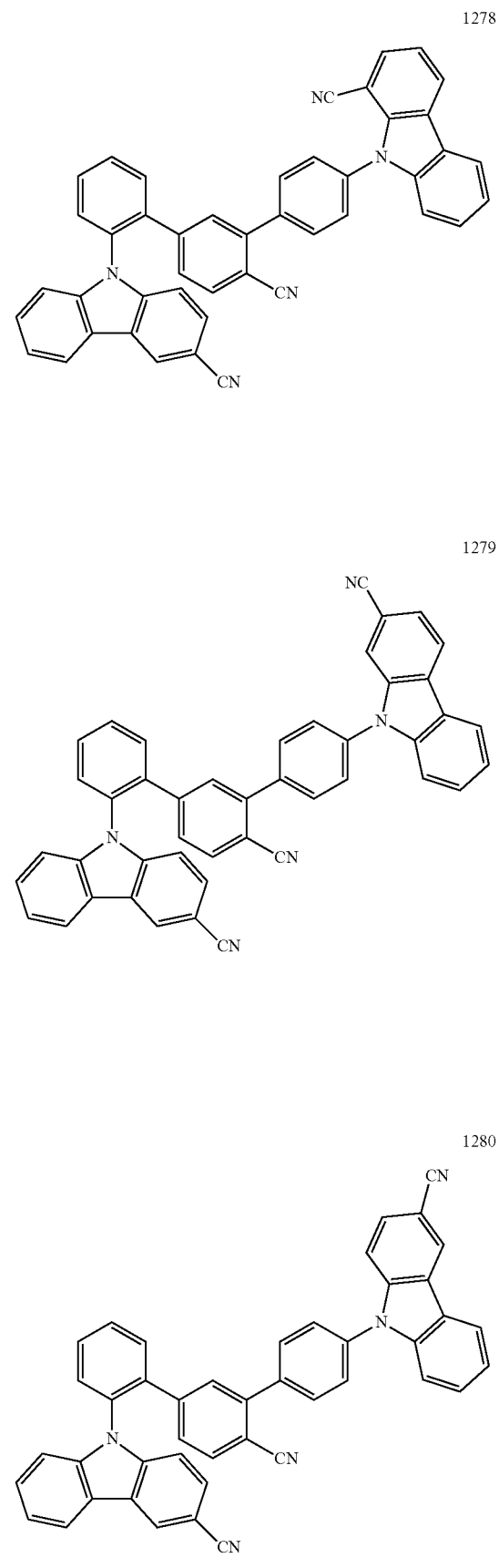

-continued
1281
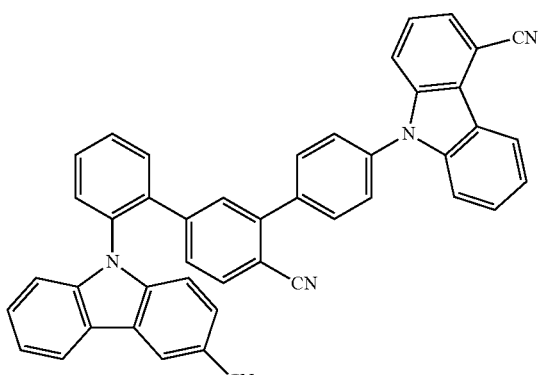
1282
1283
1284
-continued
1285
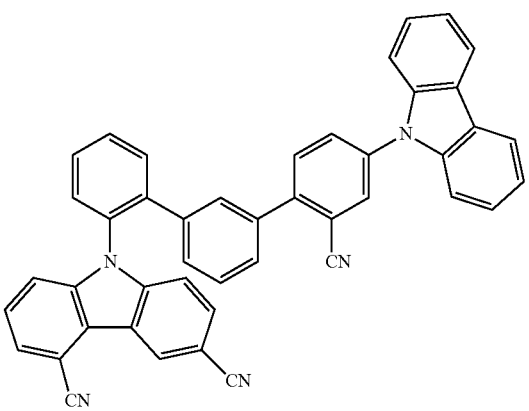
1286
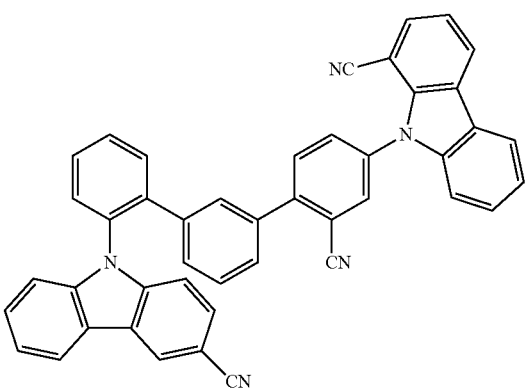
1287
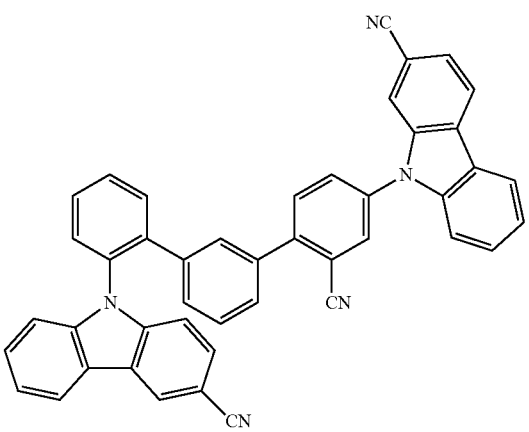

-continued
1288
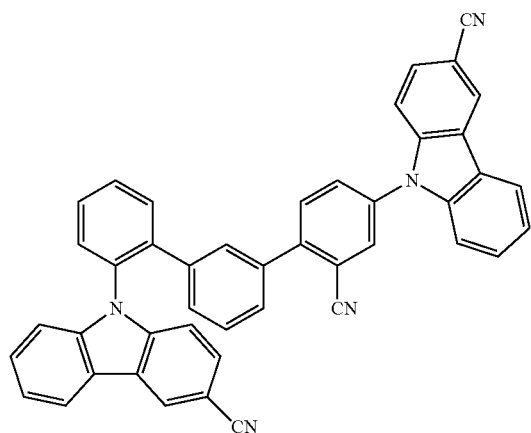
1289
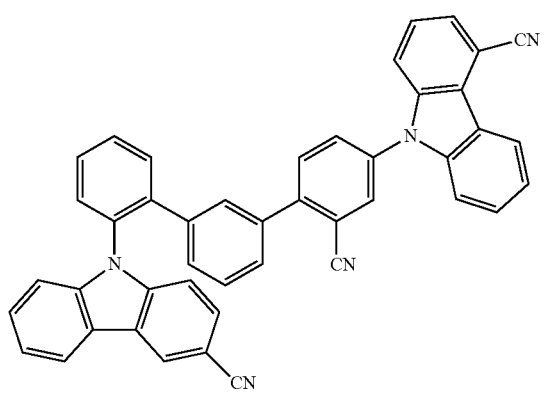
1290
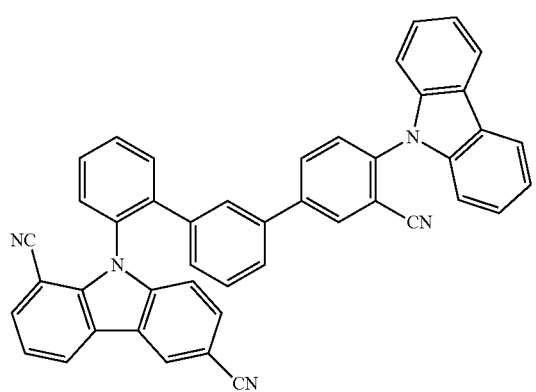
1291
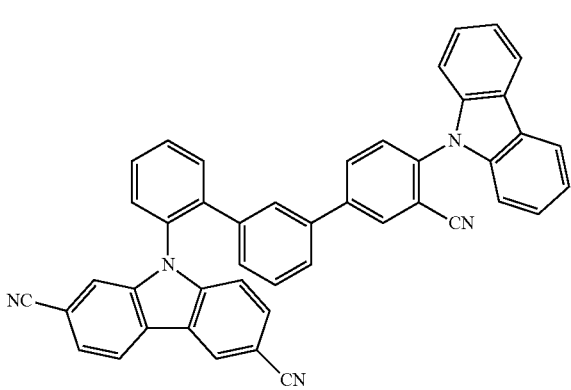
-continued
1292
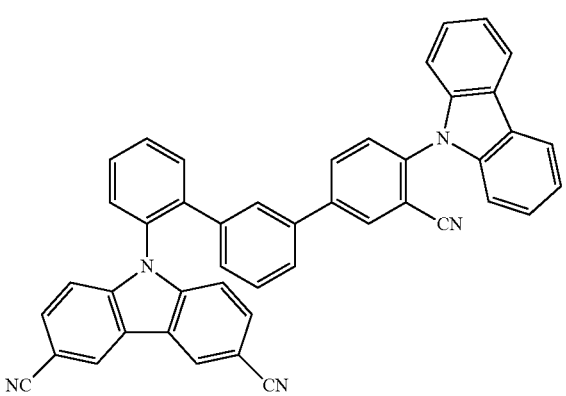
1293
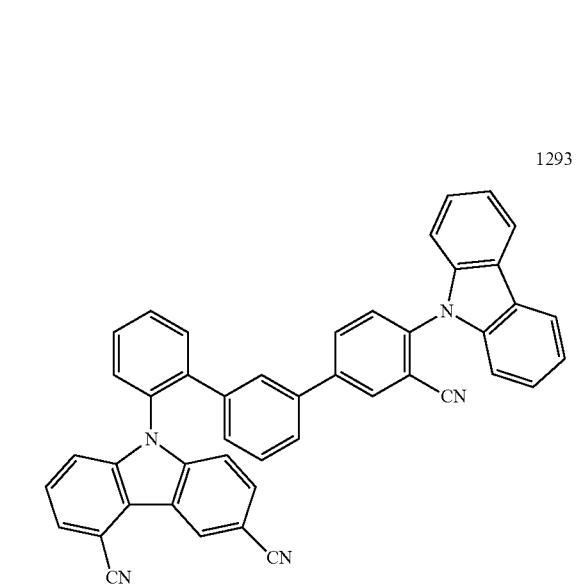
1294
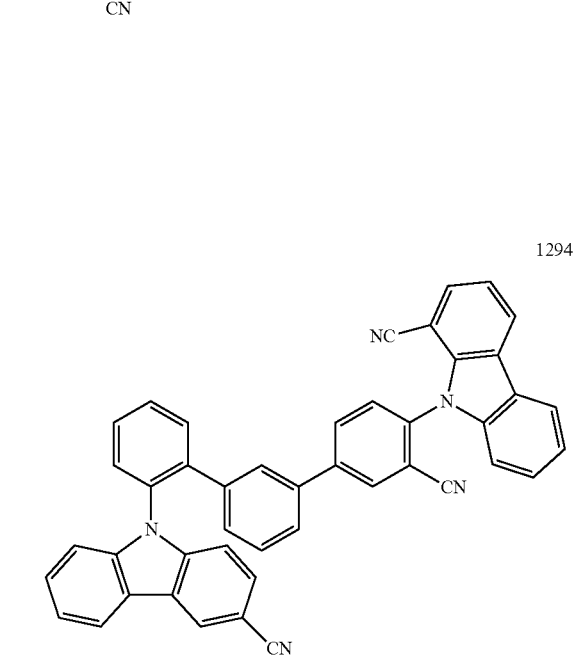

1295
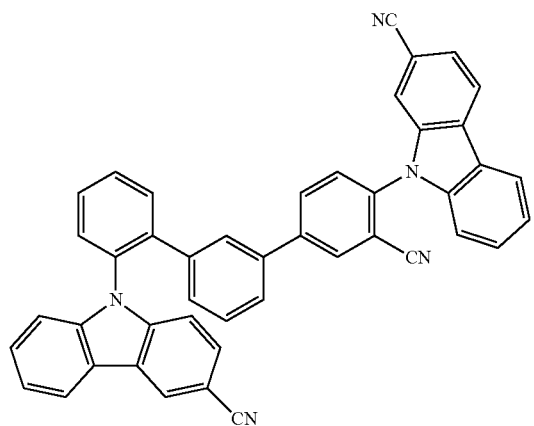
1296
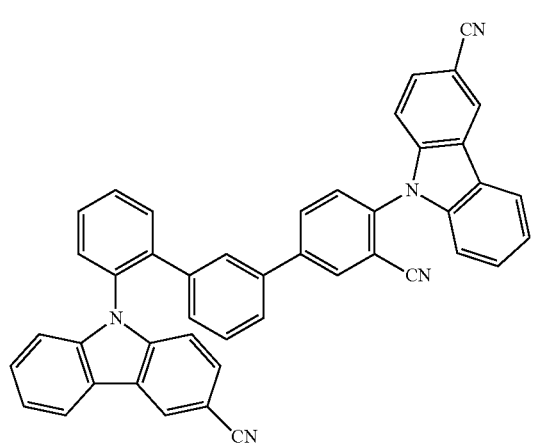
1297
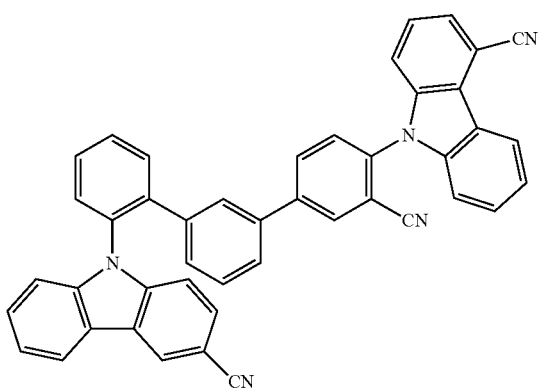
1298
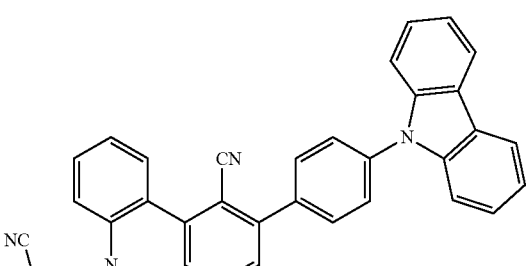
1299
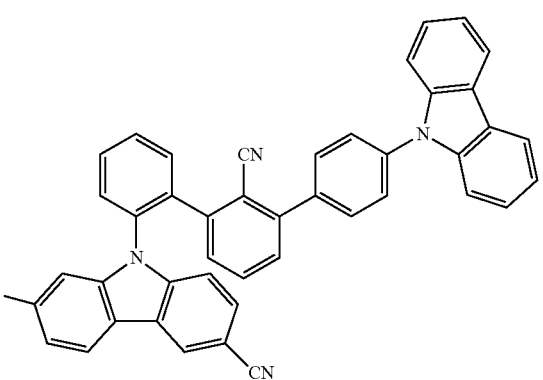
1300
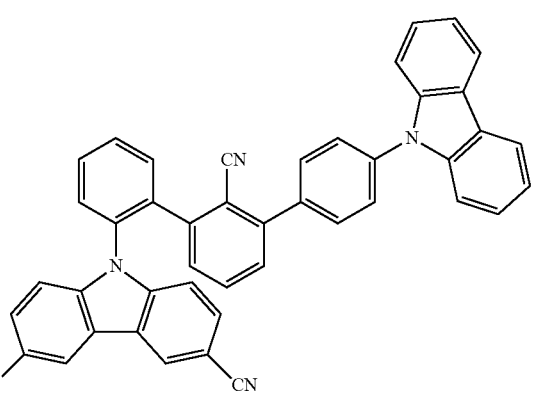
1301
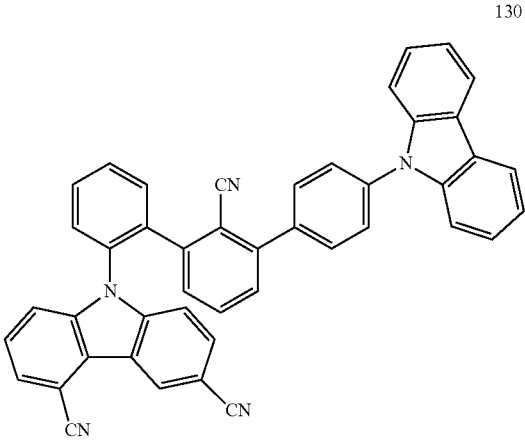

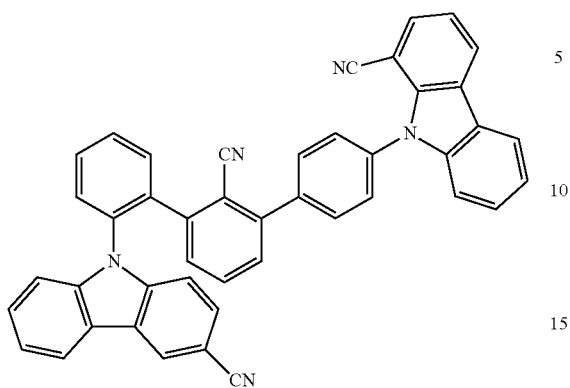
1302
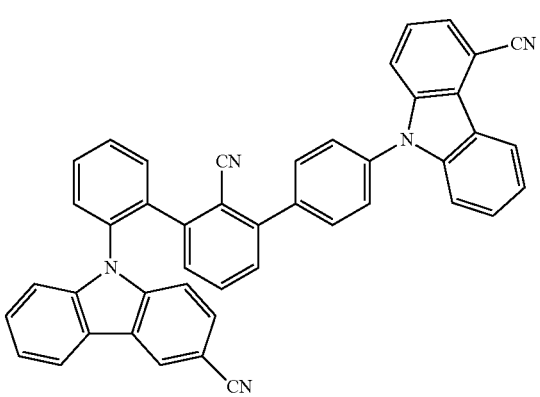
1305
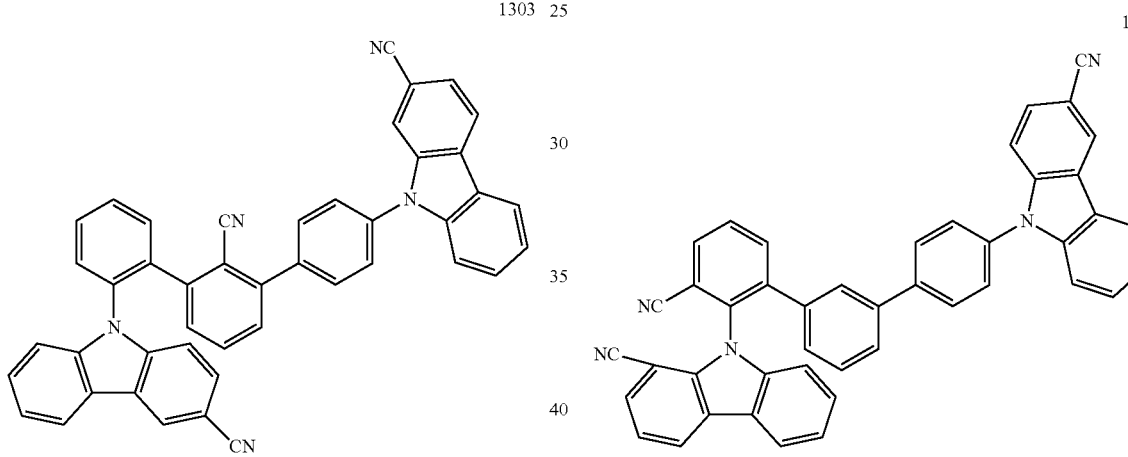
1303
1306
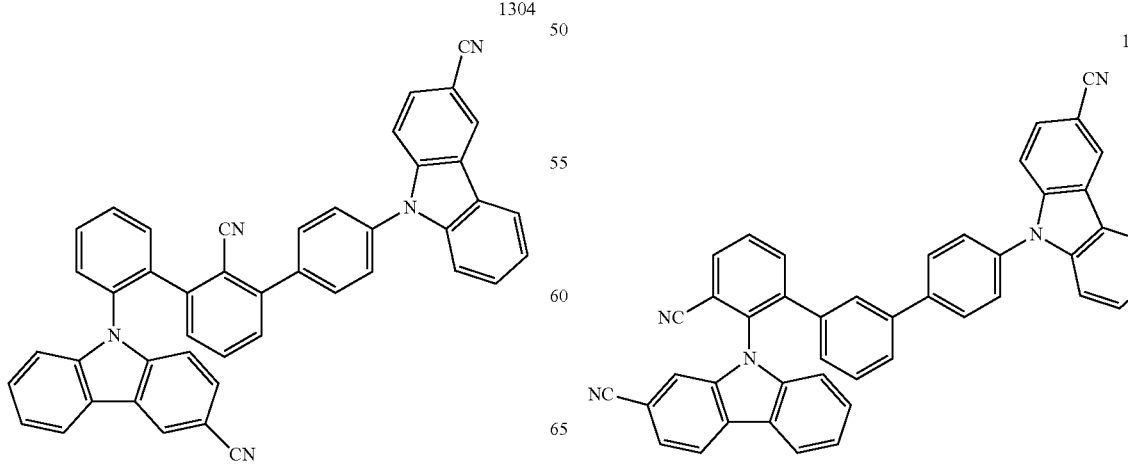
1304
1307

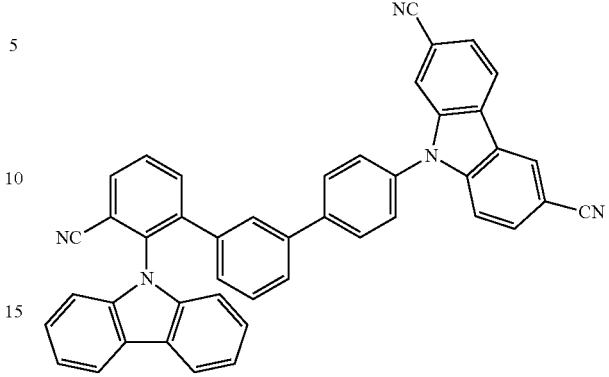
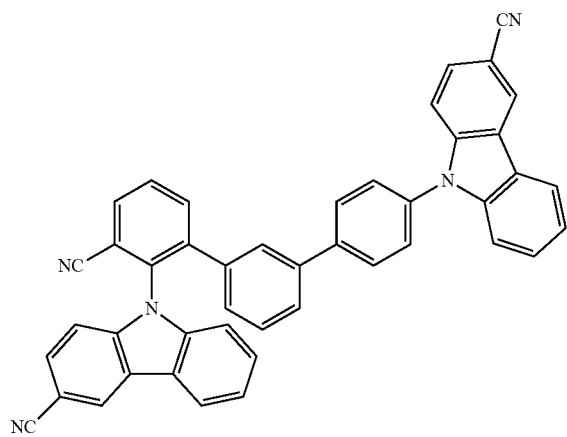
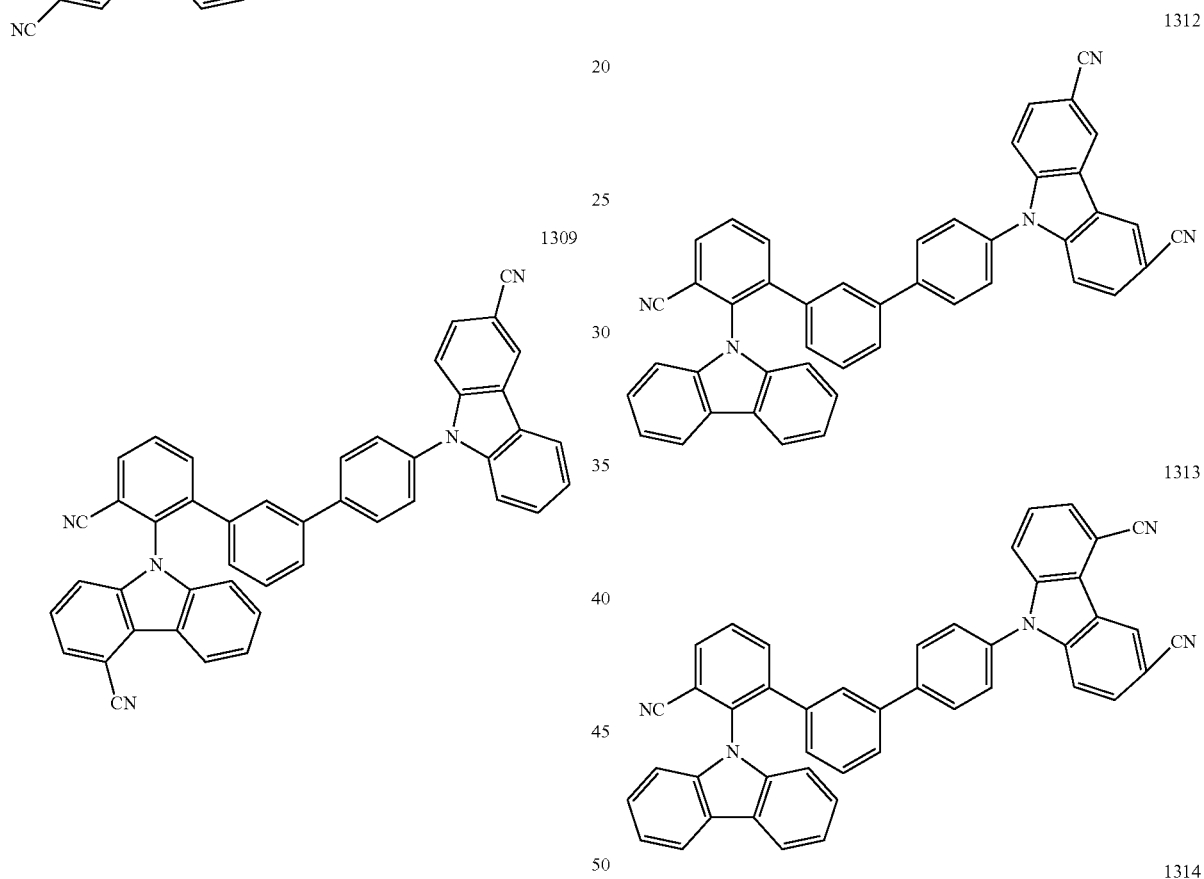
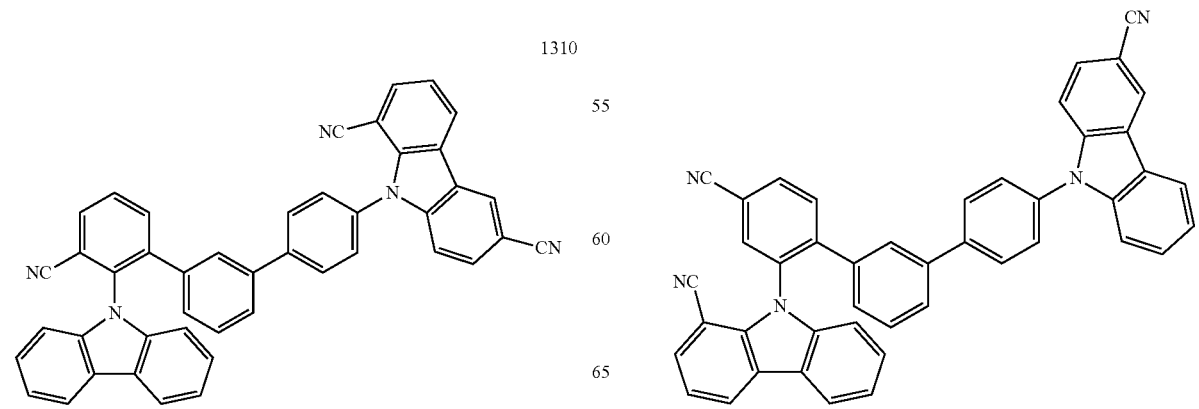

1315
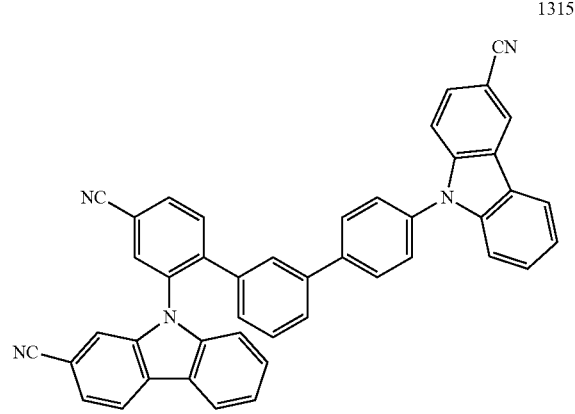
1316
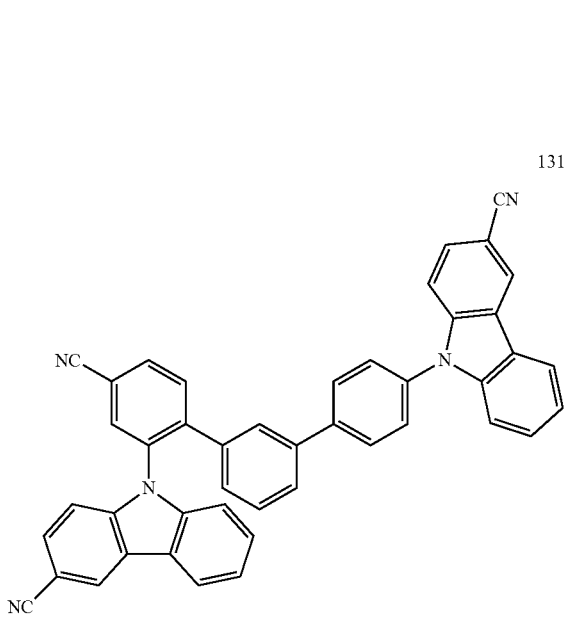
1317
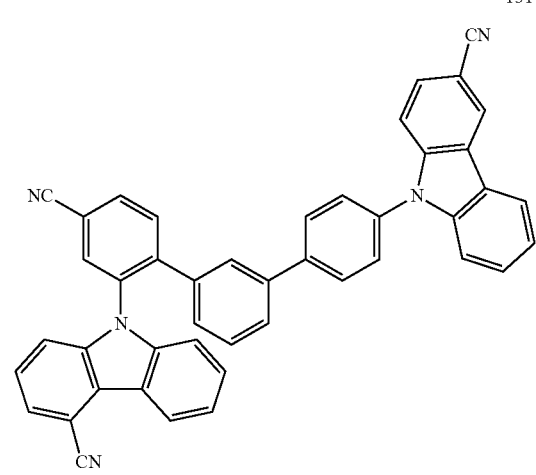
1318
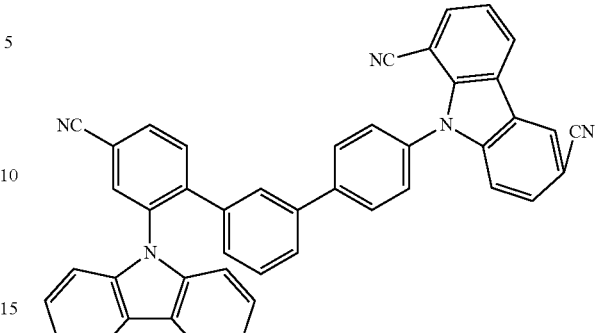
1319
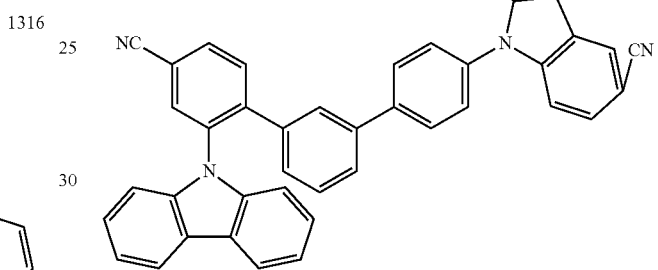
1320
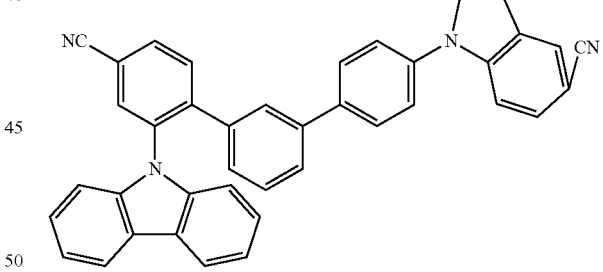
1321
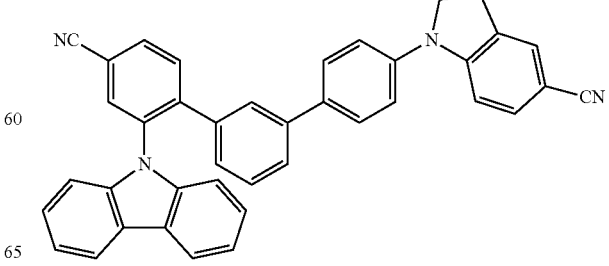

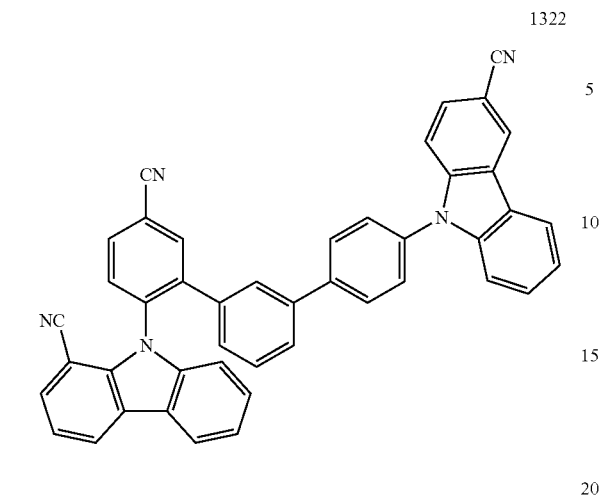
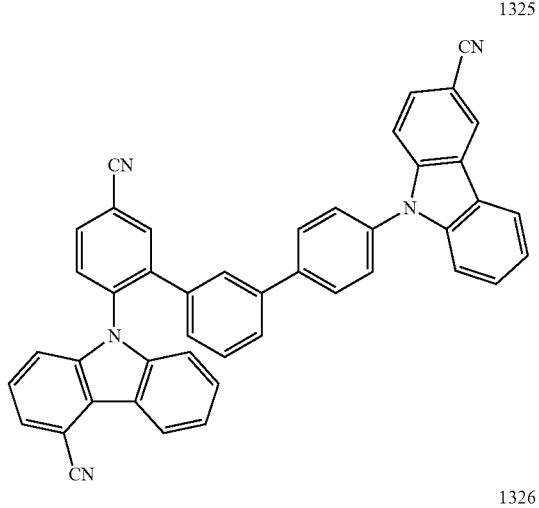
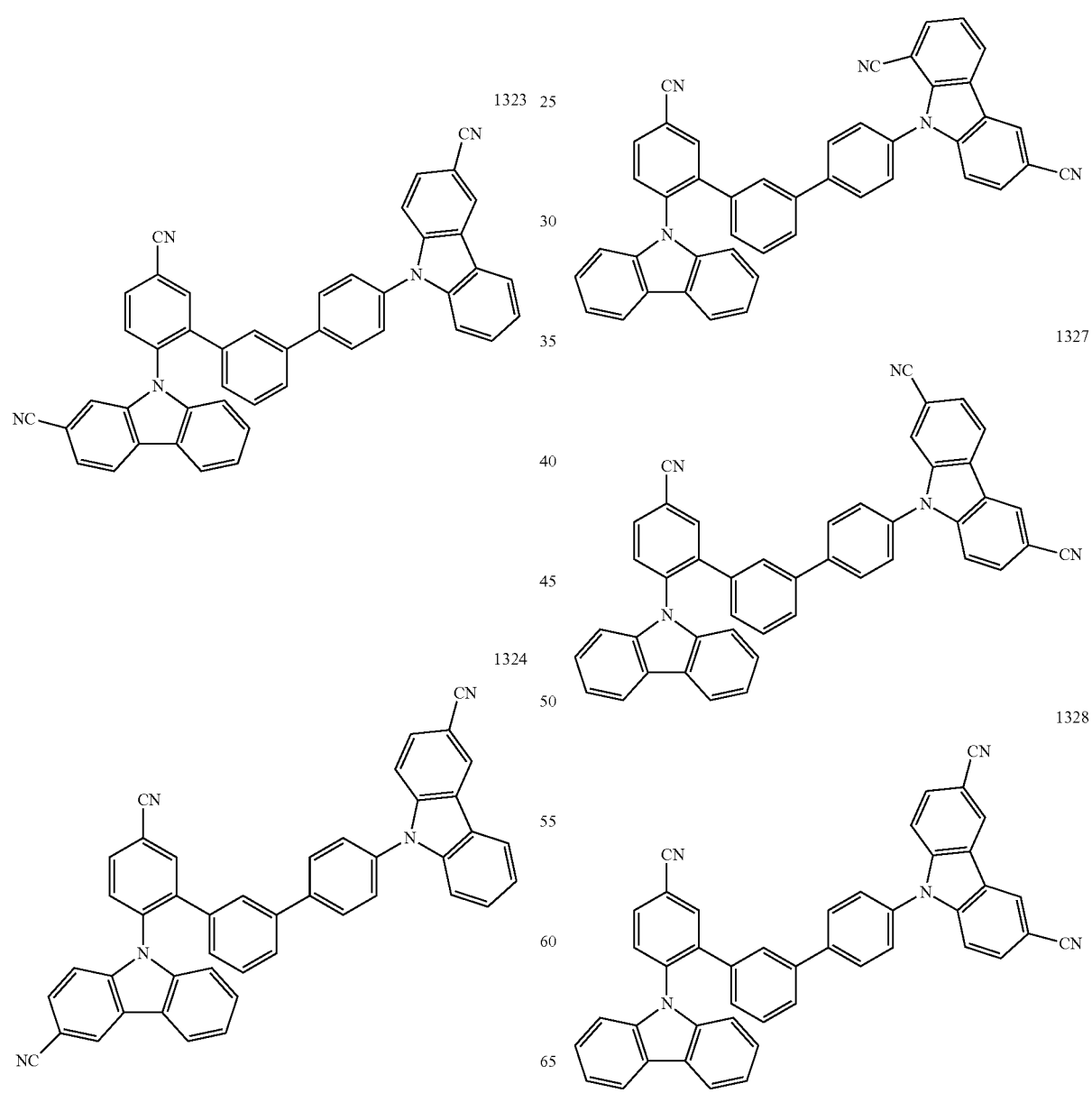

1329
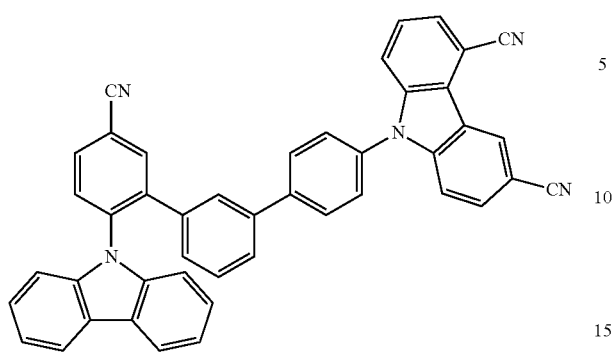
1330
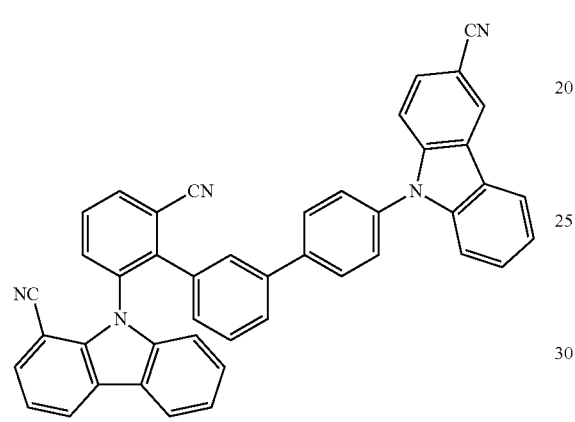
1331
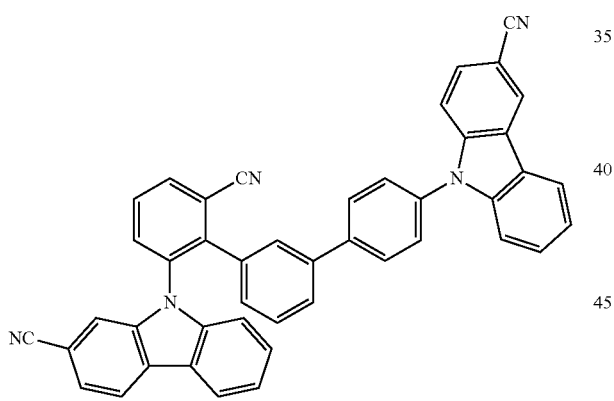
1332
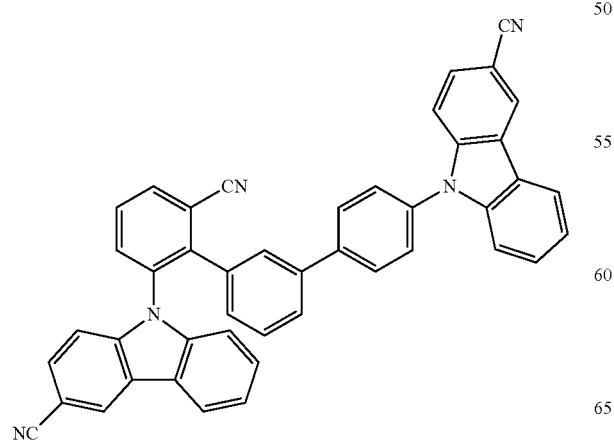
1333
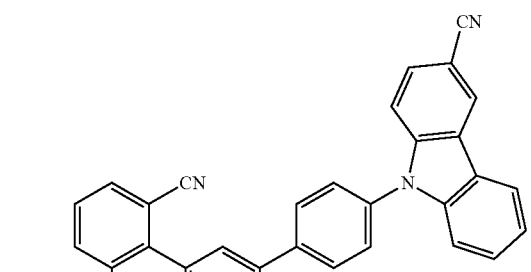
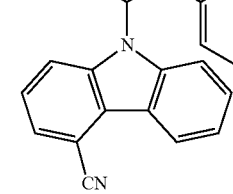
1334
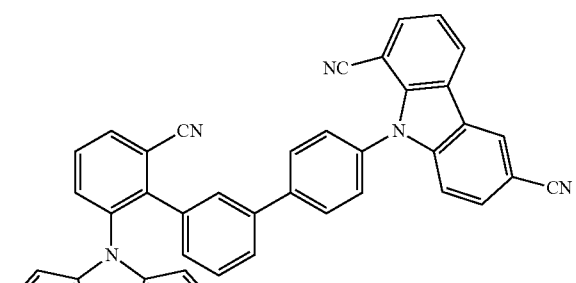
1335
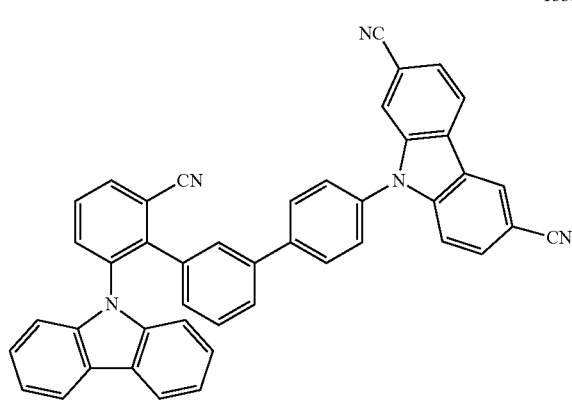
1336

-continued
1337
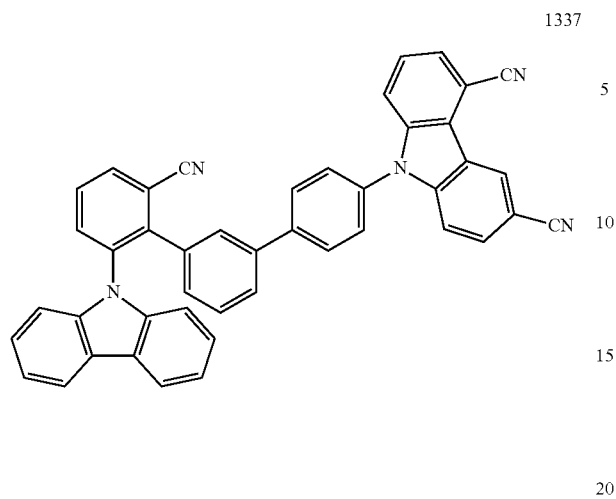
1338
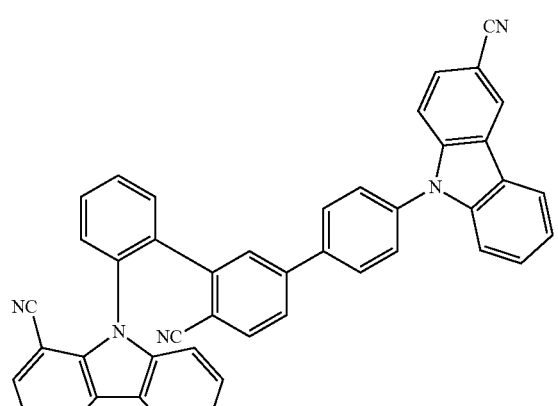
1339
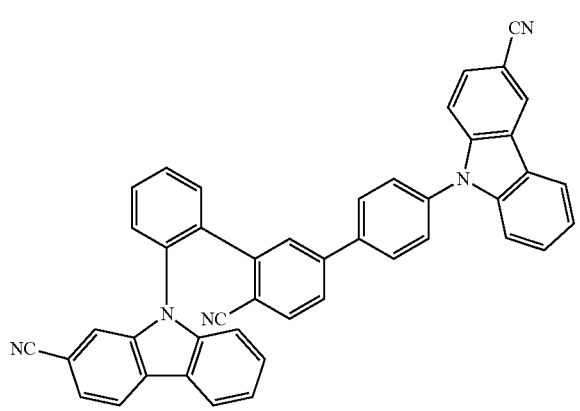
-continued
1340
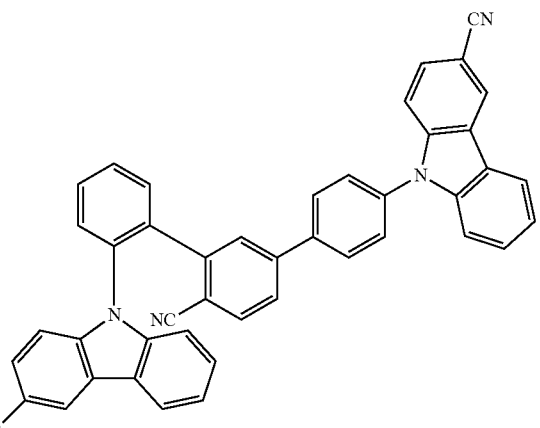
1341
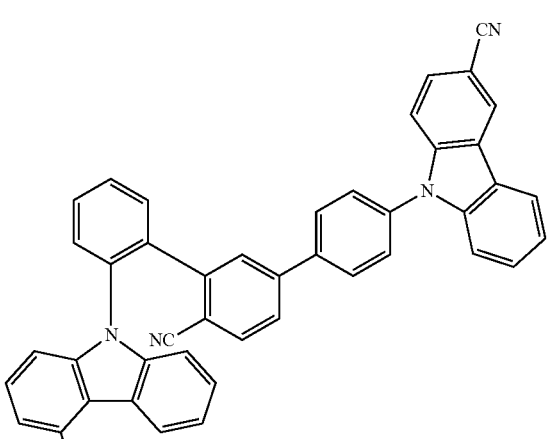
1342
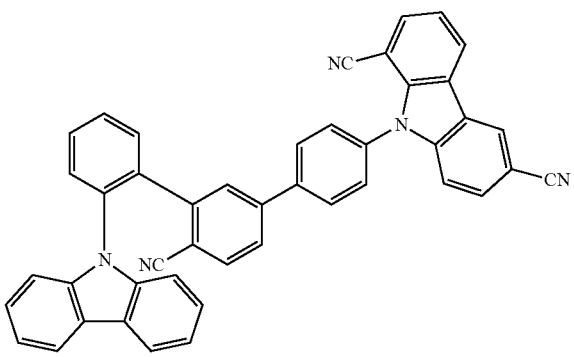

-continued
1343
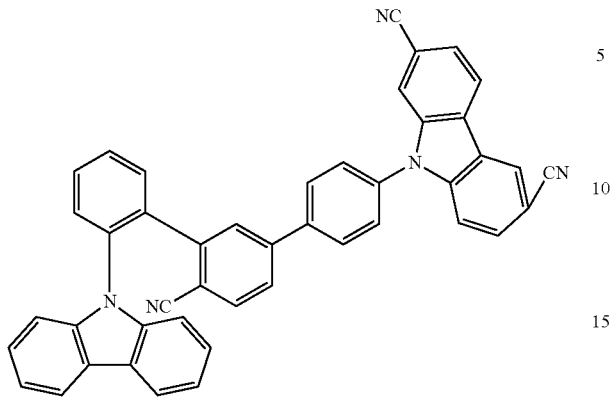
1344
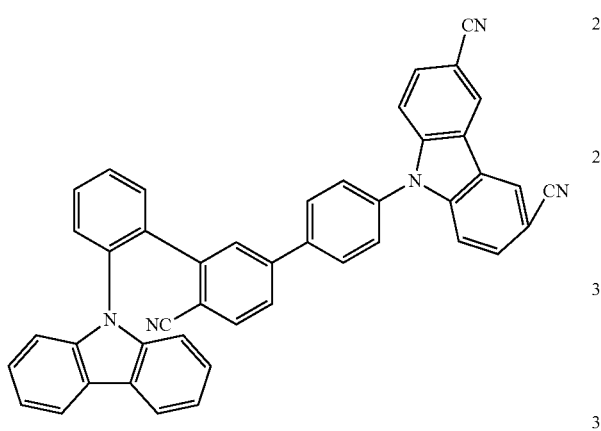
1345
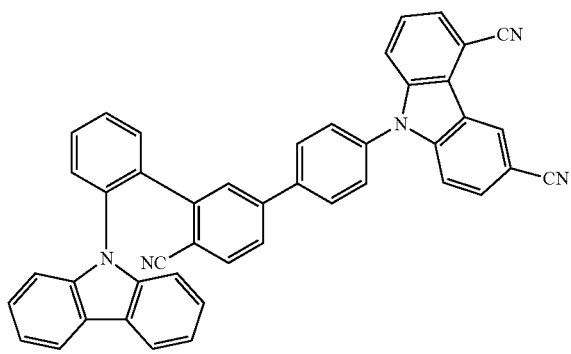
1346
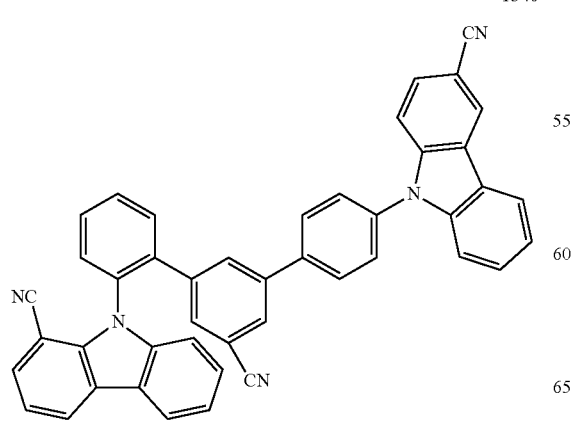
-continued
1347
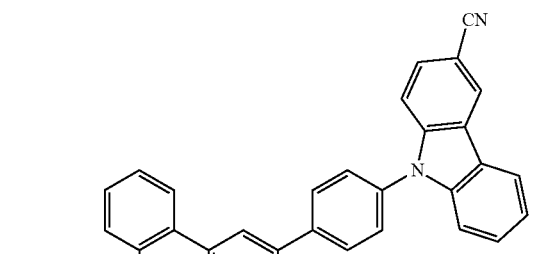
1348
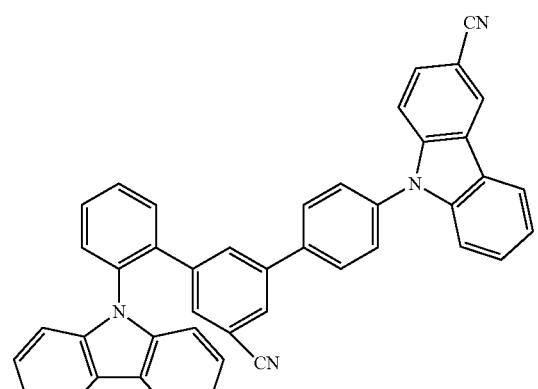
1349
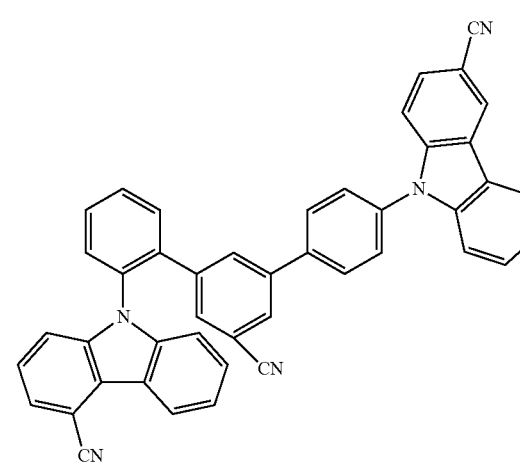

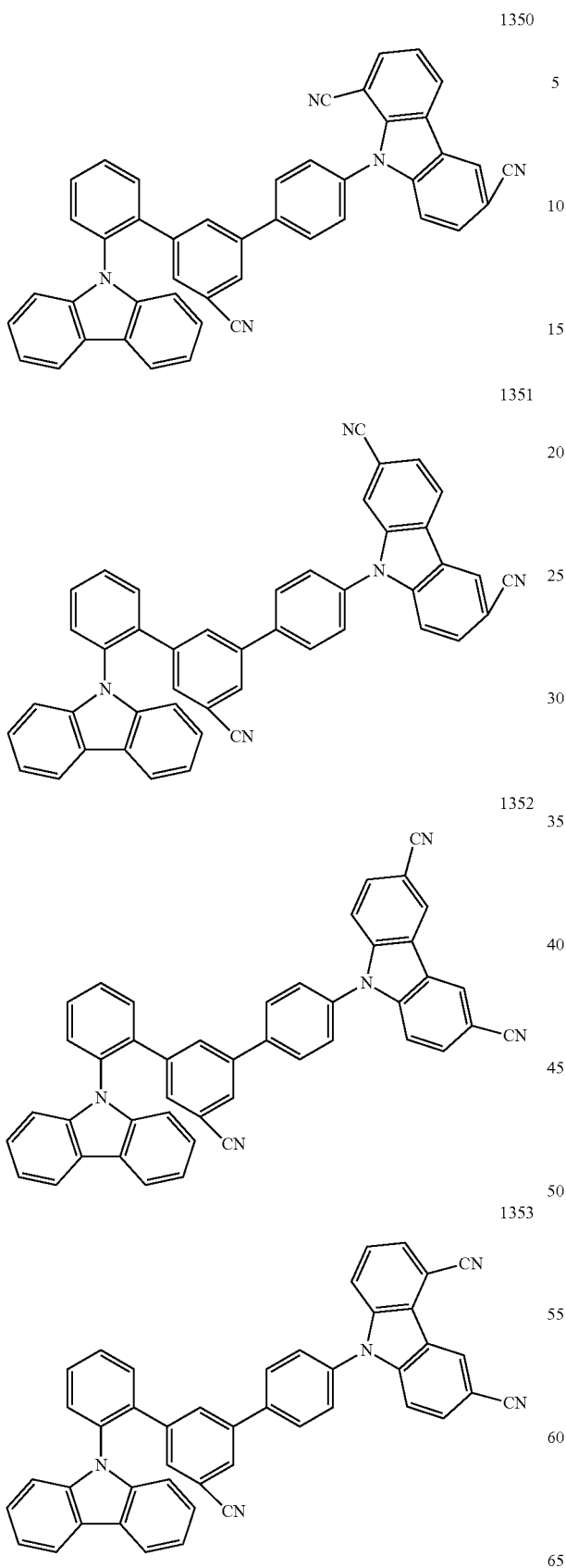
1350
1351
1352
1353
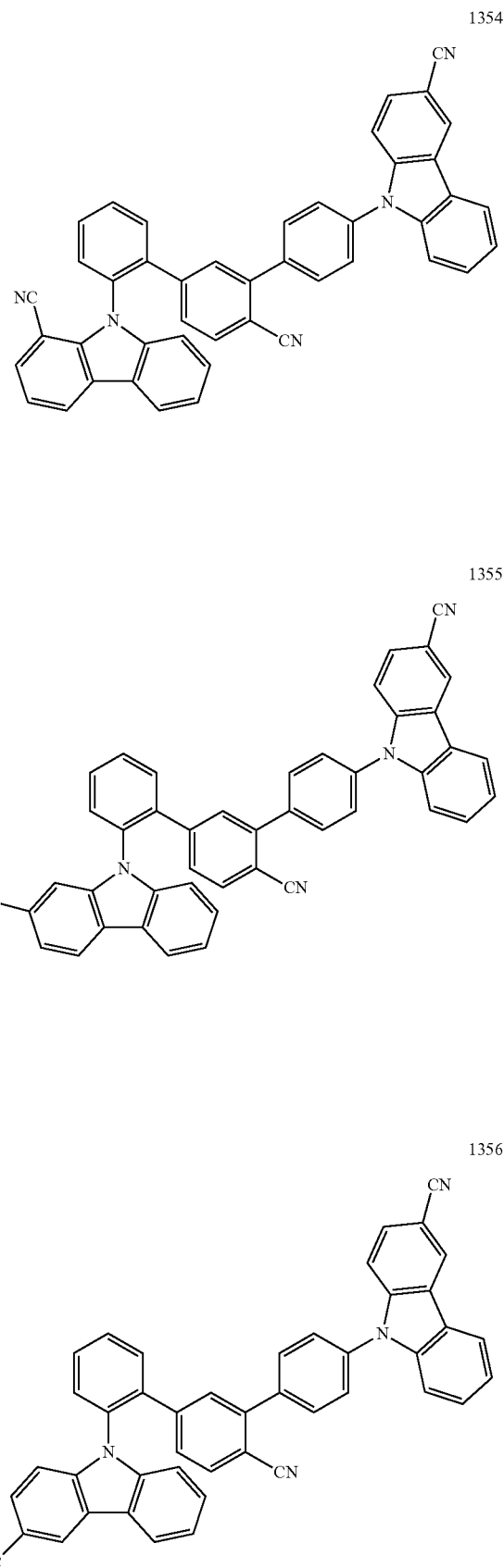
1354
1355
1356

-continued
1357
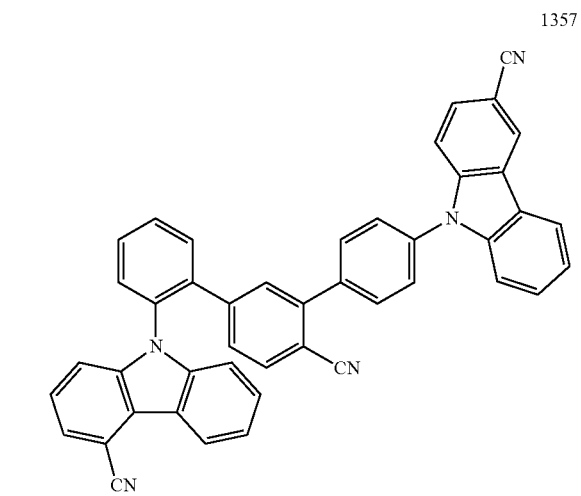
1358
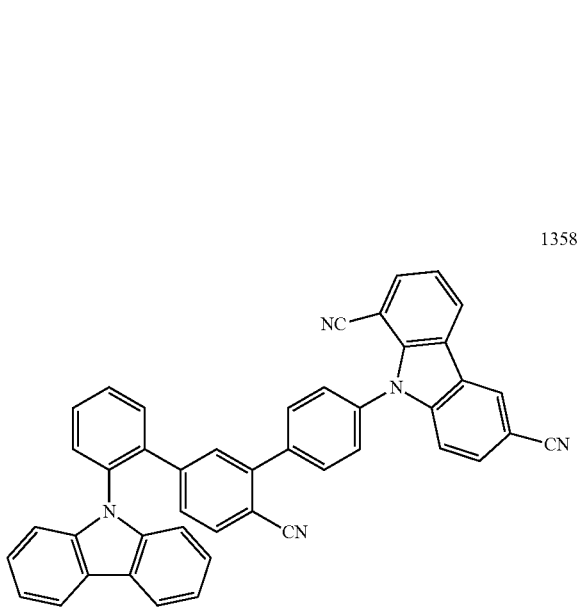
1359
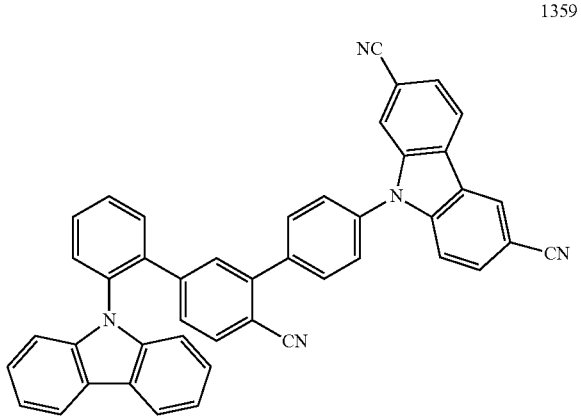
-continued
1360
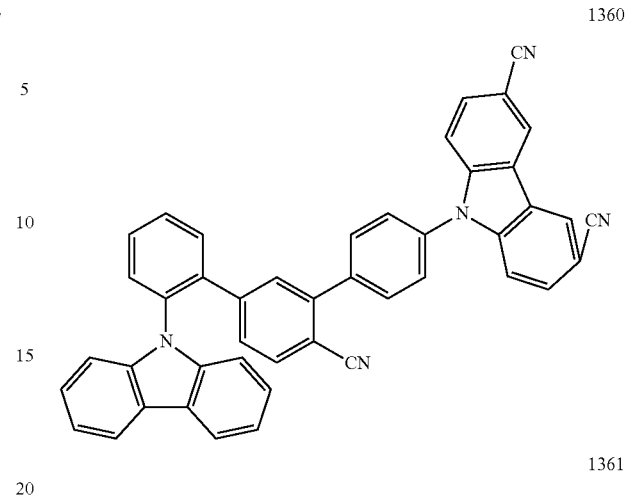
1361
1362
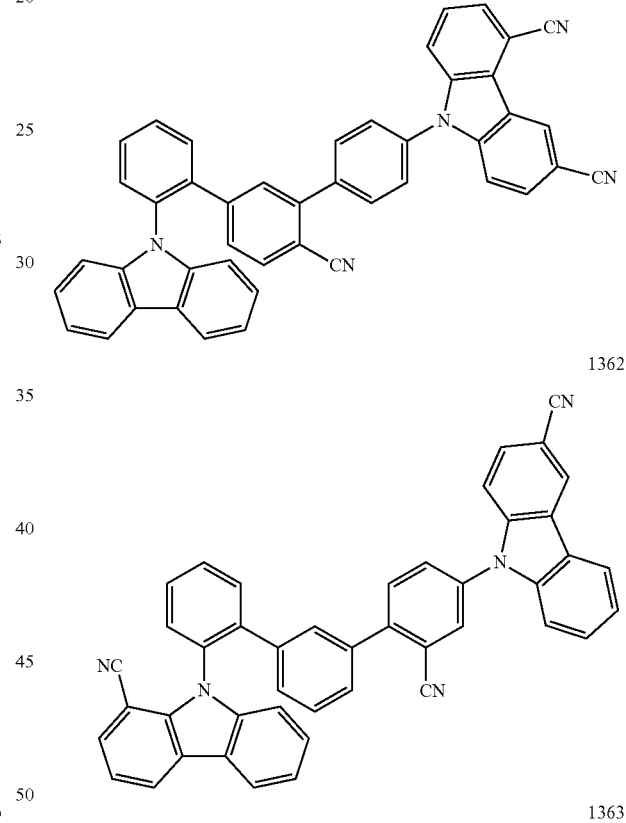
1363
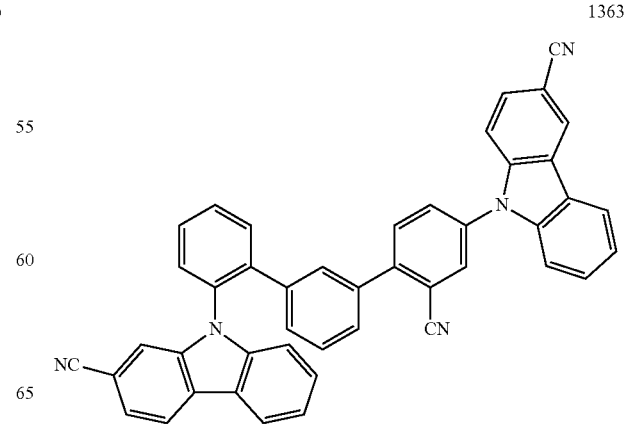

-continued
1364
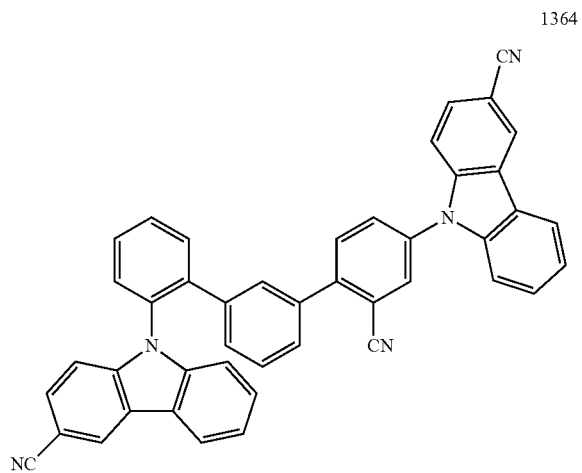
1365
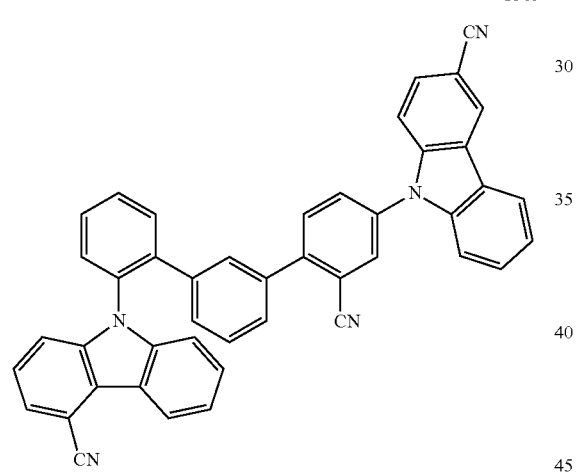
1366
1367
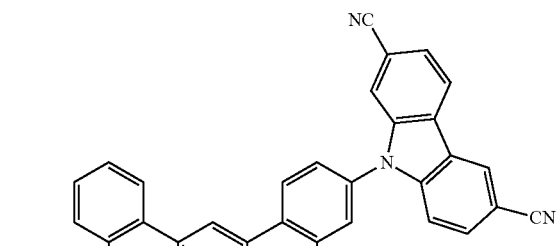
1368
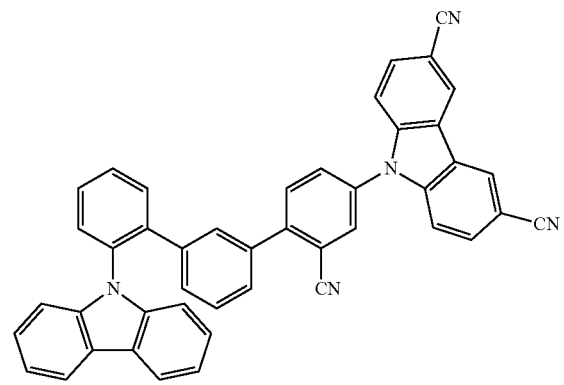
1369
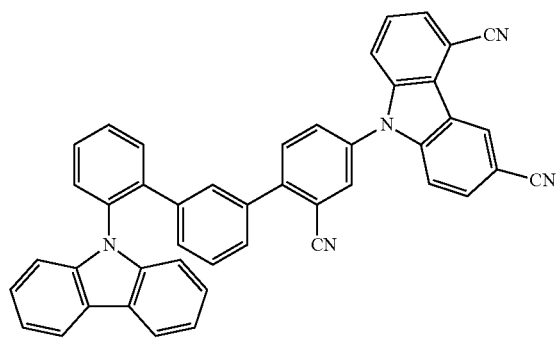
1370
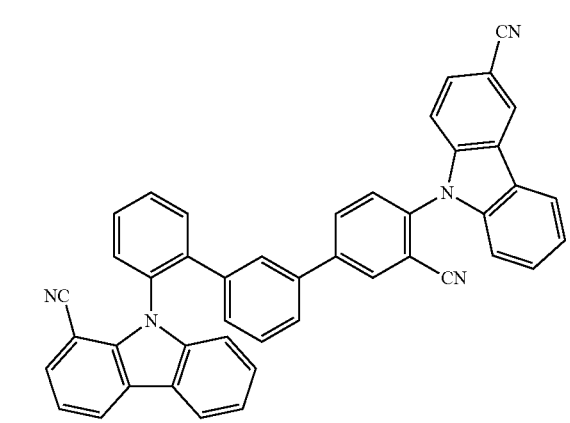
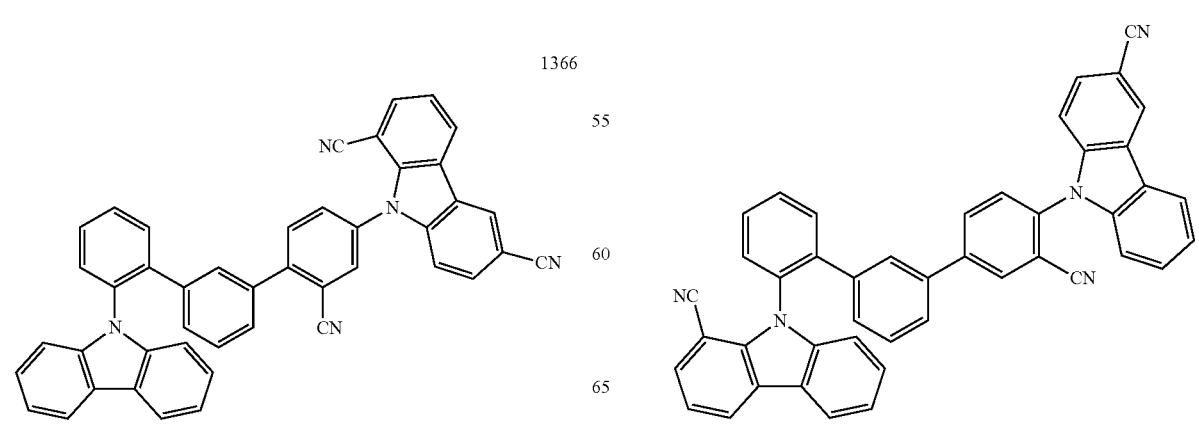

1371
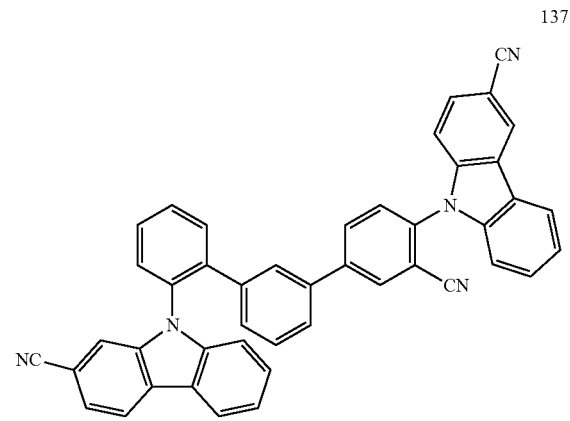
1372
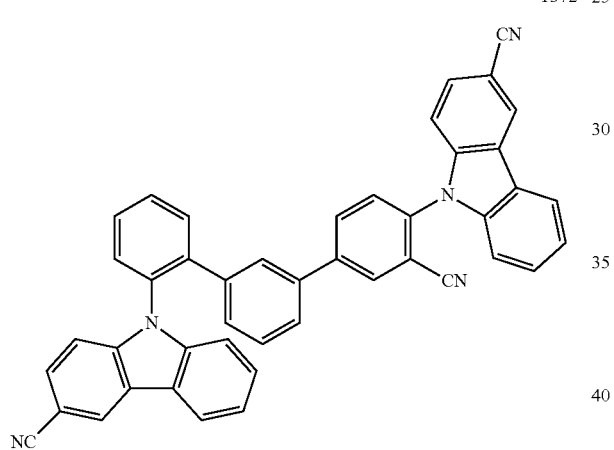
1373
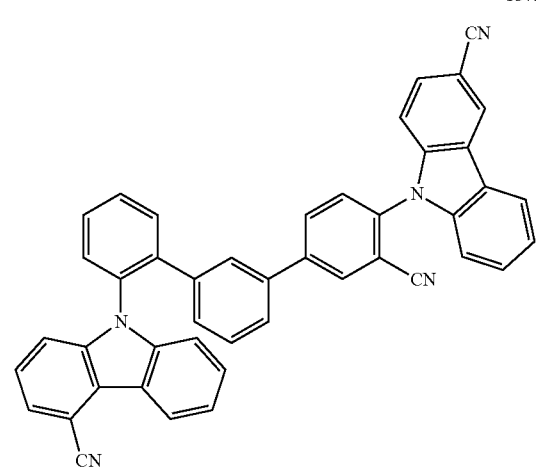
1374
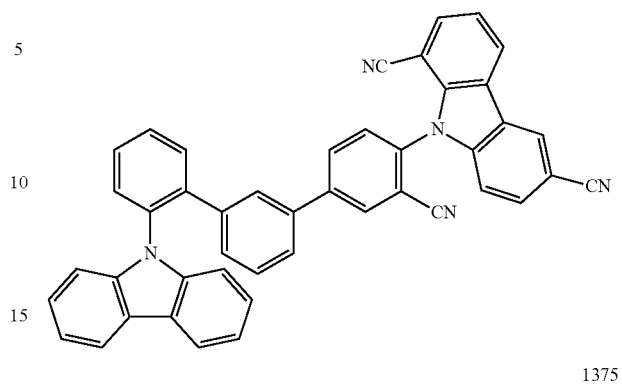
1375
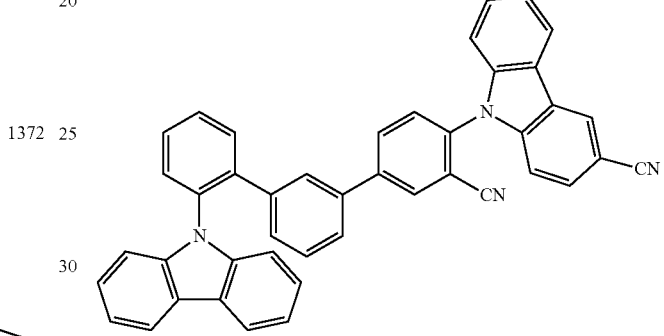
1376
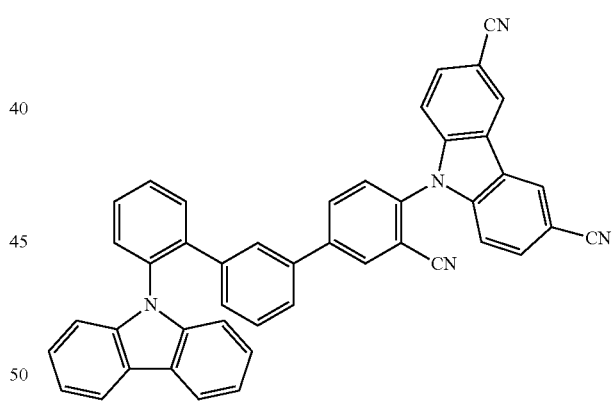
1377
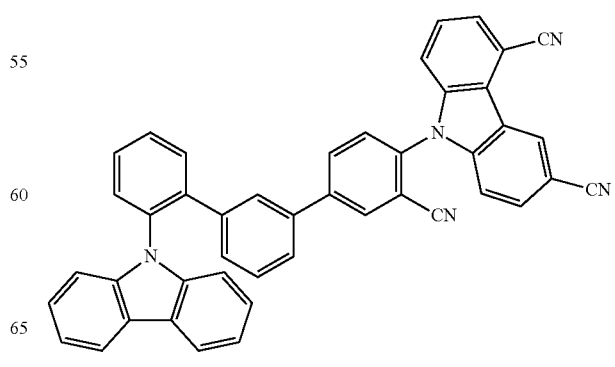

-continued
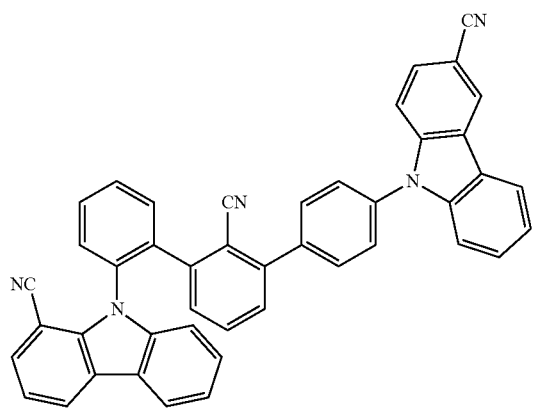
1378
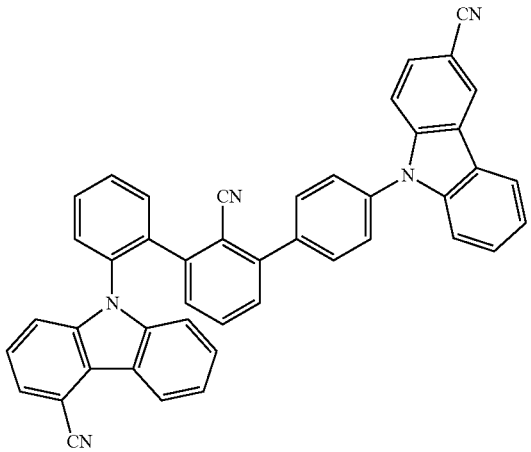
1381
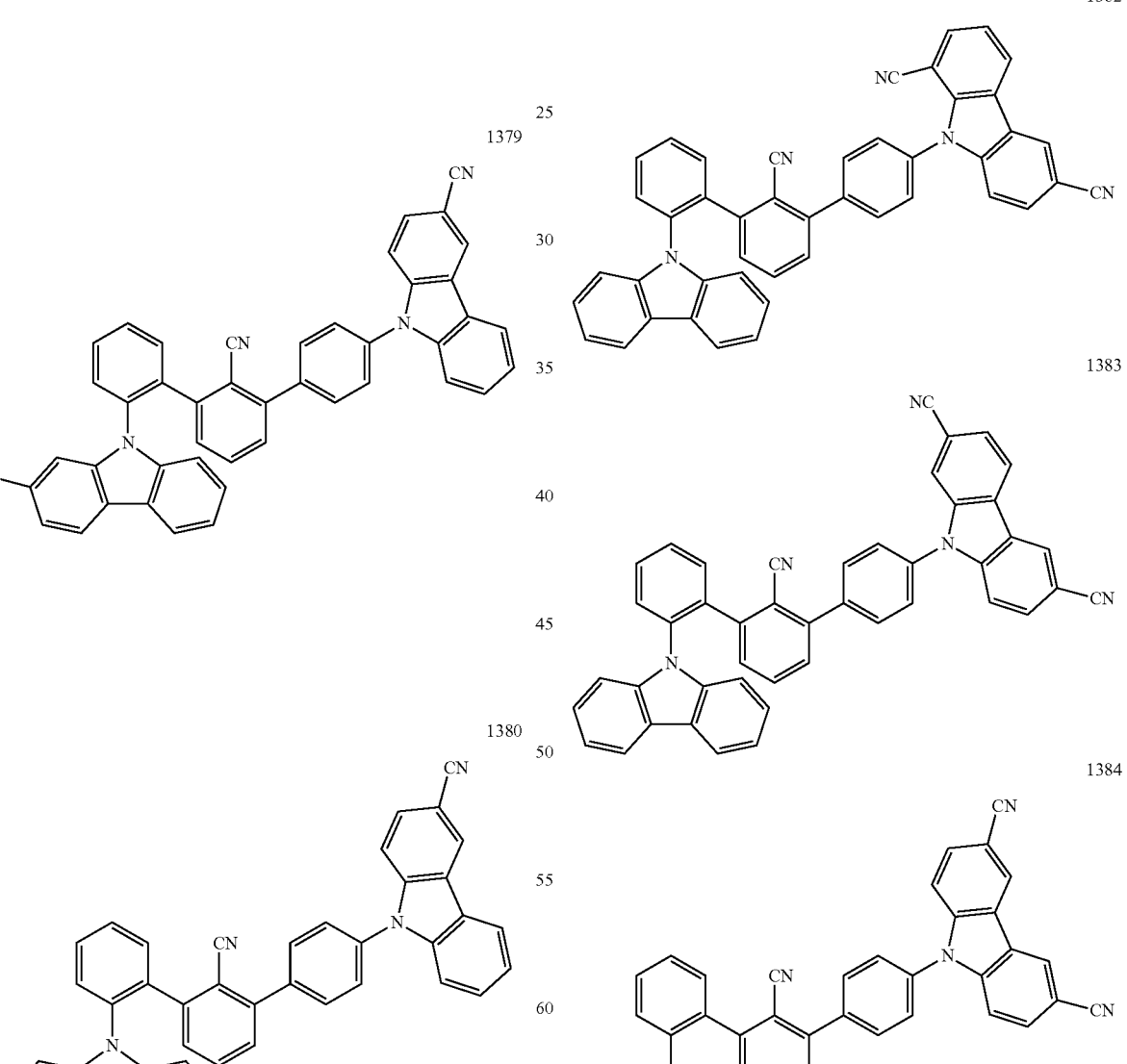
1379
1382
1380
1383
1384

| 1385 | 1389 |
|---|---|
| 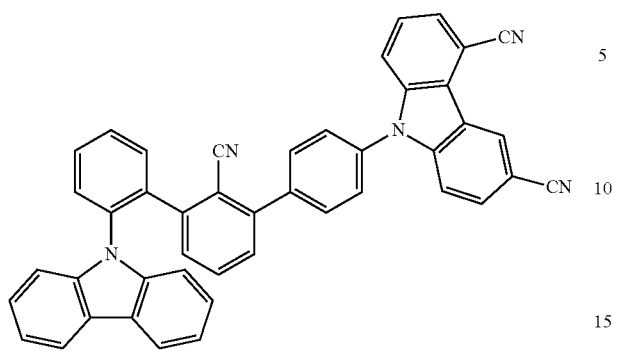 | 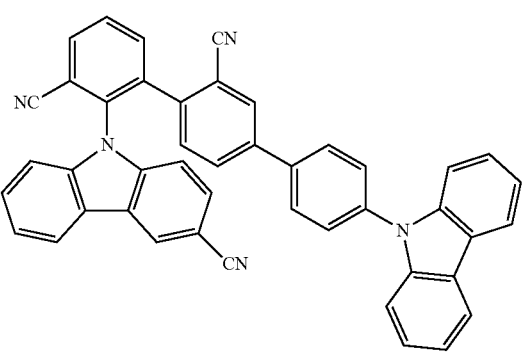 |
| 1386 | 1390 |
| 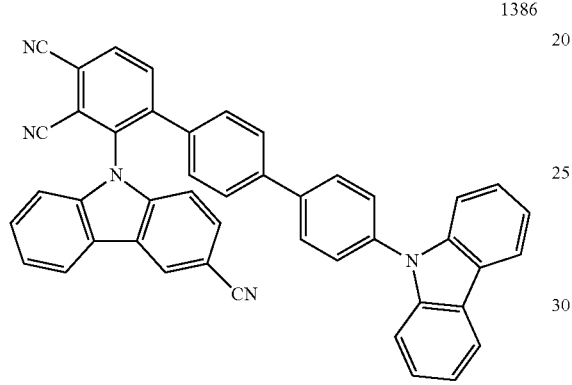 | 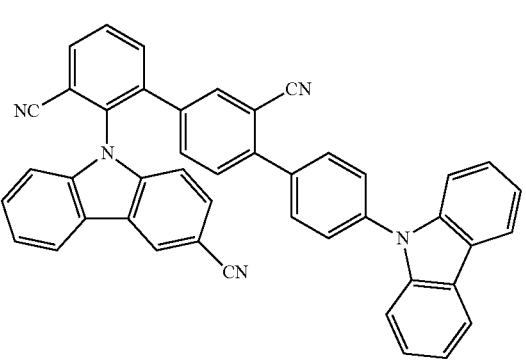 |
| 1387 | 1391 |
| 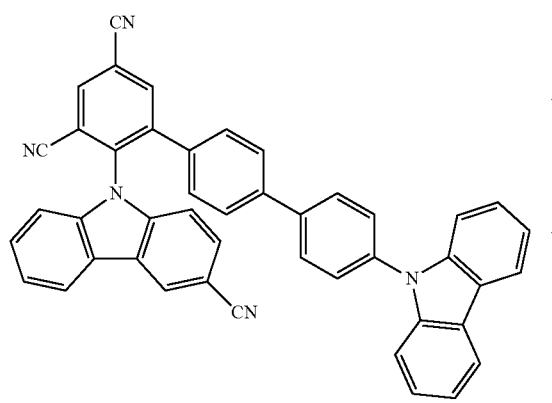 | 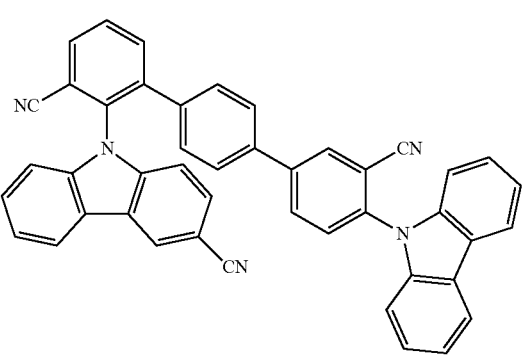 |
| 1388 | 1392 |
| 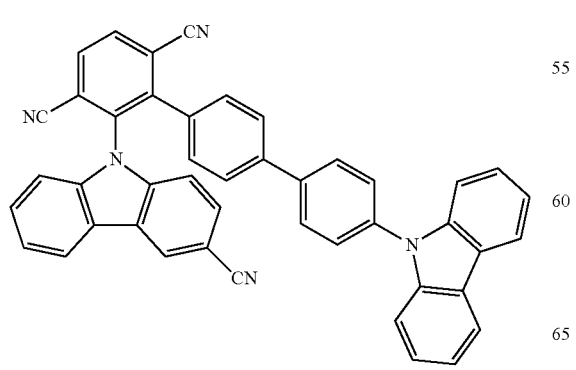 | 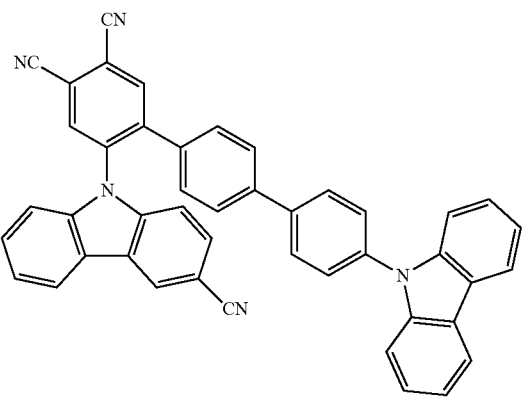 |

1393
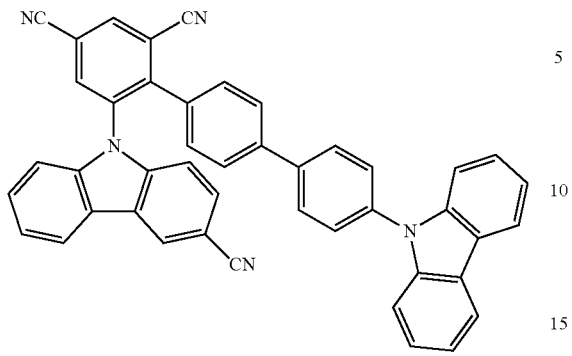
1397
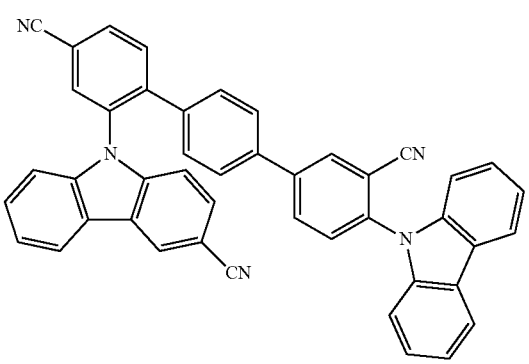
1394
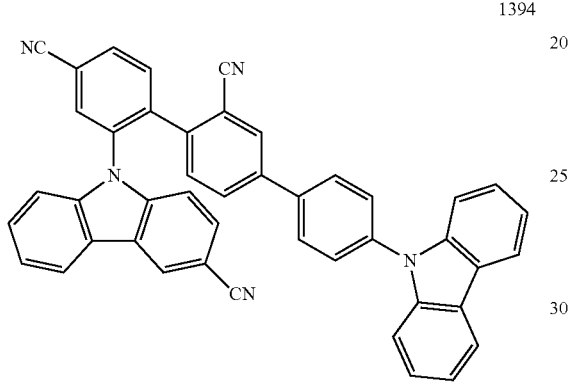
1398
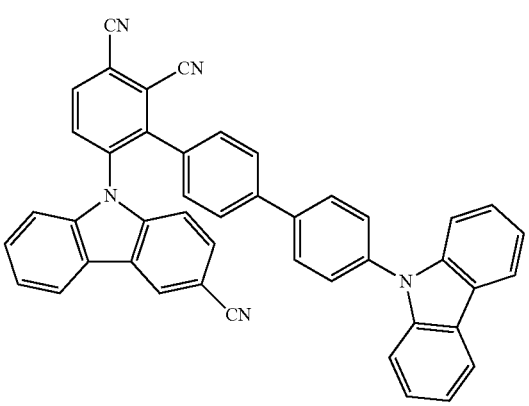
1395
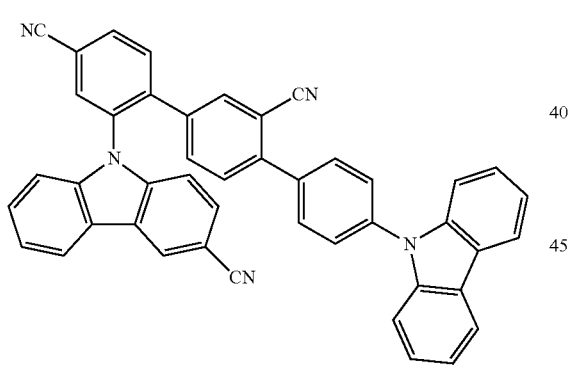
1399
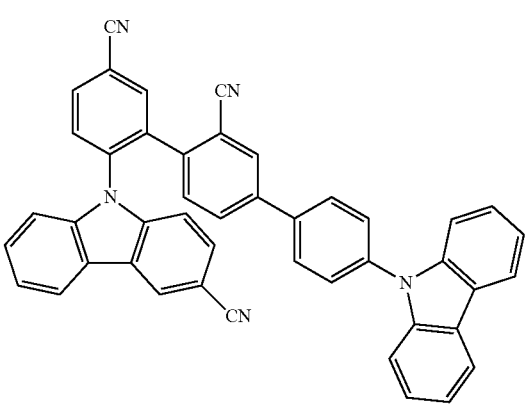
1396
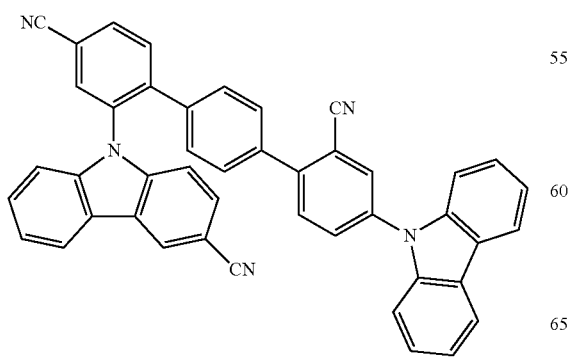
1400
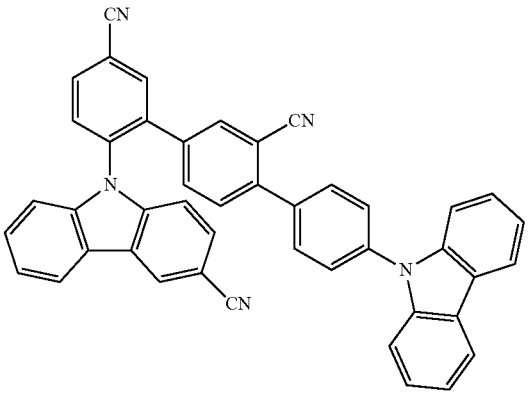

| 1401 | 1405 |
| --- | --- |
| 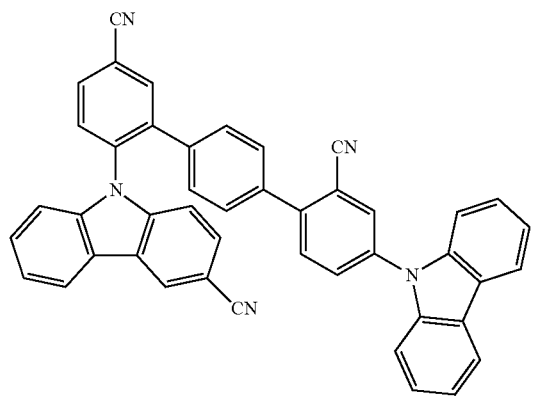 | 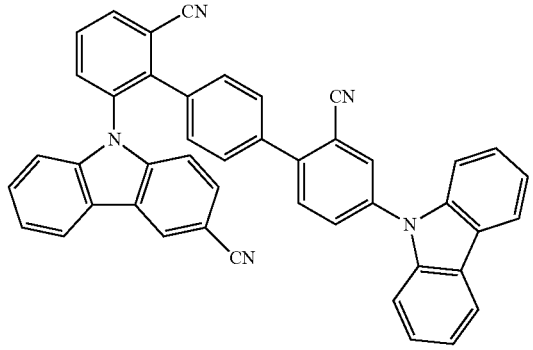 |
| 1402 | 1406 |
| 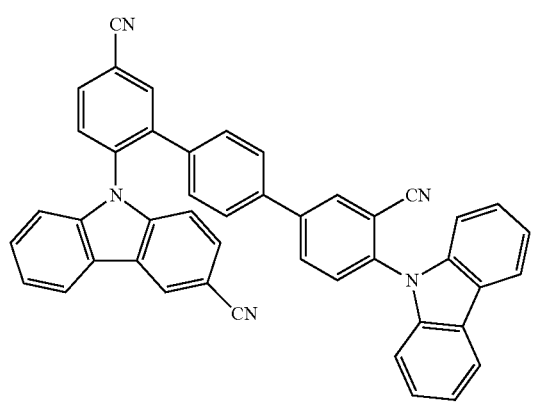 |  |
| 1403 | 1407 |
| 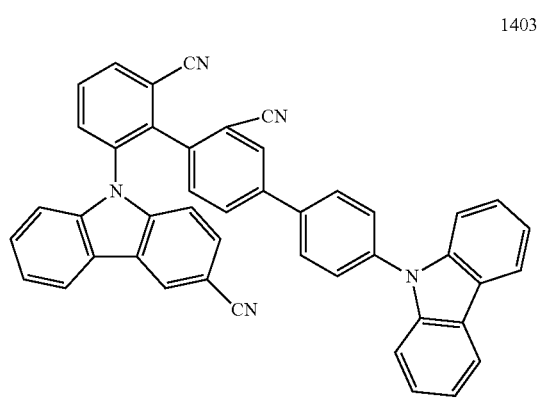 | 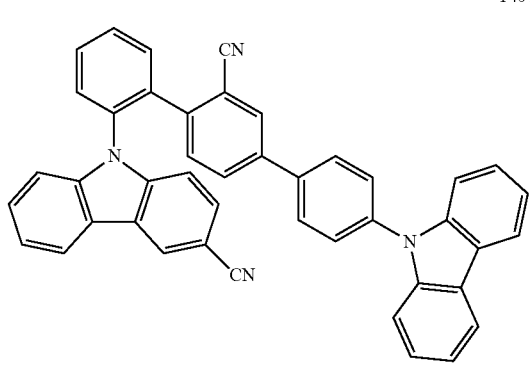 |
| 1404 | 1408 |
| 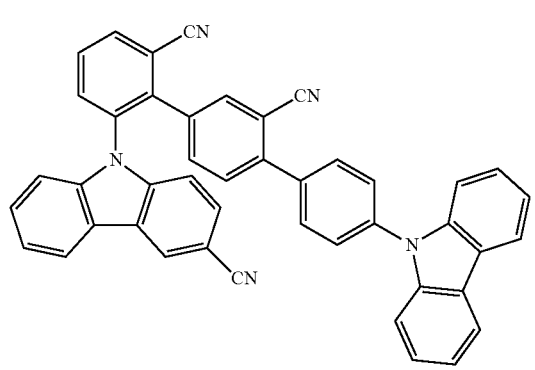 | 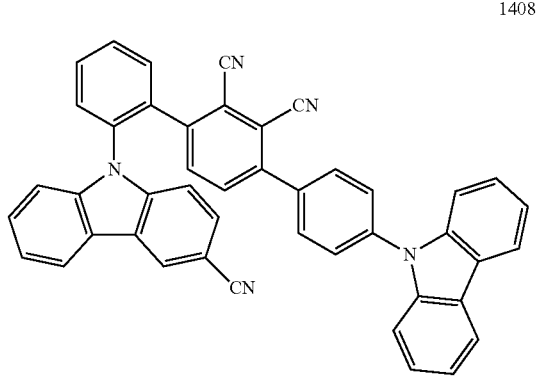 |

401
-continued
1409
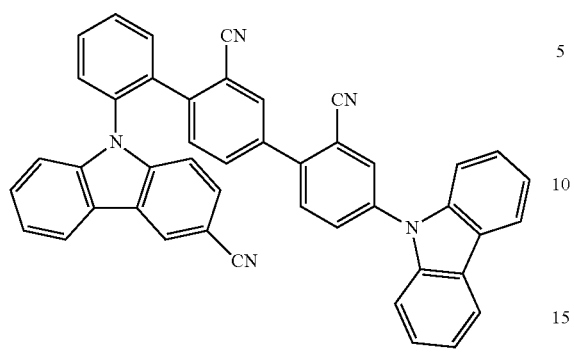
1410
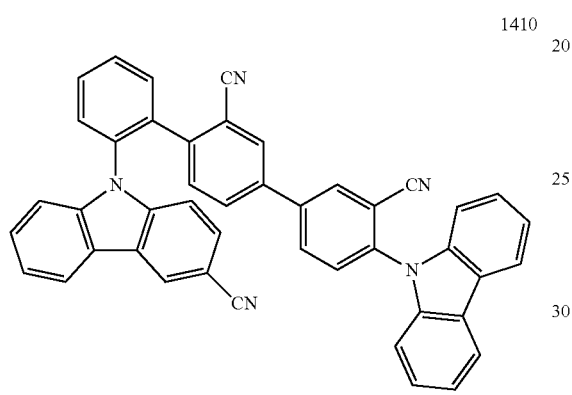
1411
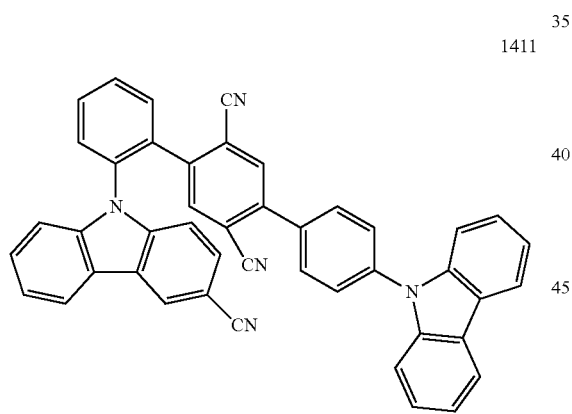
1412
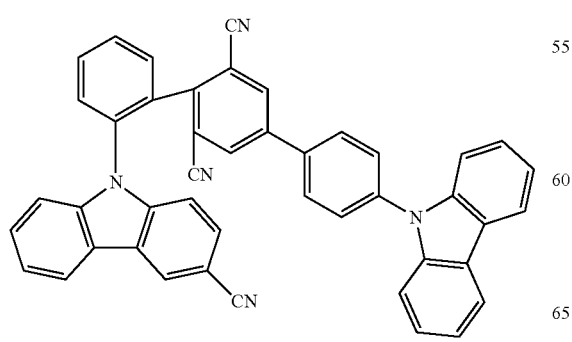
402
-continued
1413
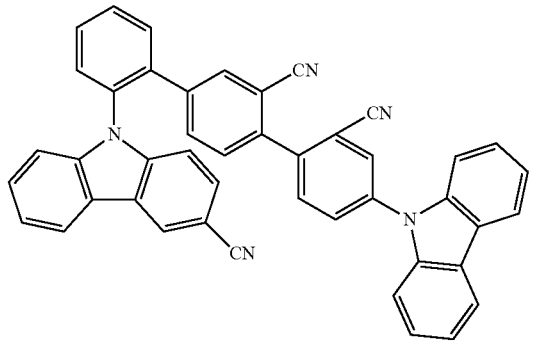
1414
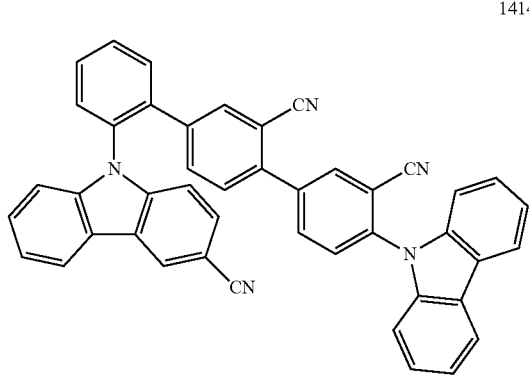
1415
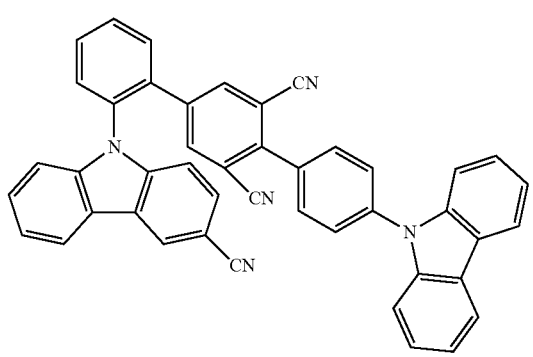
1416
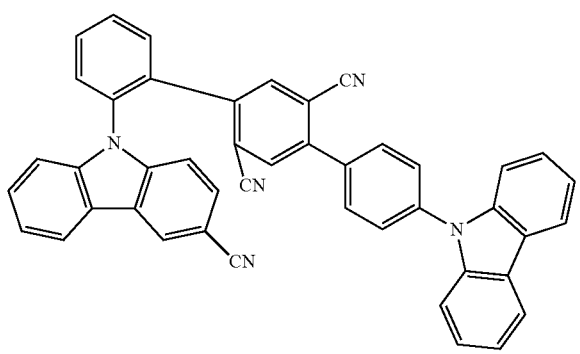

-continued
1417
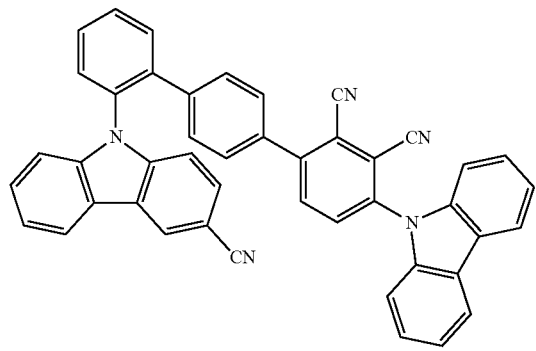
1421
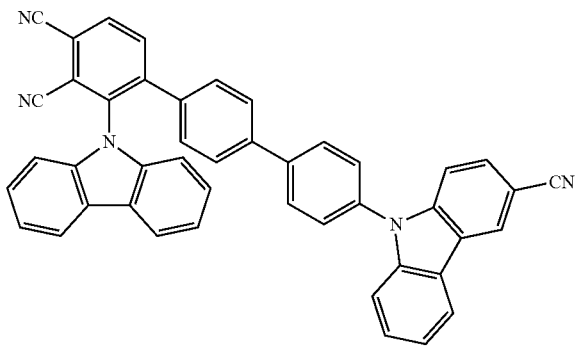
1418
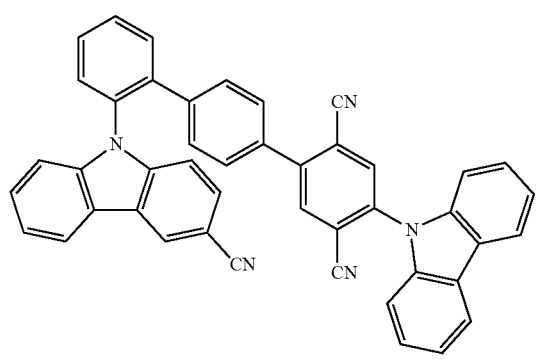
1422
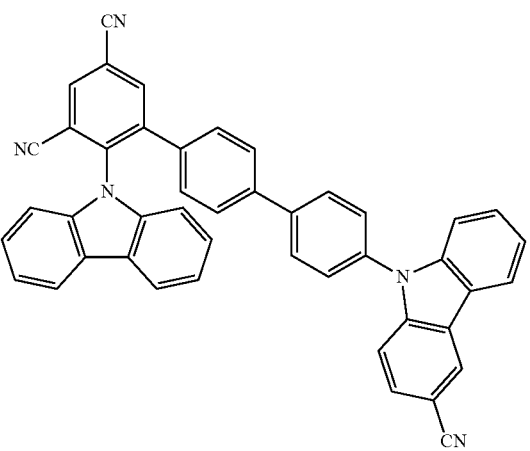
1419
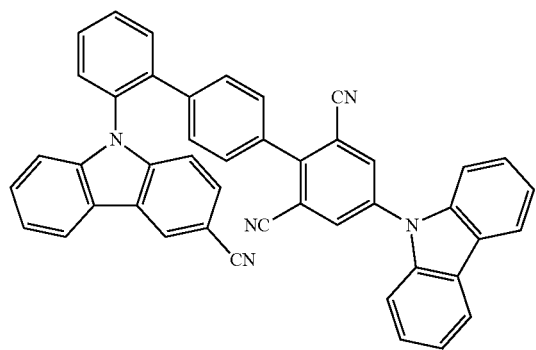
1420
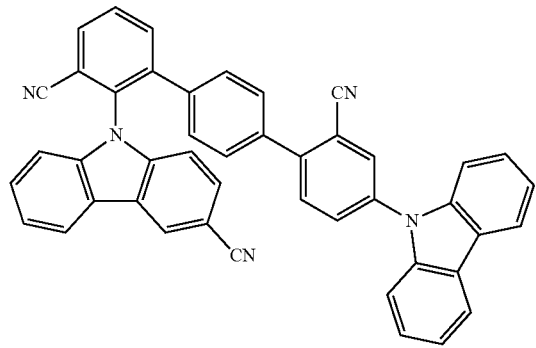
1423
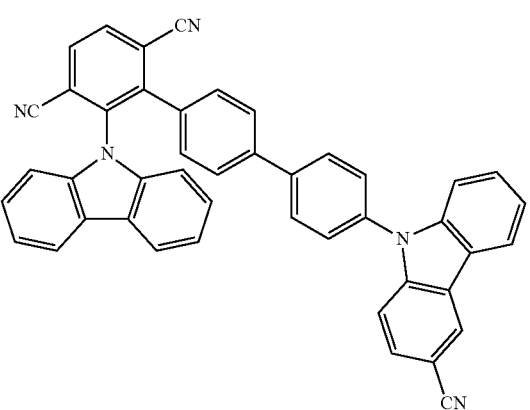

1424
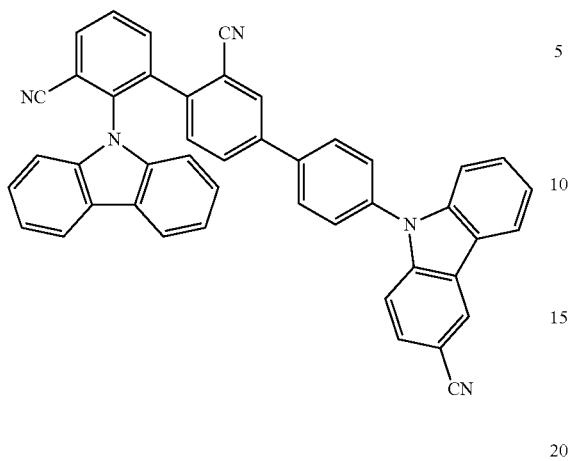
1425
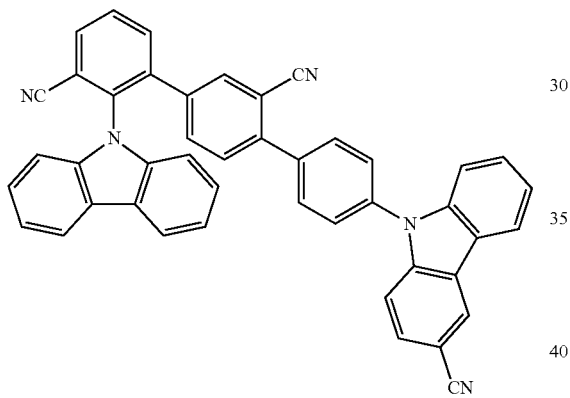
1426
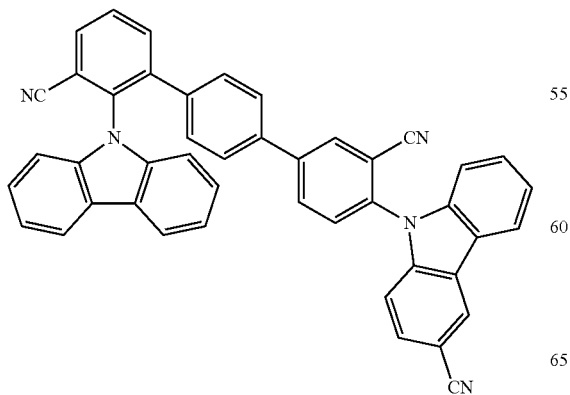
1427
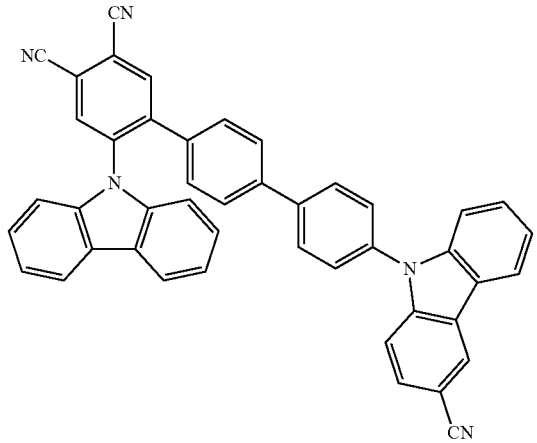
1428
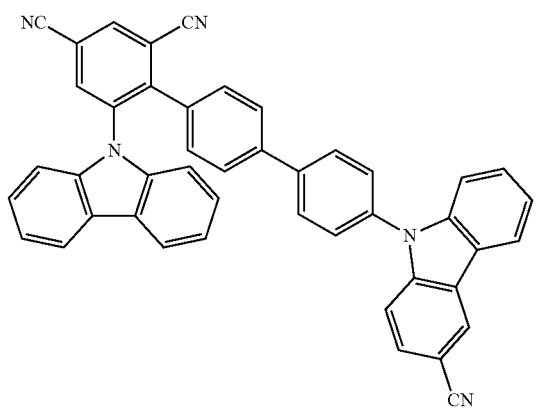
1429
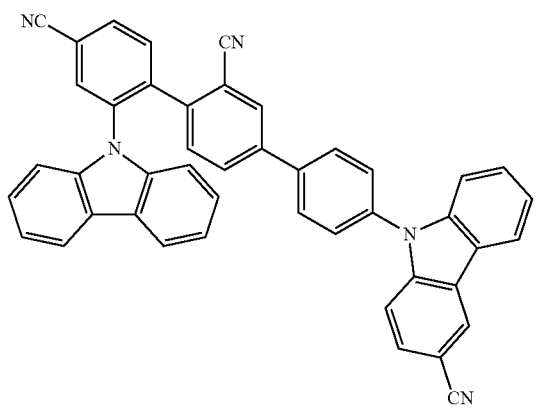

1430
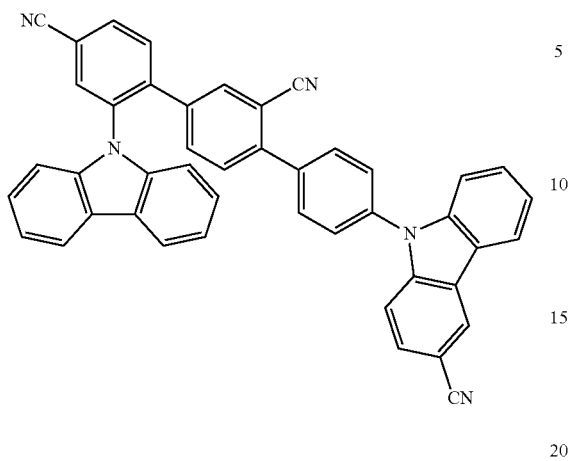
1431
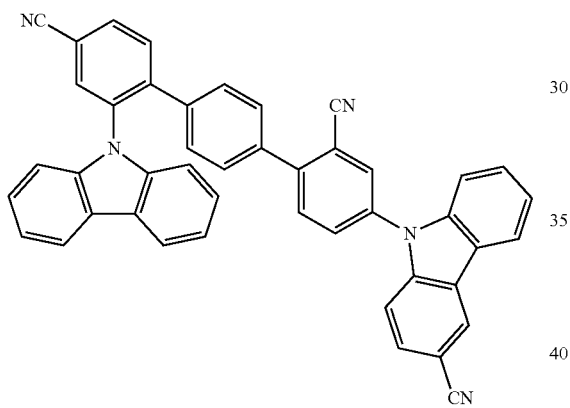
1432
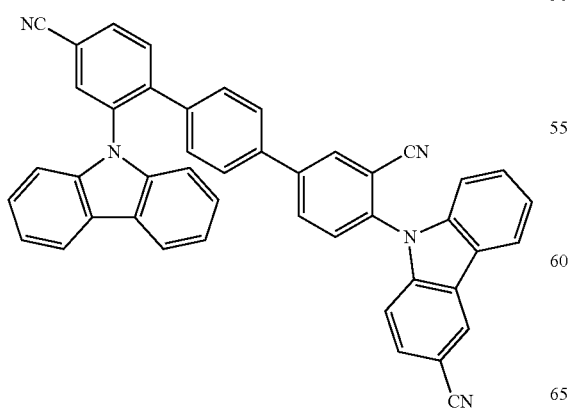
1433
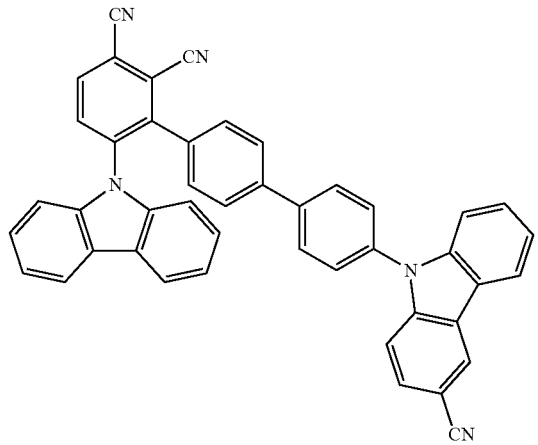
1434
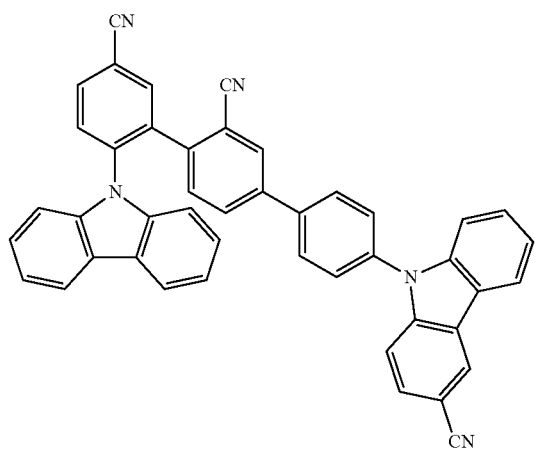
1435
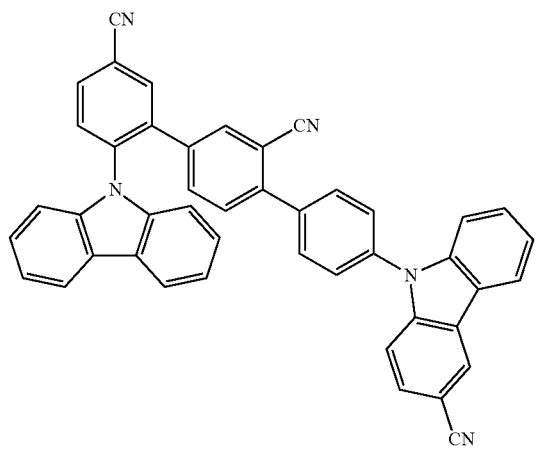

-continued
1436
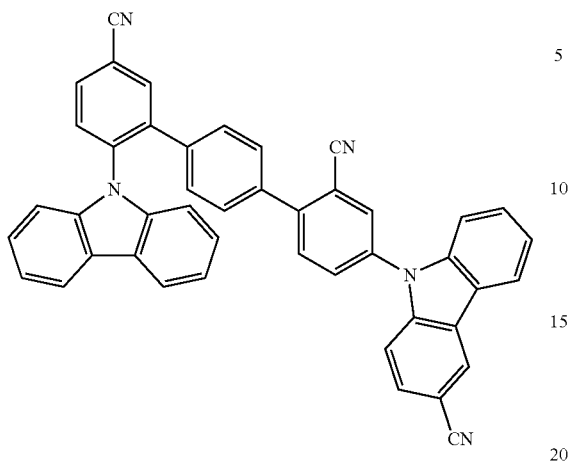
1437
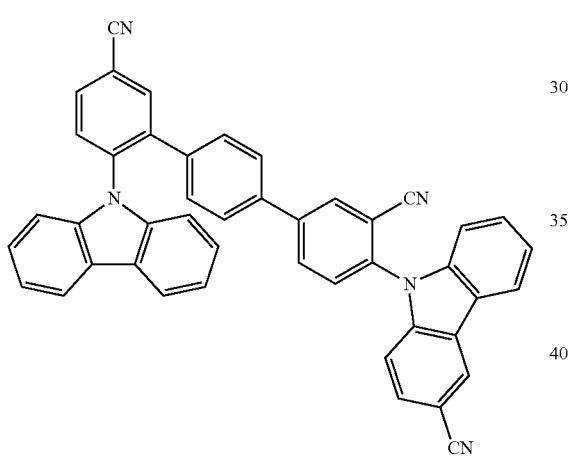
1438
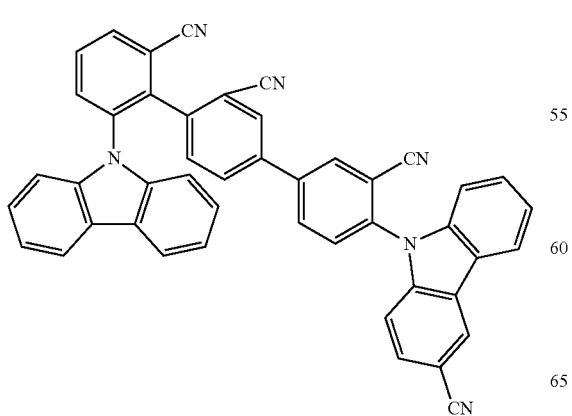
-continued
1439
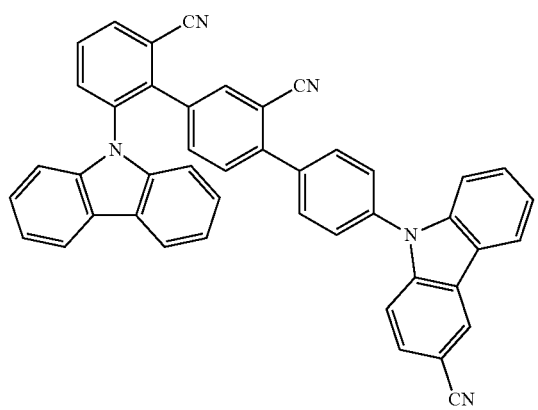
1440
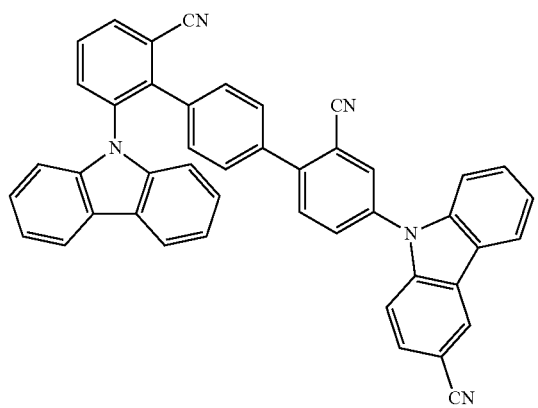
1441
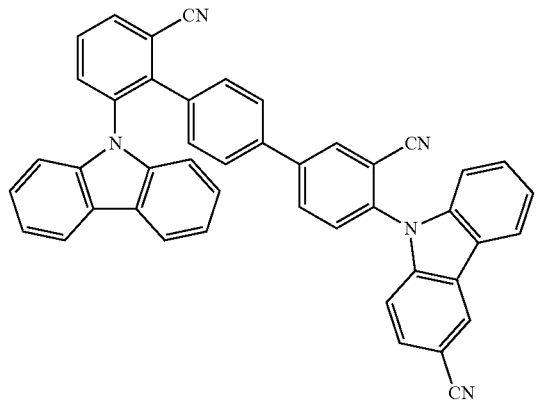

1442
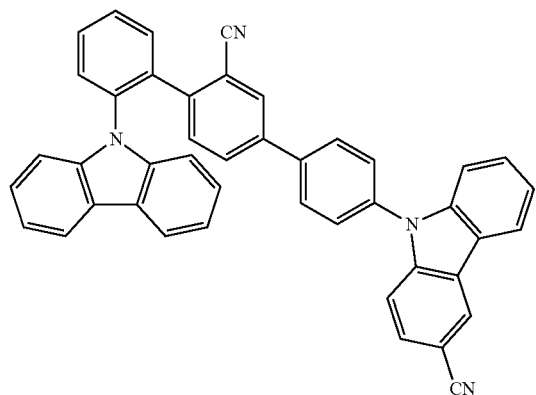
1443
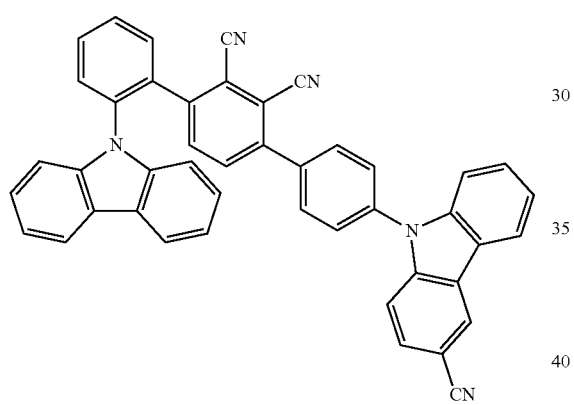
1444
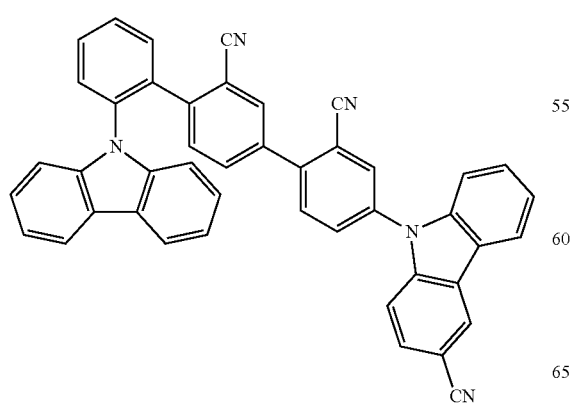
1445
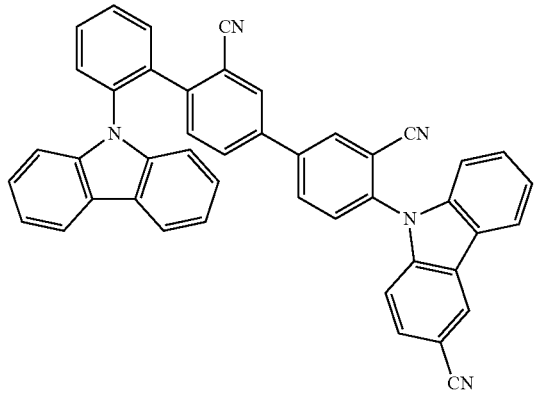
1446
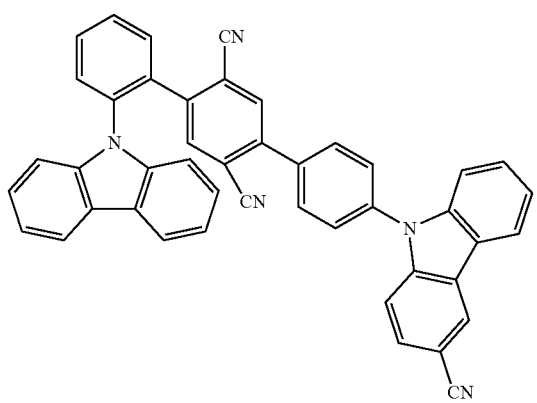
1447
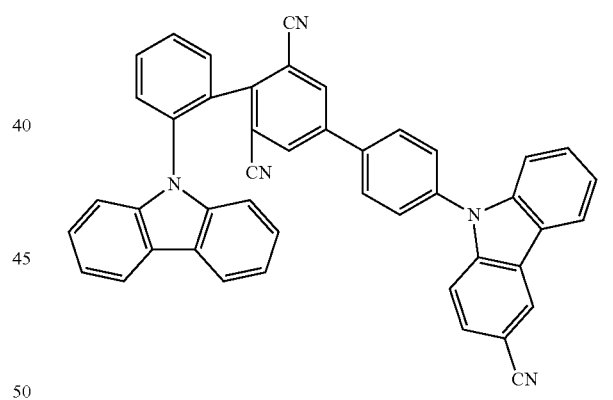
1448
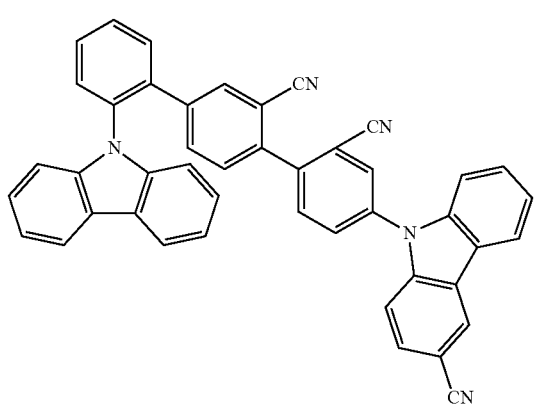

-continued
1449
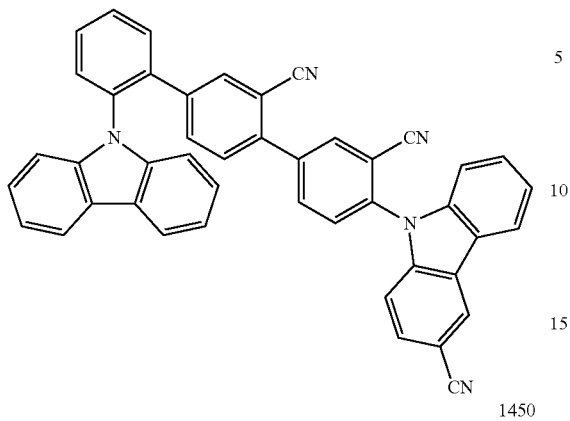
1450
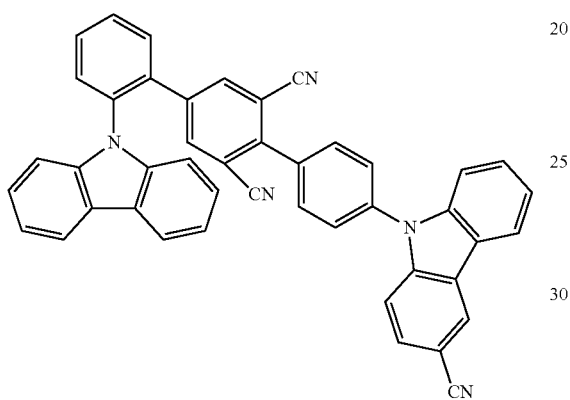
1451
1452
-continued
1453
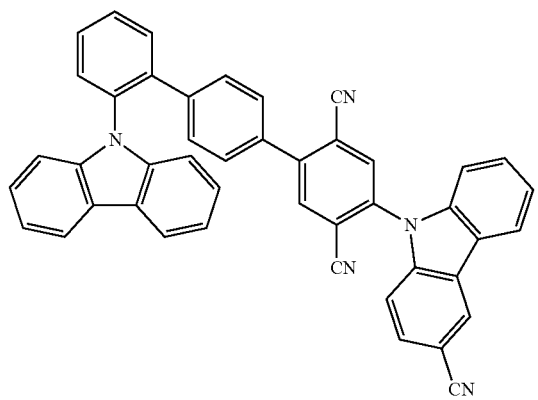
1454
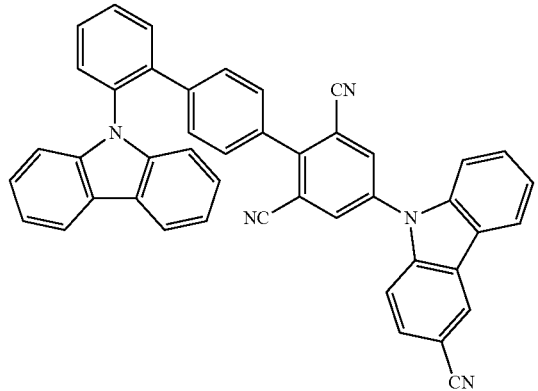
1455
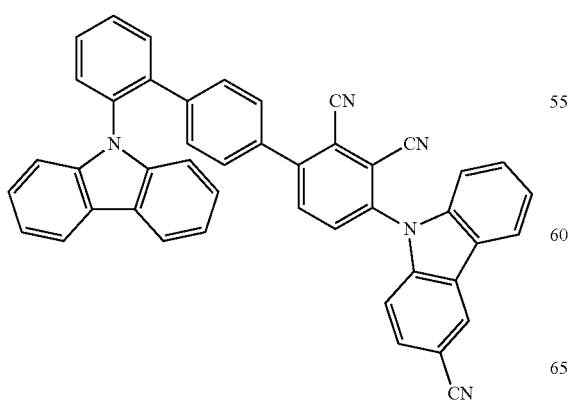
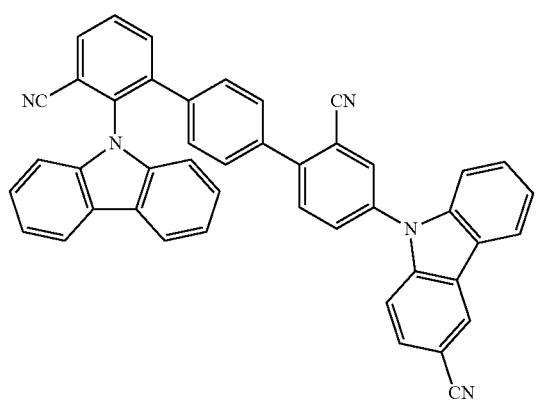

1456 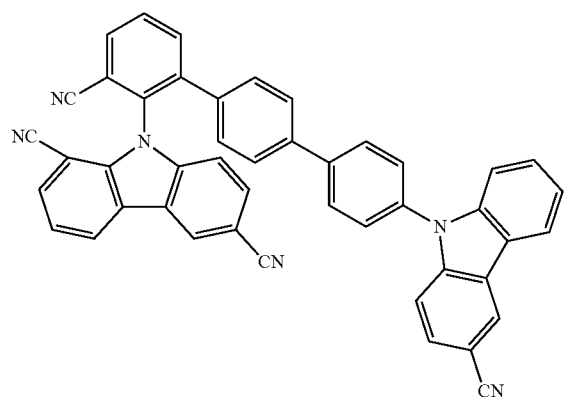
1460 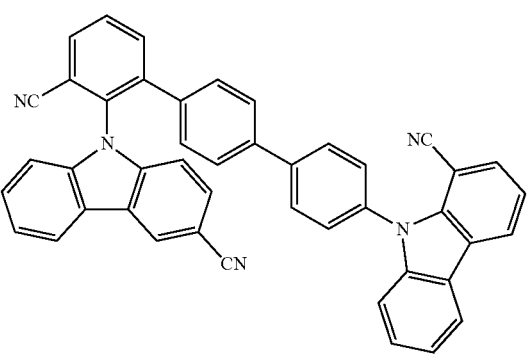
1457 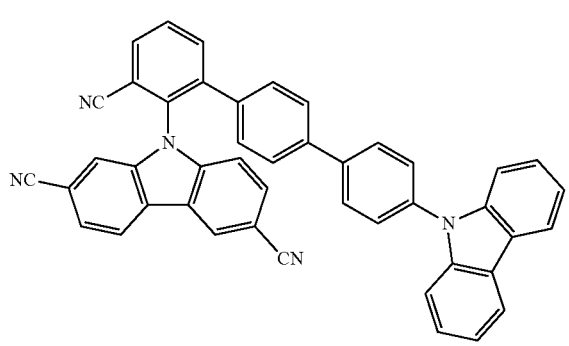
1461 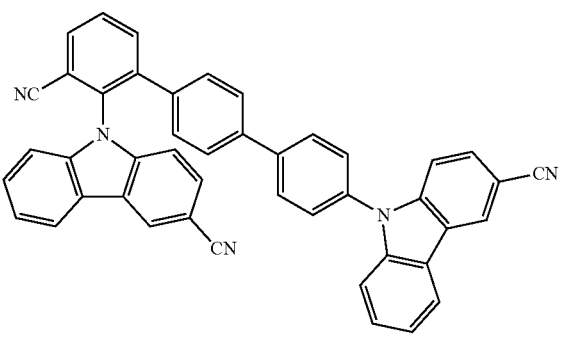
1458 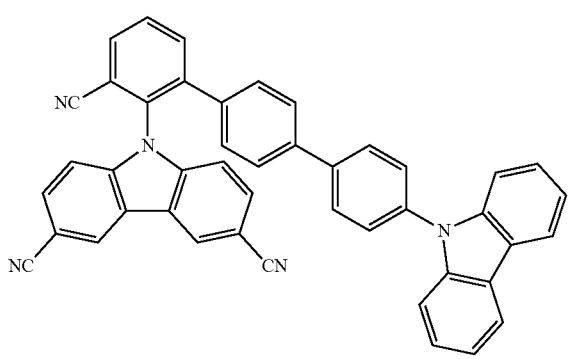
1462 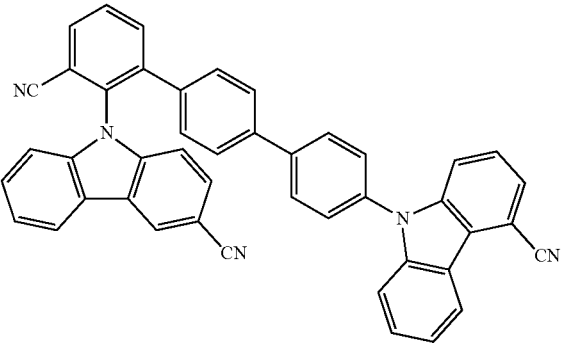
1459 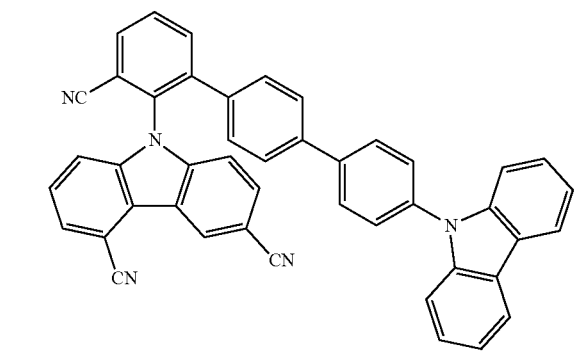
1463 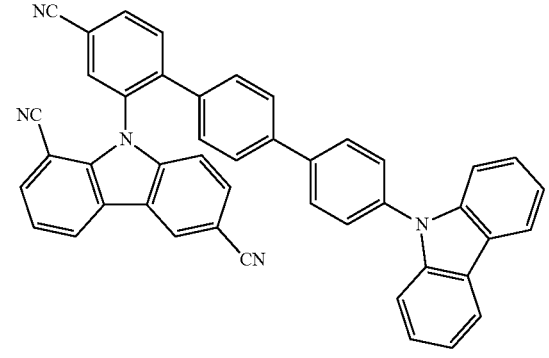

1464
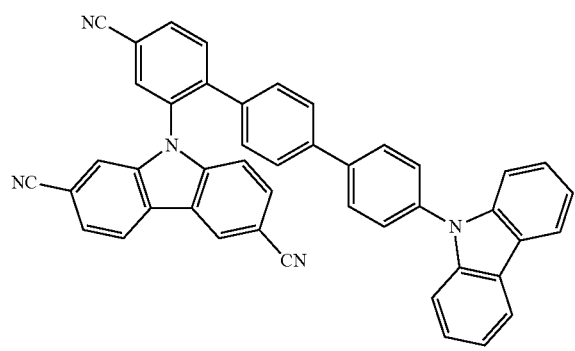
1465
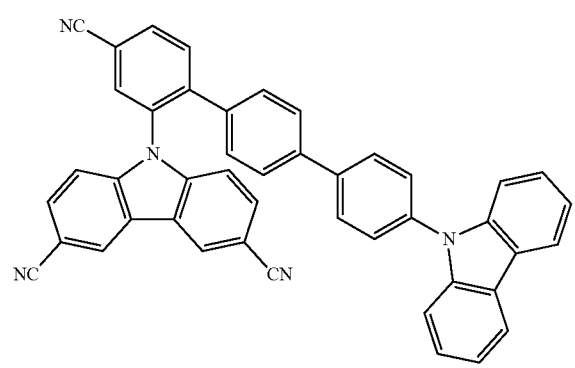
1466
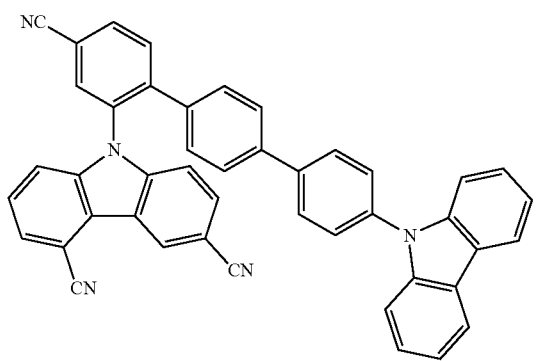
1467
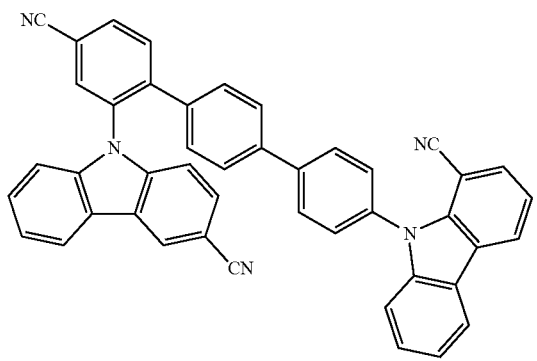
1468
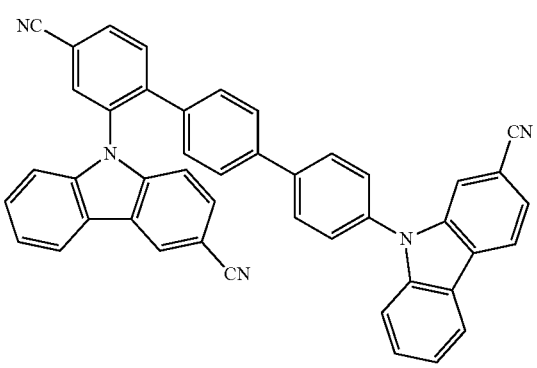
1469
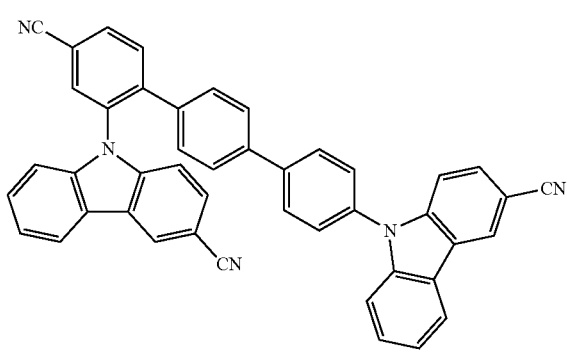
1470
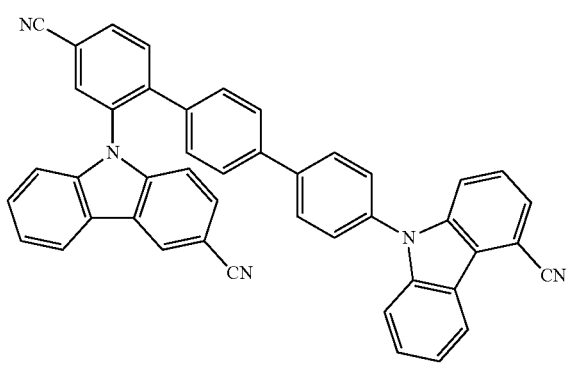
1471
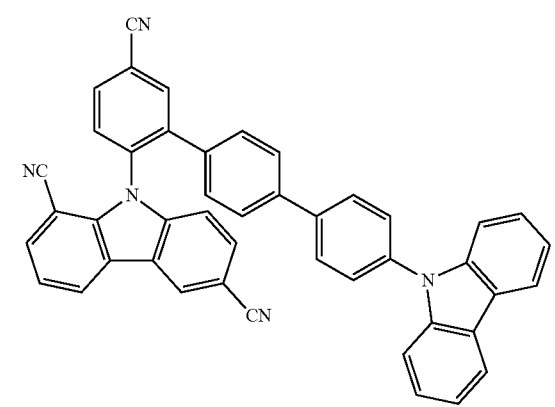

1472
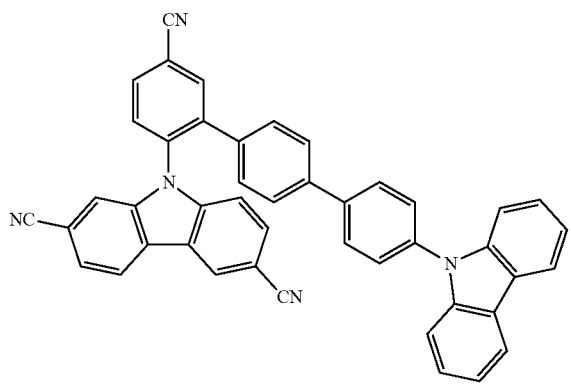
1473
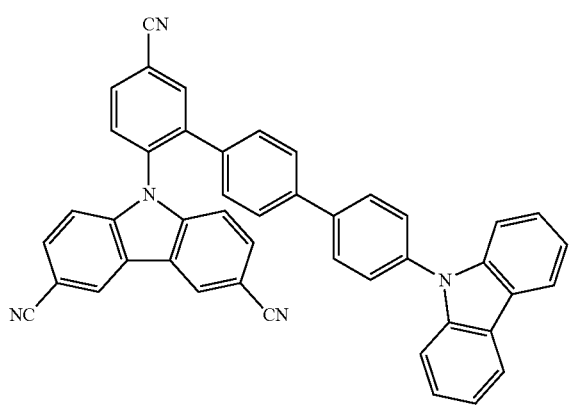
1474
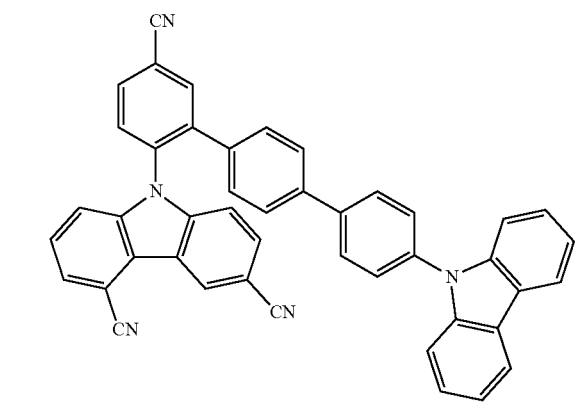
1475
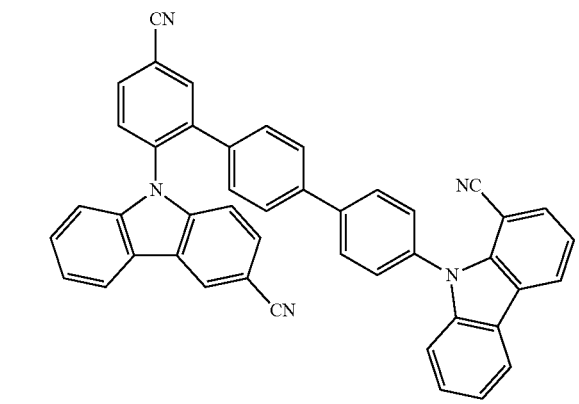
1476
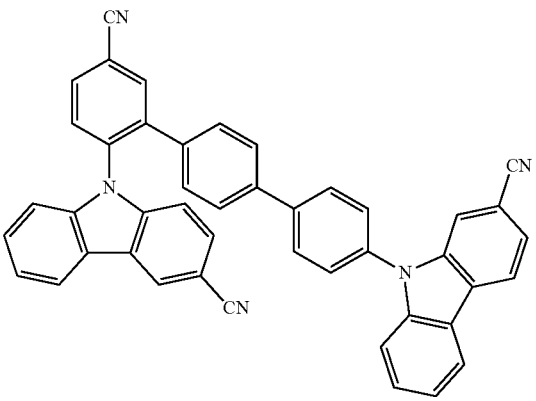
1477
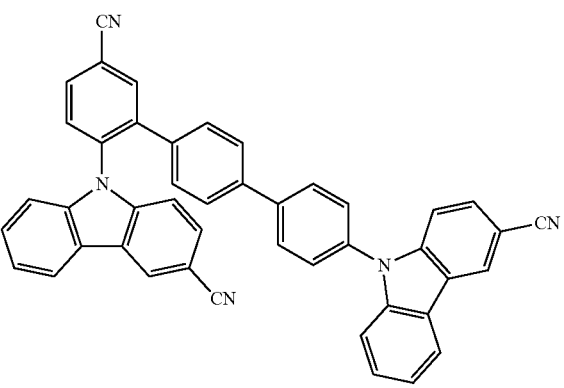
1478
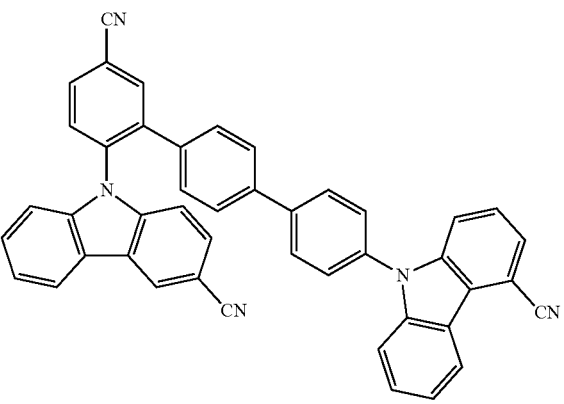
1479
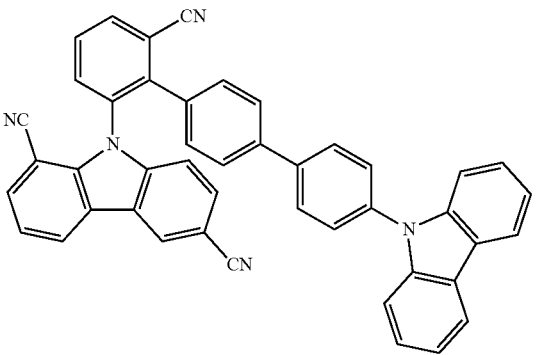

1480
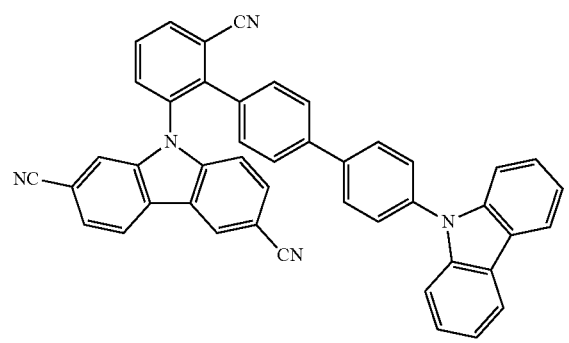
1481
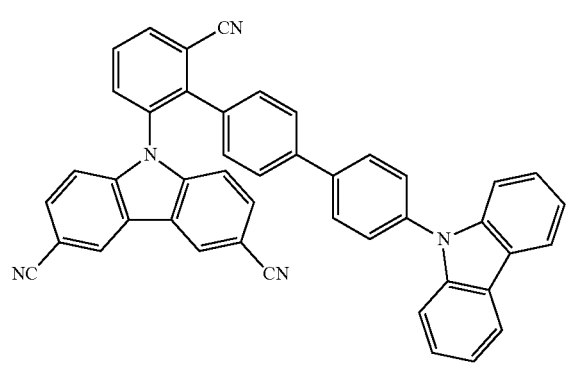
1482
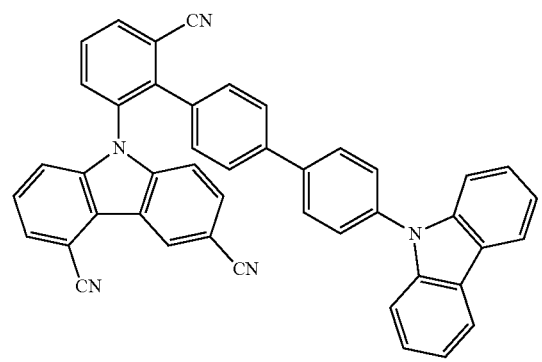
1483
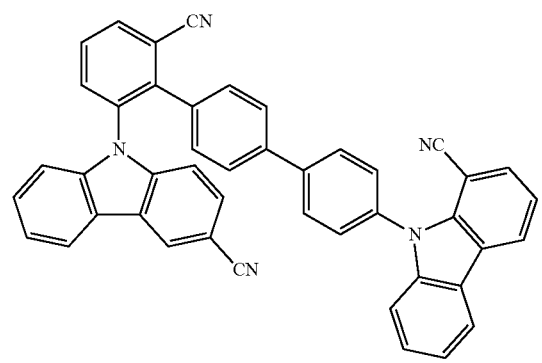
1484
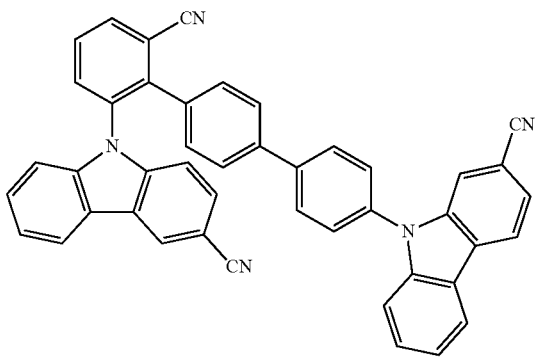
1485
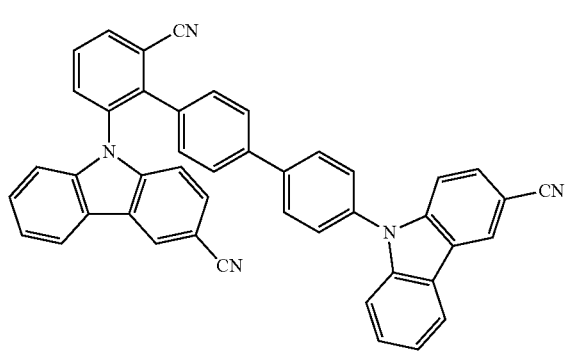
1486
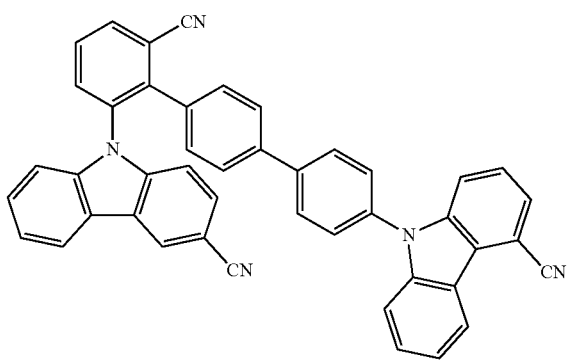
1487
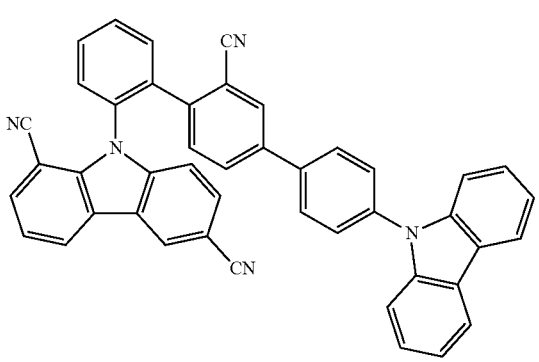

1488
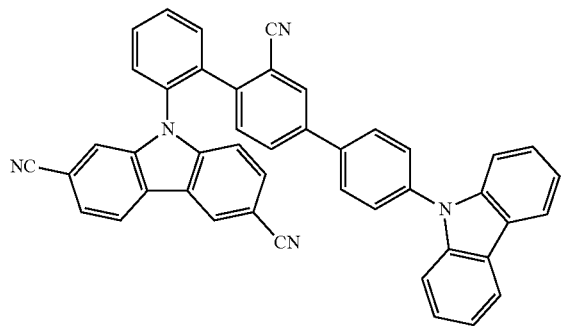
1489
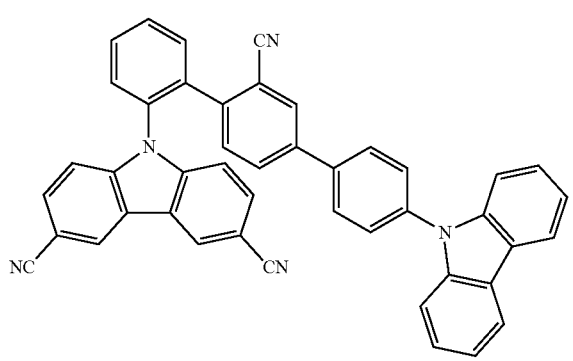
1490
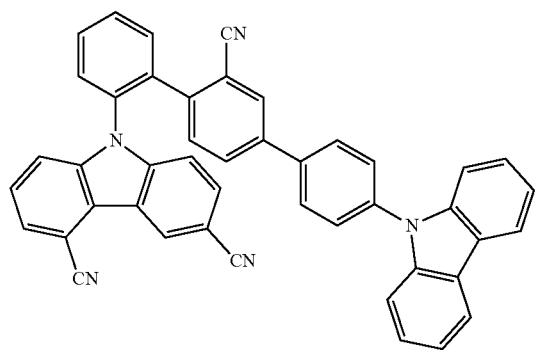
1491
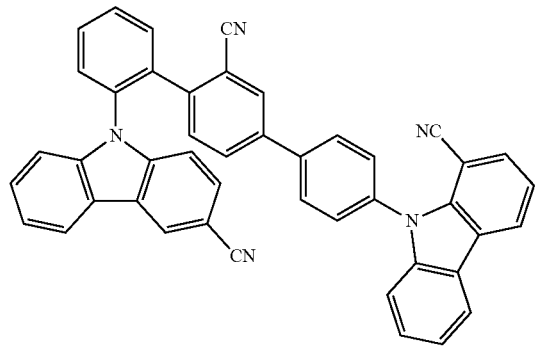
1492
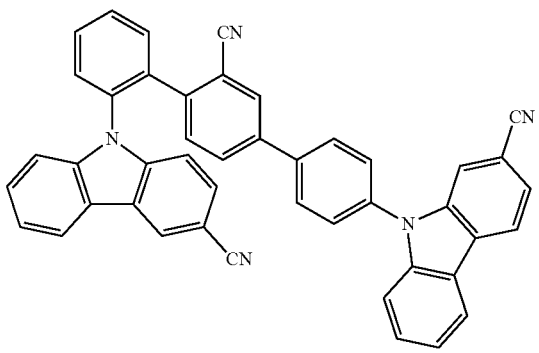
1493
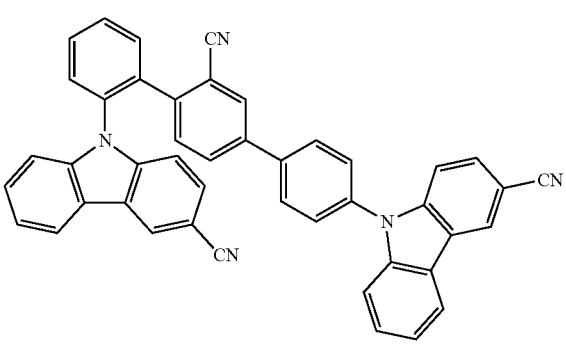
1494
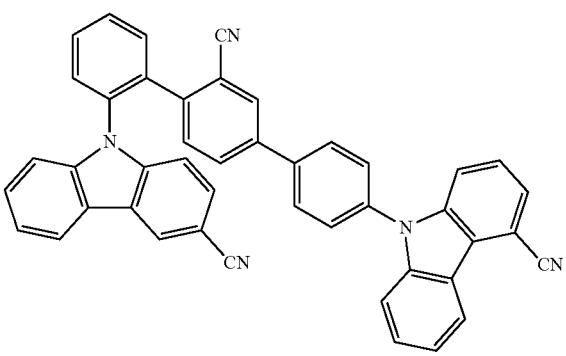
1495
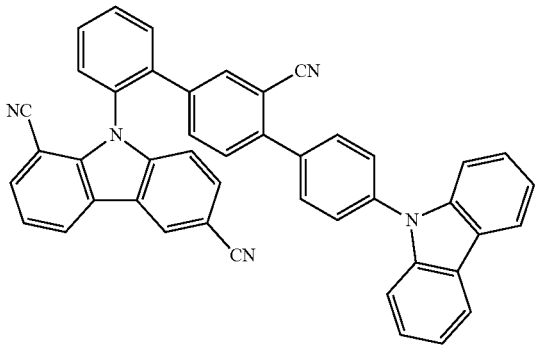

1496
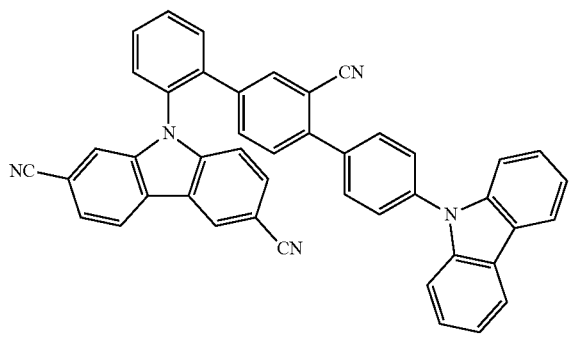
1497
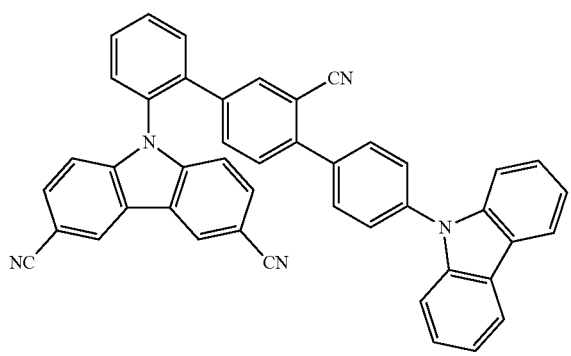
1498
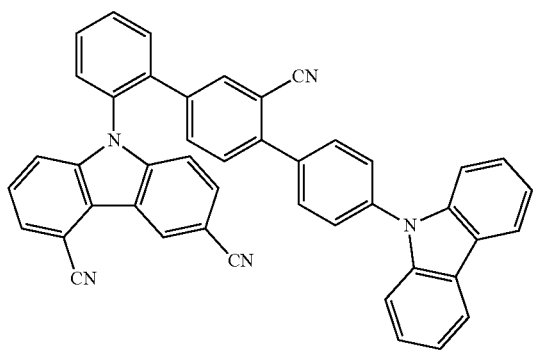
1499
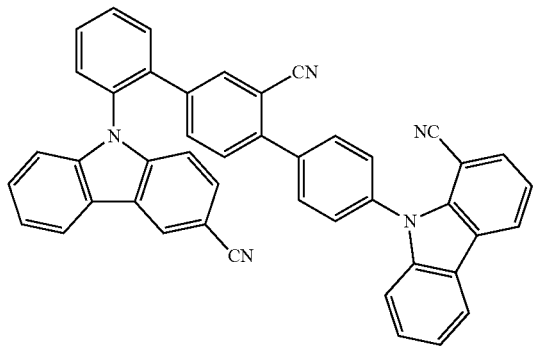
1500
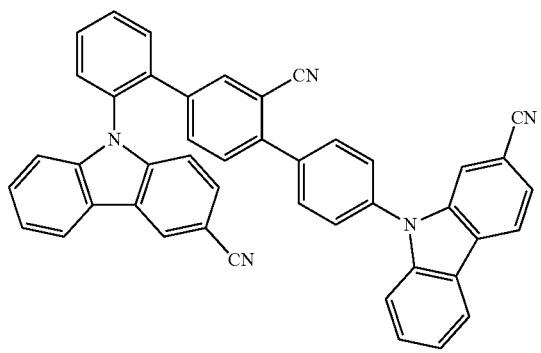
1501
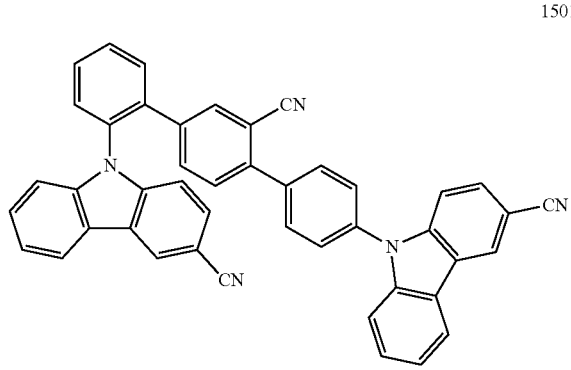
1502
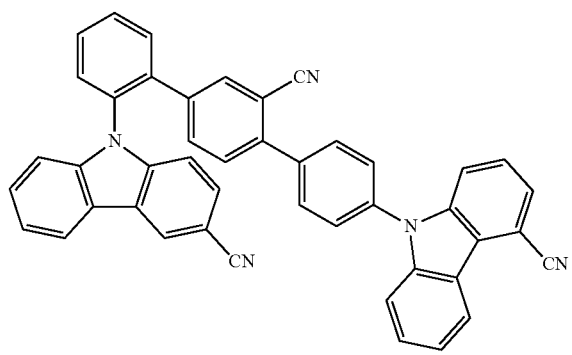
1503
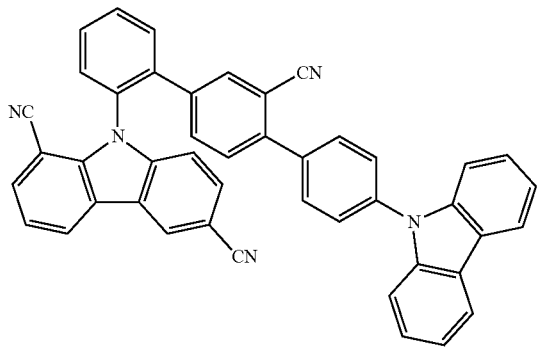

-continued
1504
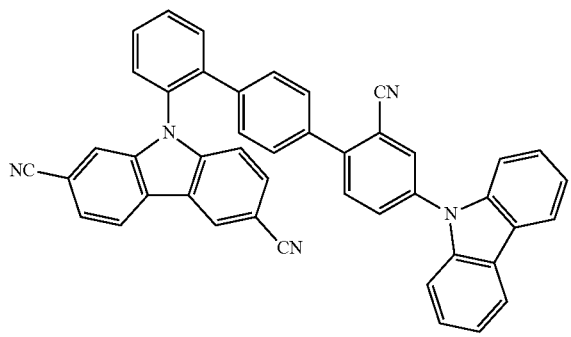
1505
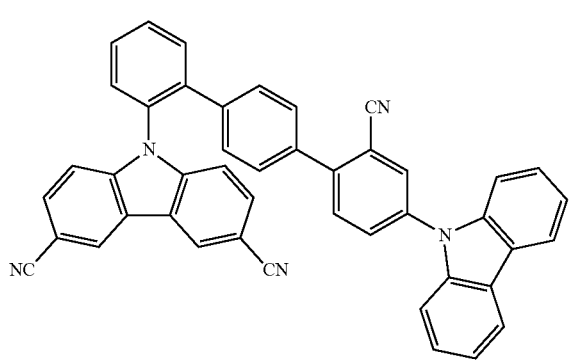
1506
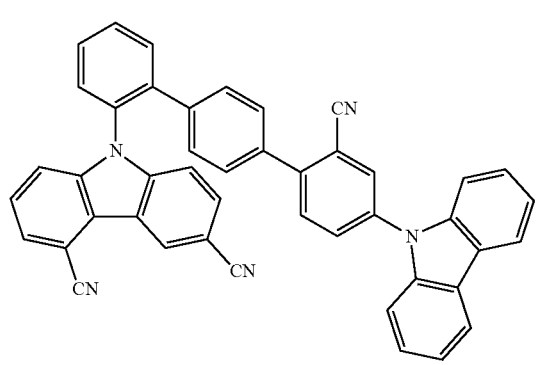
1507
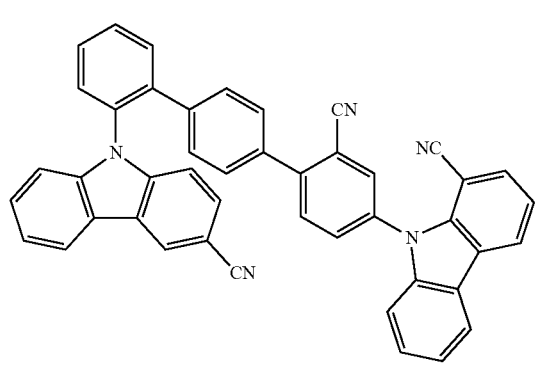
-continued
1508
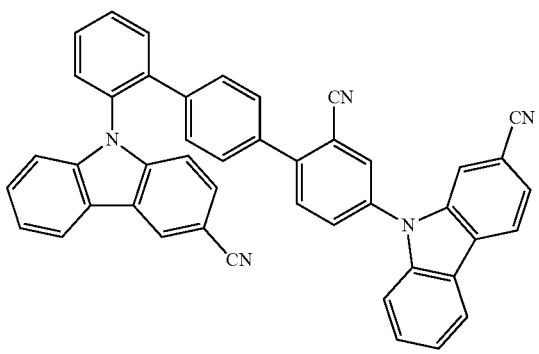
1509
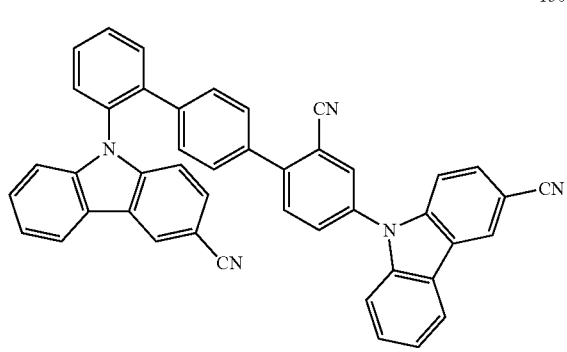
1510
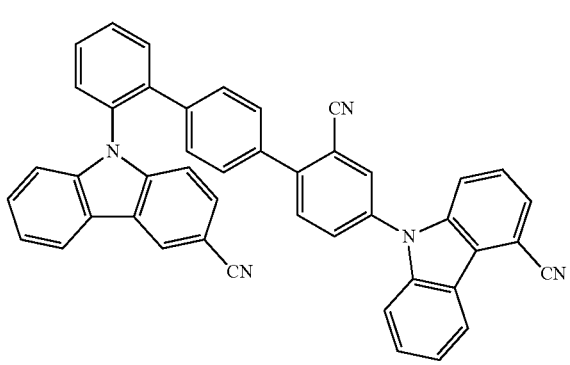
1511
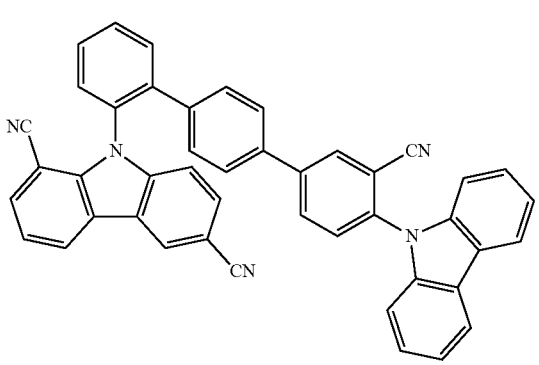

1512
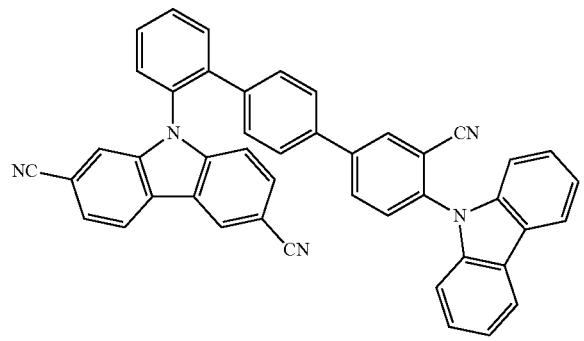
1516
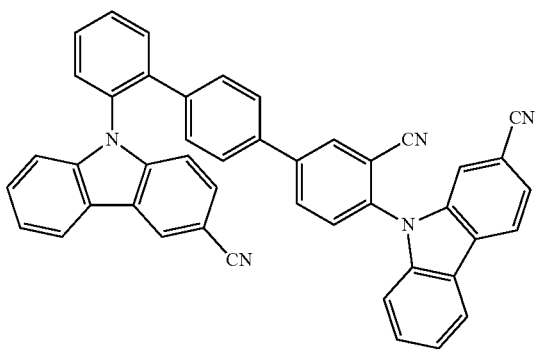
1513
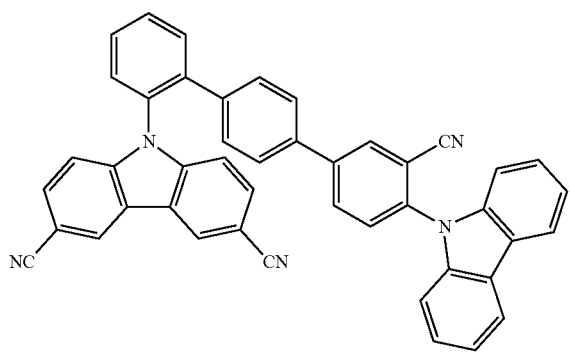
1517
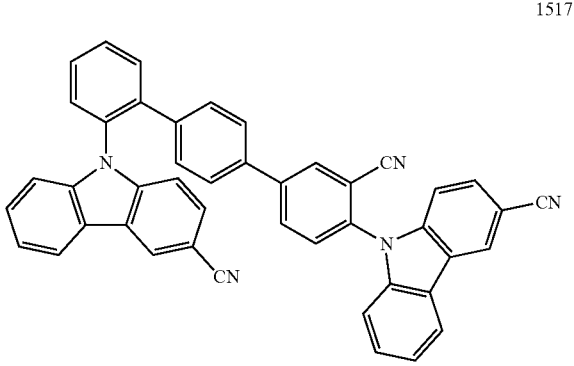
1514
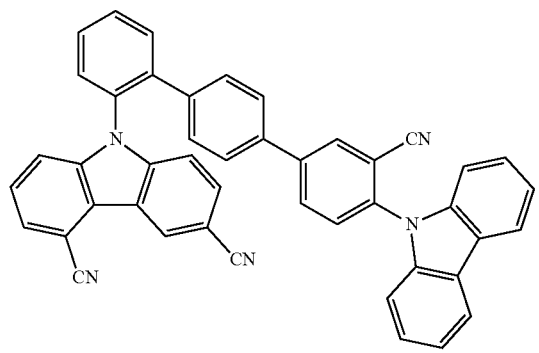
1518
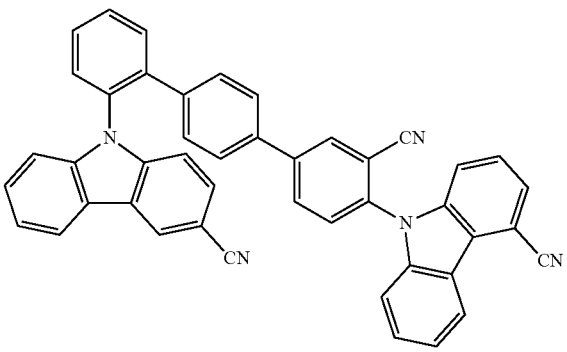
1515
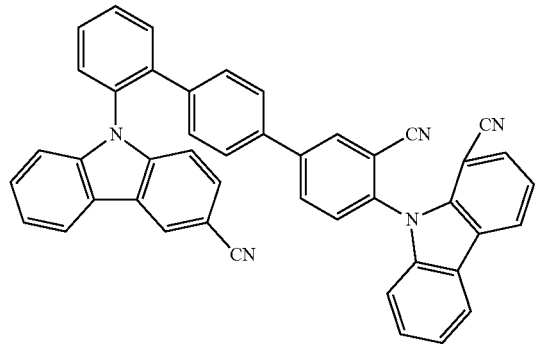
1519
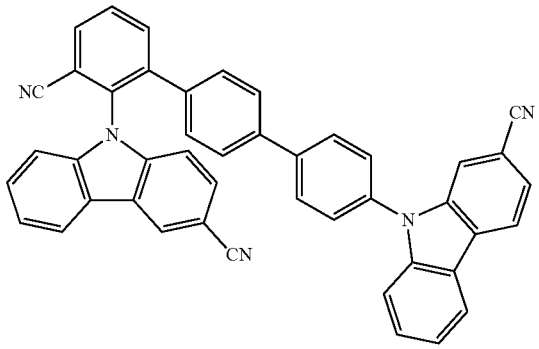

1520
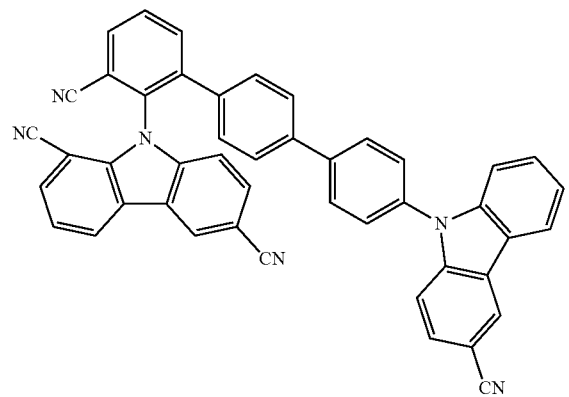
1521
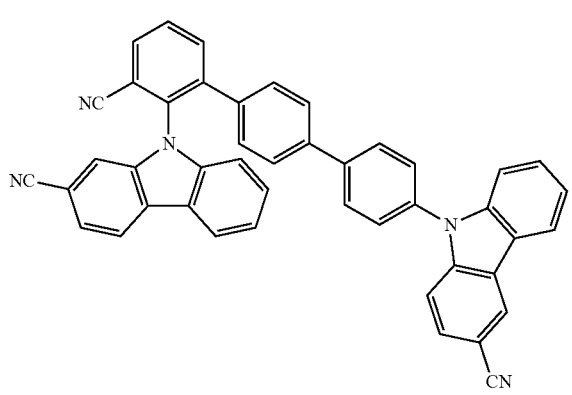
1522
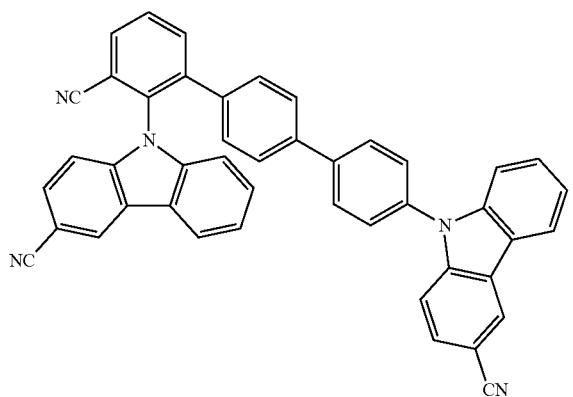
1523
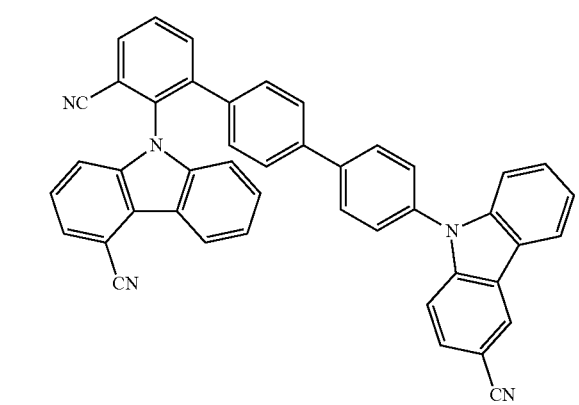
1524
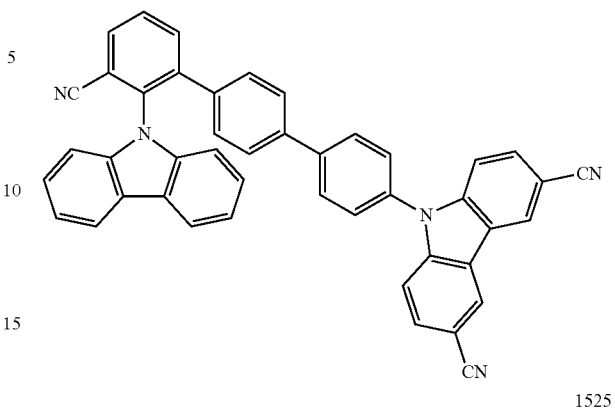
1525
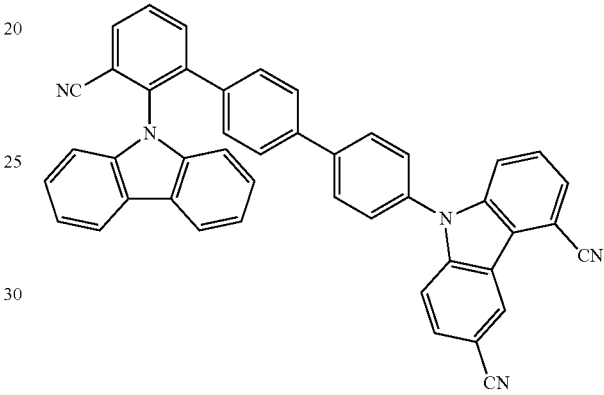
1526
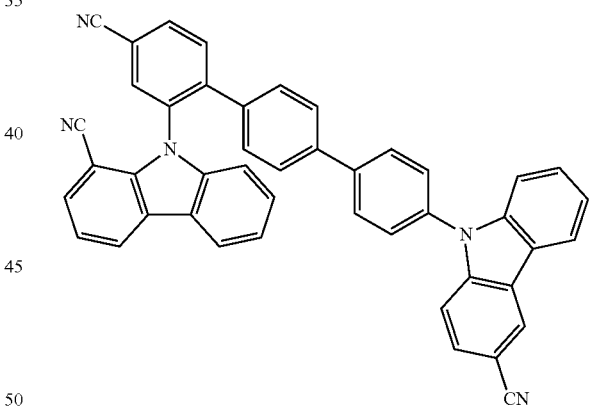
1527
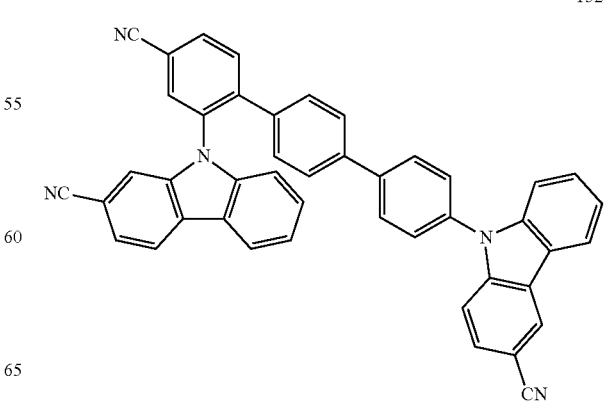

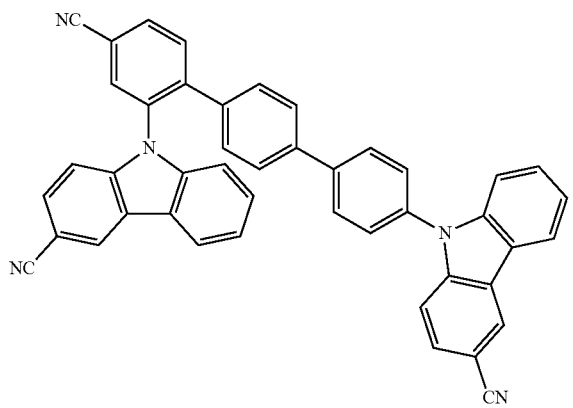
1528
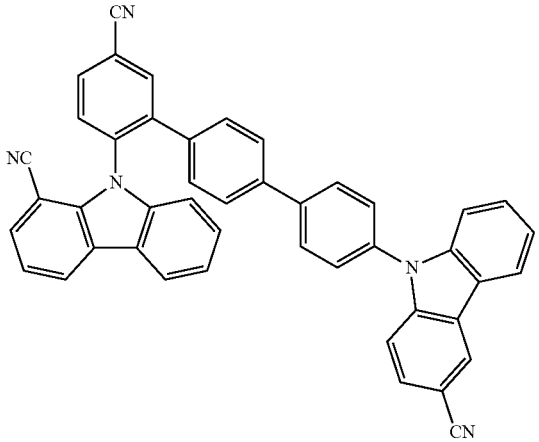
1534
1529
1535
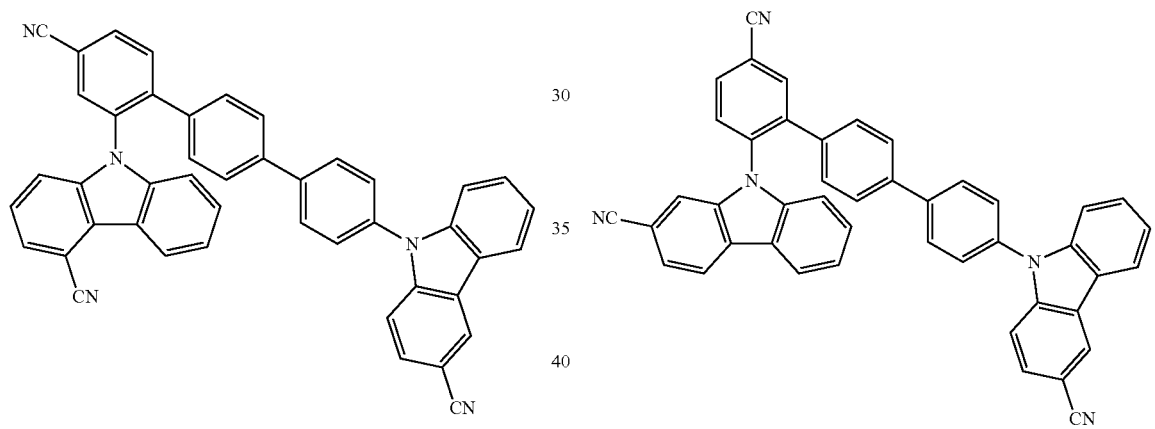
1530
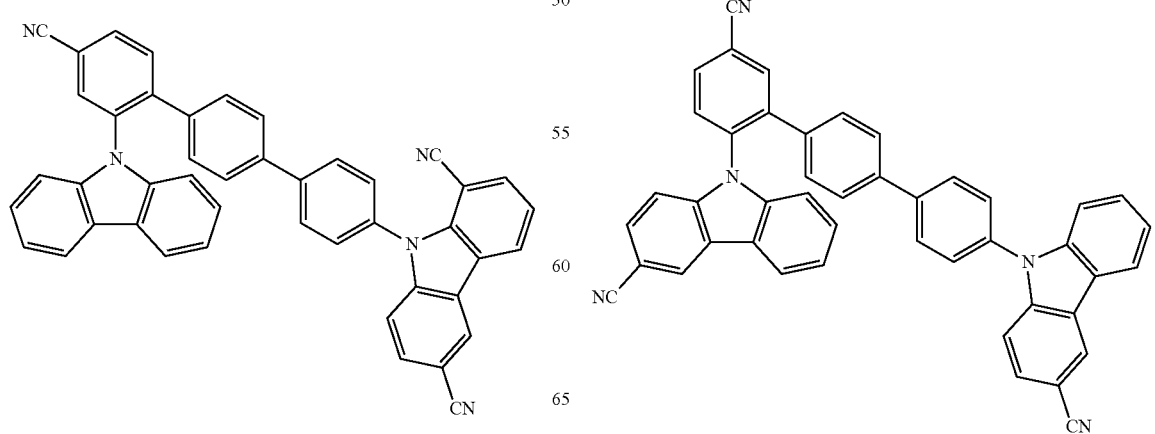
1536

435
-continued
1537
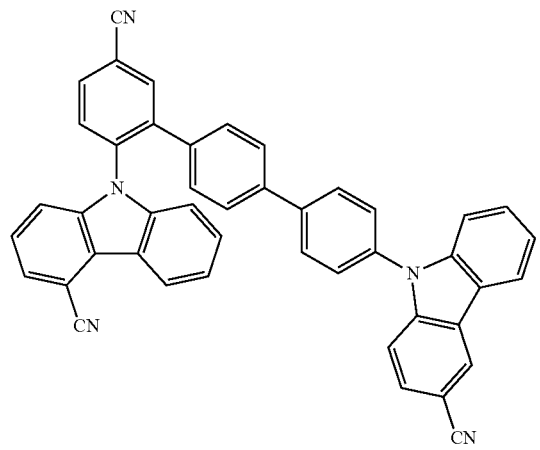
1538
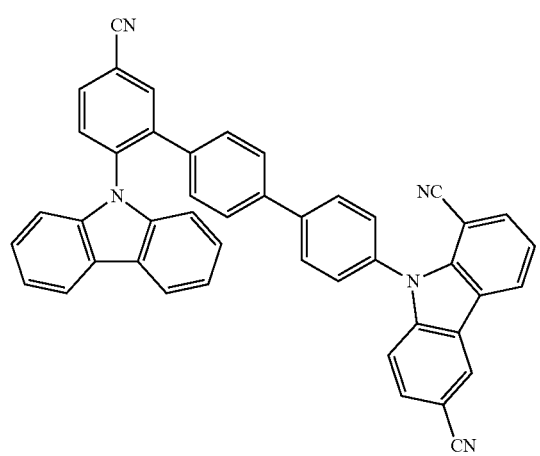
1539
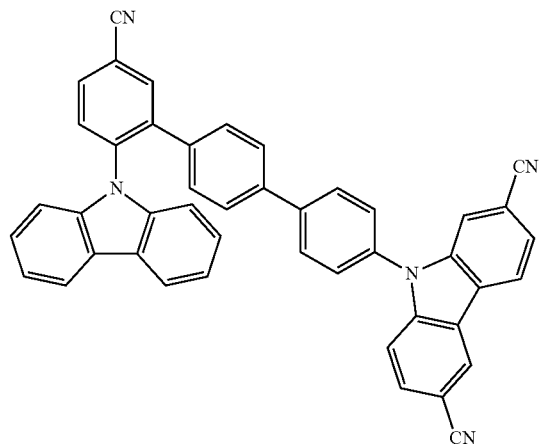
436
-continued
1540
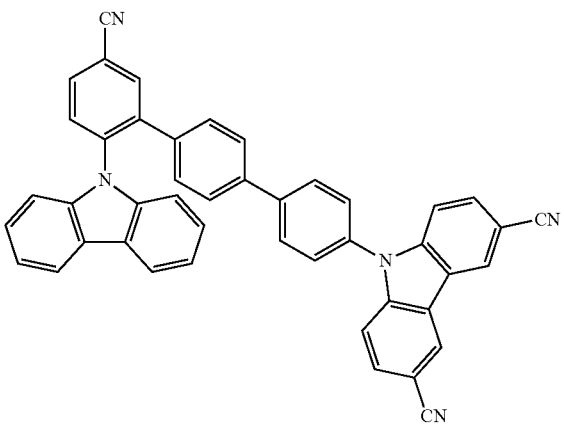
1541
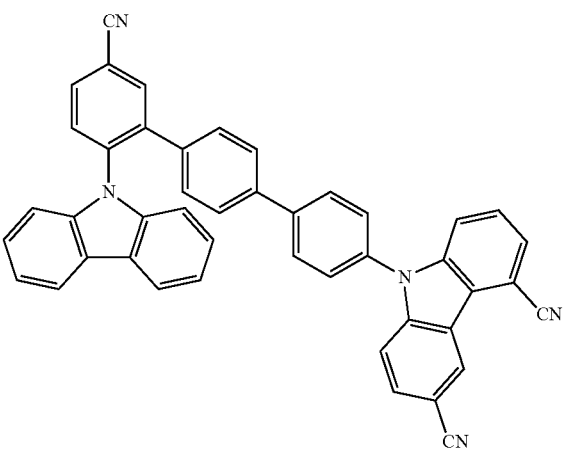
1542
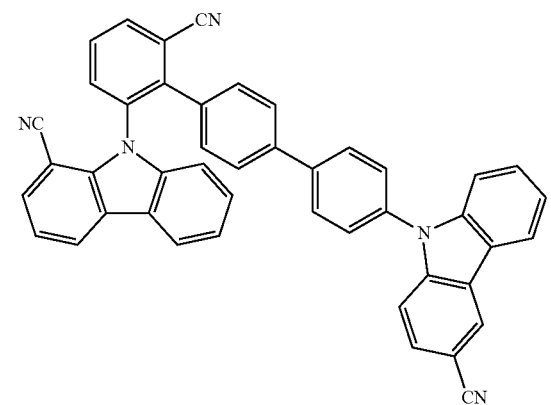

-continued
1543
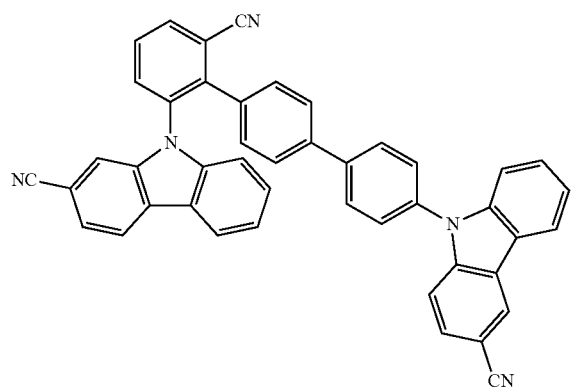
1544
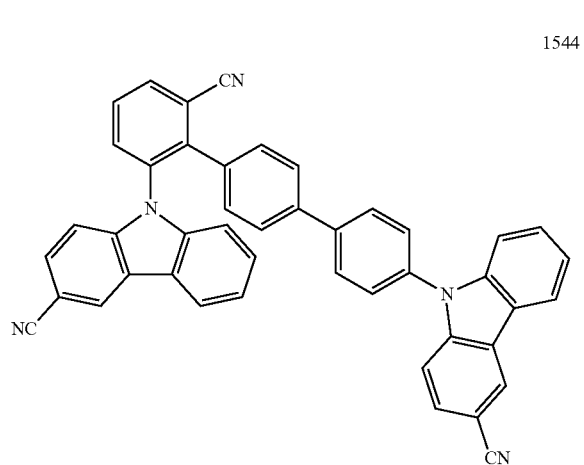
1545
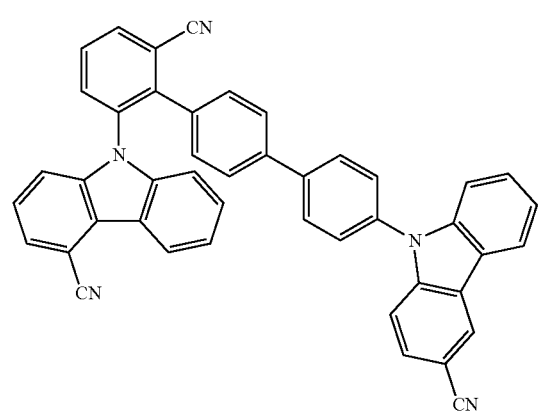
-continued
1546
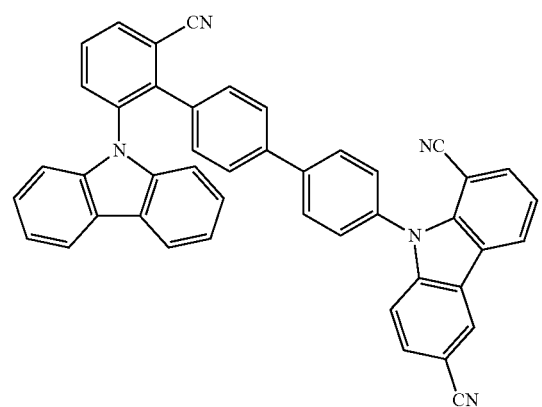
1547
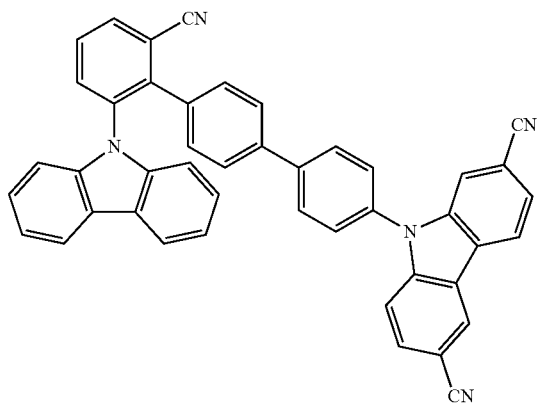
1548
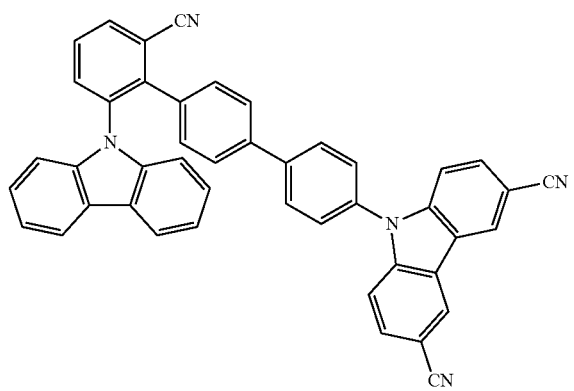

1549 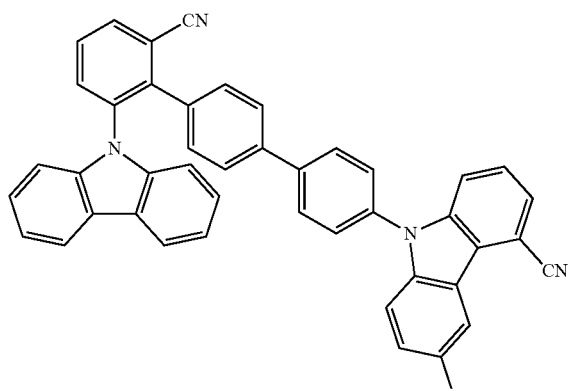
1550 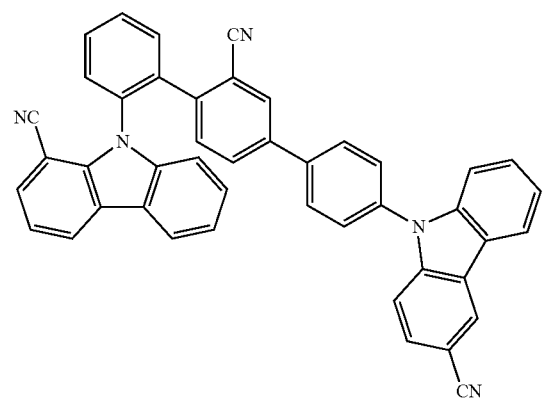
1551 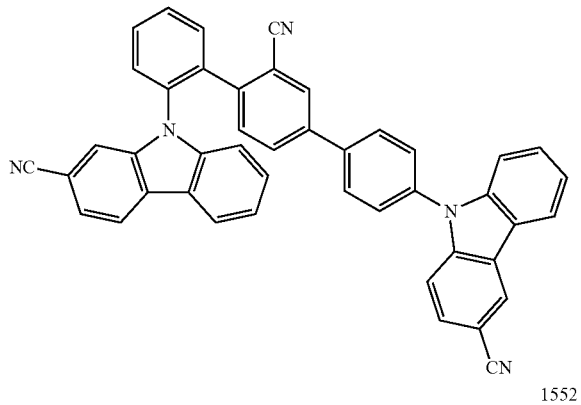
1552 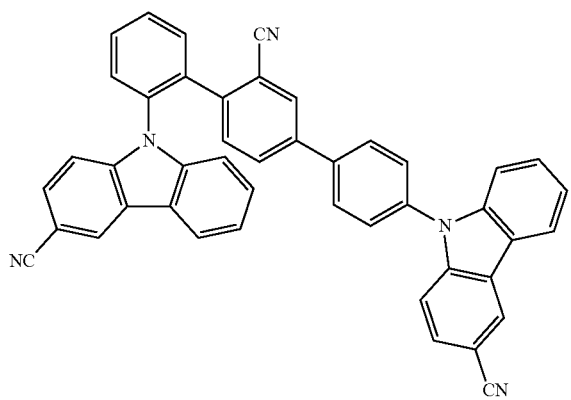
1553 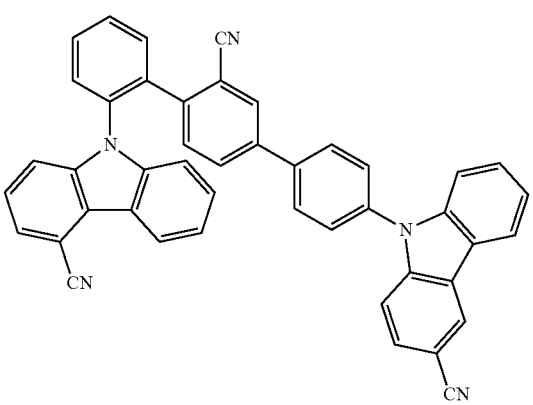
1554 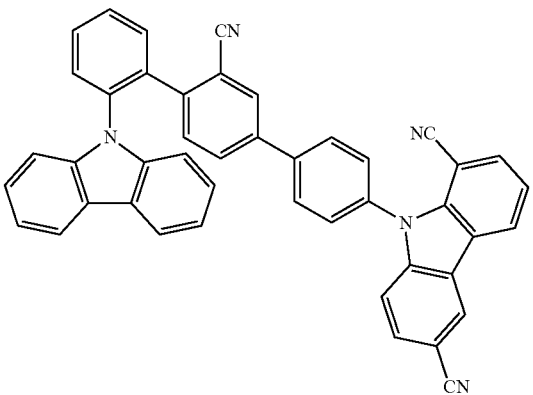
1555 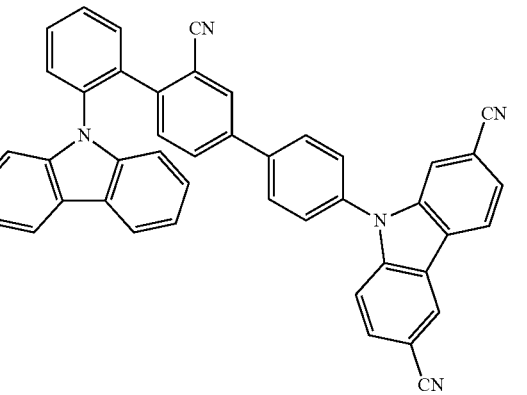
1556 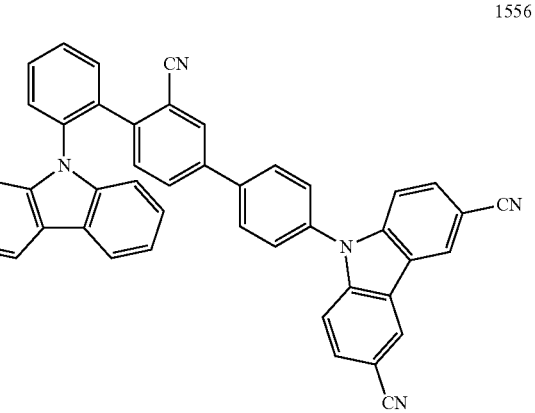

441
-continued
1557
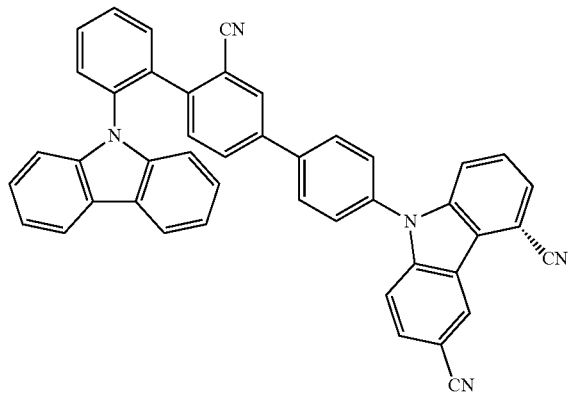
1558
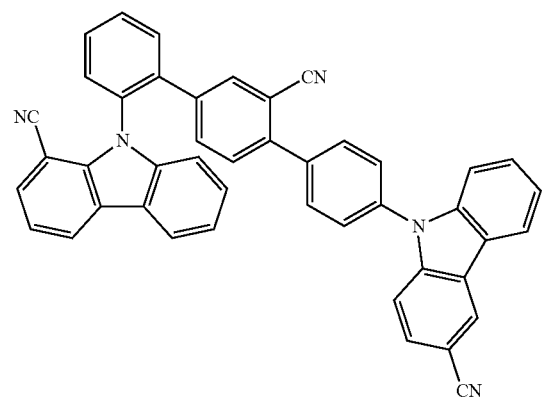
1559
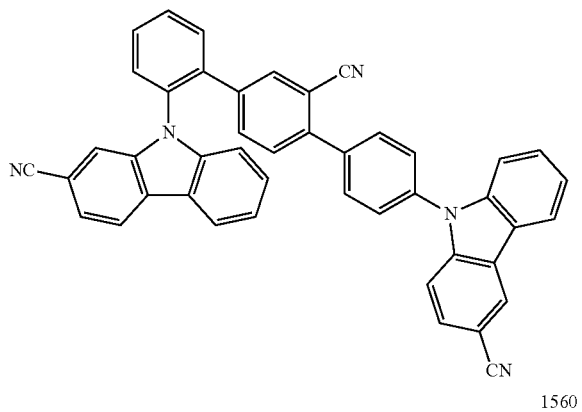
1560
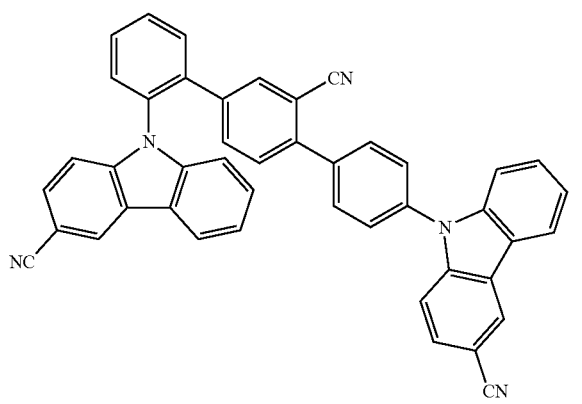
442
-continued
1561
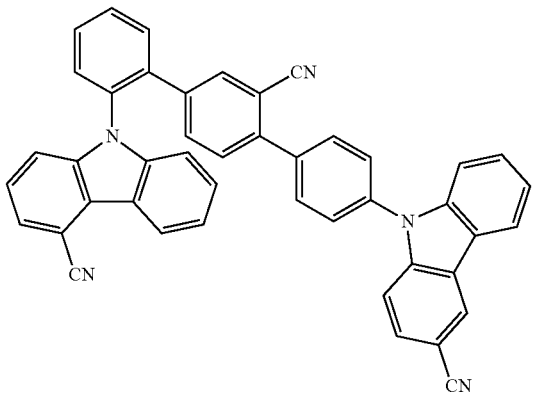
1562
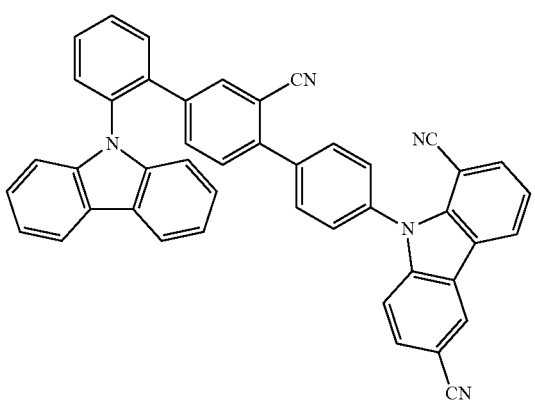
1563
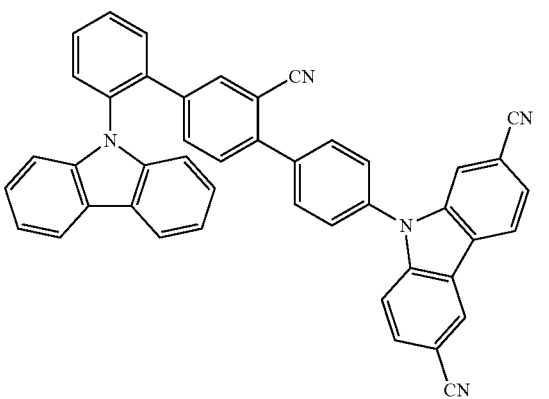
1564

-continued
1565
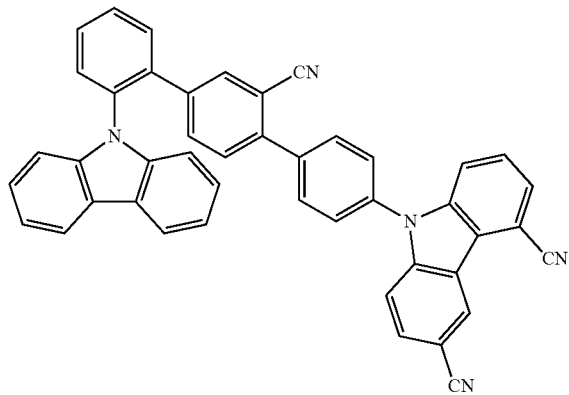
1566
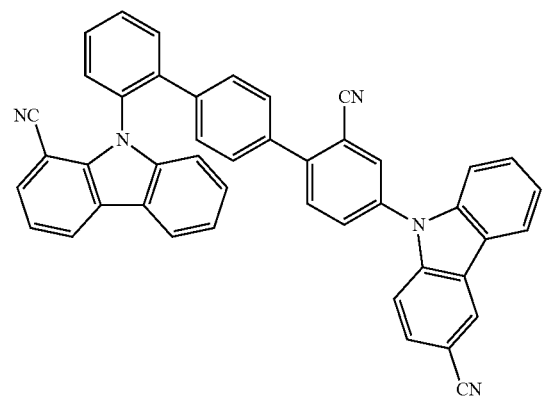
1567
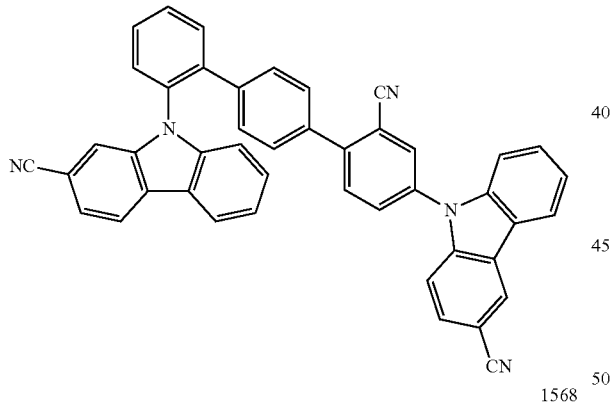
1568
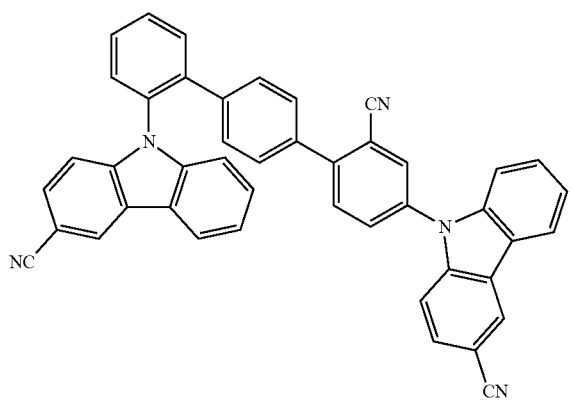
-continued
1569
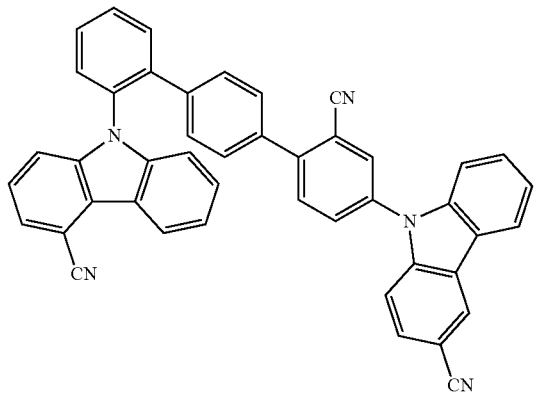
1570
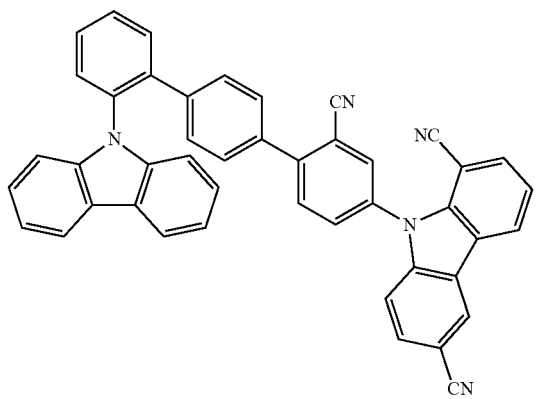
1571
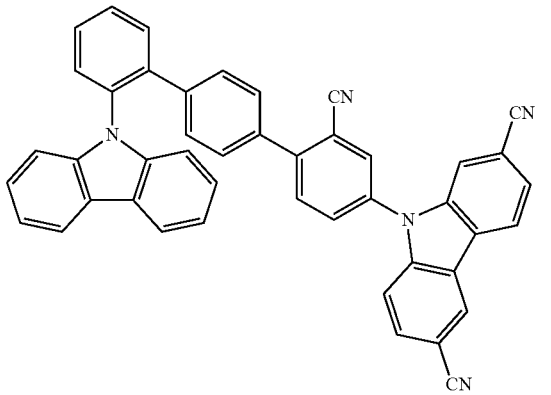
1572
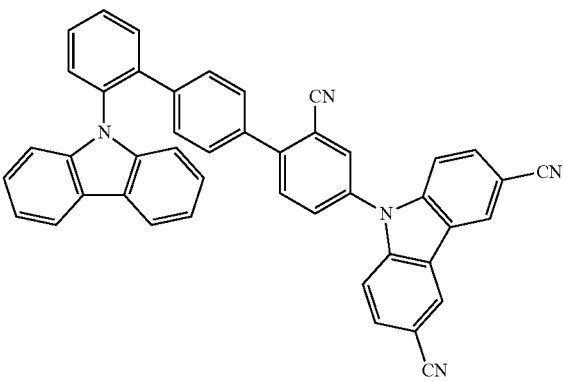

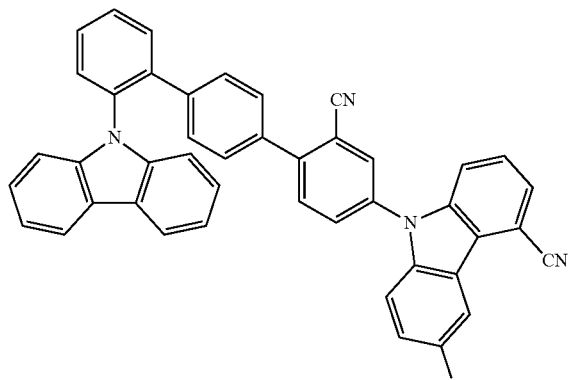
1573
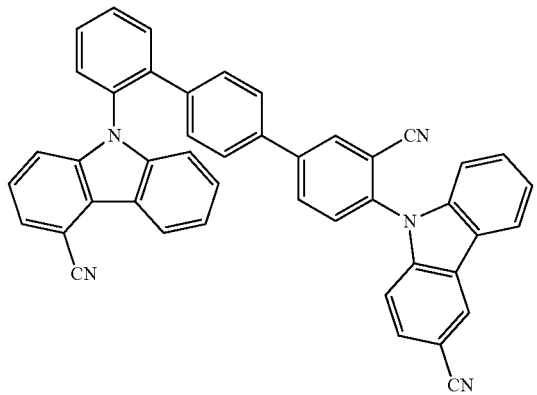
1577
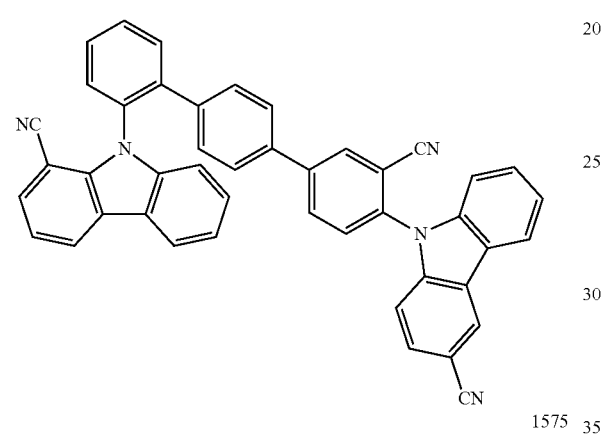
1574
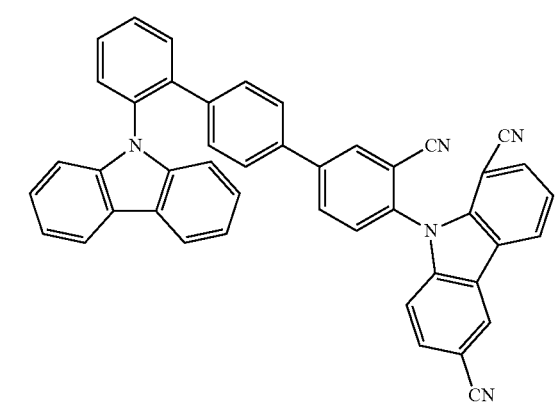
1578
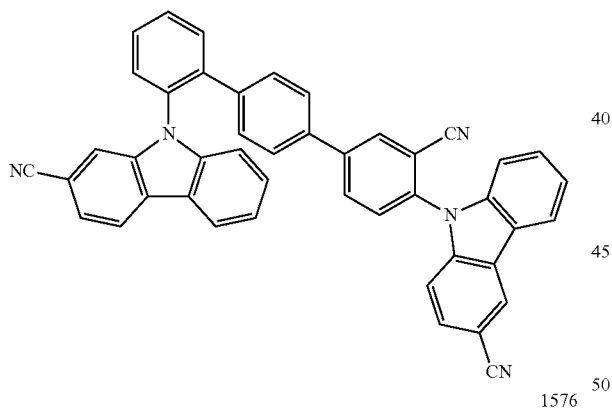
1575
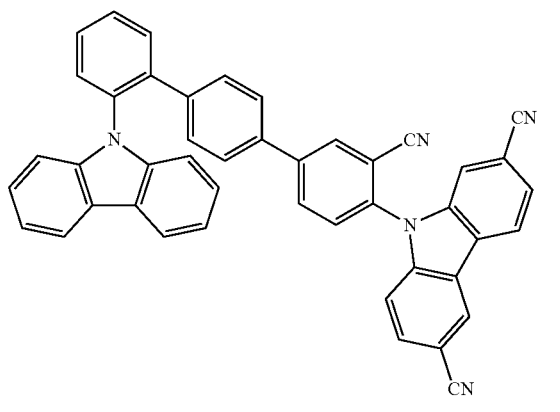
1579
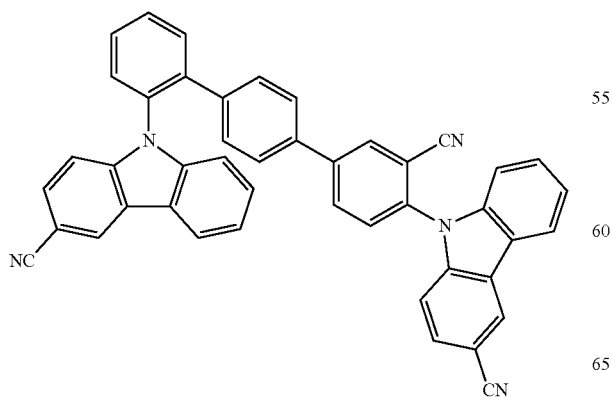
1576
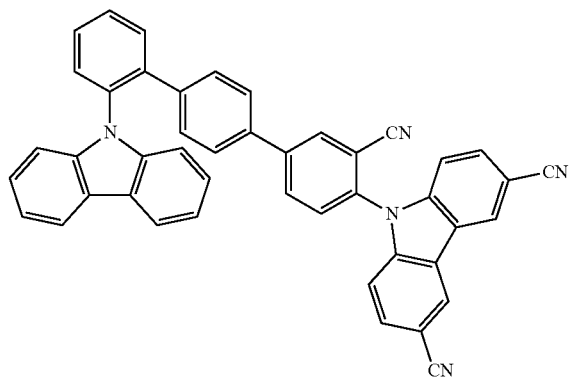
1580

1581 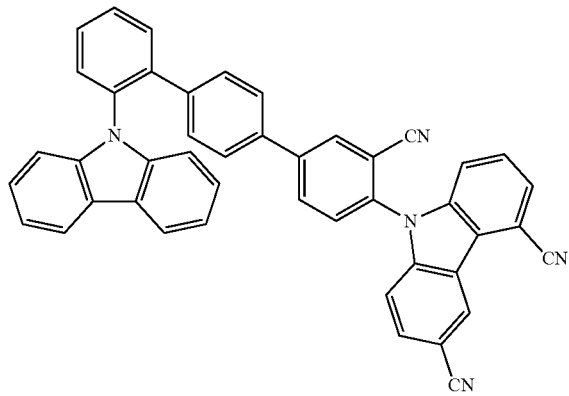
1582 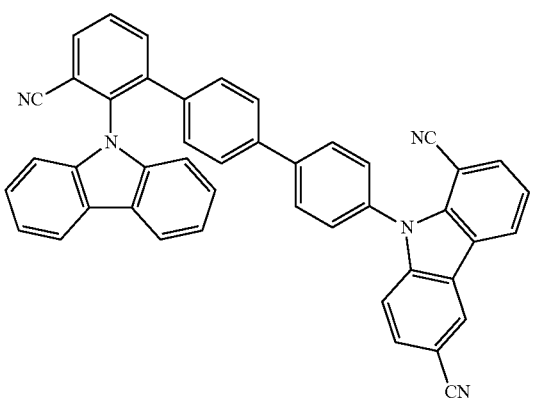
1583 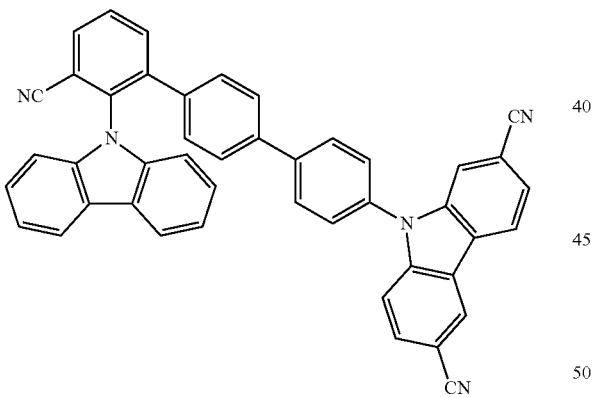
1584 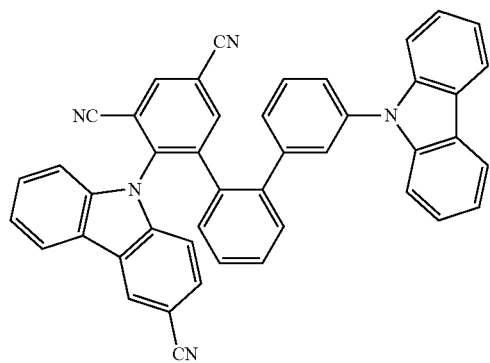
1585 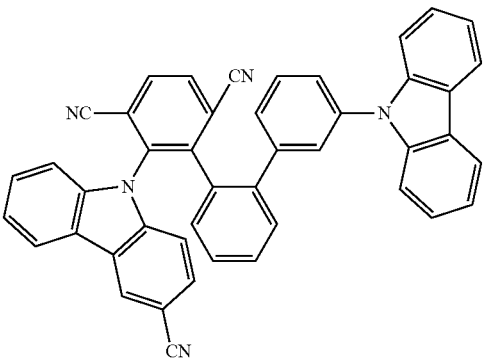
1586 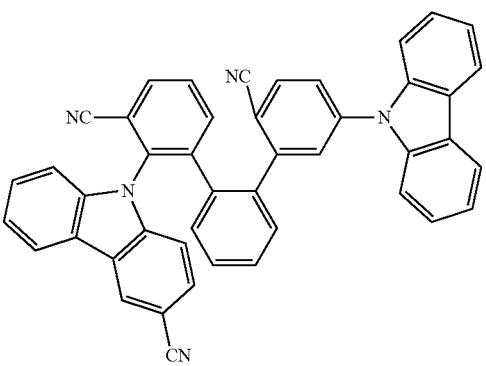
1587 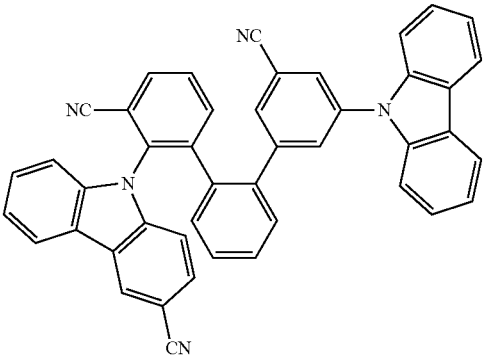
1588 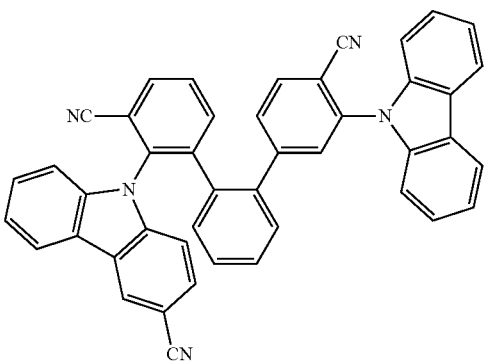

1589
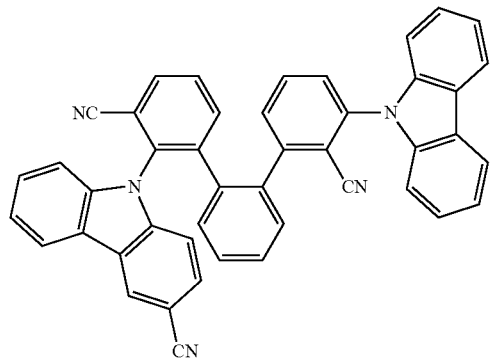
1590
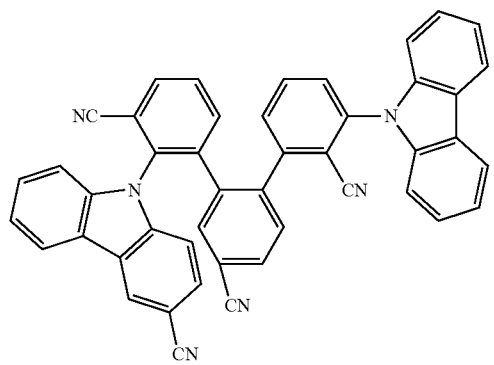
1591
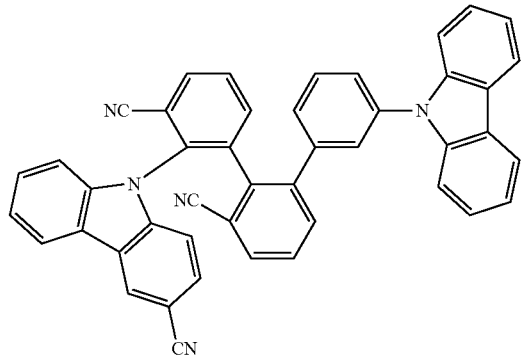
1593
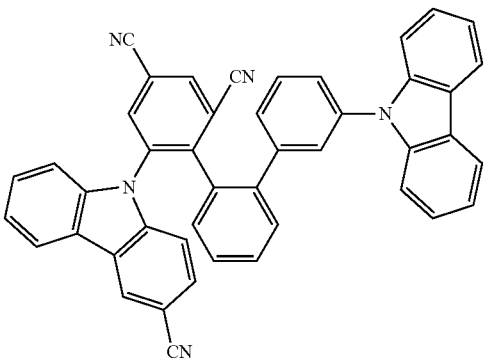
1594
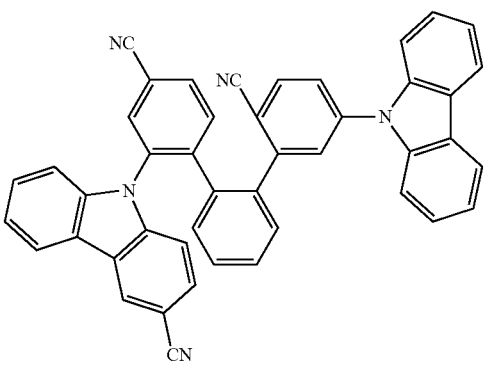
1595
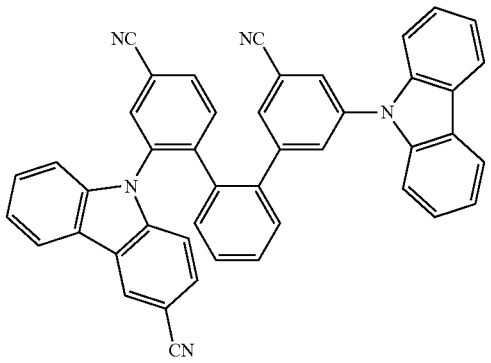
1596
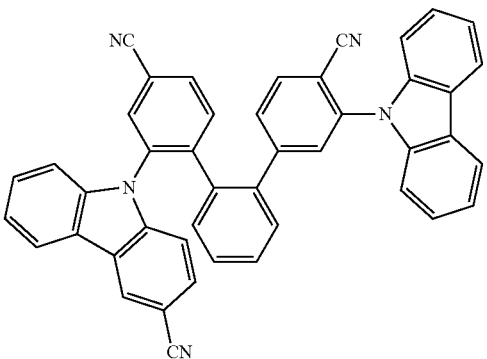

1597
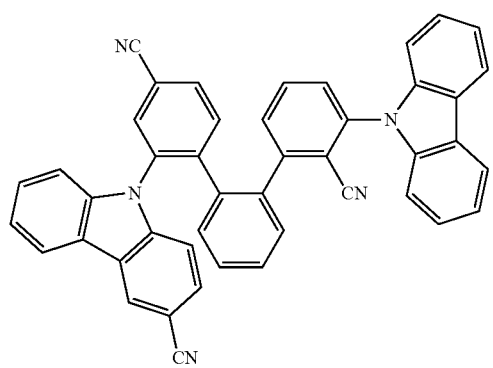
1598
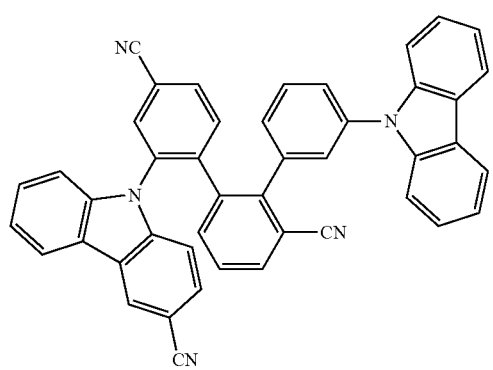
1599
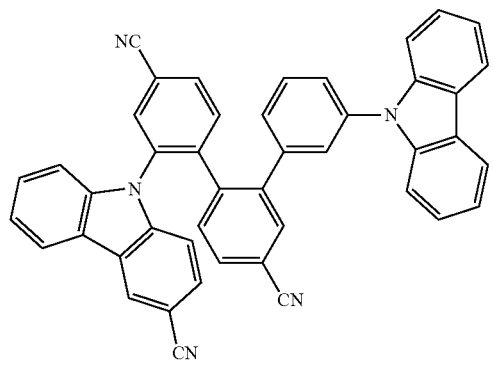
1600
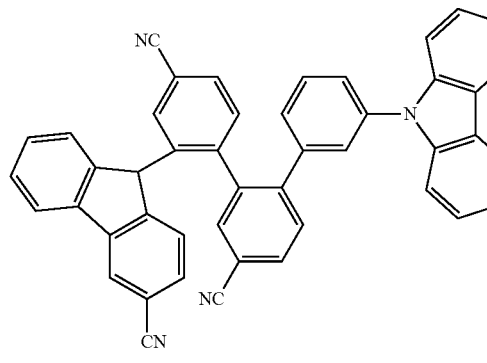
1601
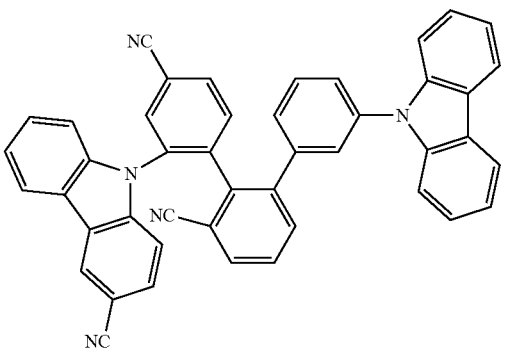
1602
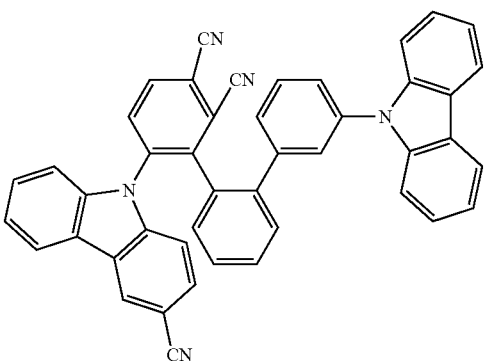
1603
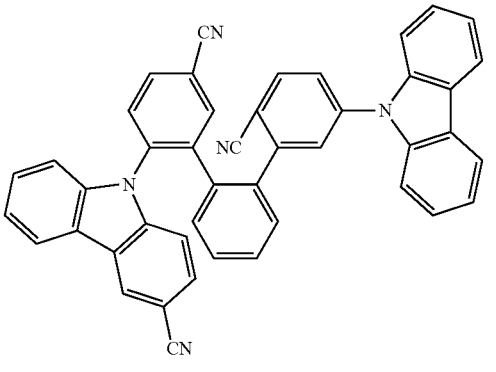
1604
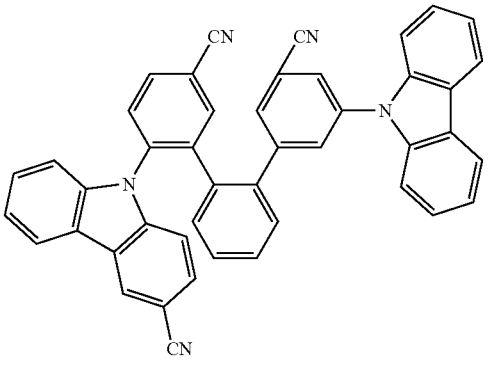

-continued
1605
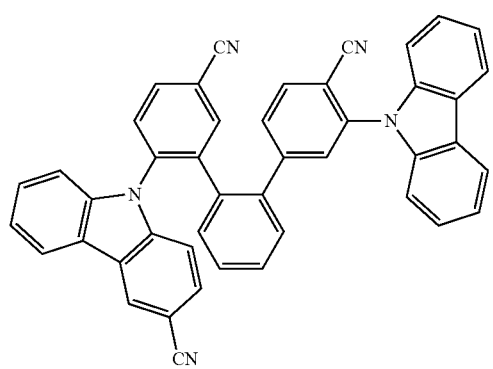
1606
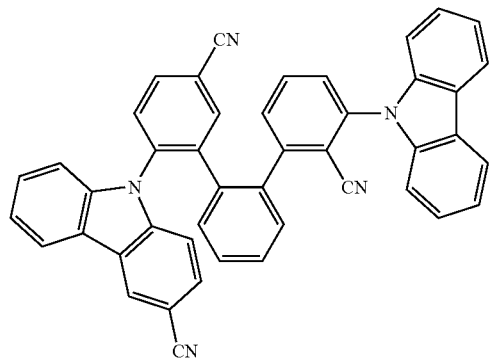
1607
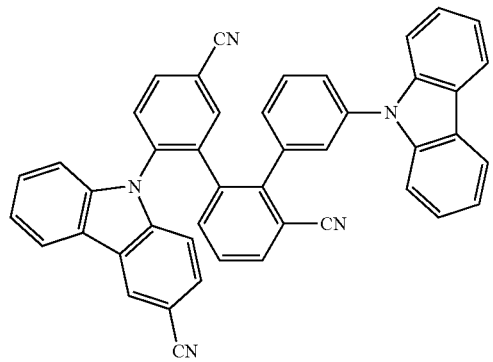
1608
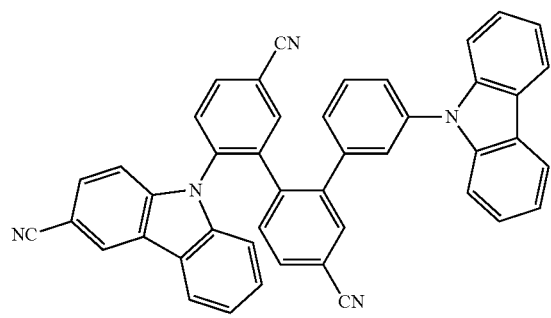
-continued
1609
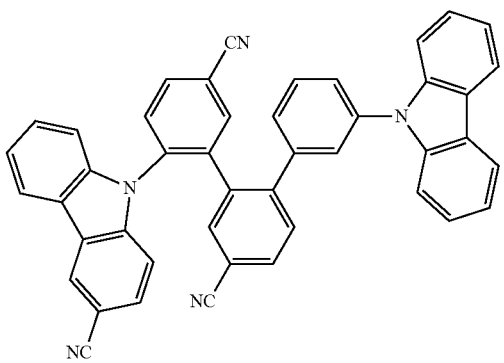
1610
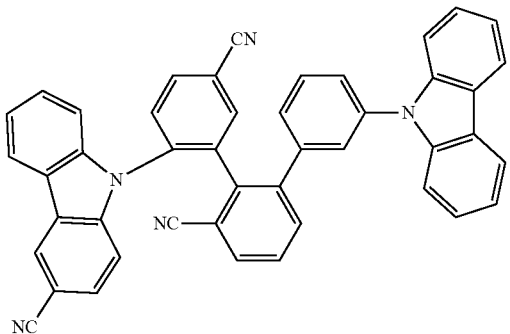
1611
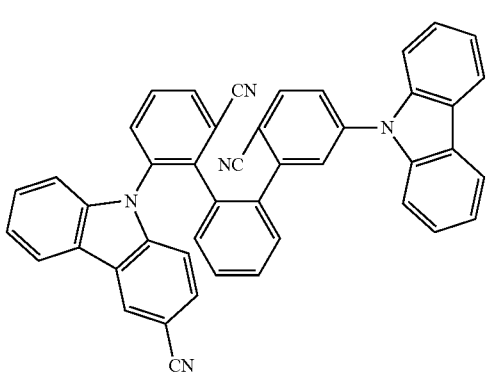
1612
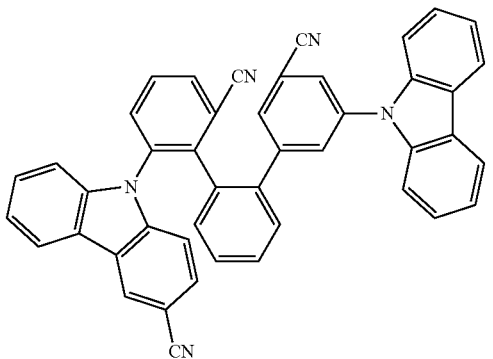

1613
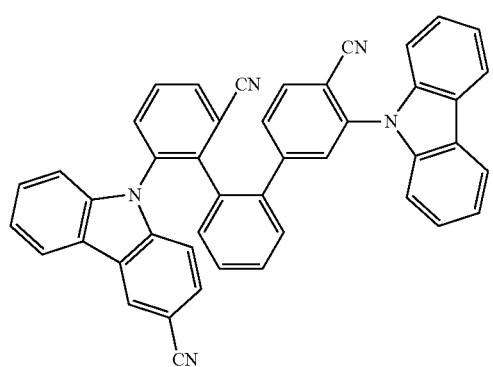
1614
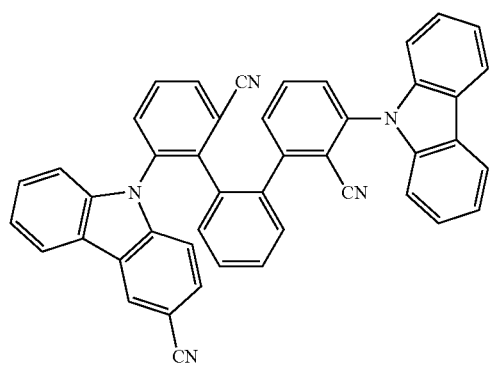
1615
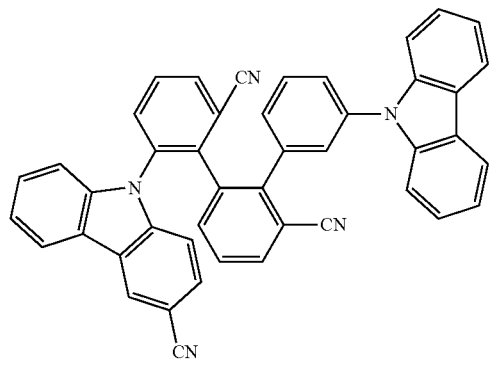
1616
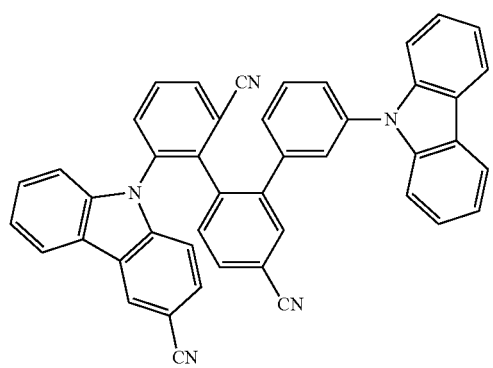
1617
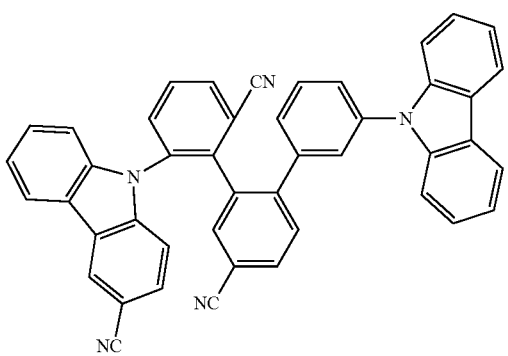
16118
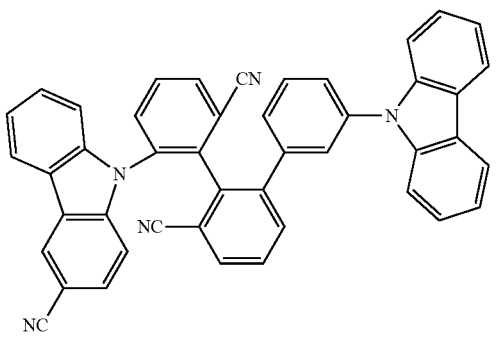
1619
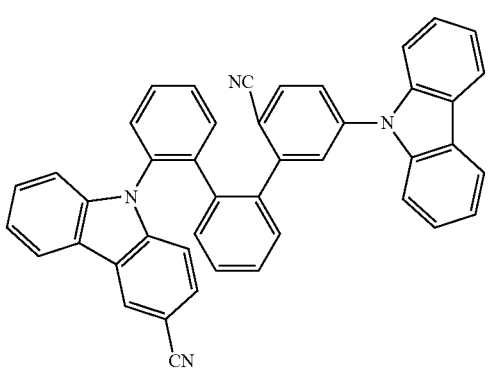
1620
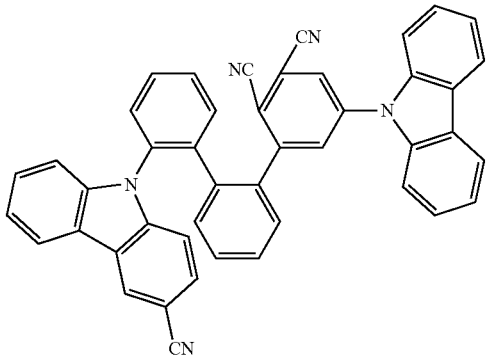

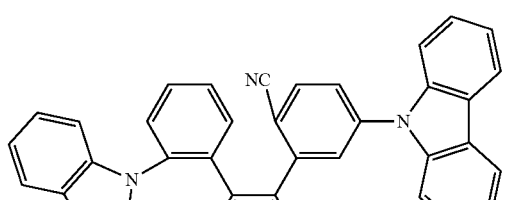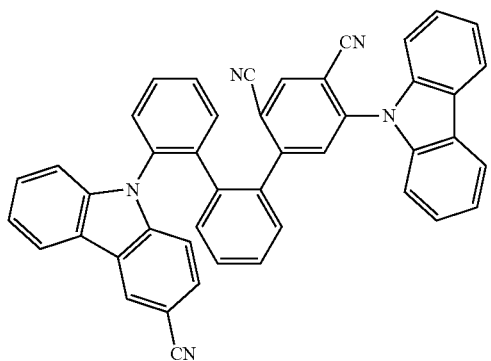

1629 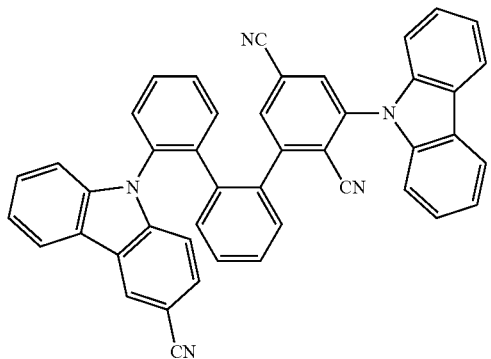
1630 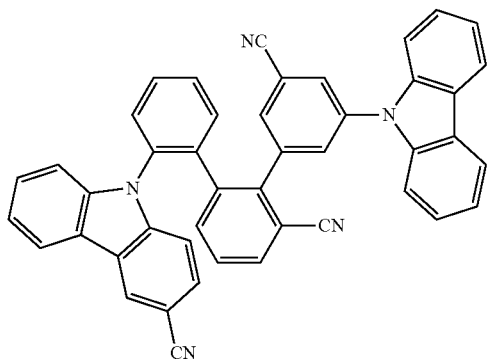
1631 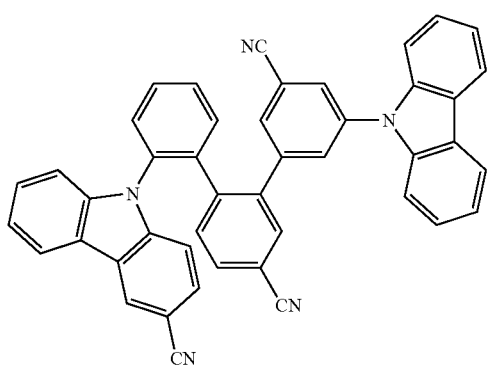
1632 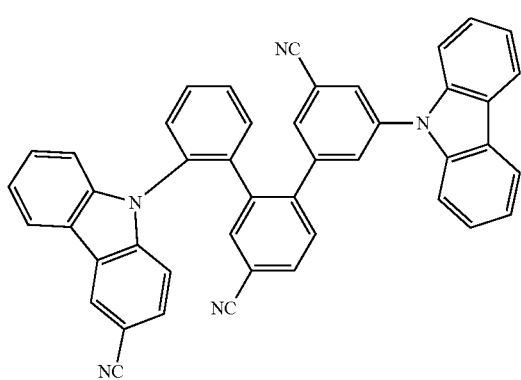
1633 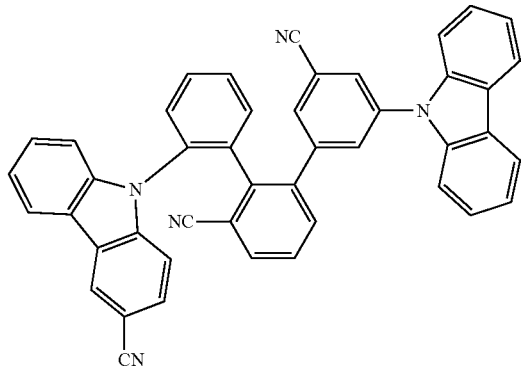
1634 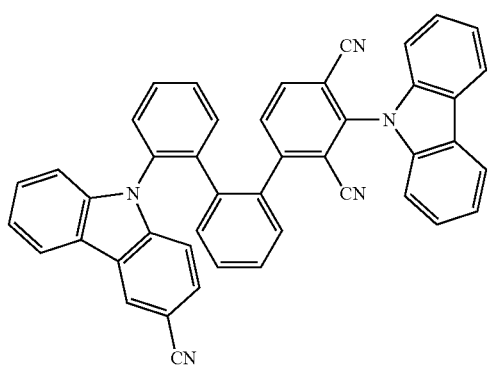
1635 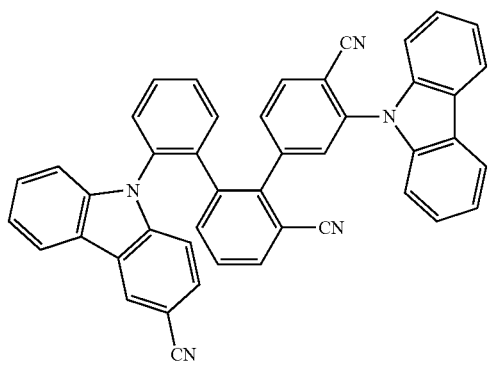
1636 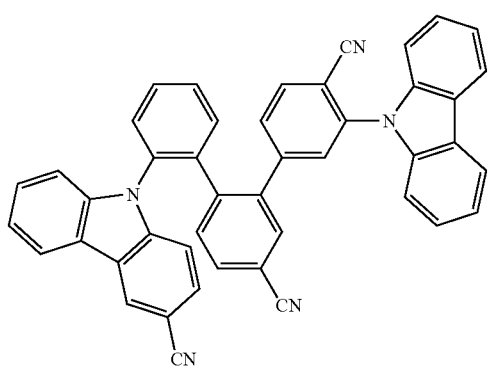

461
-continued
1637
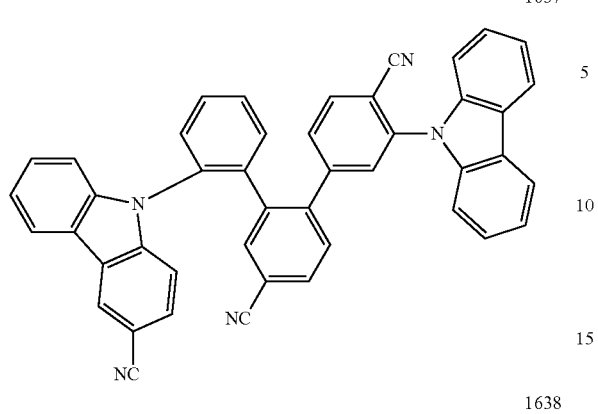
1638
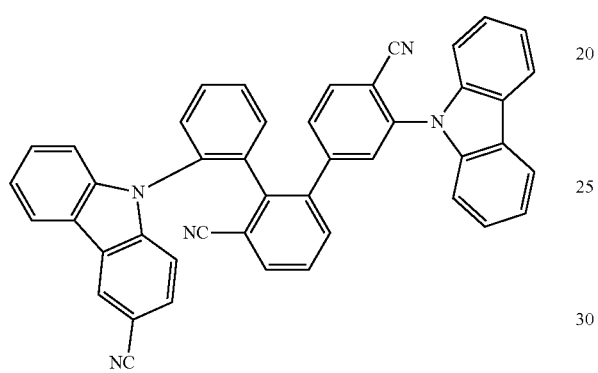
1639
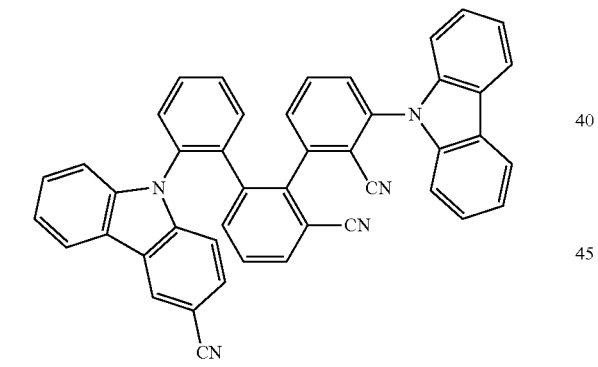
1640
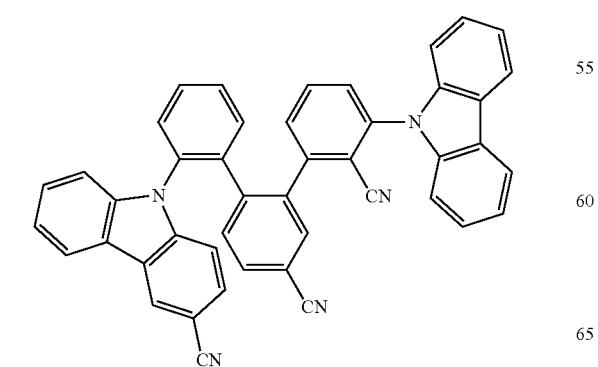
462
-continued
1641
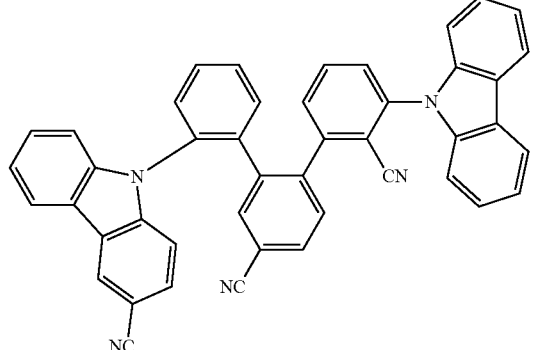
1642
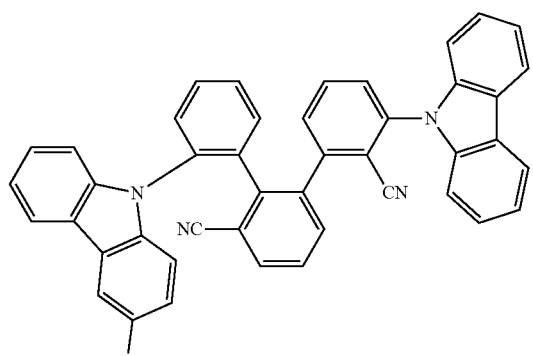
1643
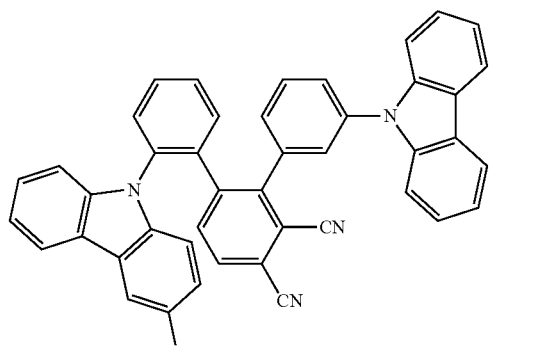
1644
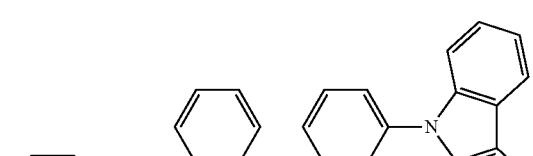

-continued
1645
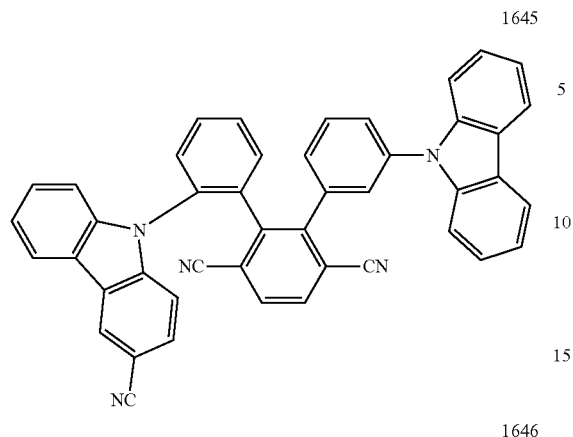
1646
1647
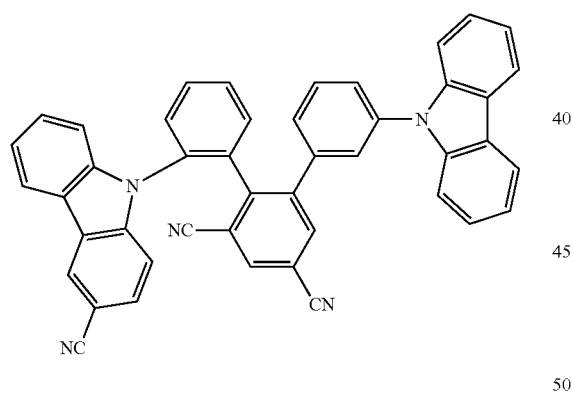
1648
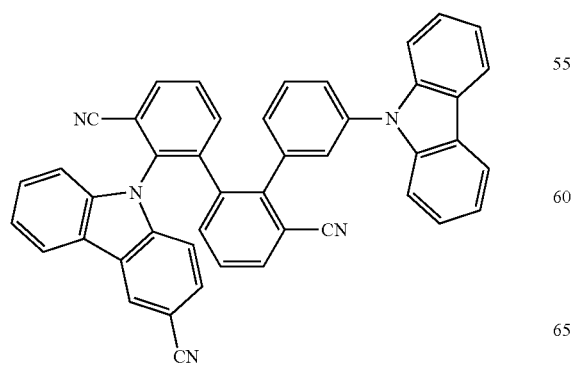
-continued
1649
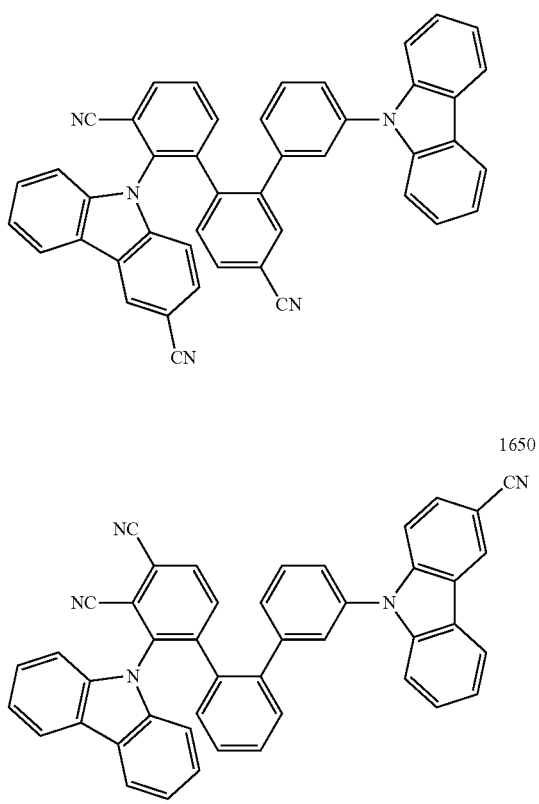
1650
1651
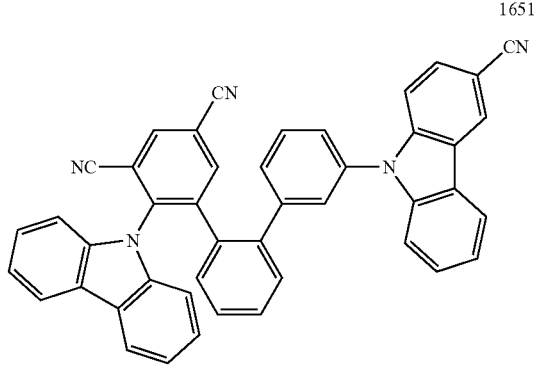
1652
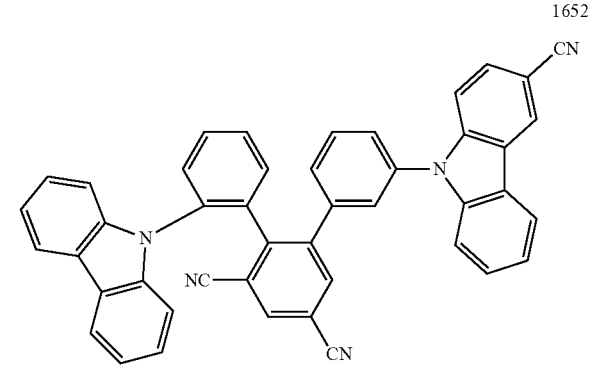

1653
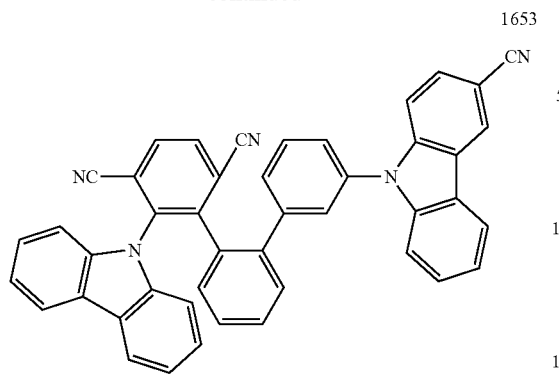
1657
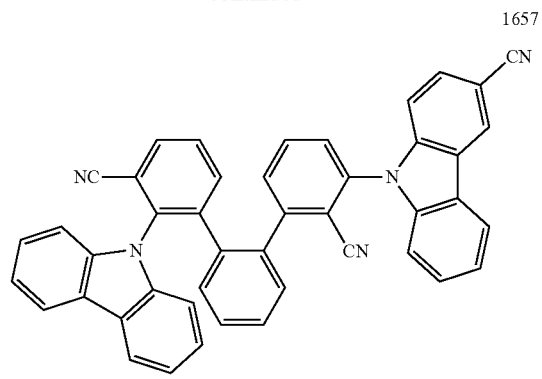
1654
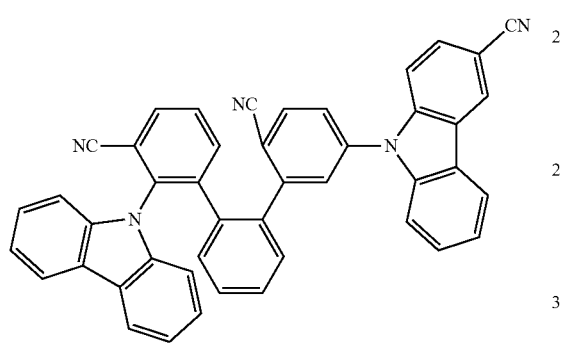
1658
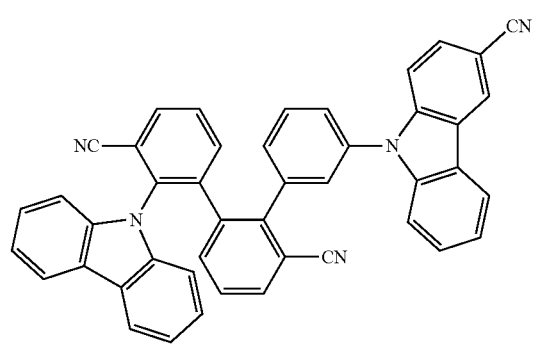
1655
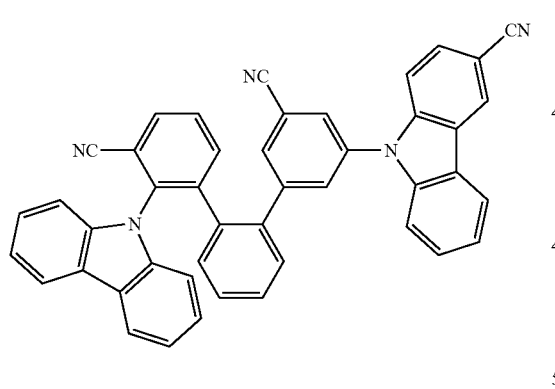
1659
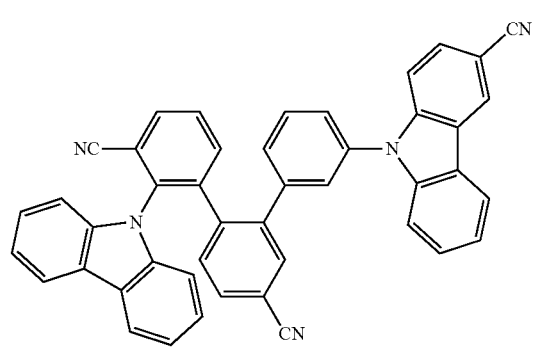
1656
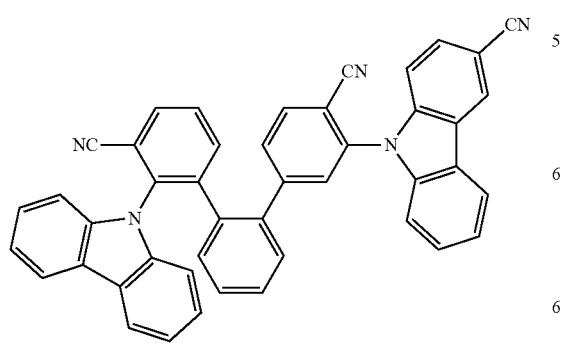
1660
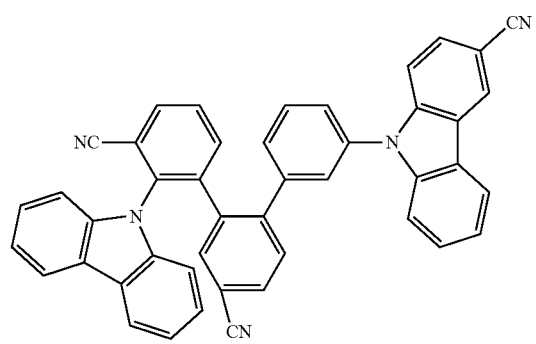

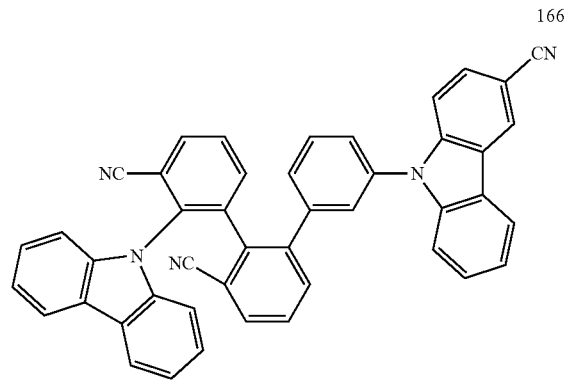
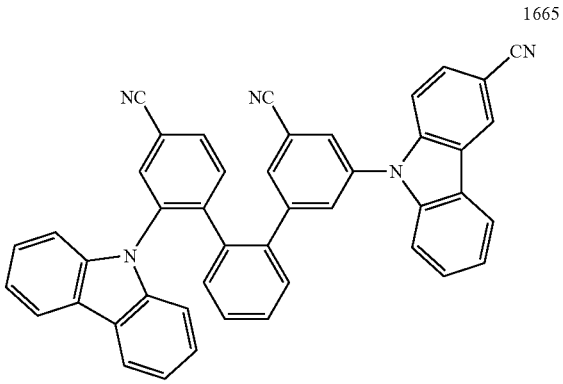

-continued
1669
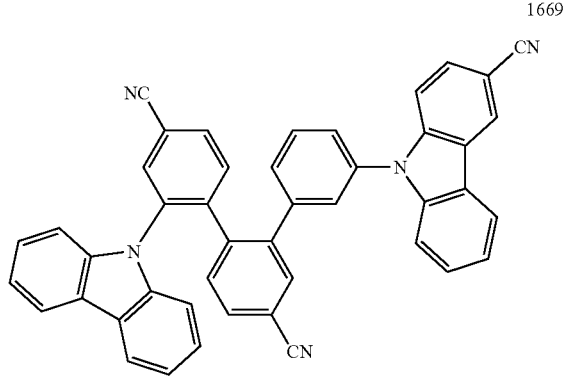
1670
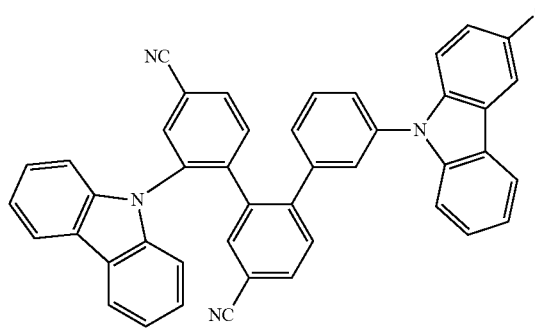
1671
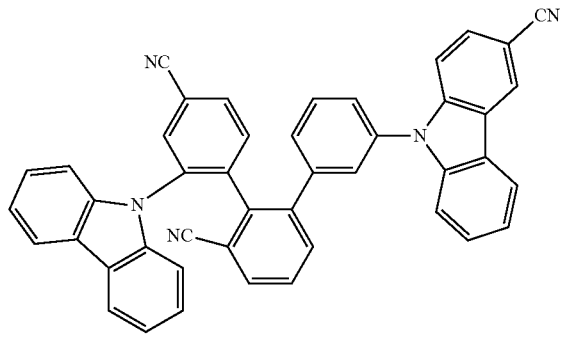
1672
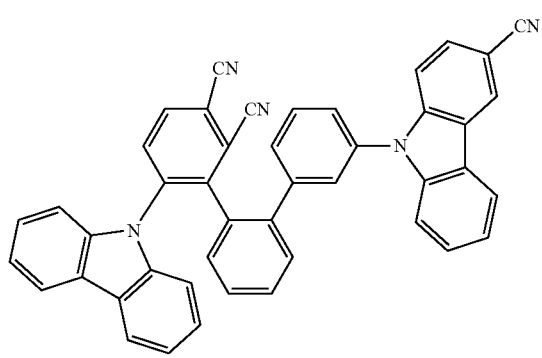
-continued
1673
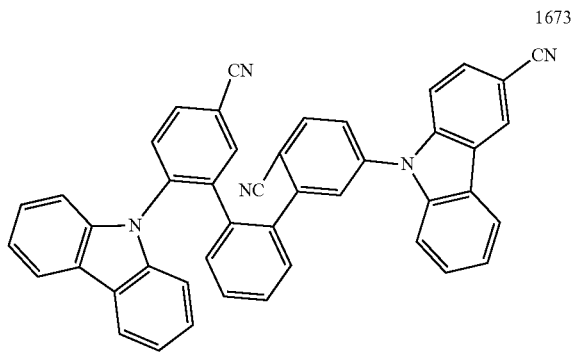
1674
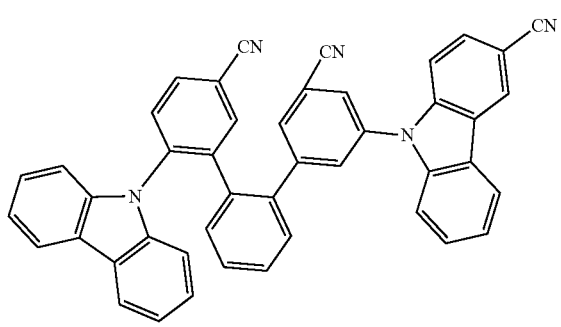
1675
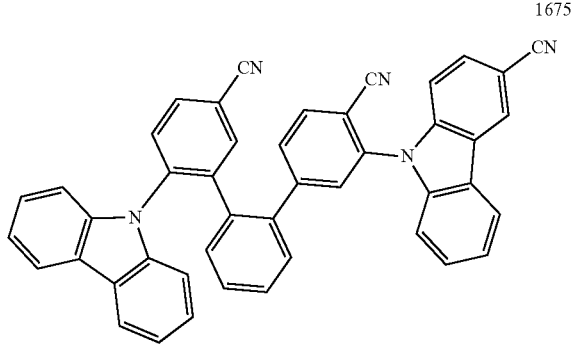
1676
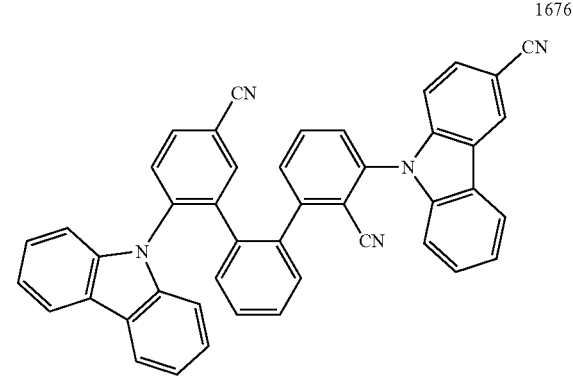

-continued
1677
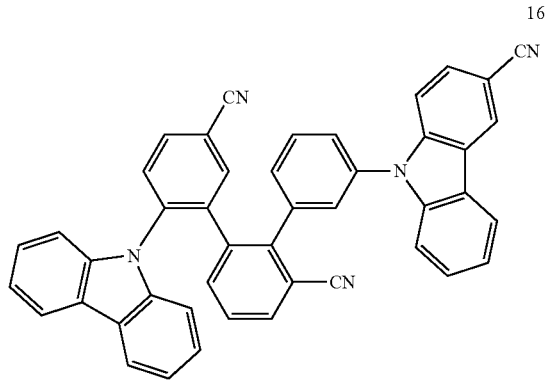
1681
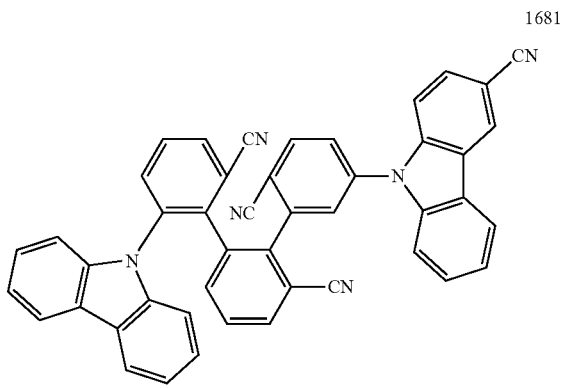
1678
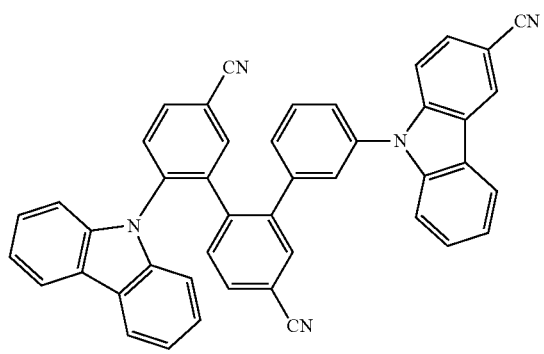
1682
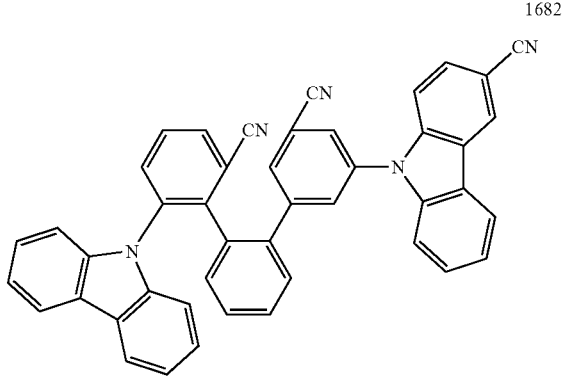
1679
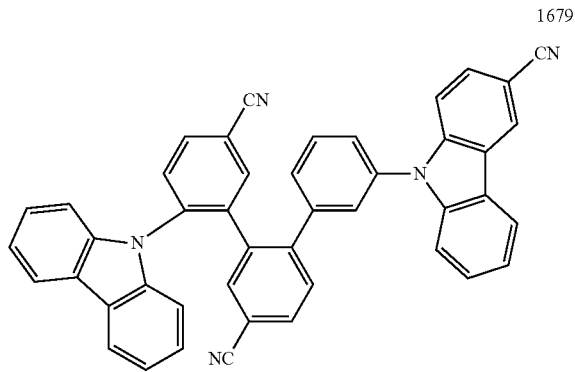
1683
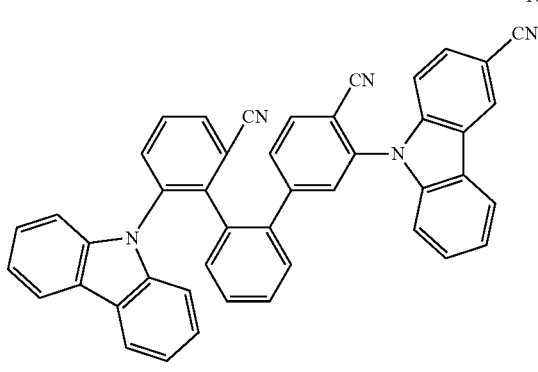
1680
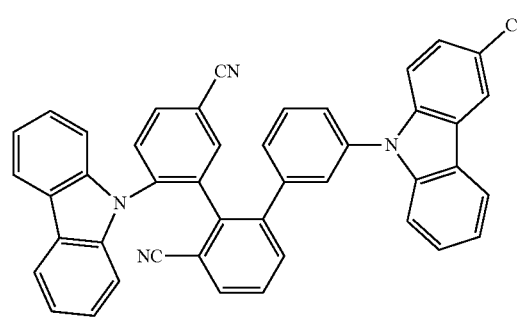
1684
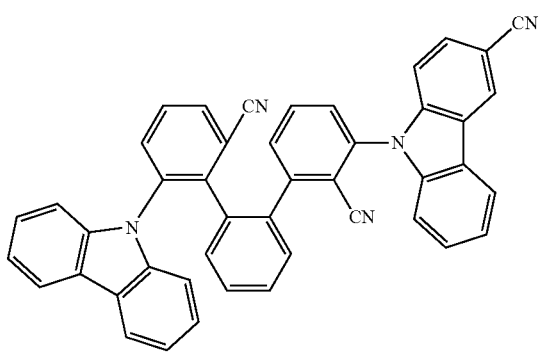

-continued
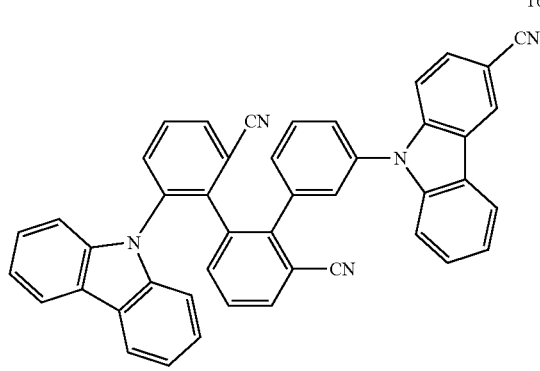
1685
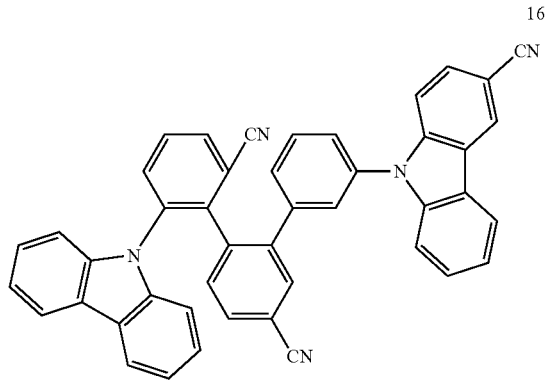
1686
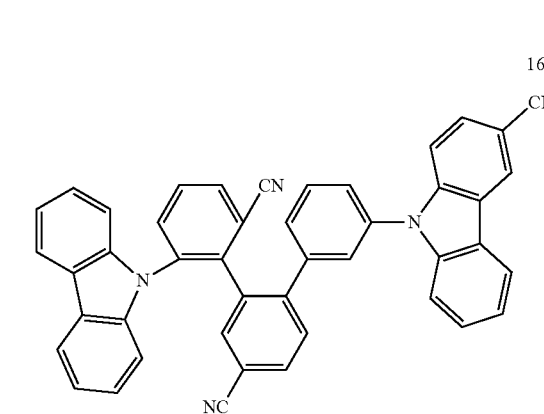
1687
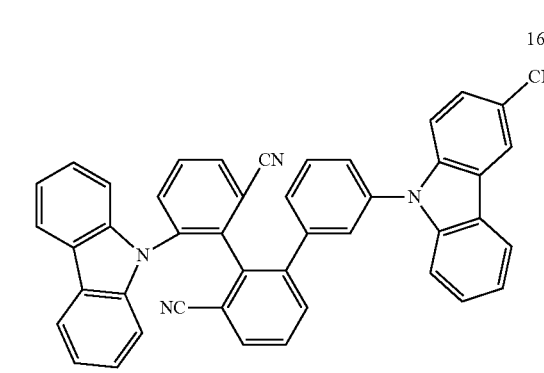
1688
-continued
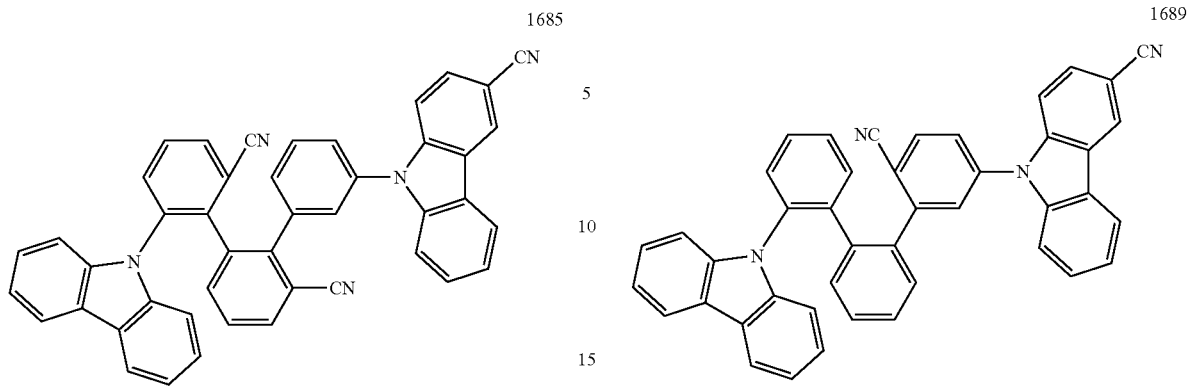
1689
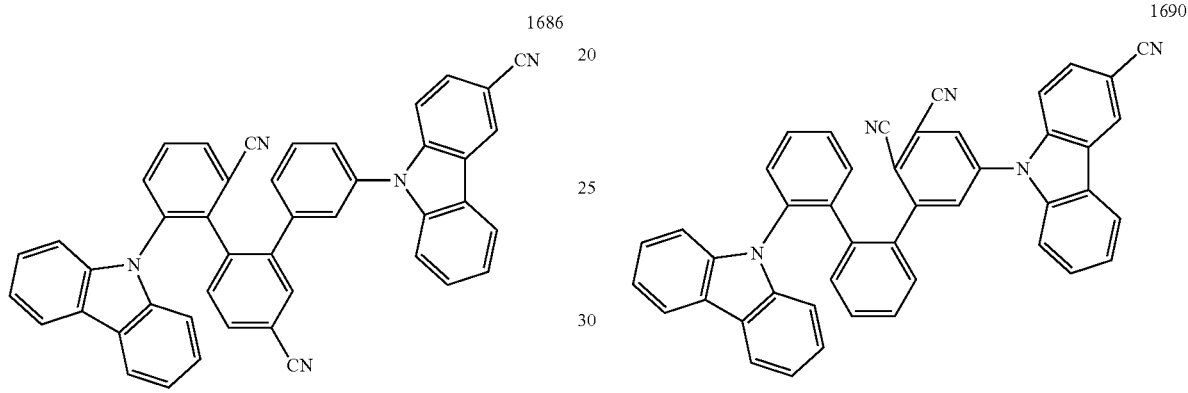
1690
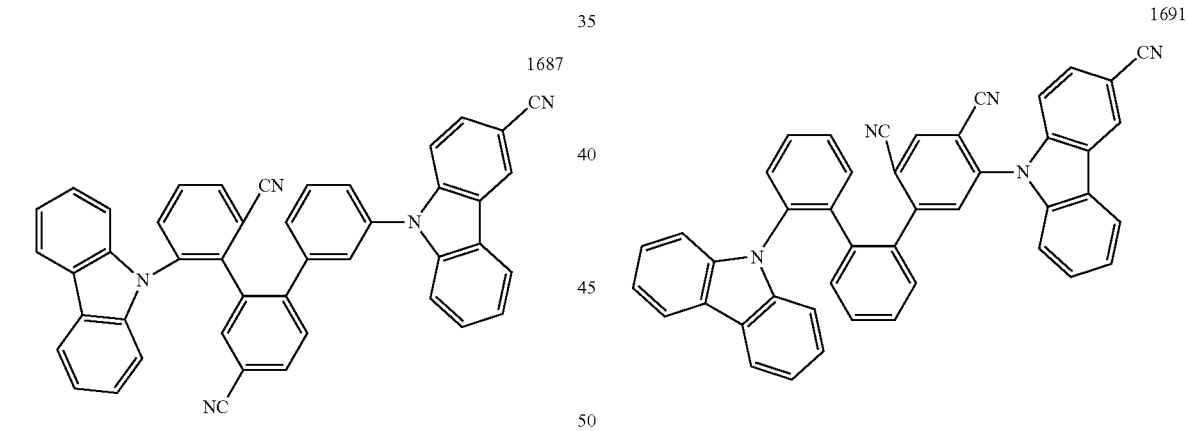
1691
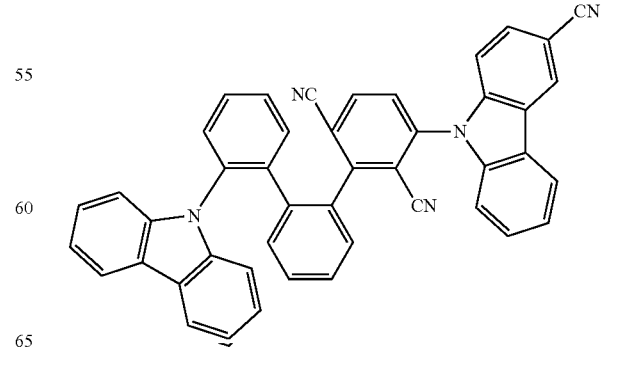
1692

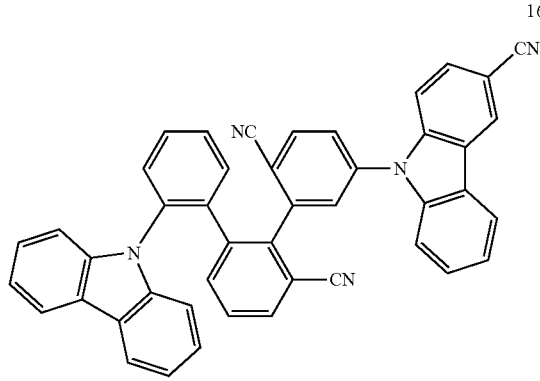
1693
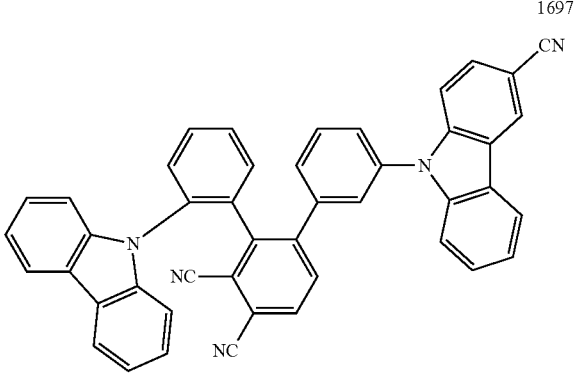
1697
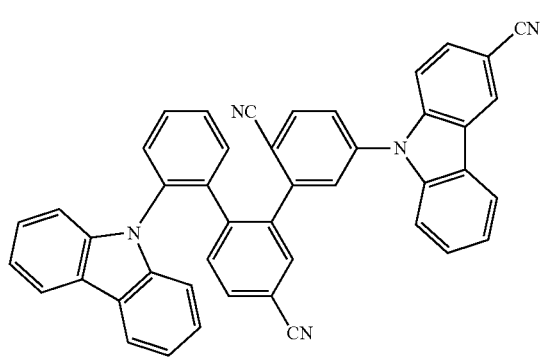
1694
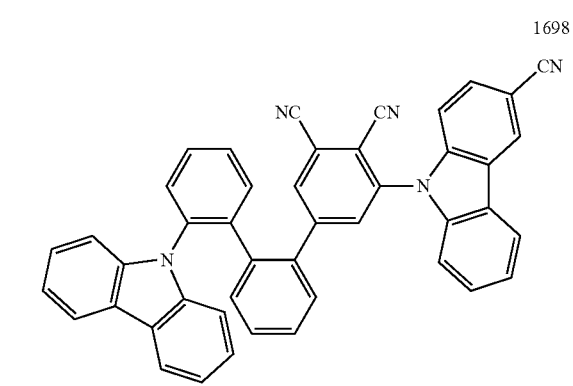
1698
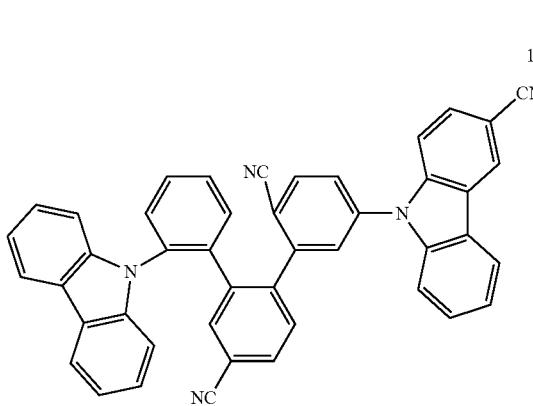
1695
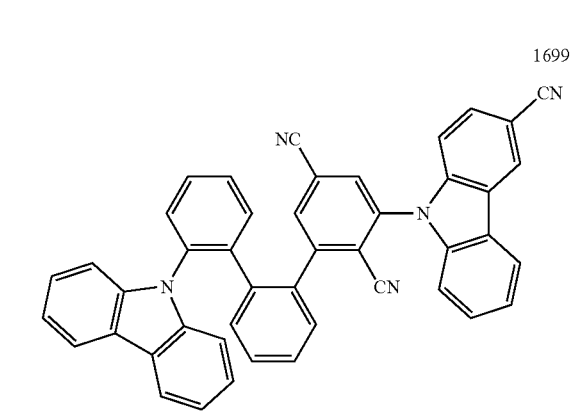 [SMILES: N#Cc1ccc2c(c1)c1ccccc1n2-c1c(C#N)ccc(-c2ccccc2-c2ccccc2-n2c3ccccc3c3ccccc32)c1C#N]
1699
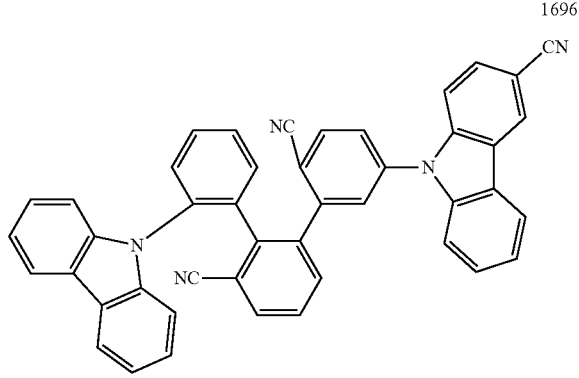
1696
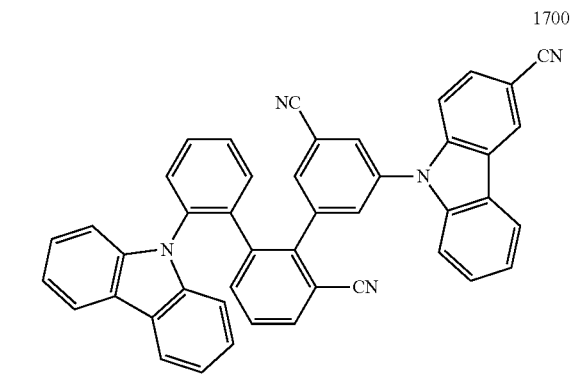
1700

1701 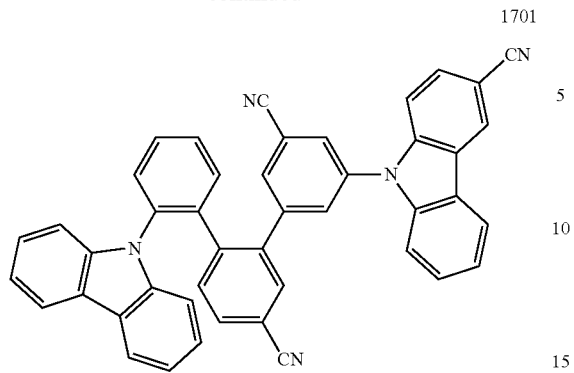
1705 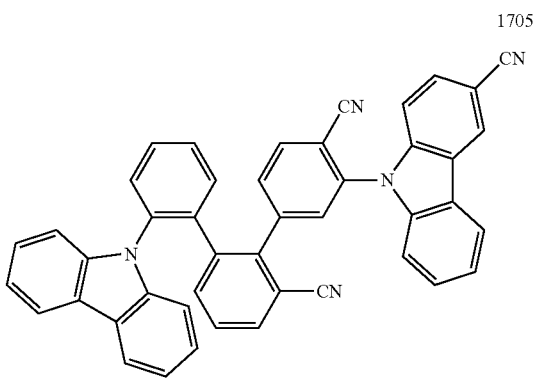
1702 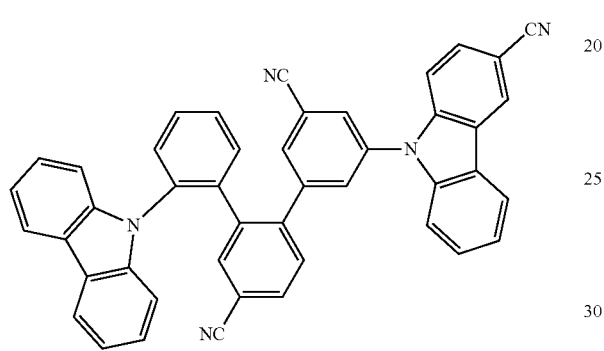
1706 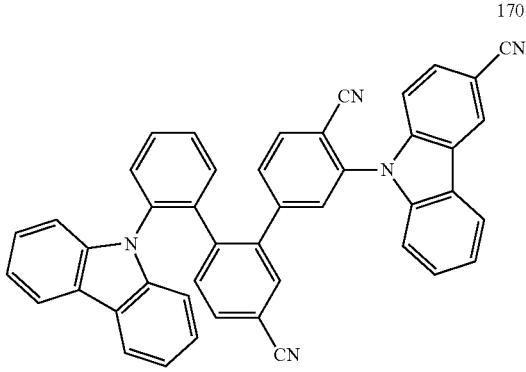
1703 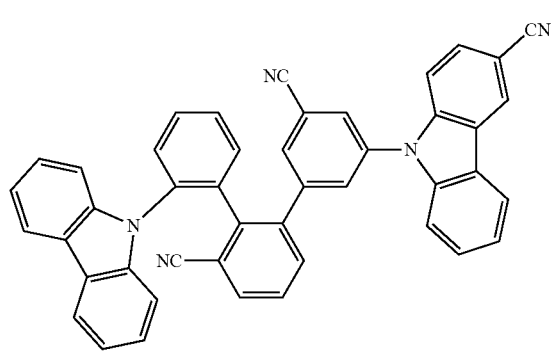
1707 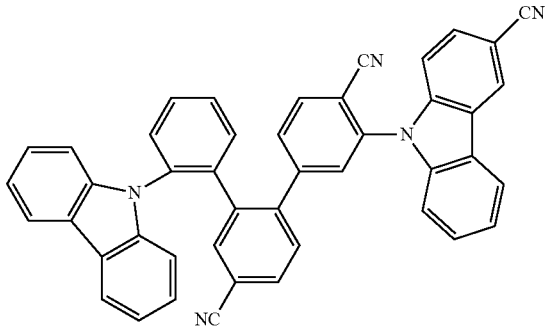
1704 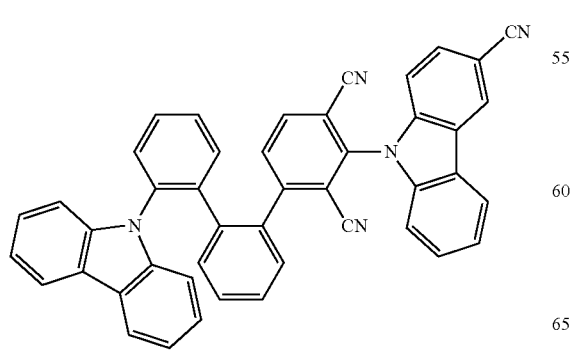
1708 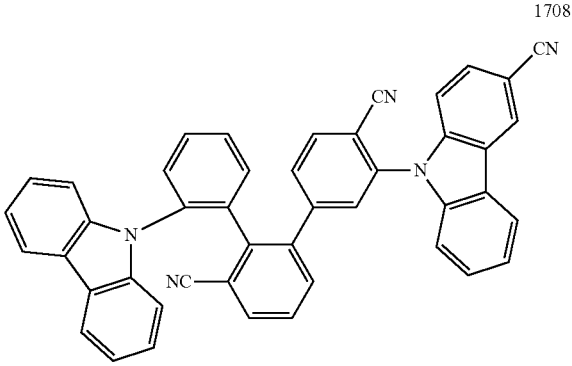

479
-continued
480
-continued
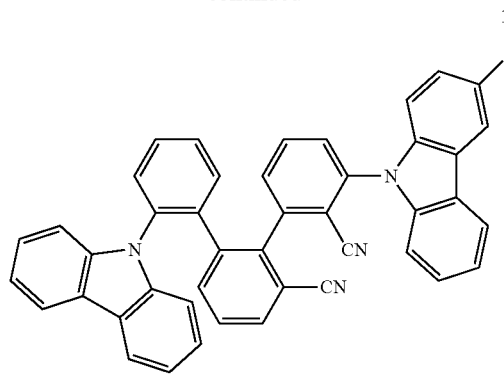
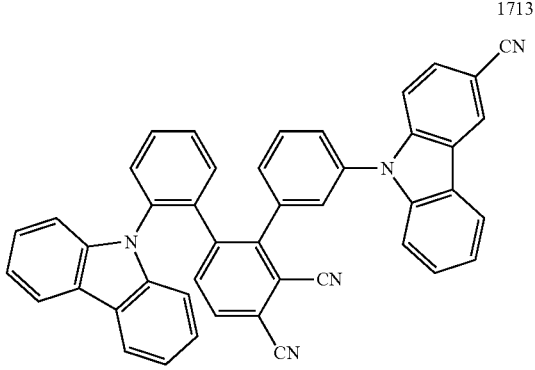

-continued
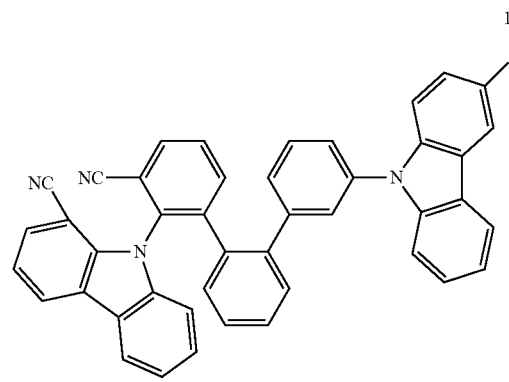
1717
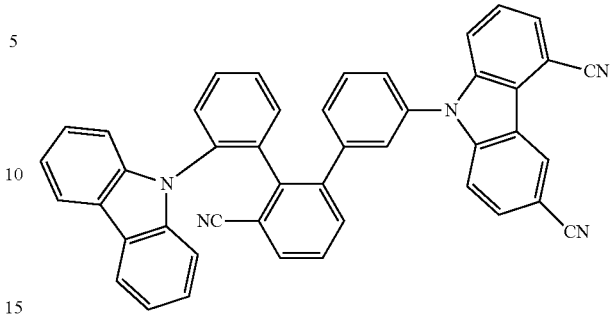
1721
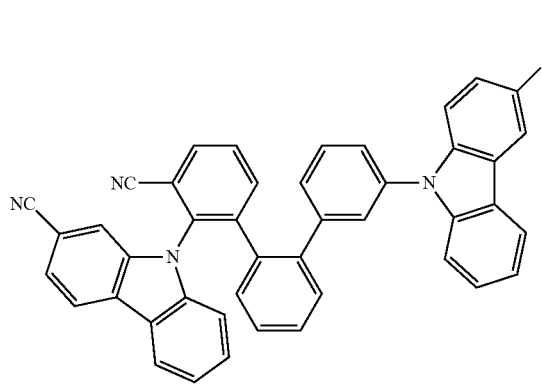
1718
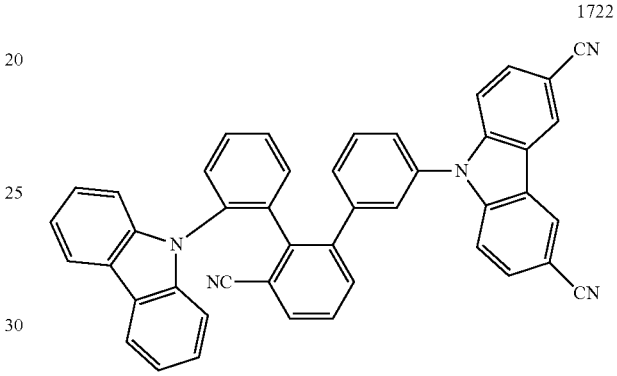
1722
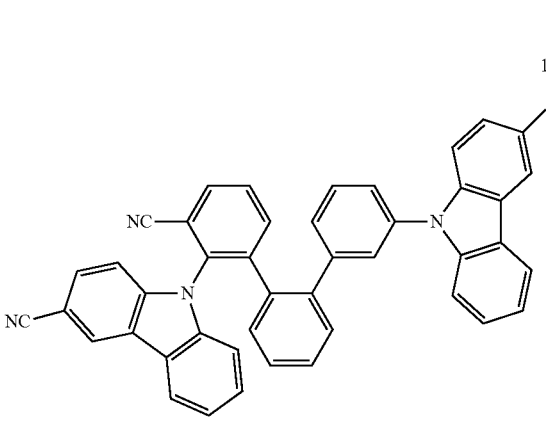
1719
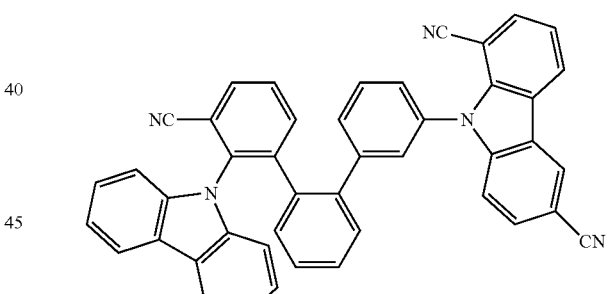
1723
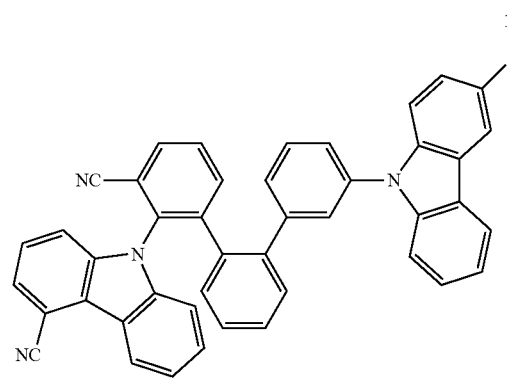
1720
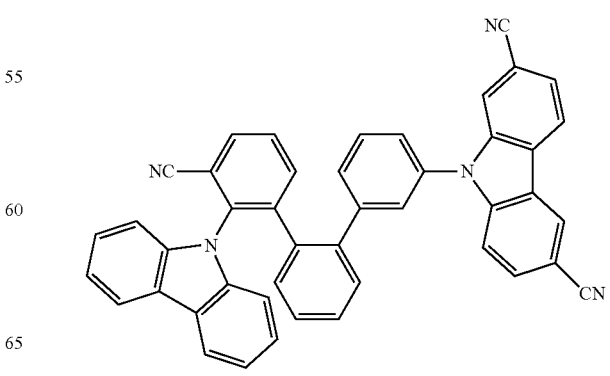
1724

1725
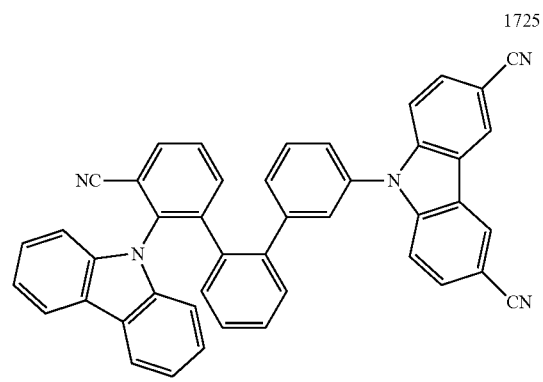
1729
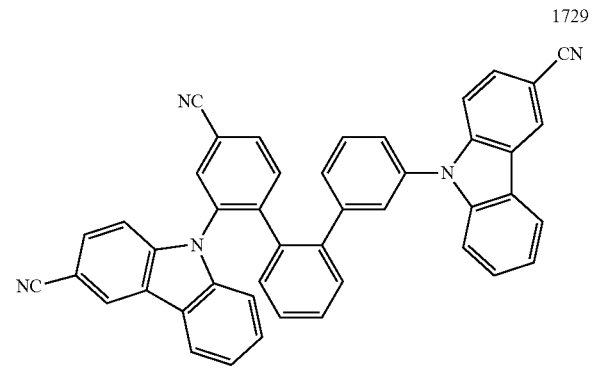
1726
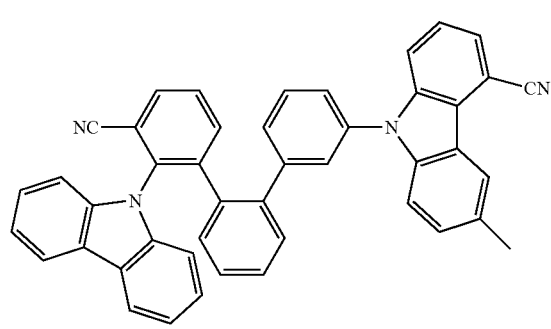
1730
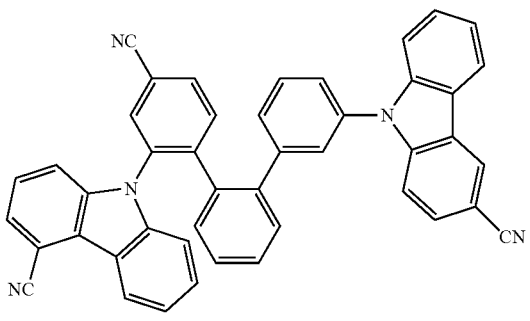
1727
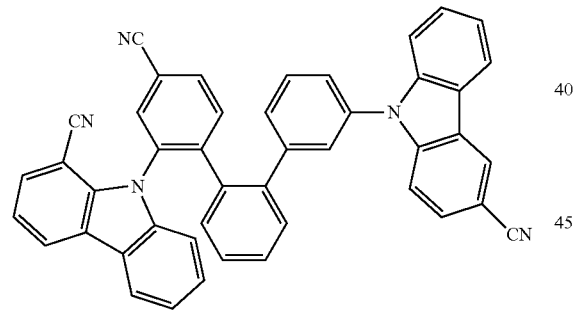
1731
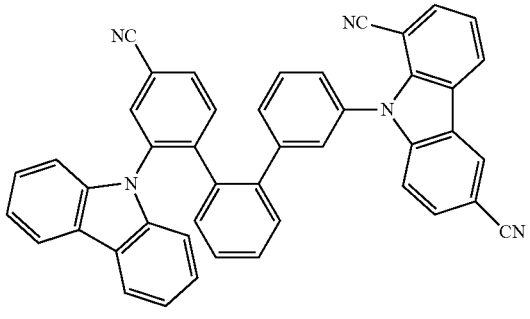
1728
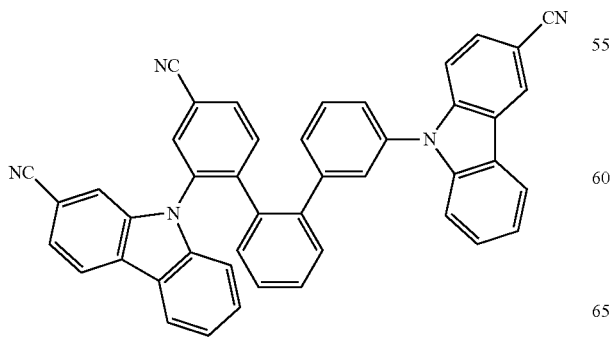
1732
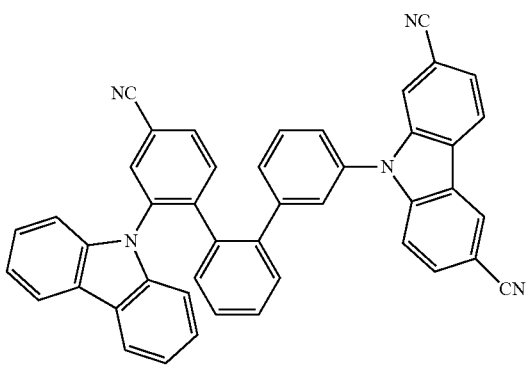

1733
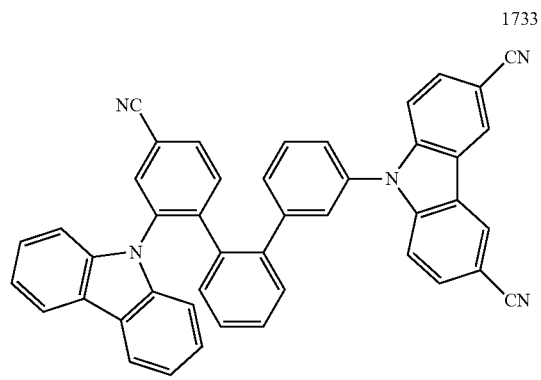
1737
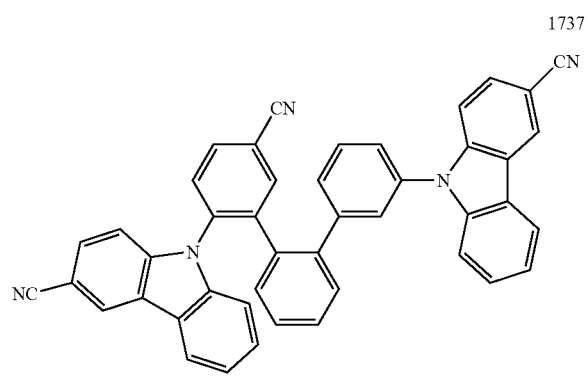
1734
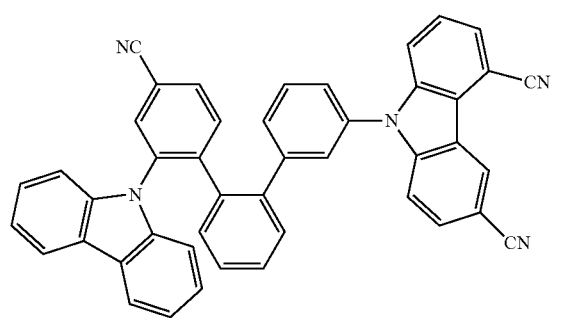
1738
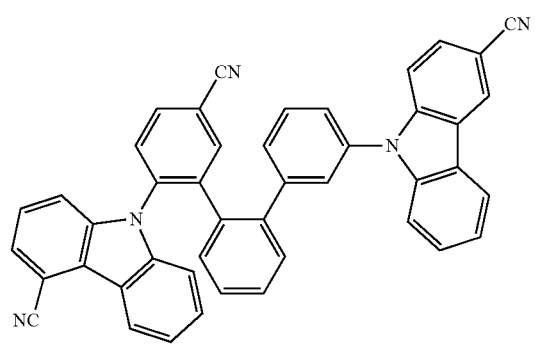
1735
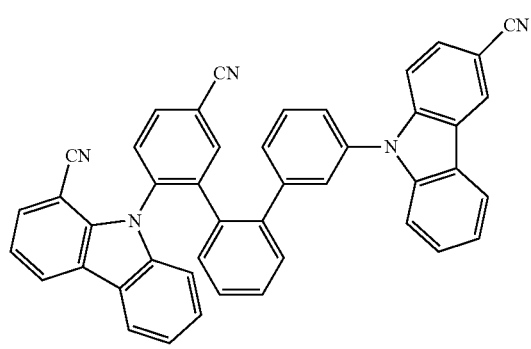
1739
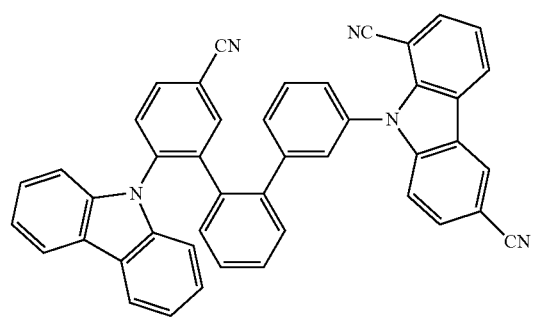
1736
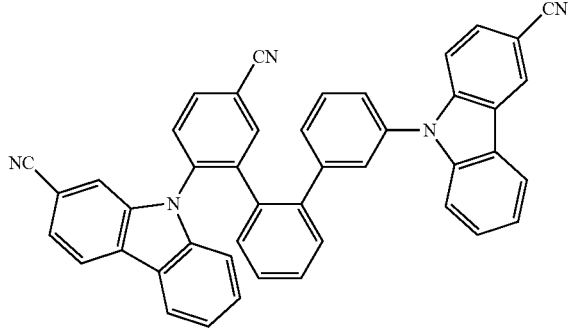
1740
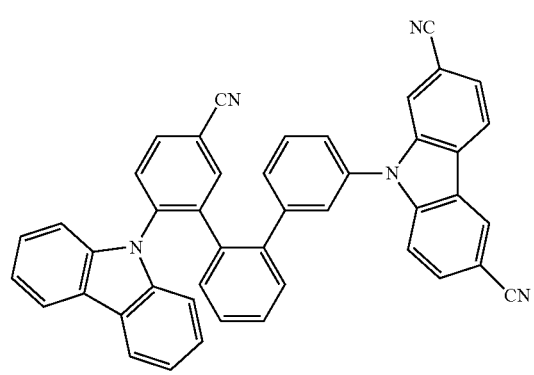

487
-continued
1741
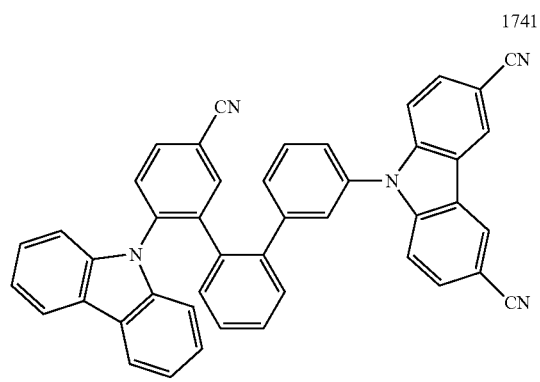
1742
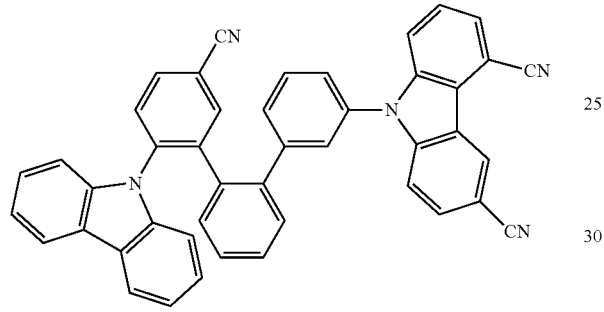
1743
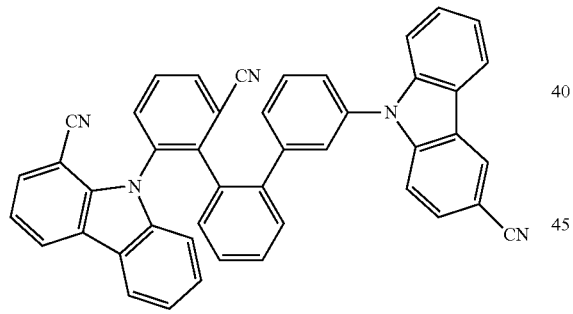
1744
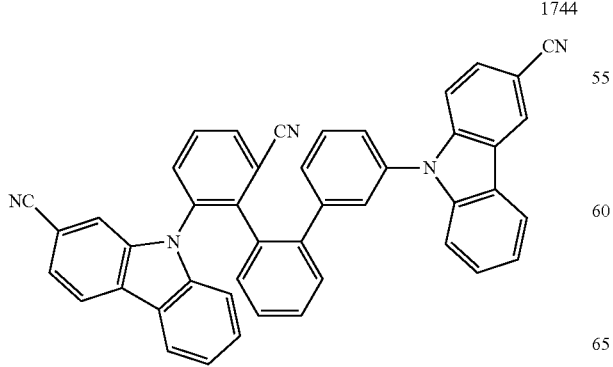
488
-continued
1745
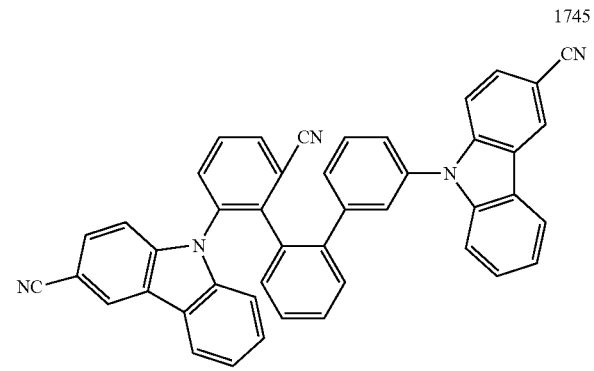
1746
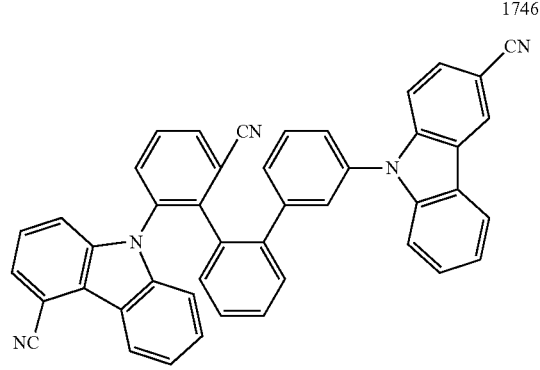
1747
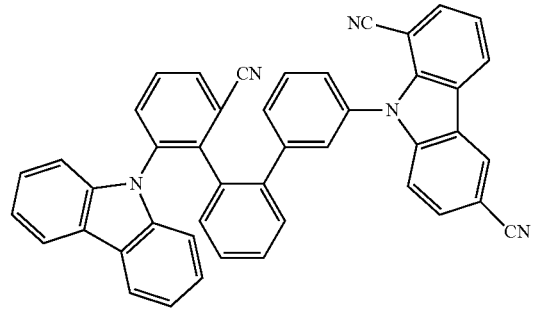
1748
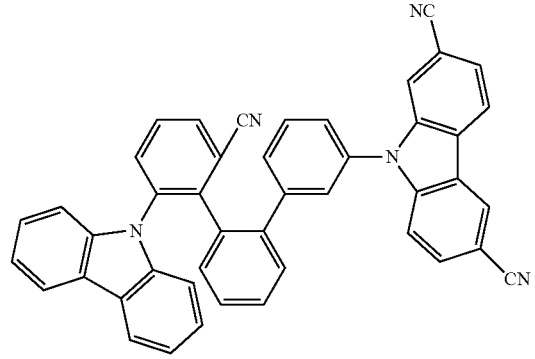

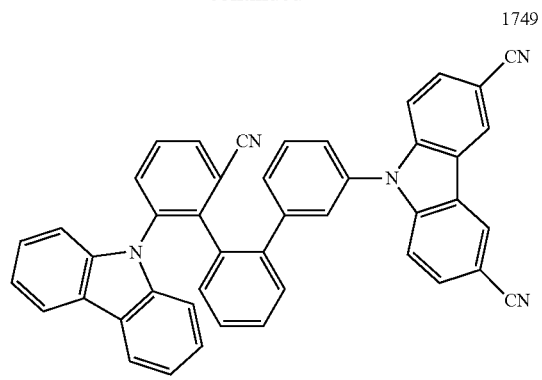
1749
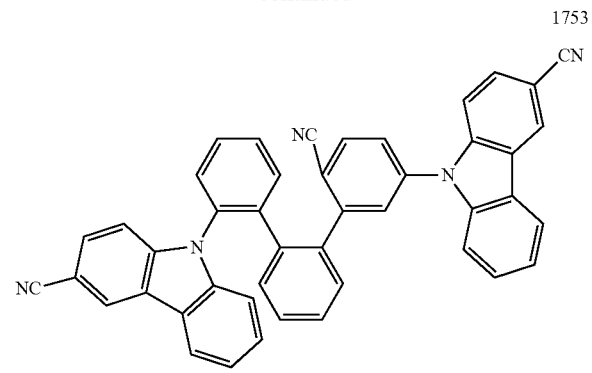
1753
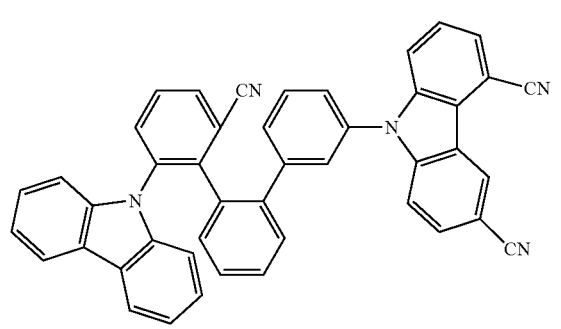
1750
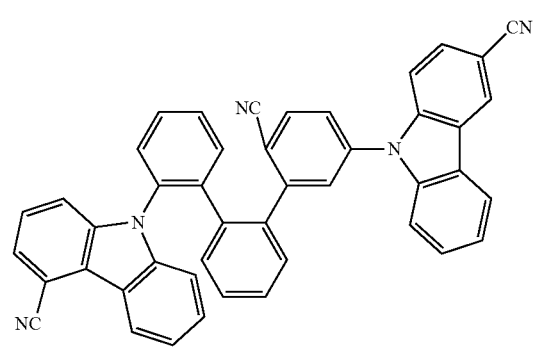
1754
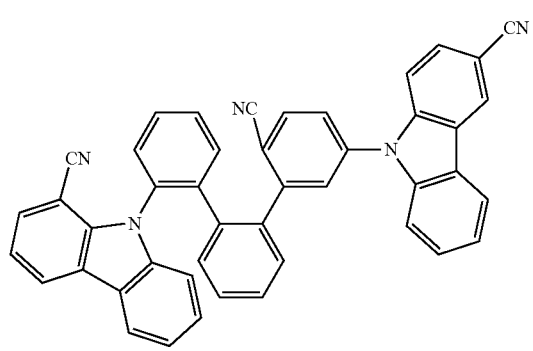
1751
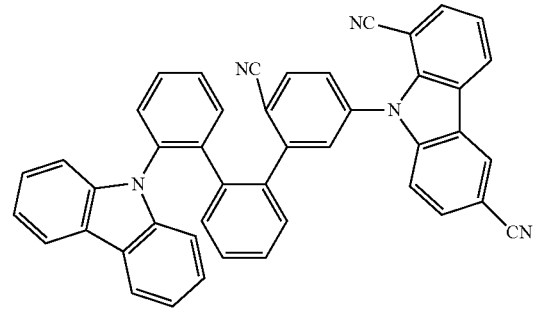
1755
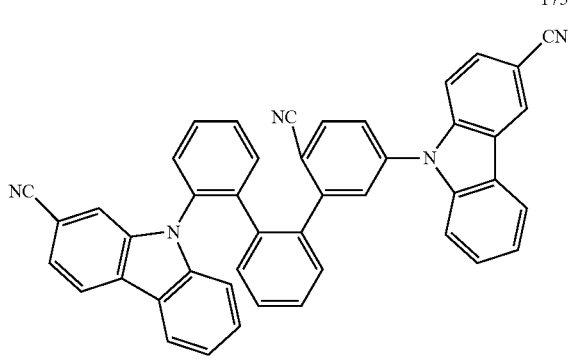
1752
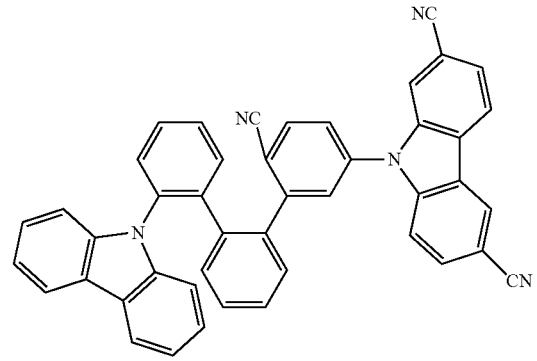
1756

491
-continued
1757
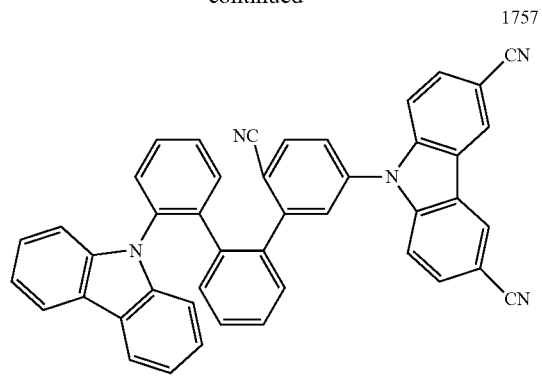
1758
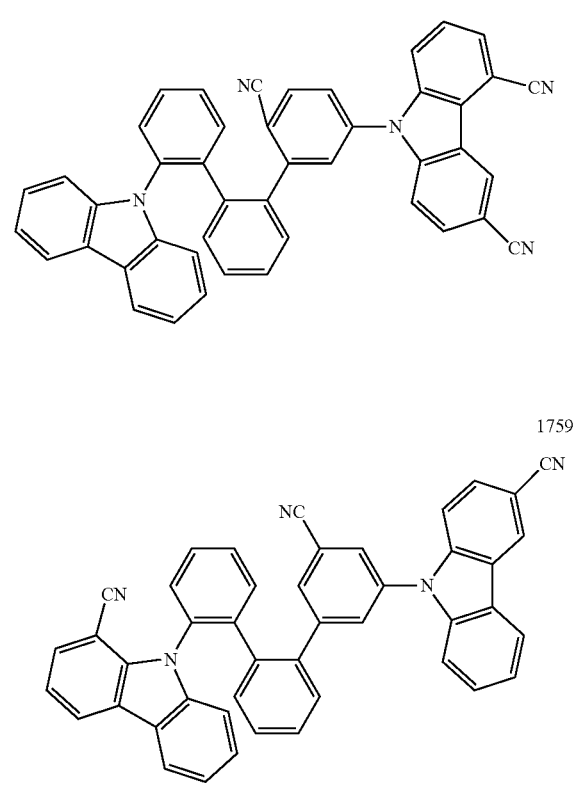
1759
1760
492
-continued
1761
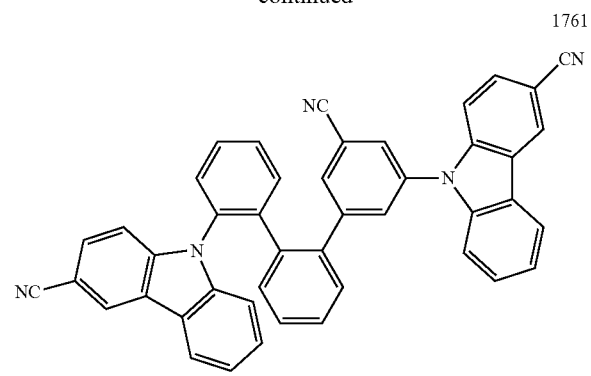
1762
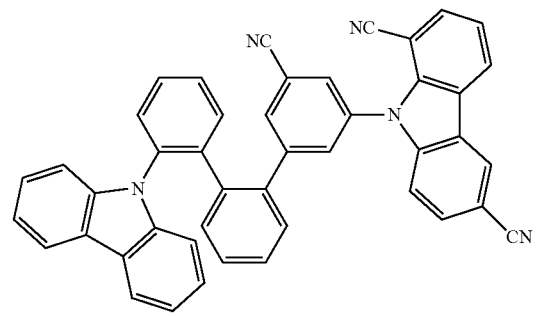
1763
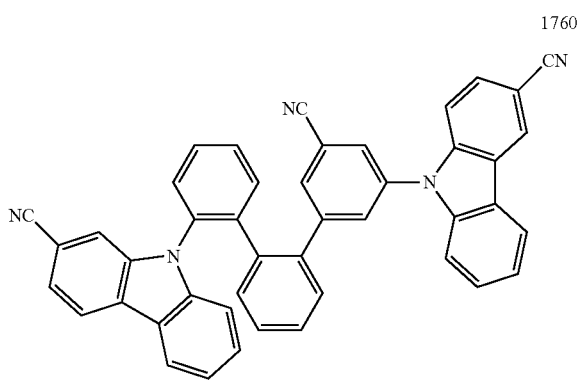
1764
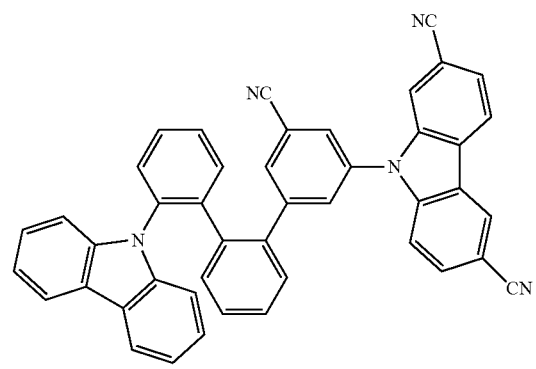

493
-continued
1765
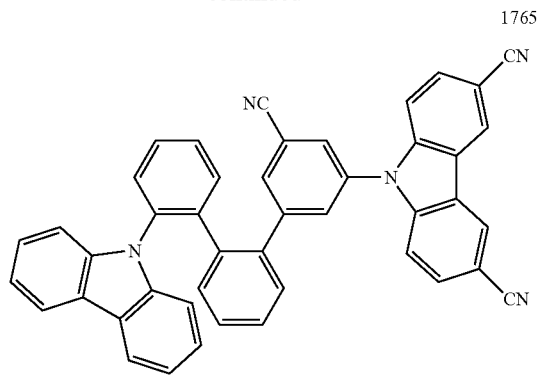
1766
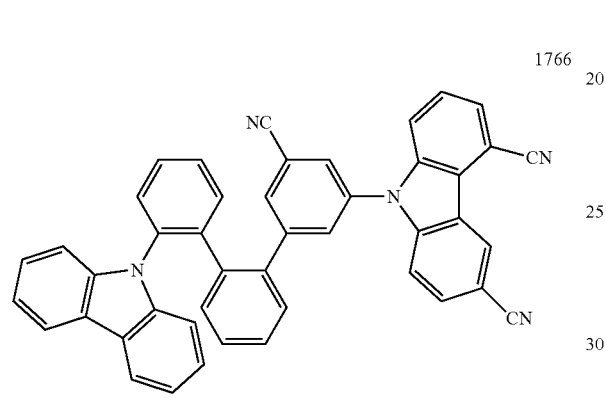
1767
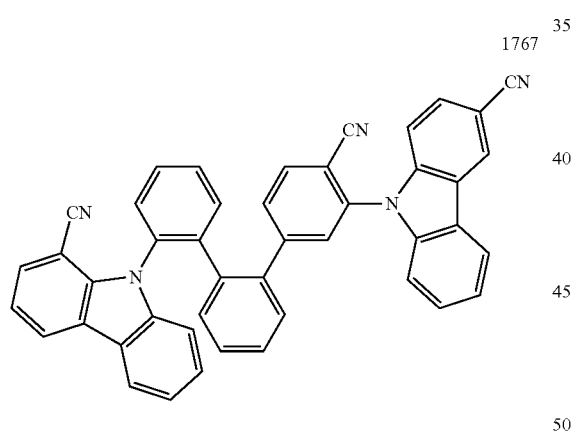
1768
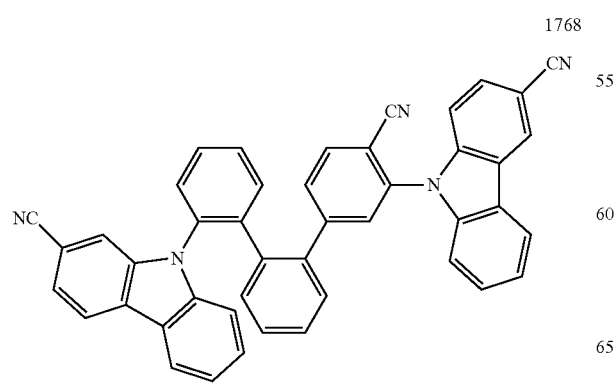
494
-continued
1769
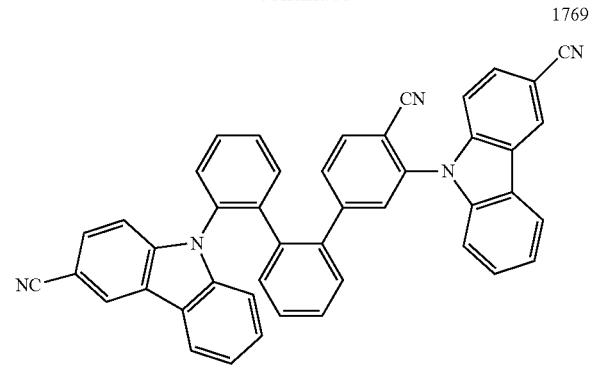
1770
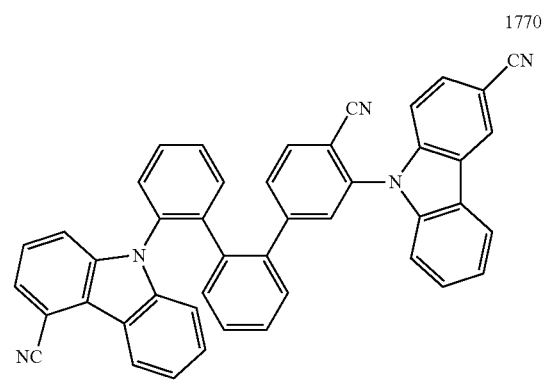
1771
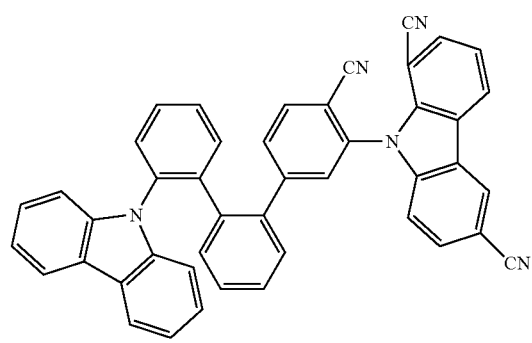
1772
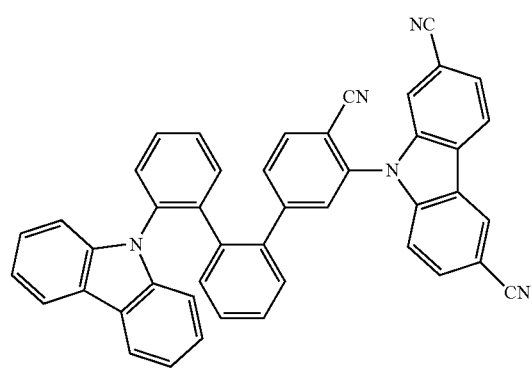

495
-continued
1773
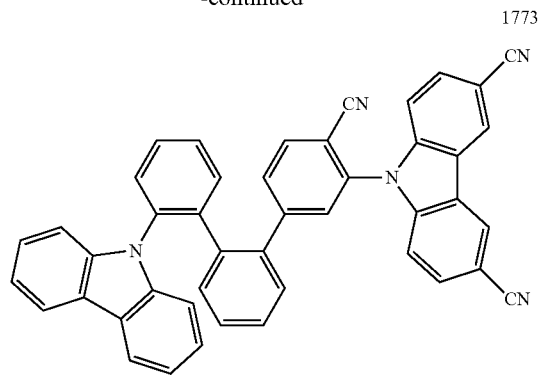
1774
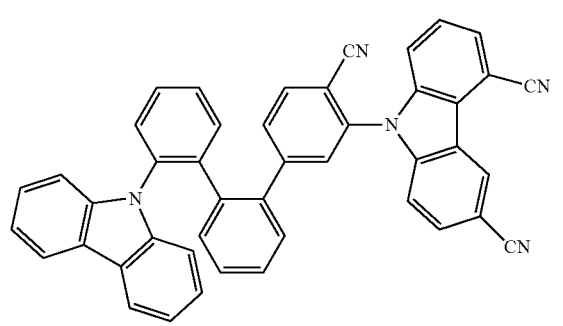
1775
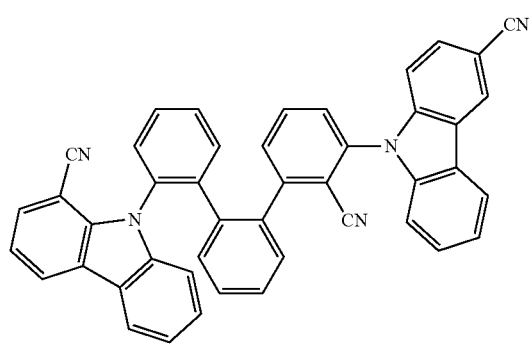
1776
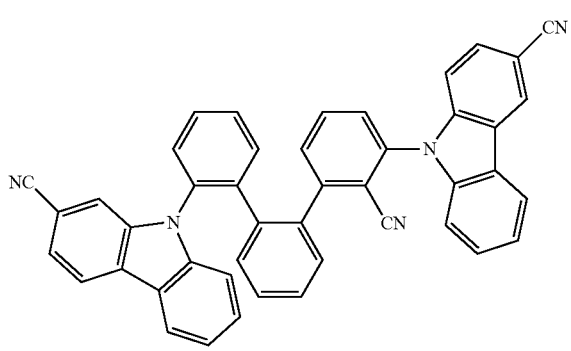
496
-continued
1777
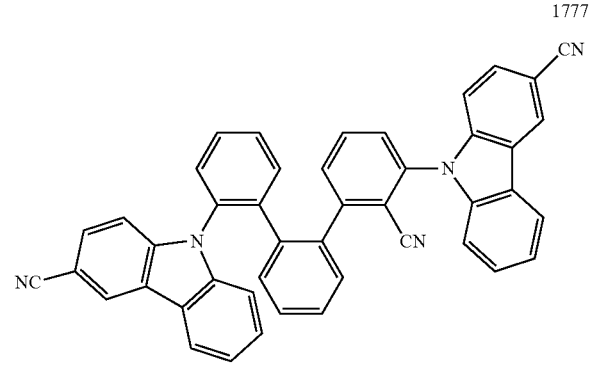
1778
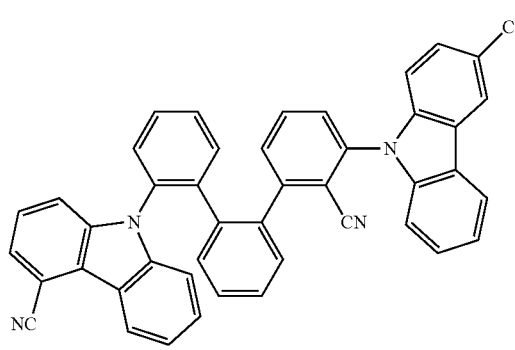
1779
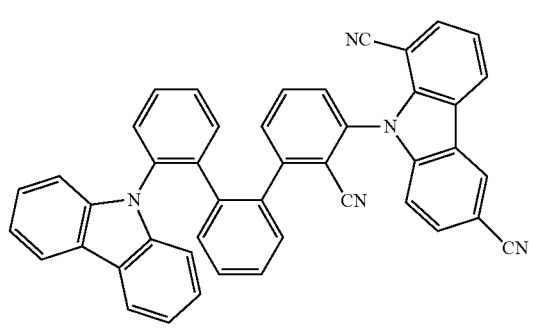
1780
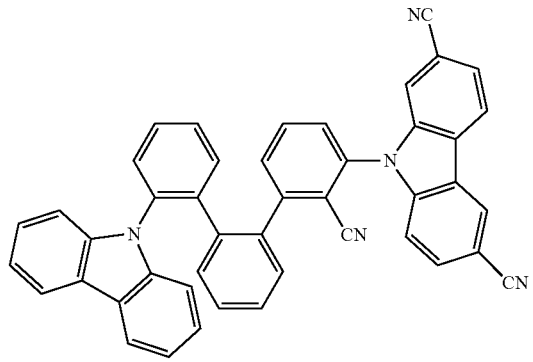

497
-continued
1781
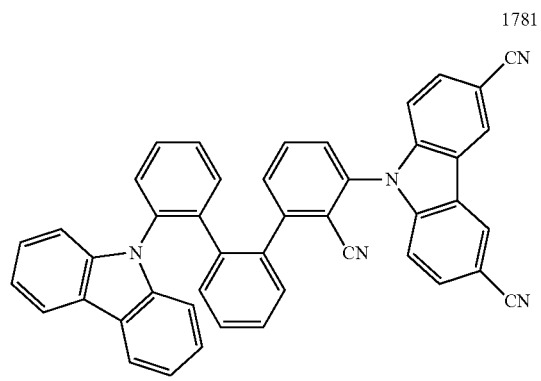
1782
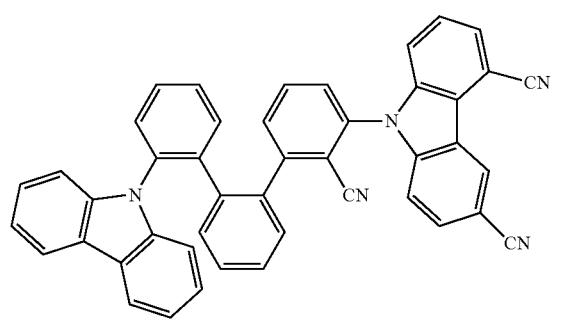
1783
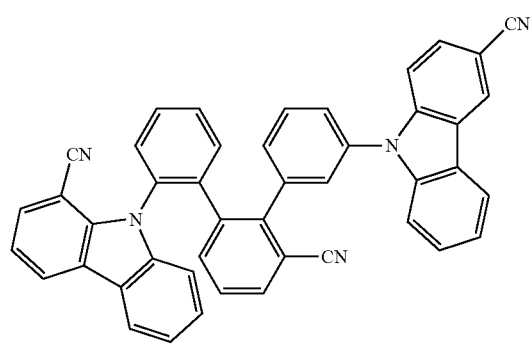
1784
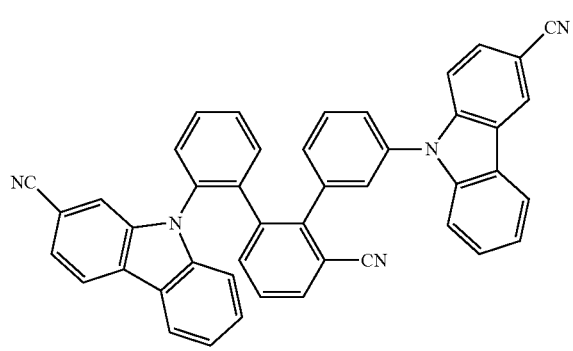
498
-continued
1785
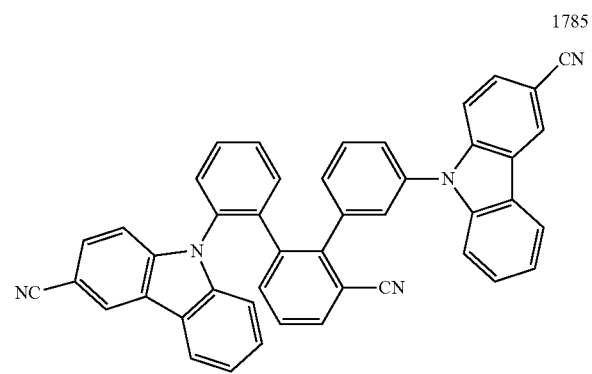
1786
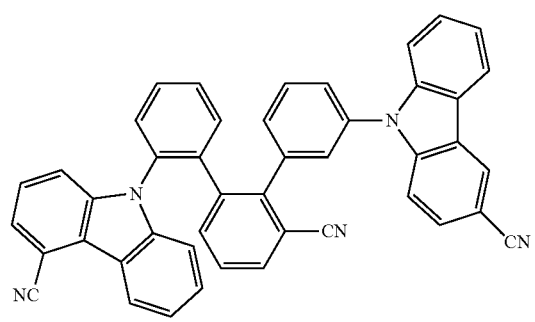
1787
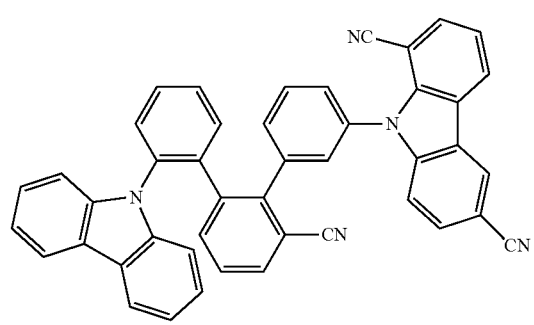
1788
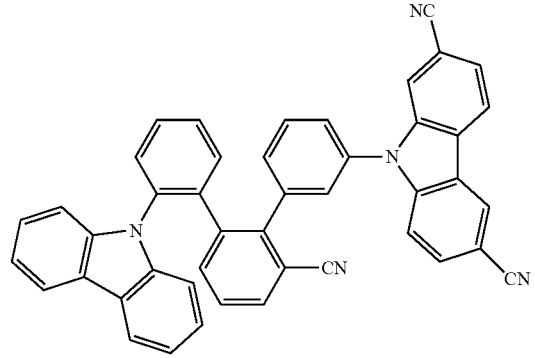

499
-continued
1789
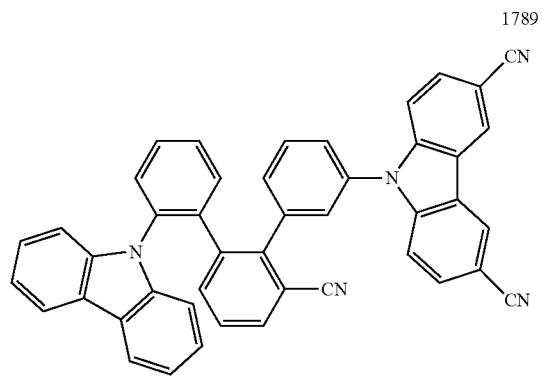
1790
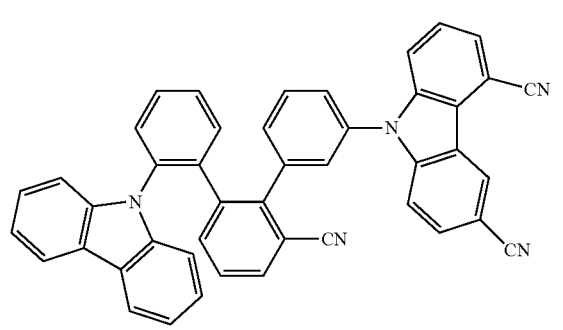
1791
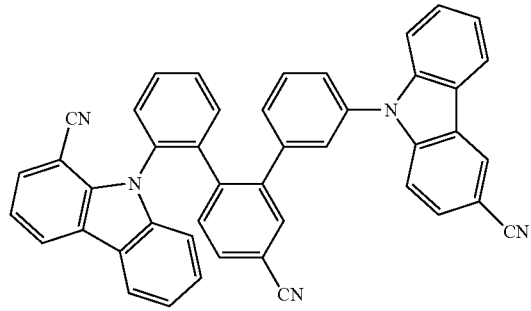
1792
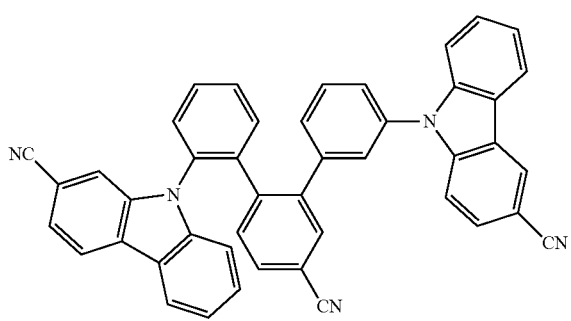
500
-continued
1793
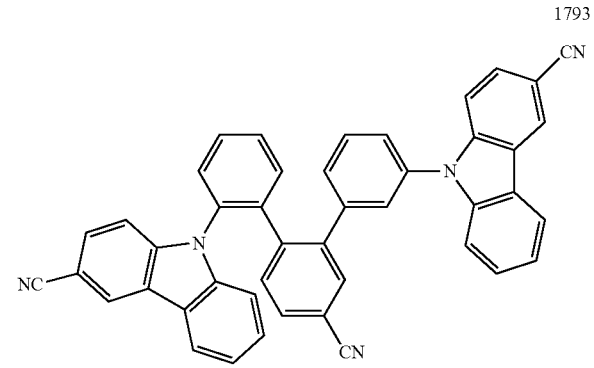
1794
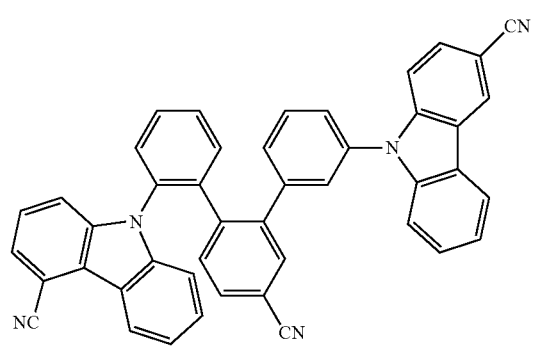
1795
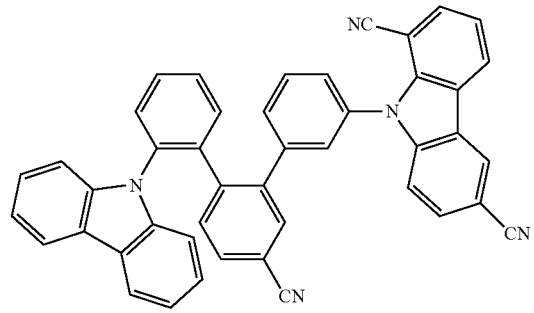
1796
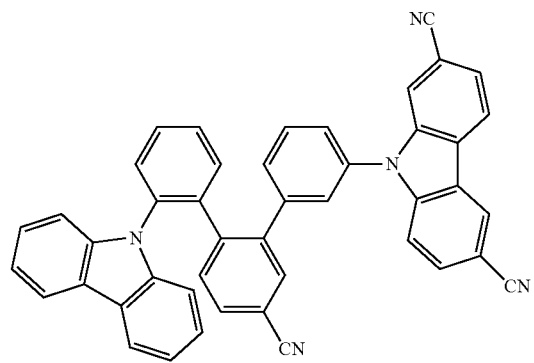

501
-continued
1797
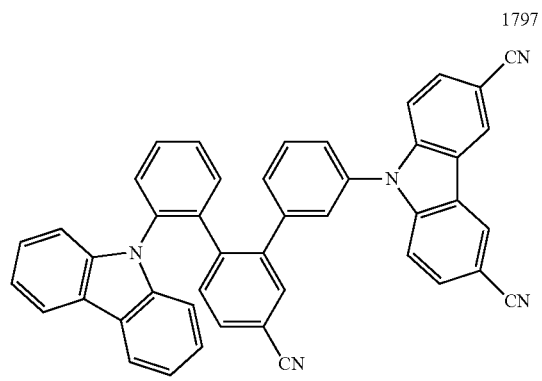
1798
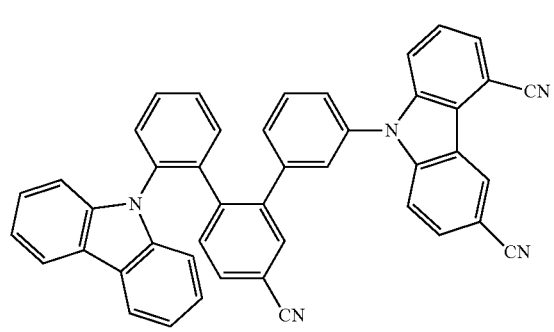
1799
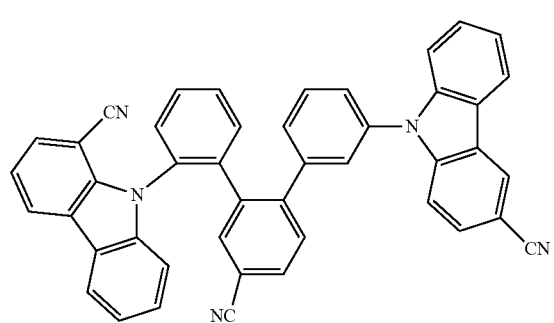
1800
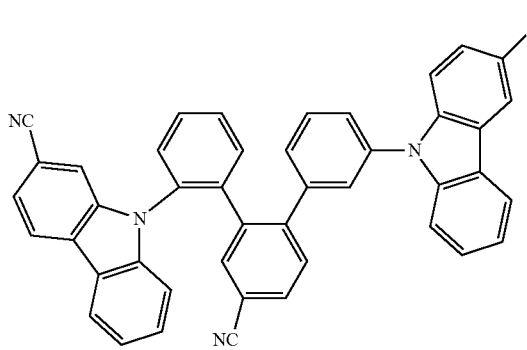
502
-continued
1801
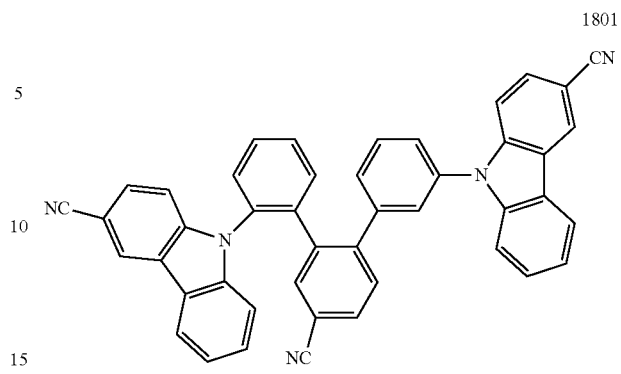
1802
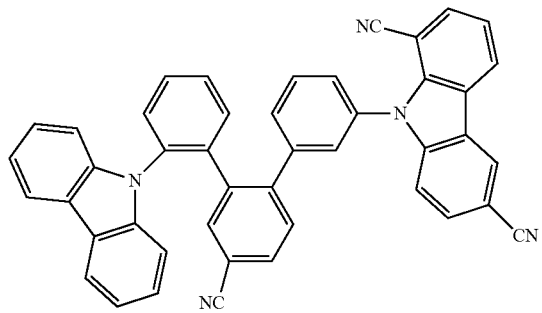
1803
1804
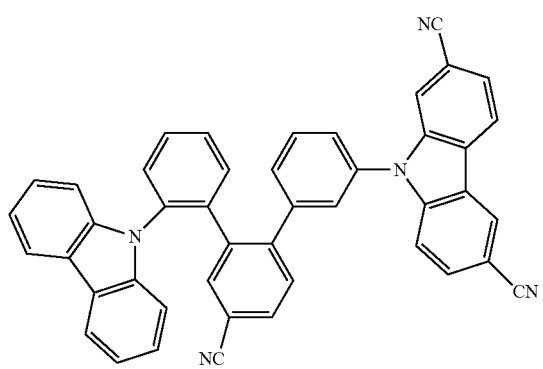

-continued
1805
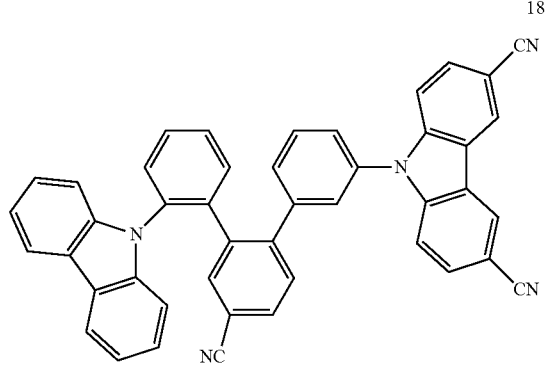
1806
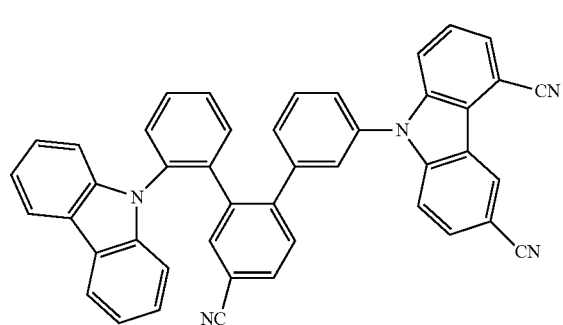
1807
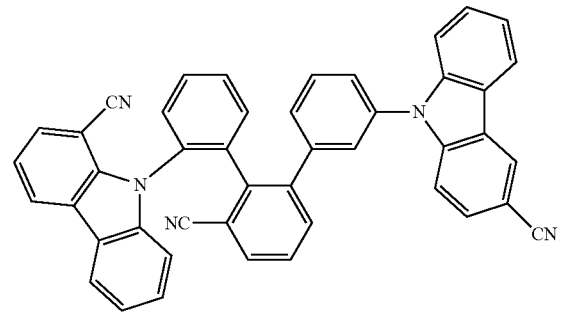
1808
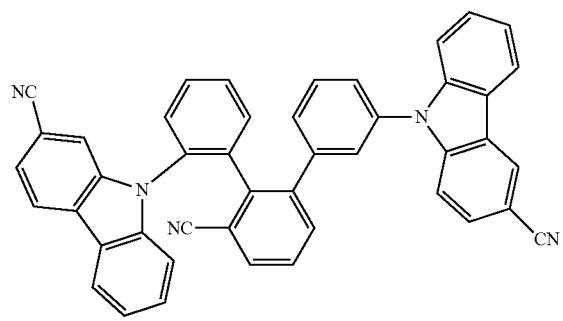
-continued
1809
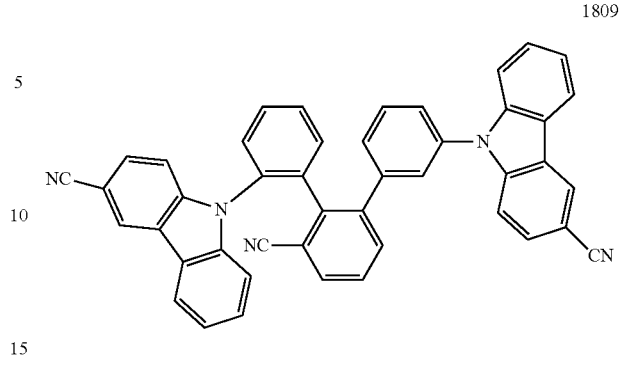
1810
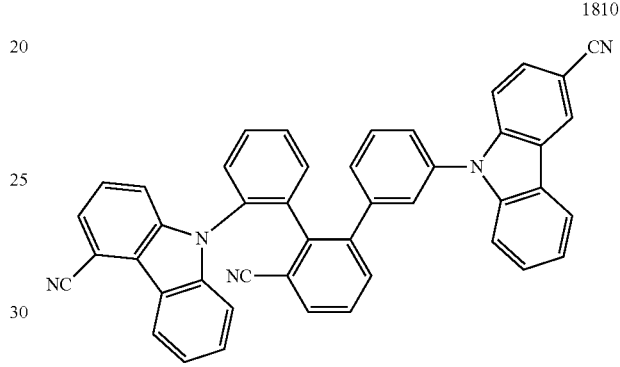
1811
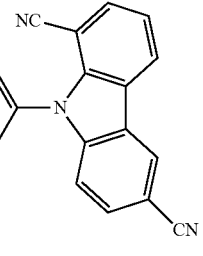
1812
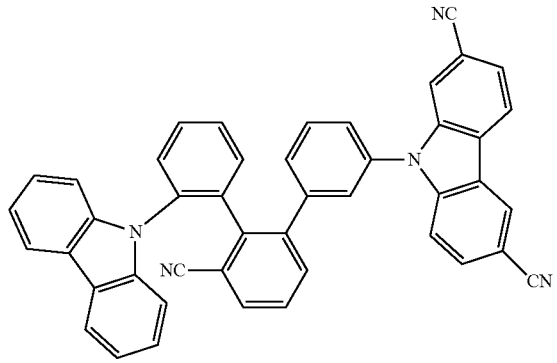

1813
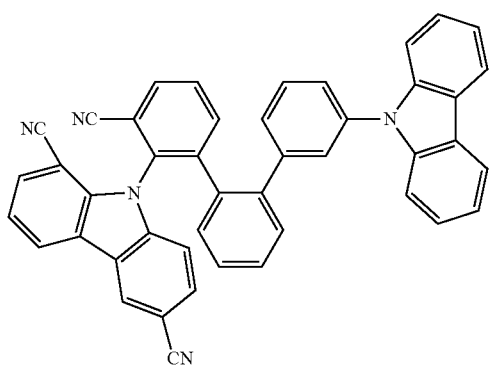
1817
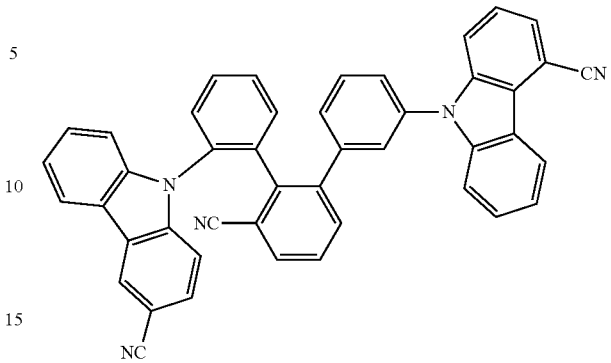
1814
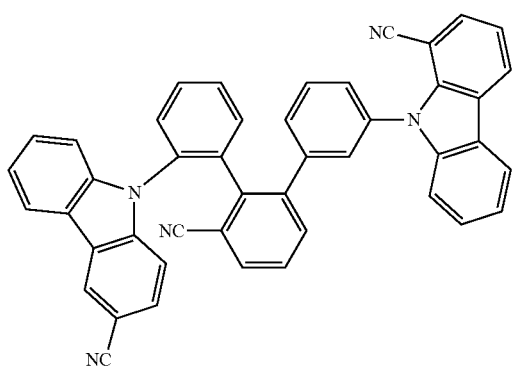
1818
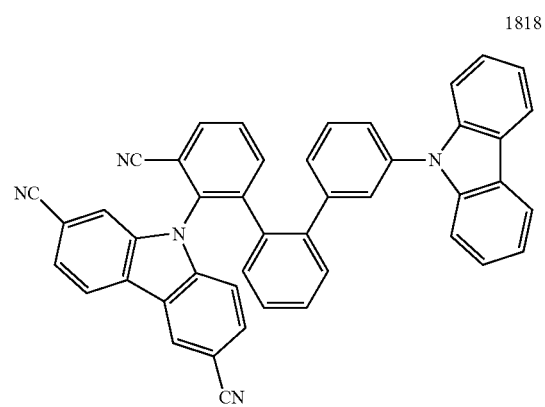
1815
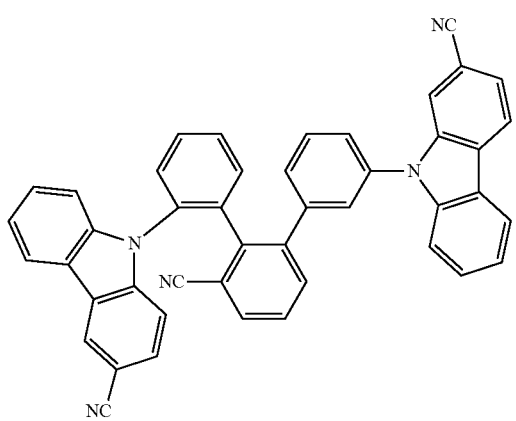
1819
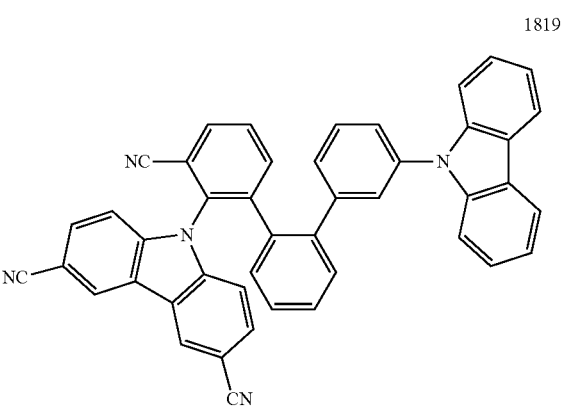
1816
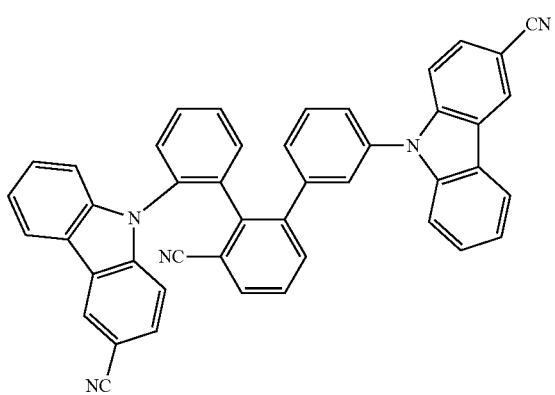
1820
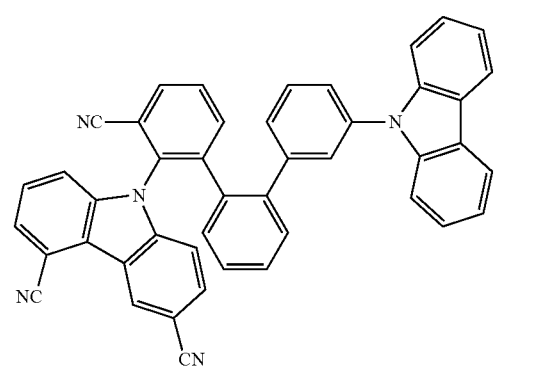

1821
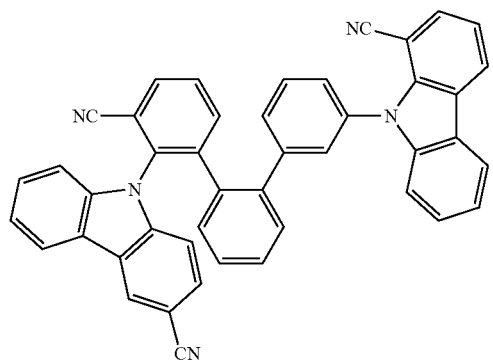
1822
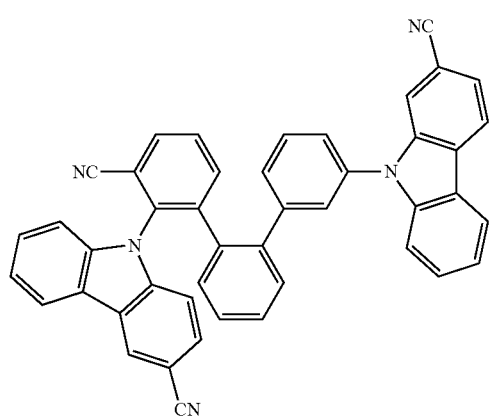
1823
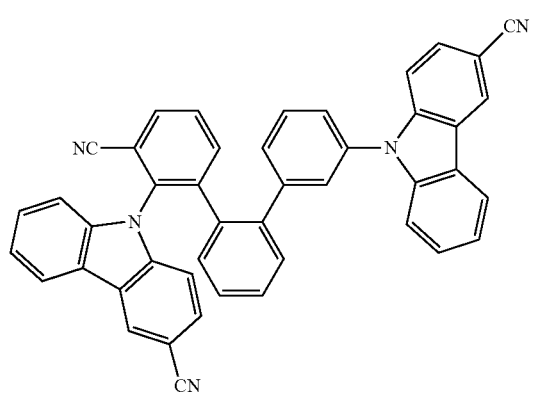
1824
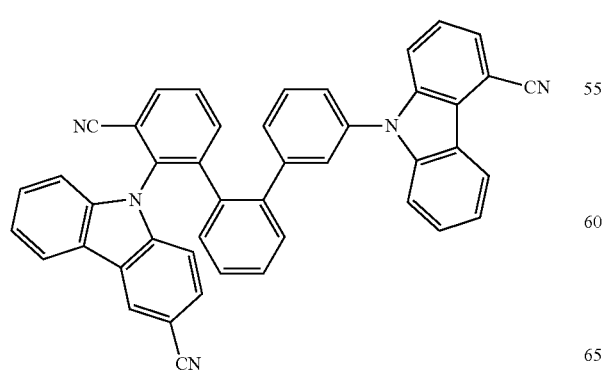
1825
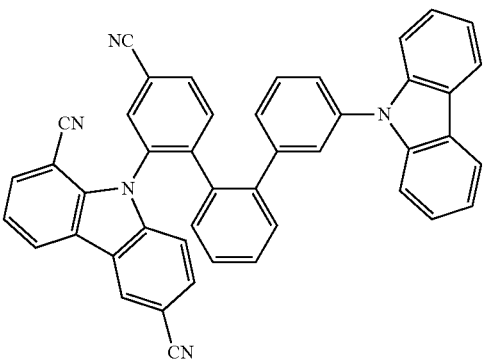
1826
1827
1828
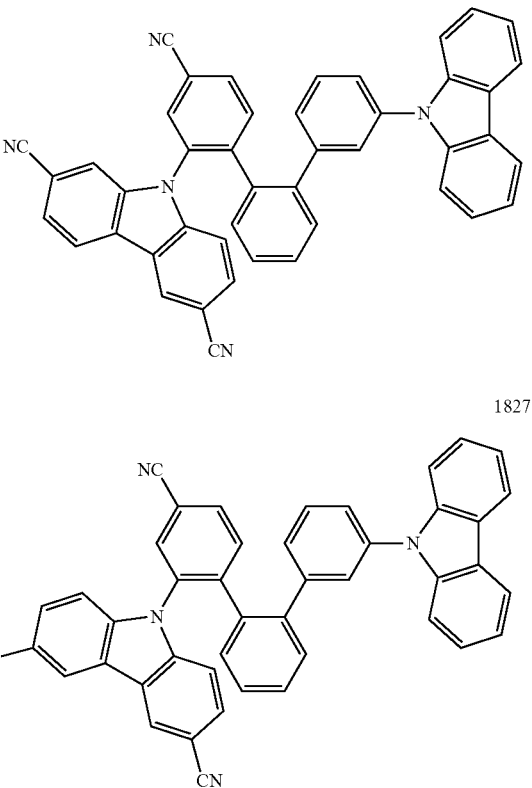
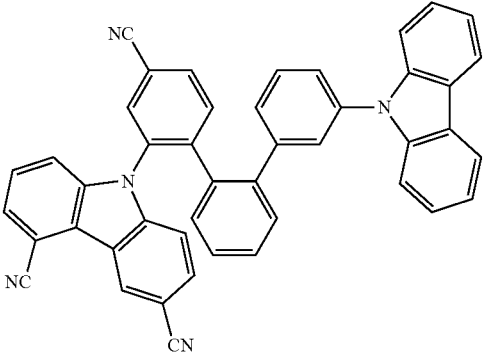

-continued
1829
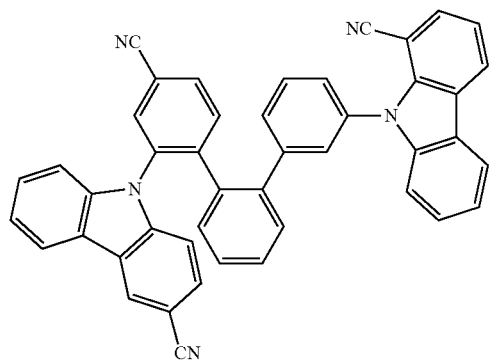
1830
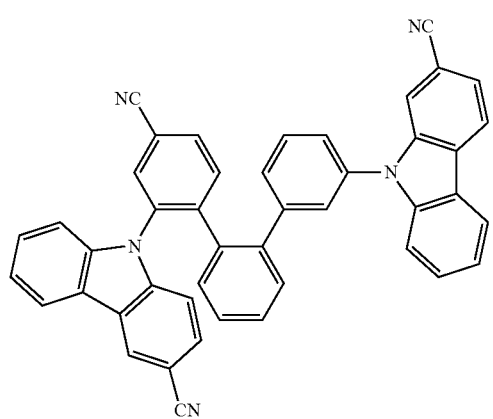
1831
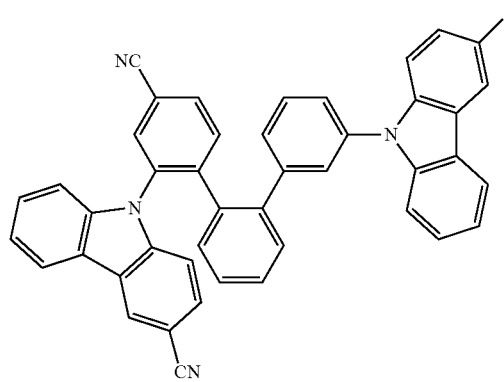
1832
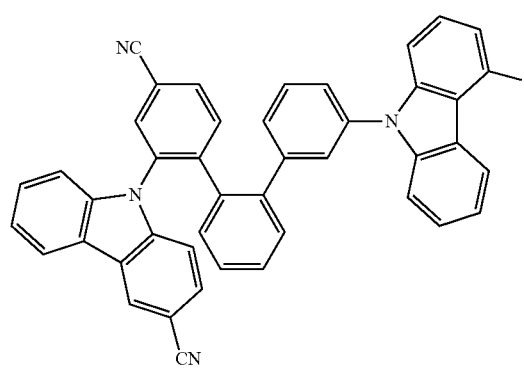
-continued
1833
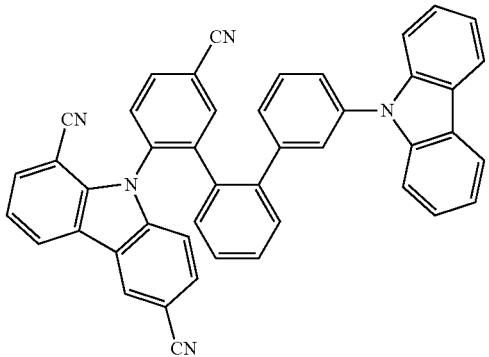
1834
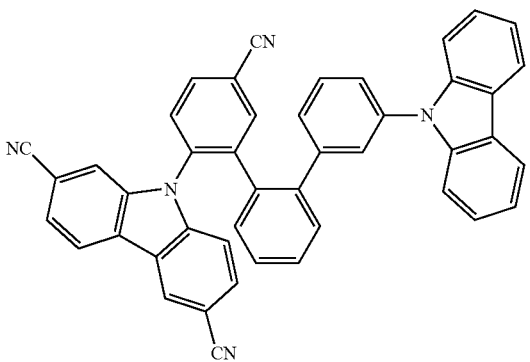
1835
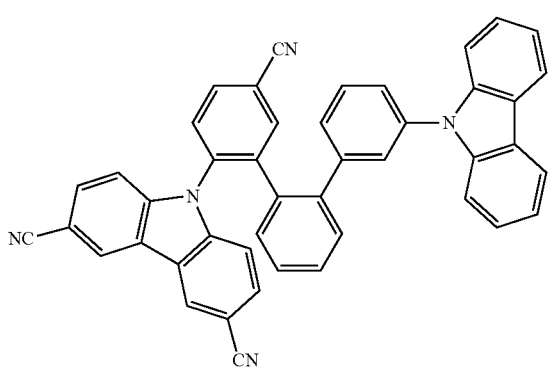
1836
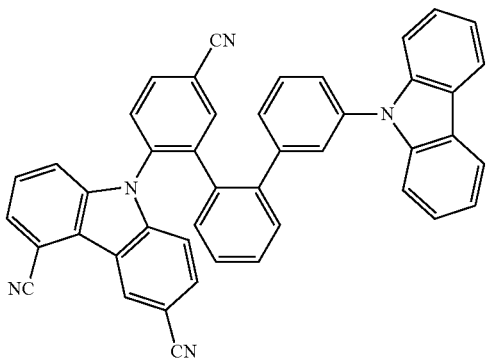

1837
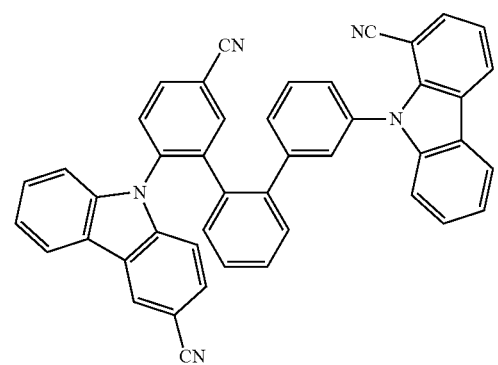
1838
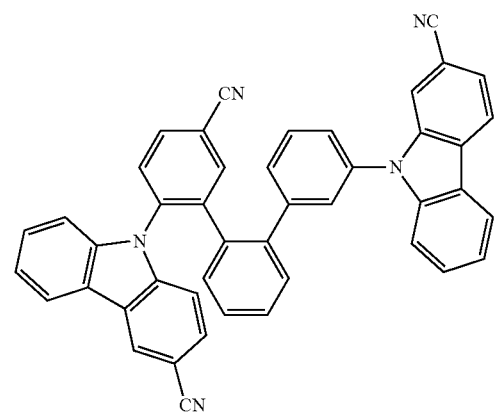
1839
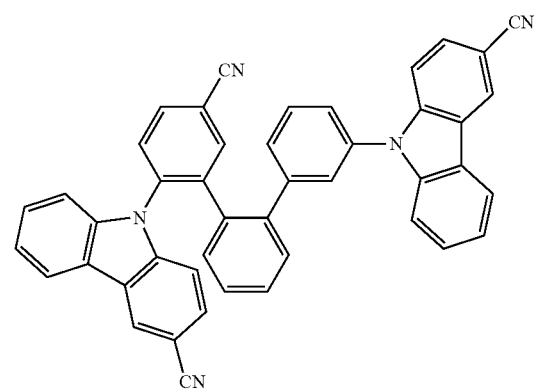
1840
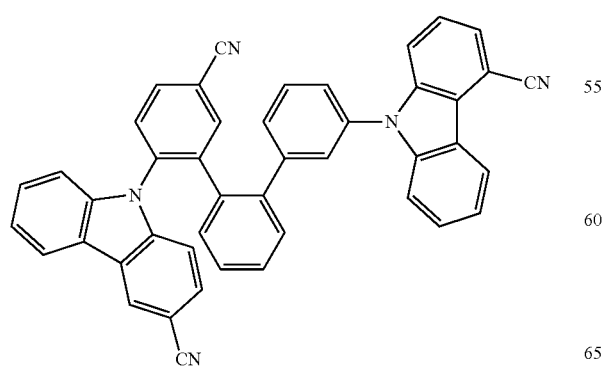
1841
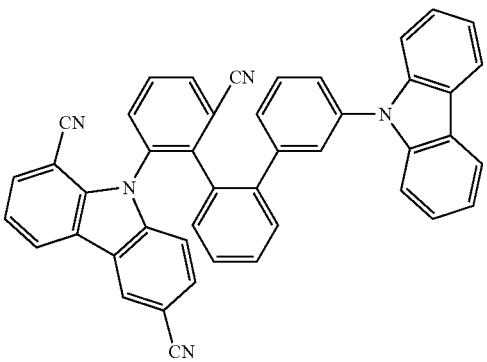
1842
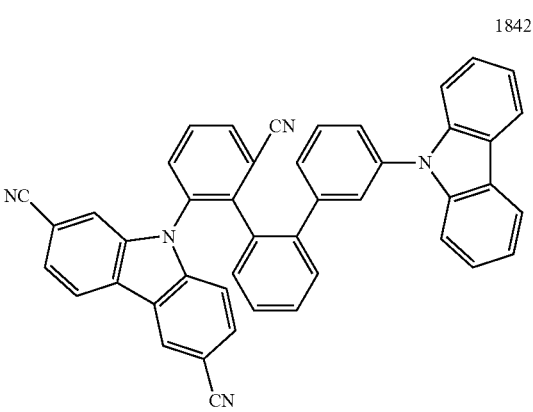
1843
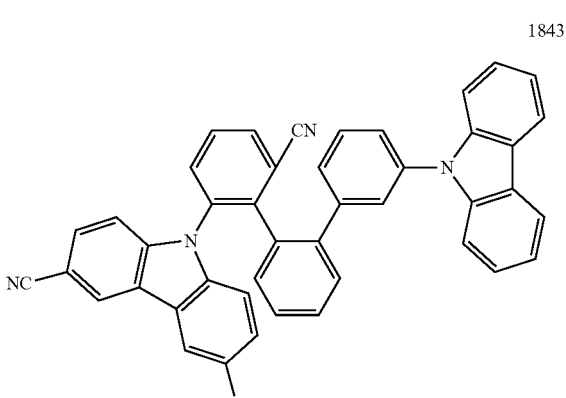
1844
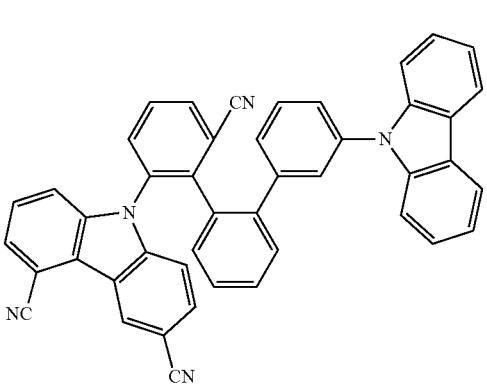

513
-continued
1845
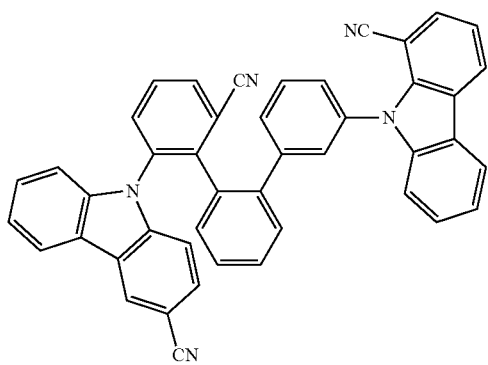
1846
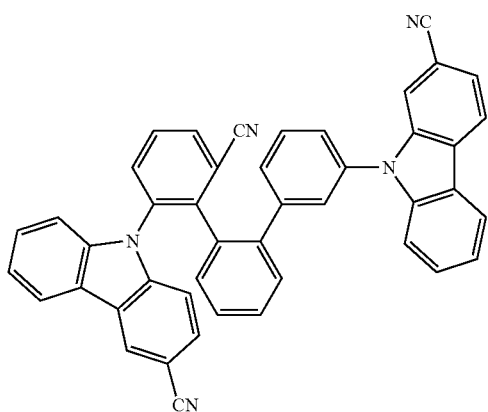
1847
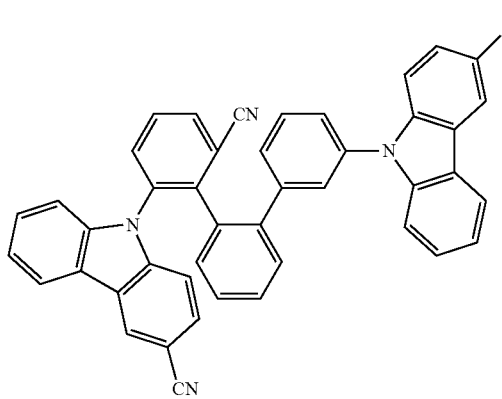
1848
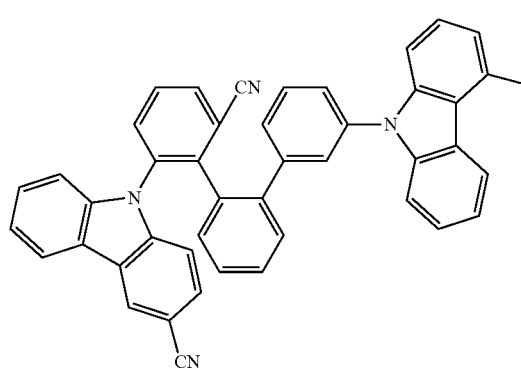
514
-continued
1849
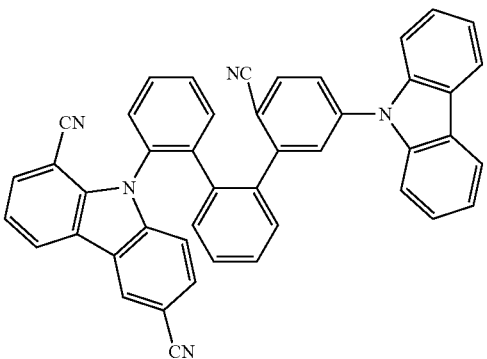
1850
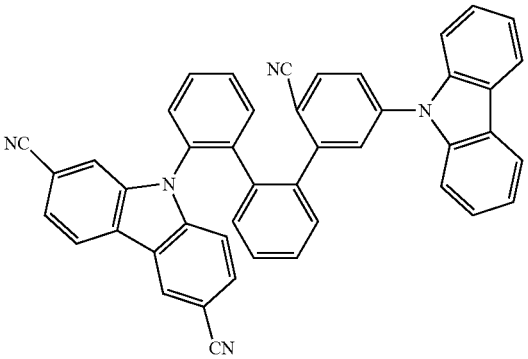
1851
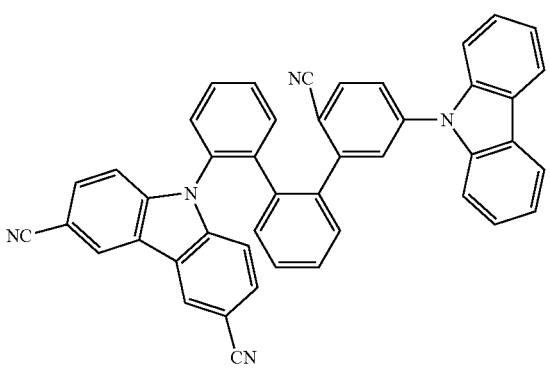
1852
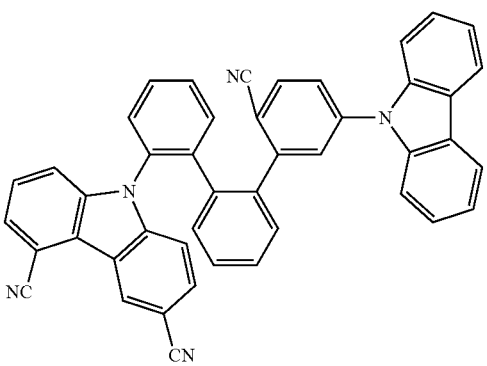

1853
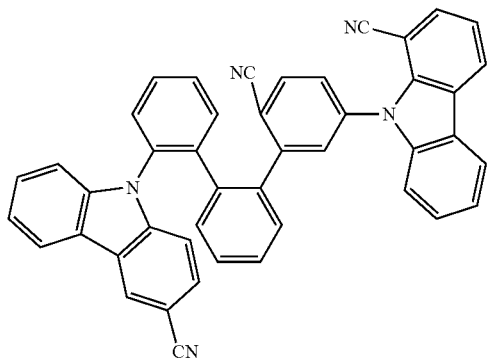
1854
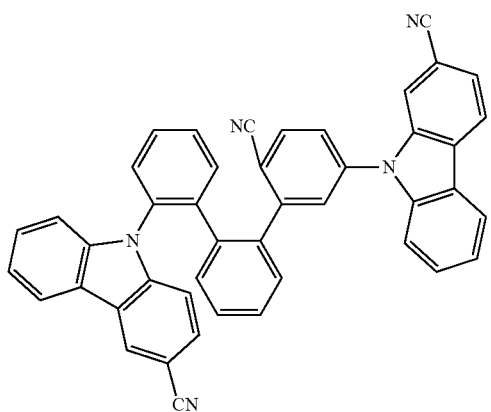
1855
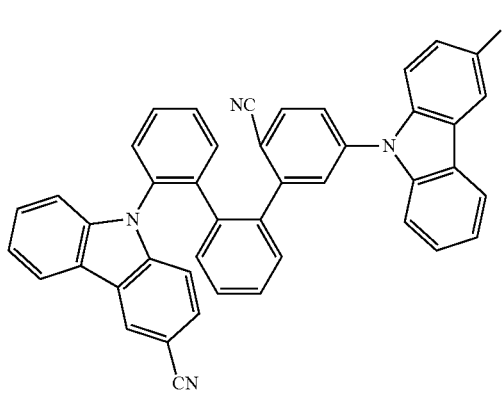
1856
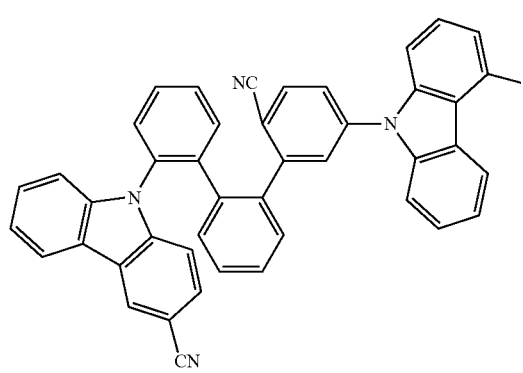
1857
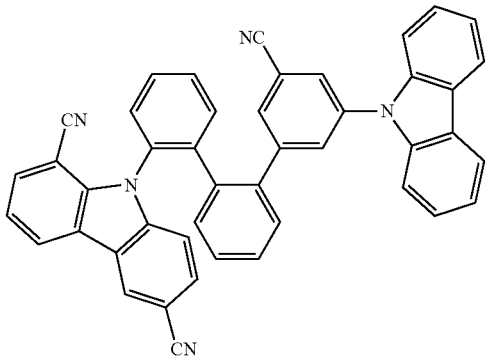
1858
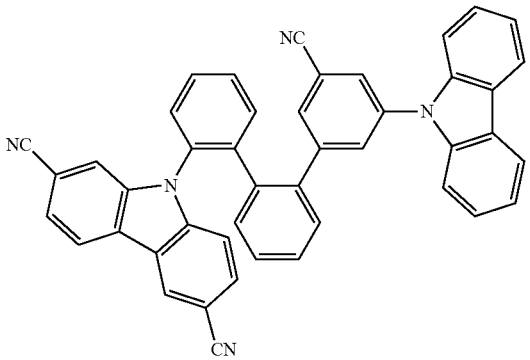
1859
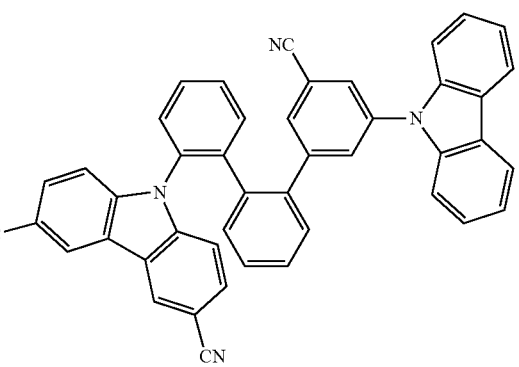
1860
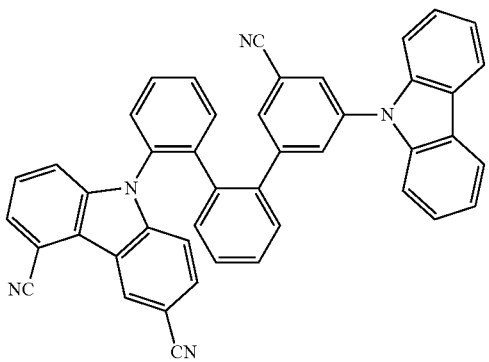

1861
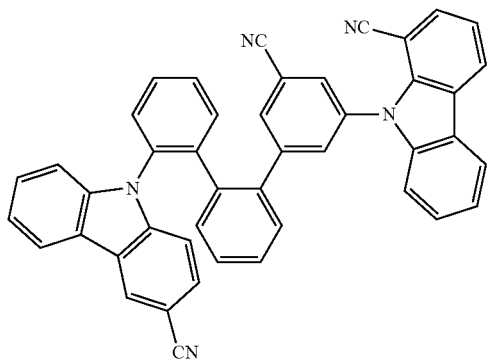
1862
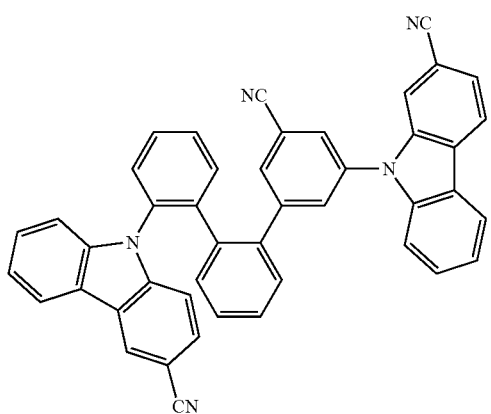
1863
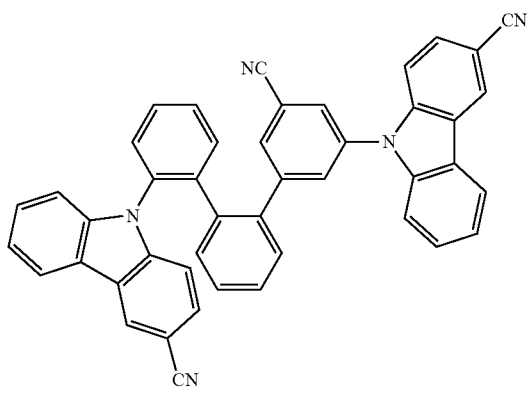
1864
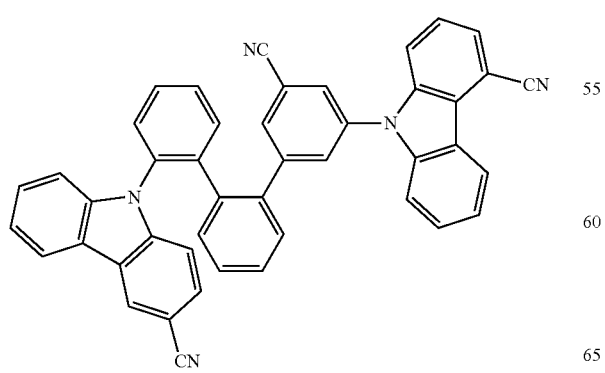
1865
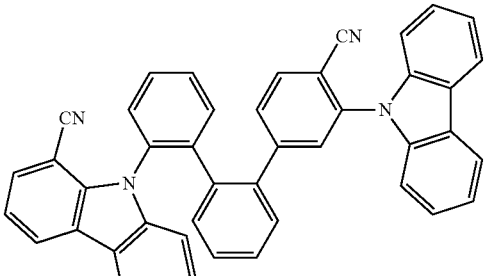
1866
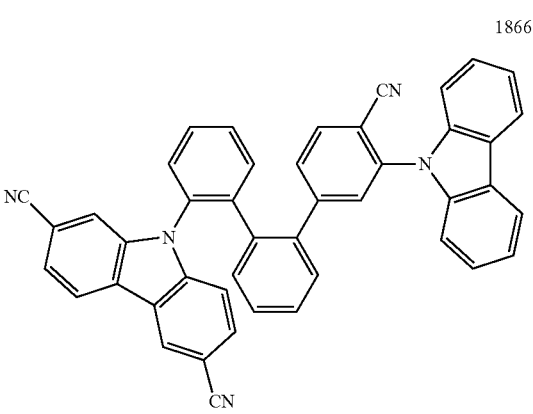
1867
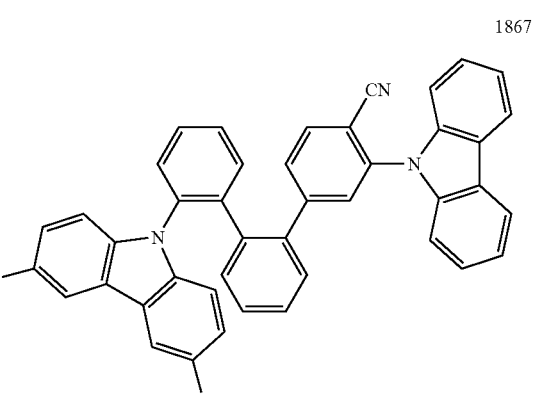
1868
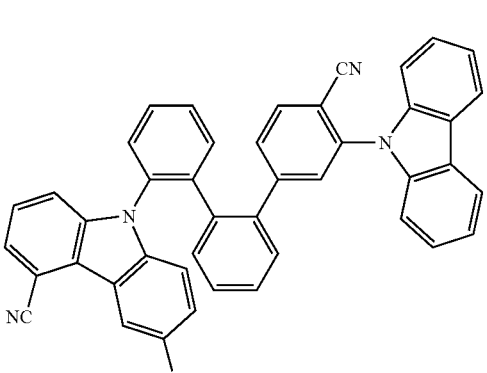

1869
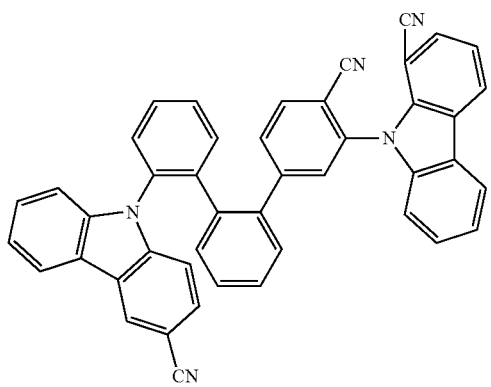
1870
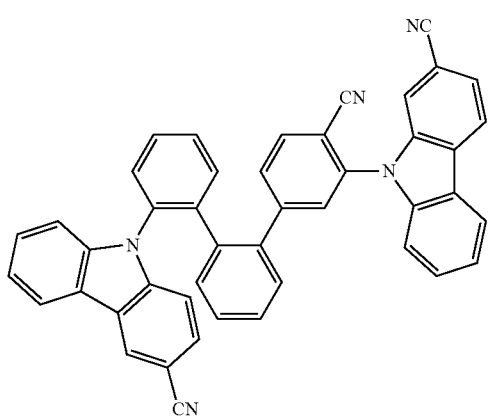
1871
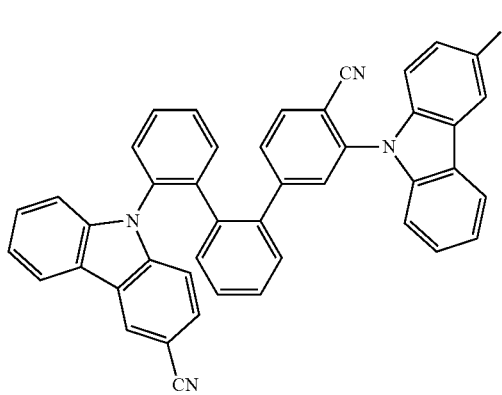
1872
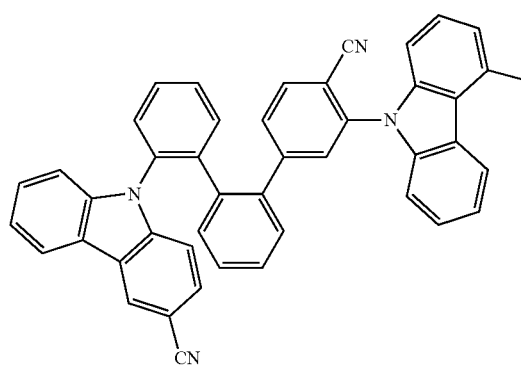
1873
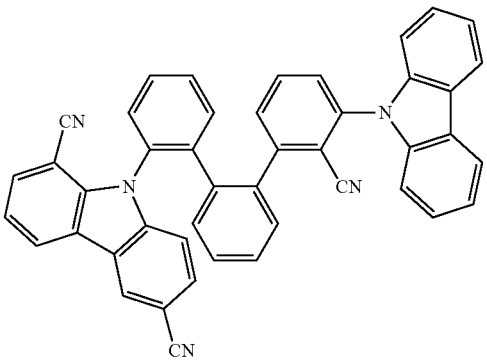
1874
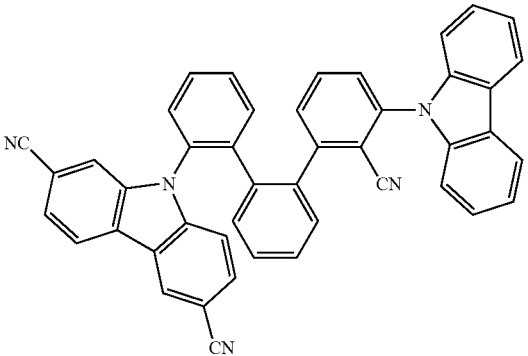
1875
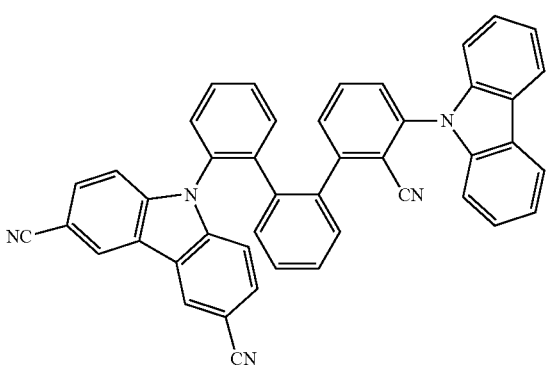
1876
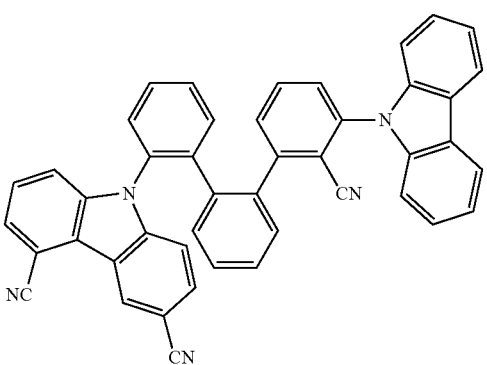

-continued
1877
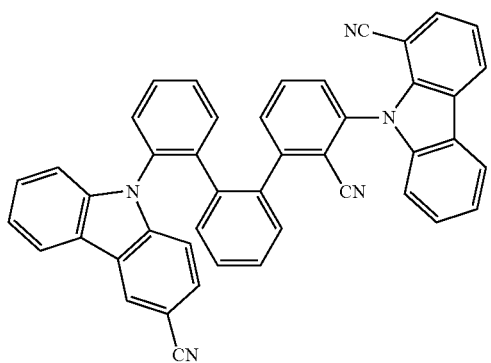
1878
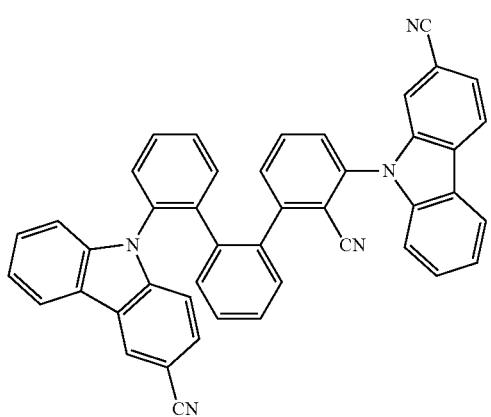
1879
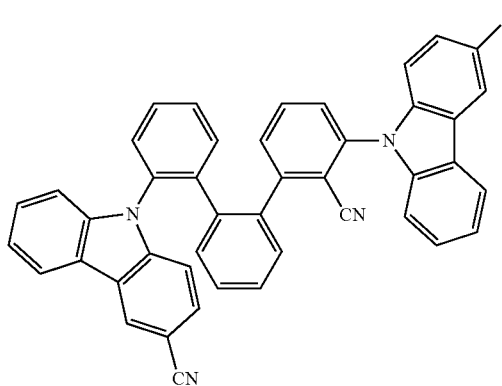
1880
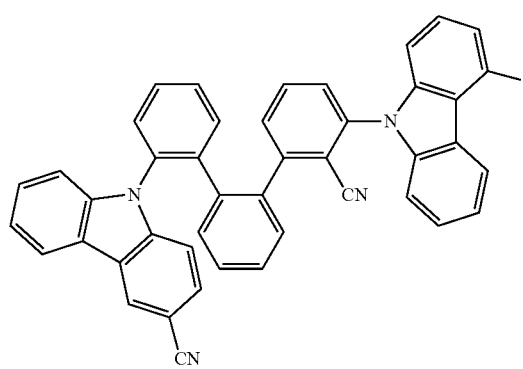
-continued
1881
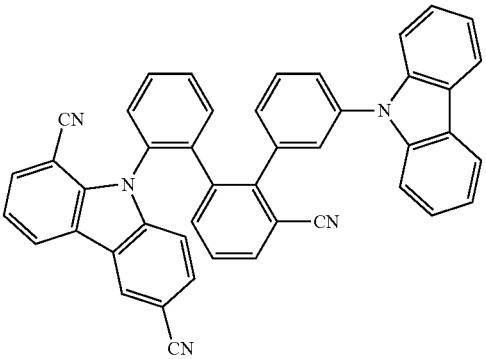
1882
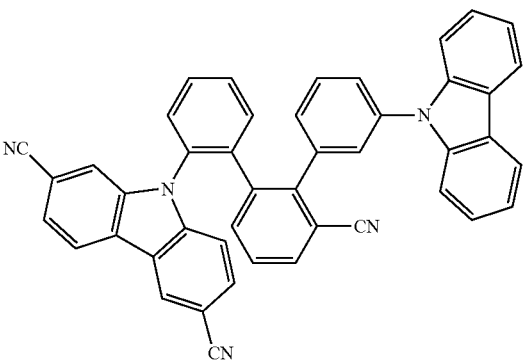
1883
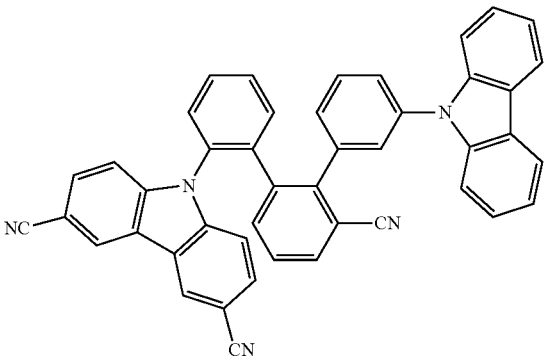
1884
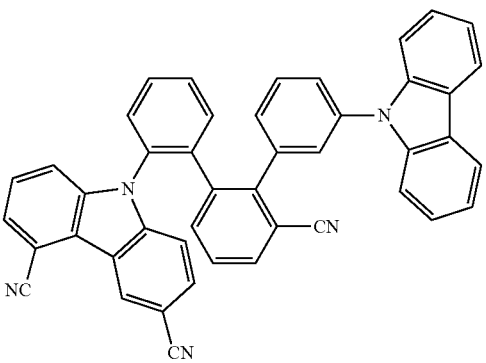

-continued
1885
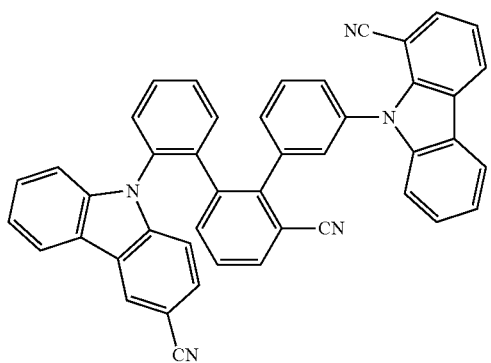
1886
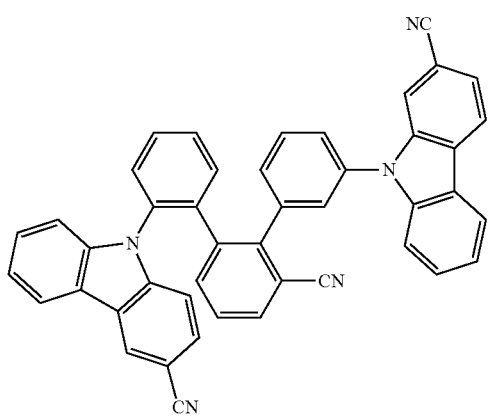
1887
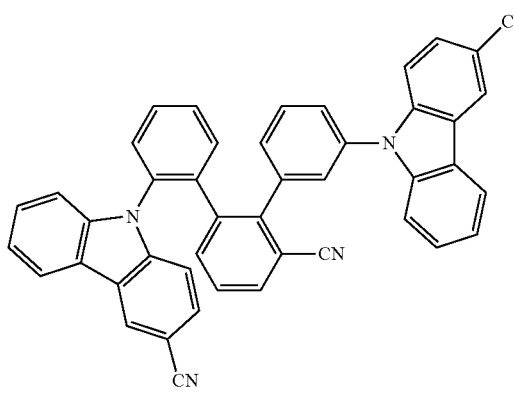
1888
-continued
1889
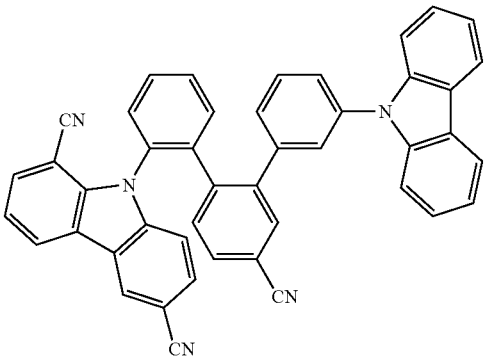
1890
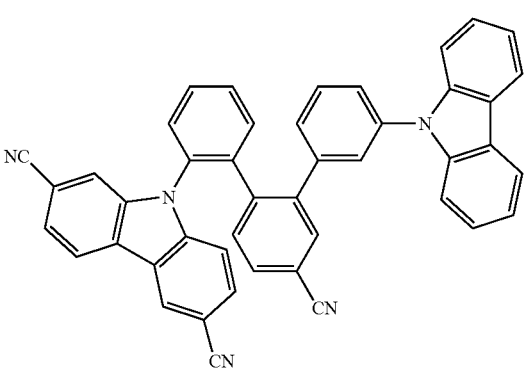
1891
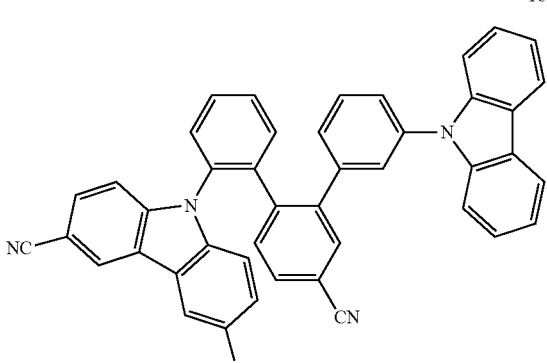
1892
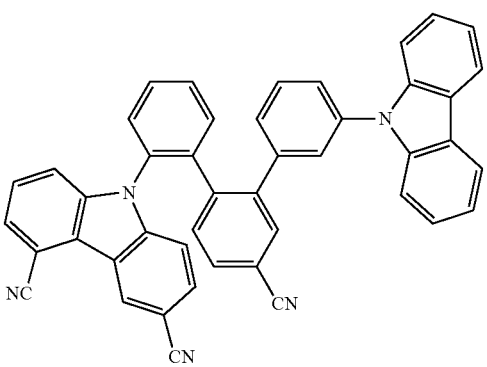

1893
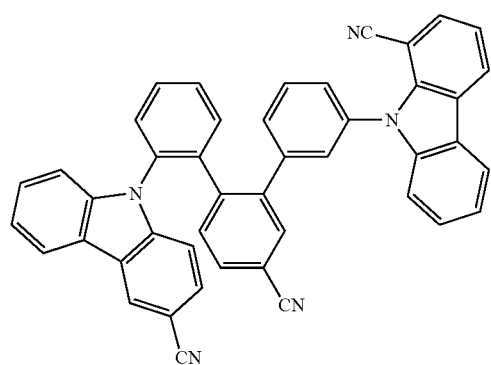
1894
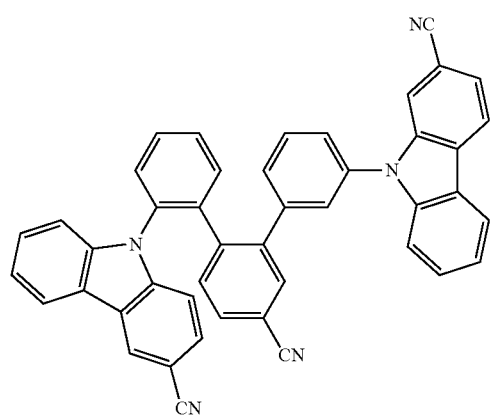
1895
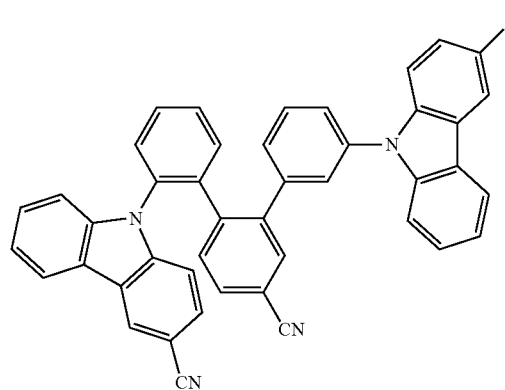
1896
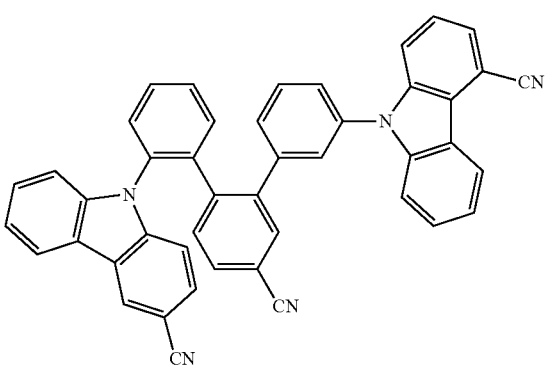
1897
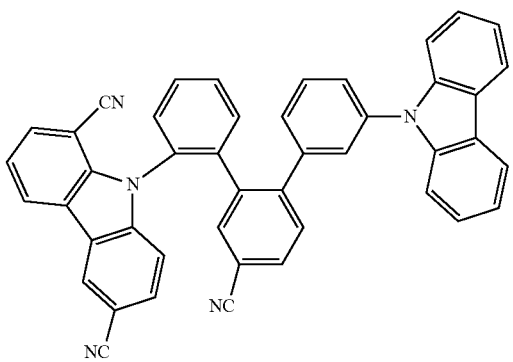
1898
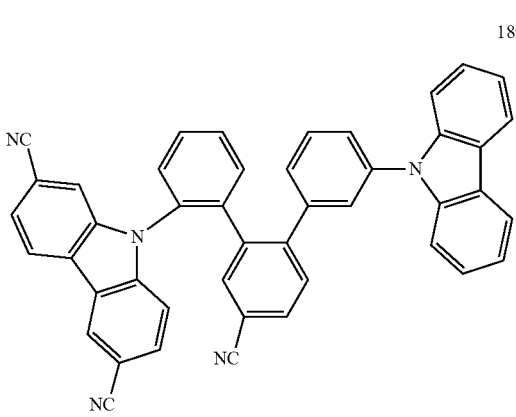
1899
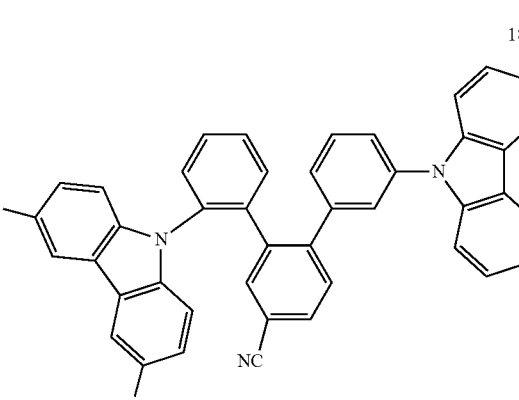
1900
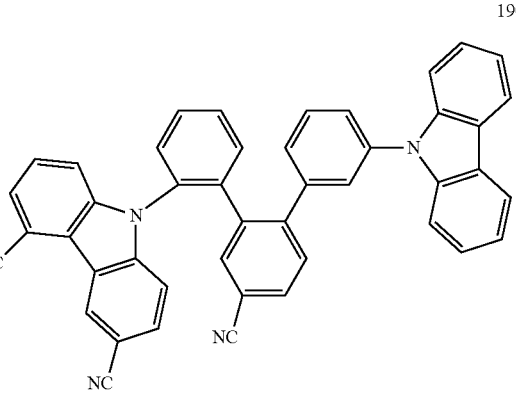

1901
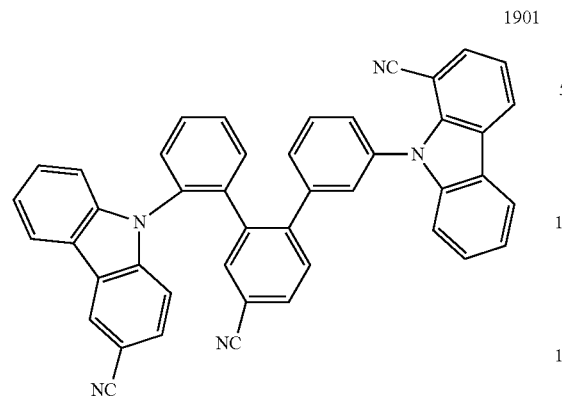
1902
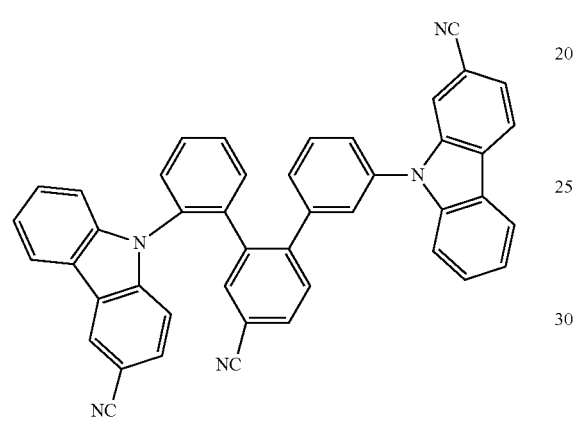
1903
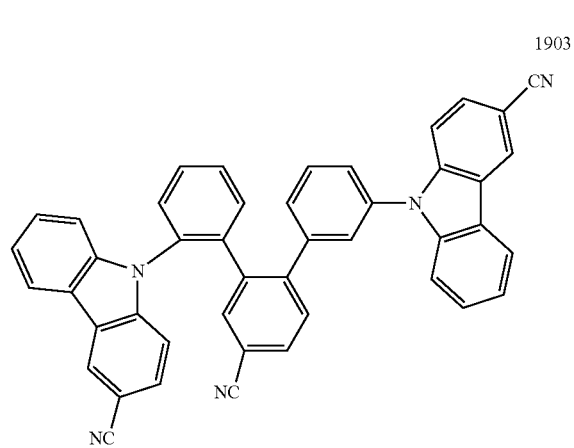
1904
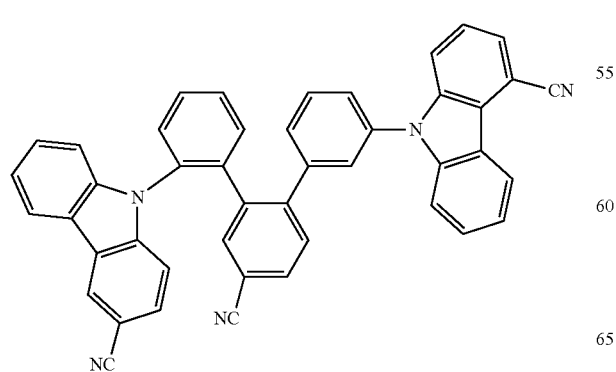
1905
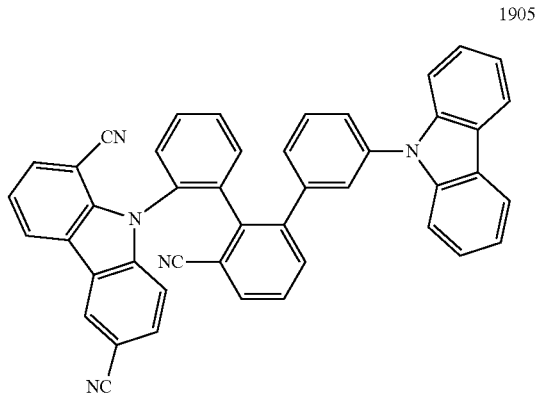
1906
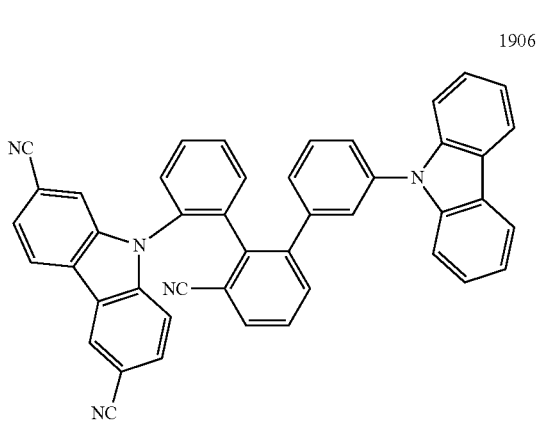
1907
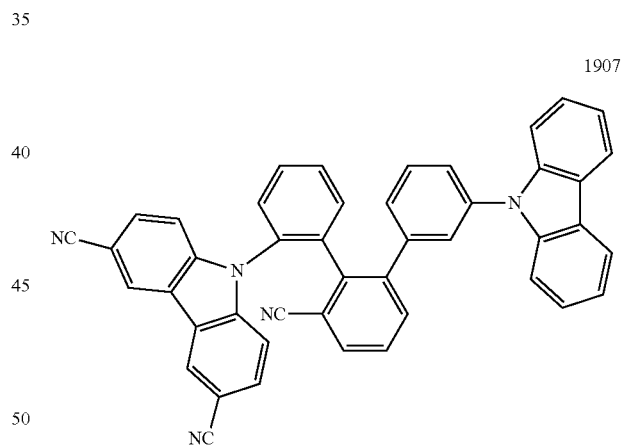
1908
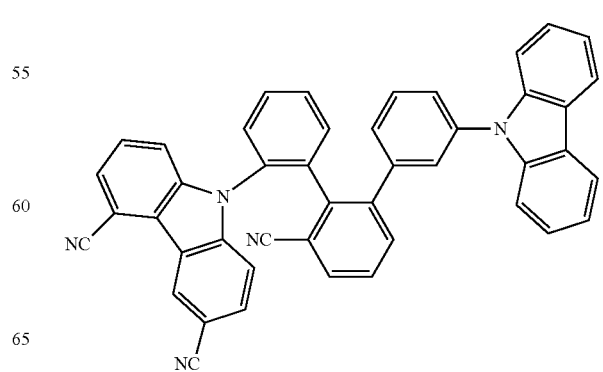

529
-continued
1909
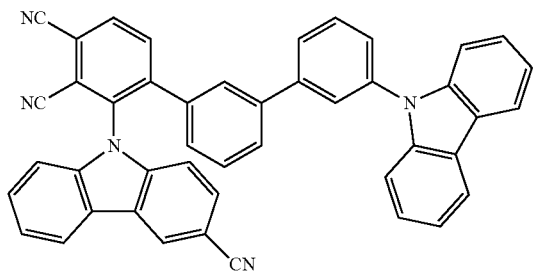
1910
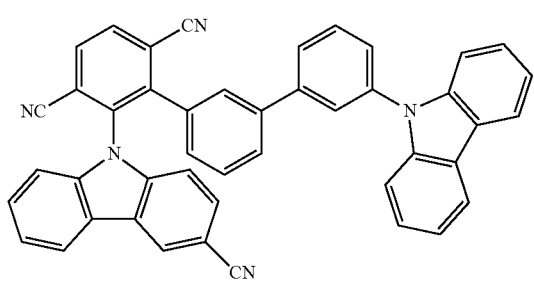
1911
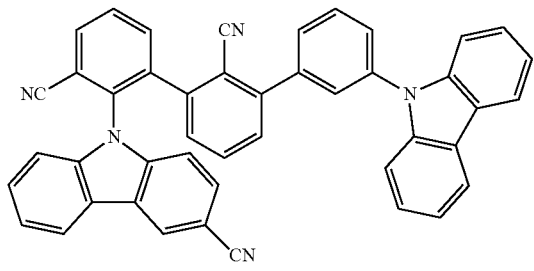
1912
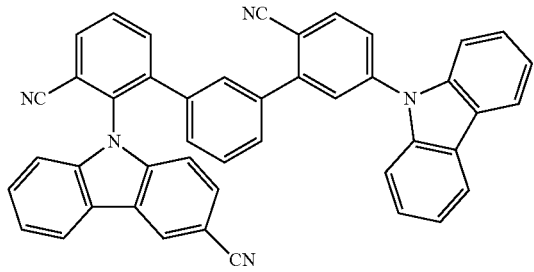
1913
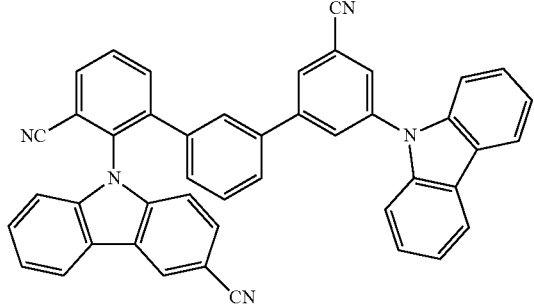
530
-continued
1914
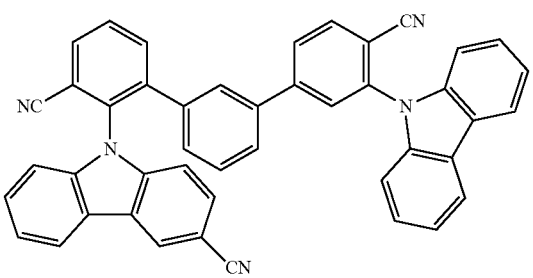
1915
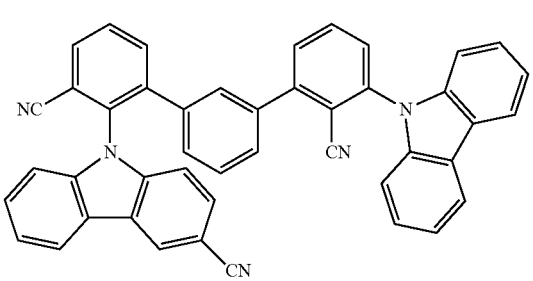
1916
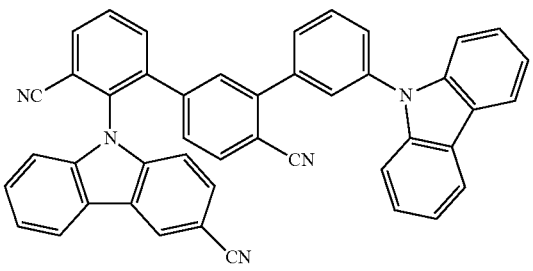
1917
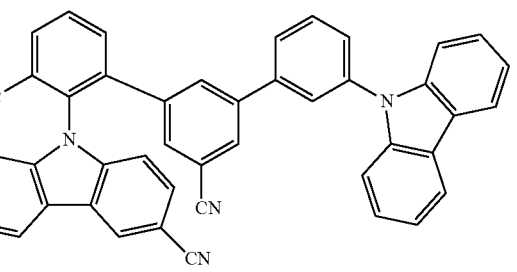
1918
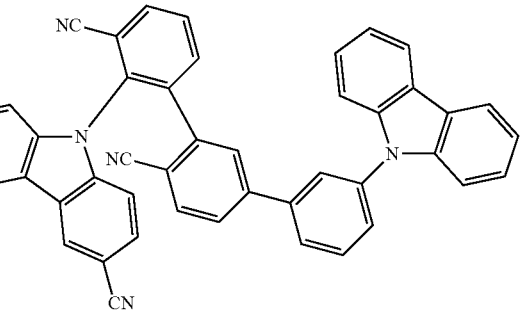

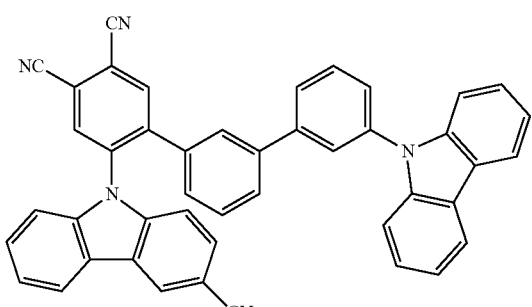
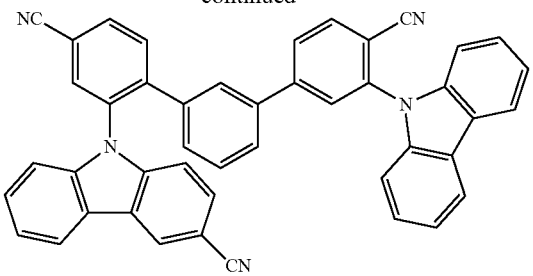
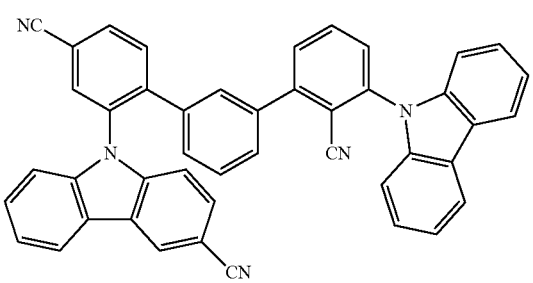
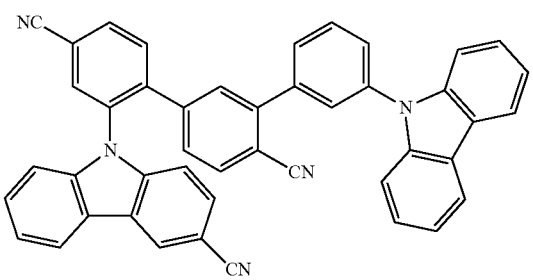
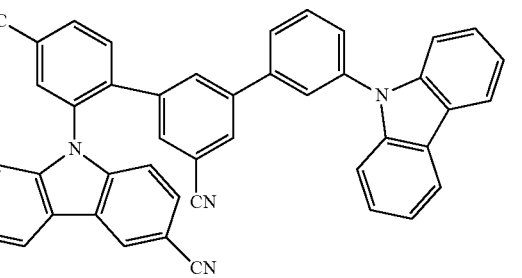
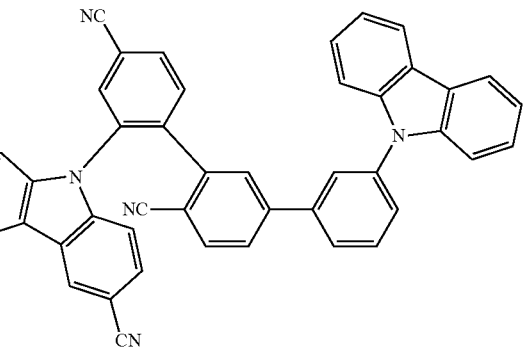

533
-continued
1929
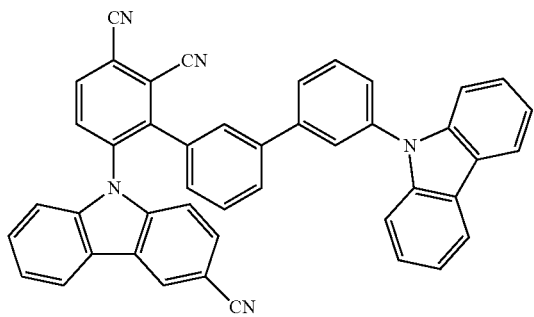
1930
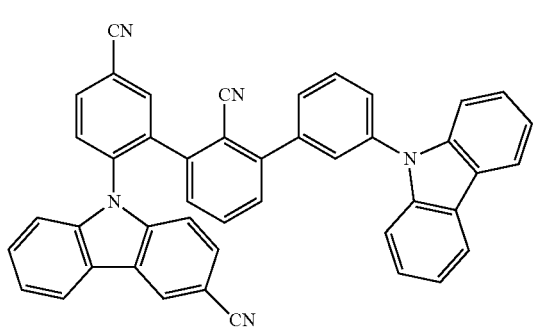
1931
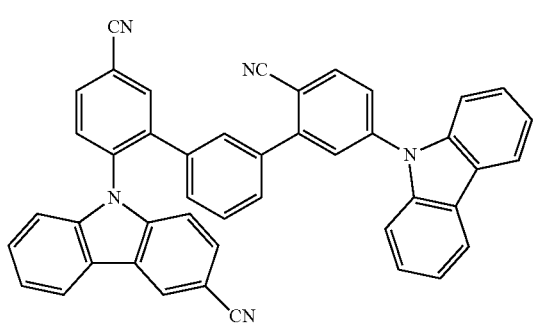
1932
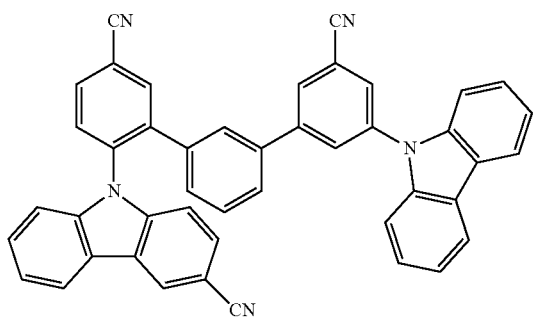
534
-continued
1933
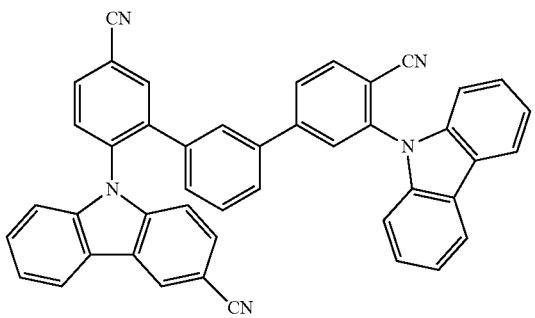
1934
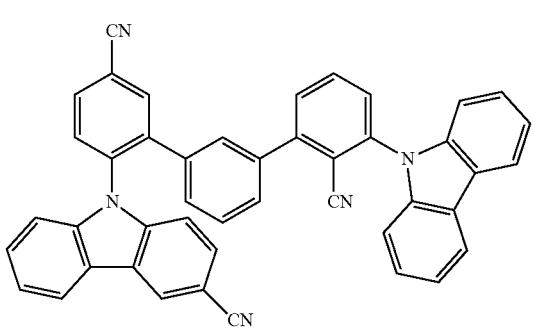
1935
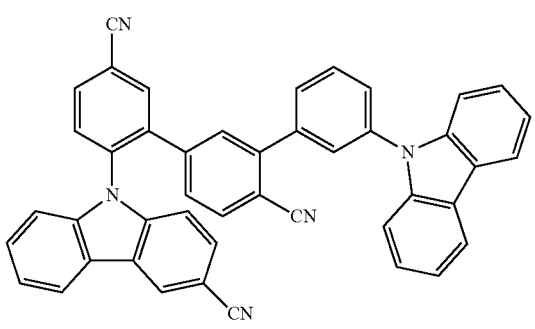
1936
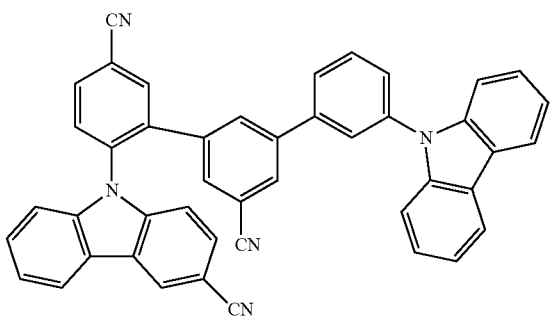

535
-continued
1937
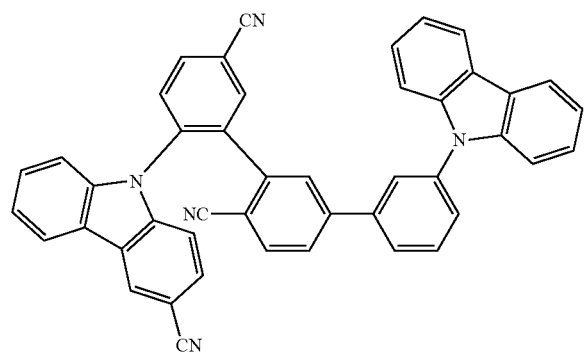
1938
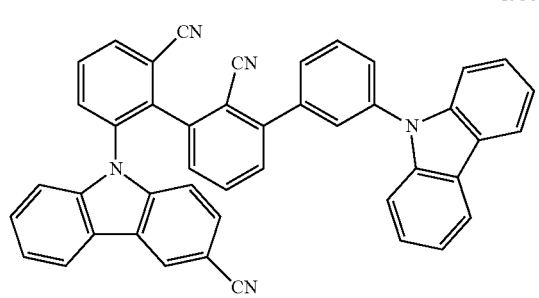
1939
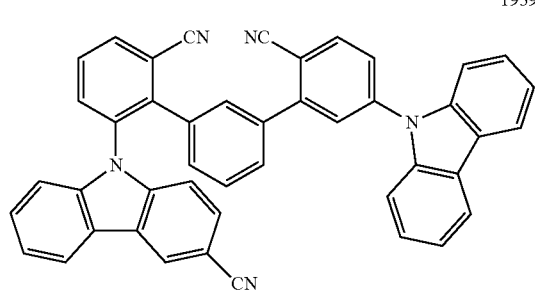
1940
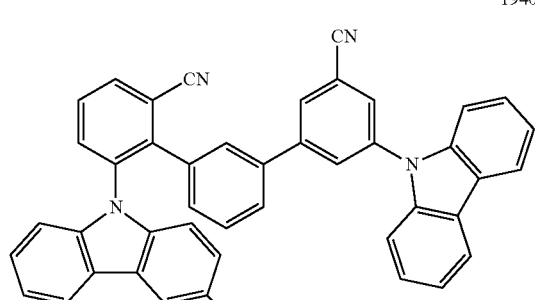
1941
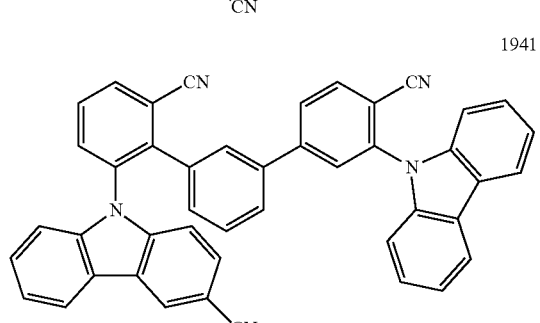
536
-continued
1942
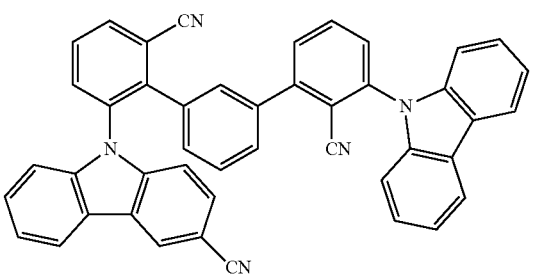
1943
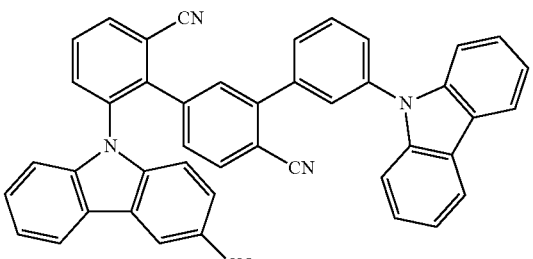
1944
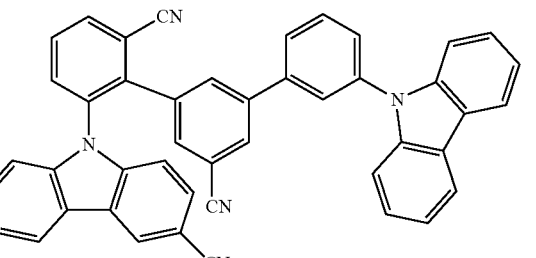
1945
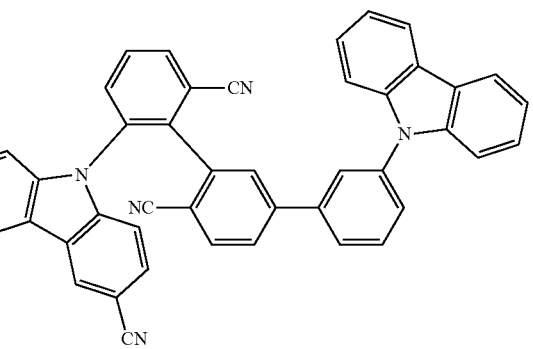
1946
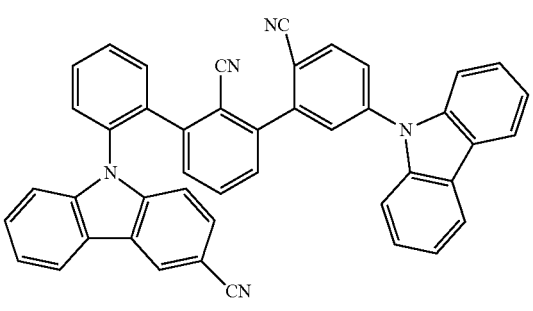

537
-continued
1947
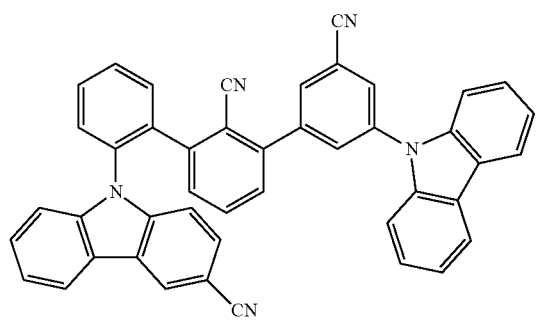
1948
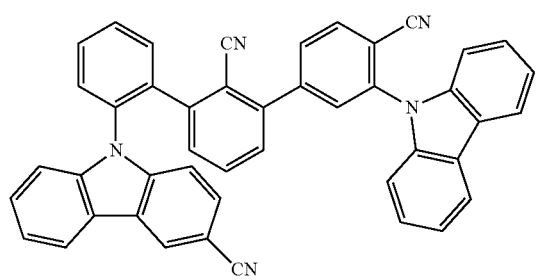
1949
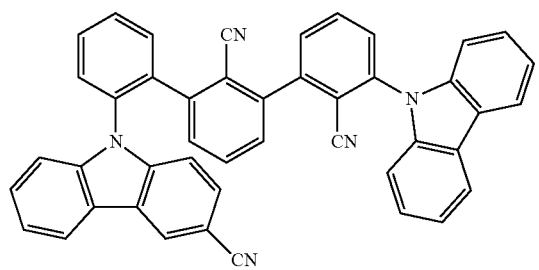
1950
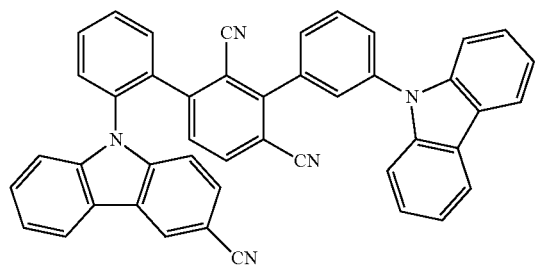
1951
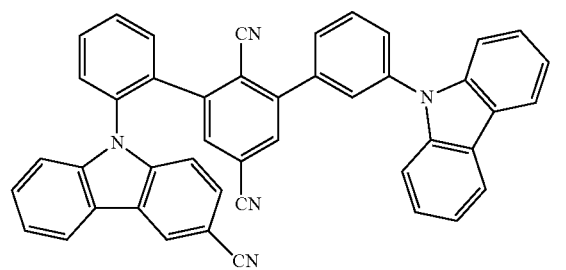
538
-continued
1952
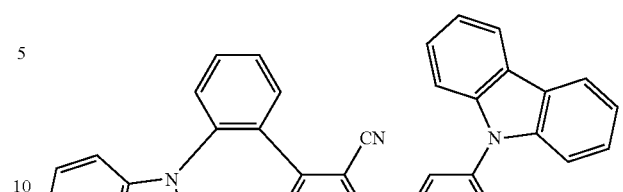
1953
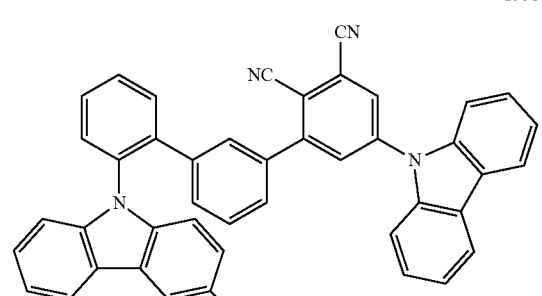
1954
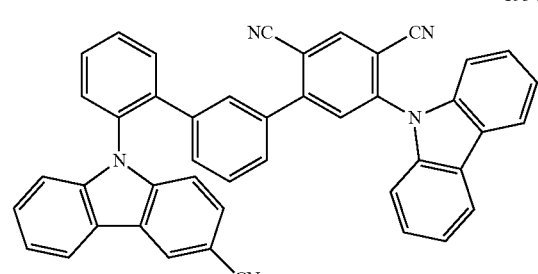
1955
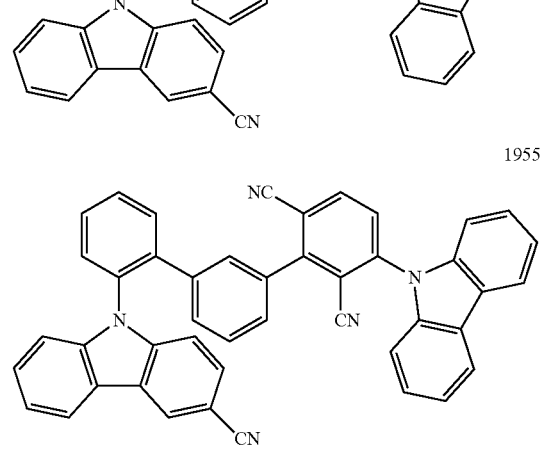
1956
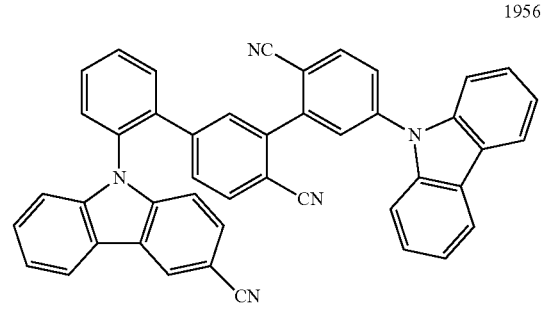

1957
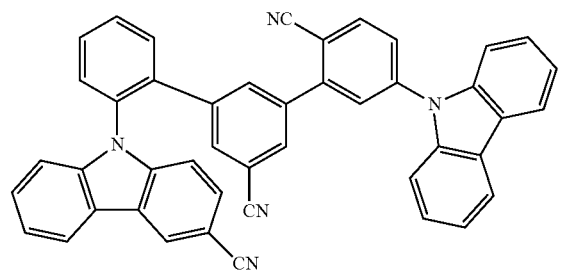
1958
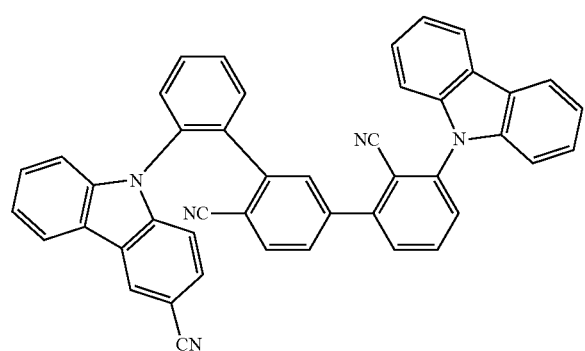
1959
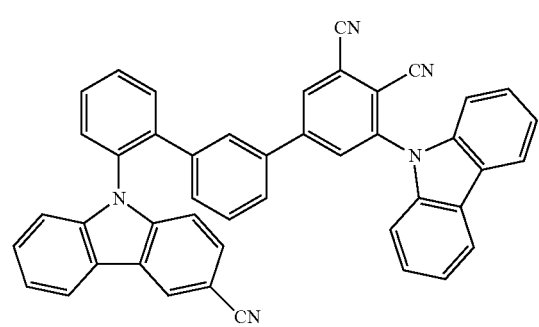
1960
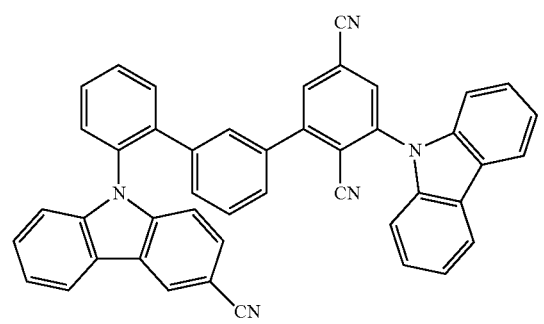
1961
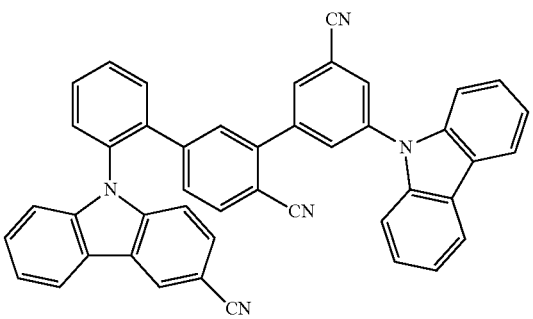
1962
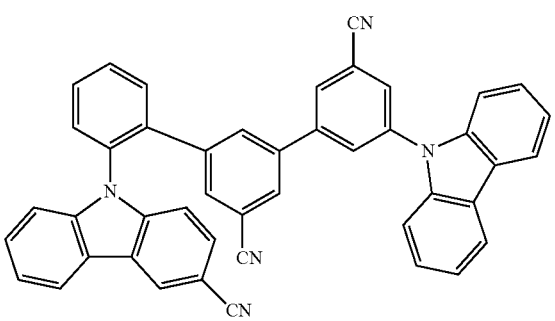
1963
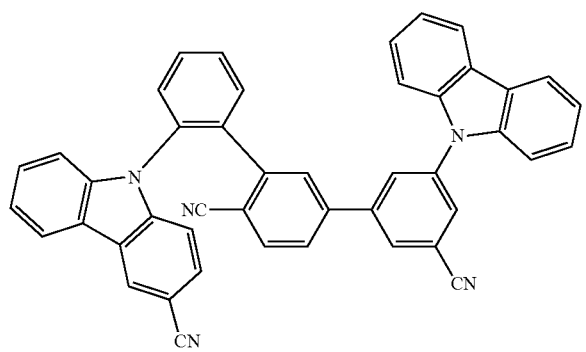
1964
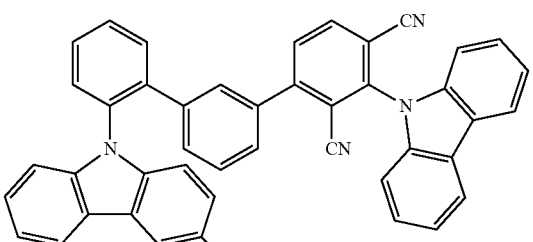
1965
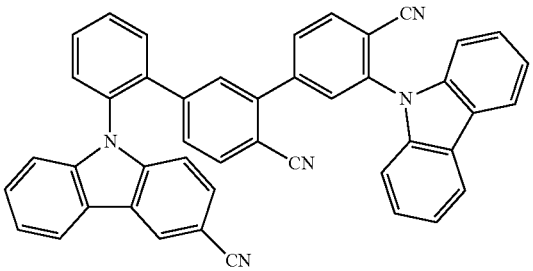

541
-continued
1966
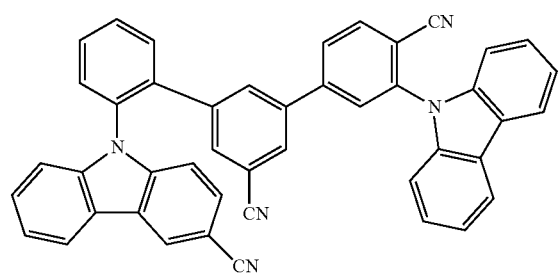
1967
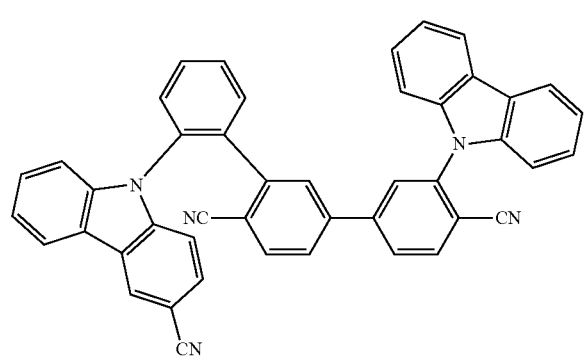
1968
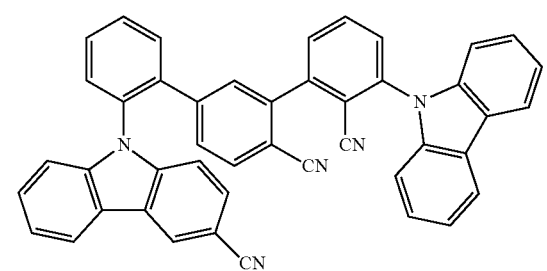
1969
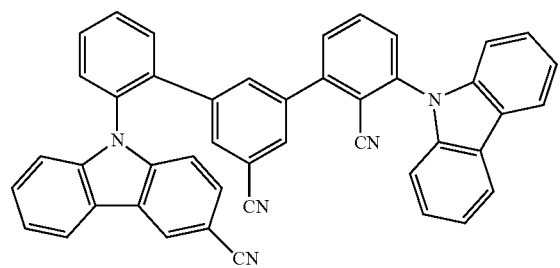
1970
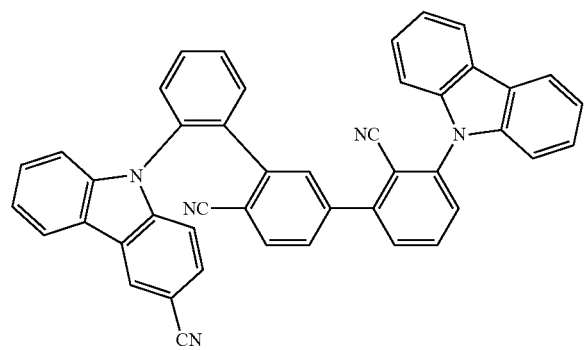
542
-continued
1971
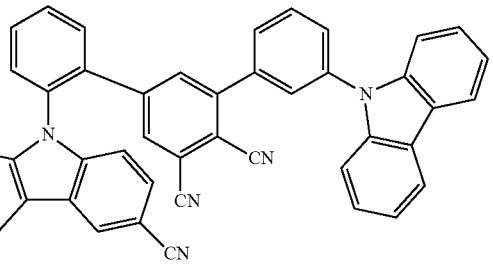
1972
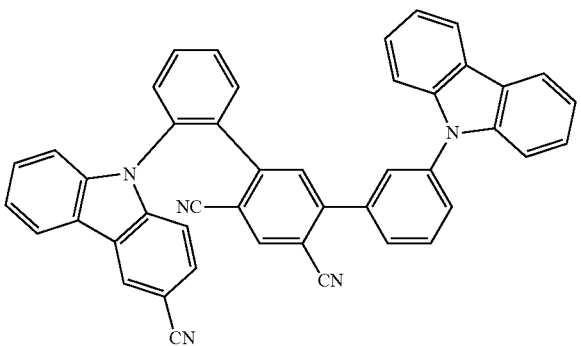
1973
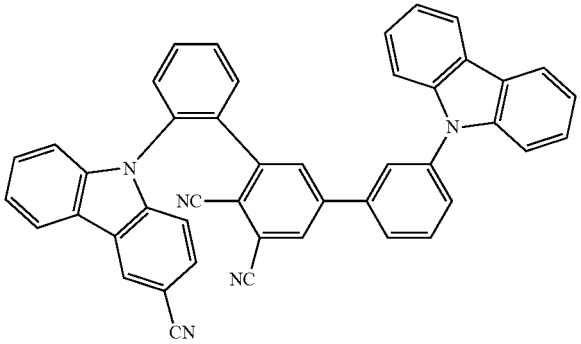
1974
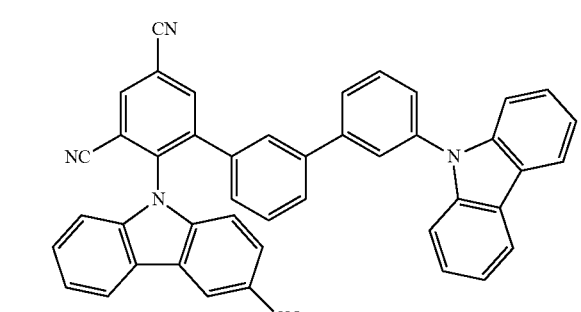
1975
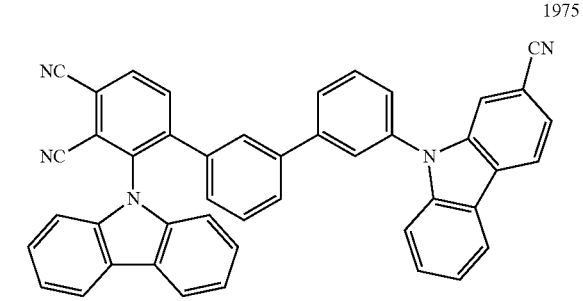

1976
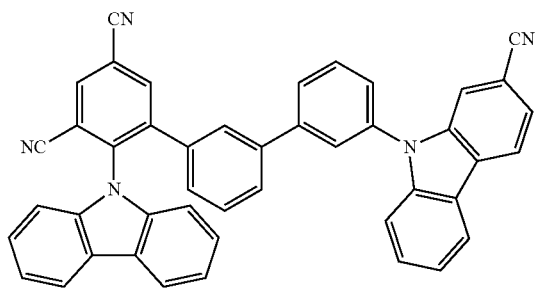
1977
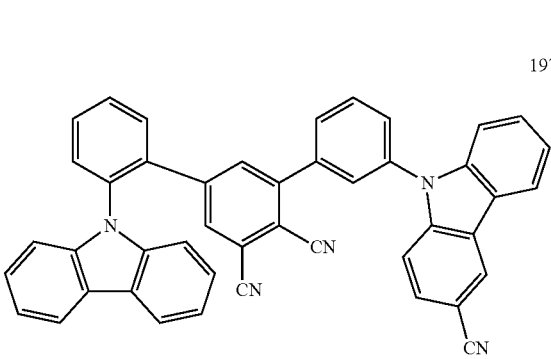
1978
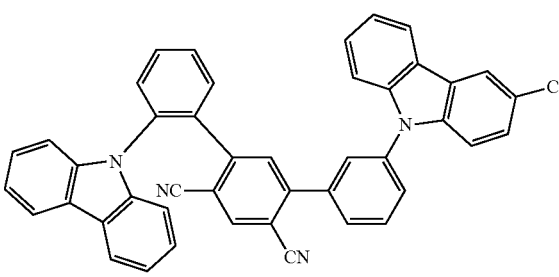
1979
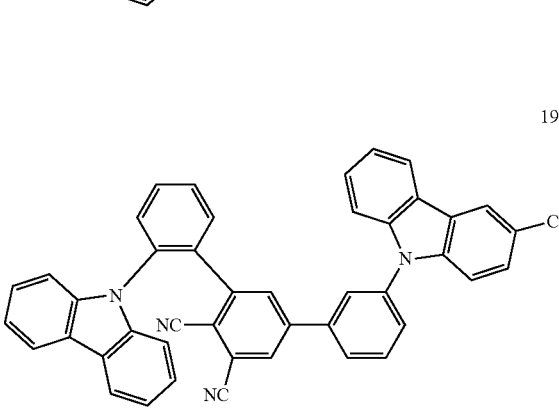
1980
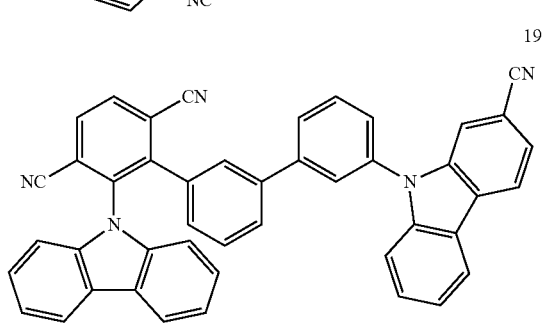
1981
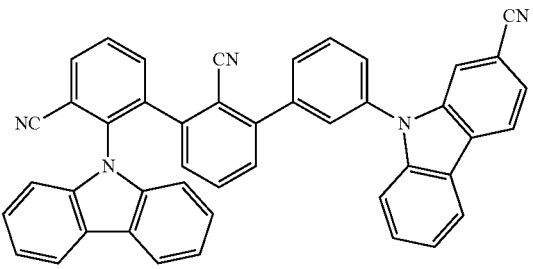
1982
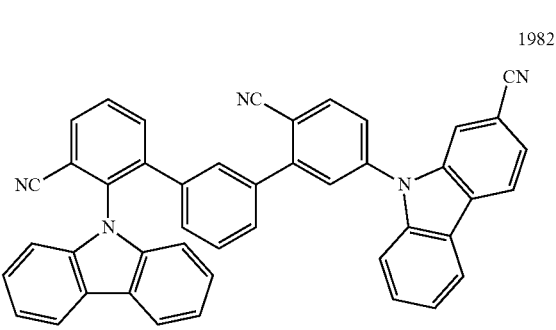
1983
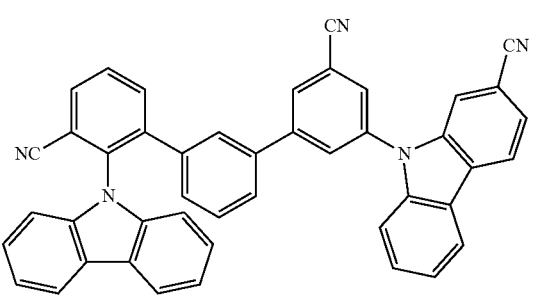
1984
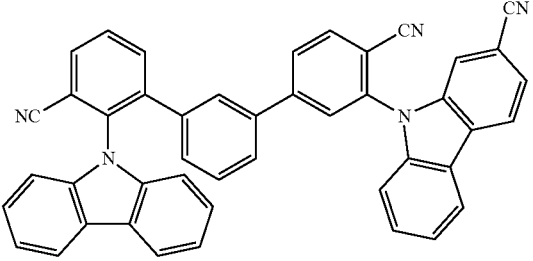
1985
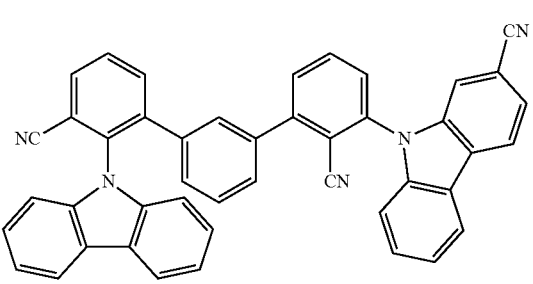

1986
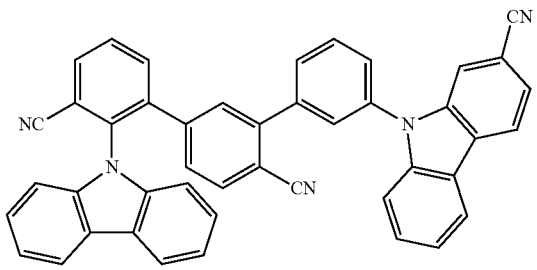
1987
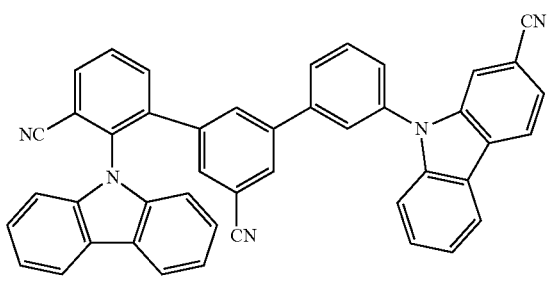
1988
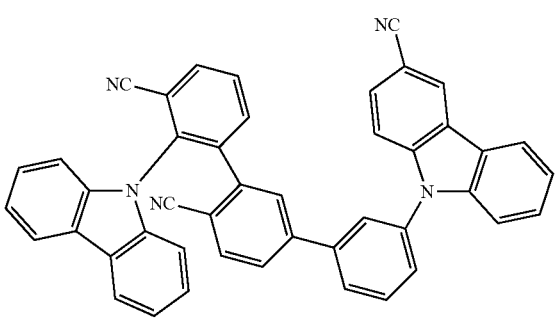
1989
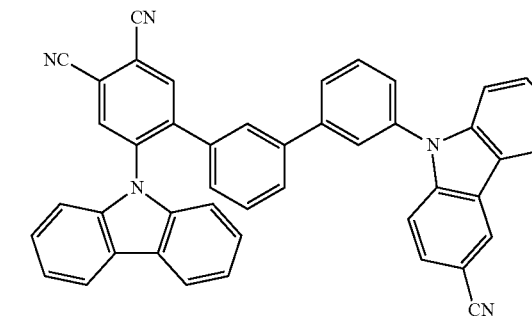
1990
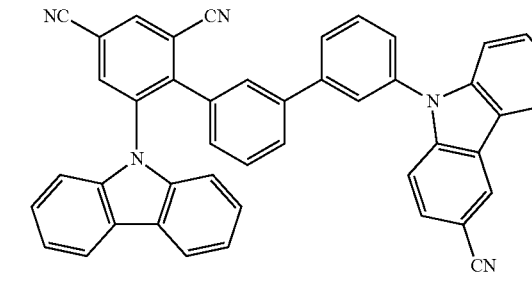
1991
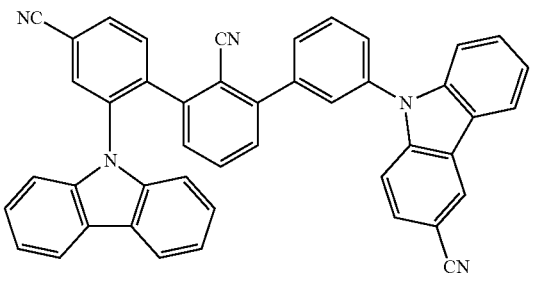
1992
1993
1994
1995

547
-continued
1996
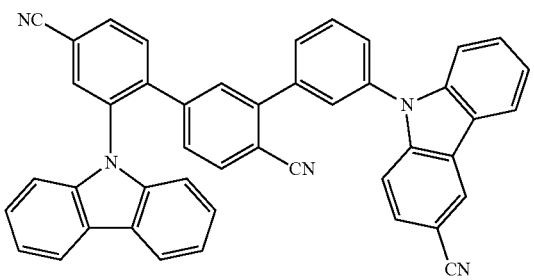
1997
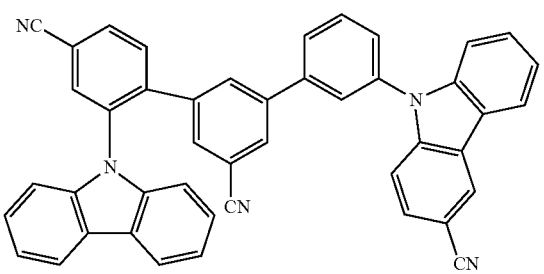
1998
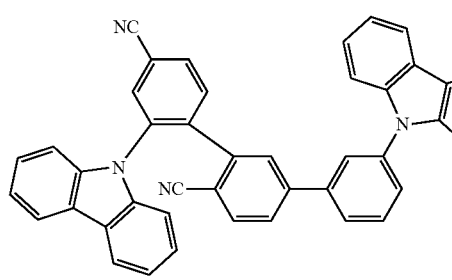
1999
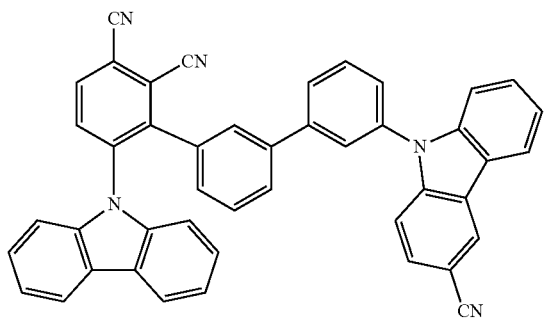
2000
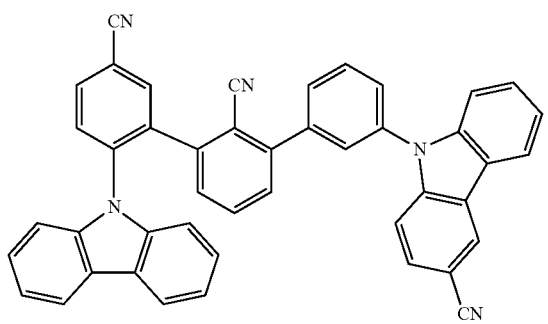
548
-continued
2001
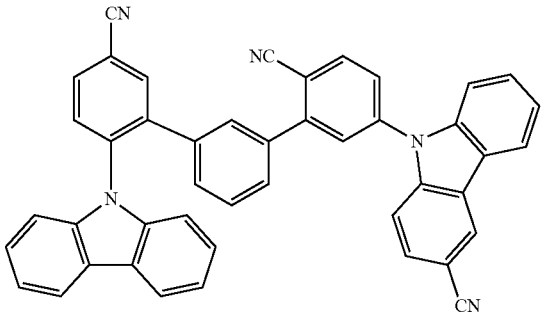
2002
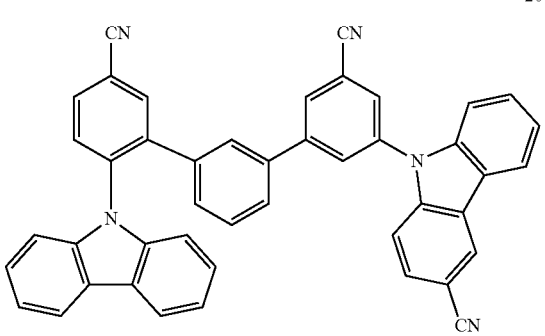
2003
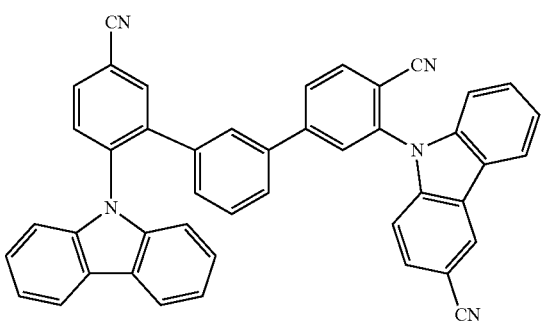
2004
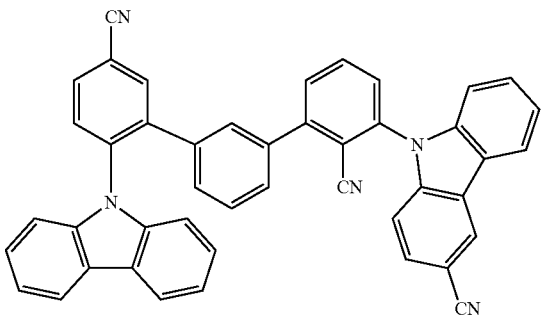

549
-continued
2005
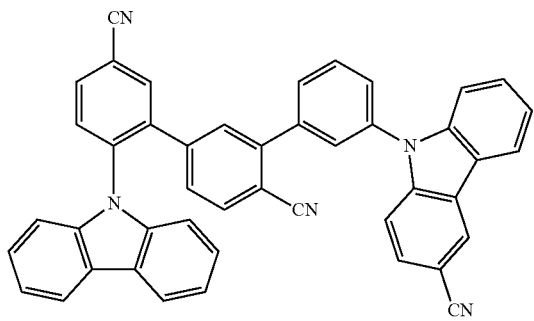
2006
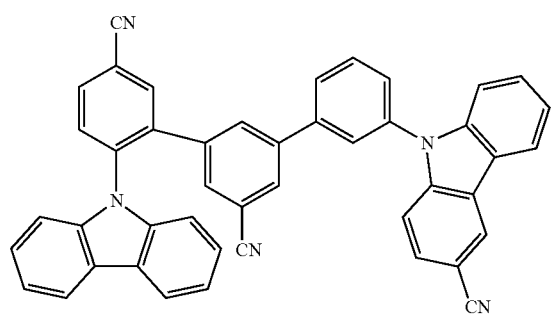
2007
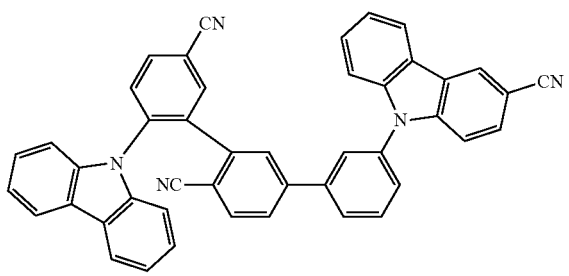
2008
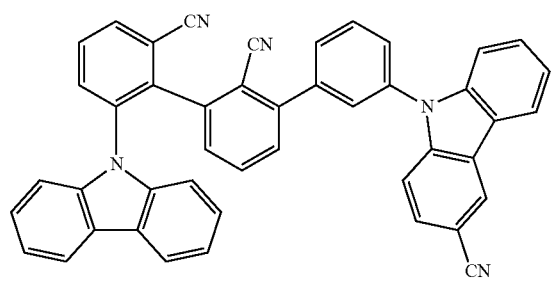
2009
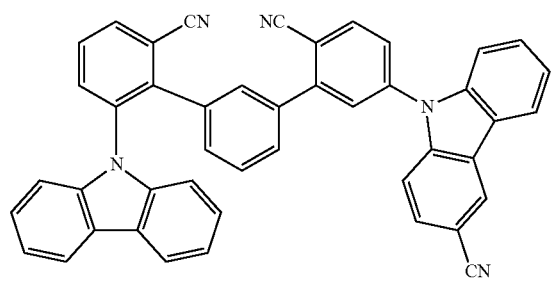
550
-continued
2010
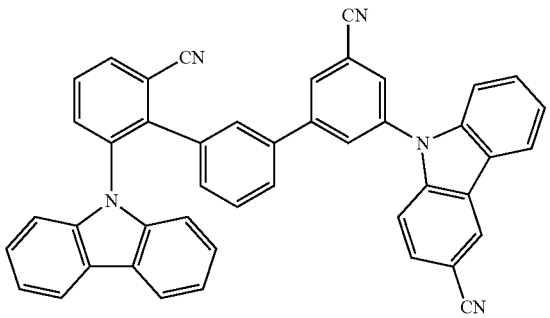
2011
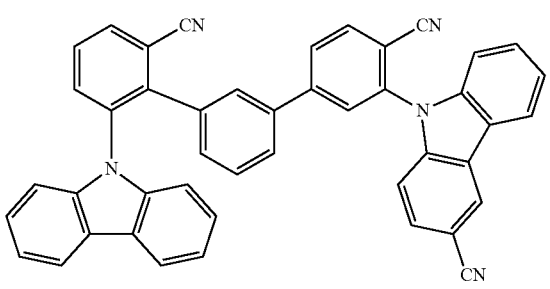
2012
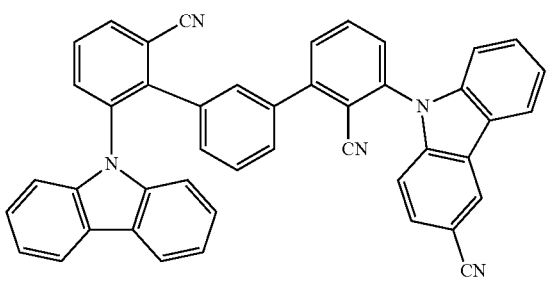
2013
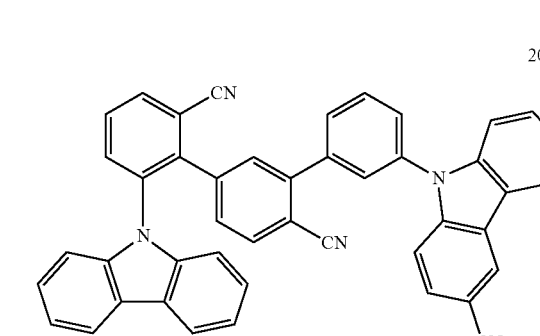
2014
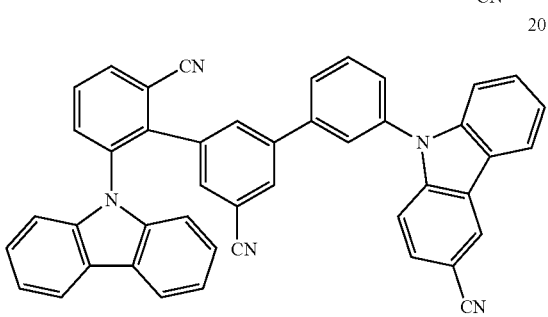

| 551 -continued | 552 -continued |
|---|---|
| 2015 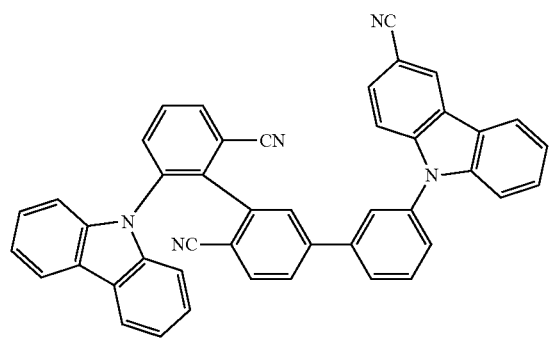 | 2020 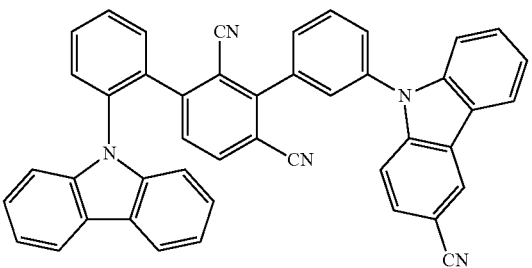 |
| 2016 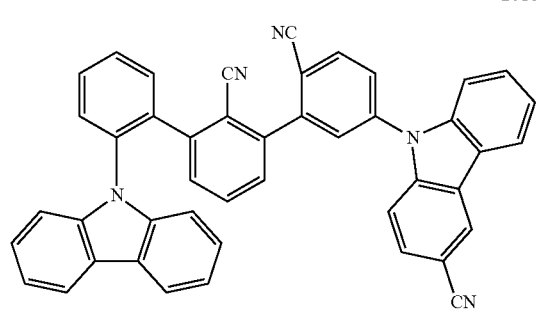 | 2021 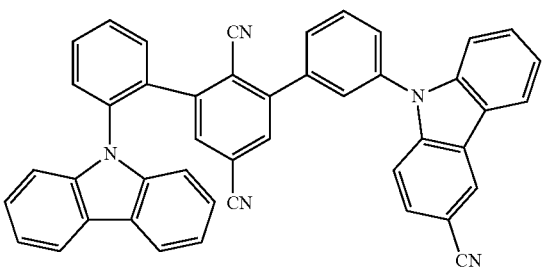 |
| 2017 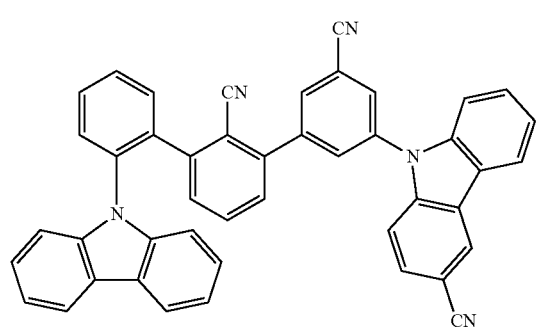 | 2022 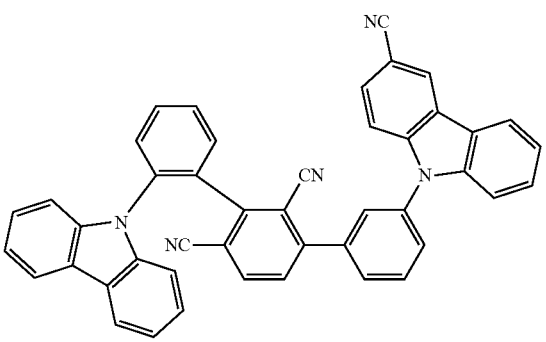 |
| 2018 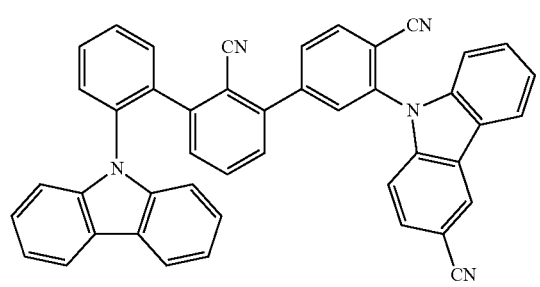 | 2023 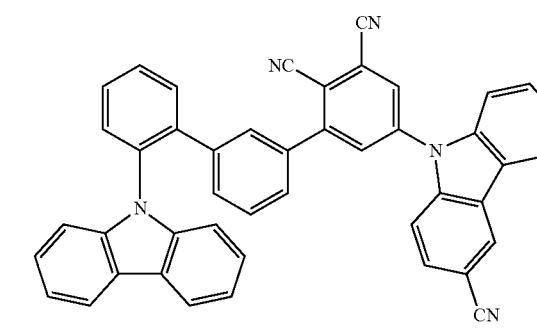 |
| 2019 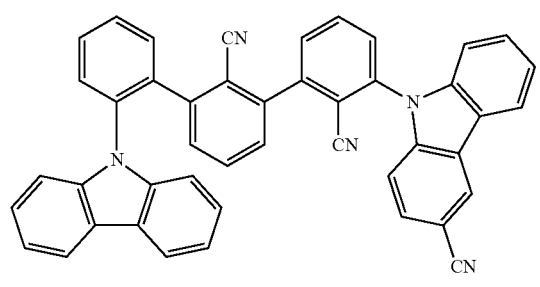 | 2024 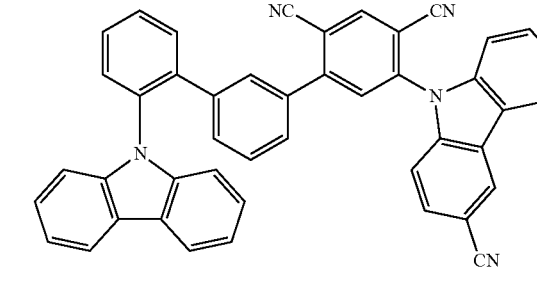 |

2025
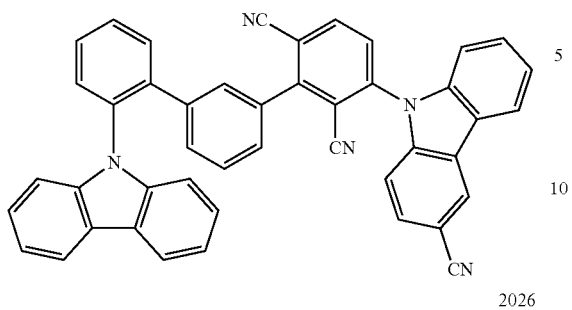
2026
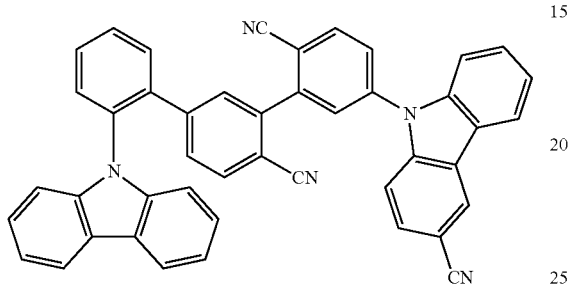
2027
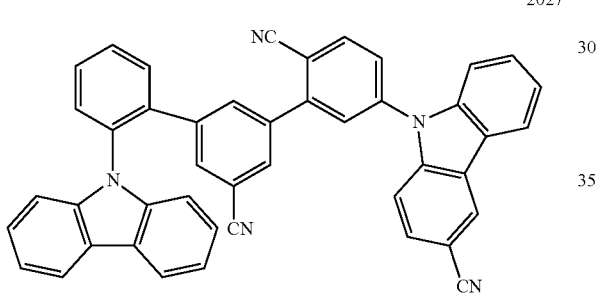
2028
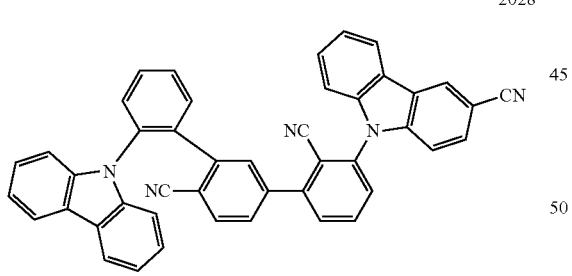
2029
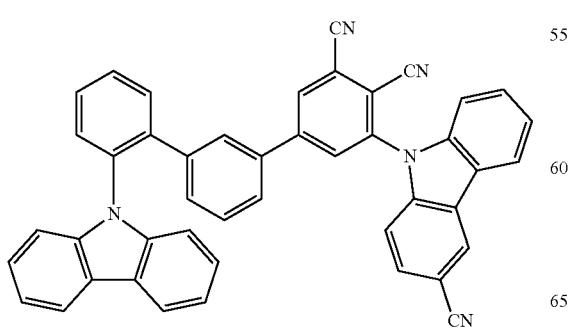
2030
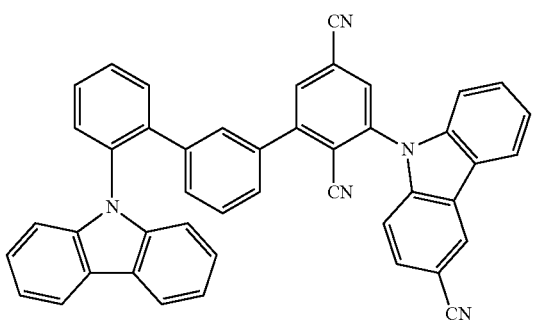
2031
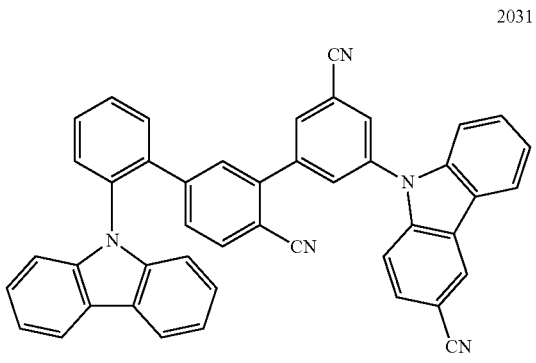
2032
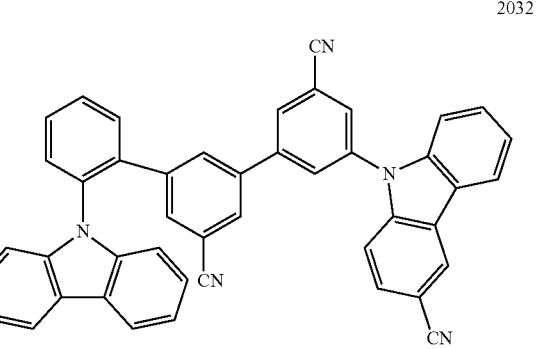
2033
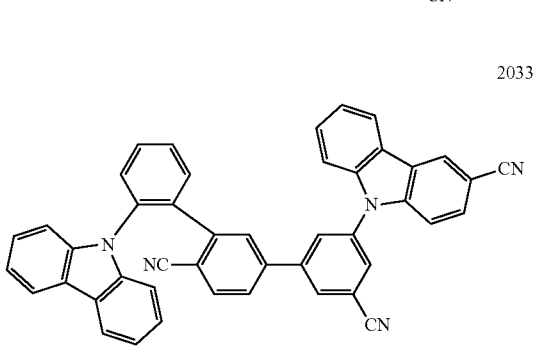
2034
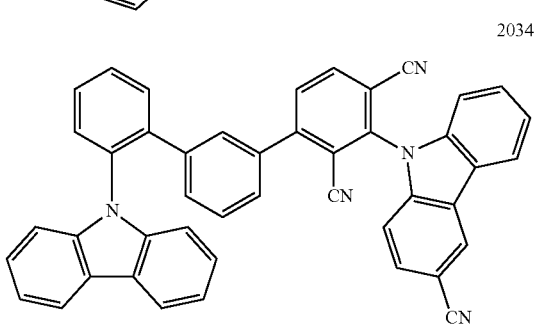

555
-continued
2035
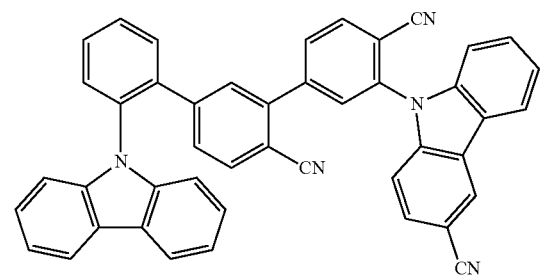
2036
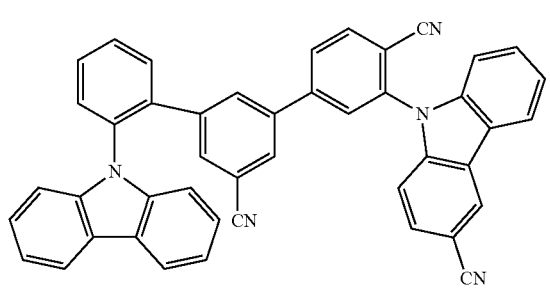
2037
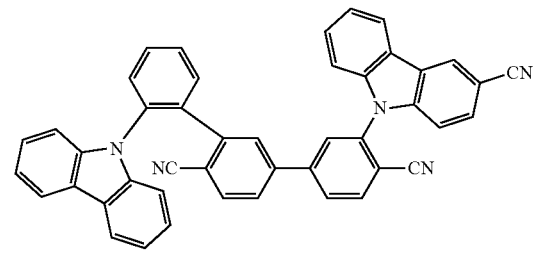
2038
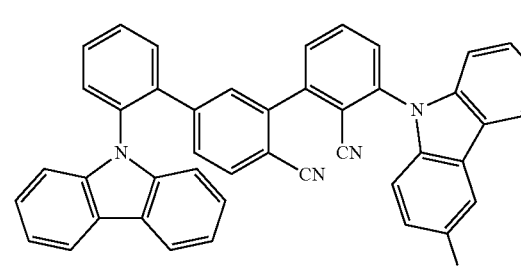
2039
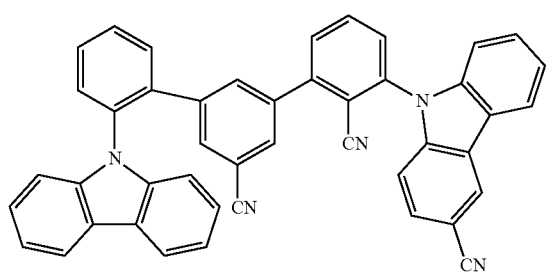
556
-continued
2040
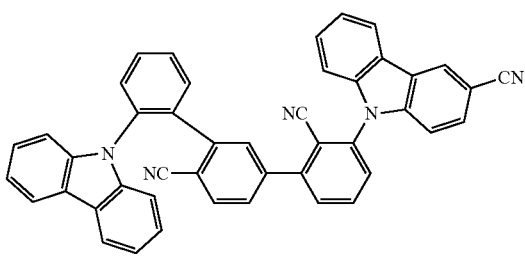
2041
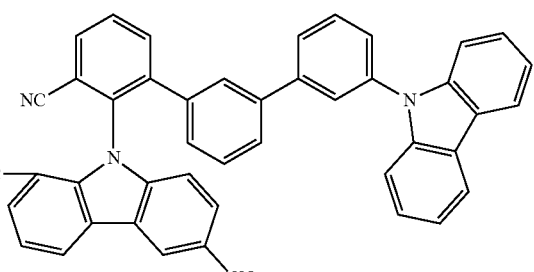
2042
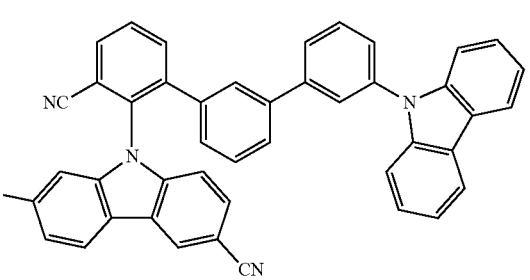
2043
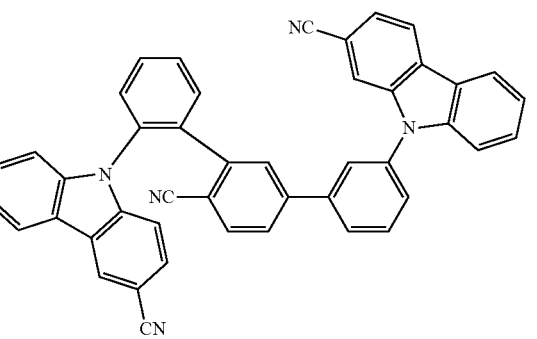
2044
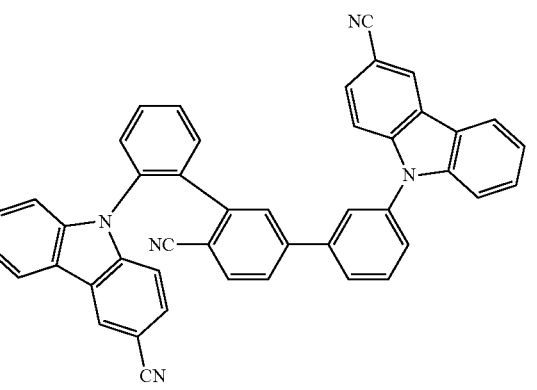

557
-continued
2045
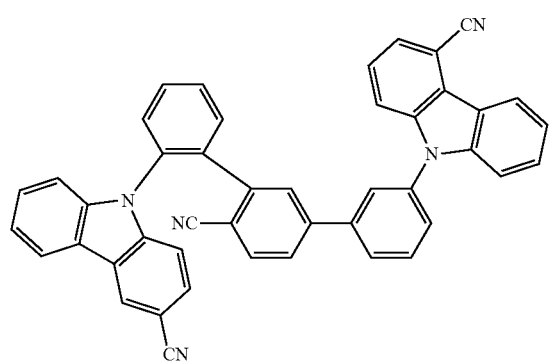
2046
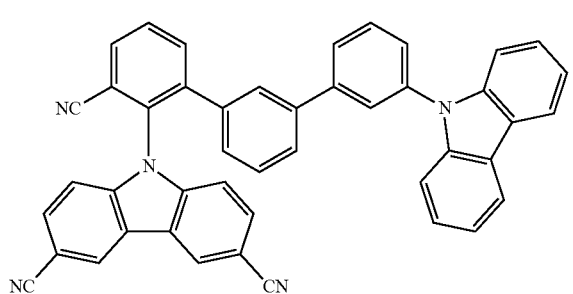
2047
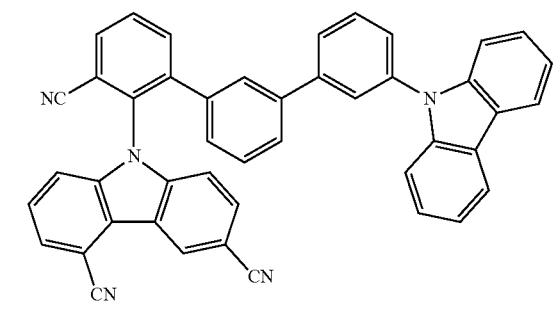
2048
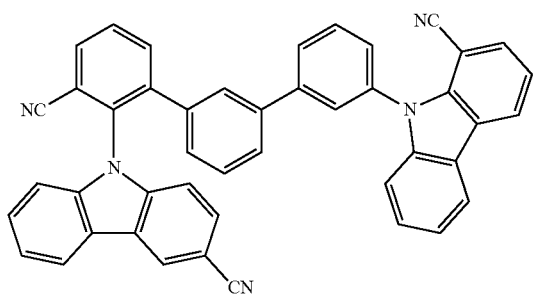
2049
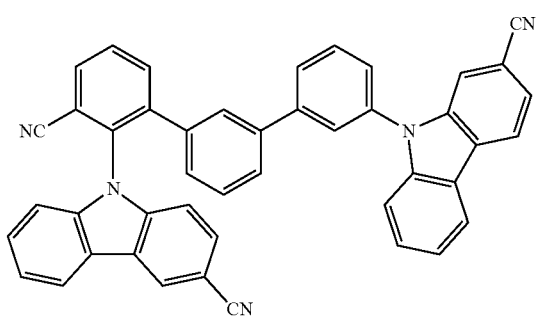
558
-continued
2050
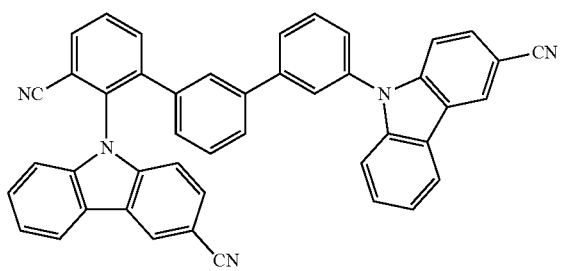
2051
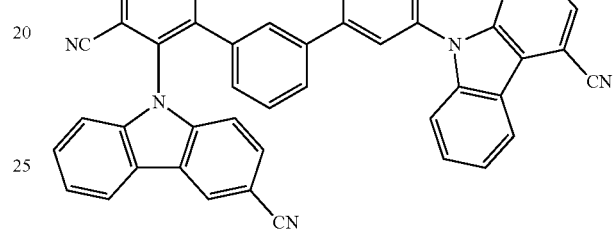
2052
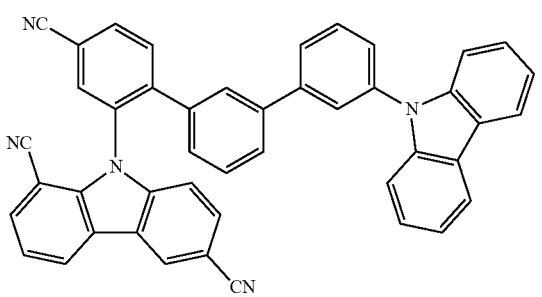
2053
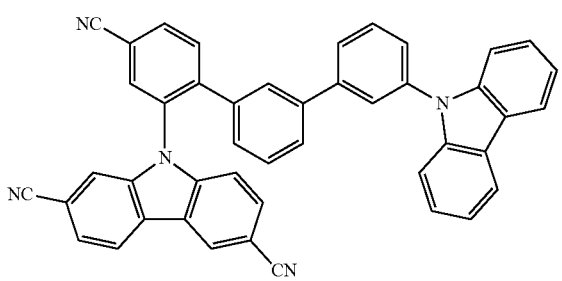
2054
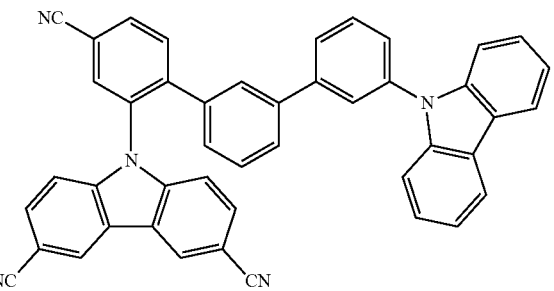

559
-continued
2055
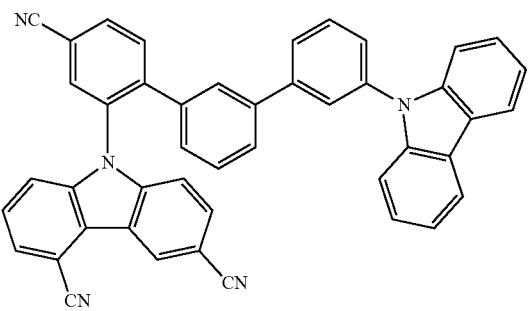
2056
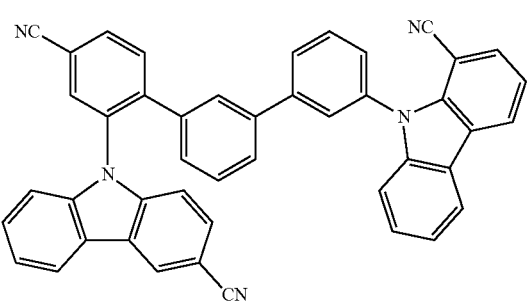
2057
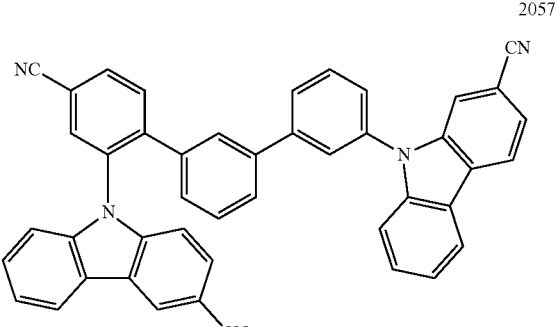
2058
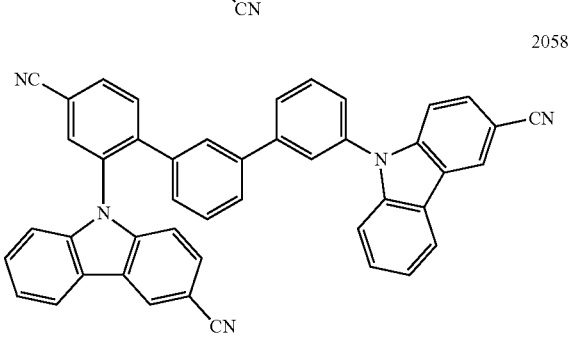
2059
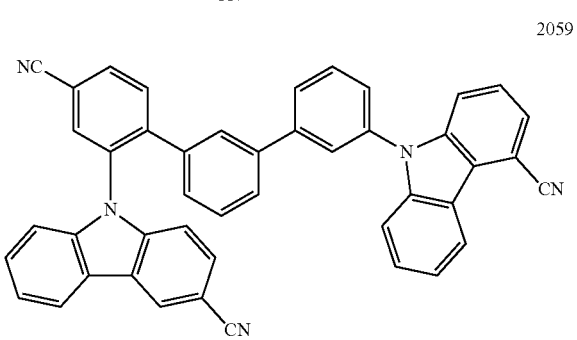
560
-continued
2060
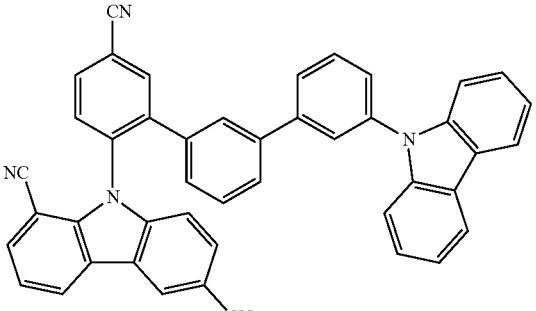
2061
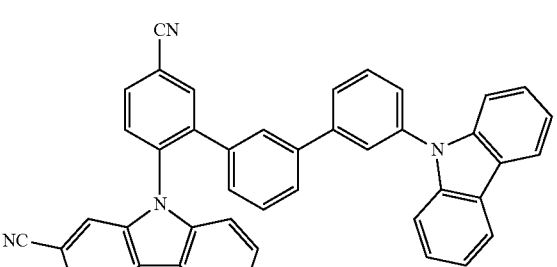
2062
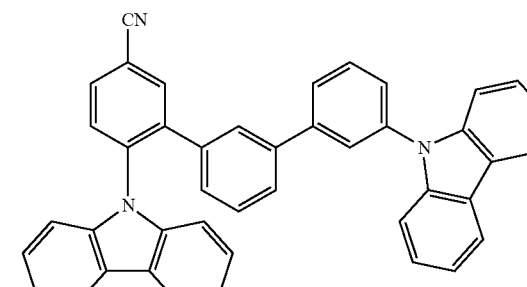
2063
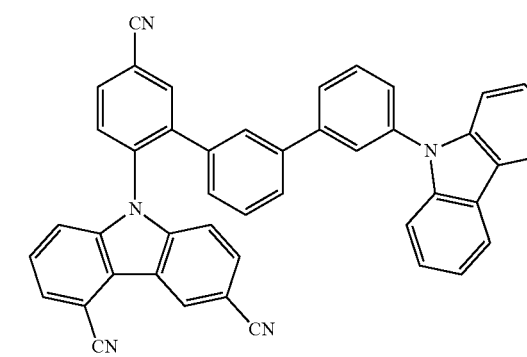

2064
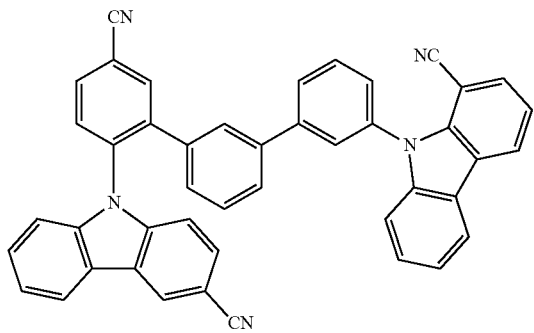
2065
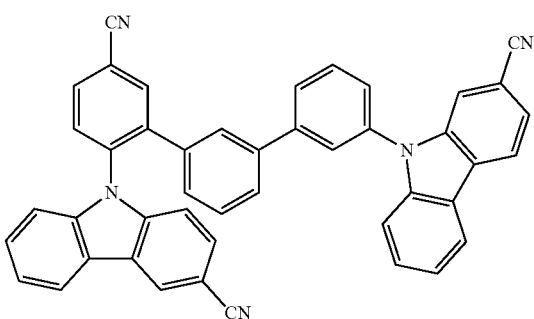
2066
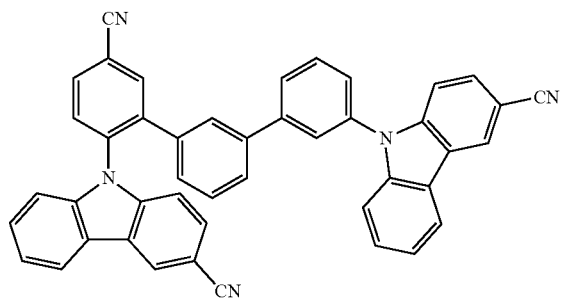
2067
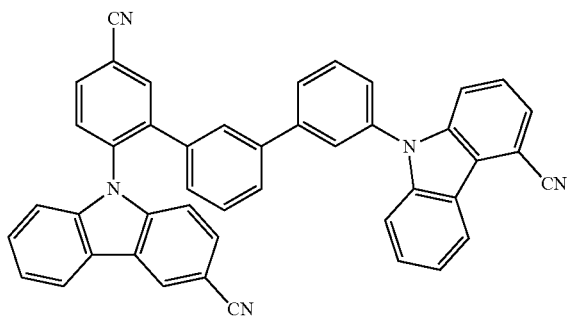
2068
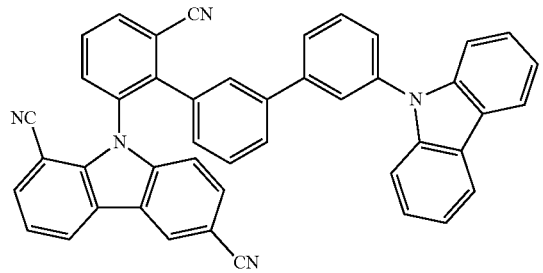
2069
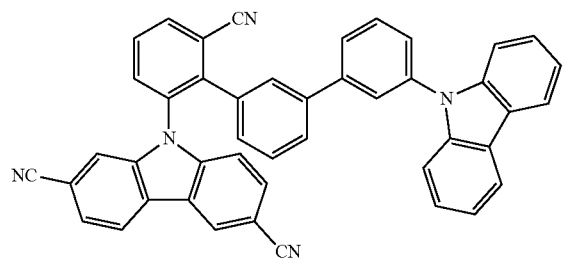
2070
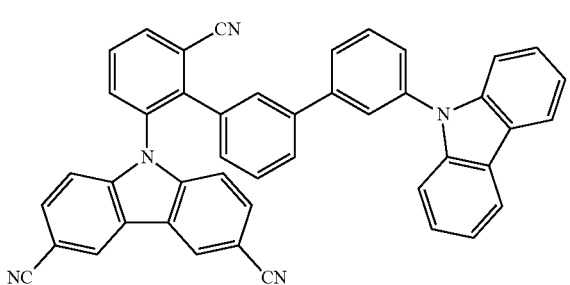
2071
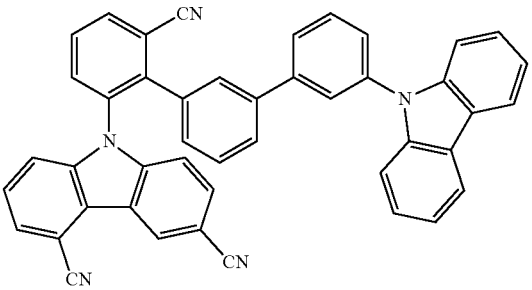
2072
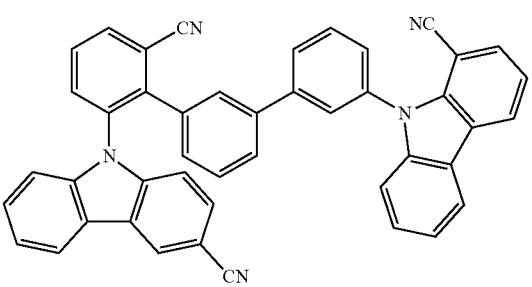
2073
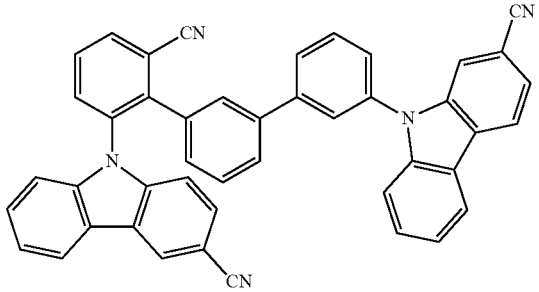

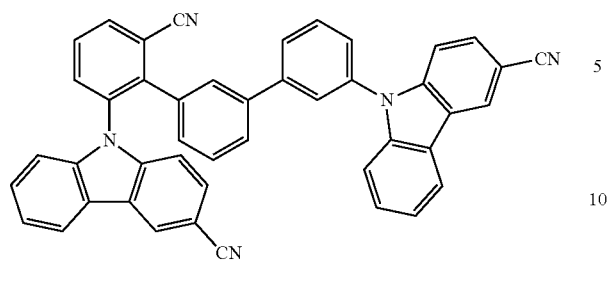
2074
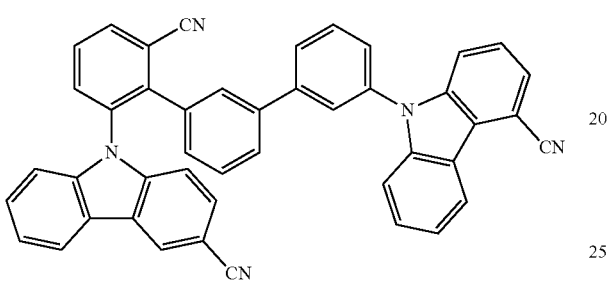
2075
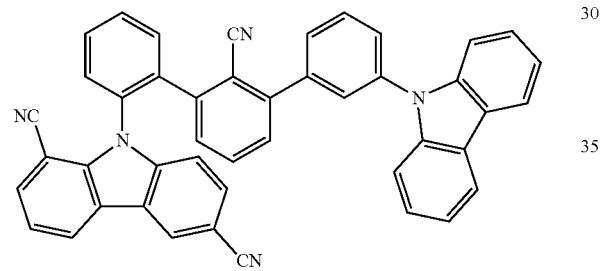
2076
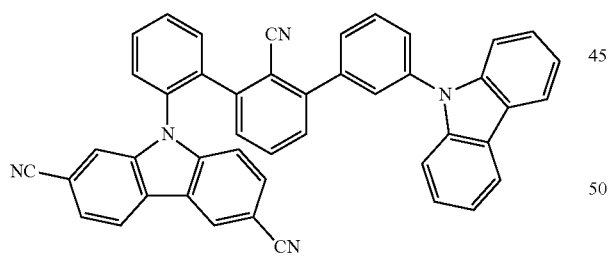
2077
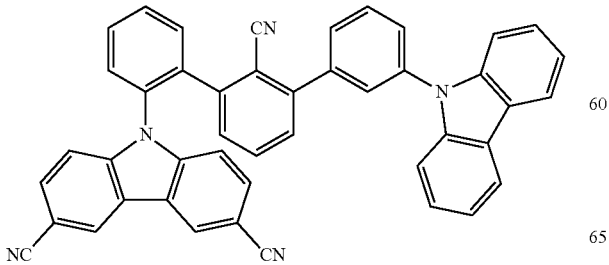
2078
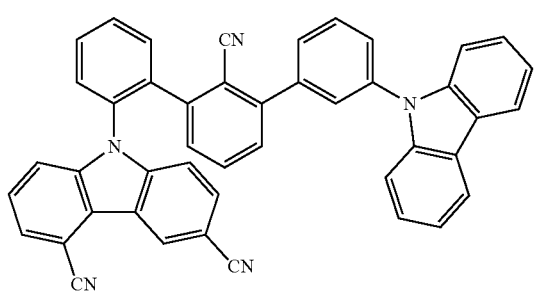
2079
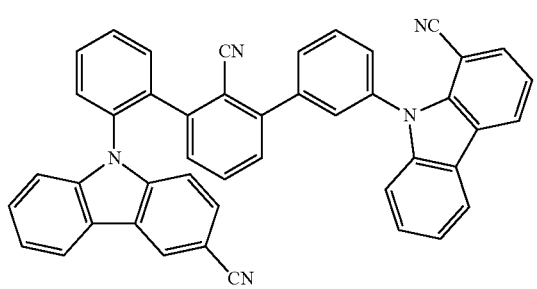
2080
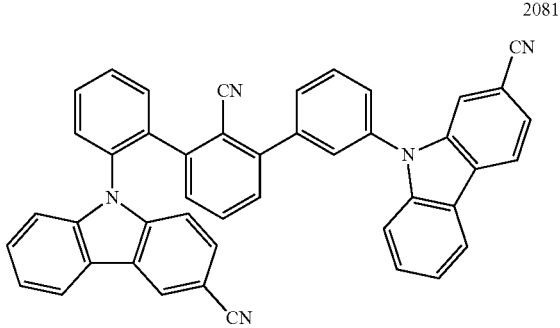
2081
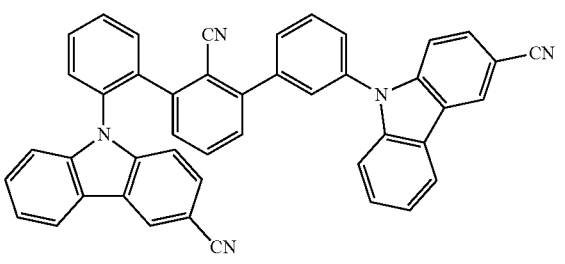
2082
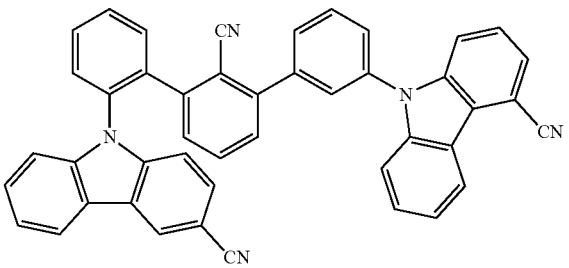
2083

-continued
2084
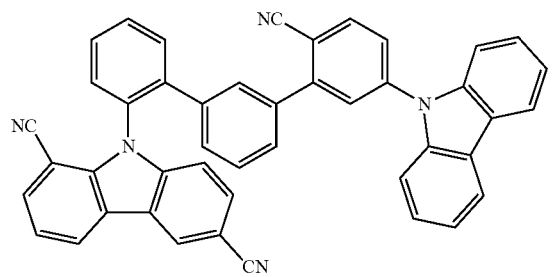
2085
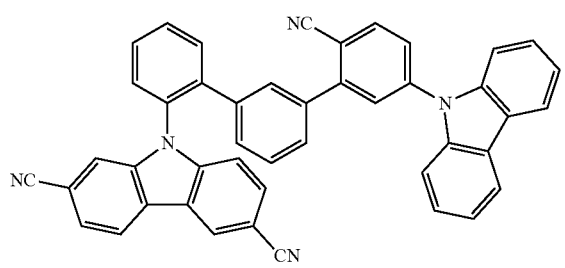
2086
2087
2088
-continued
2089
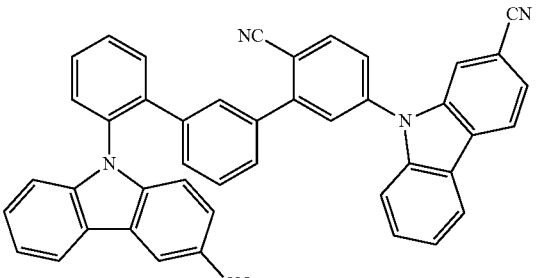
2090
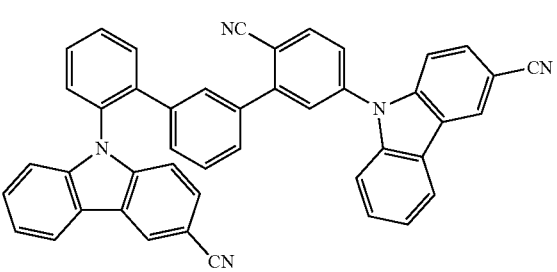
2091
2092
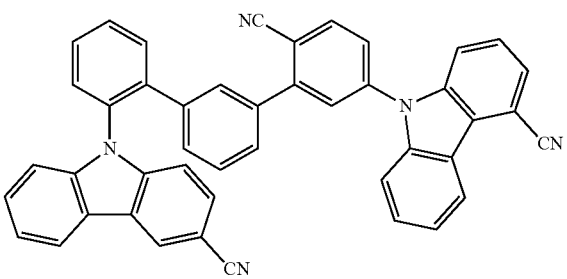
2093
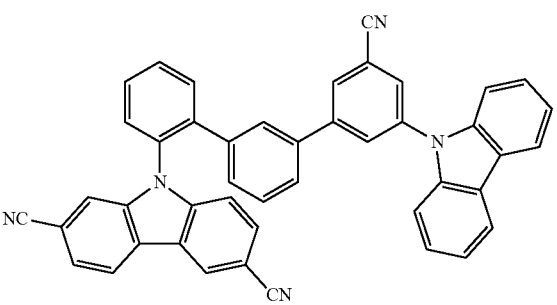

2094
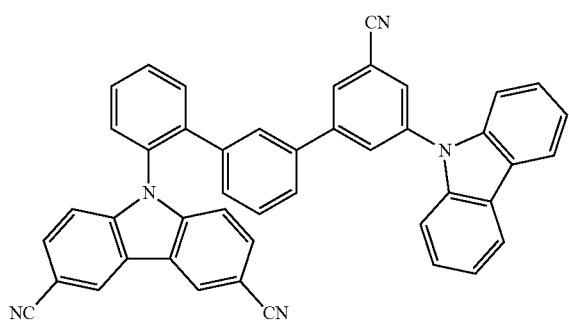
2098
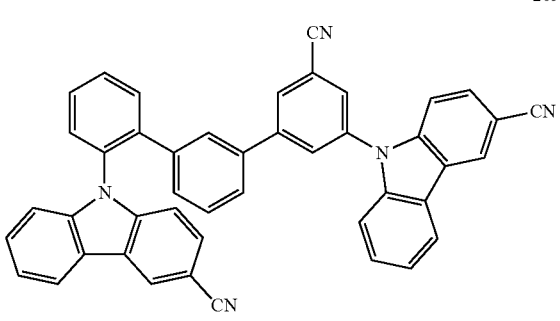
2095
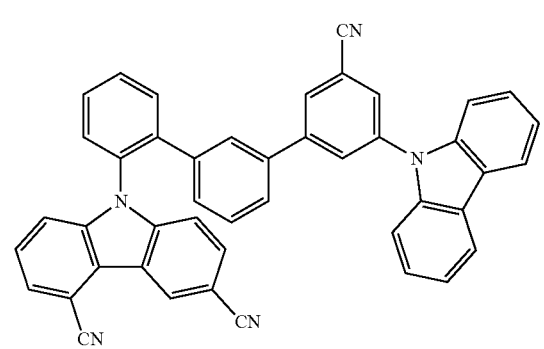
2099
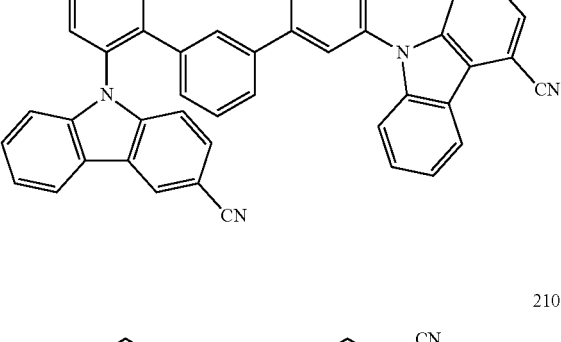
2096
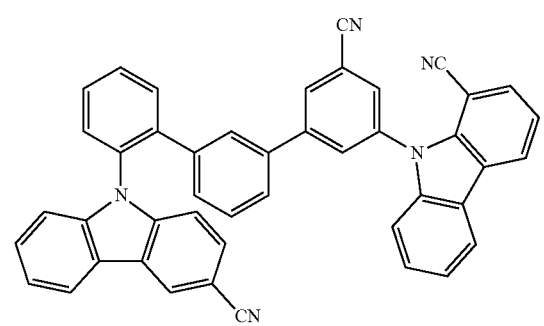
2100
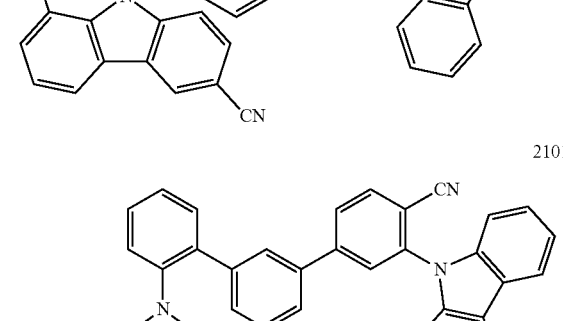
2097
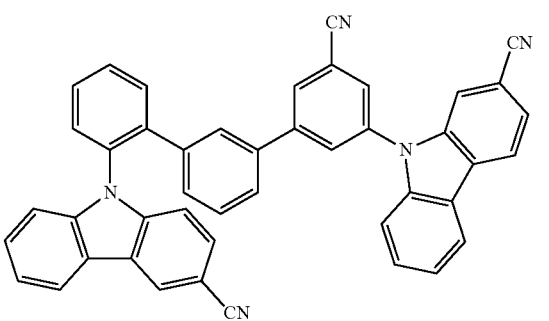
2101
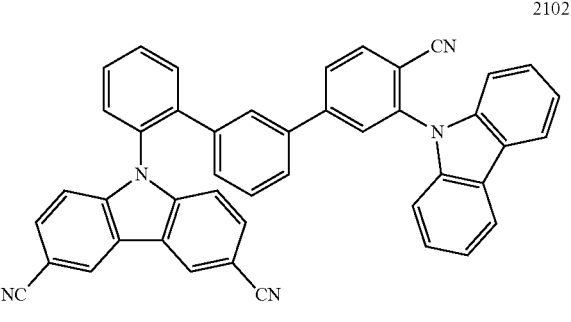

| 569 -continued | 570 -continued |
|---|---|
| 2103 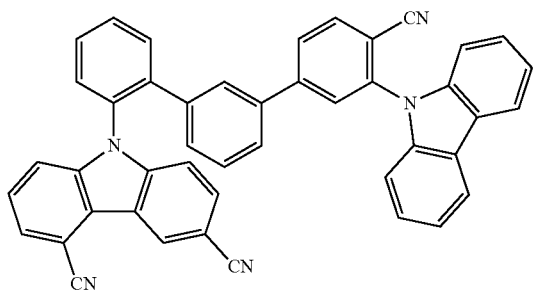 | 2108 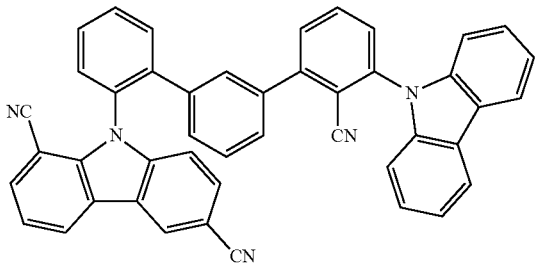 |
| 2104 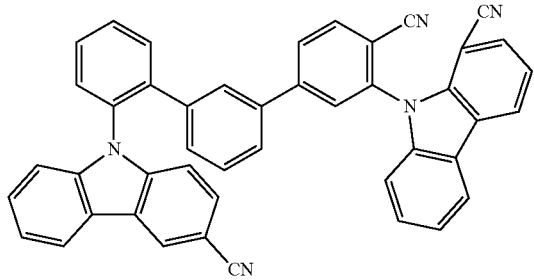 | 2109 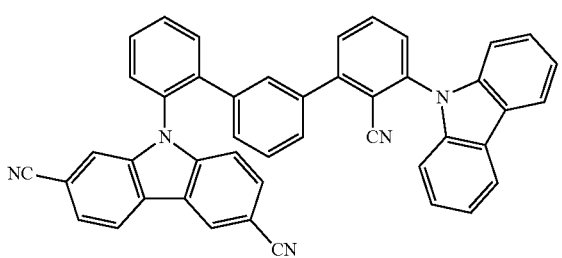 |
| 2105 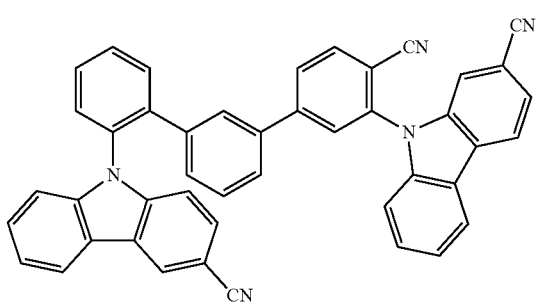 | 2110 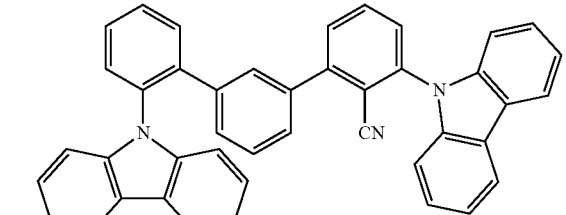 |
| 2106 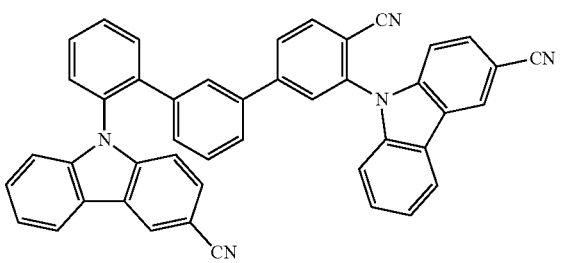 | 2111 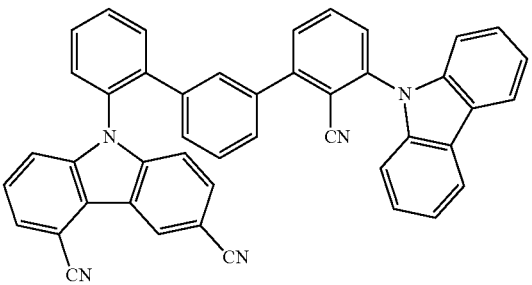 |
| 2107 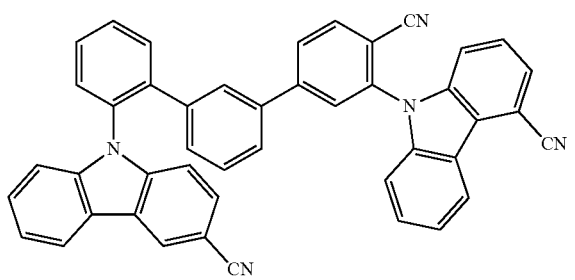 | 2112 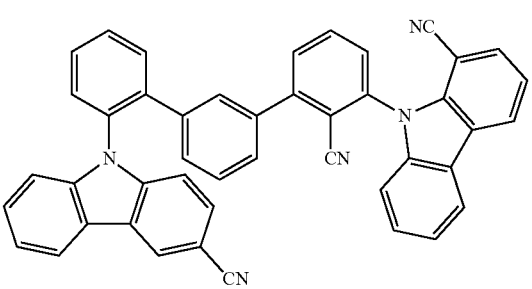 |

-continued
2113
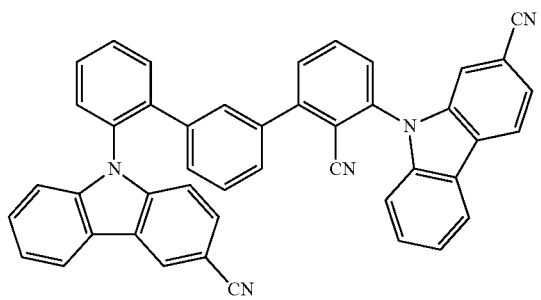
2114
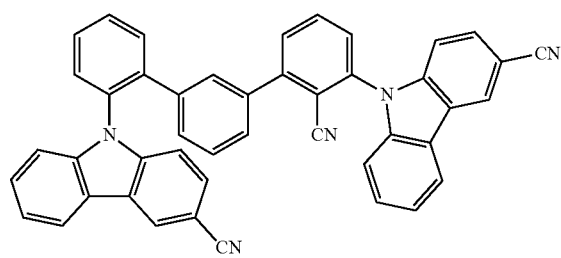
2115
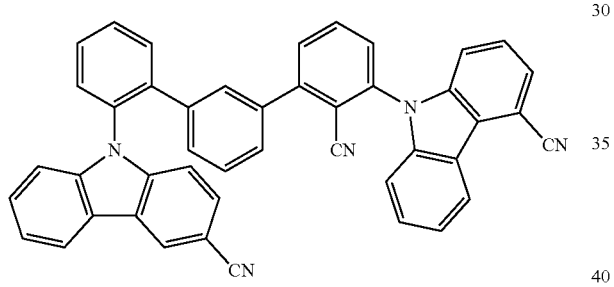
2116
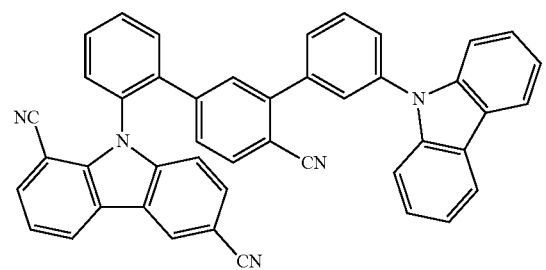
2117
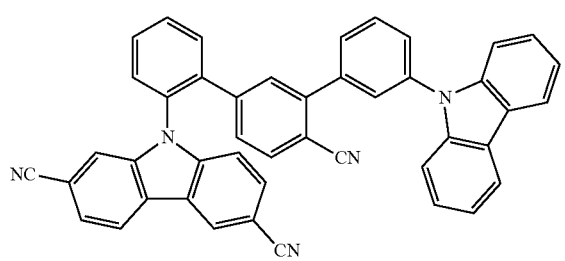
-continued
2118
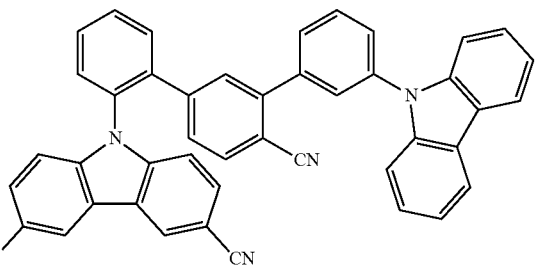
2119
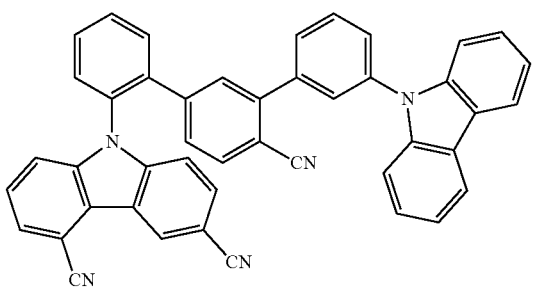
2120
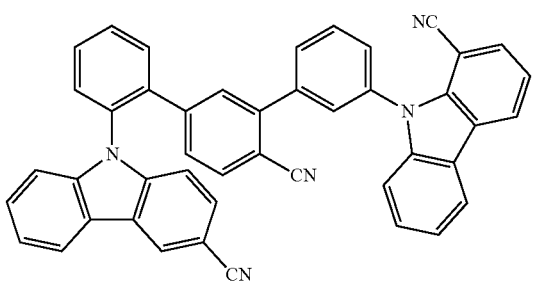
2121
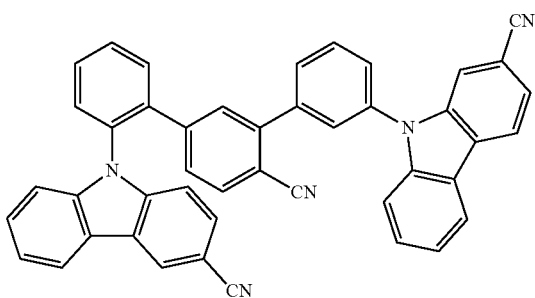
2122
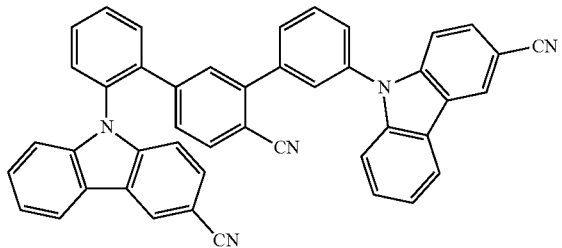

2123
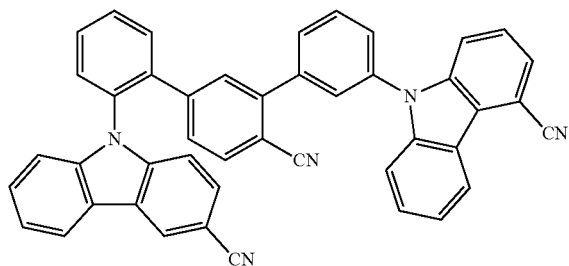
2124
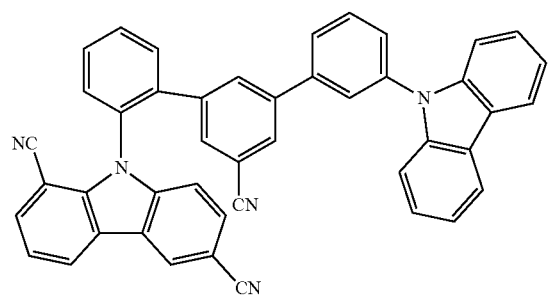
2125
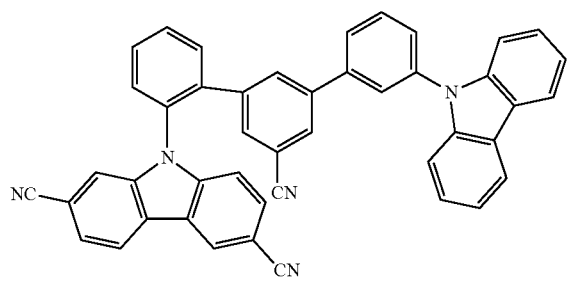
2126
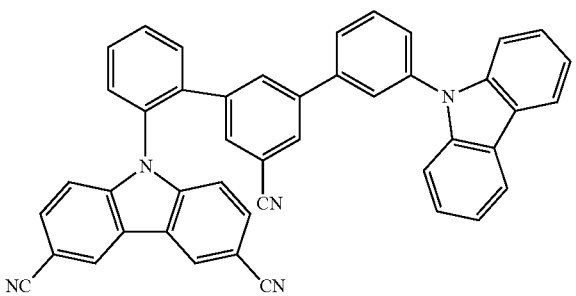
2127
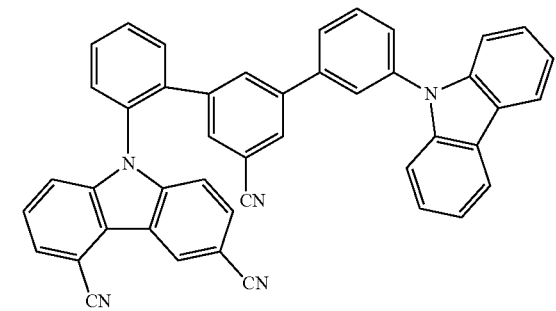
2128
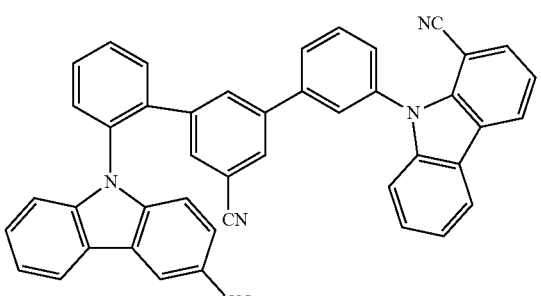
2129
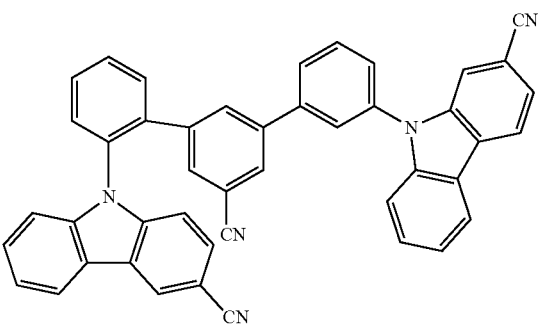
2130
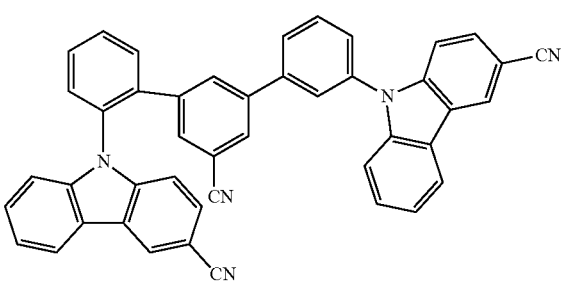
2131
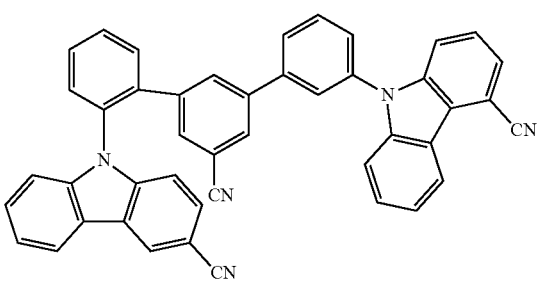
2132
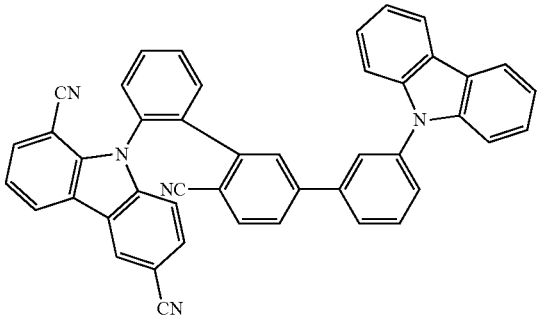

2133
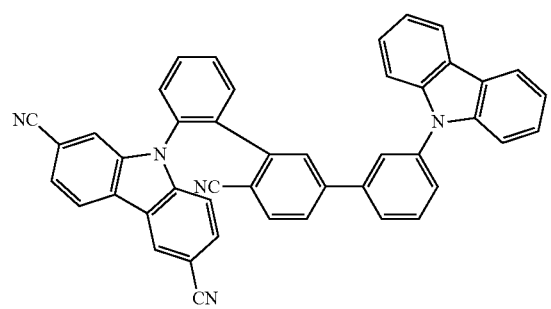
2134
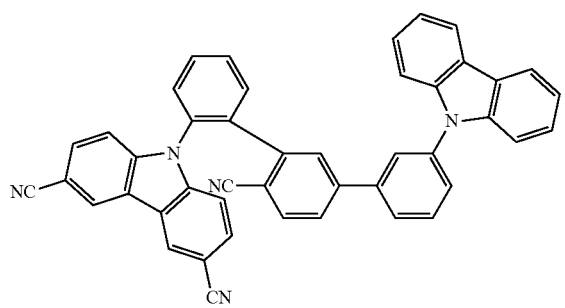
2135
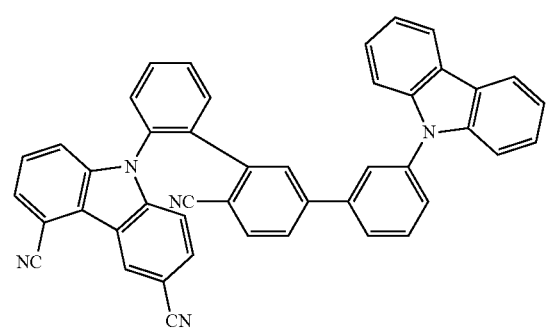
2136
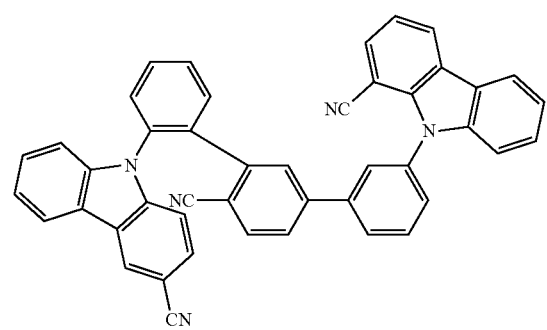
2137
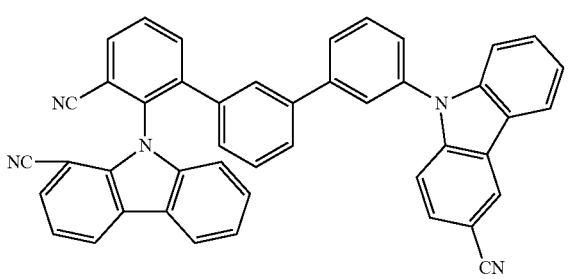
2138
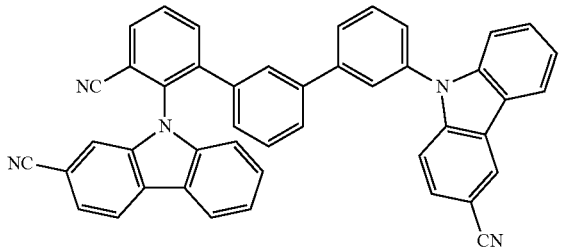
2139
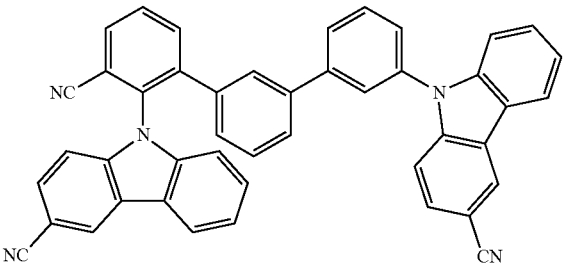
2140
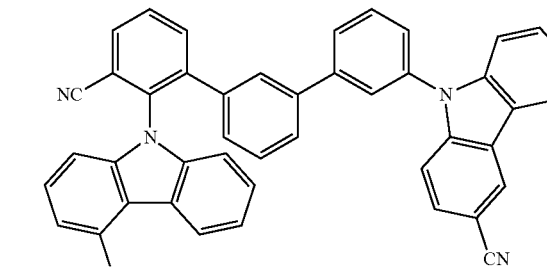
2141
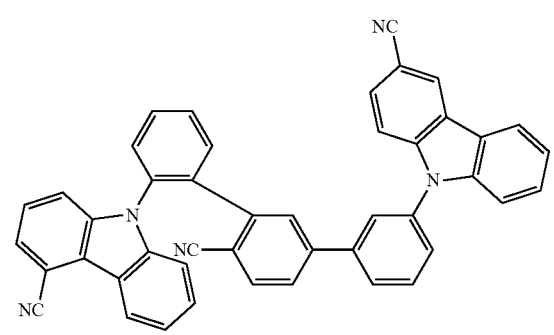
2142
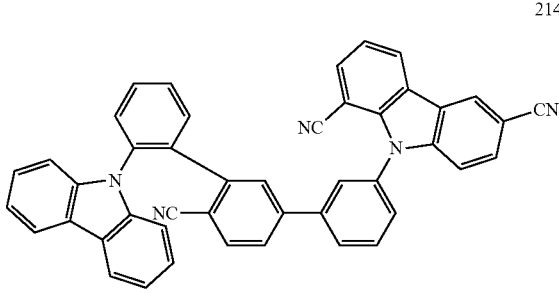

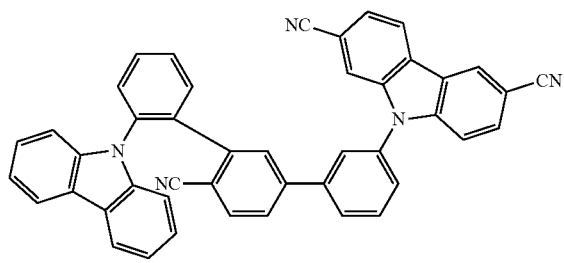
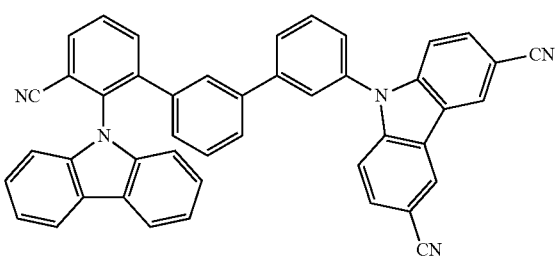
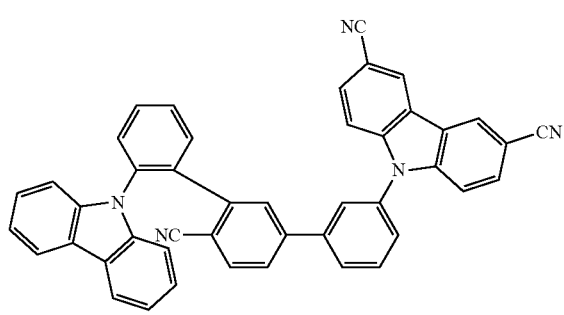

2153
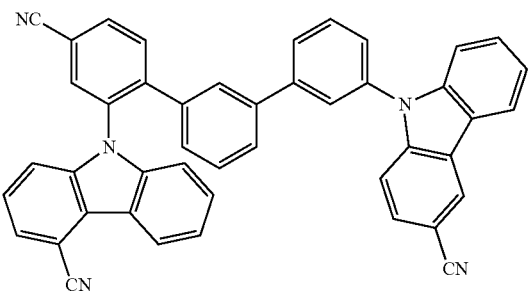
2154
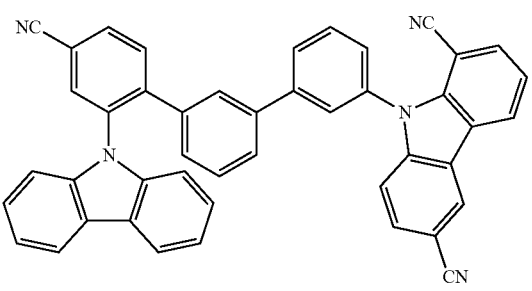
2155
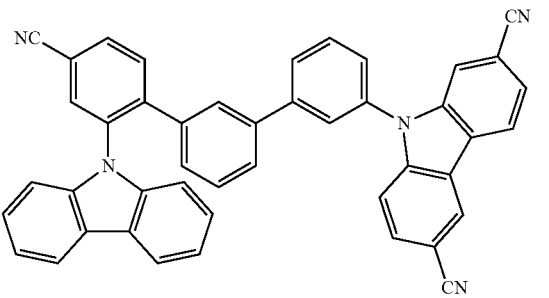
2156
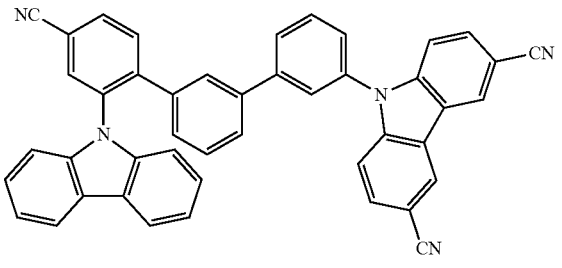
2157
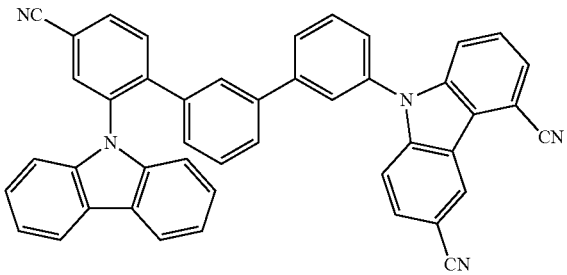
2158
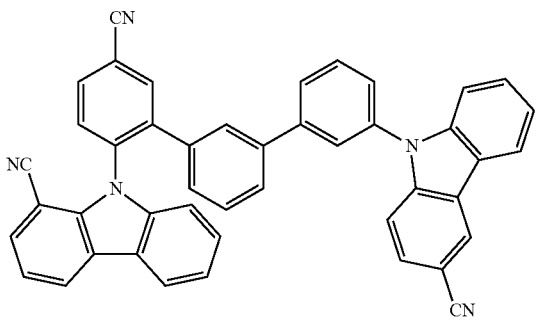
2159
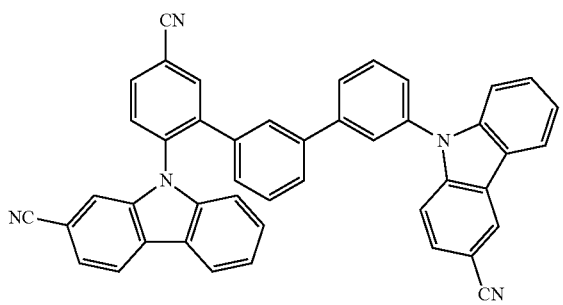
2160
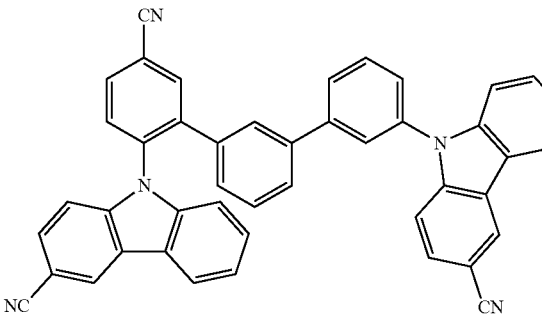
2161
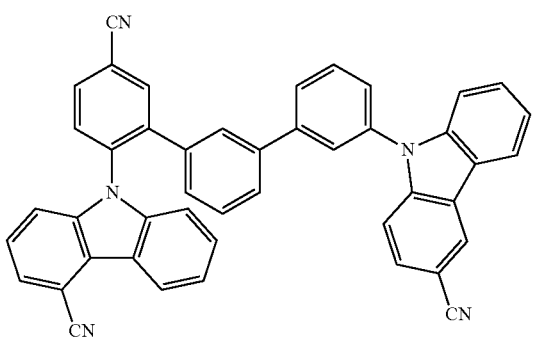

-continued
2162
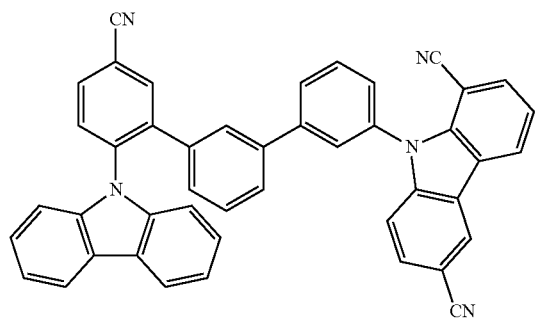
2163
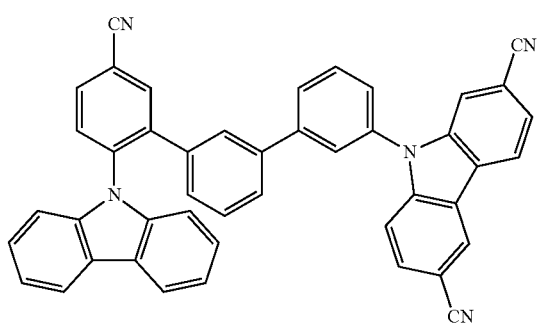
2164
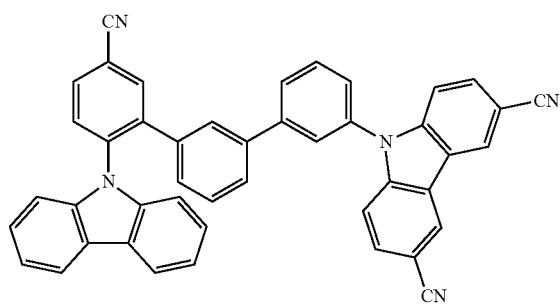
2165
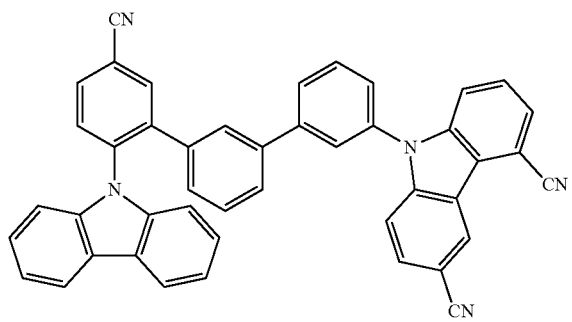
2166
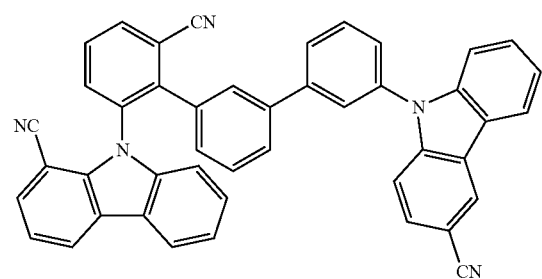
-continued
2167
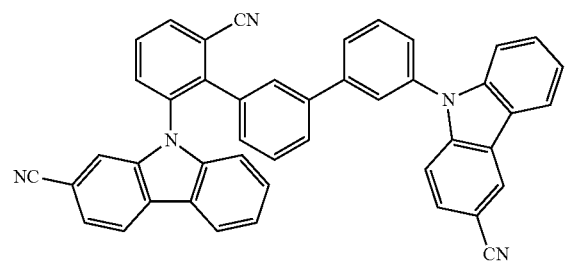
2168
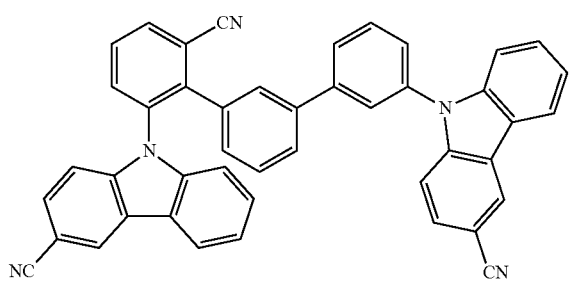
2169
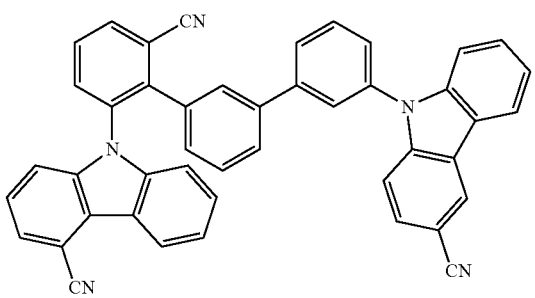
2170
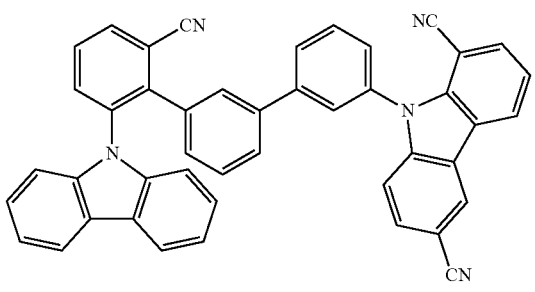
2171
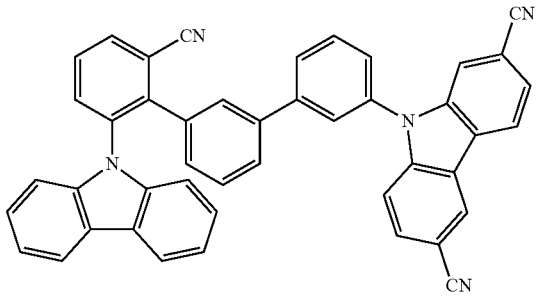

-continued
2172
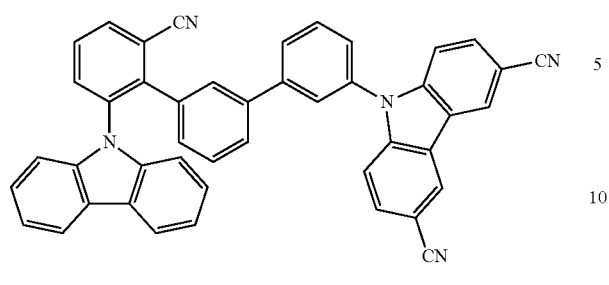
2177
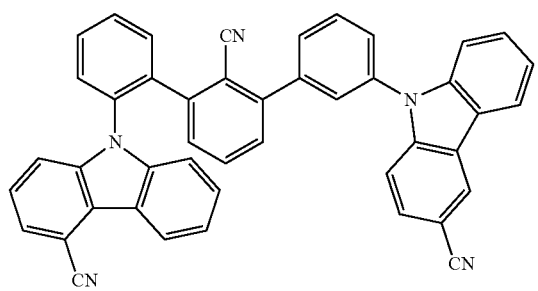
2173
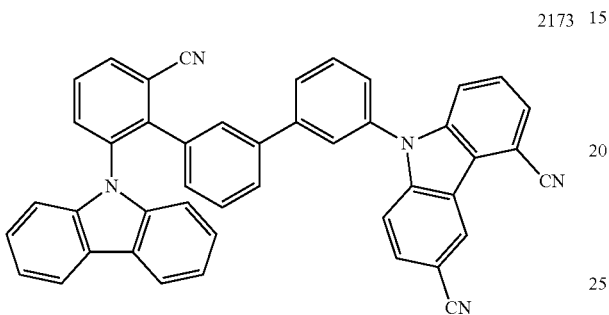
2178
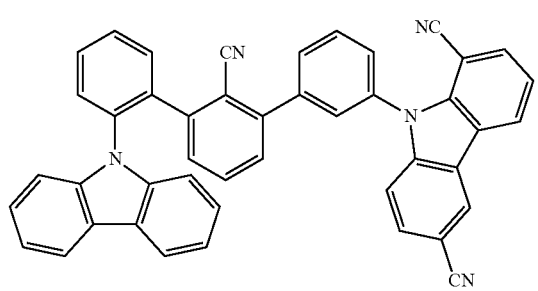
2174
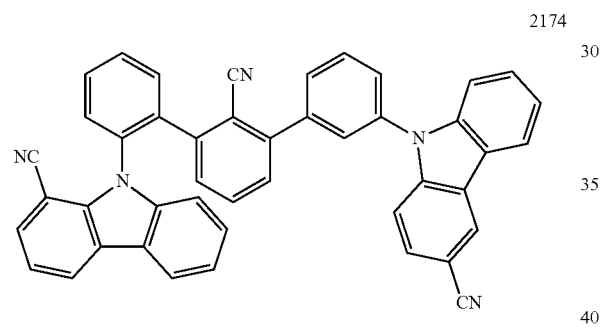
2179
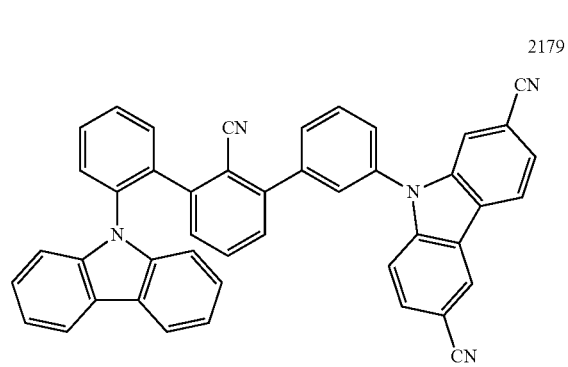
2175
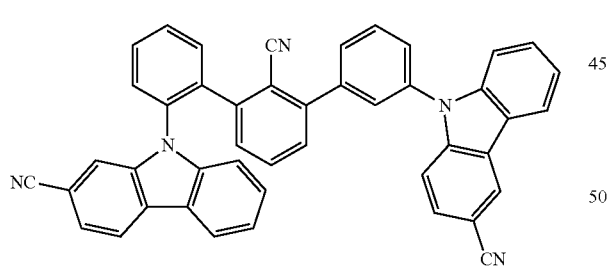
2180
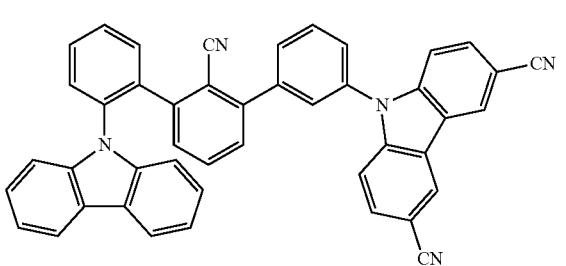
2176
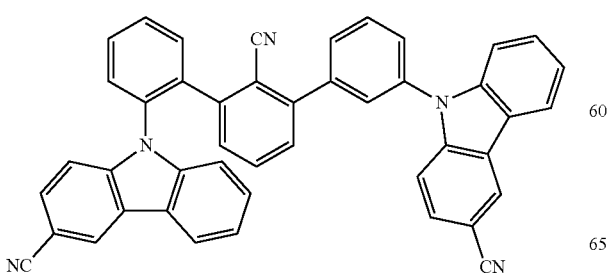
2181
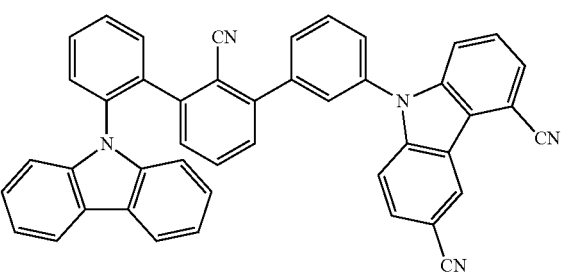

585
-continued
2182
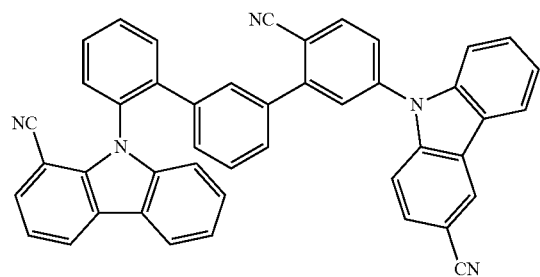
2183
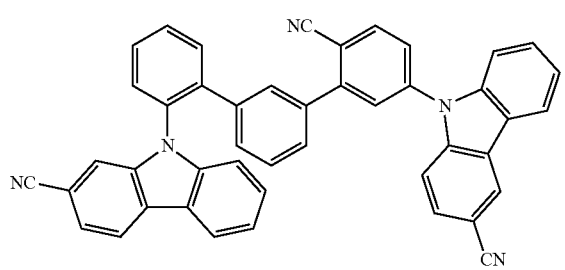
2184
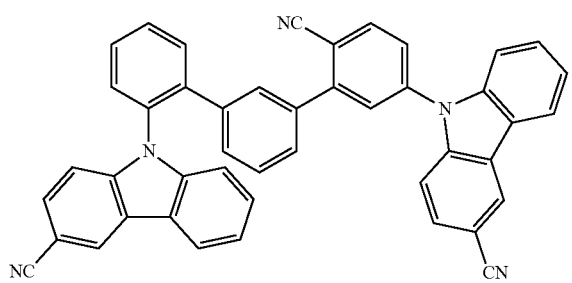
2185
2186
586
-continued
2187
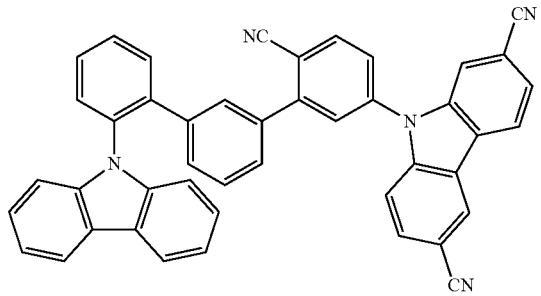
2188
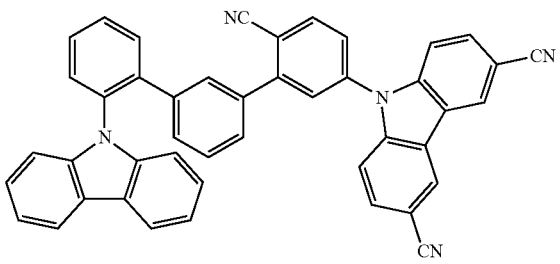
2189
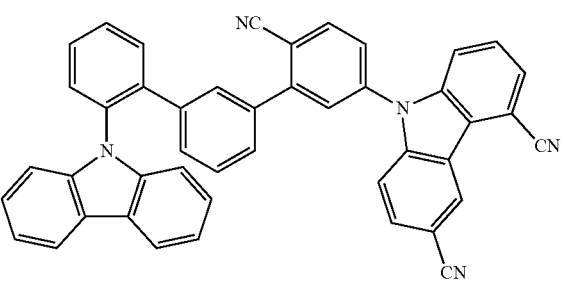
2190
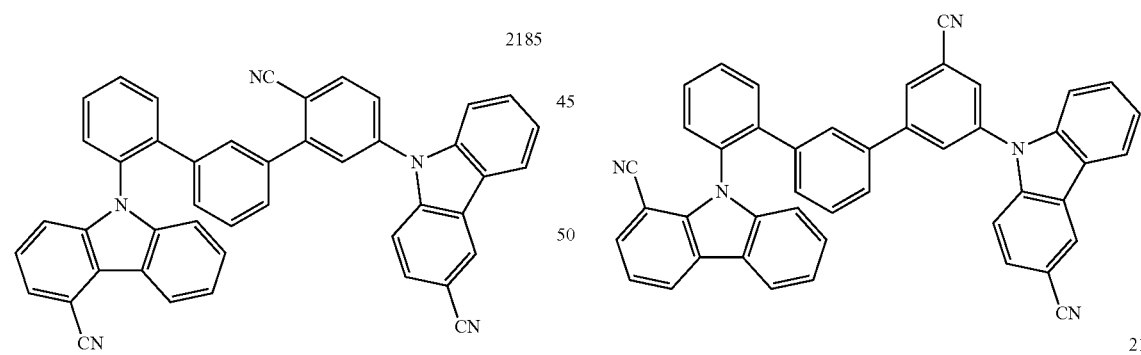
2191
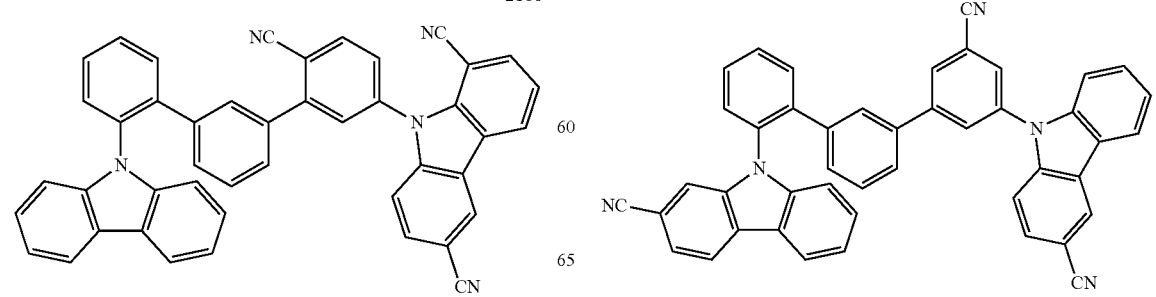

2192
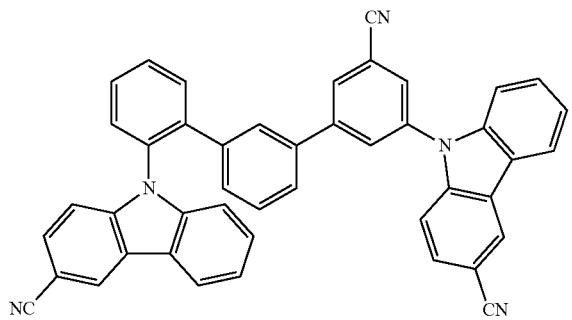
2193
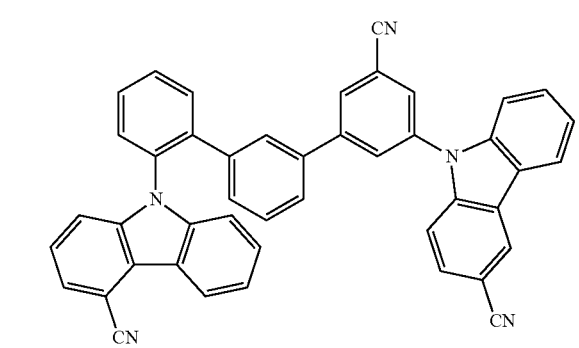
2194
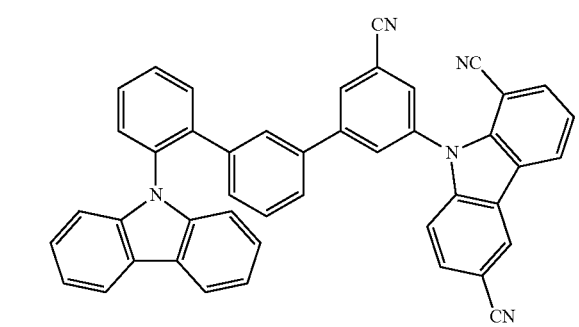
2195
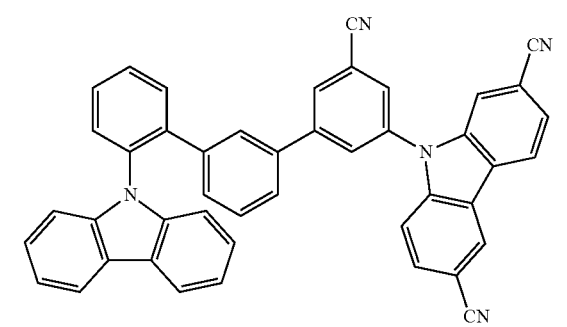
2196
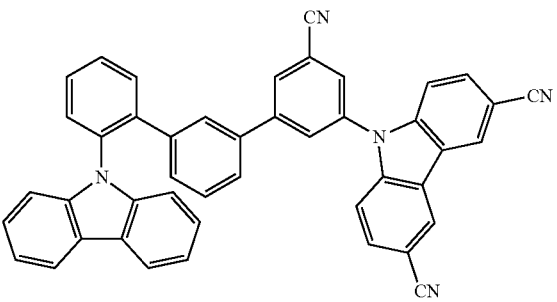
2197
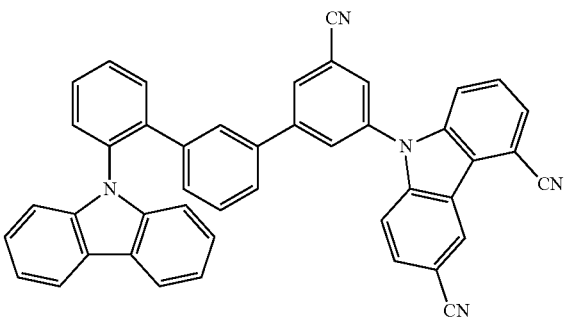
2198
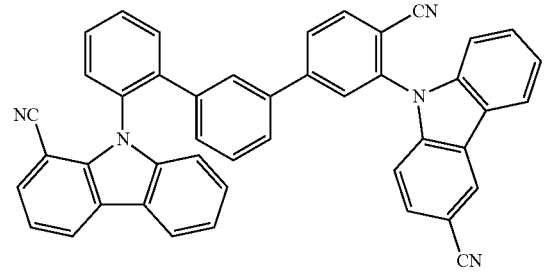
2199
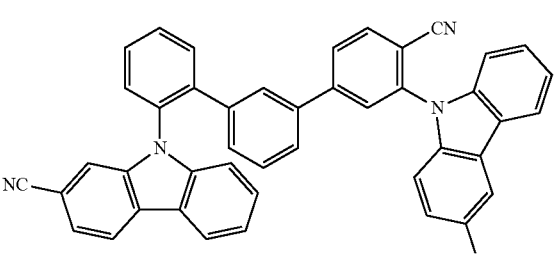
2200
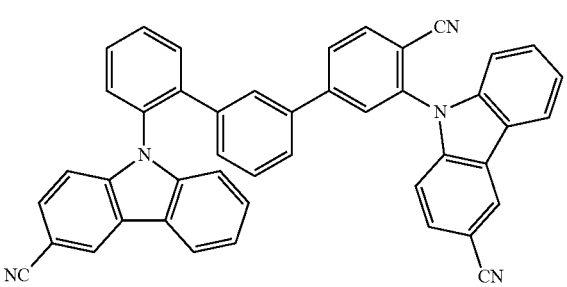

589
-continued
2201
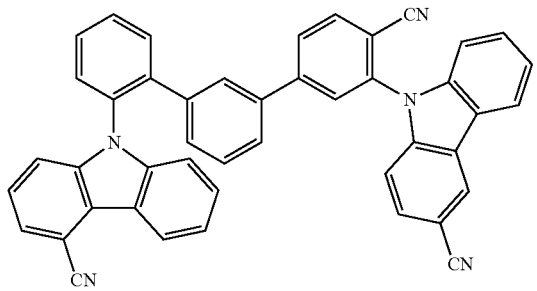
2202
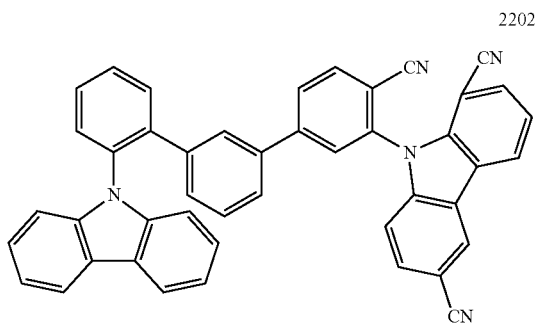
2203
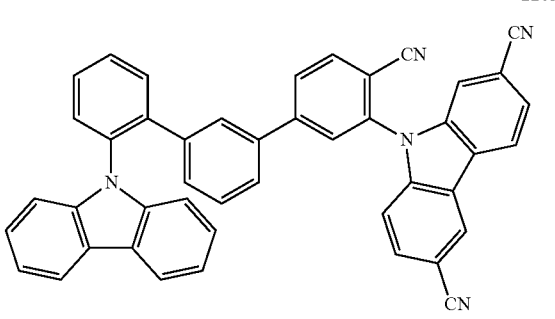
2204
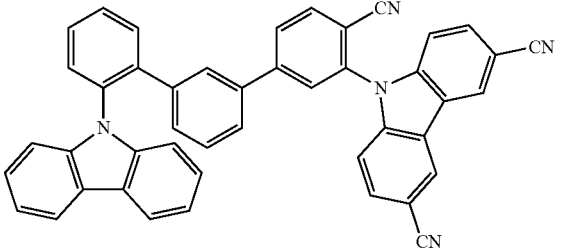
2205
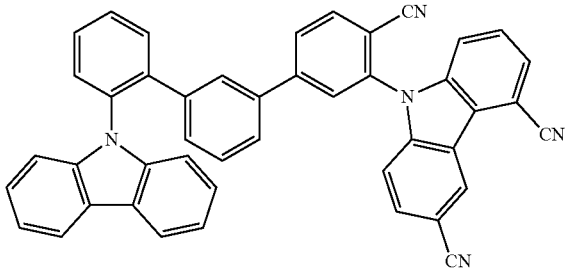
590
-continued
2206
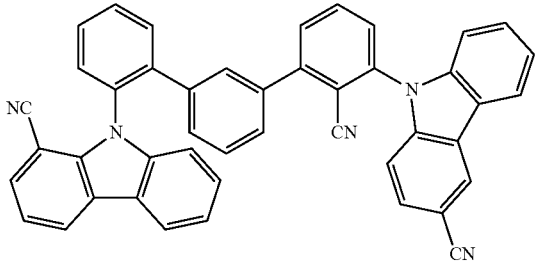
2207
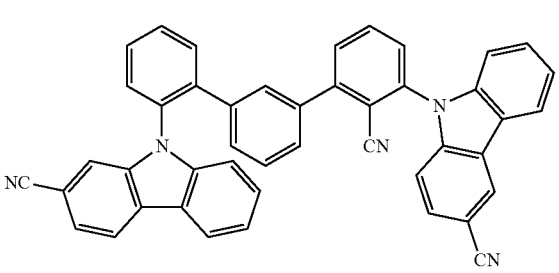
2208
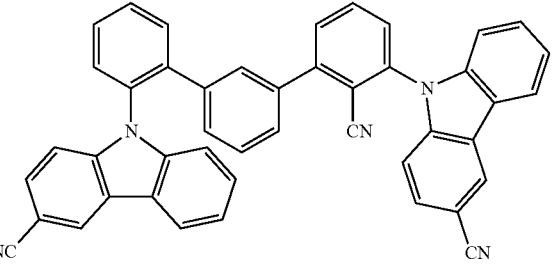
2209
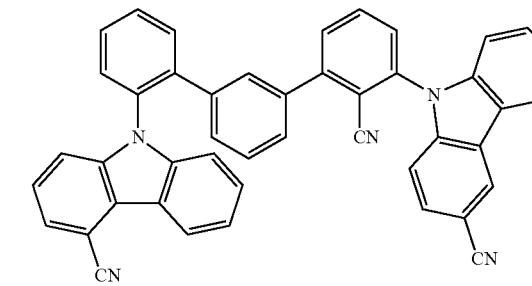
2210
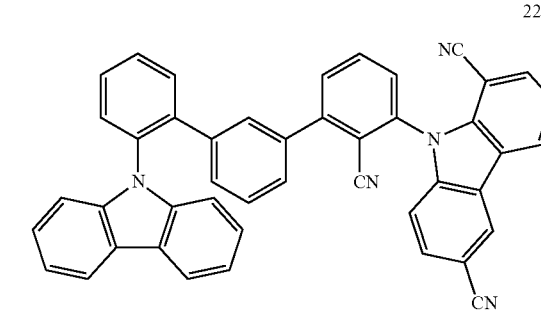

2211
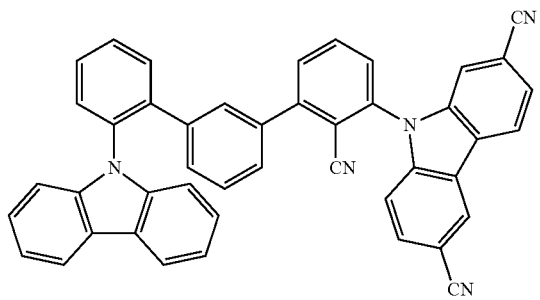
2212
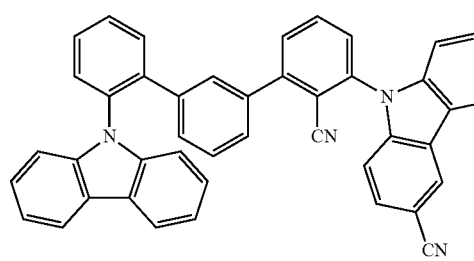
2213
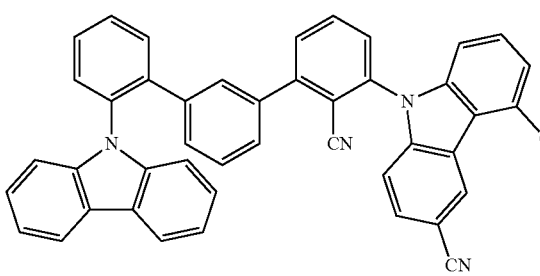
2214
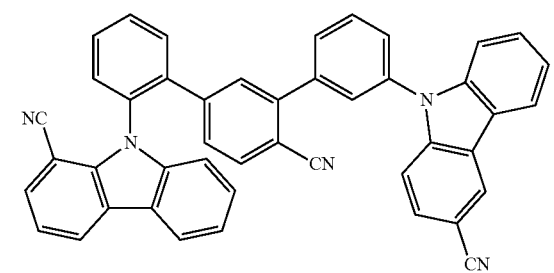
2215
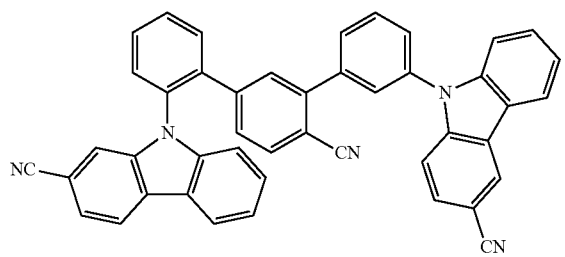
2216
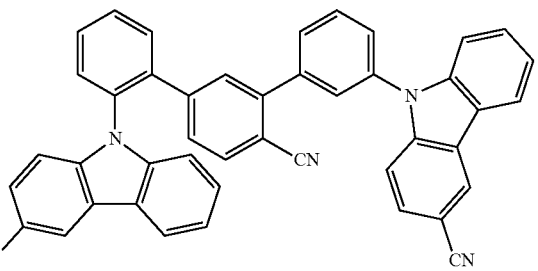
2217
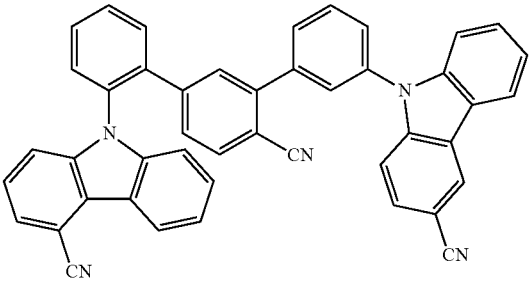
2218
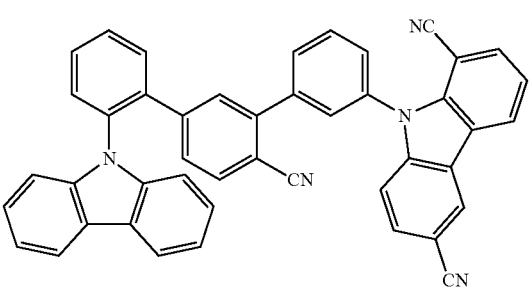
2219
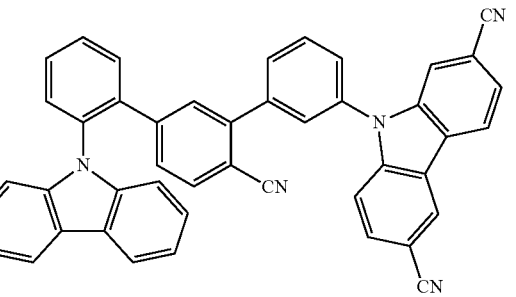
2220
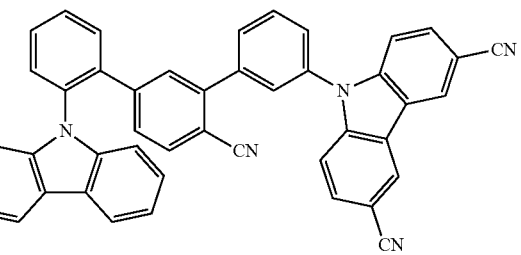

593
-continued
2221
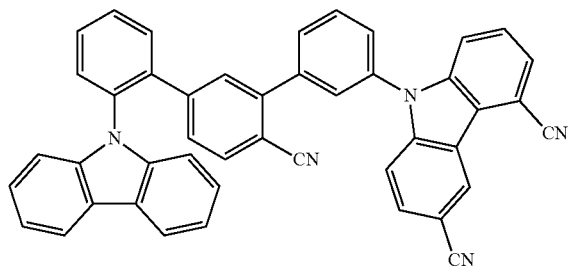
2222
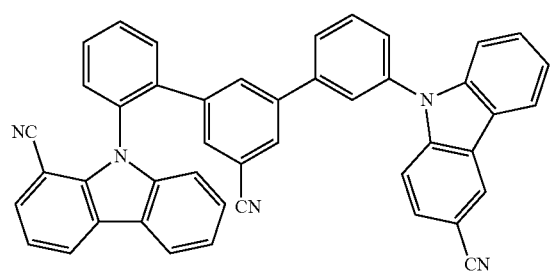
2223
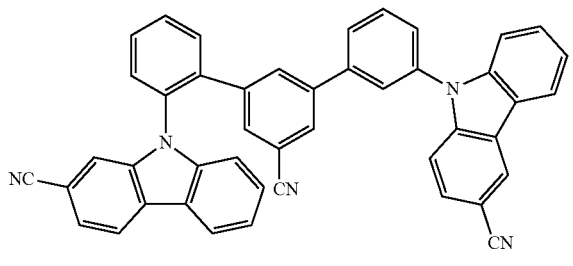
2224
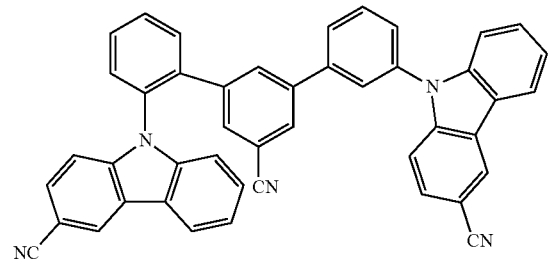
2225
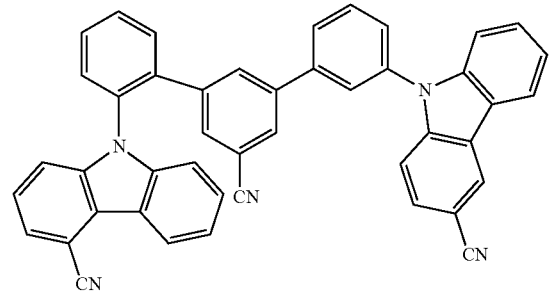
594
-continued
2226
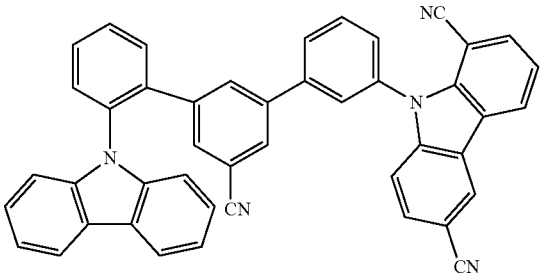
2227
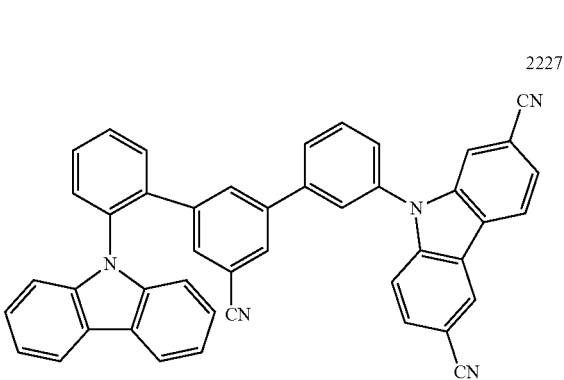
2228
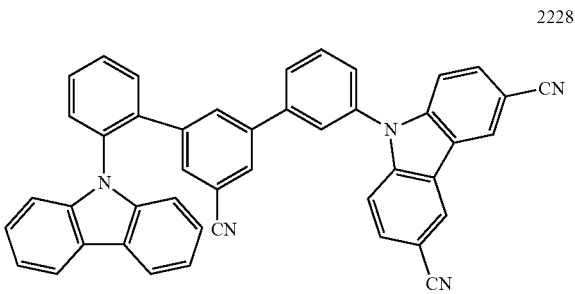
2229
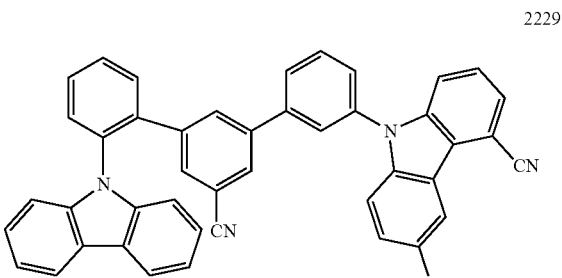
2230
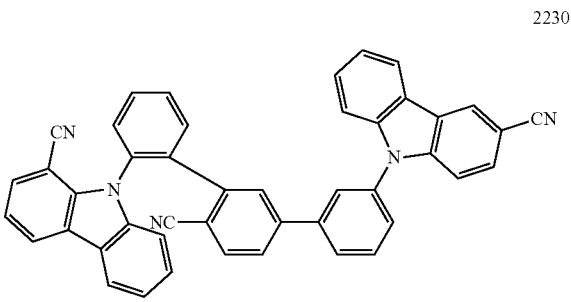

2231
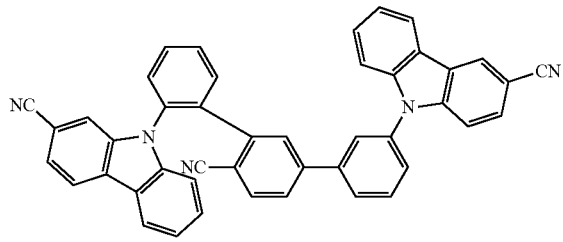
2232
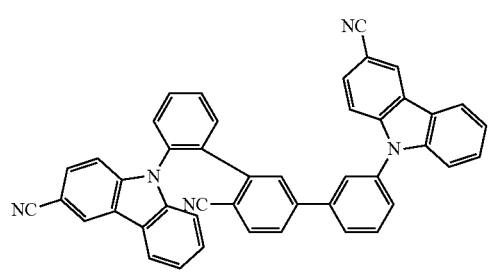
2233
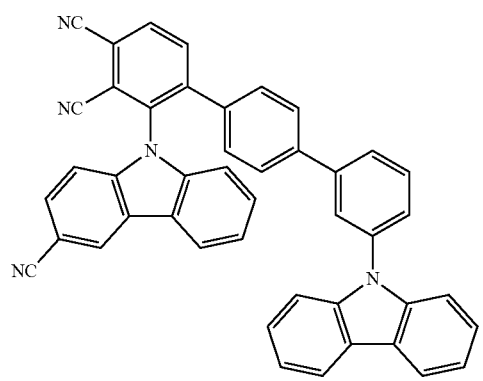
2234
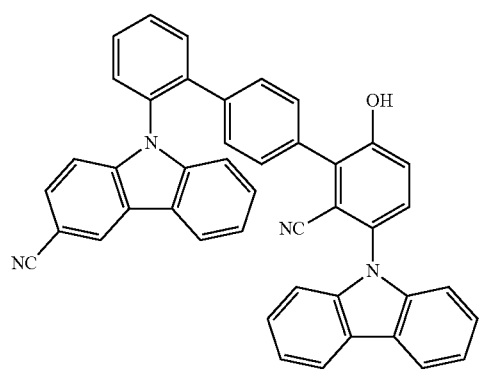
2235
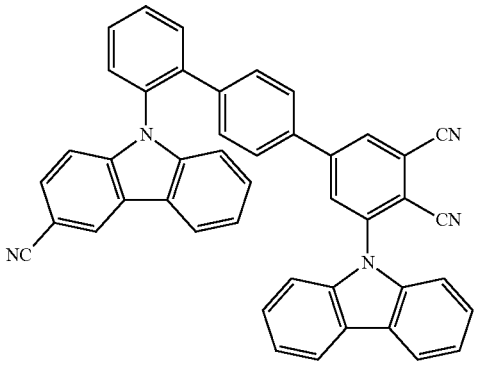
2236
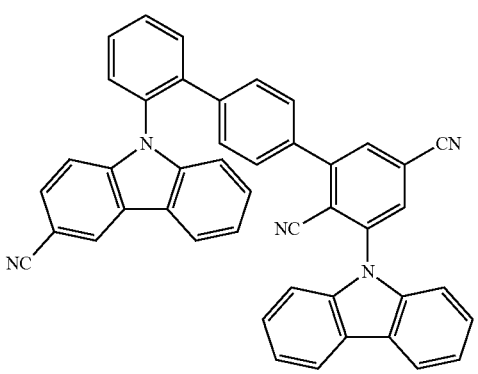
2237
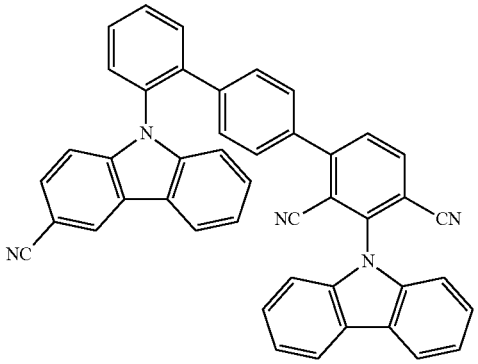
2238
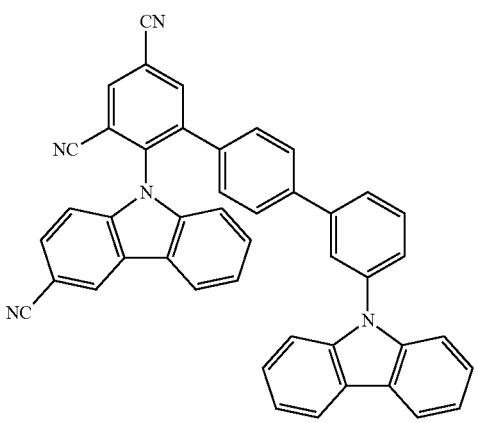

597 -continued
598 -continued

| 599 -continued | 600 -continued |
|---|---|
| 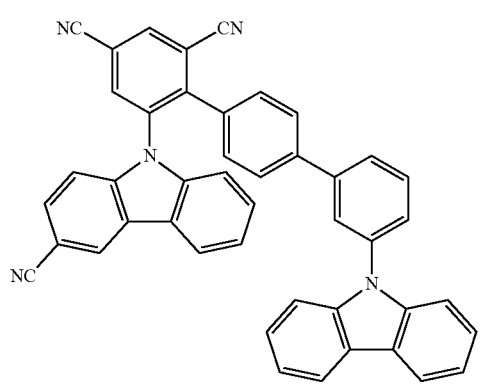 2247 | 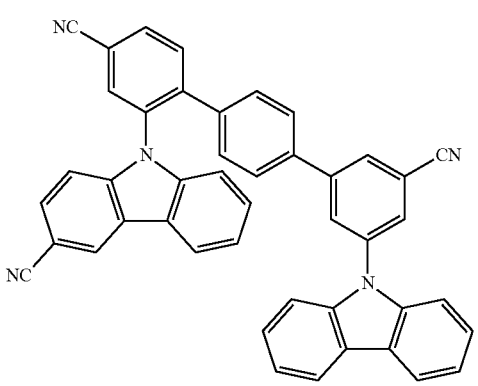 2251 |
| 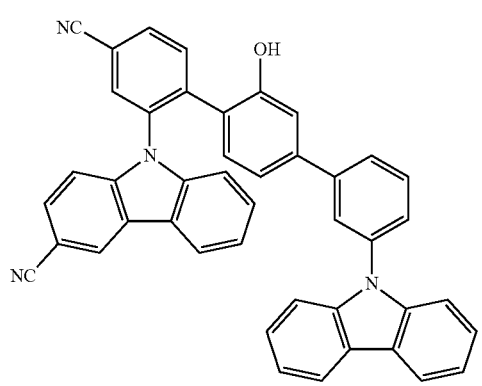 2248 | 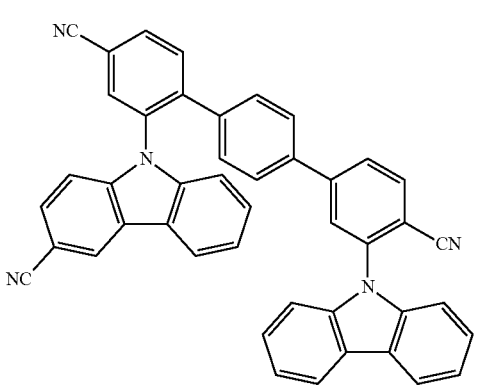 2252 |
| 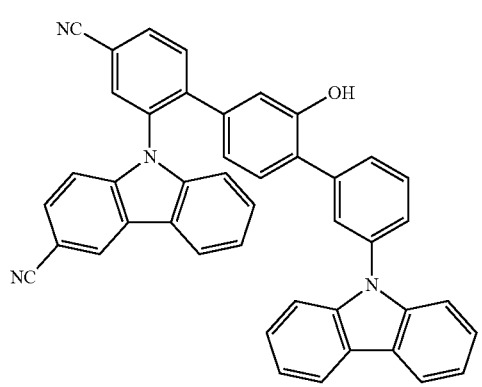 2249 | 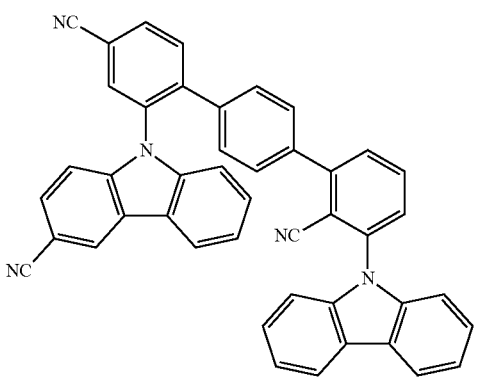 2253 |
| 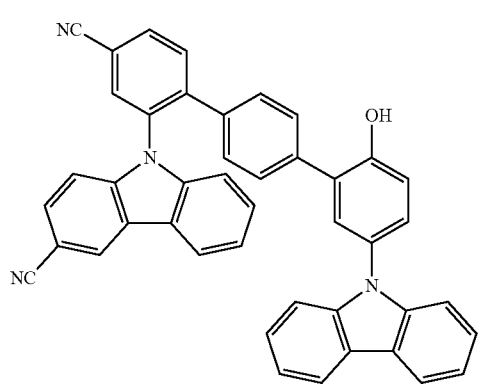 2250 | 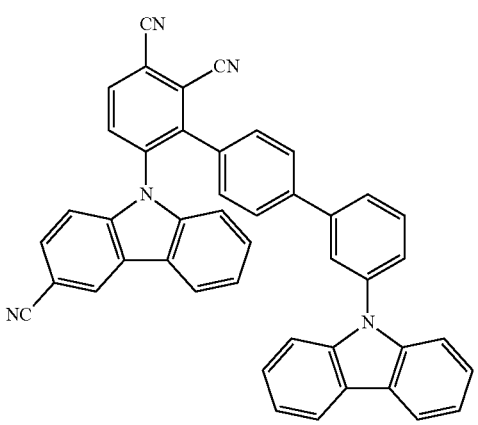 2254 |

-continued
2255
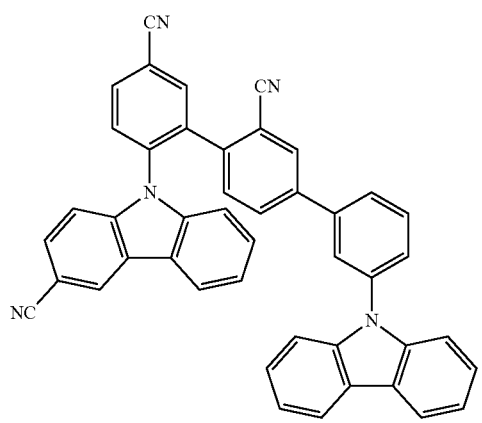
2256
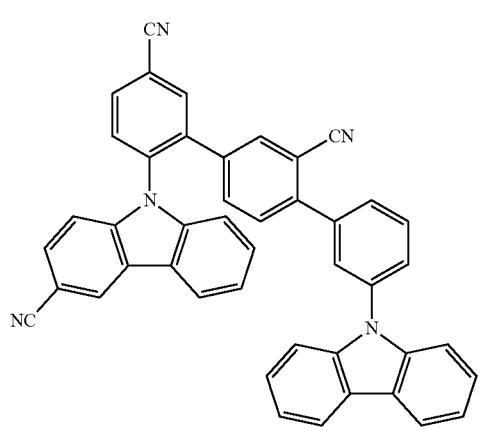
2257
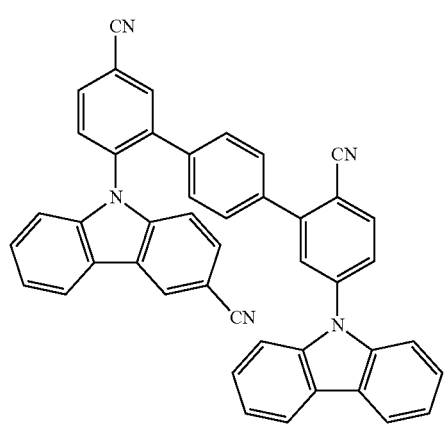
-continued
2258
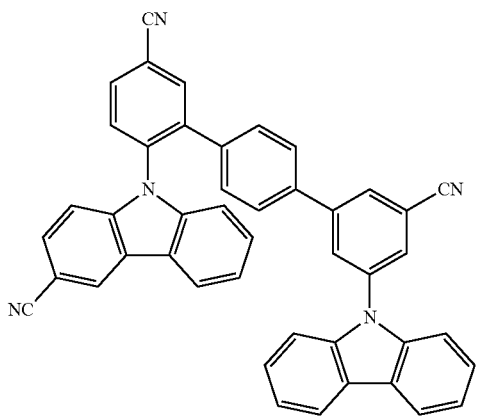
2259
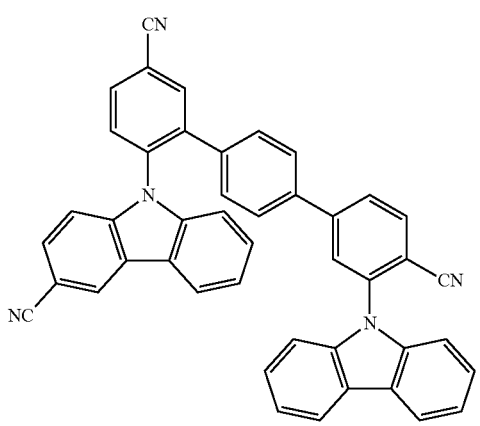
2260
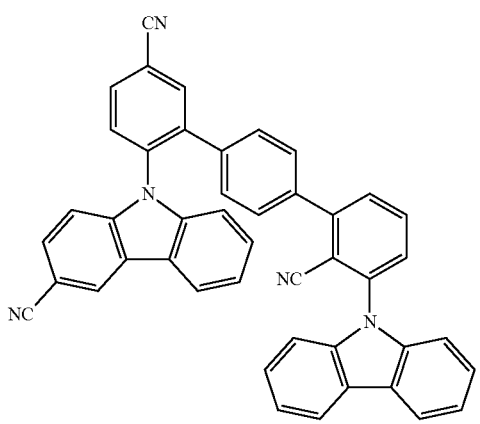
2261
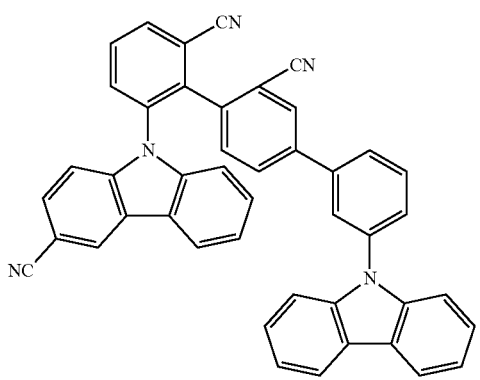

2262
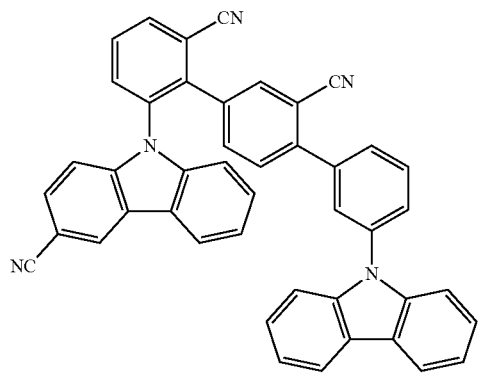
2263
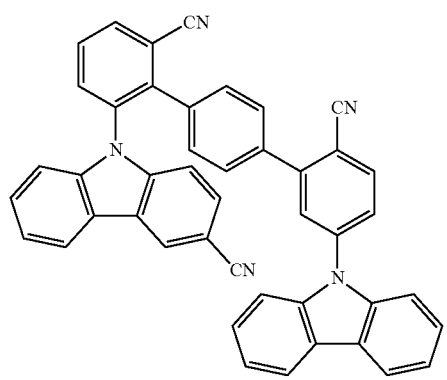
2264
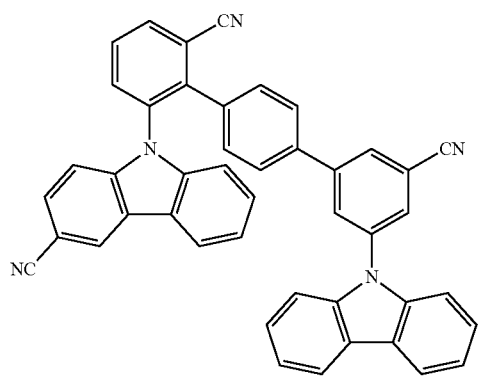
2265
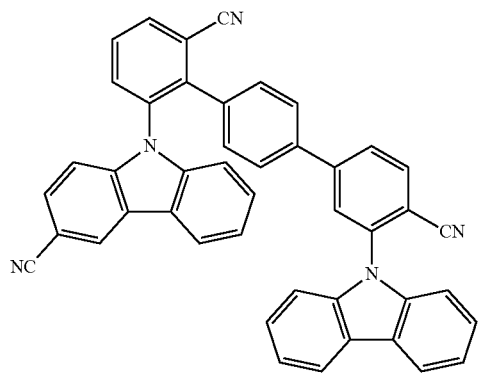
2266
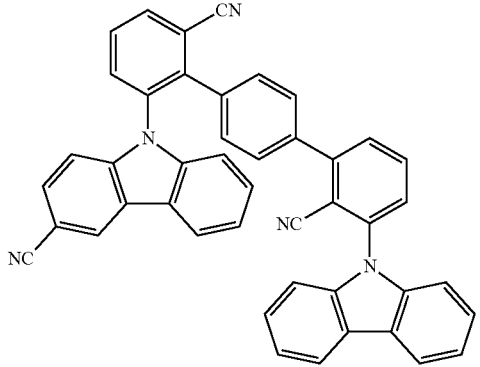
2267
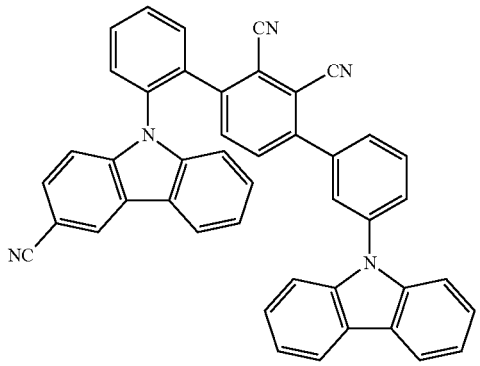
2268
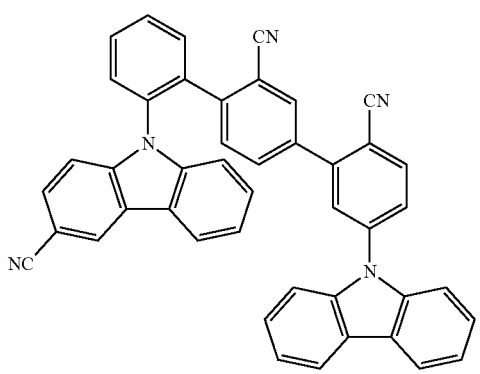
2269
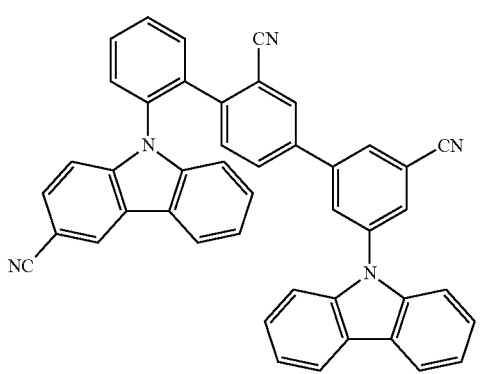

-continued
2270
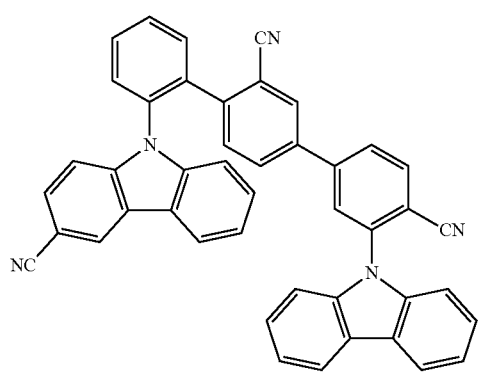
2271
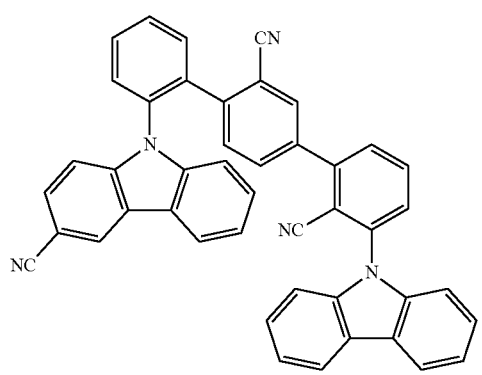
2272
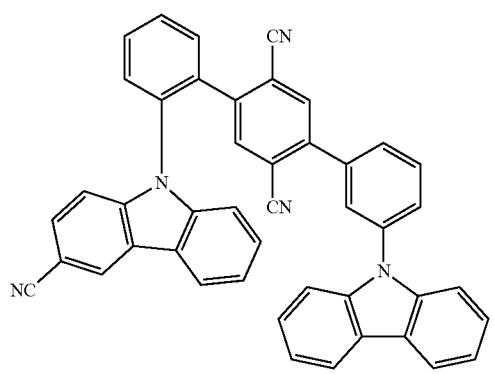
2273
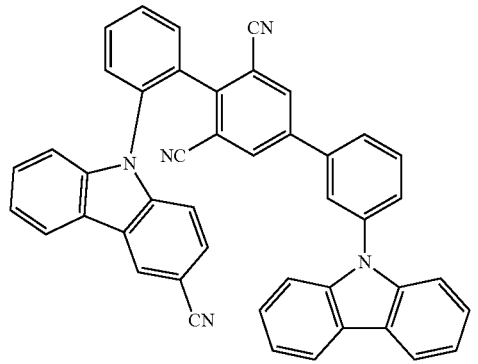
-continued
2274
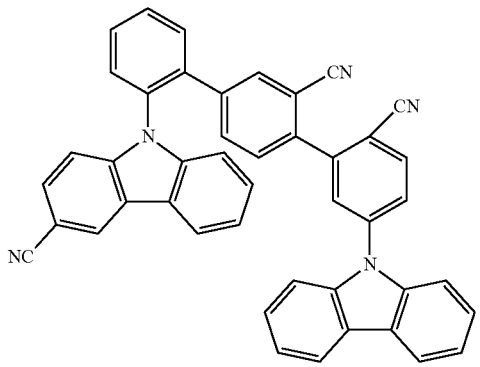
2275
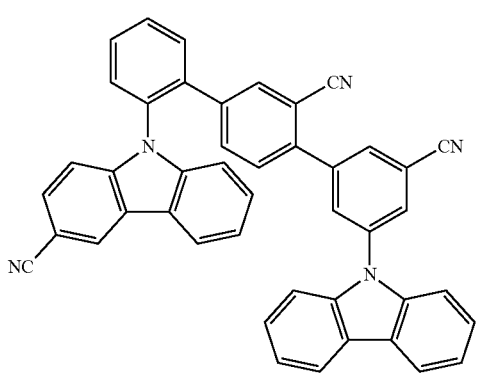
2276
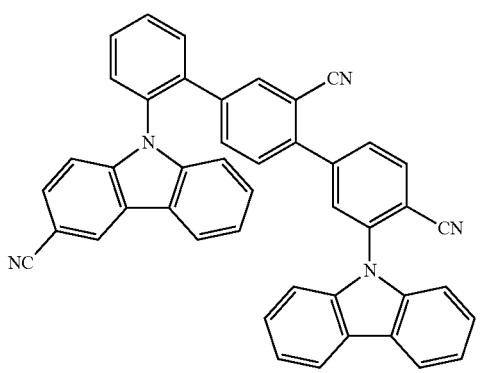
2277
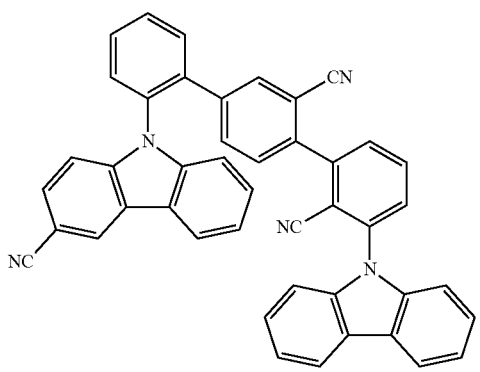

2278
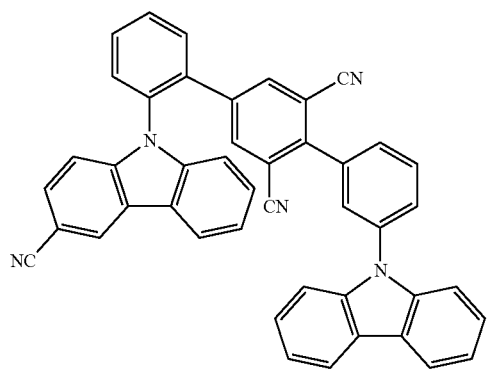
2279
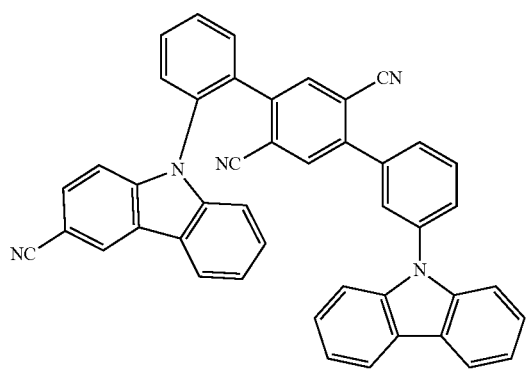
2280
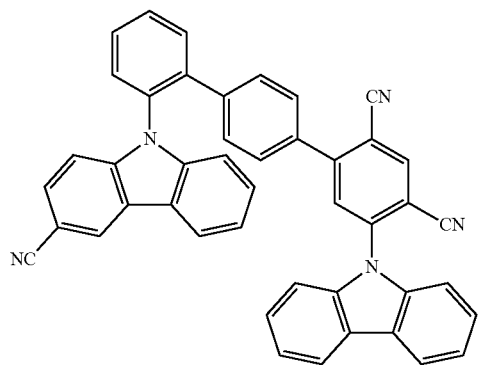
2281
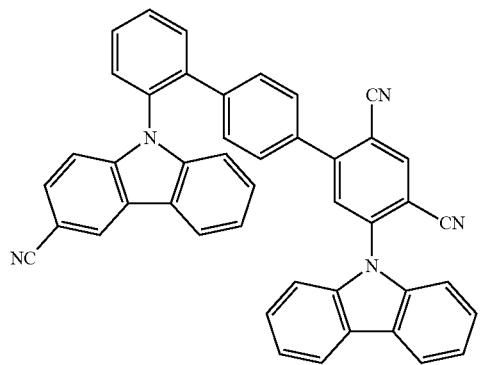
2282
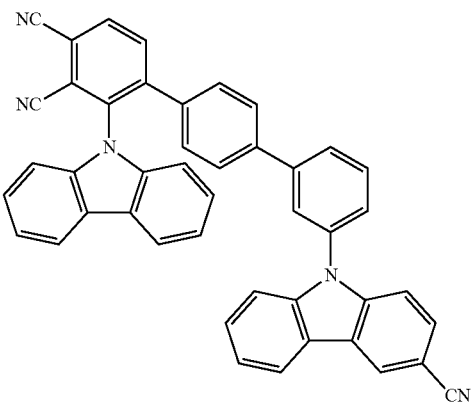
2283
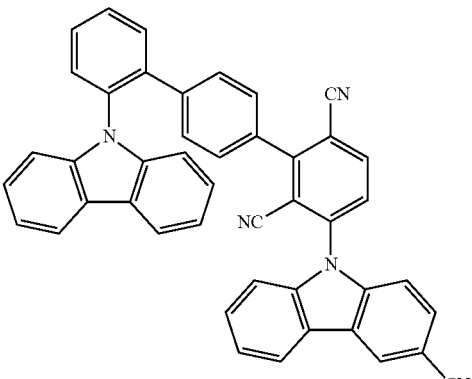
2284
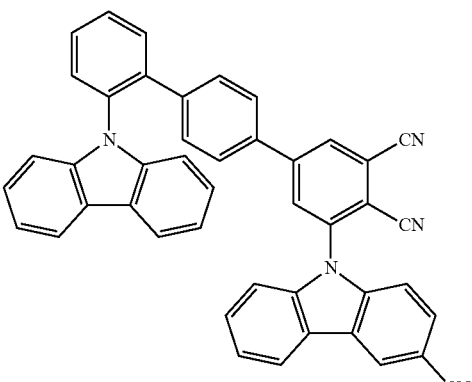
2285
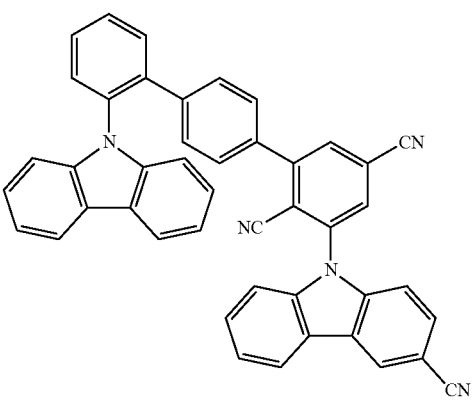

| 2286 | 2290 |
|---|---|
| 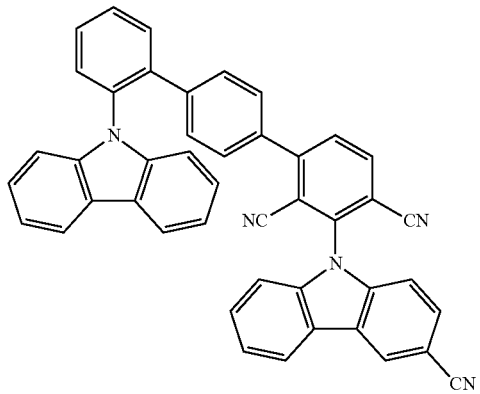 | 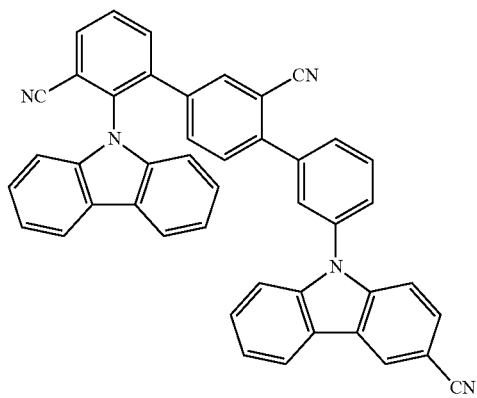 |
| 2287 | 2291 |
| 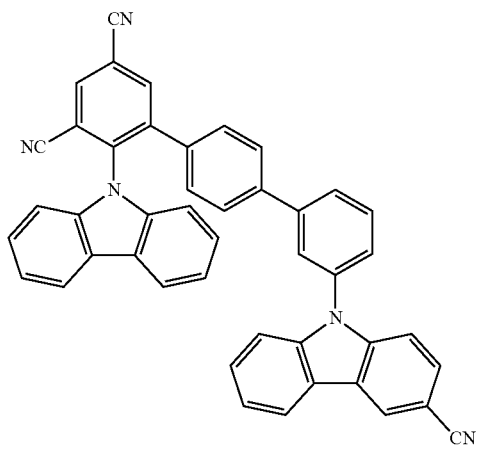 | 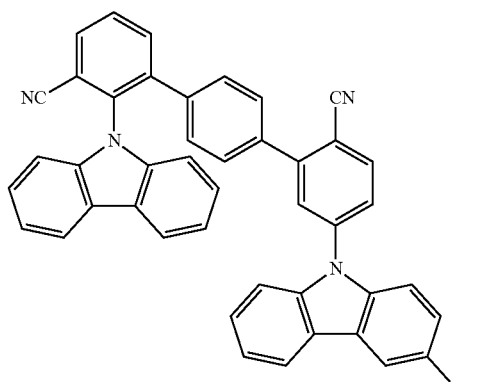 |
| 2288 | 2292 |
| 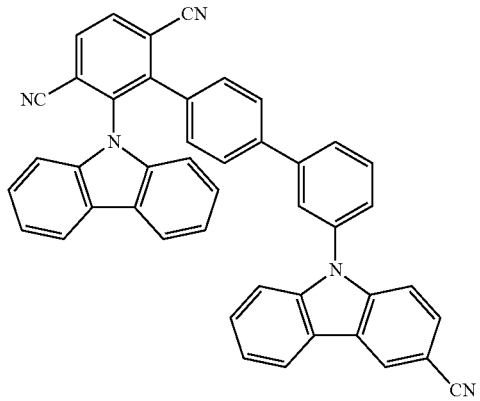 | 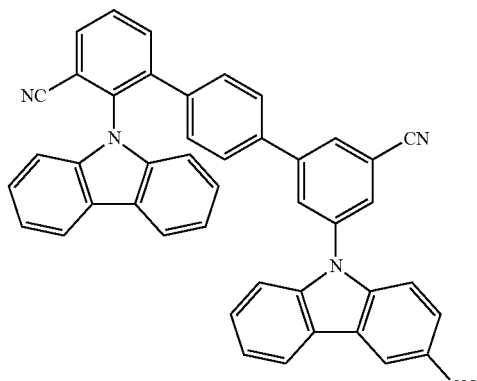 |
| 2289 | 2293 |
| 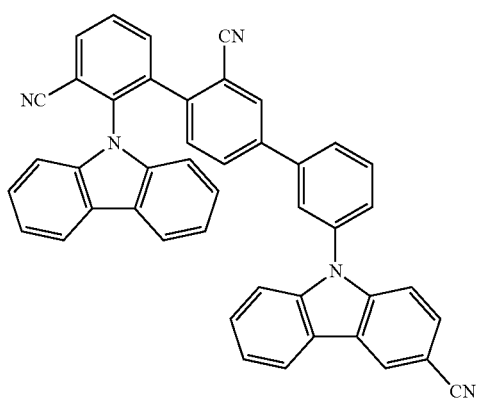 | 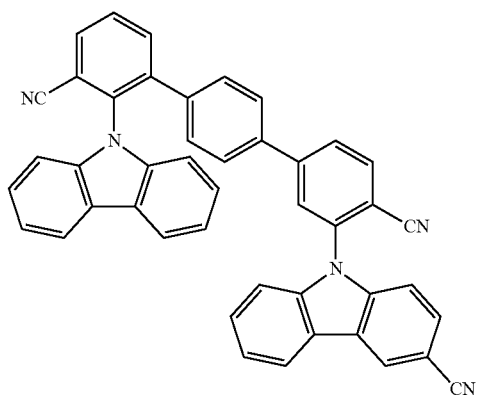 |

611
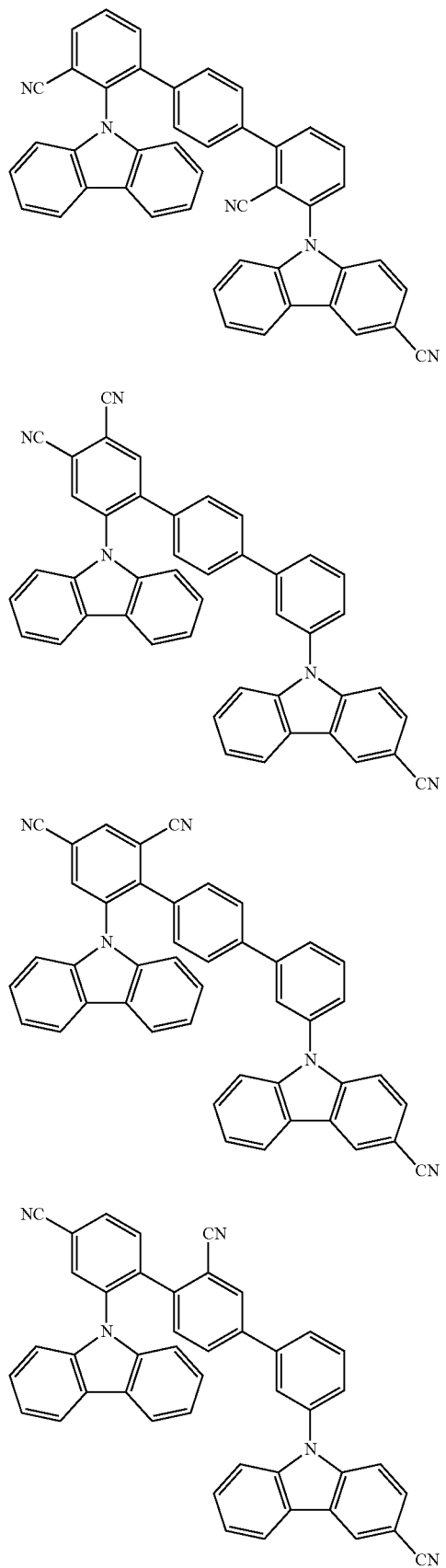
2294
2295
2296
2297
612
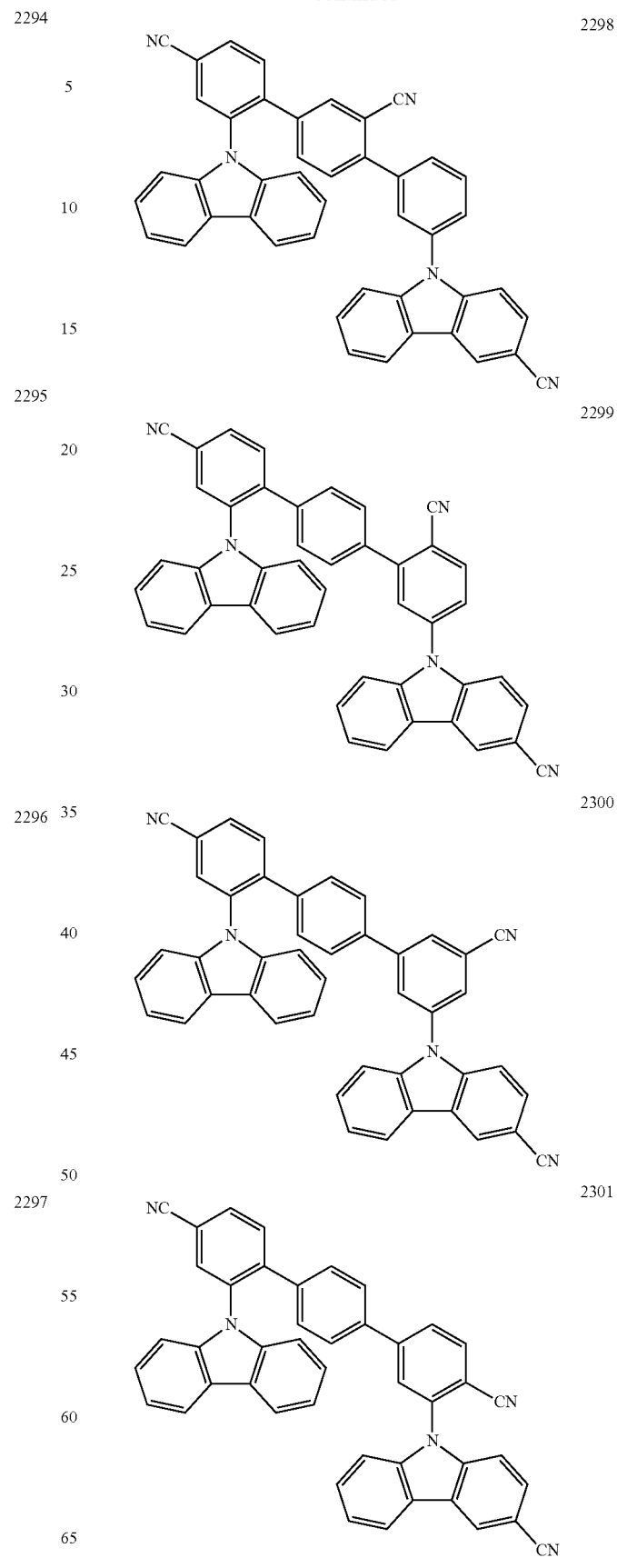
2298
2299
2300
2301

613
-continued
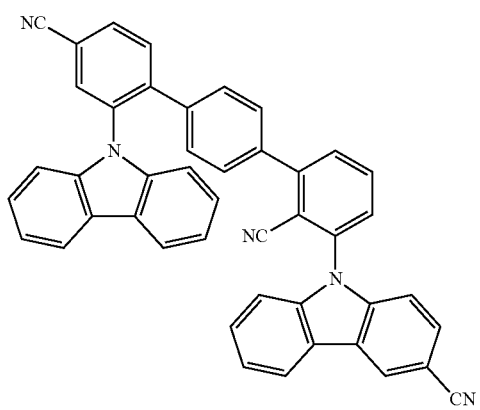
2302
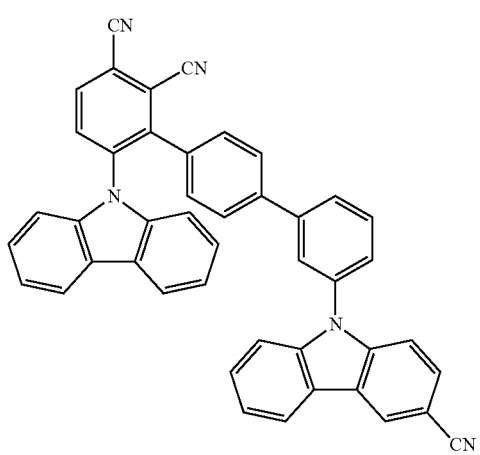
2303
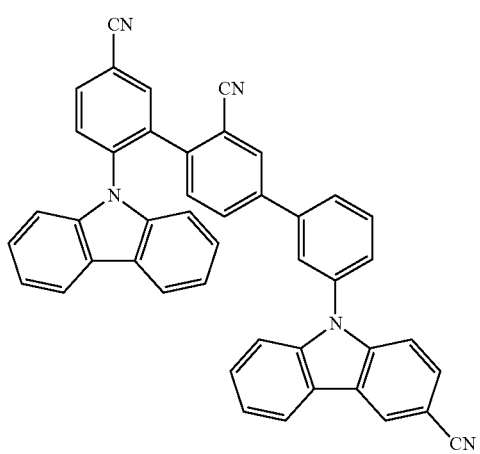
2304
614
-continued
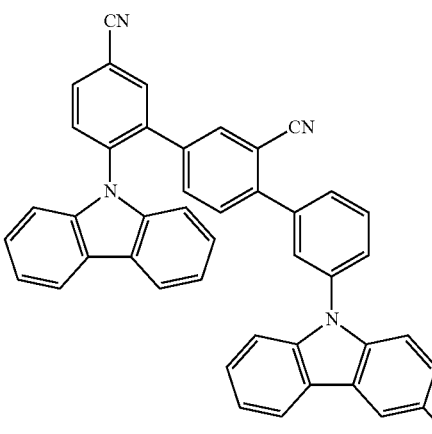
2305
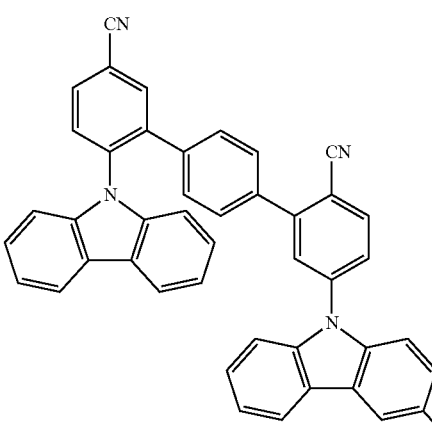
2306
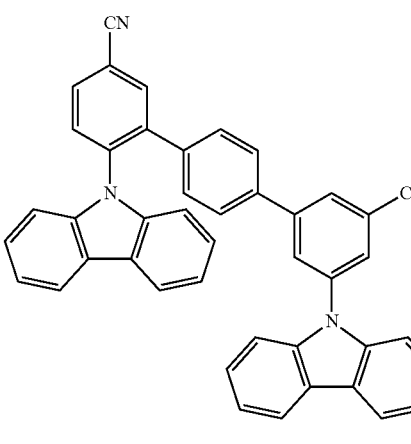
2307

-continued
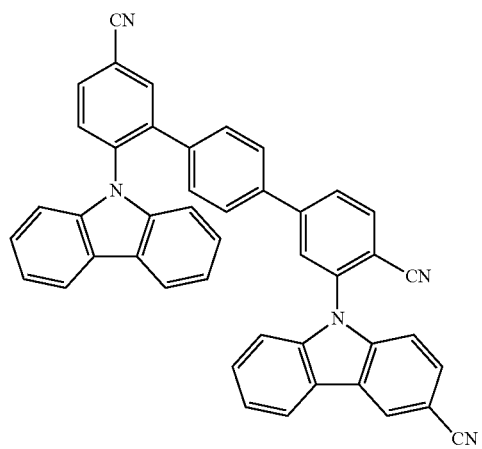
2308
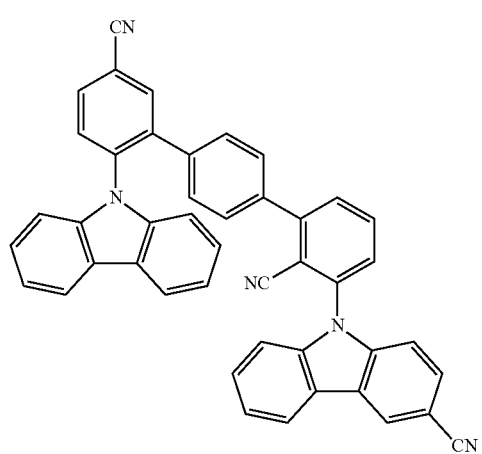
2309
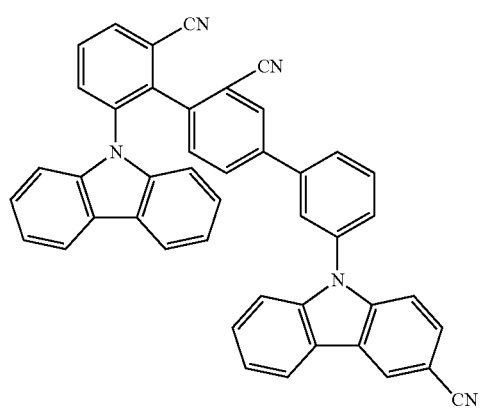
2310
-continued
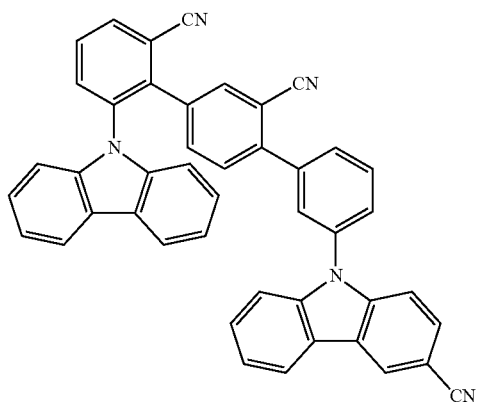
2311
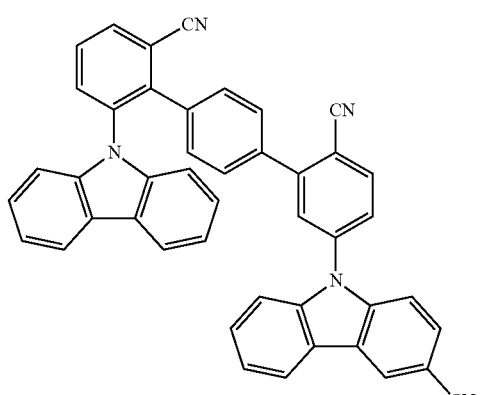
2312
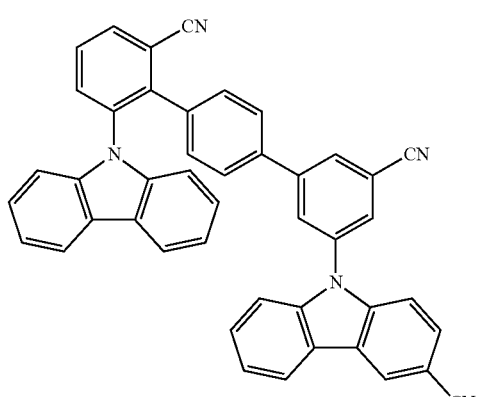
2313
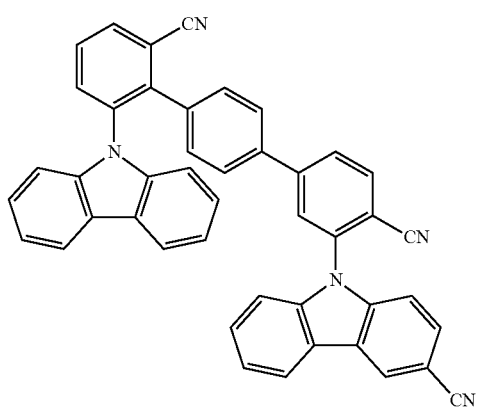
2314

2315 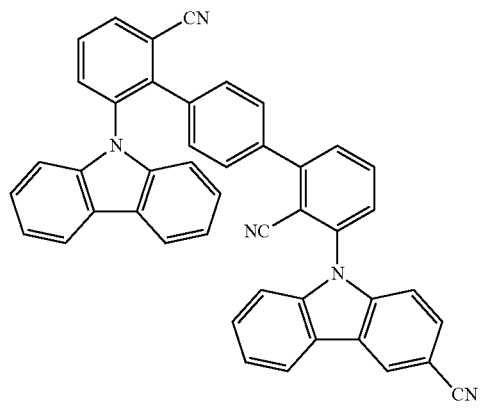
2316 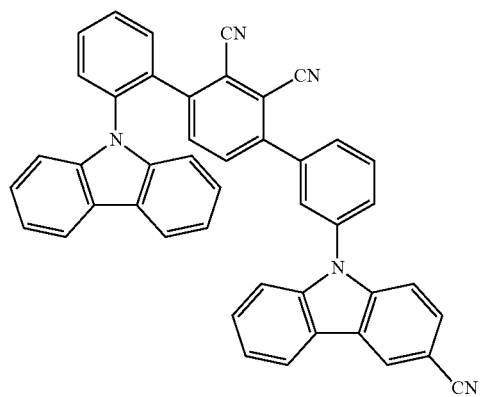
2317 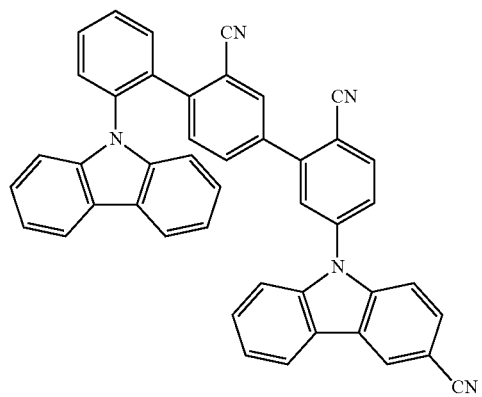
2320 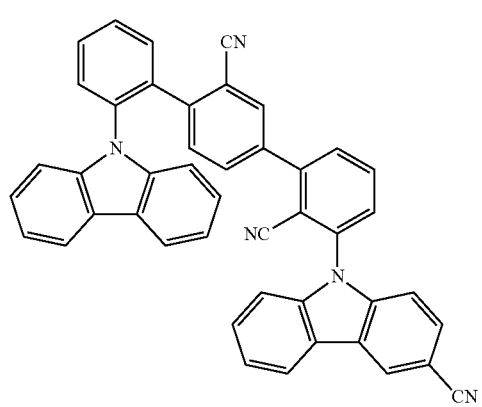
2321 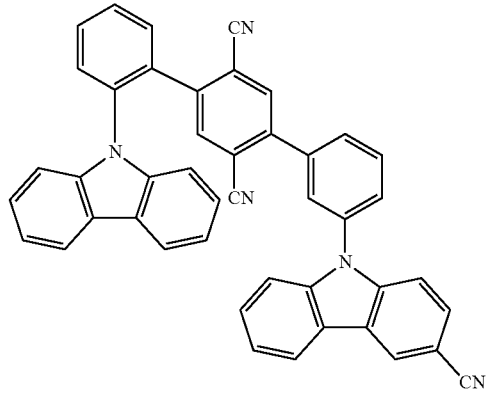
2322 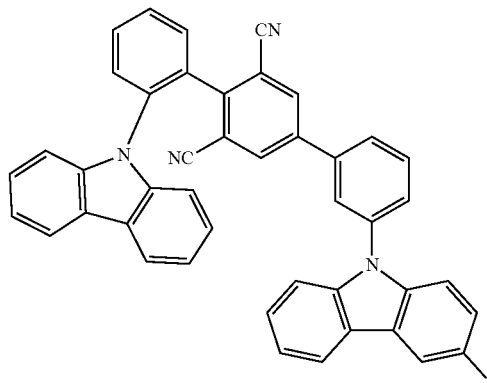
2323 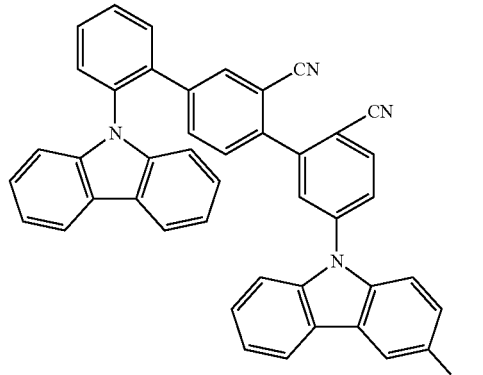
2324 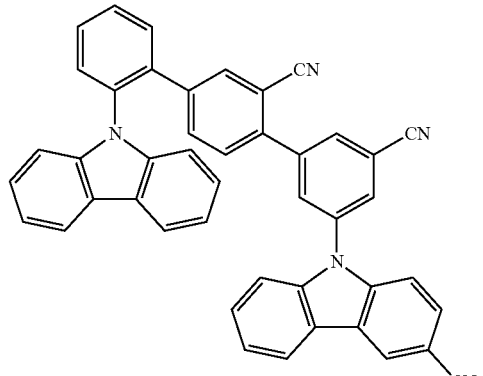

619
-continued
2325
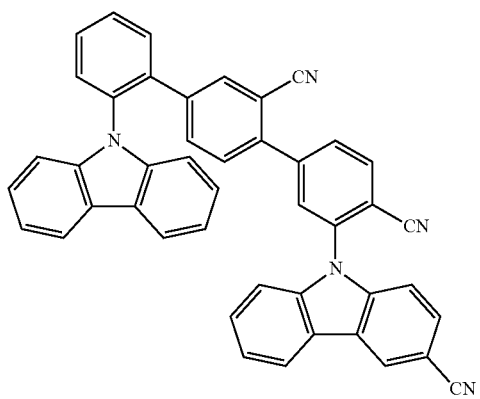
2326
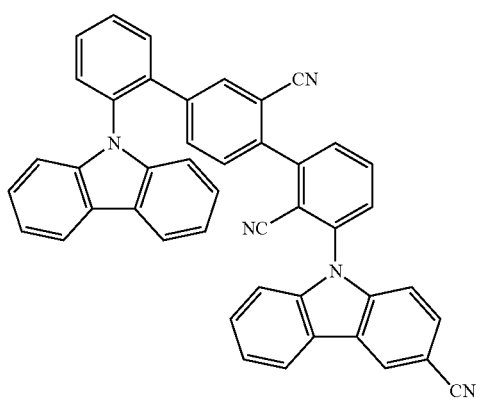
2327
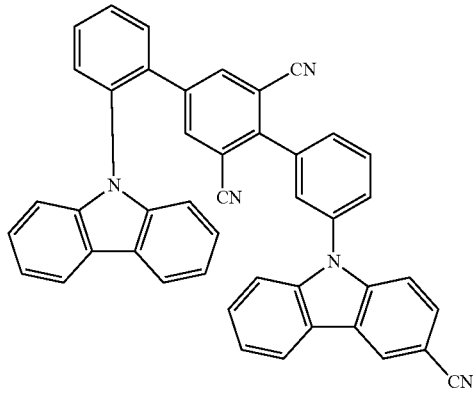
2328
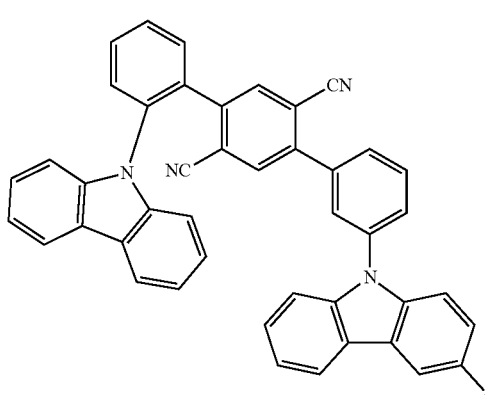
620
-continued
2329
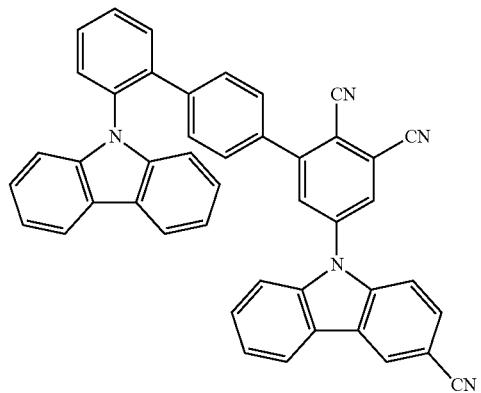
2330
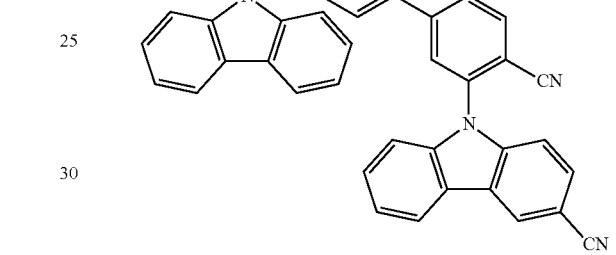
2331
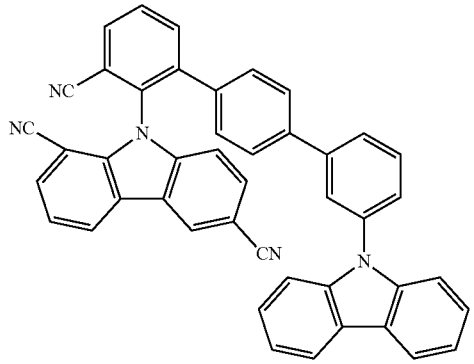
2332
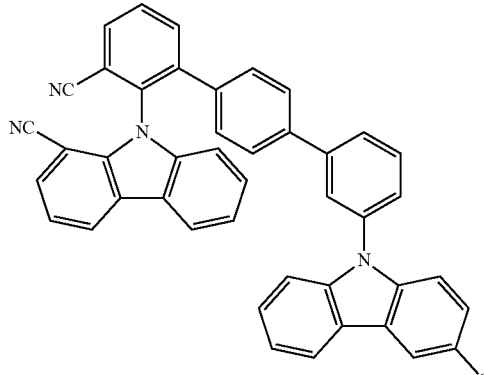

-continued
2333
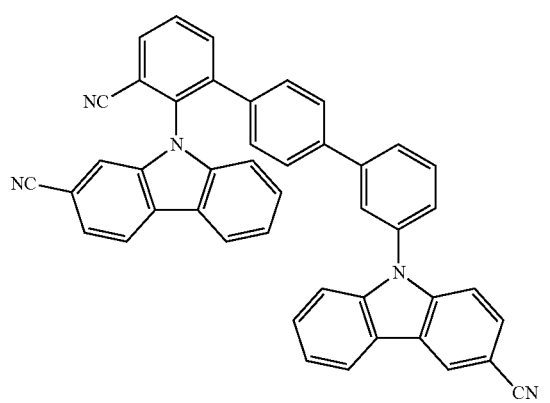
2334
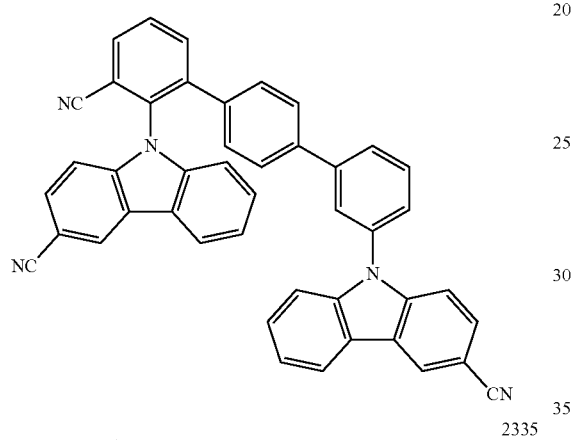
2335
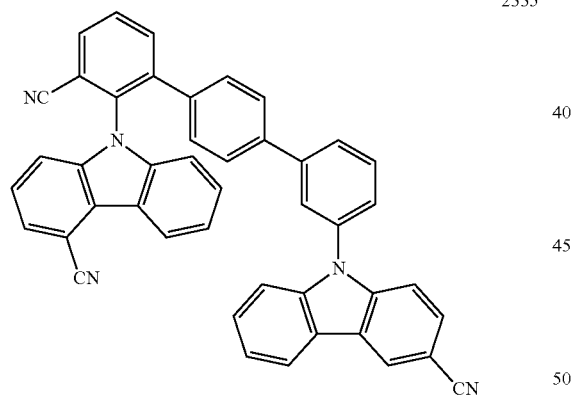
2336
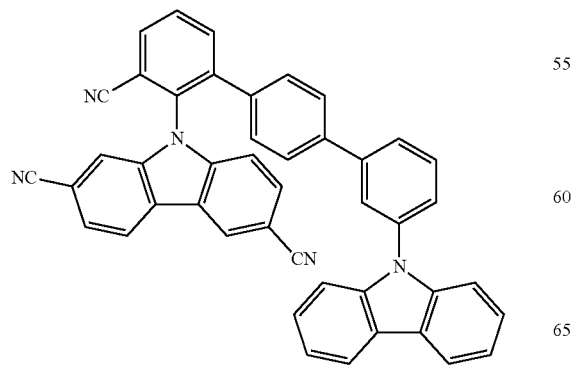
-continued
2337
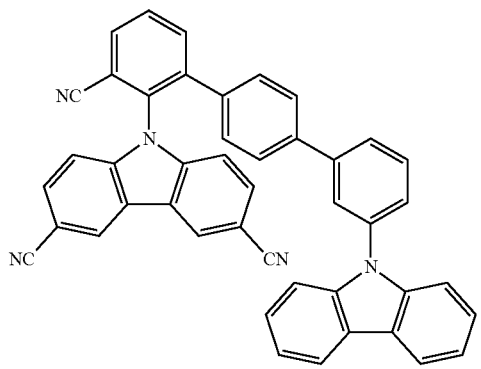
2338
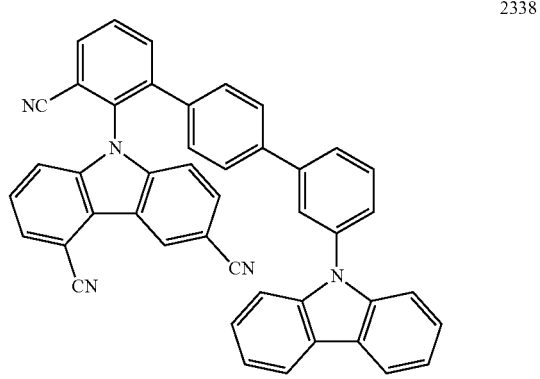
2339
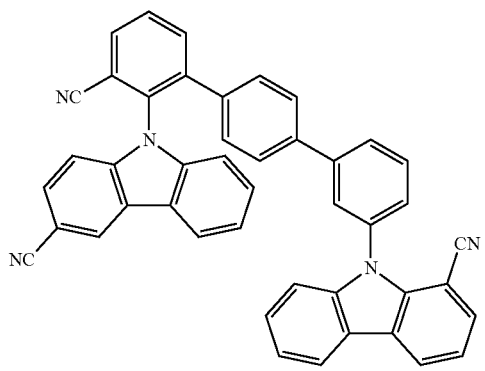
2340
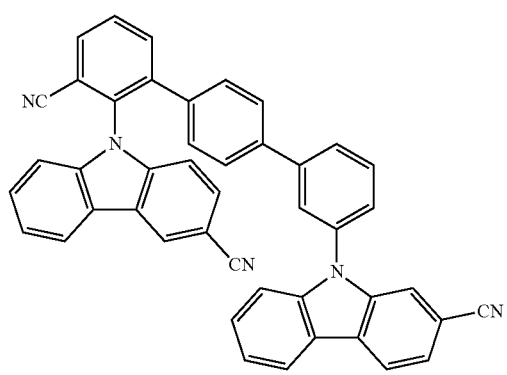

-continued
2341
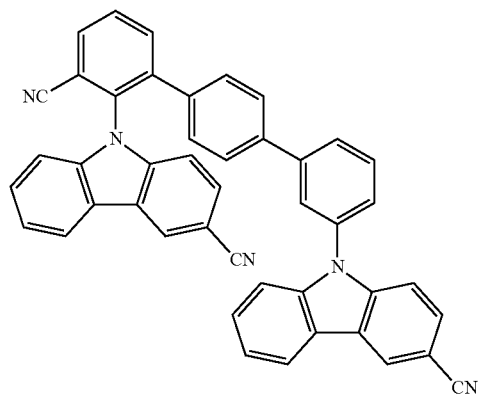
2342
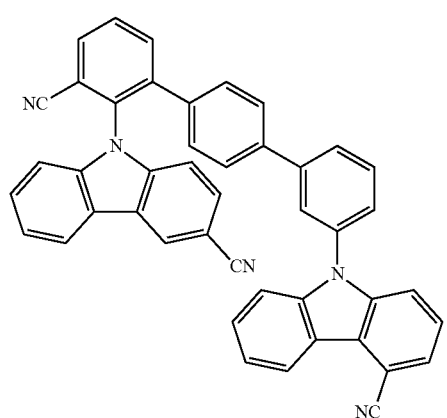
2343
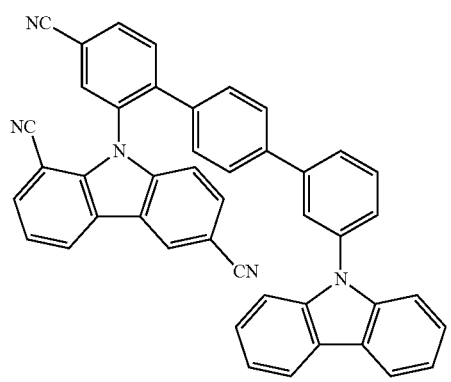
2344
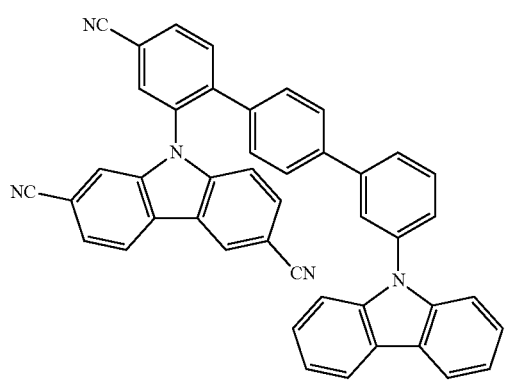
-continued
2345
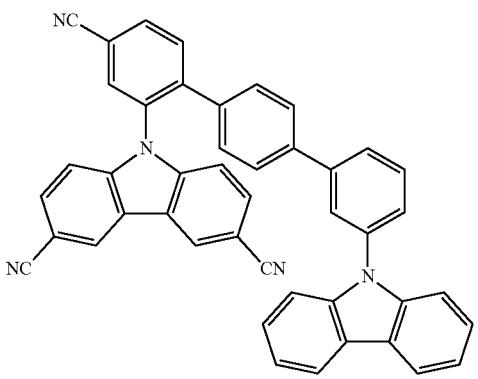
2346
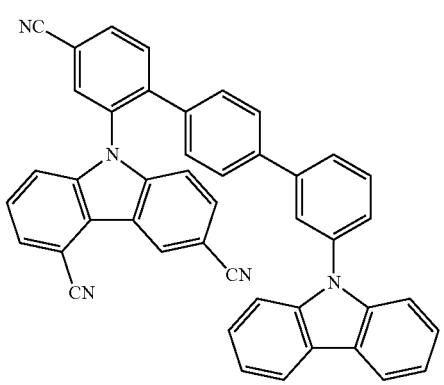
2347
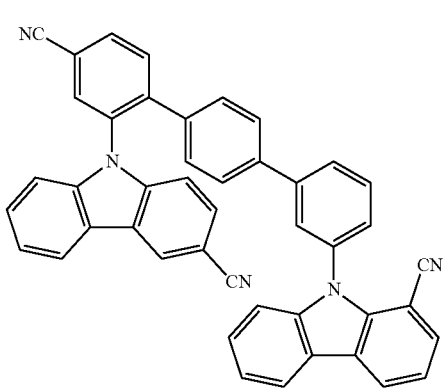
2348
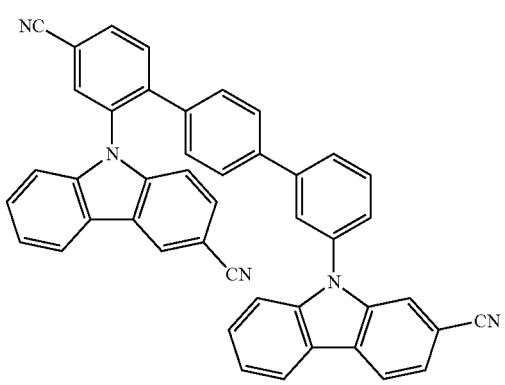

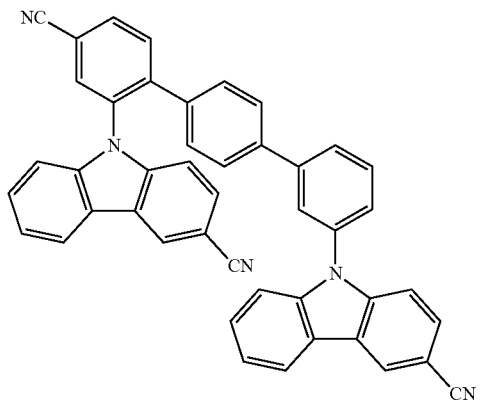
2349
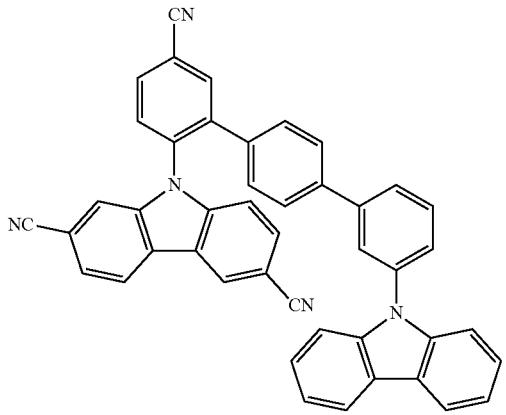
2352
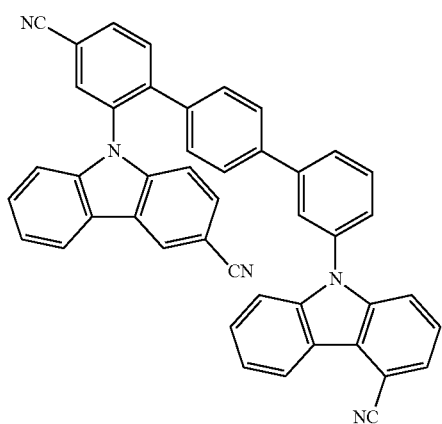
2350
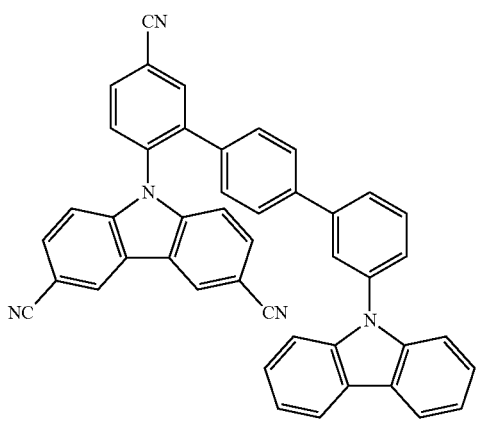
2353
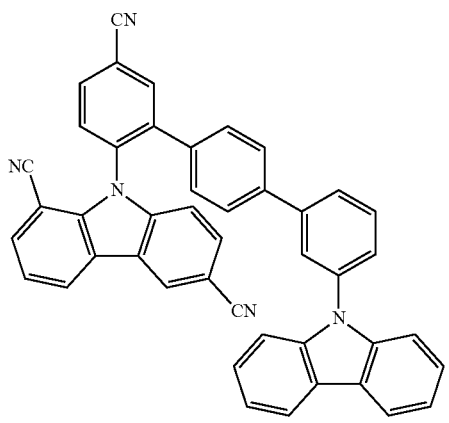
2351
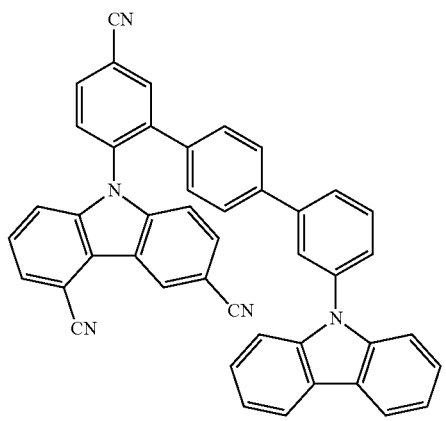
2354

-continued
2355
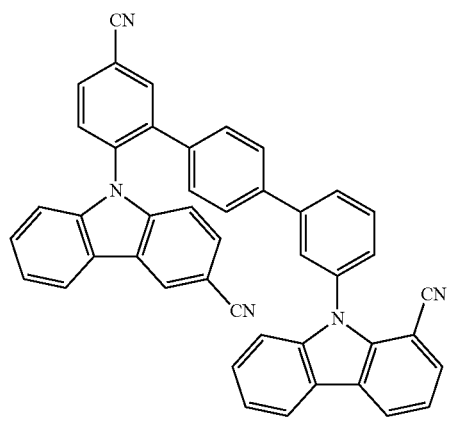
2356
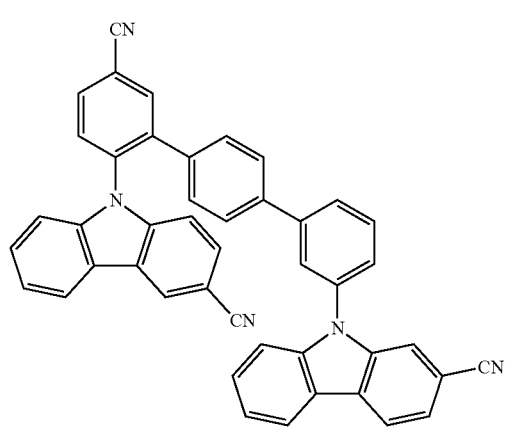
2357
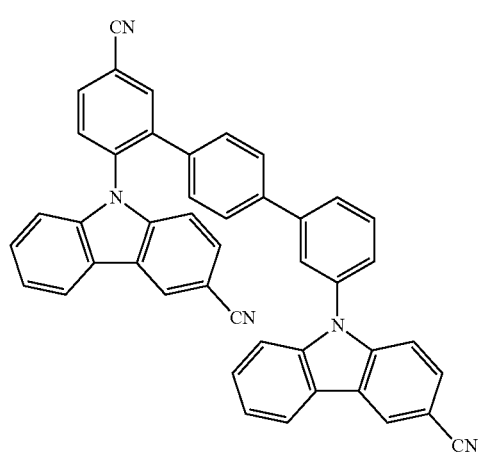
-continued
2358
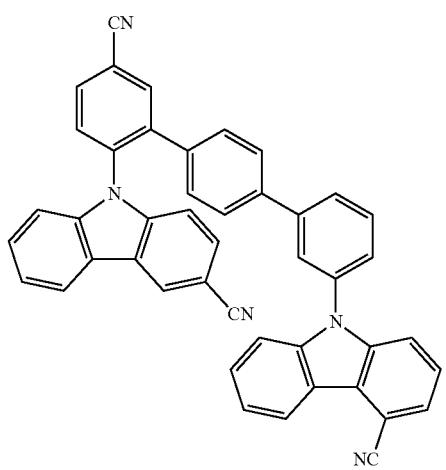
2359
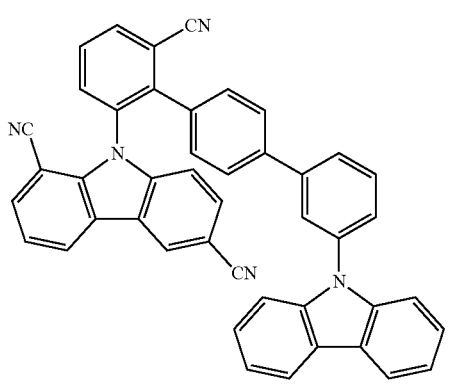
2360
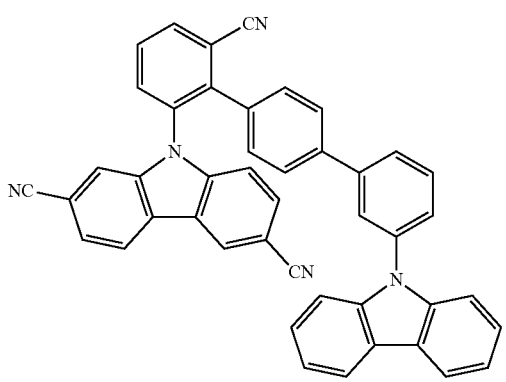
2361
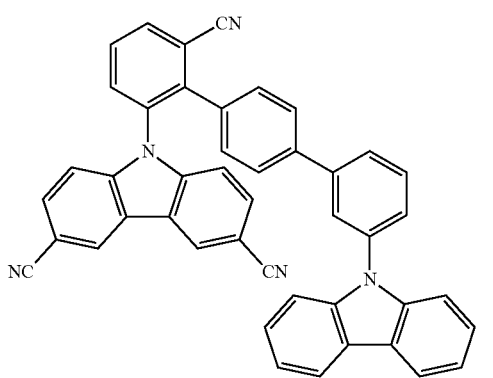

629
-continued
2362
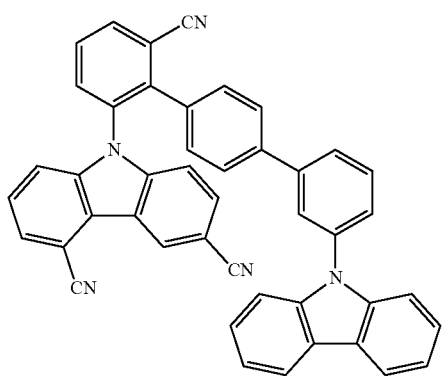
2363
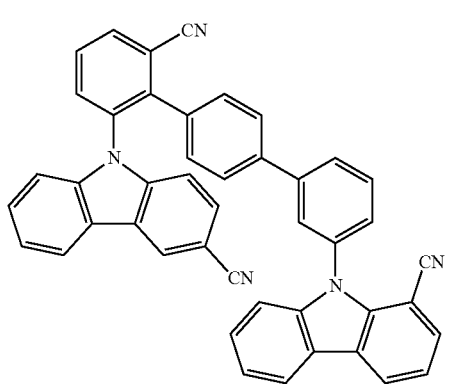
2364
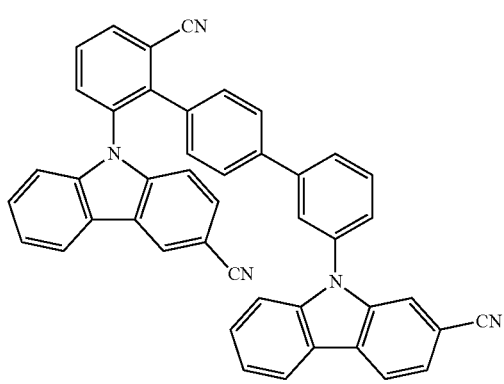
2365
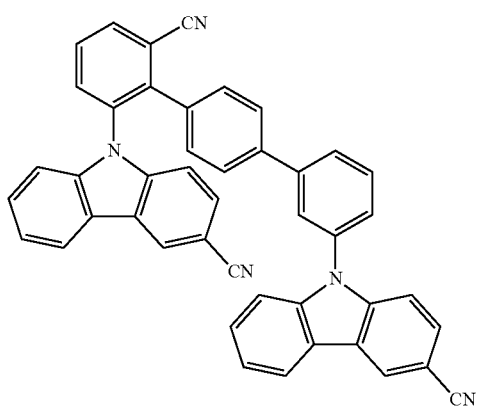
630
-continued
2366
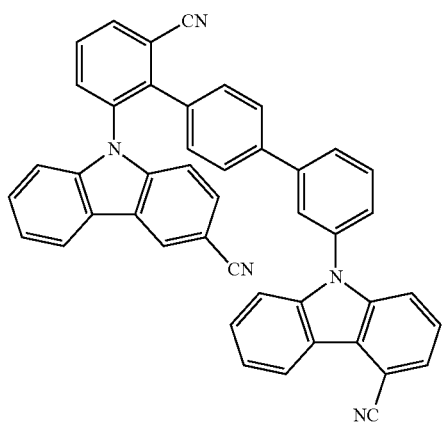
2367
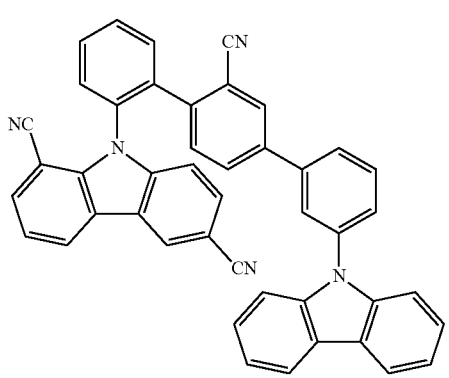
2368
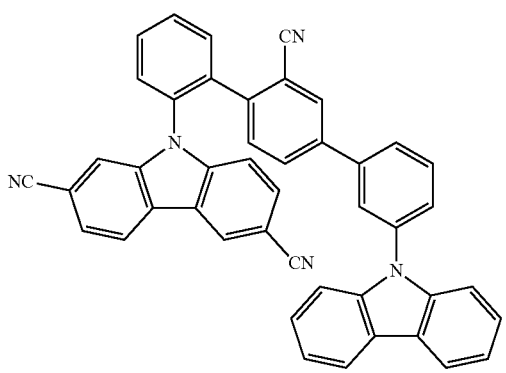
2369
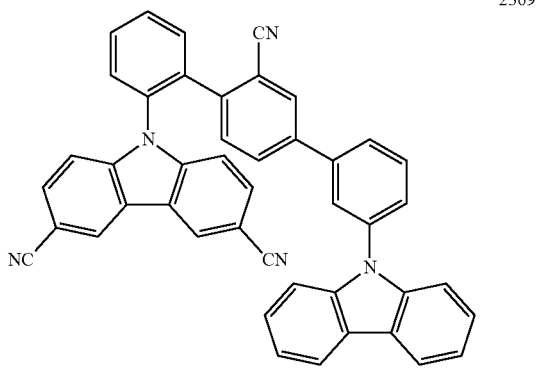

2370
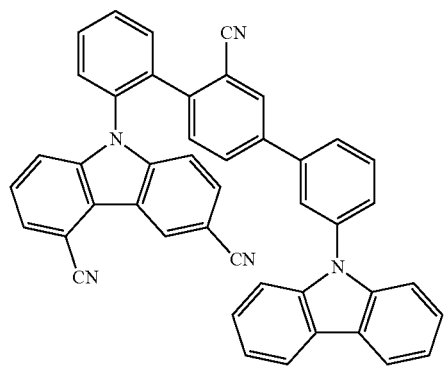
2371
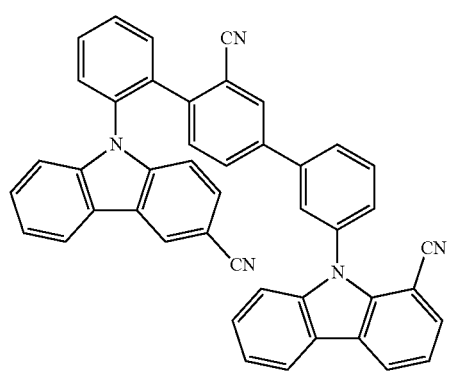
2372
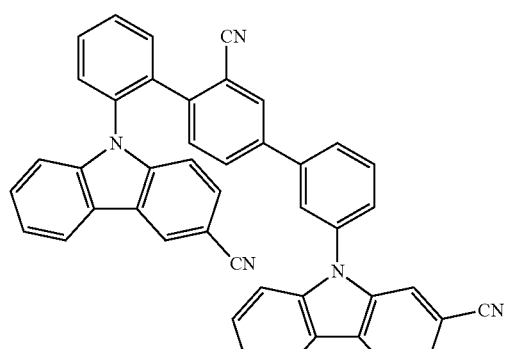
2373
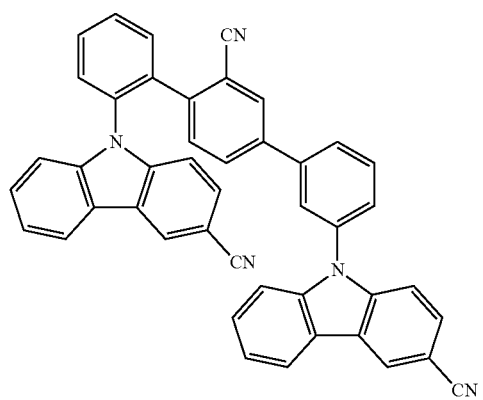
2374
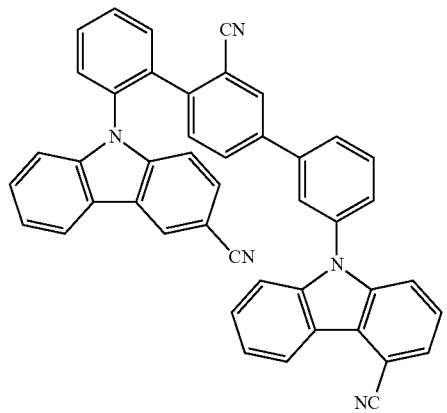
2375
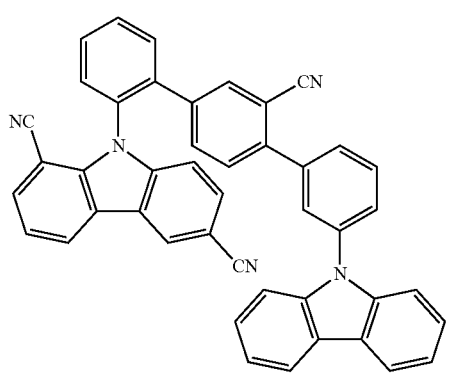
2376
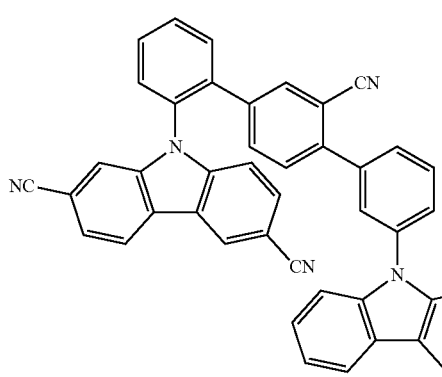
2377
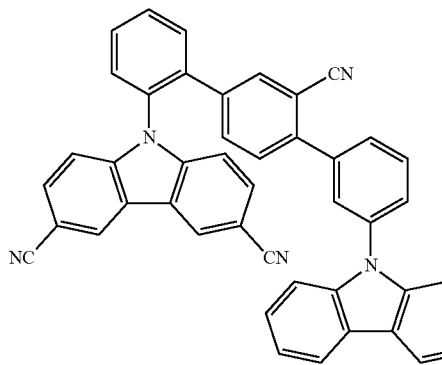

2378
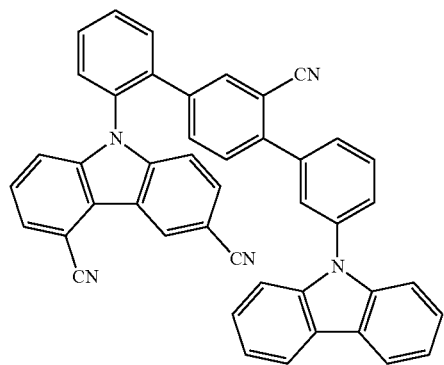
2379
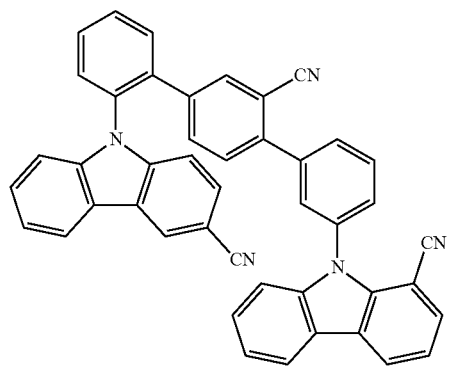
2380
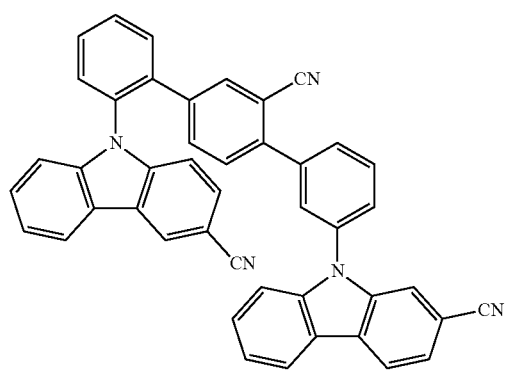
2381
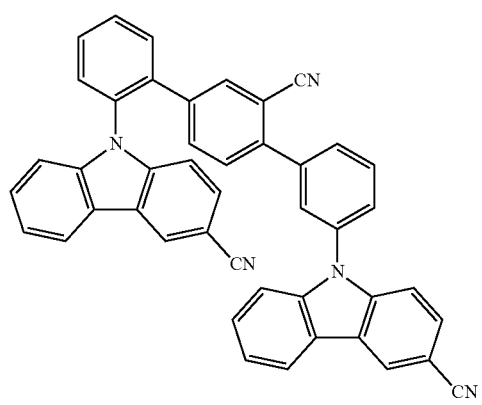
2382
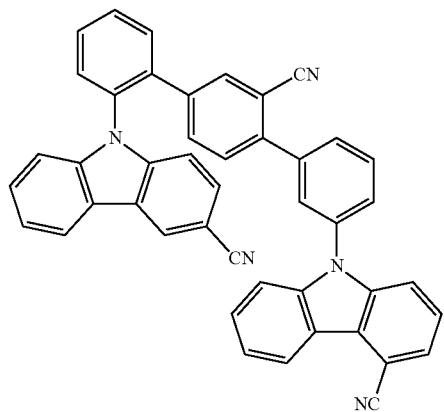
2383
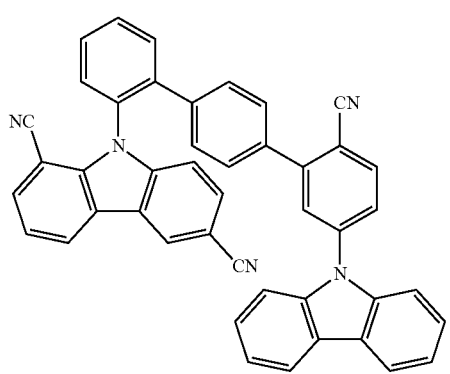
2384
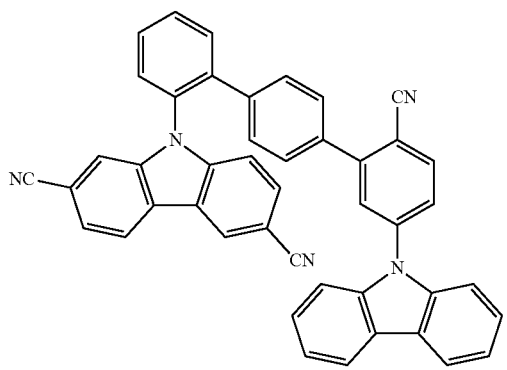
2385
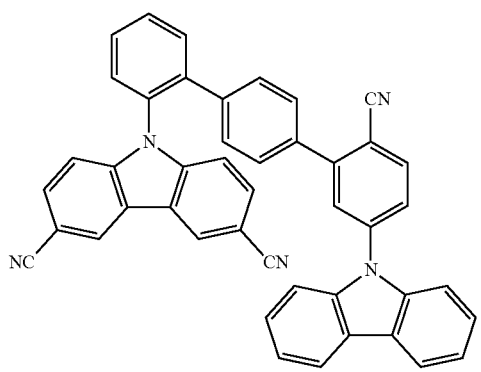

2386
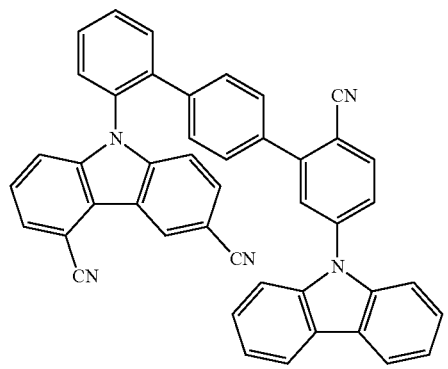
2387
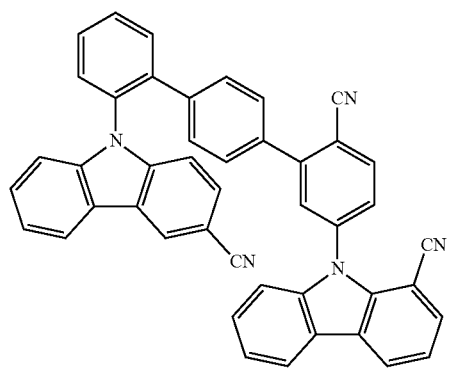
2388
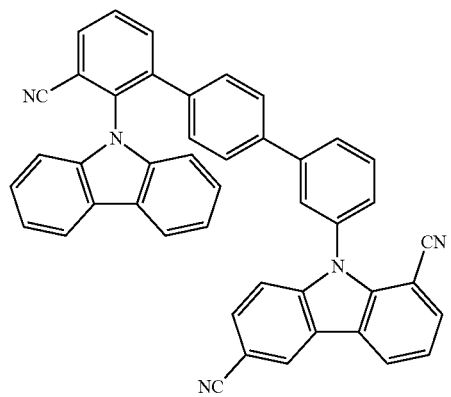
2389
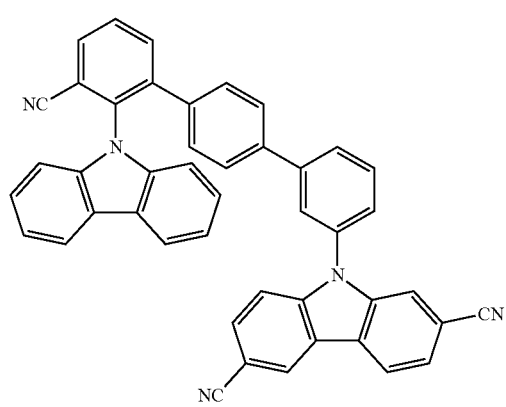
2390
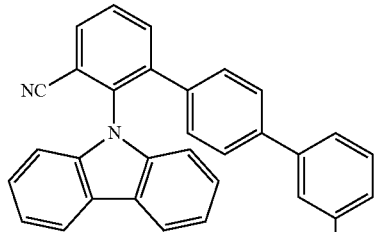
2391
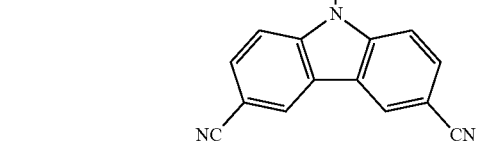
2392
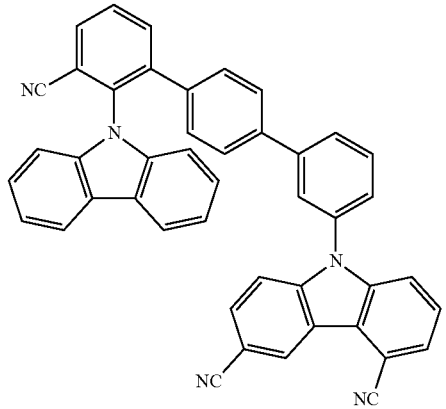
2393
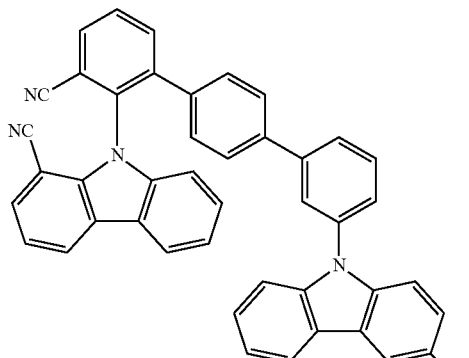

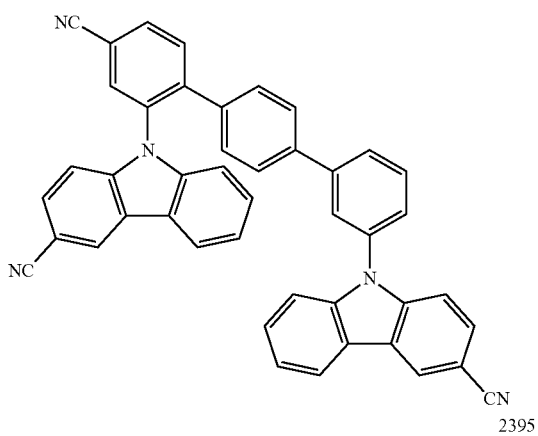
2394
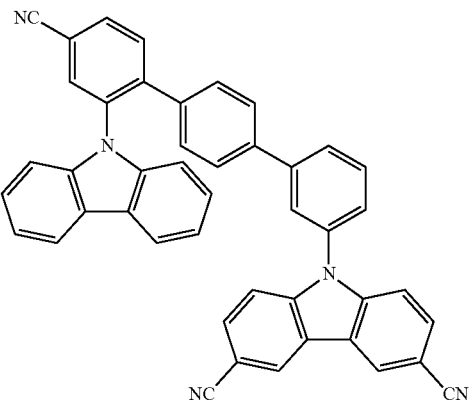
2398
2395
2399
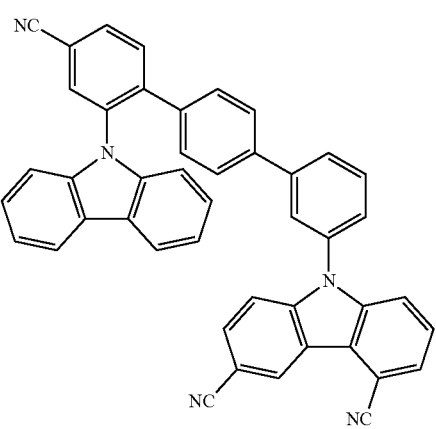
2396
2397
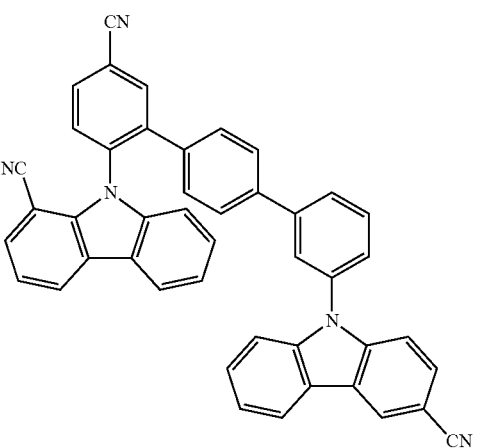
2400

-continued
2401
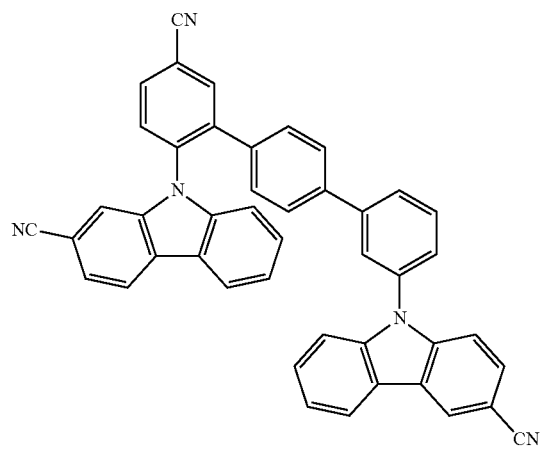
2402
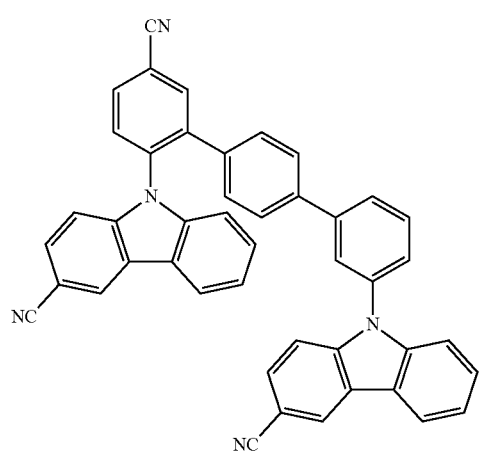
2403
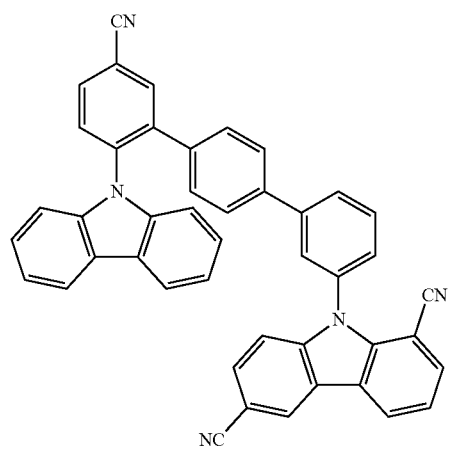
-continued
2404
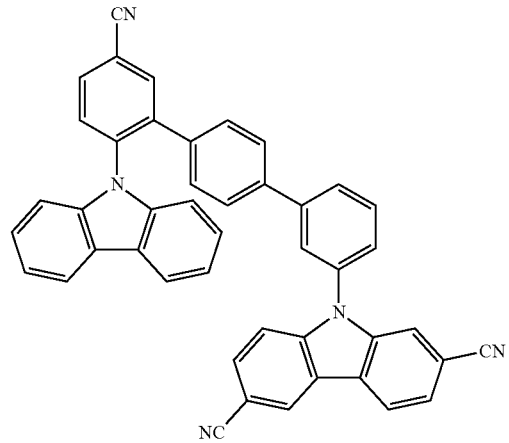
2405
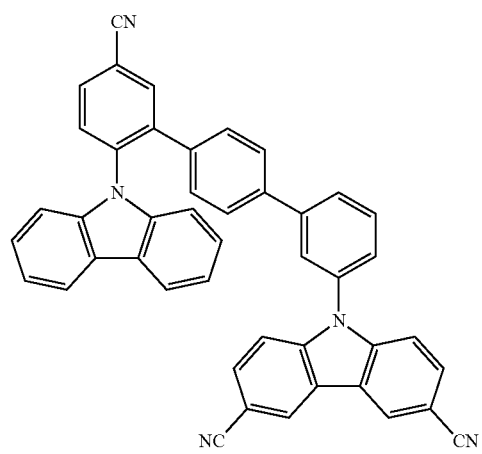
2406
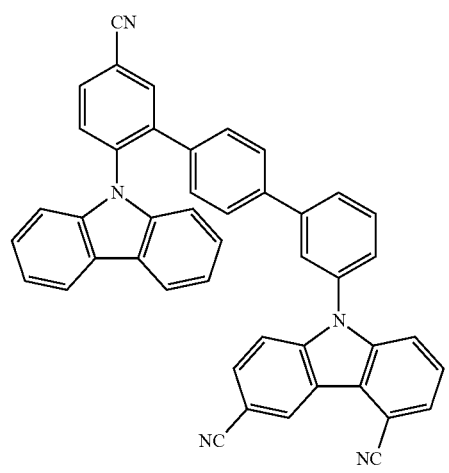

2407
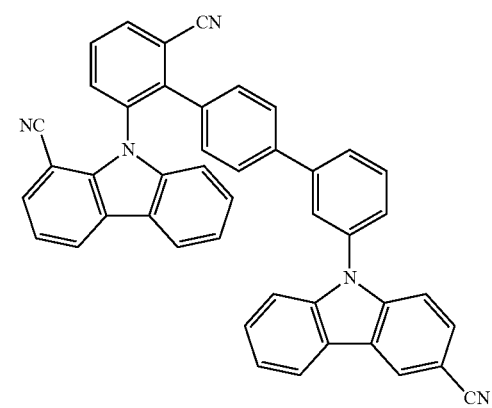
2408
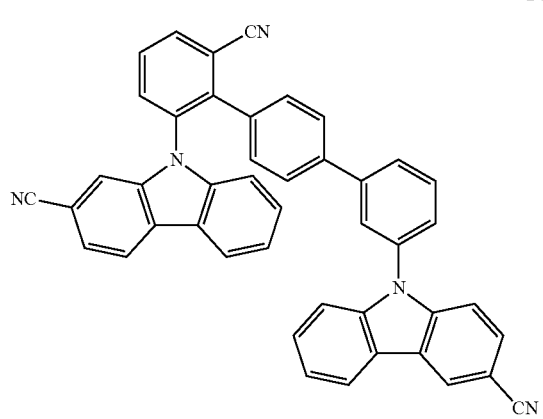
2409
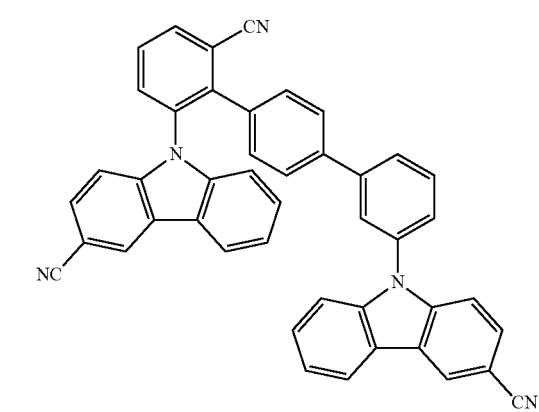
2410
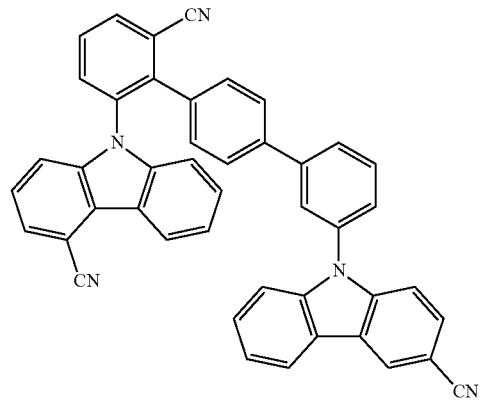
2411
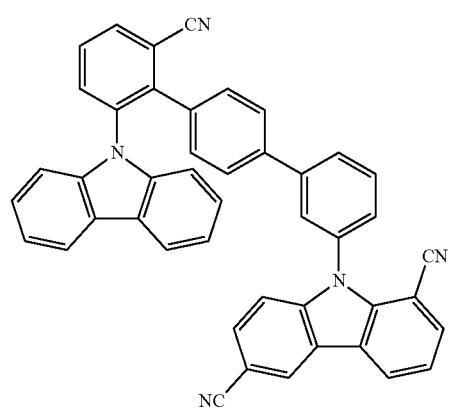
2412
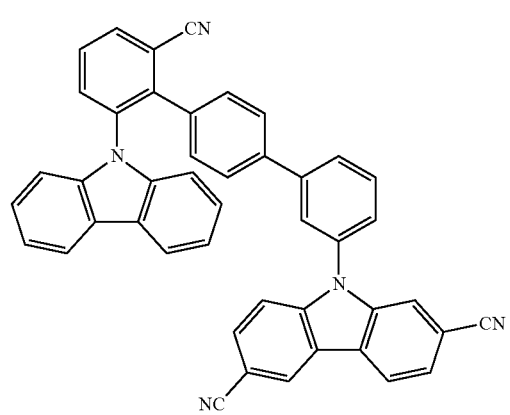
2413
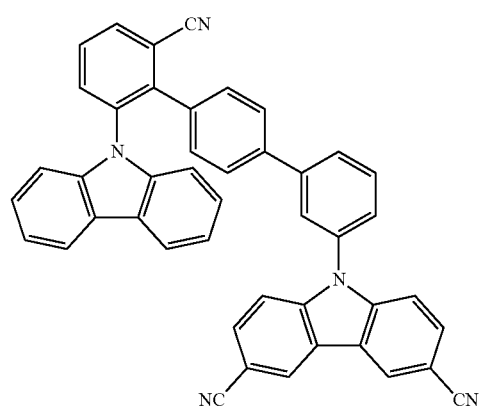

2414
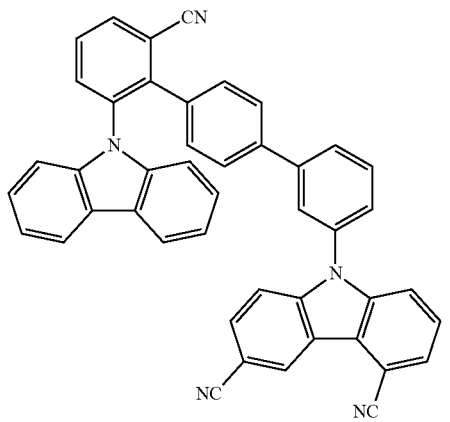
2415
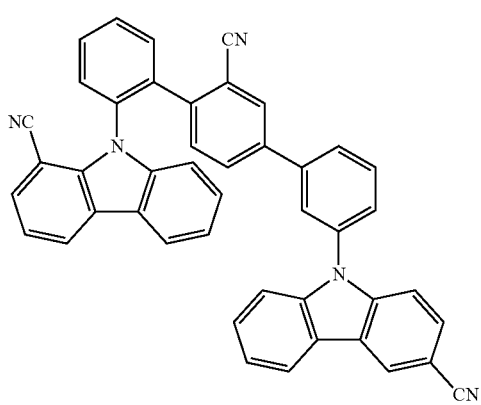
2416
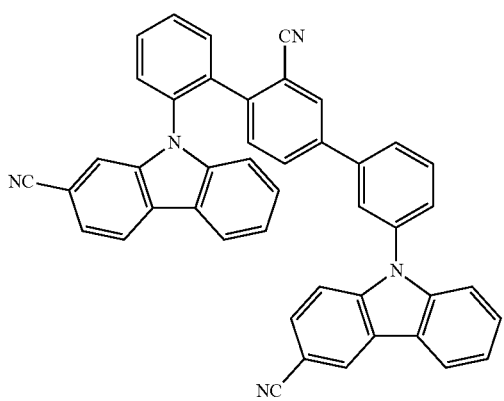
2417
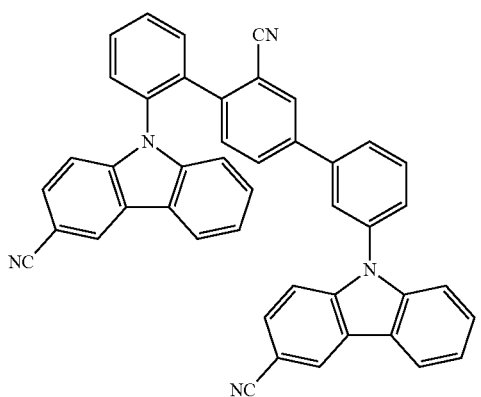
2418
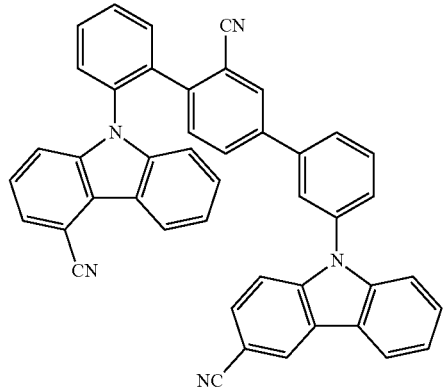
2419
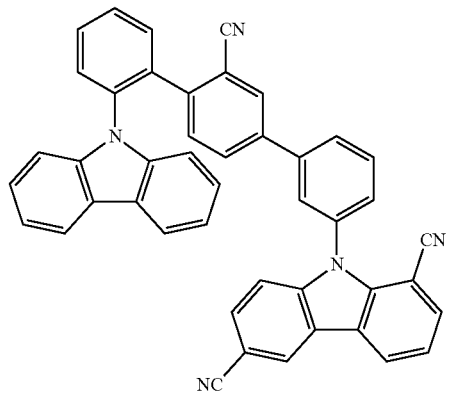
2420
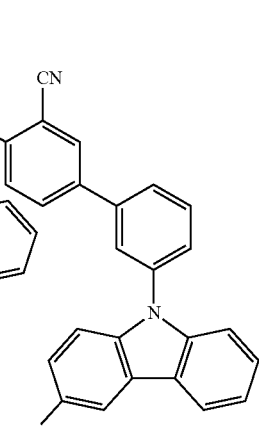
2421
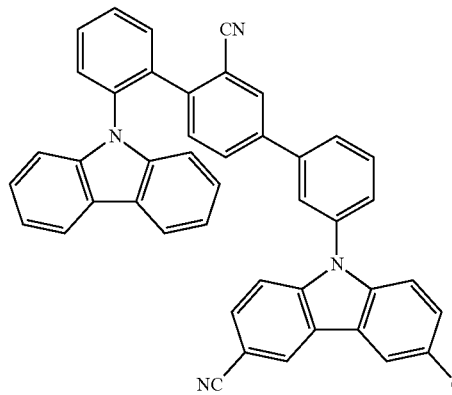

| | |
|---|---|
| 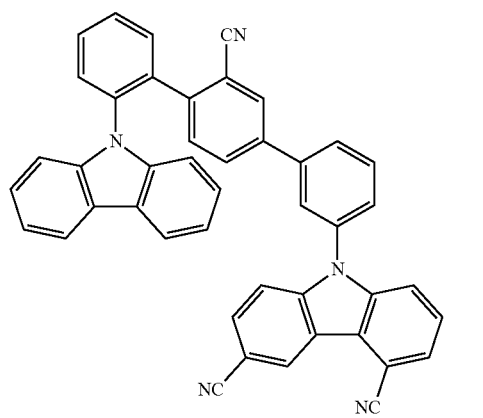 2422 | 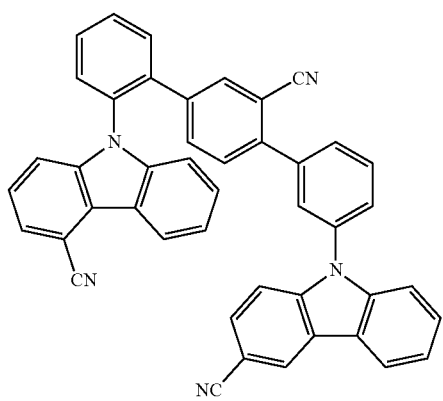 2426 |
| 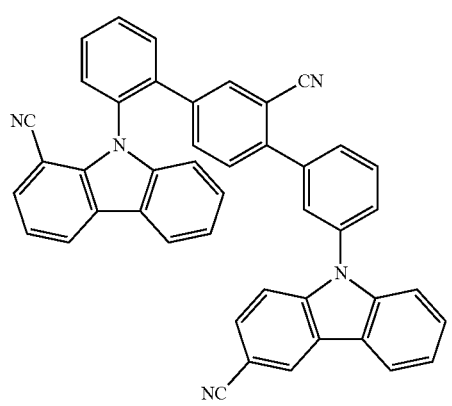 2423 | 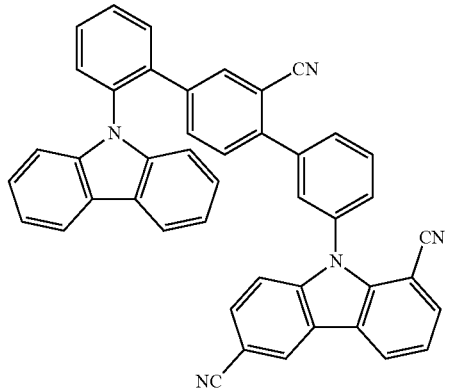 2427 |
| 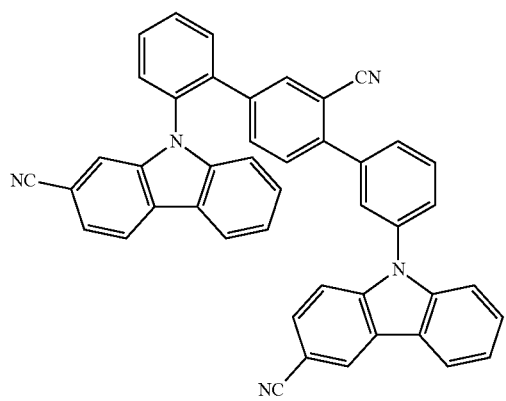 2424 | 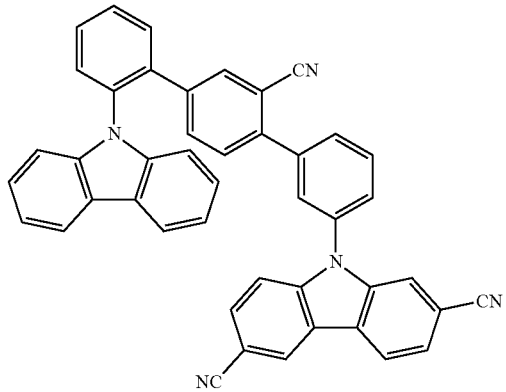 2428 |
| 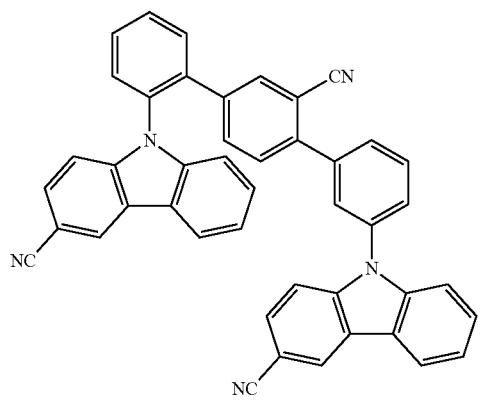 2425 | 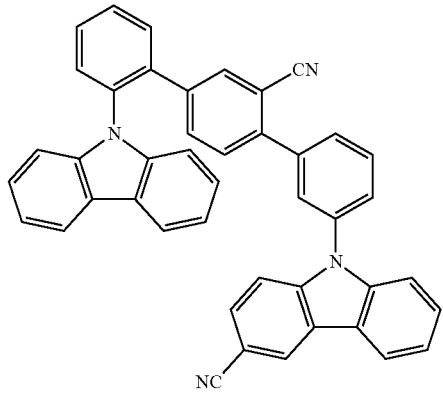 2429 |

2430
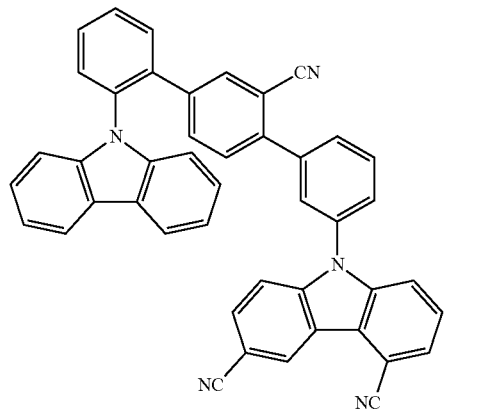
2431
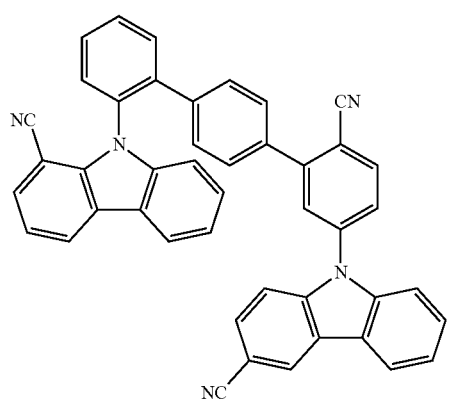
2432
2433
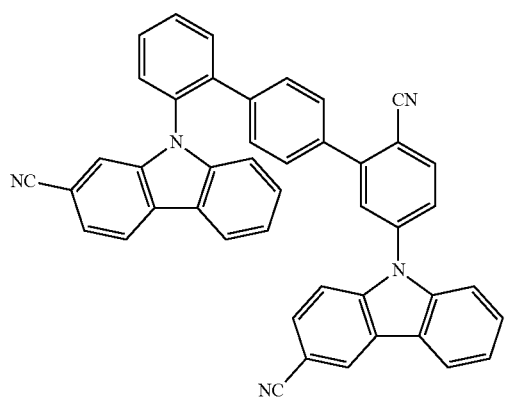
2434
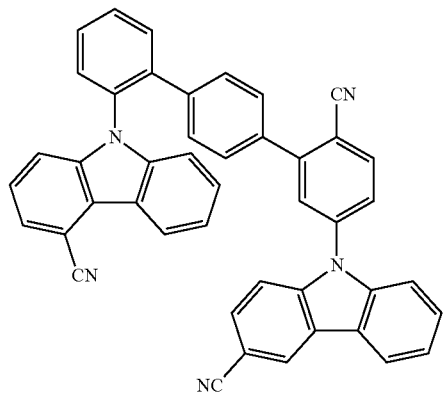
2435
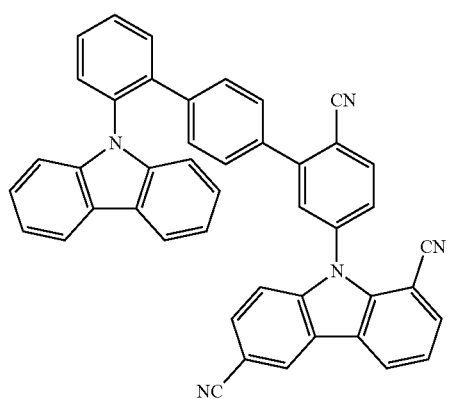
2436
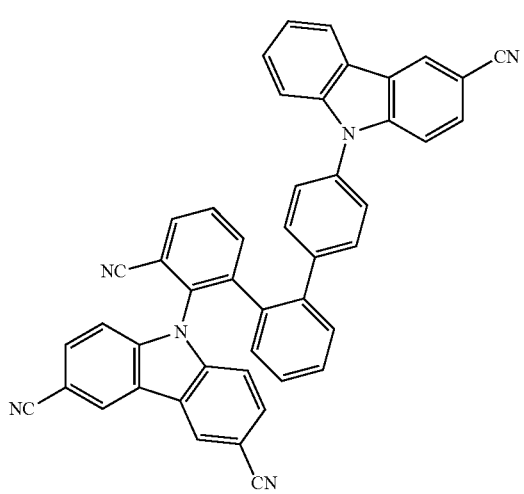

2437
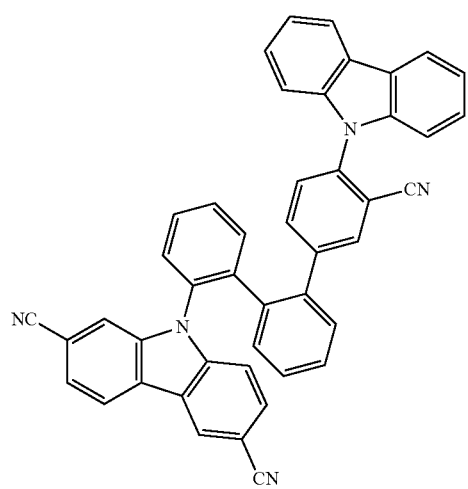
2438
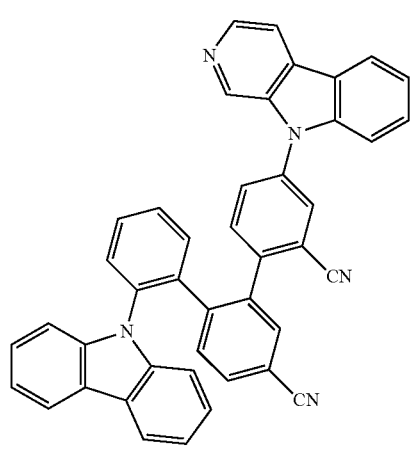
2439
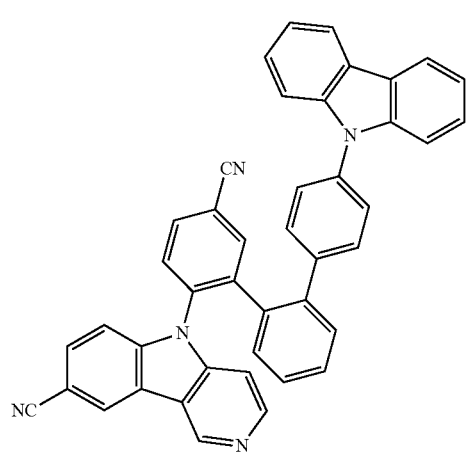
2440
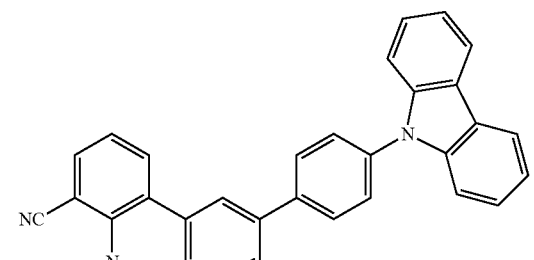
2441
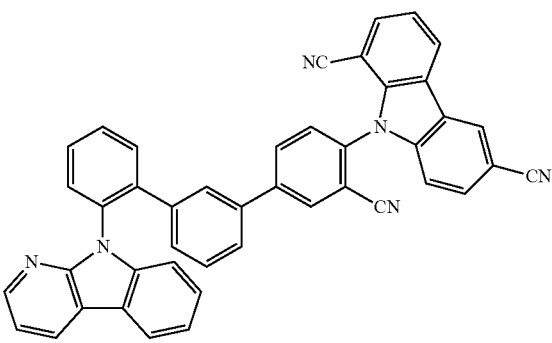
2442
2443
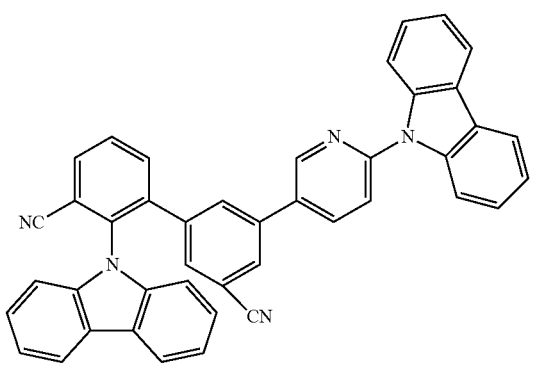

651
-continued
2444
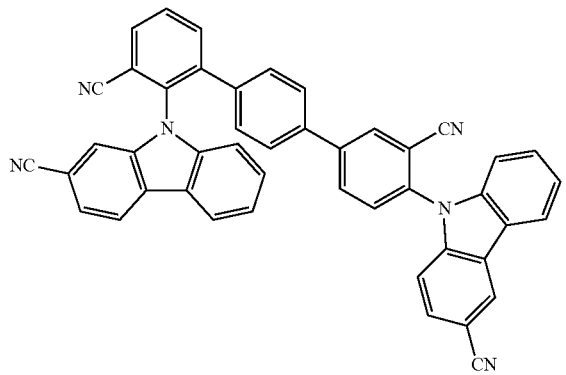
2445
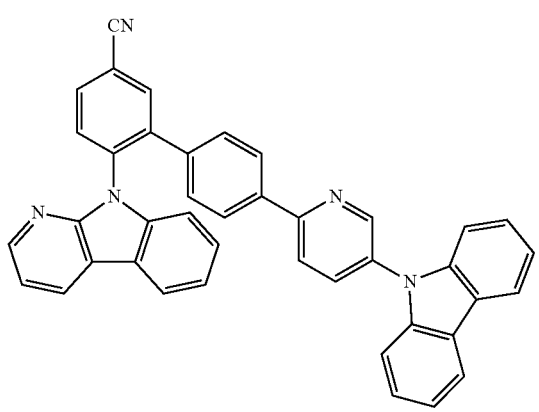
2446
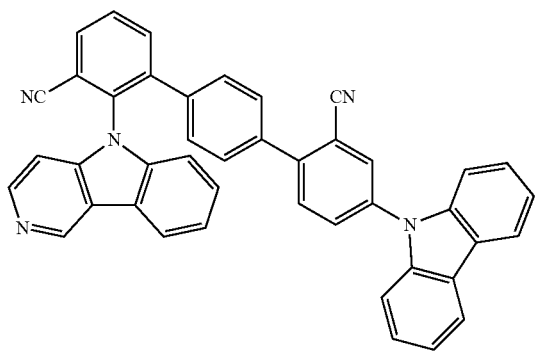
2447
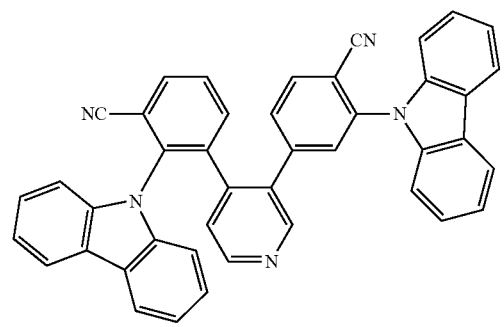
652
-continued
2448
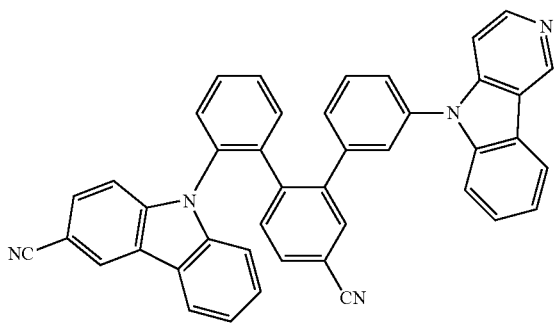
2449
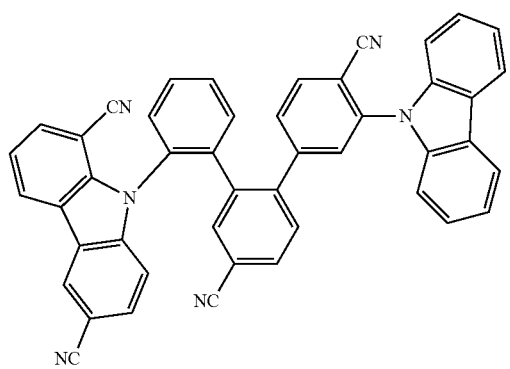
2450
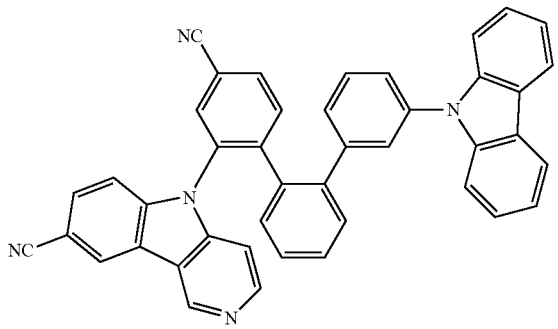
2451
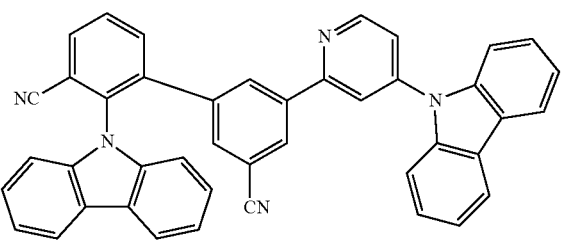

-continued
2452
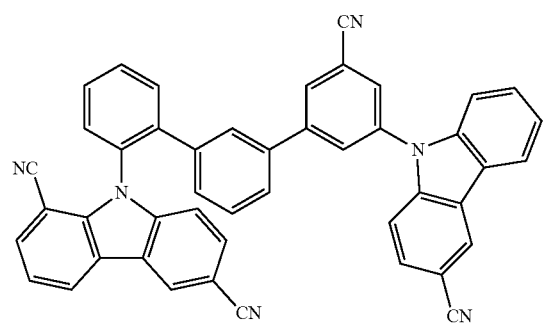
2453
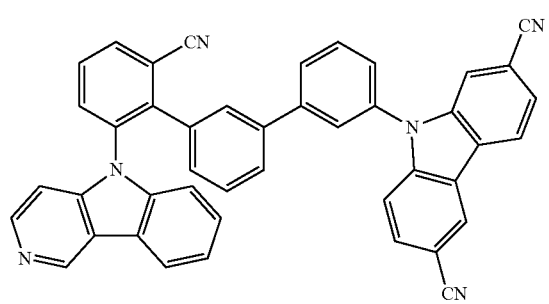
2454
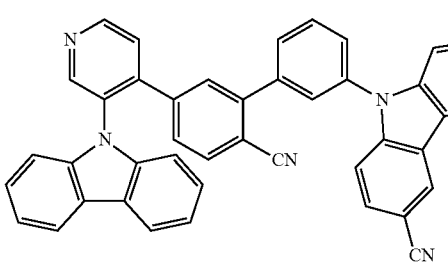
2455
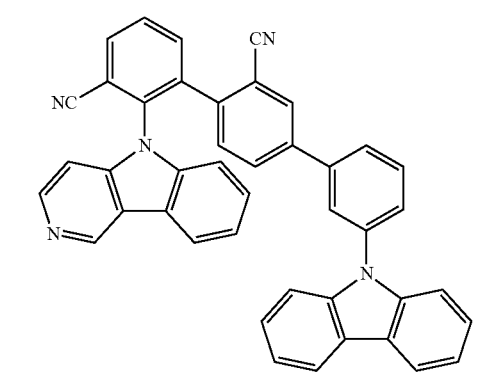
-continued
2456
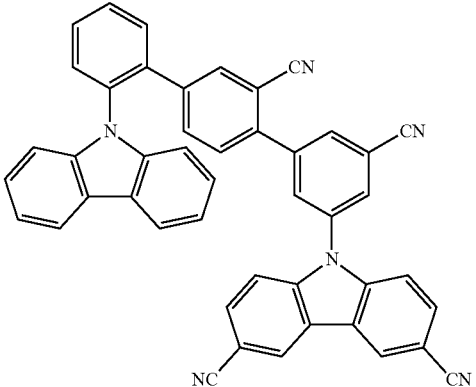
2457
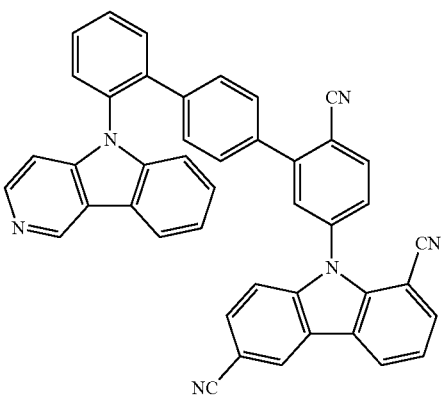
2458
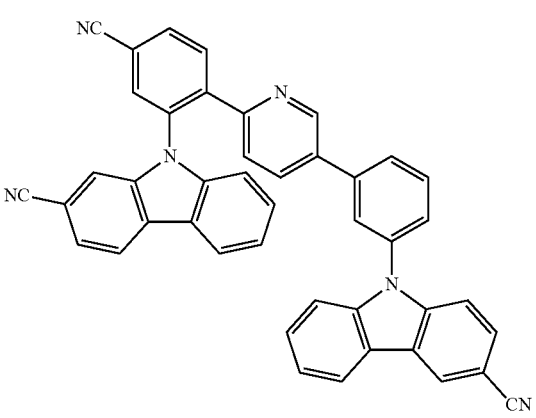
2459
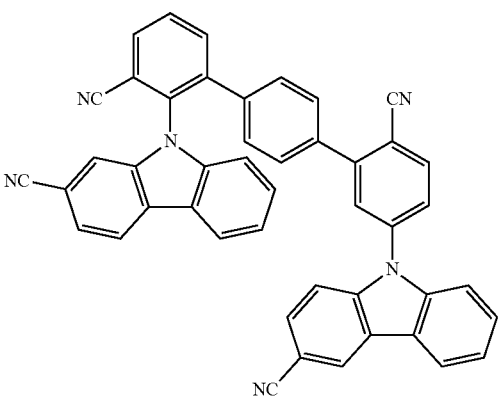

-continued

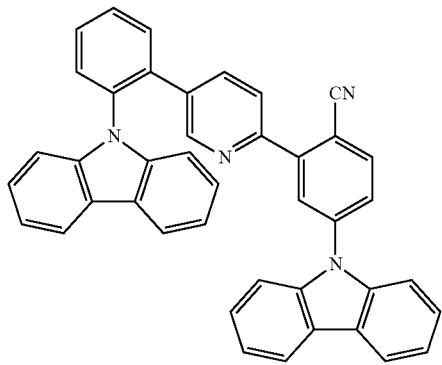

2460

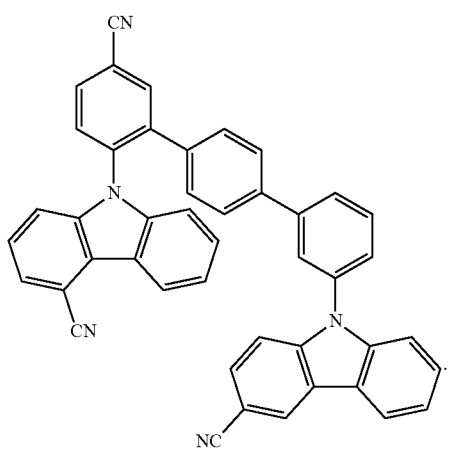

2461

The heterocyclic compound represented by Formula 1 may include a terphenyl linker, wherein an ortho position of a benzene ring at one end of the terphenyl linker may be substituted with a N-carbazole group, and a meta or para position of the benzene ring at another end thereof may be substituted with a N-carbazole group. Thus, steric hindrance may be generated asymmetrically. Accordingly, in the heterocyclic compound represented by Formula 1, characteristics of a relatively excellent amorphous thin film may be secured.

As described above, the heterocyclic compound represented by Formula 1 may have suitable electric characteristics for a material for organic light-emitting devices, e.g., a host material, a hole transport material, and an electron transport material in an emission layer. Accordingly, an organic light-emitting device including the heterocyclic compound may have high efficiency and/or a long lifespan.

For example, the highest occupied molecular orbital (HOMO), lowest unoccupied molecular orbital (LUMO), triplet ($T_1$), and singlet ($S_1$) energy levels of some of the compounds described above and a comparative compound were evaluated by using Gaussian according to a density functional theory (DFT) method (structure optimization is performed at a degree of B3LYP, and 6-31G(d,p)). The results thereof are shown in Table 1.

TABLE 1

| Compound No. | HOMO (electron volts, eV) | LUMO (eV) | $T_1$ (eV) | $S_1$ (eV) |
|---|---|---|---|---|
| 152 | −5.55 | −1.91 | 2.95 | 3.10 |
| 224 | −5.40 | −1.97 | 3.04 | 3.14 |
| 404 | −5.52 | −1.83 | 3.13 | 3.19 |

TABLE 1-continued

| Compound No. | HOMO (electron volts, eV) | LUMO (eV) | $T_1$ (eV) | $S_1$ (eV) |
|---|---|---|---|---|
| 582 | −5.53 | −1.91 | 3.02 | 3.10 |
| 670 | −5.67 | −1.81 | 3.12 | 3.24 |
| 813 | −5.33 | −2.01 | 2.97 | 3.02 |
| 857 | −5.60 | −1.97 | 2.98 | 3.20 |
| 2168 | −5.76 | −2.04 | 3.11 | 3.40 |
| 2451 | −5.71 | −1.91 | 3.04 | 3.15 |
| Compound A | −5.71 | −1.97 | 2.88 | 3.16 |

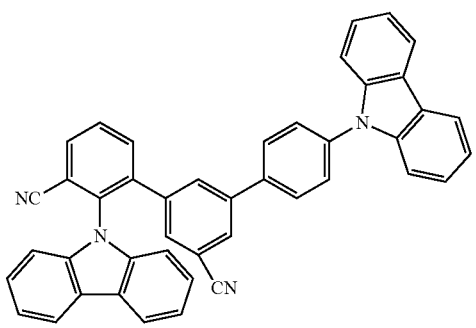 [SMILES: N#Cc1cc(-c2ccc(-n3c4ccccc4c4ccccc43)cc2)cc(-c2cccc(C#N)c2-n2c3ccccc3c3ccccc32)c1]

152

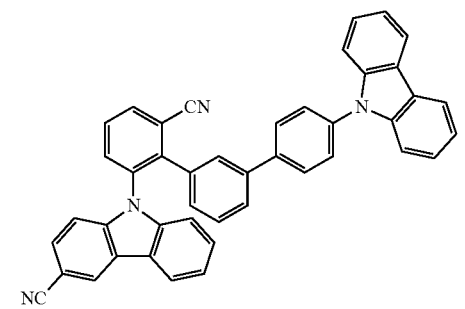 [SMILES: N#Cc1ccc2c(c1)c1ccccc1n2-c1cccc(C#N)c1-c1cccc(-c2ccc(-n3c4ccccc4c4ccccc43)cc2)c1]

224

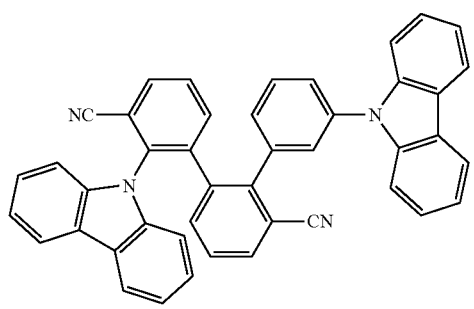 [SMILES: N#Cc1cccc(-c2cccc(C#N)c2-n2c3ccccc3c3ccccc32)c1-c1cccc(-n2c3ccccc3c3ccccc32)c1]

404

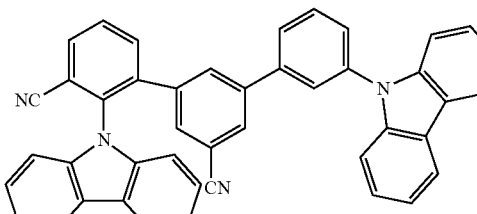

582

TABLE 1-continued

| Compound No. | HOMO (electron volts, eV) | LUMO (eV) | T₁ (eV) | S₁ (eV) |
|---|---|---|---|---|
| 670 | | | | |
| 813 | | | | |
| 857 | | | | |
| 2168 | | | | |
| 2451 | | | | |
| A | | | | |

As apparent from Table 1, the heterocyclic compounds each have a high T₁ energy level. Thus, the heterocyclic compound represented by Formula 1 may be suitable for use as an emission layer material in an electronic device, e.g., an organic light-emitting device.

A method of synthesizing the heterocyclic compound represented by Formula 1 may be understood by one of ordinary skill in the art by referring to Synthesis Examples provided herein.

The heterocyclic compound represented by Formula 1 may be suitable for use as an organic layer material of an organic light-emitting device, for example, an emission layer material, a hole transport region material, and/or an electron transport region material of the organic layer. Accordingly, according to an aspect of another embodiment, an organic light-emitting device may include: a first electrode; a second electrode; and an organic layer between the first electrode and the second electrode, the organic layer including an emission layer and at least one of the heterocyclic compound represented by Formula 1.

As the organic light-emitting device has an organic layer including the heterocyclic compound represented by Formula 1, the organic light-emitting device may have a low driving voltage, high efficiency, high luminance, high quantum efficiency, and long lifespan.

In an embodiment, in the organic light-emitting device,
the first electrode may be an anode, and the second electrode may be a cathode,
the organic layer may include a hole transport region between the first electrode and the emission layer and an electron transport region between the emission layer and the second electrode,
wherein the hole transport region may include a hole injection layer, a hole transport layer, an electron blocking layer, or any combination thereof, and
the electron transport region may include a hole blocking layer, an electron transport layer, an electron injection layer, or a combination thereof, but embodiments are not limited thereto.

In an embodiment, the emission layer in the organic light-emitting device may include at least one heterocyclic compound represented by Formula 1.

In an embodiment, the emission layer in the organic light-emitting device may include a host and a dopant, wherein the host may include at least one heterocyclic compound represented by Formula 1, and the dopant may include a phosphorescent dopant or a fluorescent dopant. In some embodiments, the dopant may include a phosphorescent dopant (e.g., an organometallic compound represented by Formula 81 provided herein). The host may further include any suitable host, in addition to the heterocyclic compound represented by Formula 1.

The emission layer may emit red light, green light, or blue light.

In an embodiment, the emission layer may include a phosphorescent dopant, but embodiments are not limited thereto.

In some embodiments, the heterocyclic compound represented by Formula 1 may be included in a hole transport region of the organic light-emitting device.

In some embodiments, a hole transport region of the organic light-emitting device may include at least one of a hole injection layer, a hole transport layer, or an electron blocking layer, wherein at least one of the hole injection layer, the hole transport layer, or the electron blocking layer may include the heterocyclic compound represented by Formula 1.

In some embodiments, the heterocyclic compound represented by Formula 1 may be included in an electron transport region of the organic light-emitting device.

In some embodiments, a hole transport region of the organic light-emitting device may include at least one of a hole blocking layer, an electron transport layer, or an electron injection layer, wherein at least one of the hole blocking layer, the electron transport layer, or the electron injection layer, may include the heterocyclic compound represented by Formula 1.

In an embodiment, a hole transport region of the organic light-emitting device may include an electron blocking layer, wherein the electron blocking layer may include the heterocyclic compound represented by Formula 1. The electron blocking layer may be in direct contact with the emission layer.

In an embodiment, an electron transport region of the organic light-emitting device may include a hole blocking layer, wherein the hole blocking layer may include the heterocyclic compound represented by Formula 1. The hole blocking layer may be in direct contact with the emission layer.

In some embodiments, the organic layer of the organic light-emitting device may further include an organometallic compound represented by Formula 81, in addition to the heterocyclic compound represented by Formula 1.

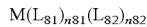

$$M(L_{81})_{n81}(L_{82})_{n82} \quad \text{Formula 81}$$

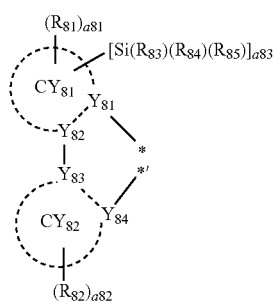

Formula 81A wherein, in Formulae 81 and 81A,

M may be iridium (Ir), platinum (Pt), osmium (Os), titanium (Ti), zirconium (Zr), hafnium (Hf), europium (Eu), terbium (Tb), thulium (Tm), or rhodium (Rh), $L_{81}$ may be a ligand represented by Formula 81A, n81 may be an integer from 1 to 3; and when n81 is 2 or greater, at least two $L_{81}$(s) may be identical to or different from each other, $L_{82}$ may be an organic ligand, n82 may be an integer from 0 to 4; and when n82 is 2 or greater, at least two $L_{82}$(s) may be identical to or different from each other, $Y_{81}$ to $Y_{84}$ may each independently be carbon (C) or nitrogen (N), $Y_{81}$ and $Y_{82}$ may be linked to each other via a single bond or a double bond, and $Y_{83}$ and $Y_{84}$ are linked to each other via a single bond or a double bond, $CY_{81}$ and $CY_{82}$ may each independently be a $C_5$-$C_{30}$ carbocyclic group or a $C_{2-30}$ heterocarbocyclic group, $CY_{81}$ and $CY_{82}$ may optionally be bound via an organic linking group, $R_{81}$ to $R_{85}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{81}$)($Q_{82}$)($Q_{83}$), —N($Q_{84}$)($Q_{85}$), —B($Q_{86}$)($Q_{87}$), or —P(=O)($Q_{88}$)($Q_{89}$), a81 to a83 may each independently be an integer from 0 to 5, when a81 is 2 or greater, at least two $R_{81}$(s) may be identical to or different from each other, when a82 is 2 or greater, at least two $R_{82}$(s) may be identical to or different from each other, when a81 is 2 or greater, two adjacent $R_{81}$(s) may be optionally bound to form a saturated or unsaturated $C_2$-$C_{30}$ ring (e.g., a benzene ring, a cyclopentane ring, a cyclohexane ring, a cyclopentene ring, a cyclohexene ring, a norbornane ring, a naphthalene ring, a benzoindene ring, a benzoindole ring, a benzofuran ring, a benzothiophene ring, a pyridine ring, a pyrimidine ring, or a pyrazine ring), or a saturated or unsaturated $C_2$-$C_{30}$ ring substituted with at least one $R_{88}$ (e.g., a benzene ring, a cyclopentane ring, a cyclohexane ring, a cyclopentene ring, a cyclohexene ring, a norbornane ring, a naphthalene ring, a benzoindene ring, a benzoindole ring, a benzofuran ring, a benzothiophene ring, a pyridine ring, a pyrimidine ring, or a pyrazine ring, each substituted with at least one $R_{88}$), when a82 is 2 or greater, two adjacent $R_{82}$(s) may be optionally bound to form a saturated or unsaturated $C_2$-$C_{30}$ ring (e.g., a benzene ring, a cyclopentane ring, a cyclohexane ring, a cyclopentene ring, a cyclohexene ring, a norbornane ring, a naphthalene ring, a benzoindene ring, a benzoindole ring, a benzofuran ring, a benzothiophene ring, a pyridine ring, a pyrimidine ring, or a pyrazine ring), or a saturated or unsaturated $C_2$-$C_{30}$ ring substituted with at least one $R_{89}$ (e.g., a benzene ring, a cyclopentane ring, a cyclohexane ring, a cyclopentene ring, a cyclohexene ring, a norbornane ring, a naphthalene ring, a benzoindene ring, a benzoindole ring, a benzofuran ring, a benzothiophene ring, a pyridine ring, a pyrimidine ring, or a pyrazine ring, each substituted with at least one $R_{89}$), $R_{88}$ may be understood by referring to the descriptions for $R_{81}$ provided herein, $R_{89}$ may be understood by referring to the descriptions for $R_{82}$ provided herein,

* and *' in Formula 81A each indicate a binding site to M in Formula 81, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_{3-10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or —Si($Q_{91}$)($Q_{92}$)($Q_{93}$), wherein $Q_{81}$ to $Q_{89}$ and $Q_{91}$ to $Q_{93}$ may each independently be hydrogen, deuterium, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In an embodiment, in Formula 81A, a83 may be 1 or 2, and $R_{83}$ to $R_{85}$ may each independently be —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group; or an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group, each substituted with at least one deuterium, a $C_1$-$C_{10}$ alkyl group, or a phenyl group, but embodiments are not limited thereto.

In some embodiments, in Formula 81A, $Y_{81}$ may be N, $Y_{82}$ and $Y_{83}$ may each be C, $Y_{84}$ may be N or C, and $CY_{81}$ and $CY_{82}$ may each independently be a cyclopentadiene group, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, a thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an iso-benzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilole group, or a 2,3-dihydro-1H-imidazole group.

In some embodiments, in Formula 81A, $Y_{81}$ may be N, $Y_{82}$ to $Y_{84}$ may each be C, $CY_{81}$ may be a 5-membered ring including two N atoms as ring-forming atoms, and $CY_{82}$ may be a benzene group, a naphthalene group a fluorene group, a dibenzofuran group, or a dibenzothiophene group, but embodiments are not limited thereto.

In some embodiments, in Formula 81A, $Y_{81}$ may be N, $Y_{82}$ to $Y_{84}$ may each be C, $CY_{81}$ may be an imidazole group or a 2,3-dihydro-1H-imidazole group, and $CY_{82}$ may be a benzene group, a naphthalene group a fluorene group, a dibenzofuran group, or a dibenzothiophene group, but embodiments are not limited thereto.

In some embodiments, in Formula 81A, $Y_{81}$ may be N, $Y_{82}$ to $Y_{84}$ may each be C, $CY_{81}$ may be a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an iso-benzothiazole group, a benzoxazole group, or an isobenzoxazole group, and $CY_{82}$ may be a cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group, or a dibenzosilole group.

In some embodiments, in Formula 81A, $R_{81}$ and $R_{82}$ may be each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, or a C$_1$-C$_{20}$ alkoxy group;

a C$_1$-C$_{20}$ alkyl group and a C$_1$-C$_{20}$ alkoxy group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a pyridinyl group, or a pyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or —B(Q$_{86}$)(Q$_{87}$) or —P(=O)(Q$_{88}$)(Q$_{89}$), wherein Q$_{86}$ to Q$_{89}$ may each independently be —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, or —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with at least one deuterium, a C$_1$-C$_{10}$ alkyl group, or a phenyl group.

In some embodiments, in Formula 81A, at least one R$_{81}$(s) in the number of a81 or R$_{82}$(s) in the number of a82 may be a cyano group.

In some embodiments, in Formula 81A, at least one R$_{82}$(s) in the number of a82 may be a cyano group.

In some embodiments, in Formula 81A, at least one of R$_{81}$(s) in the number of a81 or R$_{82}$(s) in the number of a82 may be deuterium.

In some embodiments, in Formula 81, L$_{82}$ may be a ligand represented by Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114):

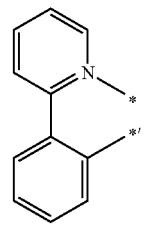

3-1(1)

665
-continued
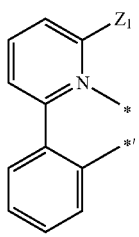
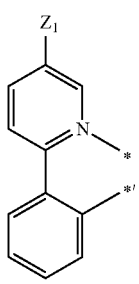
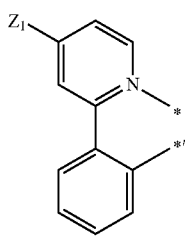
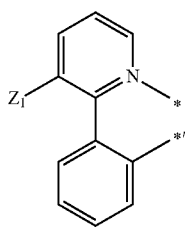
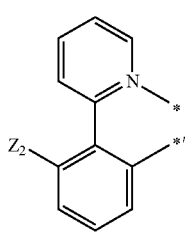
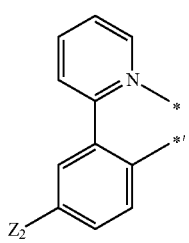
666
-continued
3-1(2)
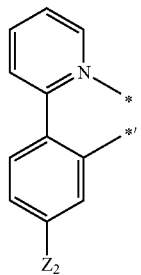
3-1(3)
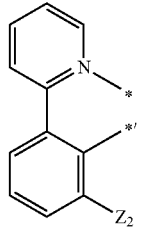
3-1(4)
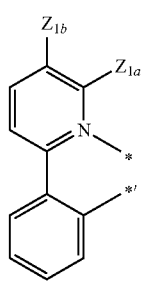
3-1(5)
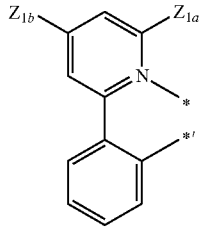
3-1(6)
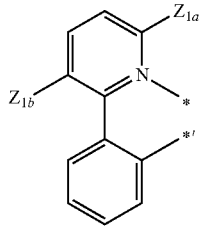
3-1(7)
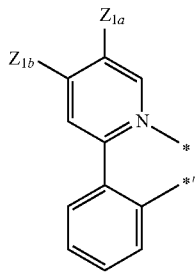
3-1(8)
3-1(9)
3-1(10)
3-1(11)
3-1(12)
3-1(13)

3-1(14)
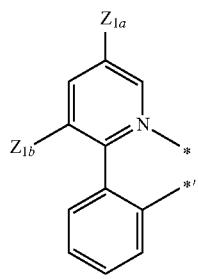
3-1(15)
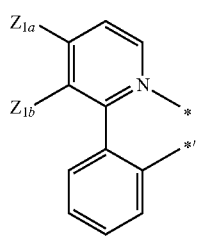
3-1(16)
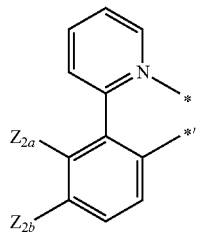
3-1(17)
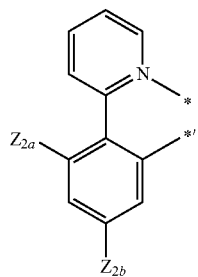
3-1(18)
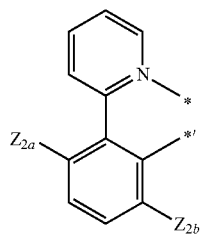
3-1(19)
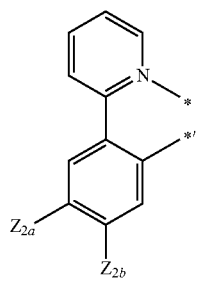
3-1(20)
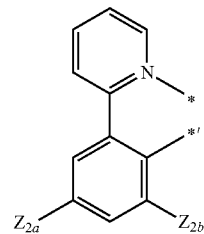
3-1(21)
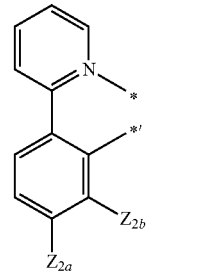
3-1(22)
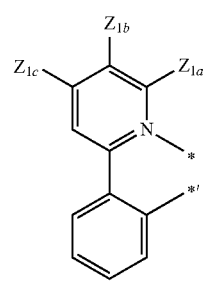
3-1(23)
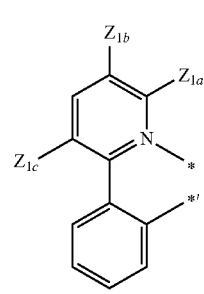
3-1(24)
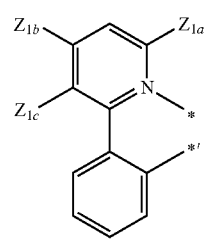
3-1(25)
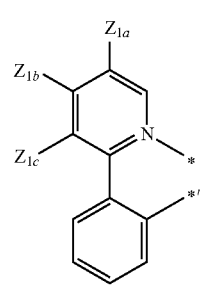

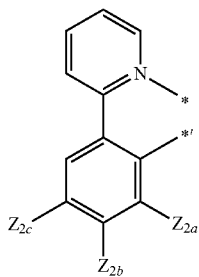
3-1(26)
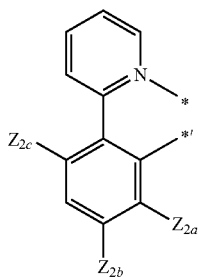
3-1(27)
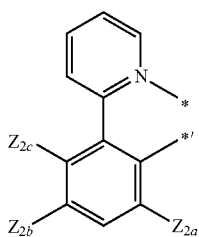
3-1(28)
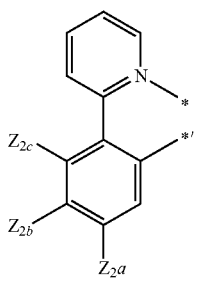
3-1(29)
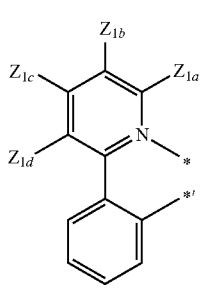
3-1(30)
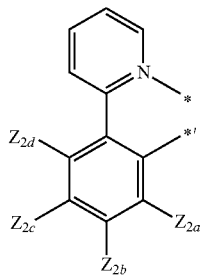
3-1(31)
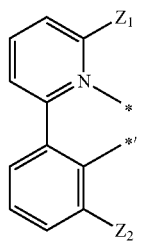
3-1(32)
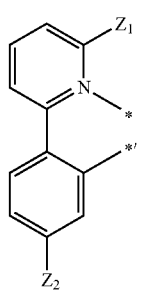
3-1(33)
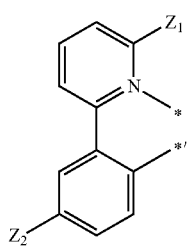
3-1(34)
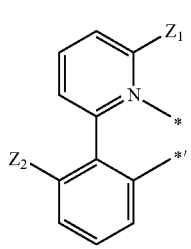
3-1(35)
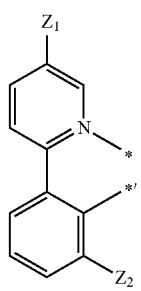
3-1(36)

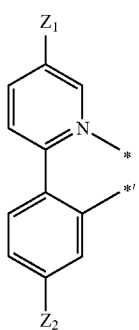 3-1(37)
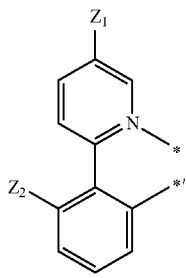 3-1(38)
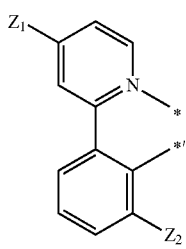 3-1(39)
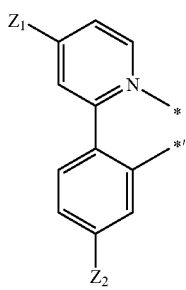 3-1(40)
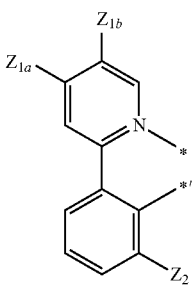 3-1(41)
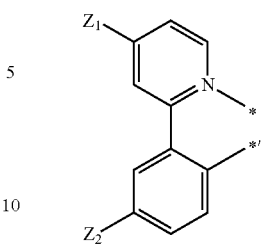 3-1(42)
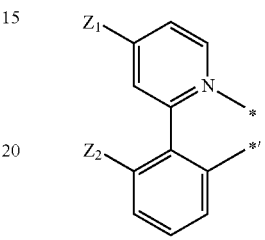 3-1(43)
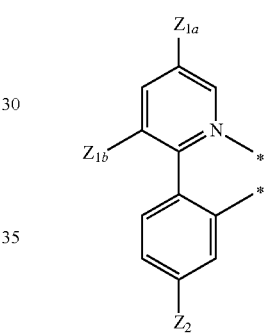 3-1(44)
3-1(45)
3-1(46)

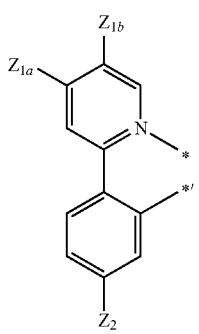
3-1(47)
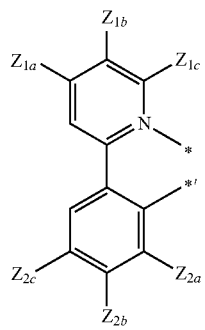
3-1(52)
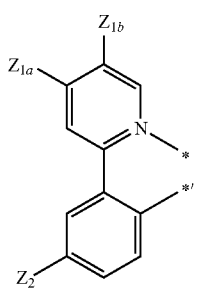
3-1(48)
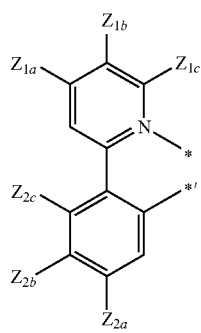
3-1(53)
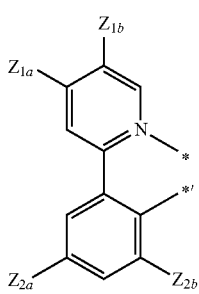
3-1(49)
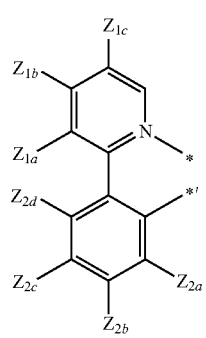
3-1(54)
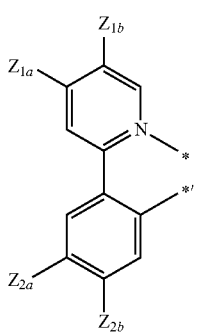
3-1(50)
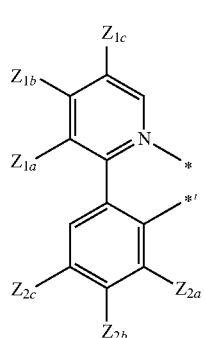
3-1(55)
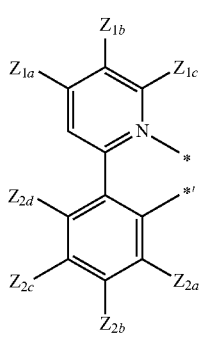
3-1(51)
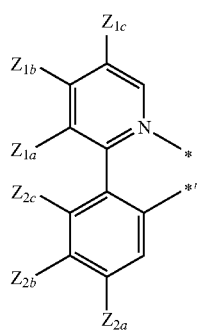
3-1(56)

-continued
3-1(57) 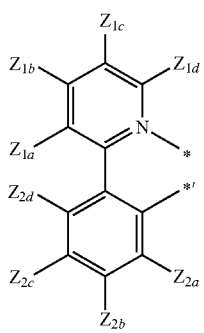
3-1(58) 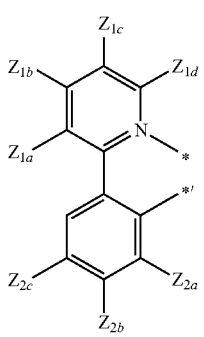
3-1(59) 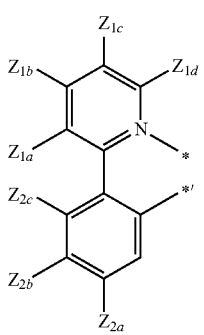
3-1(60) 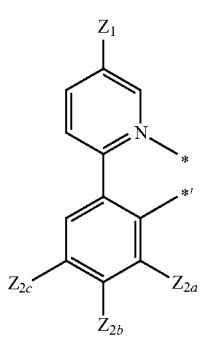
3-1(61) 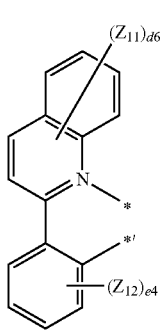
-continued
3-1(62) 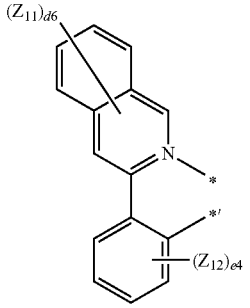
3-1(63) 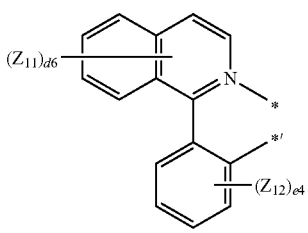
3-1(64) 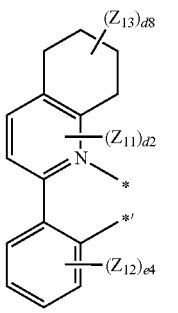
3-1(65) 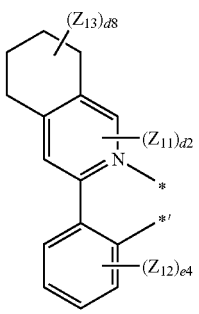
3-1(66) 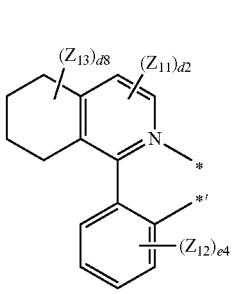

-continued
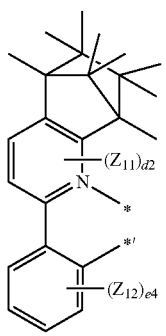
3-1(67)
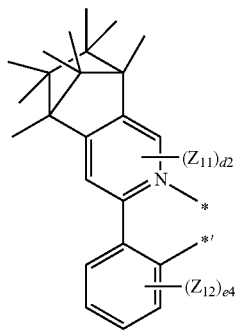
3-1(68)
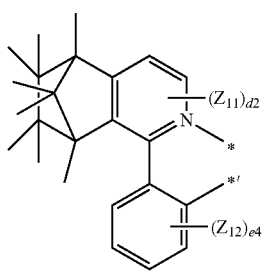
3-1(69)
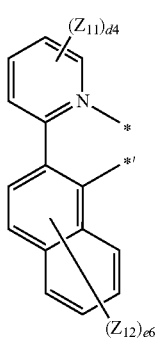
3-1(71)
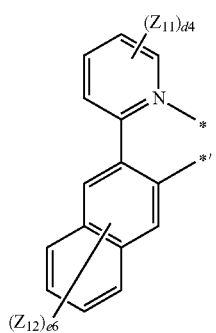
3-1(72)
-continued
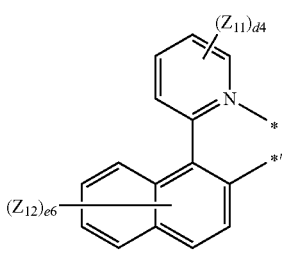
3-1(73)
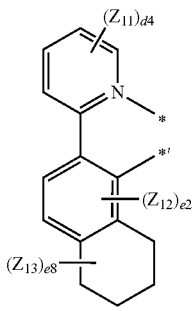
3-1(74)
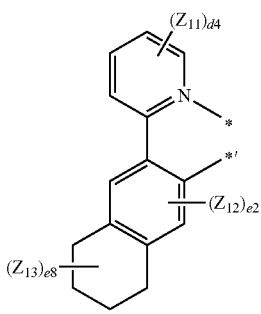
3-1(75)
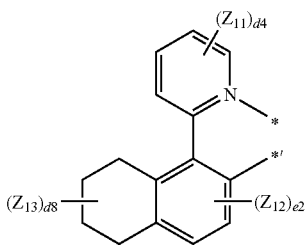
3-1(76)
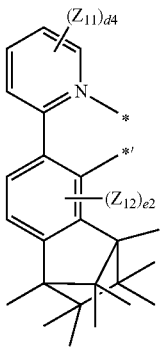
3-1(77)

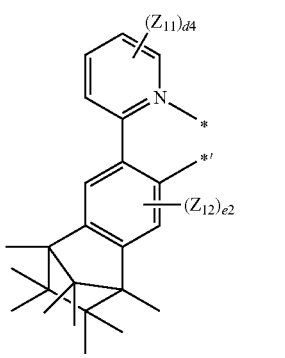
3-1(78)
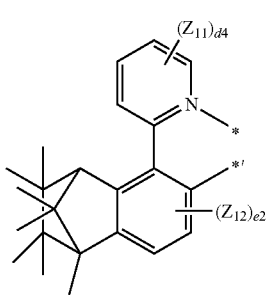
3-1(79)
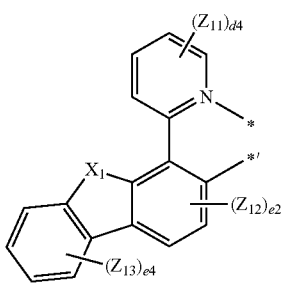
3-1(81)
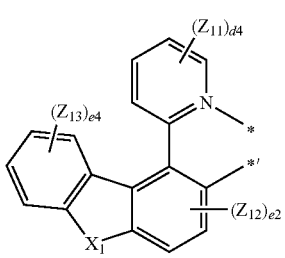
3-1(82)
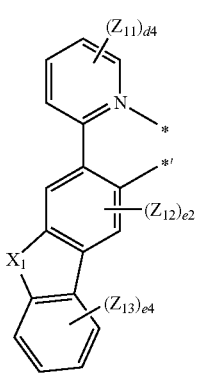
3-1(83)
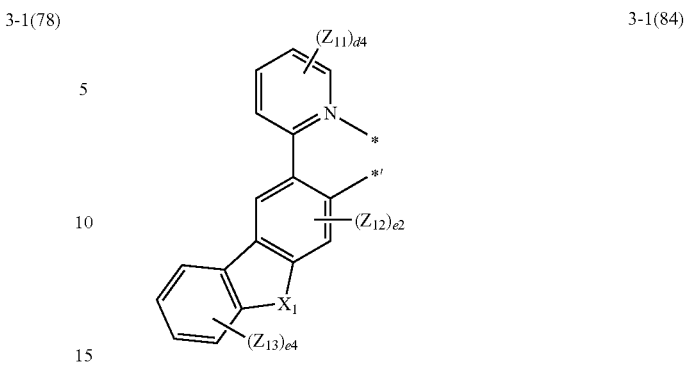
3-1(84)
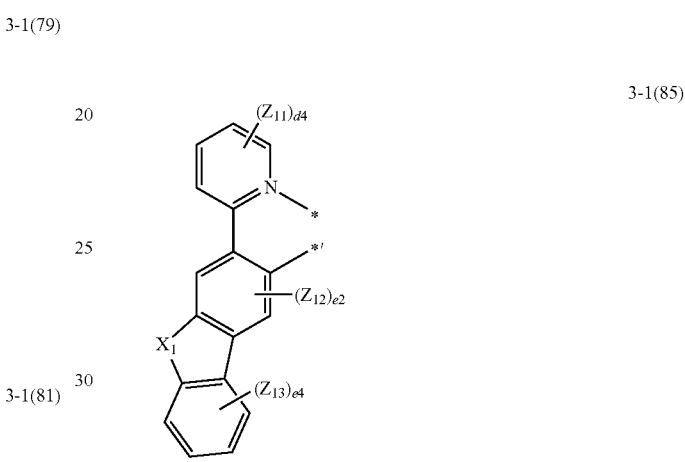
3-1(85)
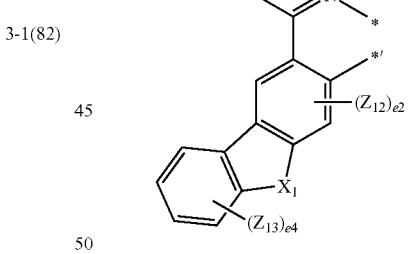
3-1(86)
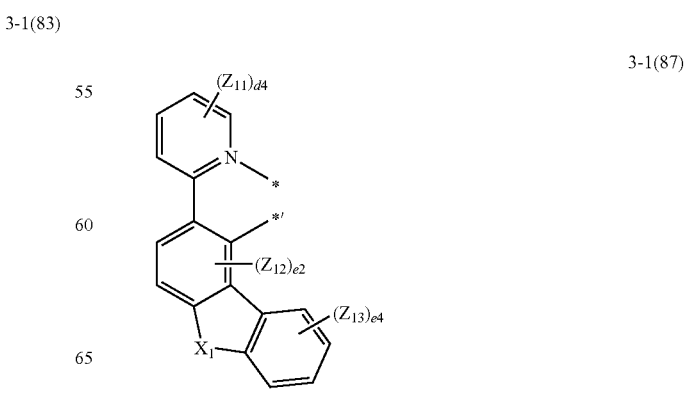
3-1(87)

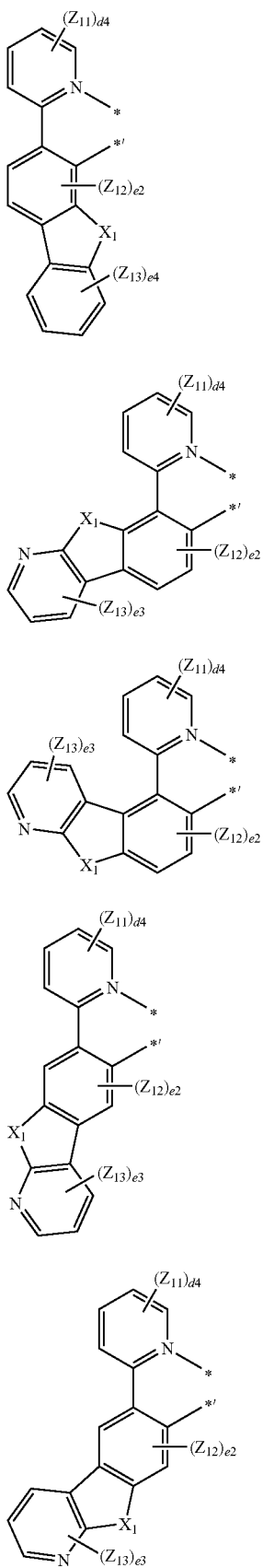
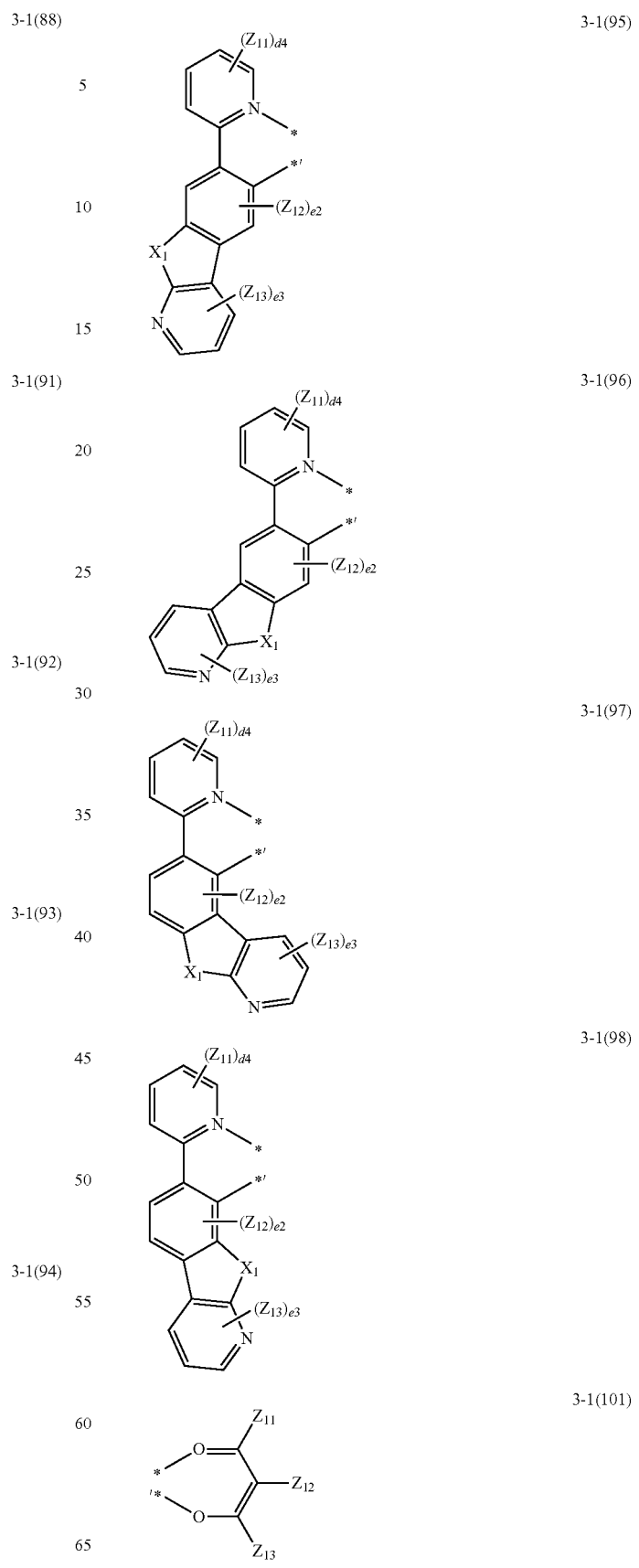

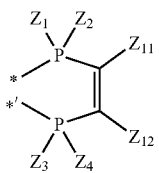 3-1(102)

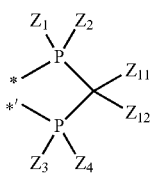 3-1(103)

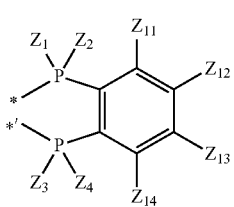 3-1(104)

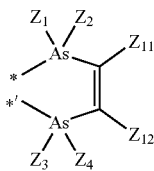 3-1(105)

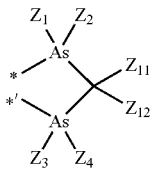 3-1(106)

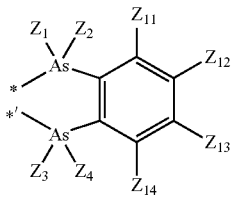 3-1(107)

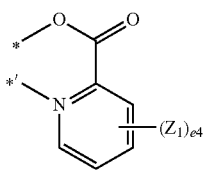 3-1(108)

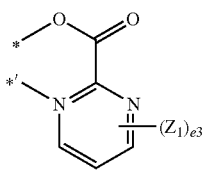 3-1(109)

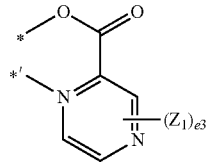 3-1(110)

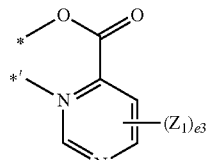 3-1(111)

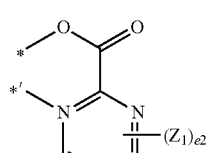 3-1(112)

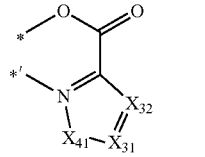 3-1(113)

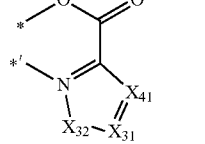 3-1(114)

wherein, in Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ may be O, S, $C(Z_{21})(Z_{22})$, or $N(Z_{23})$, $X_{31}$ may be N or $C(Z_{1a})$, $X_{32}$ may be N or $C(Z_{1b})$, $X_{41}$ may be O, S, $N(Z_{1a})$, or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a pyridinyl group, or a pyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or $B(Q_{86})(Q_{87})$ or —$P(=O)(Q_{88})(Q_{89})$, wherein $Q_{86}$ to $Q_{89}$ may each independently be CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, or —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, or a naphthyl group; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with at least one deuterium, a $C_1$-$C_{10}$ alkyl group, or a phenyl group, d2 and e2 may each independently be 0 or 2, e3 may be an integer from 0 to 3, d4 and e4 may each independently be an integer from 0 to 4, d6 and e6 may each independently be an integer from 0 to 6, d8 and e8 may each independently be an integer from 0 to 8, and

* and *' each indicate a binding site to M in Formula 1.

In some embodiments, in Formula 81, M may be Ir, and a sum of n81 and n82 may be 3. In some embodiments, in Formula 81, M may be Pt, and a sum of n81 and n82 may be 2.

In some embodiments, the organometallic compound represented by Formula 81 may be neutral and may not include ion pairs of cations and anions.

In some embodiments, the organometallic compound represented by Formula 81 may include at least one of Compounds PD1 to PD78 or Flr$_6$, but embodiments are not limited thereto:

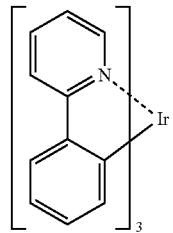

PD1

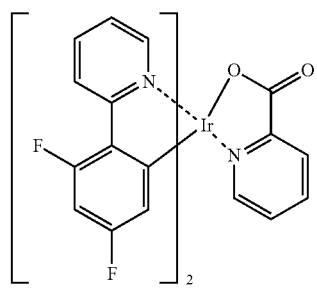

PD2

PD3 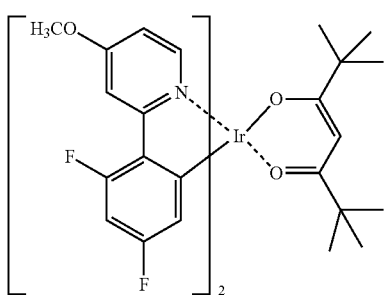
PD4 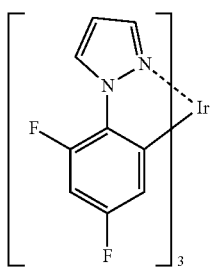
PD5 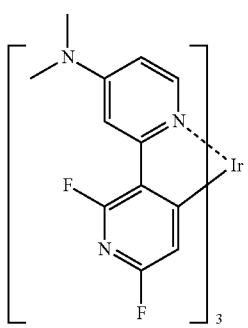
PD6 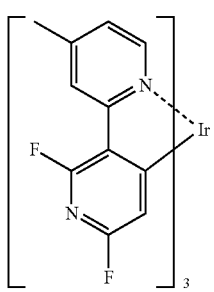
PD7 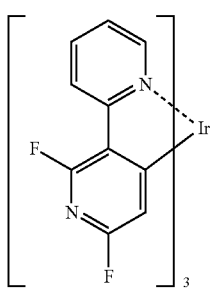
PD8 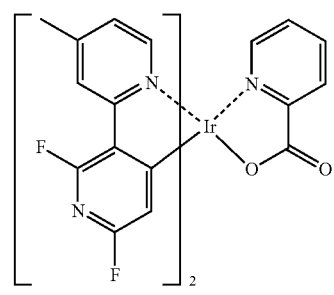
PD9 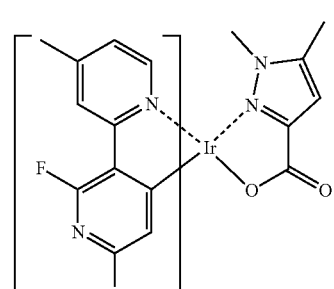
PD10 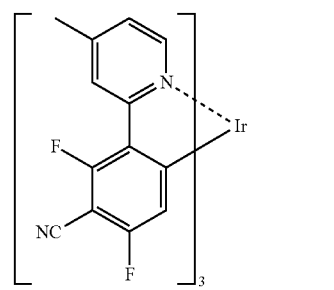
PD11 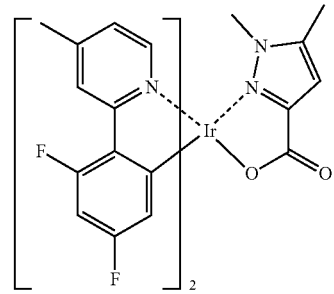
PD12 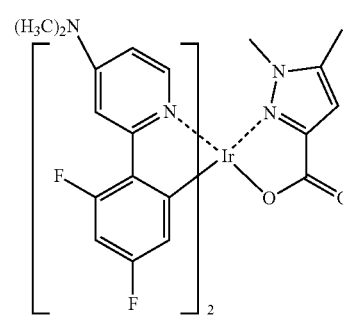

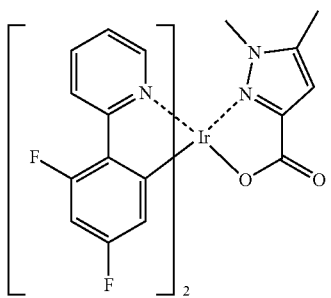
PD13
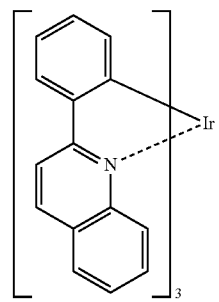
PD18
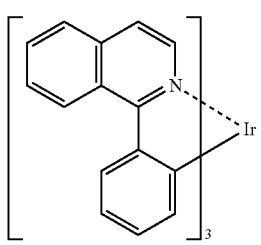
PD14
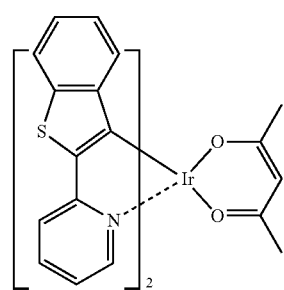
PD19
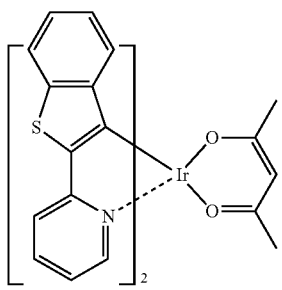
PD15
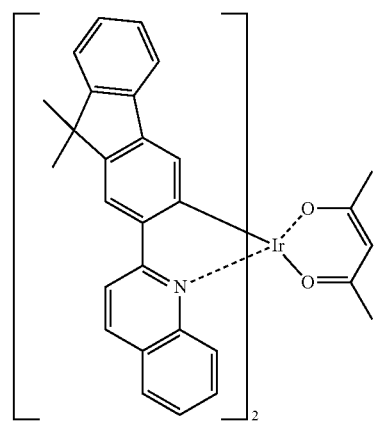
PD20
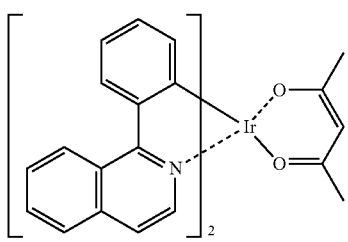
PD16
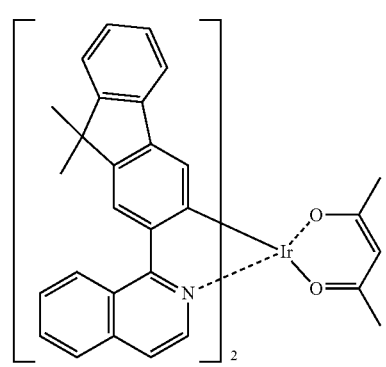
PD21
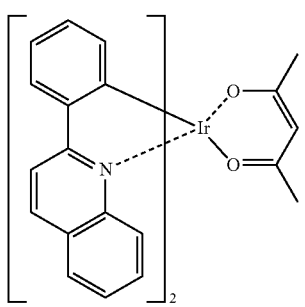
PD17
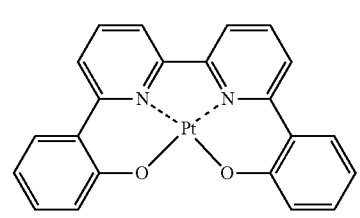
PD22

PD23 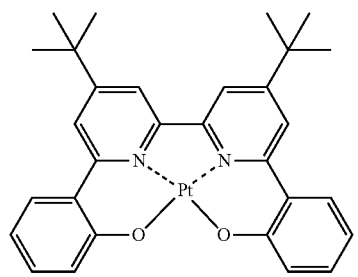
PD24 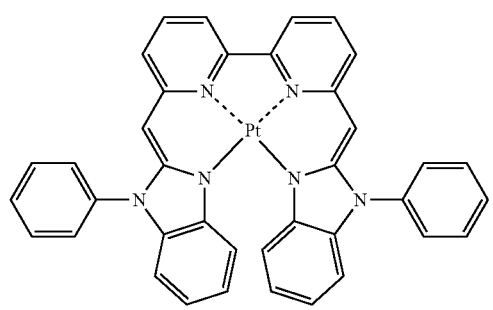
PD25 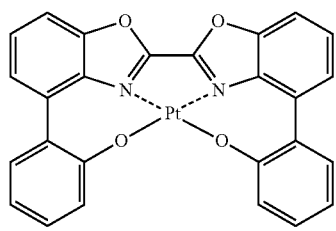
PD26 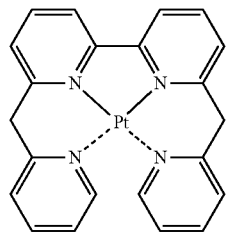
PD27 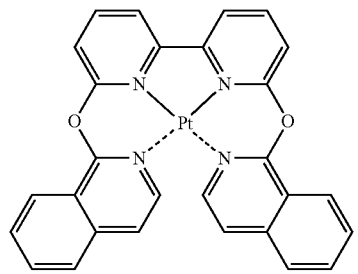
PD28 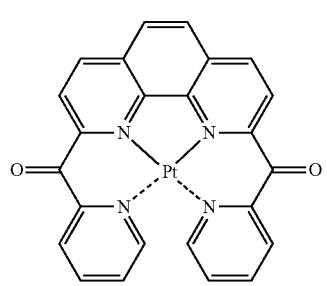
PD29 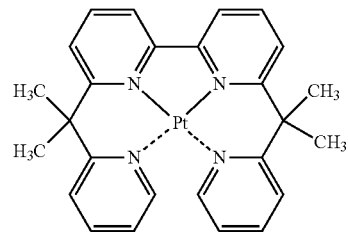
PD30 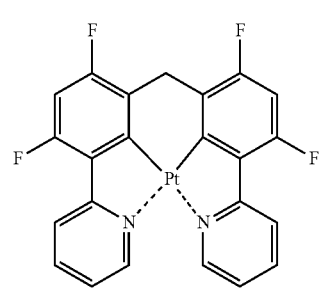
PD31 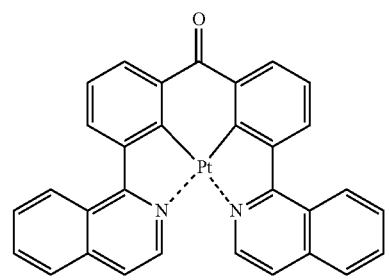
PD32 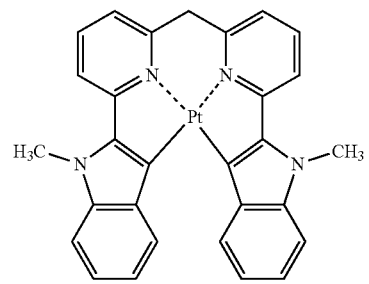
PD33 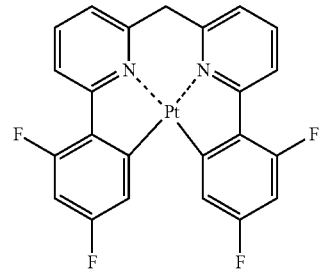
PD34 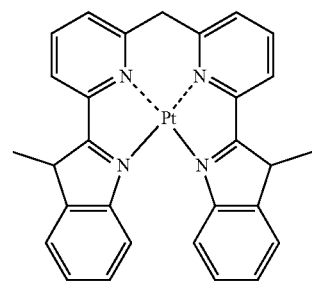

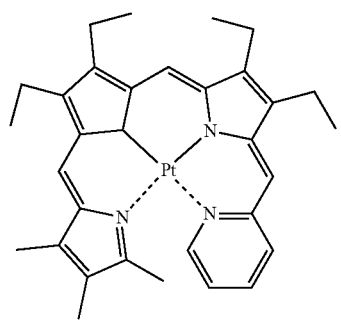
PD35
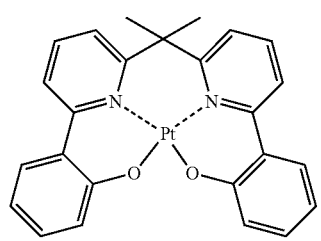
PD36
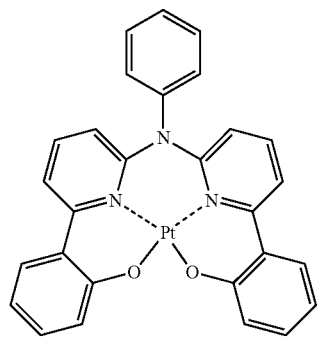
PD37
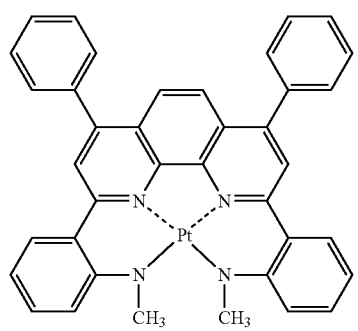
PD38
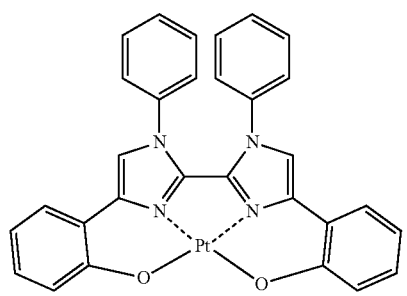
PD39
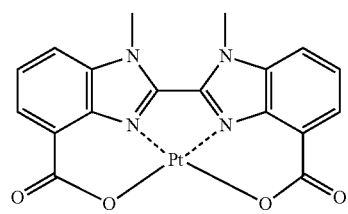
PD40
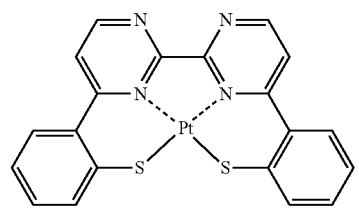
PD41
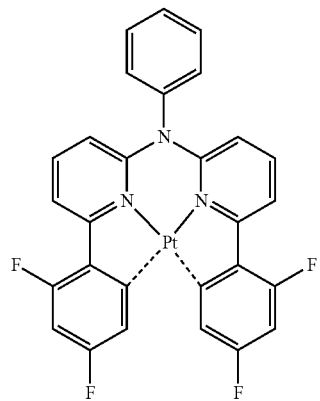
PD42
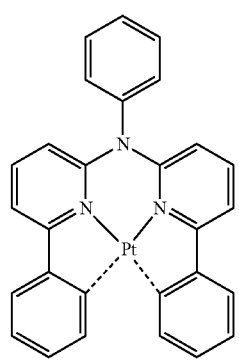
PD43
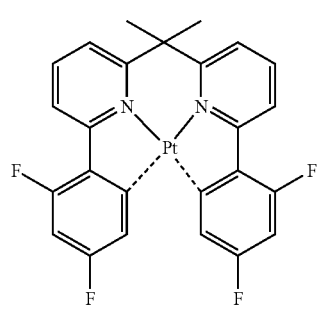
PD44

-continued
PD45
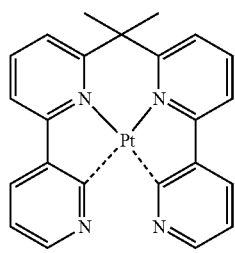
PD46
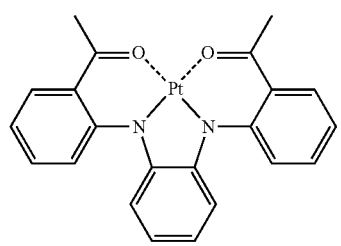
PD47
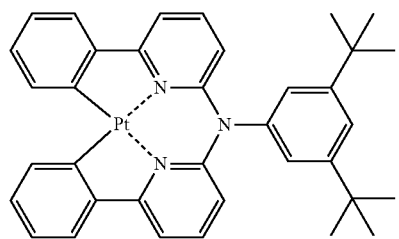
PD48
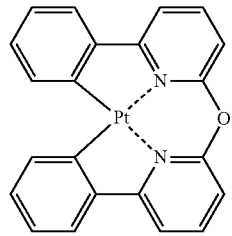
PD49
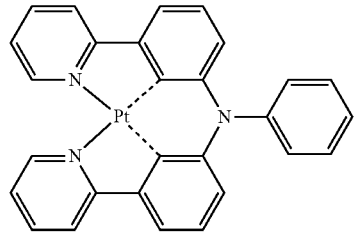
PD50
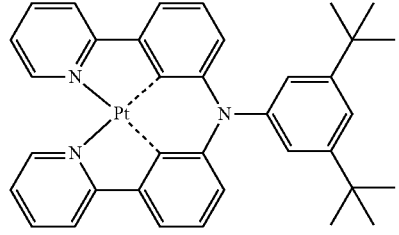
-continued
PD51
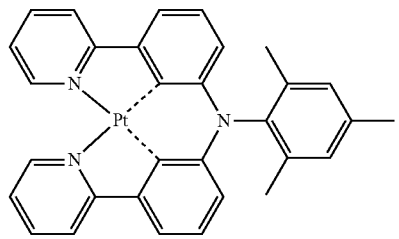
PD52
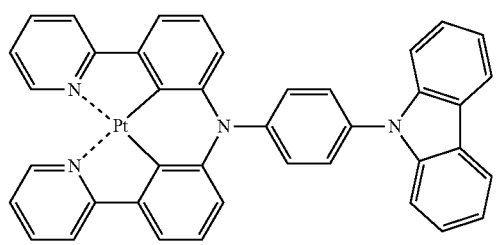
PD53
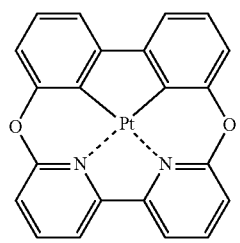
PD54
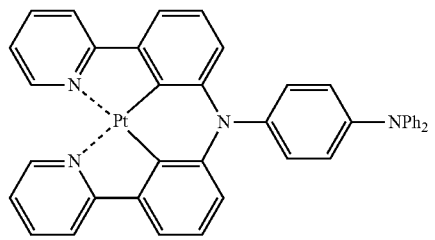
PD55
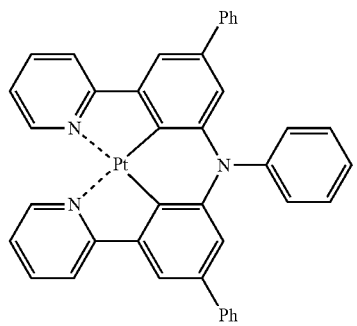
PD56
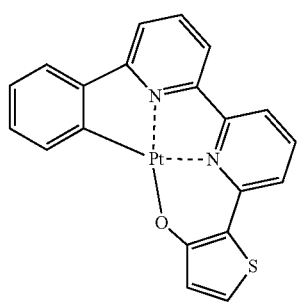

PD57
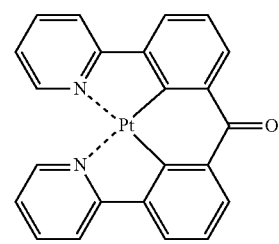
PD58
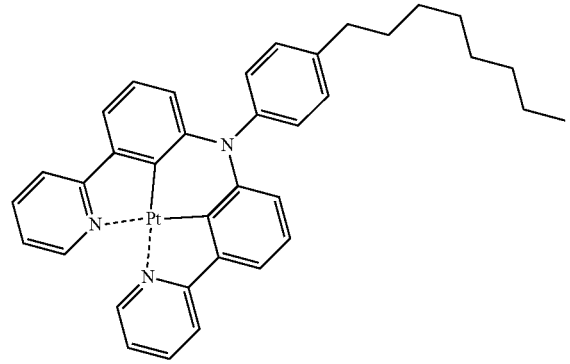
PD59
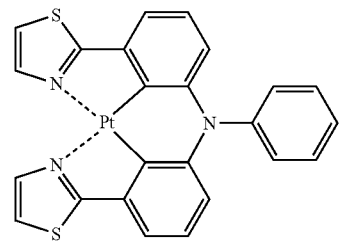
PD60
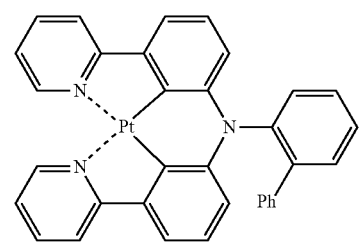
PD61
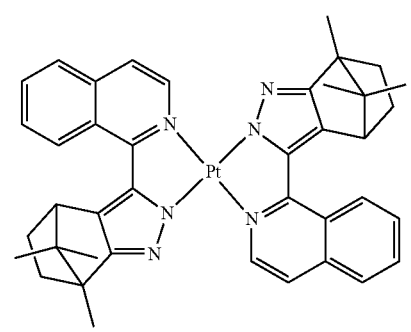
PD62
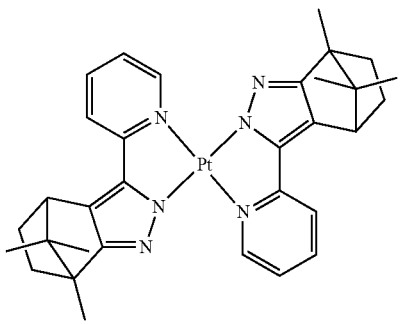
PD63
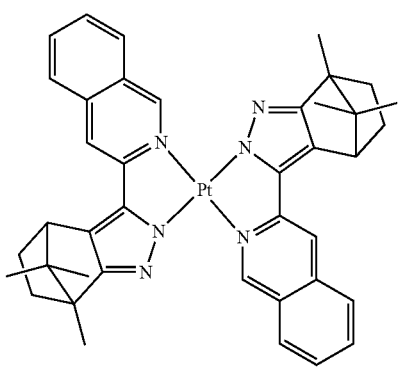
PD64
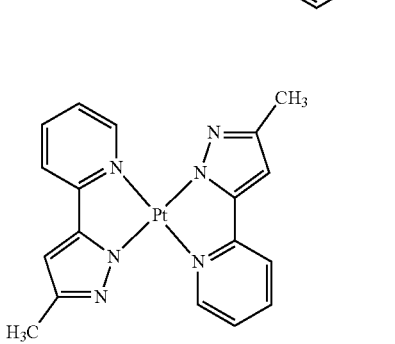
PD65
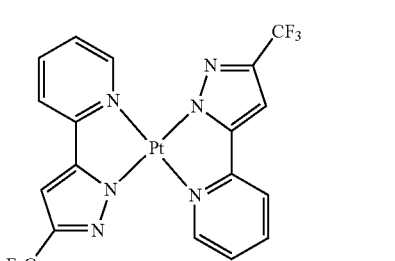
PD66
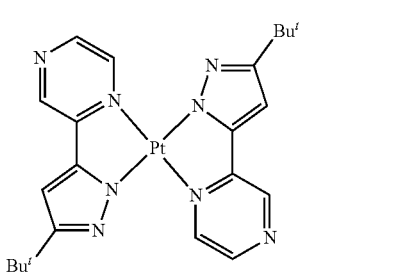

-continued
PD67 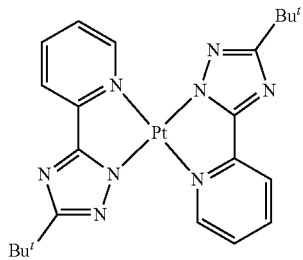
PD68 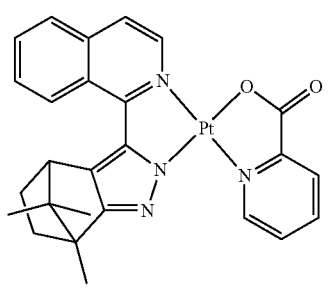
PD69 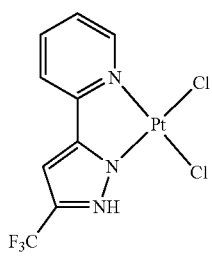
PD70 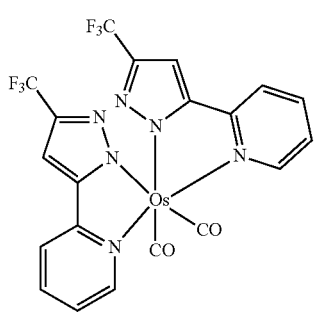
PD71 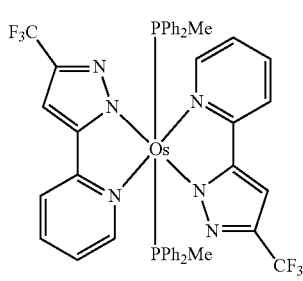
-continued
PD72 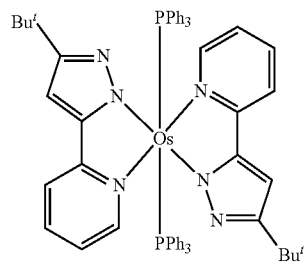
PD73 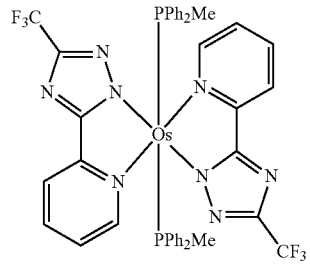
PD74 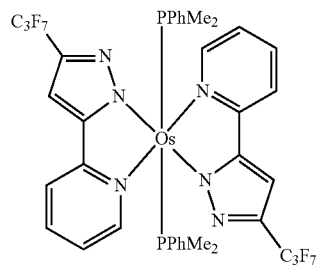
PD75 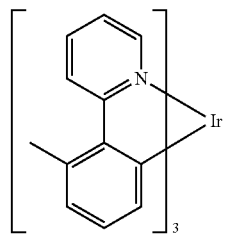
PD76 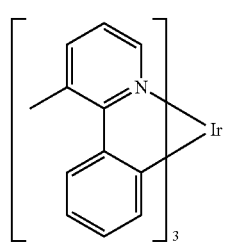
PD77

-continued

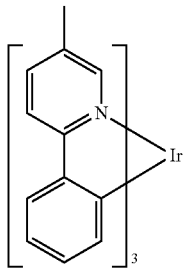
PD78

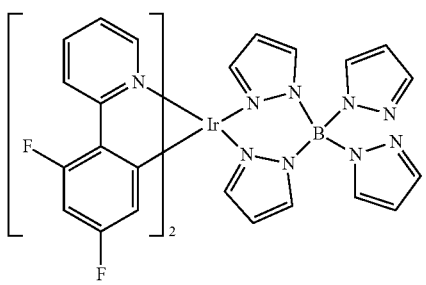
FIr6

As used herein, "(for example, the organic layer) including at least one of the heterocyclic compound" means that "(the organic layer) including a heterocyclic compound of Formula 1, or at least two different heterocyclic compounds of Formula 1".

For example, the organic layer may include Compound 1 only as the heterocyclic compound. In this embodiment, Compound 1 may be included in the emission layer of the organic light-emitting device. In some embodiments, the organic layer may include Compounds 1 and 2 as the heterocyclic compounds. In this embodiment, Compounds 1 and 2 may be present in the same layer (for example, Compounds 1 and 2 may be both present in an emission layer), or in different layers (for example, Compound 1 may be present in an emission layer, and Compound 2 may be present in a hole blocking layer).

The first electrode may be an anode, which is a hole injection electrode, and the second electrode may be a cathode, which is an electron injection electrode. In some embodiments, the first electrode may be a cathode, which is an electron injection electrode, and the second electrode may be an anode, which is a hole injection electrode.

The term "organic layer" as used herein refers to a single and/or a plurality of layers between the first electrode and the second electrode in an organic light-emitting device. The "organic layer" may include not only organic compounds but also organometallic complexes including metals.

The FIGURE illustrates a schematic cross-sectional view of an organic light-emitting device 10 according to an embodiment. Hereinafter, a structure of an organic light-emitting device according to one or more embodiments and a method of manufacturing the organic light-emitting device will be described with reference to The FIGURE. The organic light-emitting device 10 may include a first electrode 11, an organic layer 15, and a second electrode 19, which may be sequentially layered in this stated order.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

The first electrode 11 may be formed by depositing or sputtering, onto the substrate, a material for forming the first electrode 11. The first electrode 11 may be an anode. The material for forming the first electrode 11 may be materials with a high work function for easy hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), and zinc oxide (ZnO). In some embodiments, the material for forming the first electrode 11 may be a metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including a plurality of layers. In some embodiments, the first electrode 11 may have a triple-layered structure of ITO/Ag/ITO, but embodiments are not limited thereto.

The organic layer 15 may be on the first electrode 11.

The organic layer 15 may include a hole transport region, an emission layer, and an electron transport region.

The hole transport region may be disposed between the first electrode 11 and the emission layer.

The hole transport region may include at least one a hole injection layer, a hole transport layer, an electron blocking layer, and a buffer layer.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer, the hole injection layer may be formed on the first electrode 11 by using one or more suitable methods, such as vacuum deposition, spin coating, casting, and Langmuir-Blodgett (LB) deposition.

When a hole injection layer is formed by vacuum-deposition, for example, the vacuum deposition may be performed at a temperature in a range of about 100° C. to about 500° C., at a vacuum degree in a range of about $10^{-8}$ torr to about $10^{-3}$ torr, and at a rate in a range of about 0.01 Angstroms per second (Å/sec) to about 100 Å/sec, though the conditions may vary depending on a compound used as a hole injection material and a structure and thermal properties of a desired hole injection layer, but embodiments are not limited thereto.

When a hole injection layer is formed by spin coating, the spin coating may be performed at a rate in a range of about 2,000 revolutions per minute (rpm) to about 5,000 rpm and at a temperature in a range of about 80° C. to 200° C. to facilitate removal of a solvent after the spin coating, though the conditions may vary depending on a compound used as a hole injection material and a structure and thermal properties of a desired hole injection layer, but embodiments are not limited thereto.

The conditions for forming a hole transport layer and an electron blocking layer may be inferred from the conditions for forming the hole injection layer.

The hole transport region may include at least one of m-MTDATA, TDATA, 2-TNATA, NPB, β-NPB, TPD, spiro-TPD, spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor-sulfonic acid (PANI/CSA), polyaniline/poly(4-styrenesulfonate) (PANI/PSS), a compound represented by Formula 201, or a compound represented by Formula 202:

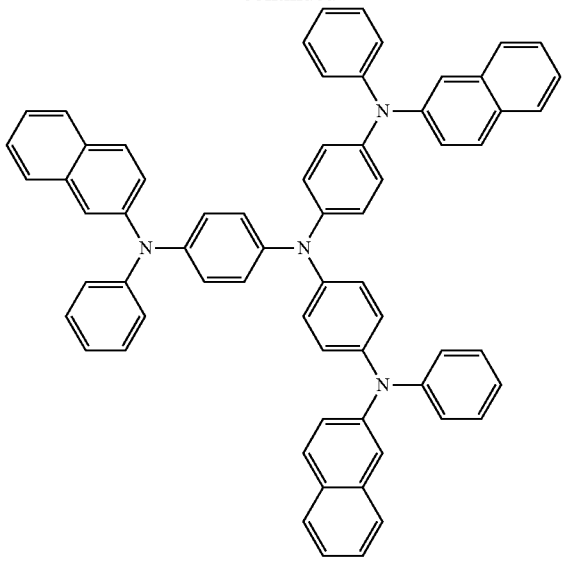

2-TNATA

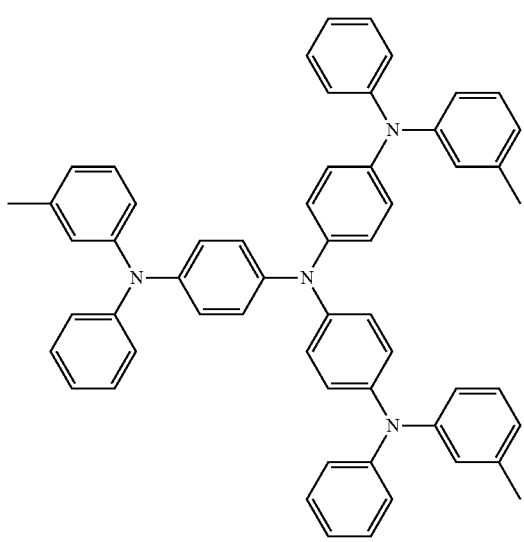

m-MTDATA

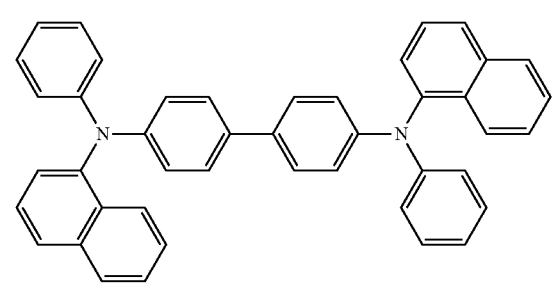

NPB

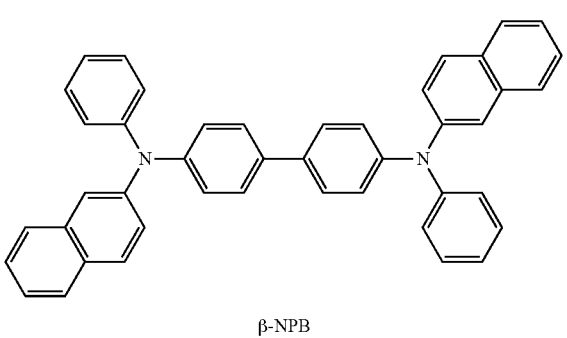

β-NPB

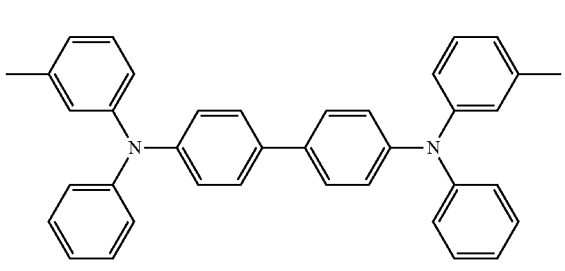

TPD

TDATA

-continued

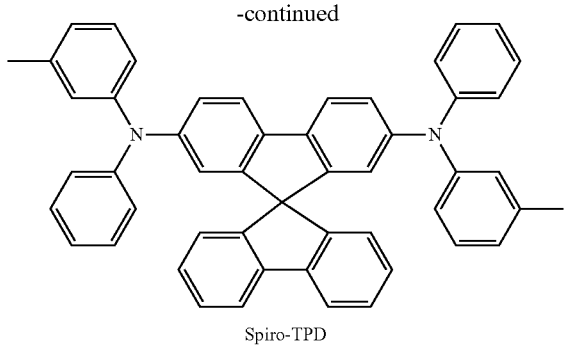

Spiro-TPD

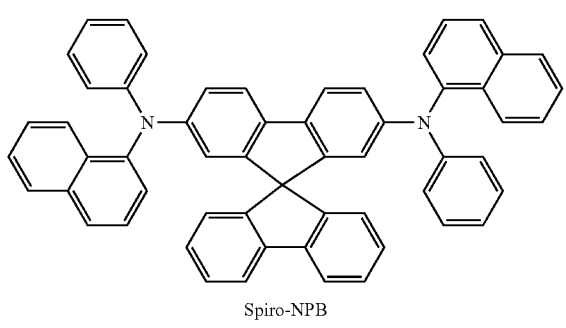

Spiro-NPB

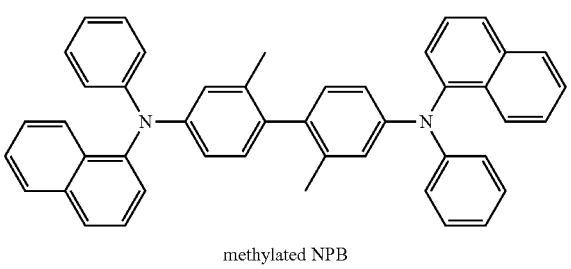

methylated NPB

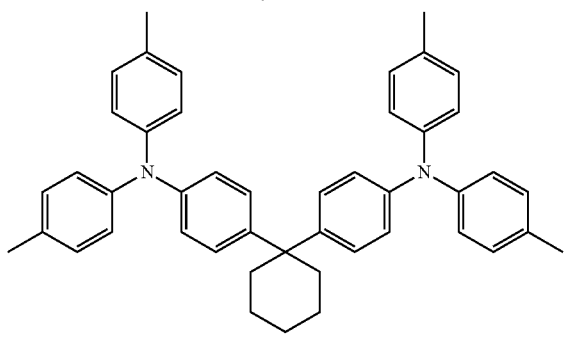

TAPC

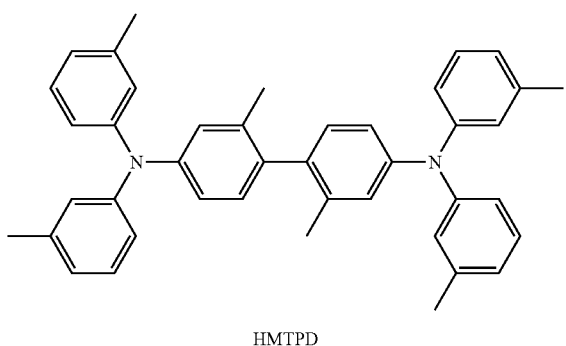

HMTPD

-continued

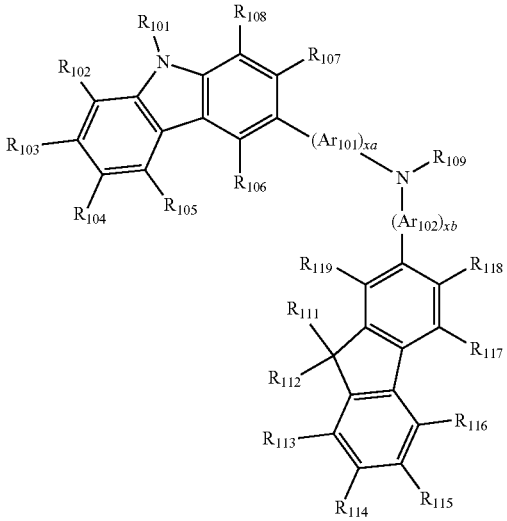

Formula 201

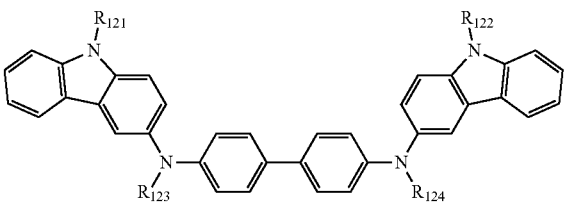

Formula 202 wherein, in Formula 201, $Ar_{101}$ and $Ar_{102}$ may each independently be a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

In Formula 201, xa and xb may each independently be an integer from 0 to 5. In some embodiments, xa and xb may each independently be an integer from 0 to 2. In some embodiments, xa may be 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), or a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, or a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but embodiments are not limited thereto.

In Formula 201, $R_{109}$ may be a phenyl group, a naphthyl group, an anthracenyl group, or a pyridinyl group; or a phenyl group, a naphthyl group, an anthracenyl group, or a pyridinyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, or a pyridinyl group.

In some embodiments, the compound represented by Formula 201 may be represented by Formula 201A, but embodiments are not limited thereto:

Formula 201A

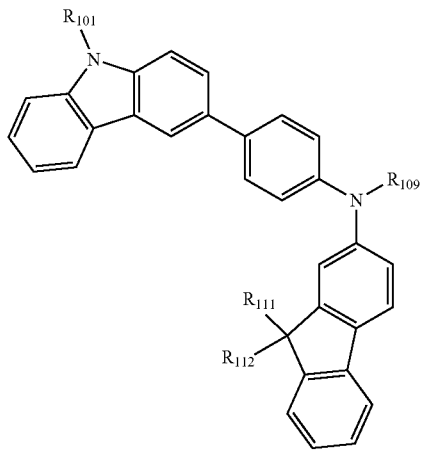

wherein, in Formula 201A, $R_{101}$, $R_{111}$, $R_{112}$, and $R_{109}$ may respectively be understood by referring to the descriptions therefor provided herein.

In some embodiments, the compounds represented by Formulae 201 and 202 may include Compounds HT1 to HT20, but embodiments are not limited thereto:

HT1

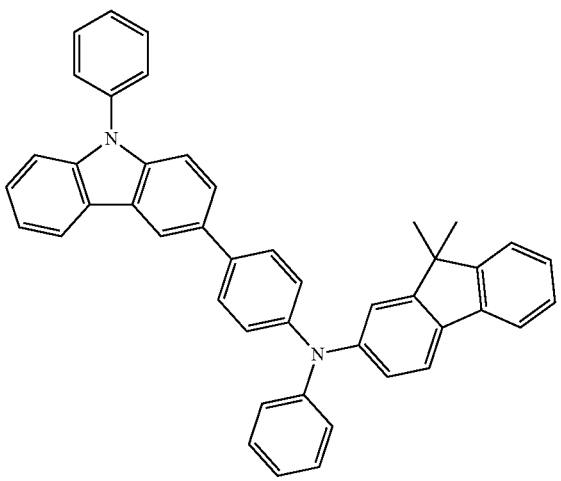

HT2

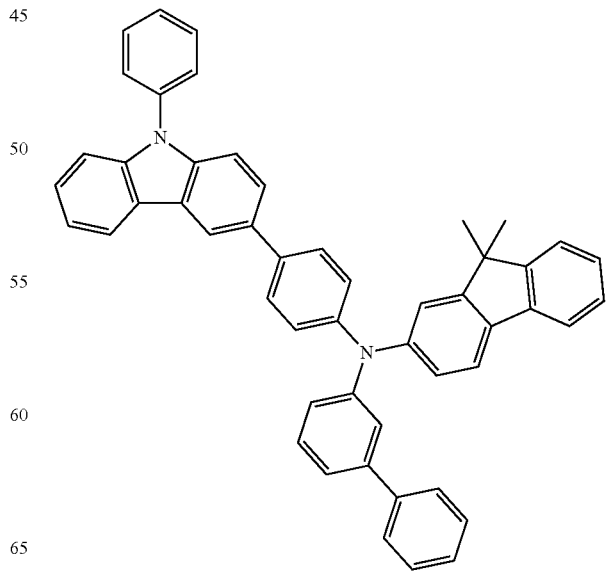

709
-continued
HT3
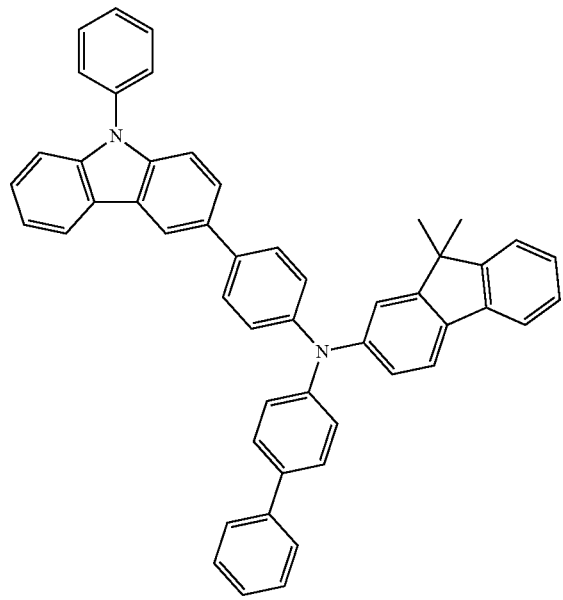
HT4
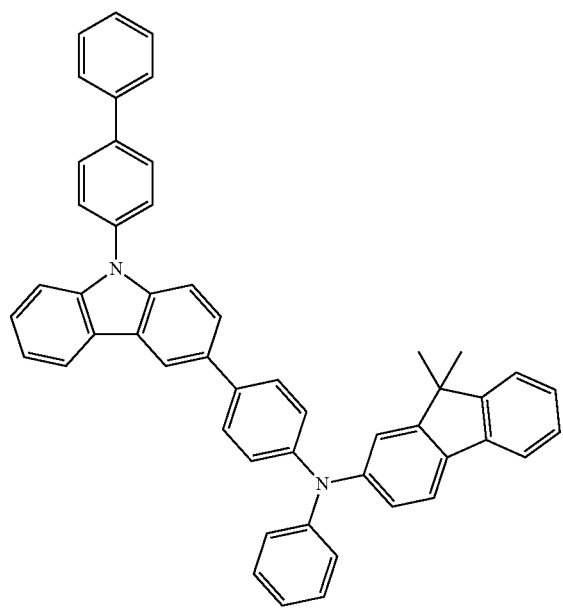
710
-continued
HT5
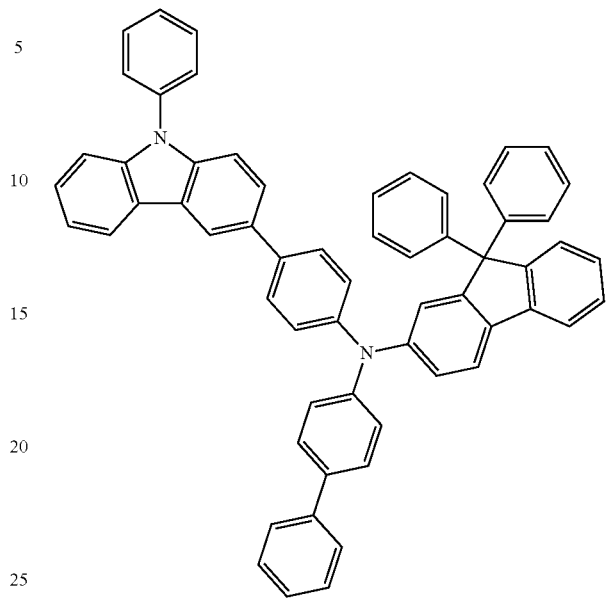
HT6
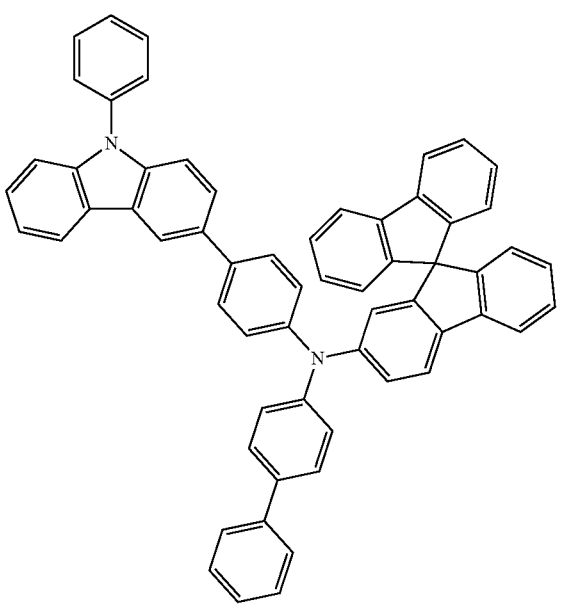

711
-continued
712
-continued
HT7
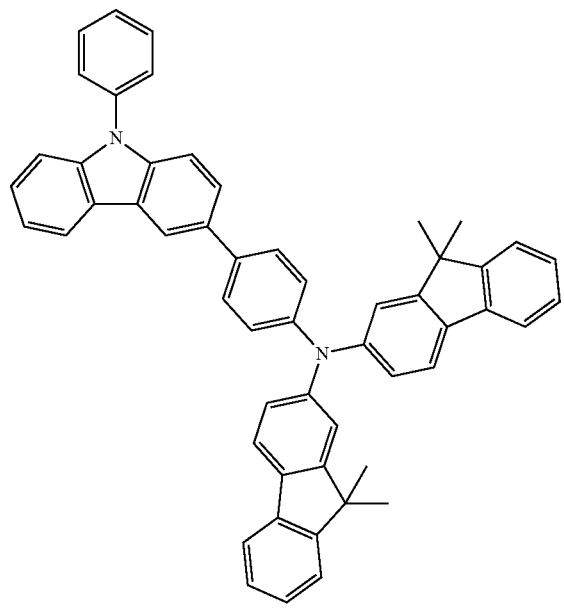
HT10
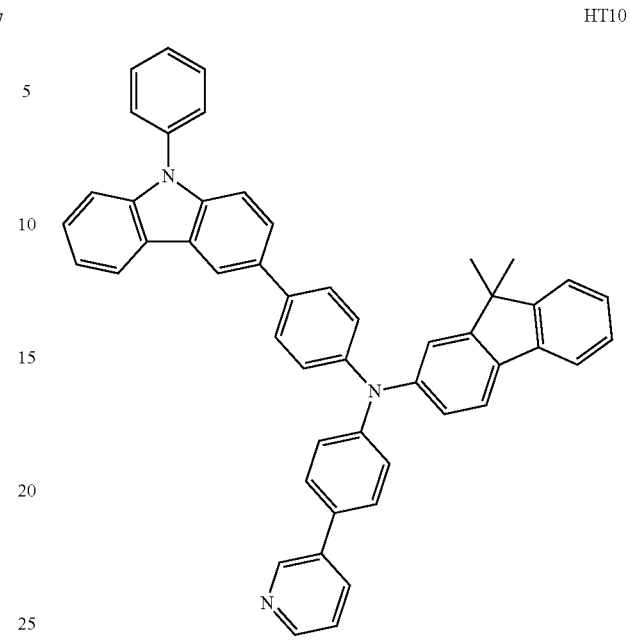
HT8
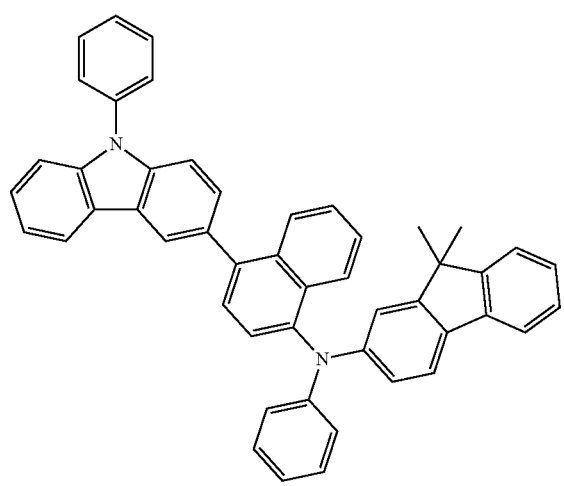
HT9
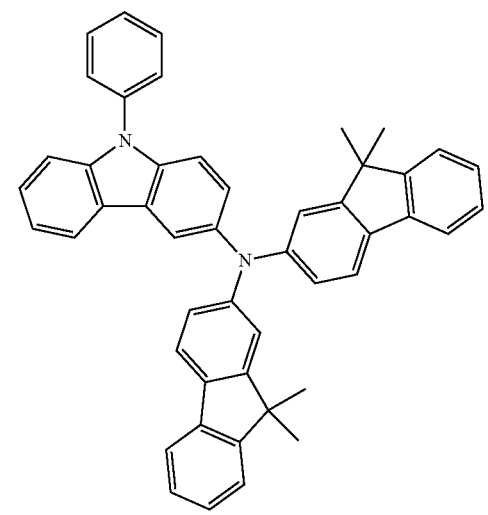
HT11
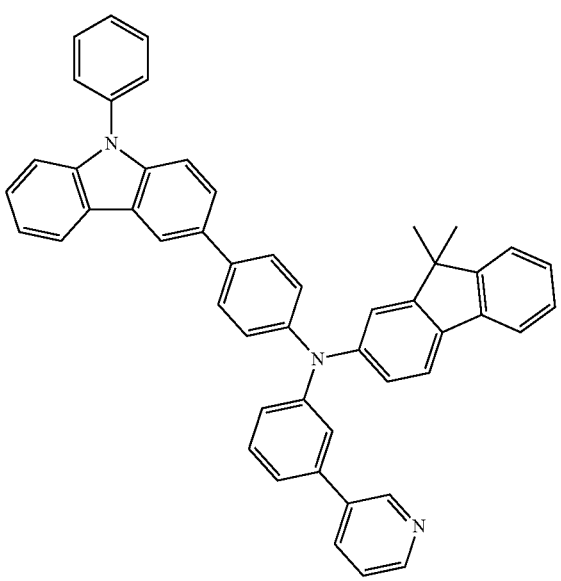

HT12
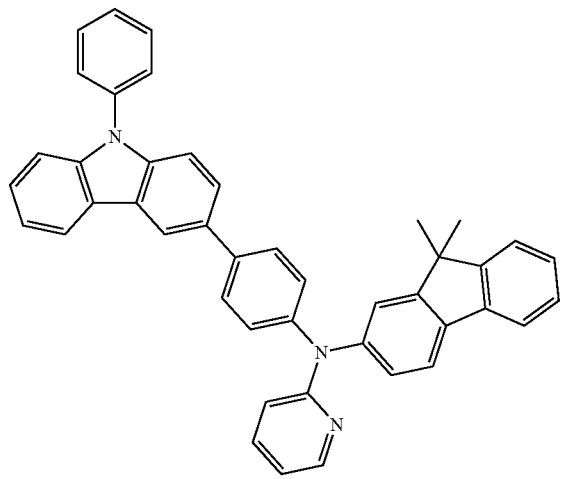
HT13
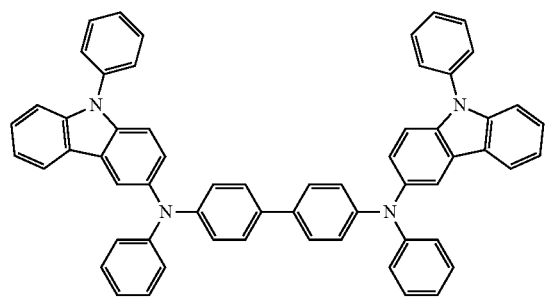
HT14
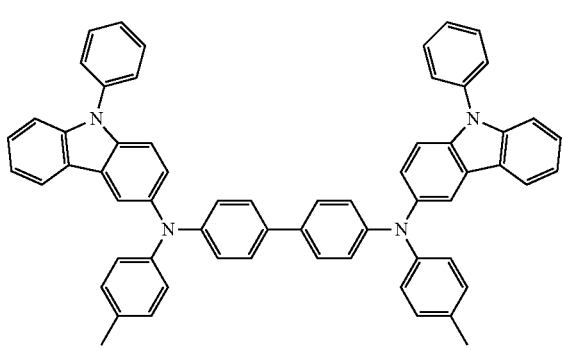
HT15
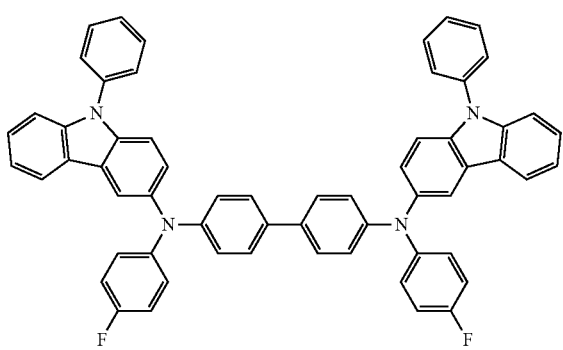
HT16
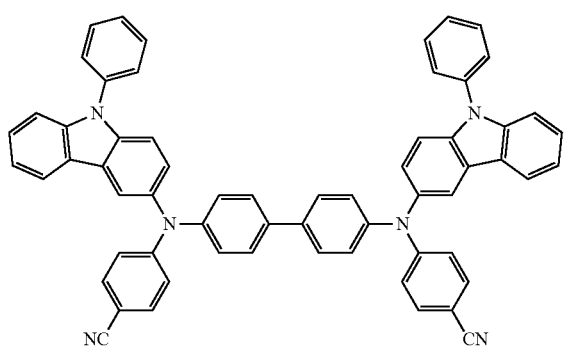
HT17
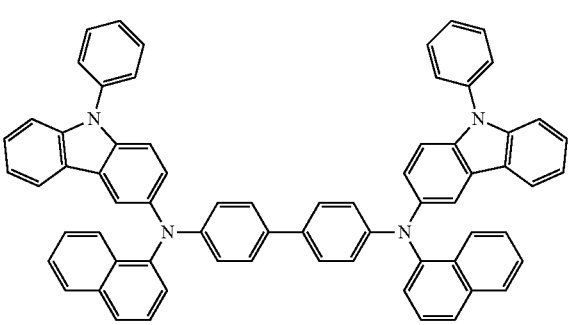
HT18
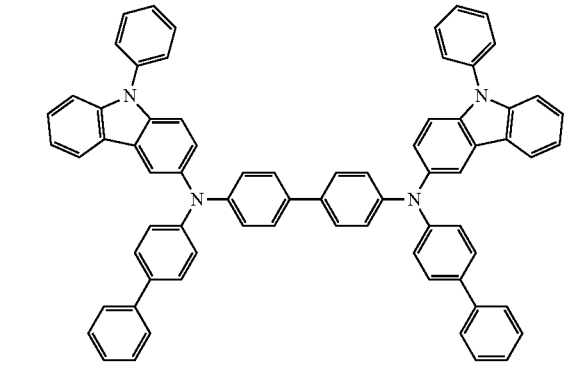
HT19
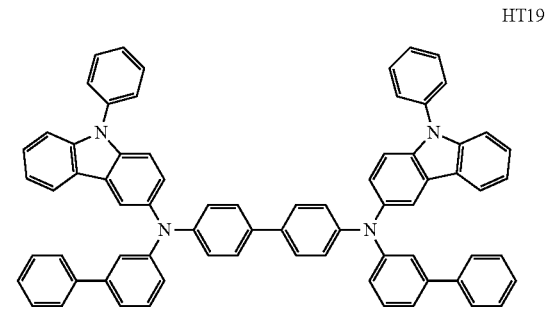

-continued

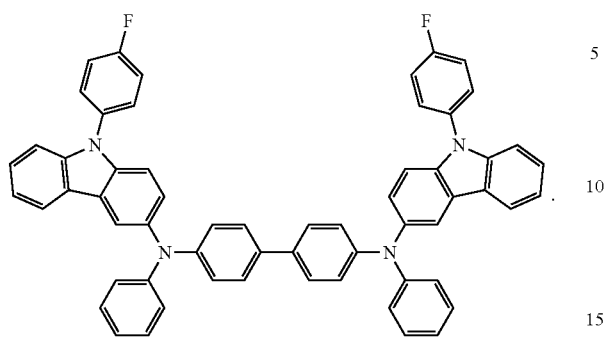

HT20

The thickness of the hole transport region may be in a range of about 100 Angstroms (Å) to about 10,000 Å, for example, about 100 Å to about 1,000 Å. When the hole transport region includes at least one a hole injection layer and a hole transport layer, the thickness of the hole injection layer may be in a range of about 100 Å to about 10,000 Å, for example, about 100 Å to about 1,000 Å, the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, excellent hole transport characteristics may be obtained without a substantial increase in driving voltage.

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant. The p-dopant may include one of a quinone derivative, a metal oxide, and a compound containing a cyano group, but embodiments are not limited thereto. For example, non-limiting examples of the p-dopant include a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or Compound HT-D2, but embodiments are not limited thereto:

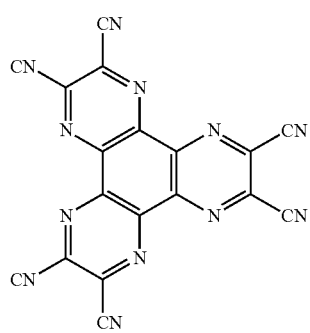

HT-D1

-continued

F4-TCNQ

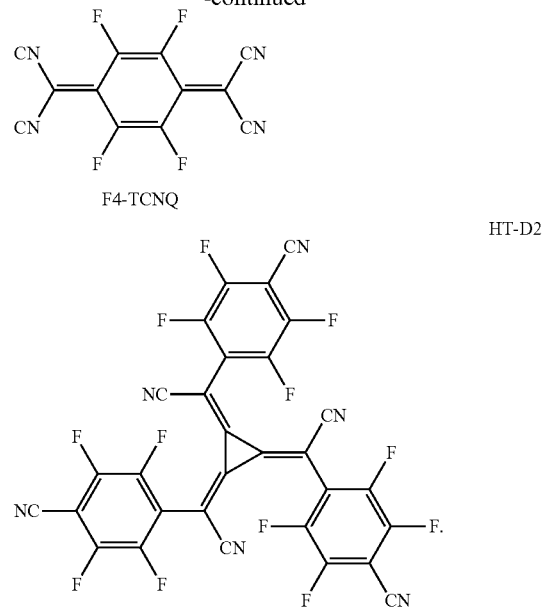

HT-D2

The hole transport region may further include a buffer layer.

The buffer layer may compensate for an optical resonance distance depending on a wavelength of light emitted from the emission layer to improve the efficiency of an organic light-emitting device.

An emission layer may be formed on the hole transport region by using one or more suitable methods, such as vacuum deposition, spin coating, casting, or LB deposition. When the emission layer is formed by vacuum deposition or spin coating, vacuum deposition and coating conditions for forming the emission layer may be generally similar to those conditions for forming a hole injection layer, though the conditions may vary depending on a compound that is used.

The hole transport region may further include an electron blocking layer. The electron blocking layer may include any suitable known material, e.g., mCP, but embodiments are not limited thereto:

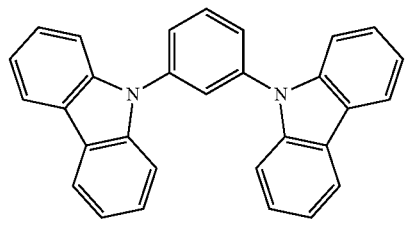

mCP

The thickness of the electron blocking layer may be in a range of about 50 Å to about 1,000 Å, and in some embodiments, about 70 Å to about 500 Å. When the thickness of the electron blocking layer is within any of these ranges, excellent electron blocking characteristics may be obtained without a substantial increase in driving voltage.

When the organic light-emitting device 10 is a full-color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light. In some embodiments, the structure of the emission layer may vary.

The emission layer may include the heterocyclic compound represented by Formula 1.

In some embodiments, the emission layer may include the heterocyclic compound represented by Formula 1 only.

In some embodiments, the emission layer may include the heterocyclic compound represented by Formula 1,
i) the second compound (e.g., a compound represented by Formula H-1);
ii) the organometallic compound represented by Formula 81; or
iii) any combination of i) and ii).

The heterocyclic compound represented by Formula 1, the second compound, and the organometallic compound represented by Formula 81 may respectively be understood by referring to the descriptions for those provided herein.

When the emission layer includes the host and the dopant, an amount of the dopant may be in a range of about 0.01 parts to about 20 parts by weight based on about 100 parts by weight of the emission layer, but embodiments are not limited thereto. When the amount of the dopant is within this range, light emission without quenching may be realized.

When the emission layer includes the heterocyclic compound represented by Formula 1 and the second compound, a weight ratio of the heterocyclic compound represented by Formula 1 to the second compound may be in a range of about 1:99 to about 99:1, for example, about 70:30 to about 30:70. In some embodiments, a weight ratio of the heterocyclic compound represented by Formula 1 to the second compound may be in a range of about 60:40 to about 40:60. When the weight ratio of the heterocyclic compound represented by Formula 1 to the second compound in the emission layer is within any of these ranges, the charge transport balance may be efficiently achieved in the emission layer.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Next, an electron transport region may be formed on the emission layer.

The electron transport region may include at least one a hole blocking layer, an electron transport layer, or an electron injection layer.

In some embodiments, the electron transport region may have a hole blocking layer/an electron transport layer/an electron injection layer structure or an electron transport layer/an electron injection layer structure, but embodiments are not limited thereto. The electron transport layer may have a single-layered structure or a multi-layered structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer, for example, may include at least one of BCP or Bphen, but embodiments are not limited thereto:

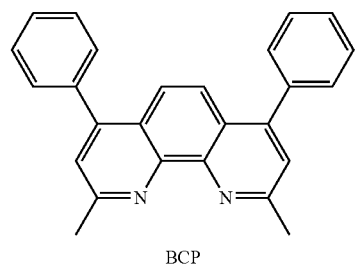

BCP

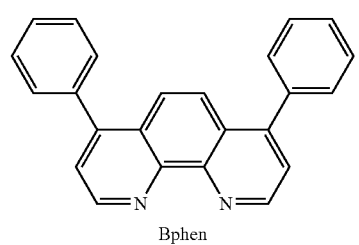

Bphen

The hole blocking layer may include the heterocyclic compound represented by Formula 1.

The thickness of the hole blocking layer may be in a range of about 20 Å to about 1,000 Å, for example, about 30 Å to about 300 Å. When the thickness of the hole blocking layer is within any of these ranges, excellent hole blocking characteristics may be obtained without a substantial increase in driving voltage.

The electron transport layer may further include at least one of BCP, Bphen, Alq$_3$, BAlq, TAZ, or NTAZ:

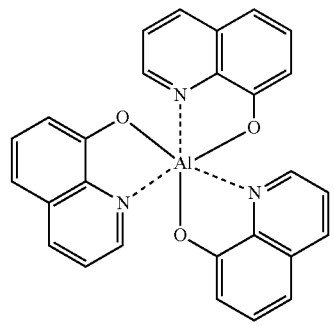

Alq$_3$

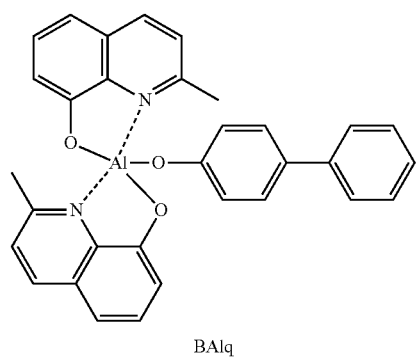

BAlq

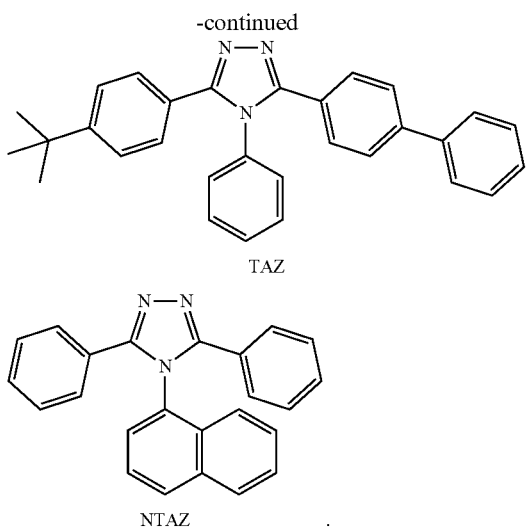

TAZ

NTAZ

In some embodiments, the electron transport layer may include at least one of Compounds ET1, ET2, and ET3, but embodiments are not limited thereto:

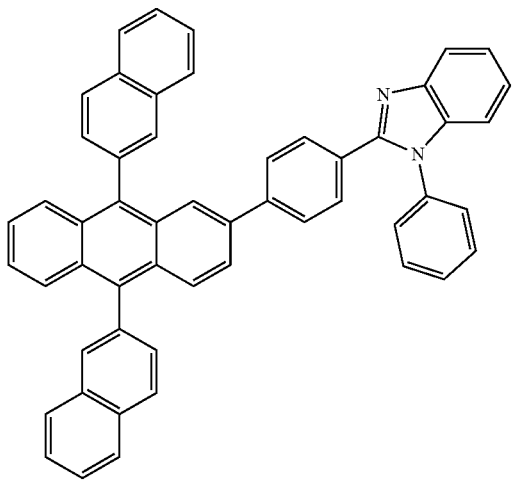

ET1

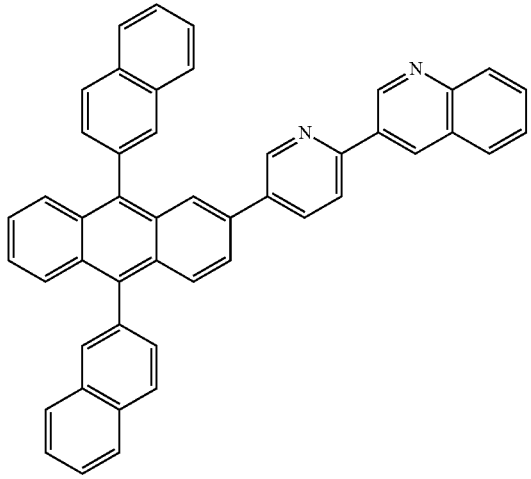

ET2

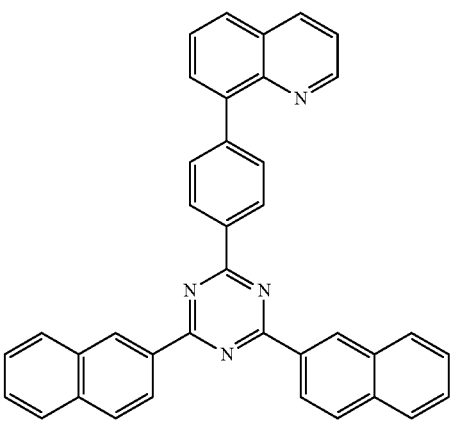

ET3

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport layer may further include a material containing metal, in addition to the materials described above.

The material containing metal may include a Li complex. The Li complex may include, e.g., Compound ET-D1 (LiQ) or Compound ET-D2:

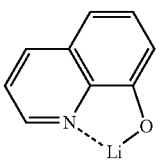

ET-D1

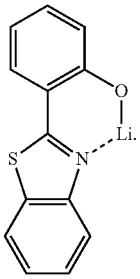

ET-D2

The electron transport region may include an electron injection layer that facilitates electron injection from the second electrode 19.

The electron injection layer may include at least one of LiQ, LiF, NaCl, CsF, $Li_2O$, or BaO.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

The second electrode 19 may be on the organic layer 15. The second electrode 19 may be a cathode. A material for forming the second electrode 19 may be a material with a relatively low work function, such as a metal, an alloy, an electrically conductive compound, and a mixture thereof. Examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device. In some embodiments, the material for forming the second electrode 19 may vary.

Hereinbefore the organic light-emitting device 10 has been described with reference to The FIGURE, but embodiments are not limited thereto.

The term "$C_1$-$C_{60}$ alkyl group" as used herein refers to a linear or branched aliphatic saturated hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is a $C_1$-$C_1$ alkyl group). Examples thereof include a methoxy group, an ethoxy group, and an isopropyloxy group.

The term "$C_2$-$C_{60}$ alkenyl group" as used herein refers to a group formed by placing at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by placing at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent monocyclic group including at least one heteroatom of N, O, P, Si, Se. Ge, or S as a ring-forming atom and 2 to 10 carbon atoms. Examples thereof include a tetrahydrofuranyl group and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group including at least one heteroatom of N, O, P, Si, Se, Ge, or S as a ring-forming atom, 2 to 10 carbon atoms, and at least one double bond in its ring. Examples of the $C_2$-$C_{10}$ heterocycloalkenyl group include a 2,3-dihydrofuranyl group and a 2,3-dihydrothiophenyl group. The term "$C_2$-$C_{10}$ heterocycloalkylene group" as used herein refers to a divalent group having the same structure as the $C_2$-$C_{10}$ heterocycloalkyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

The term "$C_1$-$C_{60}$ heteroaryl group" as used herein refers to a monovalent group having a carbocyclic aromatic system having at least one heteroatom of N, O, P, Si, Se, Ge, or S as a ring-forming atom and 1 to 60 carbon atoms. The term "$C_1$-$C_{60}$ heteroarylene group" as used herein refers to a divalent group having a carbocyclic aromatic system having at least one heteroatom of N, O, P, Se, Ge, or S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein is represented by —$OA_{102}$ (wherein $A_{102}$ is the $C_6$-$C_{60}$ aryl group). The term "$C_6$-$C_{60}$ arylthio group" as used herein is represented by —$SA_{103}$ (wherein $A_{103}$ is the $C_6$-$C_{60}$ aryl group).

The term "monovalent non-aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is non-aromatic. Examples of the non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group having at least two rings condensed and a heteroatom of N, O, P, Si, Se, Ge, or S as well as carbon atoms (for example, the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{60}$ carbocyclic group" as used herein refers to a saturated or unsaturated cyclic group including 5 to 60 carbon atoms only as ring-forming atoms. The $C_5$-$C_{60}$ carbocyclic group may be a monocyclic group or a polycyclic group.

The term "$C_2$-$C_{60}$ heterocyclic group" as used herein refers to saturated or unsaturated cyclic group including 2 to 60 carbon atoms and at least one heteroatom of N, O, P, Si, Se, Ge, or S as ring-forming atoms. The $C_2$-$C_{60}$ heterocyclic group may be a monocyclic group or a polycyclic group.

In the present specification, in Formula 1, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, or —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, or —$B(Q_{26})(Q_{27})$; or —$Si(Q_{31})(Q_{32})(Q_{33})$, —$N(Q_{34})(Q_{35})$ or —$B(Q_{36})(Q_{37})$, wherein $Q_{11}$ to $Q_{17}$, $Q_{21}$ to $Q_{27}$, and $Q_{31}$ to $Q_{37}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

The symbols * and *' as used herein, unless defined otherwise, refer to a binding site to an adjacent atom in the formula.

Hereinafter, a compound and an organic light-emitting device according to an embodiment will be described in detail with reference to Synthesis Examples and Examples, however, the present disclosure is not limited thereto. The wording "B was used instead of A" used in describing Synthesis Examples means that an identical molar equivalent of B was used in place of A.

EXAMPLES

Synthesis Example 1: Synthesis of Compound 582

(1) Synthesis of Intermediate (5)

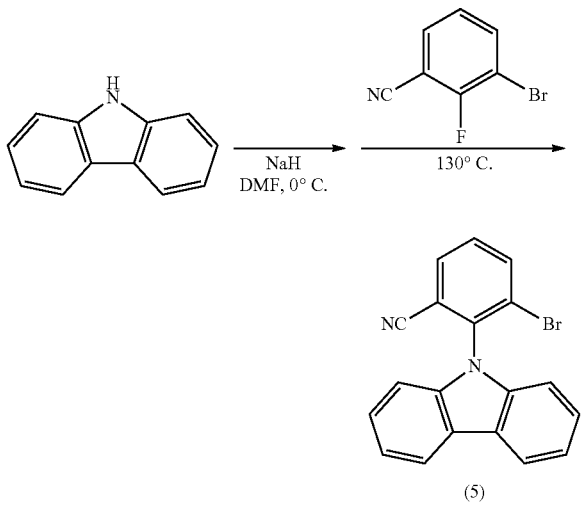 [SMILES: c1ccc2c(c1)[nH]c1ccccc12 ; N#Cc1cccc(Br)c1F ; N#Cc1cccc(Br)c1-n1c2ccccc2c2ccccc21]

(5)

7.22 grams (g) (43.2 mmol) of carbazole was mixed with 100 milliliters (mL) of dimethyl formamide, followed by slowly adding 1.73 g (43.2 mmol) of sodium hydride (60 percent (%) dispersion in mineral oil) thereto and stirring at a temperature of 0° C. for 30 minutes. A solution, in which 9.51 g (47.5 mmol) of 3-bromo-2-fluorobenzonitrile was diluted in 70 mL of dimethyl formamide, was slowly added to the resulting product for 10 minutes. Subsequently, the reaction temperature was raised to 130° C., followed by stirring for 18 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified through silica gel column chromatography to obtain a desired compound, 10.62 g of Intermediate (5) (at a yield of 71%).

LC-MS (calculated value: 346.01 g/mol, measured value: M+1=347 g/mol)

(2) Synthesis of Intermediate (6)

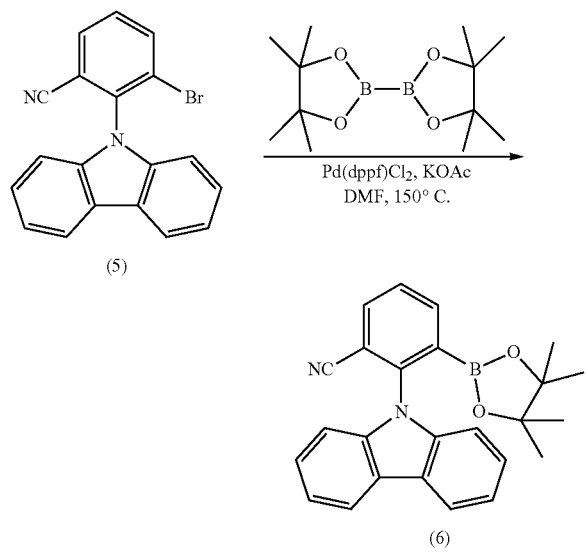

10.39 g (29.9 mmol) of Intermediate (5), 11.40 g (44.9 mmol) of 4,4,4',4',5,5,5',5'-octamethyl-2,2'-bi(1,3,2-dioxaborolane), 2.19 g (3.0 mmol) of PdCl$_2$(dppf).CH$_2$Cl$_2$, and 8.81 g (89.8 mmol) of potassium acetate were mixed with 75 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified by silica gel column chromatography and recrystallized using dichloromethane/n-hexane to obtain a desired compound, 7.95 g of Intermediate (6) (at a yield of 67%).

LC-MS (calculated value: 394.19, measured value: M+1=395)

(3) Synthesis of Intermediate (7)

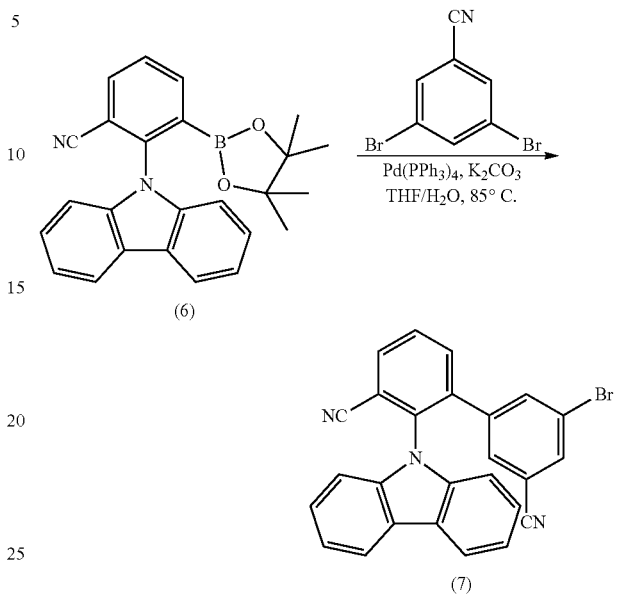

5.12 g (19.6 mmol) of 3,5-dibromobenzonitrile, 7.74 g (19.6 mmol) of Intermediate (6), 2.27 g (2.0 mmol) of tetrakis(triphenylphosphine)palladium(0), and 5.43 g (39.3 mmol) of potassium carbonate were added to a mixture solution of 50 mL of tetrahydrofuran and 20 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 5.30 g of Intermediate (7) (at a yield of 60%).

LC-MS (calculated value: 447.04, measured value: M+1=448)

(4) Synthesis of Intermediate (8)

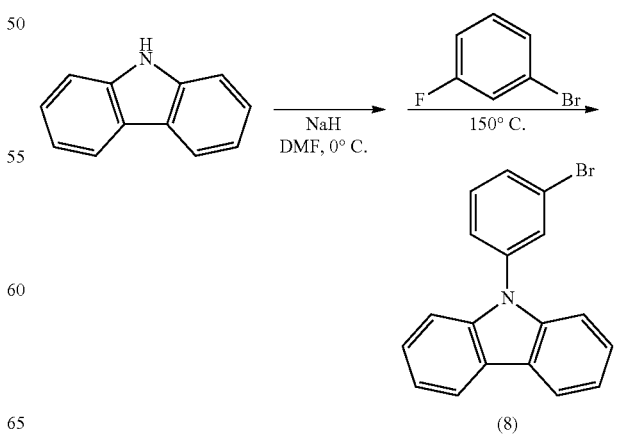

10.38 g (62.1 mmol) of carbazole was mixed with 150 mL of dimethyl formamide, followed by slowly adding 2.48 g (62.1 mmol) of sodium hydride (60% dispersion in mineral oil) thereto and stirring at a temperature of 0° C. for 30 minutes. A solution, in which 11.95 g (68.3 mmol) of 1-bromo-3-fluorobenzene was diluted in 100 mL of dimethyl formamide, was slowly added to the resulting product for 10 minutes. Subsequently, the reaction temperature was raised to 150° C., followed by stirring for 24 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography to obtain a desired compound, 9.35 g of Intermediate (8) (at a yield of 47%).

LC-MS (calculated value: 321.01, measured value: M+1=322)

(5) Synthesis of Intermediate (9)

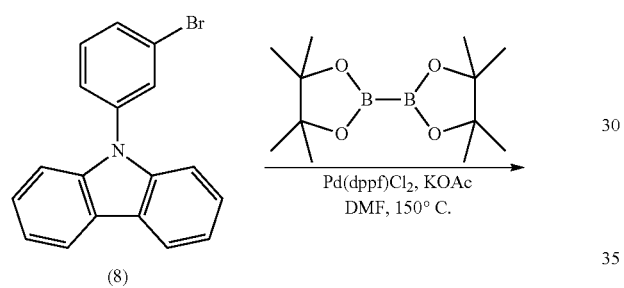

9.16 g (28.4 mmol) of Intermediate (8), 10.83 g (42.7 mmol) of 4,4,4',4',5,5,5',5'-octamethyl-2,2'-bi(1,3,2-dioxaborolane), 2.08 g (2.8 mmol) of PdCl$_2$(dppf).CH$_2$Cl$_2$, and 8.37 g (85.3 mmol) of potassium acetate were mixed with 72 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified by silica gel column chromatography and recrystallized using ethyl acetate/n-hexane to obtain a desired compound, 8.65 g of Intermediate (9) (at a yield of 82%).

LC-MS (calculated value: 369.19, measured value: M+1=370)

(6) Synthesis of Compound 582

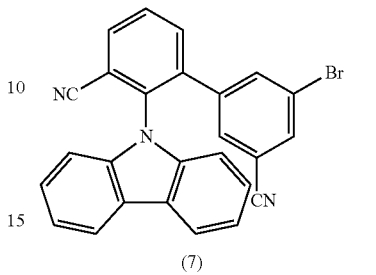

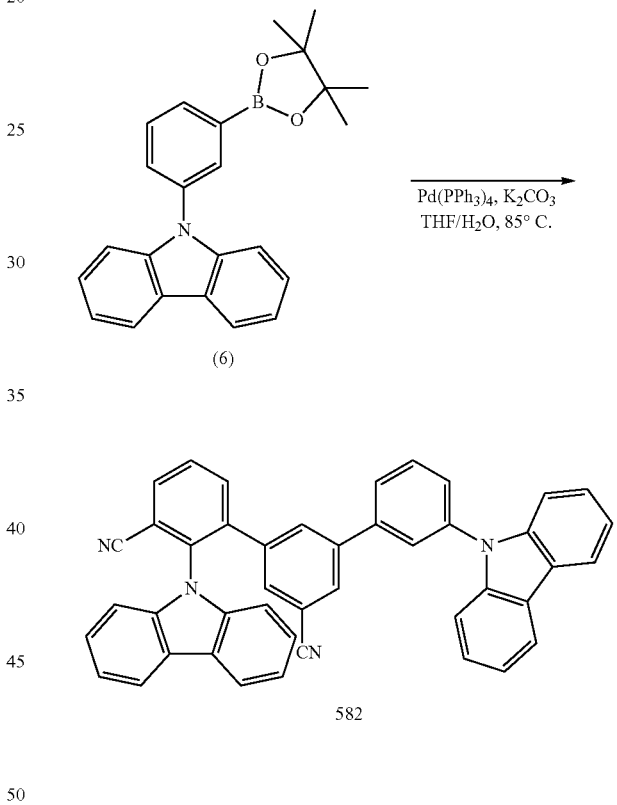

5.14 g (11.5 mmol) of Intermediate (7), 5.08 g (13.8 mmol) of Intermediate (9), 1.33 g (1.2 mmol) of tetrakis (triphenylphosphine)palladium(0), and 3.17 g (22.9 mmol) of potassium carbonate were added to a mixture solution of 30 mL of tetrahydrofuran and 12 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography and recrystallized to obtain a desired compound, 1.25 g of Compound 582 (at a yield of 18%).

LC-MS (calculated value: 610.22, measured value: M+1=611)

Synthesis Example 2: Synthesis of Compound 2451

(1) Synthesis of Intermediate (10)

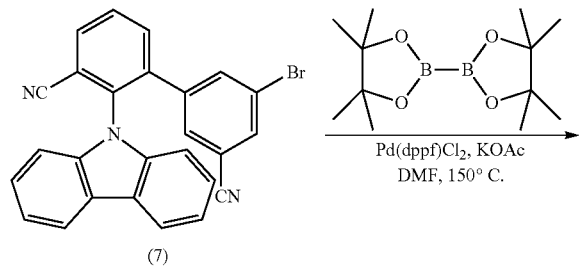

(7)

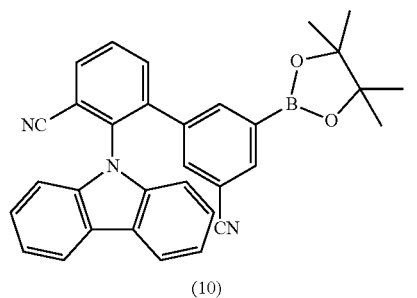

(10)

18.10 g (40.4 mmol) of Intermediate (7), 15.38 g (60.6 mmol) of 4,4,4',4',5,5,5',5'-octamethyl-2,2'-bi(1,3,2-dioxaborolane), 2.95 g (4.0 mmol) of $PdCl_2(dppf) \cdot CH_2Cl_2$, and 11.89 g (121.1 mmol) of potassium acetate were mixed with 100 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified through silica gel column chromatography and recrystallized using dichloromethane/n-hexane to obtain a desired compound, 8.79 g of Intermediate (10) (at a yield of 44%).

LC-MS (calculated value: 495.21, measured value: M+1=495)

(2) Synthesis of Intermediate (11)

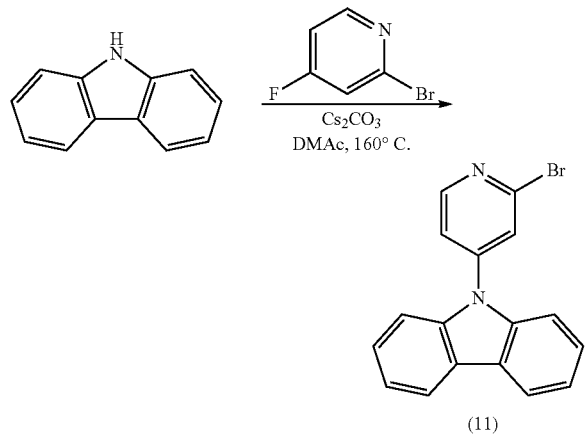

(11)

9.05 g (54.2 mmol) of carbazole, 14.29 g (81.2 mmol) of 2-bromo-4-fluoropyridine, and 35.29 g (108.3 mmol) of cesium carbonate were dissolved in 135 mL of dimethyl acetamide, followed by stirring under reflux for 15 hours at a temperature of 160° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 12.35 g of Intermediate (11) (at a yield of 71%).

LC-MS (calculated value: 322.01, measured value: M+1=323)

(3) Synthesis of Compound 2451

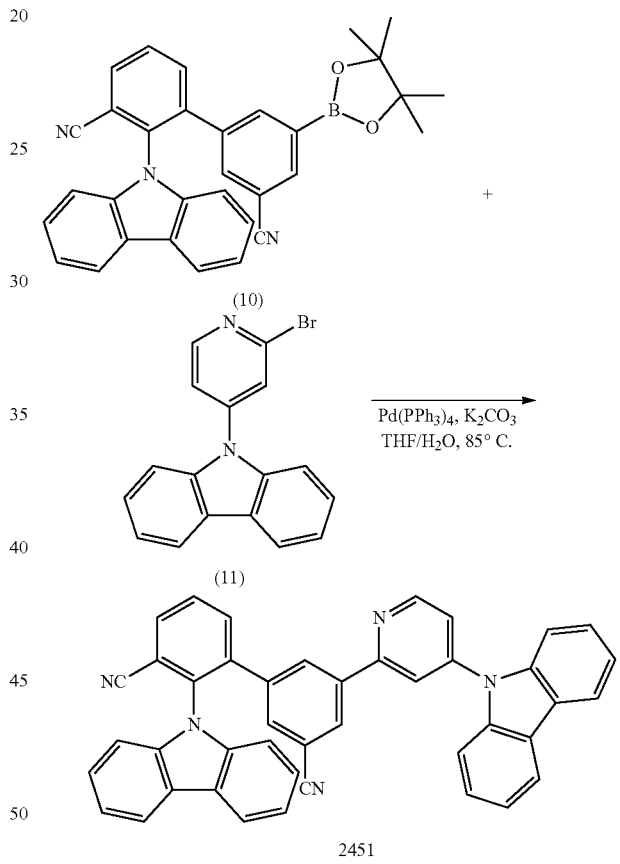

2451

8.69 g (17.5 mmol) of Intermediate (10), 8.72 g (17.5 mmol) of Intermediate (11), 2.03 g (1.8 mmol) of tetrakis(triphenylphosphine)palladium(0), and 4.85 g (35.1 mmol) of potassium carbonate were added to a mixture solution of 45 mL of tetrahydrofuran and 18 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography and recrystallized to obtain a desired compound, 2.10 g of Compound 2451 (at a yield of 20%).

LC-MS (calculated value: 611.21, measured value: M+1=612)

Synthesis Example 3: Synthesis of Compound 2168

(1) Synthesis of Intermediate (12)

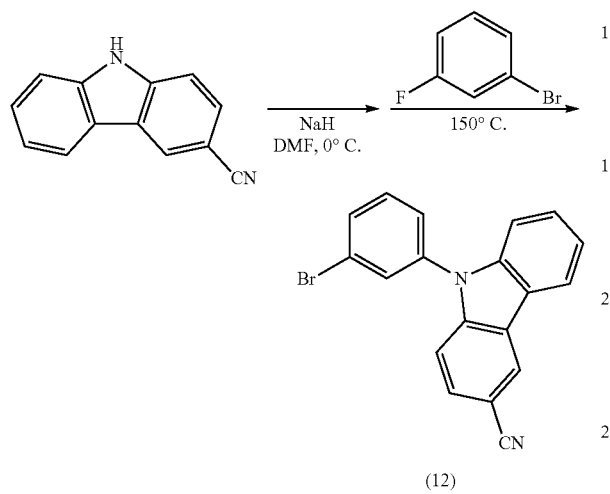

(12)

11.07 g (57.6 mmol) of 9H-carbazole-3-carbonitrile was mixed with 130 mL of dimethyl formamide, followed by slowly adding 2.30 g (57.6 mmol) of sodium hydride (60% dispersion in mineral oil) thereto and stirring at a temperature of 0° C. for 30 minutes. A solution, in which 11.09 g (63.4 mmol) of 1-bromo-3-fluorobenzene was diluted in 100 mL of dimethyl formamide, was slowly added to the resulting product for 10 minutes. Subsequently, the reaction temperature was raised to 150° C., followed by stirring for 18 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography to obtain a desired compound, 13.60 g of Intermediate (12) (at a yield of 68%).

LC-MS (calculated value: 346.01, measured value: M+1=347)

(2) Synthesis of Intermediate (13)

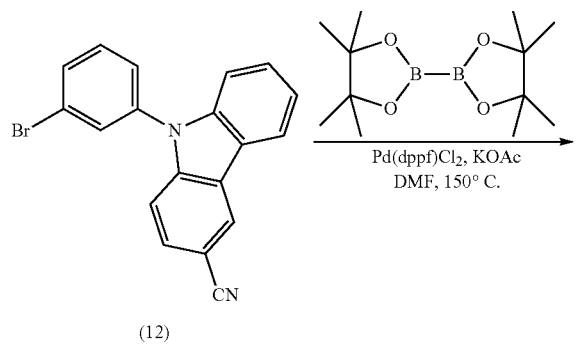

(12)

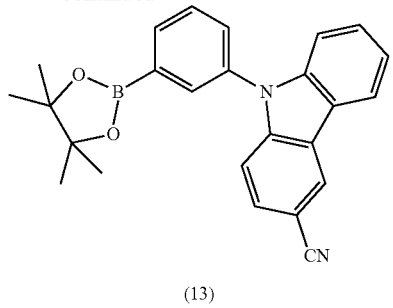

(13)

13.21 g (38.0 mmol) of Intermediate (12), 14.49 g (57.1 mmol) of 4,4,4',4',5,5,5',5'-octamethyl-2,2'-bi(1,3,2-dioxaborolane), 2.78 g (3.8 mmol) of PdCl$_2$(dppf).CH$_2$Cl$_2$, and 11.20 g (114.1 mmol) of potassium acetate were mixed with 95 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified by silica gel column chromatography and recrystallized using dichloromethane/n-hexane to obtain a desired compound, 9.63 g of Intermediate (13) (at a yield of 64%).

LC-MS (calculated value: 394.19, measured value: M+1=395)

(3) Synthesis of Intermediate (14)

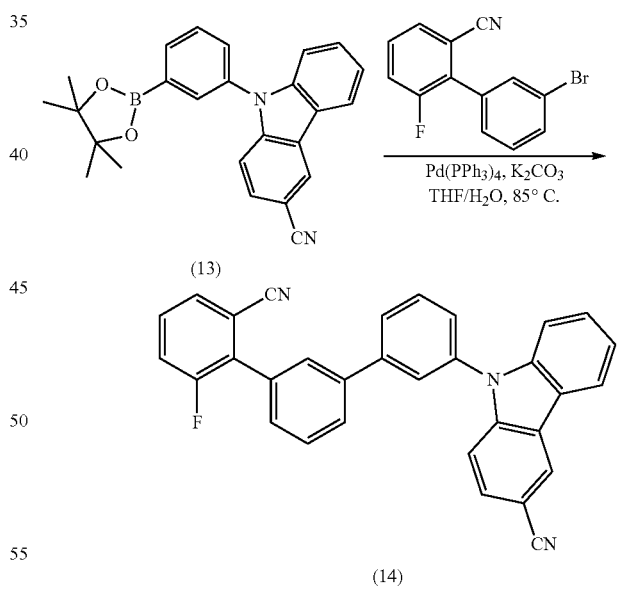

(14)

5.54 g (20.1 mmol) of 3'-bromo-6-fluoro-[1,1'-biphenyl]-2-carbonitrile, 9.49 g (24.1 mmol) of Intermediate (13), 2.32 g (2.0 mmol) of tetrakis(triphenylphosphine)palladium(0), and 55.55 g (40.1 mmol) of potassium carbonate were added to a mixture solution of 50 mL of tetrahydrofuran and 20 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 6.25 g of Intermediate (14) (at a yield of 67%).

LC-MS (calculated value: 463.15, measured value: M+1=464)

(4) Synthesis of Compound 2168

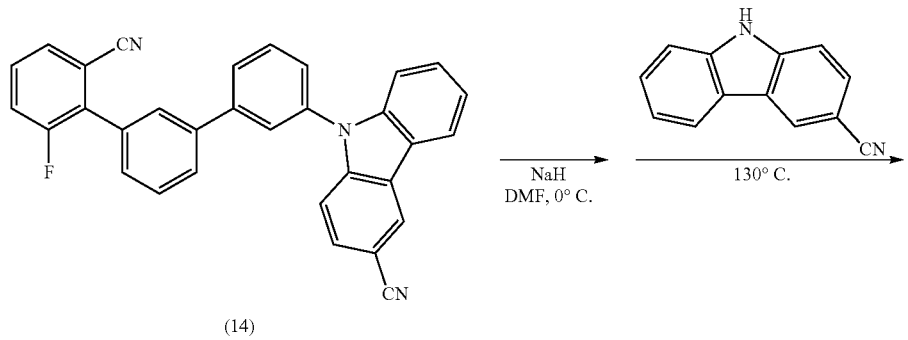

(14)

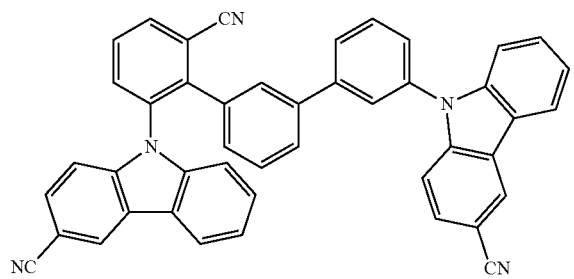

2168

2.27 g (11.8 mmol) of 9H-carbazole-3-carbonitrile was mixed with 30 mL of dimethyl formamide, followed by slowly adding 0.47 g (11.8 mmol) of sodium hydride (60% dispersion in mineral oil) thereto and stirring at a temperature of 0° C. for 30 minutes. A solution, in which 6.02 g (13.0 mmol) of Intermediate (14) was diluted in 17 mL of dimethyl formamide, was slowly added to the resulting product for 10 minutes. Subsequently, the reaction temperature was raised to 130° C., followed by stirring for 40 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography and recrystallized to obtain a desired compound, 2.36 g of Compound 2168 (at a yield of 31%).

LC-MS (calculated value: 635.21, measured value: M+1=636)

Synthesis Example 4: Synthesis of Compound 670

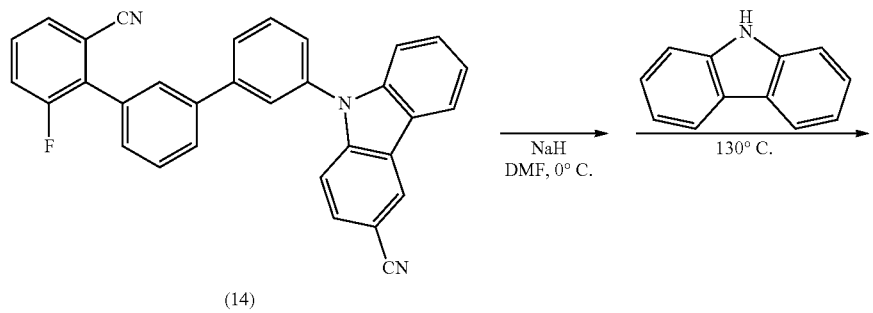

(14)

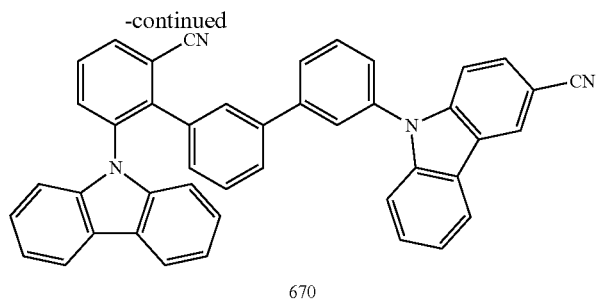

670

1.73 g (10.3 mmol) of carbazole was mixed with 25 mL of dimethyl formamide, followed by slowly adding 0.41 g (10.3 mmol) of sodium hydride (60% dispersion in mineral oil) thereto and stirring at a temperature of 0° C. for 30 minutes. A solution, in which 5.26 g (11.6.0 mmol) of Intermediate (14) was diluted in 17 mL of dimethyl formamide, was slowly added to the resulting product for 10 minutes. Subsequently, the reaction temperature was raised to 130° C., followed by stirring for 40 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography and recrystallized to obtain a desired compound, 3.21 g of Compound 670 (at a yield of 51%).

LC-MS (calculated value: 610.70, measured value: M+1=611)

Synthesis Example 5: Synthesis of Compound 813

(1) Synthesis of Intermediate (15)

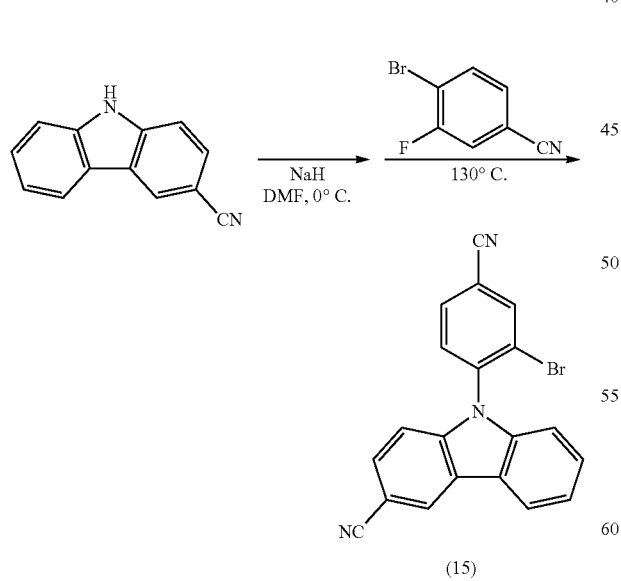

7.75 g (40.3 mmol) of 9H-carbazole-3-carbonitrile was mixed with 100 mL of dimethyl formamide, followed by slowly adding 1.61 g (40.3 mmol) of sodium hydride (60% dispersion in mineral oil) thereto and stirring at a temperature of 0° C. for 30 minutes. A solution, in which 8.87 g (44.33 mmol) of 3-bromo-4-fluorobenzonitrile was diluted in 61 mL of dimethyl formamide, was slowly added to the resulting product for 10 minutes. Subsequently, the reaction temperature was raised to 130° C., followed by stirring for 18 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography to obtain a desired compound, 11.60 g of Intermediate (15) (at a yield of 77%).

LC-MS (calculated value: 371.01, measured value: M+1=372)

(2) Synthesis of Intermediate (16)

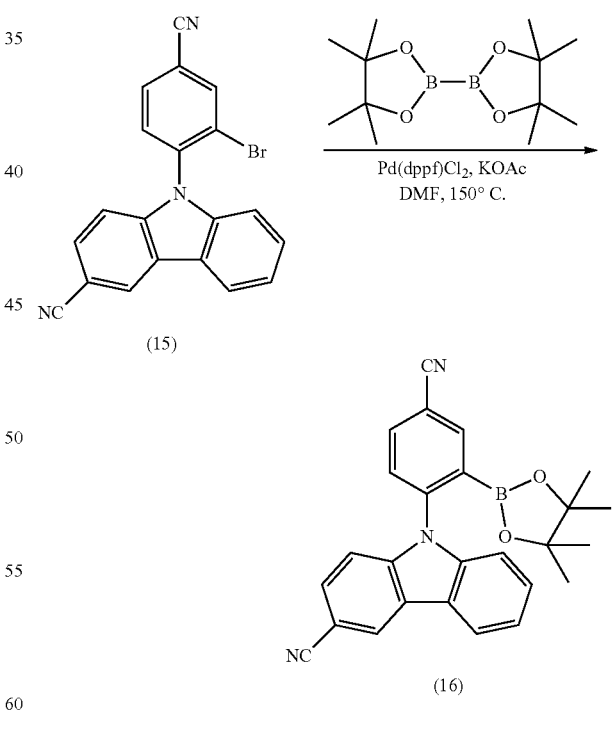

11.36 g (30.5 mmol) of Intermediate (15), 11.63 g (45.8 mmol) of 4,4,4',4',5,5,5',5'-octamethyl-2,2'-bi(1,3,2-dioxaborolane), 2.23 g (3.1 mmol) of PdCl$_2$(dppf).CH$_2$Cl$_2$, and 8.99 g (91.6 mmol) of potassium acetate were mixed with 77 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified by silica gel column chromatography and recrystallized using dichloromethane/n-hexane to obtain a desired compound, 10.63 g of Intermediate (16) (at a yield of 83%).

LC-MS (calculated value: 419.18, measured value: M+1=420)

(3) Synthesis of Intermediate (17)

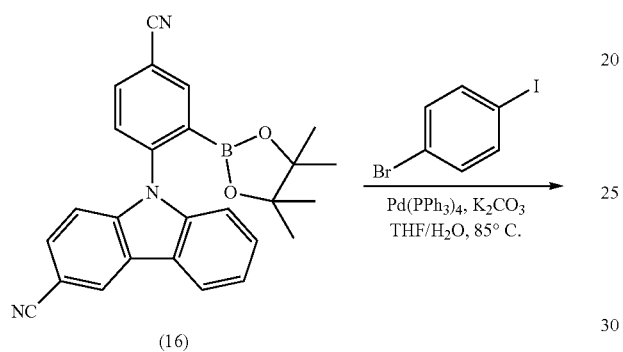

(4) Synthesis of Compound 813

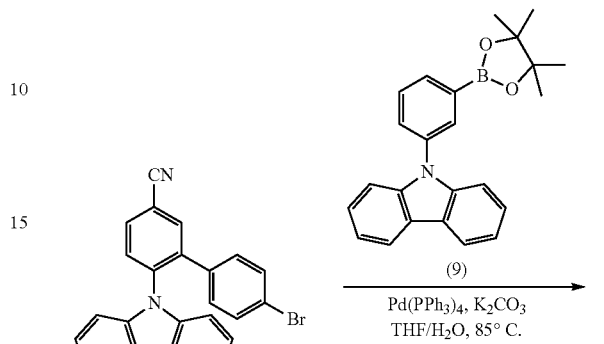

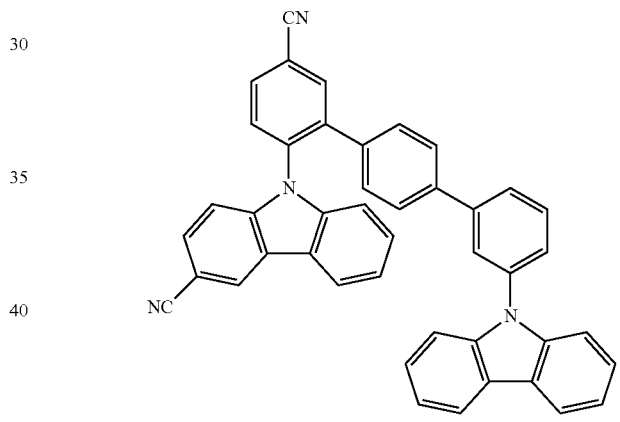

70.7 g (25.0 mmol) of 1-bromo-4-iodobenzene, 10.48 g (25.0 mmol) of Intermediate (16), 2.89 g (2.5 mmol) of tetrakis(triphenylphosphine)palladium(0), and 6.91 g (50.0 mmol) of potassium carbonate were added to a mixture solution of 63 mL of tetrahydrofuran and 25 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 5.94 g of Intermediate (17) (at a yield of 53%).

LC-MS (calculated value: 447.04, measured value: M+1=448)

5.58 g (12.4 mmol) of Intermediate (17), 5.97 g (16.2 mmol) of Intermediate (9), 1.44 g (1.2 mmol) of tetrakis(triphenylphosphine)palladium(0), and 3.44 g (24.9 mmol) of potassium carbonate were added to a mixture solution of 32 mL of tetrahydrofuran and 13 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography and recrystallized to obtain a desired compound, 3.52 g of Compound 813 (at a yield of 46%).

LC-MS (calculated value: 641.22, measured value: M+1=612)

Synthesis Example 6: Synthesis of Compound 152

(1) Synthesis of Intermediate (18)

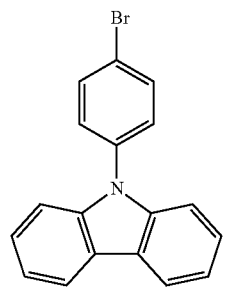 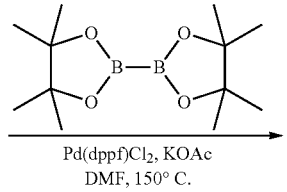 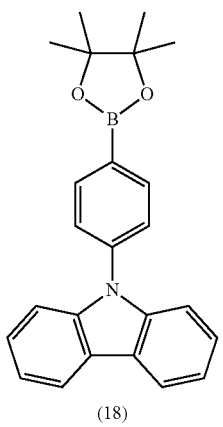

(18)

(2) Synthesis of Intermediate (19)

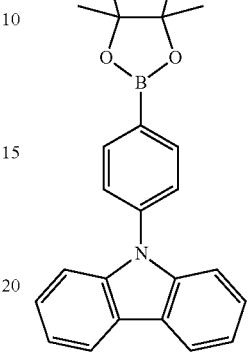 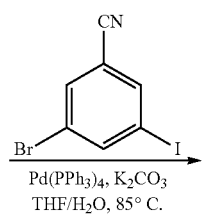

(18)

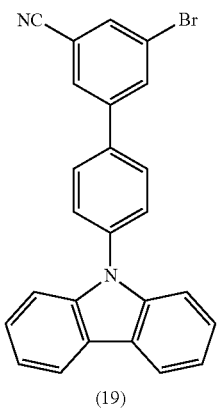

(19)

13.09 g (40.6 mmol) of 9-(4-bromophenyl)-9H-carbazole, 15.47 g (60.9 mmol) of 4,4,4',4',5,5,5',5'-octamethyl-2,2'-bi (1,3,2-dioxaborolane), 2.97 g (4.06 mmol) of PdCl$_2$(dppf) .CH$_2$Cl$_2$, and 11.96 g (121.9 mmol) of potassium acetate were mixed with 102 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified by silica gel column chromatography and recrystallized using dichloromethane/n-hexane to obtain a desired compound, 9.66 g of Intermediate (18) (at a yield of 64%).

LC-MS (calculated value: 369.19, measured value: M+1=370)

7.86 g (25.5 mmol) of 3-bromo-5-iodobenzonitrile, 9.42 g (25.5 mmol) of Intermediate (18), 2.95 g (2.6 mmol) of tetrakis(triphenylphosphine)palladium(0), and 7.05 g (51.0 mmol) of potassium carbonate were added to a mixture solution of 65 mL of tetrahydrofuran and 25 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 7.12 g of Intermediate (19) (at a yield of 66%).

LC-MS (calculated value: 422.04, measured value: M+1=423)

(3) Synthesis of Compound 152

Synthesis Example 7: Synthesis of Compound 224

(1) Synthesis of Intermediate (20)

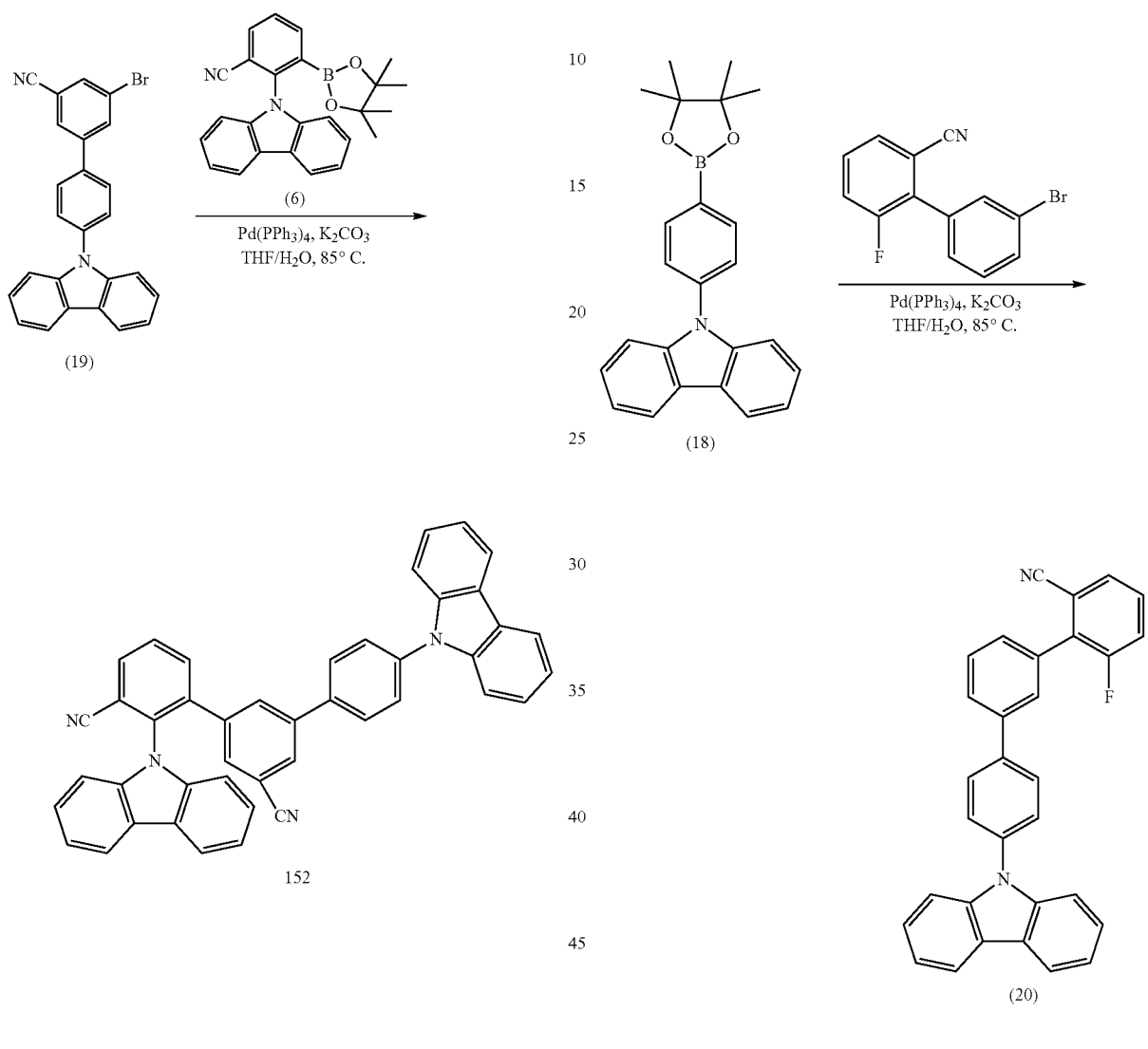

6.79 g (16.1 mmol) of Intermediate (19), 8.23 g (20.9 mmol) of Intermediate (6), 1.85 g (1.6 mmol) of tetrakis(triphenylphosphine)palladium(0), and 4.44 g (32.1 mmol) of potassium carbonate were added to a mixture solution of 40 mL of tetrahydrofuran and 16 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography and recrystallized to obtain a desired compound, 1.55 g of Compound 152 (at a yield of 16%).

LC-MS (calculated value: 610.22, measured value: M+1=611)

6.30 g (22.8 mmol) of 3'-bromo-6-fluoro-[1,1'-biphenyl]-2-carbonitrile, 10.11 g (27.4 mmol) of Intermediate (18), 2.64 g (2.3 mmol) of tetrakis(triphenylphosphine)palladium (0), and 6.30 g (45.6 mmol) of potassium carbonate were added to a mixture solution of 60 mL of tetrahydrofuran and 23 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 7.17 g of Intermediate (20) (at a yield of 72%).

LC-MS (calculated value: 438.15, measured value: M+1=439)

(2) Synthesis of Compound 224

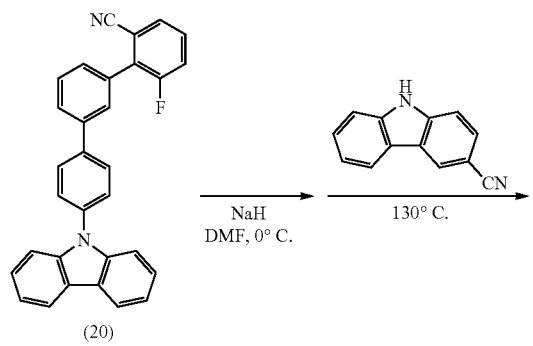

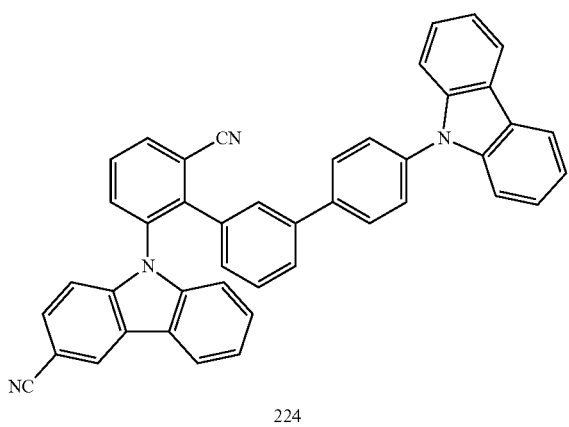

2.68 g (13.9 mmol) of 9H-carbazole-3-carbonitrile was mixed with 40 mL of dimethyl formamide, followed by slowly adding 0.56 g (13.9 mmol) of sodium hydride (60% dispersion in mineral oil) thereto and stirring at a temperature of 0° C. for 30 minutes. A solution, in which 6.71 g (15.3 mmol) of Intermediate (20) was diluted in 20 mL of dimethyl formamide, was slowly added to the resulting product for 10 minutes. Subsequently, the reaction temperature was raised to 130° C., followed by stirring for 18 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography and recrystallized to obtain a desired compound, 2.99 g of Compound 224 (at a yield of 35%).

LC-MS (calculated value: 610.22, measured value: M+1=611)

Synthesis Example 8: Synthesis of Compound 857

(1) Synthesis of Intermediate (21)

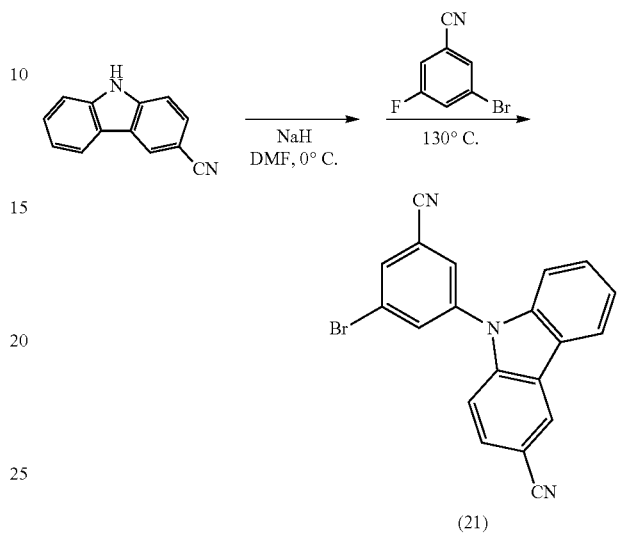

4.65 g (24.2 mmol) of 9H-carbazole-3-carbonitrile was mixed with 55 mL of dimethyl formamide, followed by slowly adding 0.97 g (24.2 mmol) of sodium hydride (60% dispersion in mineral oil) thereto and stirring at a temperature of 0° C. for 30 minutes. A solution, in which 5.32 g (26.6 mmol) of 3-bromo-5-fluorobenzonitrile was diluted in 40 mL of dimethyl formamide, was slowly added to the resulting product for 10 minutes. Subsequently, the reaction temperature was raised to 130° C., followed by stirring for 18 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography to obtain a desired compound, 6.55 g of Intermediate (21) (at a yield of 73%).

LC-MS (calculated value: 371.01 g/mol, measured value: M+1=372 g/mol)

(2) Synthesis of Intermediate (22)

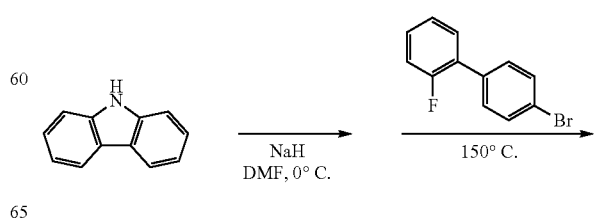

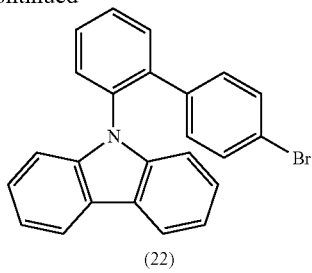

(22)

6.30 g (37.7 mmol) of carbazole was mixed with 100 mL of dimethyl formamide, followed by slowly adding 1.51 g (37.7 mmol) of sodium hydride (60% dispersion in mineral oil) thereto and stirring at a temperature of 0° C. for 30 minutes. A solution, in which 10.82 g (41.4 mmol) of 4'-bromo-2-fluoro-1,1'-biphenyl was mixed with 50 mL of dimethyl formamide, was slowly added to the resulting product for 10 minutes. Subsequently, the reaction temperature was raised to a temperature of 150° C., followed by stirring for 40 hours. Once the reaction was complete, the resulting mixture was cooled to room temperature, followed by addition of ammonium chloride aqueous solution to extract an organic layer using dichloromethane. From the resulting product, water was removed using magnesium sulfate. Subsequently, the obtained filtrate was concentrated under reduced pressure, and the resulting product was separated and purified by silica gel column chromatography to obtain a desired compound, 7.30 g of Intermediate (22) (at a yield of 49%).

LC-MS (calculated value: 397.05 g/mol, measured value: M+1=398 g/mol)

(3) Synthesis of Intermediate (23)

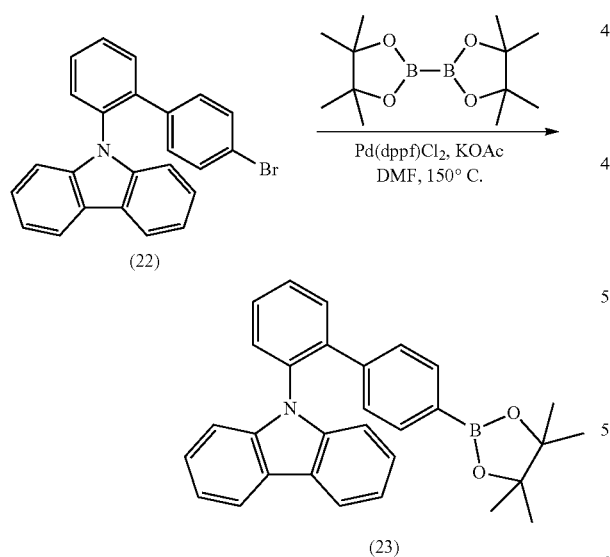

7.15 g (18.0 mmol) of Intermediate (22), 6.84 g (26.9 mmol) of 4,4,4',4',5,5,5',5'-octamethyl-2,2'-bi(1,3,2-dioxaborolane), 1.31 g (1.8 mmol) of PdCl₂(dppf).CH₂Cl₂, and 5.29 g (53.9 mmol) of potassium acetate were mixed with 45 mL of dimethyl formamide, followed by stirring under reflux at a temperature of 150° C. for 15 hours. Once the reaction was complete, the resulting mixture was cooled to room temperature, and was filtered through silica gel under reduced pressure. The obtained filtrate was concentrated under reduced pressure, and the resulting product was separated and purified by silica gel column chromatography and recrystallized using dichloromethane/n-hexane to obtain a desired compound, 4.93 g of Intermediate (23) (at a yield of 62%).

LC-MS (calculated value: 445.22, measured value: M+1=446)

(4) Synthesis of Compound 857

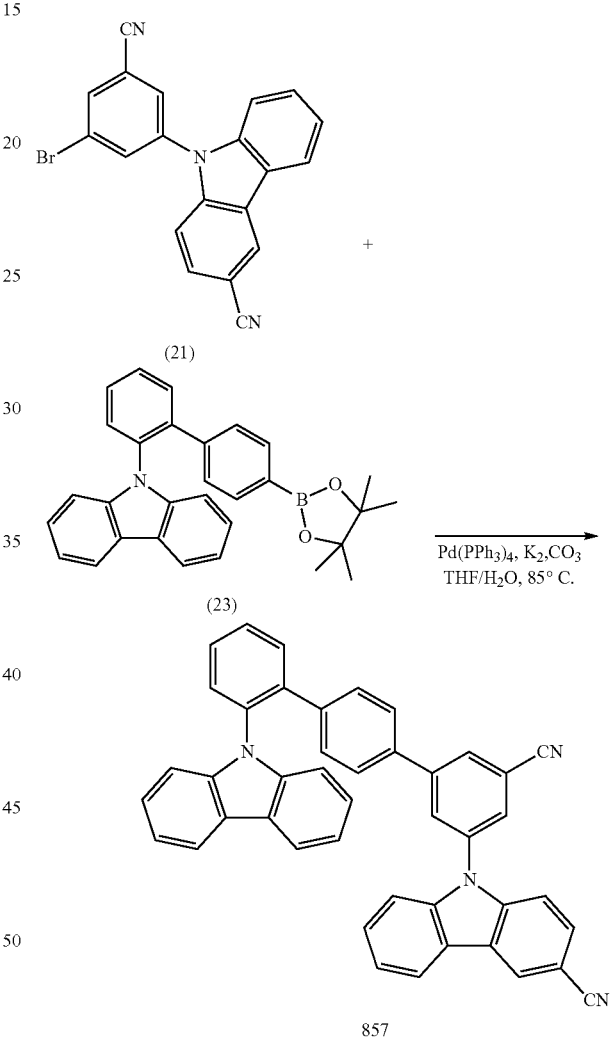

3.23 g (8.7 mmol) of Intermediate (21), 4.64 g (10.4 mmol) of Intermediate (23), 1.00 g (0.9 mmol) of tetrakis(triphenylphosphine)palladium(0), and 2.40 g (17.4 mmol) of potassium carbonate were added to a mixture solution of 23 mL of tetrahydrofuran and 9 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography and recrystallized to obtain a desired compound, 1.27 g of Compound 857 (at a yield of 24%).

LC-MS (calculated value: 610.22, measured value: M+1=611)

Synthesis Example 9: Synthesis of Compound 404

(1) Synthesis of Intermediate (24)

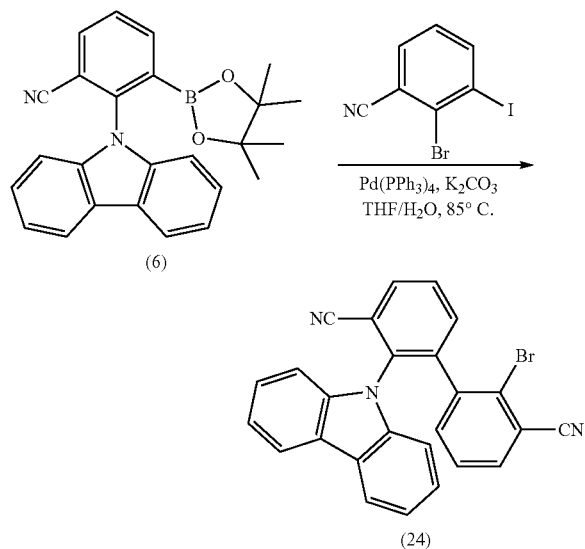

10.30 g (33.5 mmol) of 2-bromo-3-iodobenzonitrile, 6.60 g (16.7 mmol) of Intermediate (6), 3.87 g (3.4 mmol) of tetrakis(triphenylphosphine)palladium(0), and 9.25 g (66.9 mmol) of potassium carbonate were added to a mixture solution of 85 mL of tetrahydrofuran and 35 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified by silica gel column chromatography to obtain a desired compound, 5.66 g of Intermediate (24) (at a yield of 38%).

LC-MS (calculated value: 447.04, measured value: M+1=448)

(2) Synthesis of Compound 404

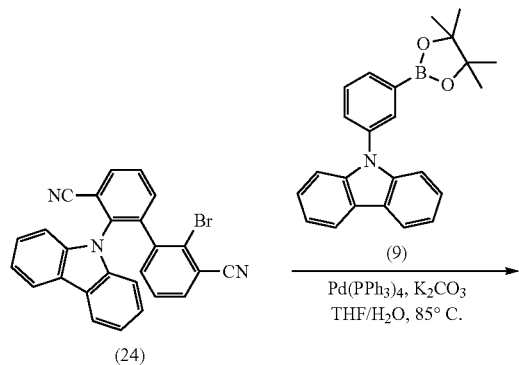

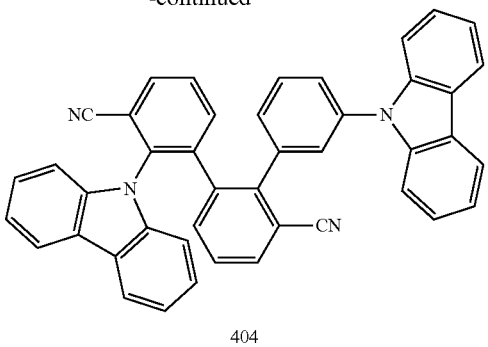

5.36 g (11.6 mmol) of Intermediate (24), 8.83 g (23.9 mmol) of Intermediate (9), 1.38 g (1.2 mmol) of tetrakis(triphenylphosphine)palladium(0), and 3.30 g (23.9 mmol) of potassium carbonate were added to a mixture solution of 30 mL of tetrahydrofuran and 12 mL of water, followed by stirring under reflux at a temperature of 85° C. Once the reaction was complete, the resulting mixture was cooled to room temperature, a solution layer was removed by extraction, and the resultant was filtered through silica gel under reduced pressure. The obtained filtrate was concentrated under reduced pressure, and the resulting product was separated and purified through silica gel column chromatography and recrystallized to obtain a desired compound, 0.94 g of Compound 404 (at a yield of 13%).

LC-MS (calculated value: 610.22 g/mol, measured value: M+1=612 g/mol)

Example 1

A glass substrate having 1,500 Å of indium tin oxide (ITO) electrode (first electrode, anode) deposited thereon was washed with distilled water in the presence of ultrasound waves. Once the washing with distilled water was complete, ultrasound wave washing was performed on the substrate using a solvent, such as isopropyl alcohol, acetone, or methanol. Subsequently, the substrate was dried, transferred to a plasma washer, washed for 5 minutes using oxygen plasma, and mounted in a vacuum depositor.

Compound HT3 and Compound HT-D2 were vacuum-deposited on the ITO electrode of the glass substrate to form a hole injection layer having a thickness of 100 Å. Then, Compound HT3 was vacuum-deposited on the hole injection layer to form a hole transport layer having a thickness of 1,300 Å. mCP was next vacuum-deposited on the hole transport layer to form an electron blocking layer having a thickness of 100 Å, thereby forming a hole transport region.

Subsequently, Compound 582 (host) and FIr6 (dopant) were co-deposited on the hole transport region to form an emission layer having a thickness of 400 Å.

BCP was vacuum-deposited on the emission layer to form a hole blocking layer having a thickness of 100 Å. Compound ET3 and Liq were then co-deposited on the hole blocking layer to form an electron transport layer having a thickness of 300 Å. Next, Liq was vacuum-deposited on the electron transport layer to form an electron injection layer having a thickness of 10 Å, and then, Al second electrode (a cathode) having a thickness of 1,200 Å was formed on the electron injection layer, thereby completing the manufacture of an organic light-emitting device.

HT3

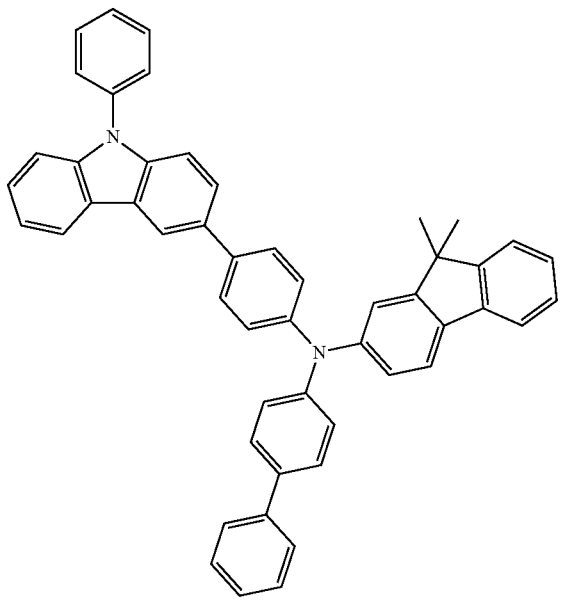

HT-D2

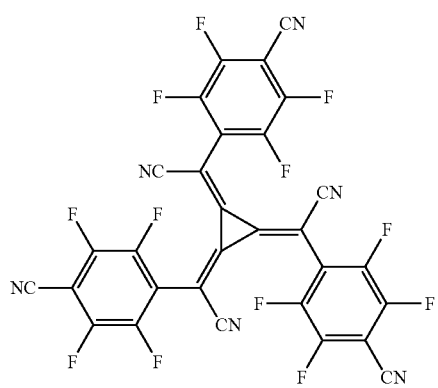

mCP

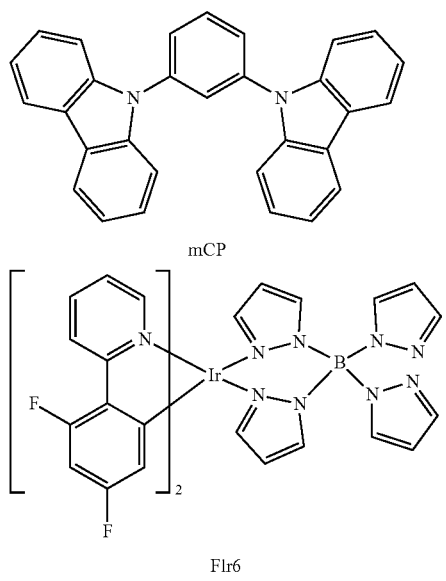

FIr6

BCP

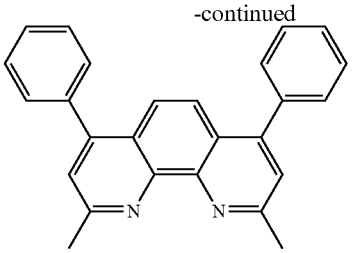

ET3

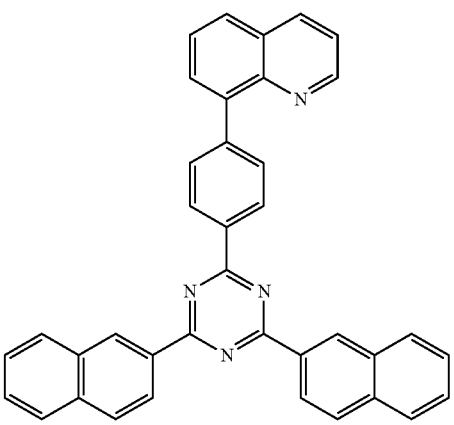

Examples 2 to 9 and Comparative Examples 1 and 2

Organic light-emitting devices were manufactured in substantially the same manner as in Example 1, except that the compounds shown in Table 2 were used instead of Compound 582 as a host in the formation of an emission layer.

Evaluation Example: Evaluation of Characteristics of Organic Light-Emitting Device Driving voltages, current density changes, luminance changes, and emission efficiencies of the organic light-emitting device manufactured in Examples 1 to 9 and Comparative Examples 1 and 2 were measured by applying various voltages thereto. The measurement method is as described in the following. The results thereof are shown in Table 2.

(1) Measurement of Driving Voltage and Current Density Changes Depending on Changes of Applied Voltages The driving voltages and current values in a unit device of the prepared organic light-emitting devices were measured by using a current voltmeter (Keithley 2400) while increasing the applied voltage from 0 volt (V) to 10 V. The result was obtained by dividing a current value by an area.

(2) Measurement of Luminance Changes Depending on Changes of Applied Voltages

Luminance values of the prepared organic light-emitting devices were measured by using a luminance meter (Minolta Cs-1000A) while increasing the applied voltage from 0V to 10 V.

(3) Measurement of Emission Efficiency

The luminance values measured from (2) and current density values and voltages measured from (1) were used in calculating the current efficiency (cd/A) under a condition of an identical current density (10 milliamperes per square meter ($mA/cm^2$)).

(4) Measurement of Durability

The time (hour) for the luminance of each organic light-emitting device to decline to 95% of its initial luminance was evaluated.

TABLE 2

| Host | Driving voltage (relative value) | Current efficiency (relative value) | Durability (relative value) | Emission color |
|---|---|---|---|---|
| Example 1 | 582 | 85 | 129 | 133 | Blue |
| Example 2 | 2451 | 88 | 121 | 109 | Blue |
| Example 3 | 2168 | 75 | 147 | 137 | Blue |
| Example 4 | 670 | 80 | 145 | 132 | Blue |
| Example 5 | 813 | 82 | 131 | 125 | Blue |
| Example 6 | 152 | 74 | 117 | 119 | Blue |
| Example 7 | 224 | 71 | 144 | 130 | Blue |
| Example 8 | 857 | 89 | 128 | 120 | Blue |
| Example 9 | 404 | 76 | 138 | 103 | Blue |
| Comparative Example 1 | Compound A | 100 | 100 | 100 | Blue |
| Comparative Example 2 | Compound B | 96 | 116 | 53 | Blue |

TABLE 2-continued

| Host | Driving voltage (relative value) | Current efficiency (relative value) | Durability (relative value) | Emission color |
|---|---|---|---|---|
| | | | 2451 | A |
| | | | | B |

As apparent from Table 2, the organic light-emitting device of Examples 1 to 9 were found to have low driving voltages and excellent current efficiency and durability, as compared with the organic light-emitting device of Comparative Examples 1 and 2.

As apparent from the foregoing description, the heterocyclic compound according to one or more embodiments has excellent electric characteristics and thermal stability. Accordingly, an organic light-emitting device including the heterocyclic compound may have a low driving voltage, high efficiency, high power, high quantum yield, and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURE, it will be understood by those of ordinary skill in the art that various changes in form and details may be made therein without departing from the spirit and scope as defined by the following claims.

What is claimed is:
1. An organic light-emitting device comprising:
a first electrode;
a second electrode; and
an organic layer between the first electrode and the second electrode, the organic layer comprising an emission layer and at least one heterocyclic compound represented by Formula 1, wherein the emission layer comprises a host and a dopant, and the host consists of the heterocyclic compound represented by Formula 1, wherein a content of the host is greater than a content of the dopant:

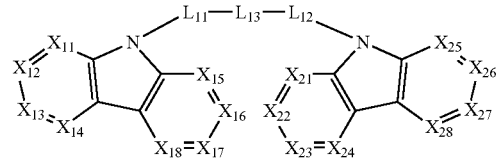

Formula 1

Formula 2

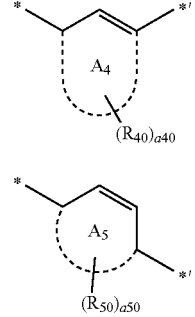

Formula 3

Formula 4

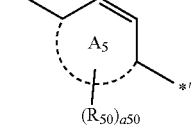

wherein, in Formula 1,
$X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, $X_{18}$ is N or $C(R_{18})$,
$X_{21}$ is N or $C(R_{21})$, $X_{22}$ is N or $C(R_{22})$, $X_{23}$ is N or $C(R_{23})$, $X_{24}$ is N or $C(R_{24})$, $X_{25}$ is N or $C(R_{25})$, $X_{26}$ is N or $C(R_{26})$, $X_{27}$ is N or $C(R_{27})$, $X_{28}$ is N or $C(R_{28})$,
$L_{11}$ is a group represented by Formula 2,
$L_{12}$ is a group represented by one of Formulae 3 and 4,
$L_{13}$ is a group represented by one of Formulae 2 to 4,
wherein in Formulae 2 to 4,
ring $A_3$ to ring $A_5$ are each independently a $C_5$-$C_{60}$ carbocyclic group or a $C_2$-$C_{60}$ heterocyclic group,
$R_{11}$ to $R_{18}$, $R_{21}$ to $R_{28}$, $R_{30}$, $R_{40}$, and $R_{50}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), at least one of $R_{30}$, $R_{40}$, or $R_{50}$ is a cyano group, $a_{30}$, $a_{40}$, and $a_{50}$ are each independently an integer from 1 to 10,

* and *' each indicate a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group is:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}O_{13}$), —N($Q_{14}$)($Q_{15}$), or —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), or —B($Q_{26}$)($Q_{27}$); or —Si($Q_{31}$)($Q_{32}$)($Q_{33}$), —N($Q_{34}$)($Q_{35}$) or —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

2. The organic light-emitting device of claim 1, wherein $X_{11}$ to $X_{18}$ and $X_{21}$ to $X_{28}$ are each not N, and one or two of $X_{11}$ to $X_{18}$ and $X_{21}$ to $X_{28}$ are each N.

3. The organic light-emitting device of claim 1, wherein ring $A_3$ to ring $A_5$ are each independently a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group.

4. The organic light-emitting device of claim 1, wherein ring $A_3$ to ring $A_5$ are each independently a benzene group, a pyridine group, a pyrazine group, a pyrimidine group, a pyridazine group, or a triazine group.

5. The organic light-emitting device of claim 1, wherein $L_{11}$ is one of Formulae O-1 to O-6, $L_{12}$ is one of Formulae M-1 to M-9 and P-1 to P-5, and $L_{13}$ is one of Formulae O-1 to O-6, M-1 to M-9, and P-1 to P-5:

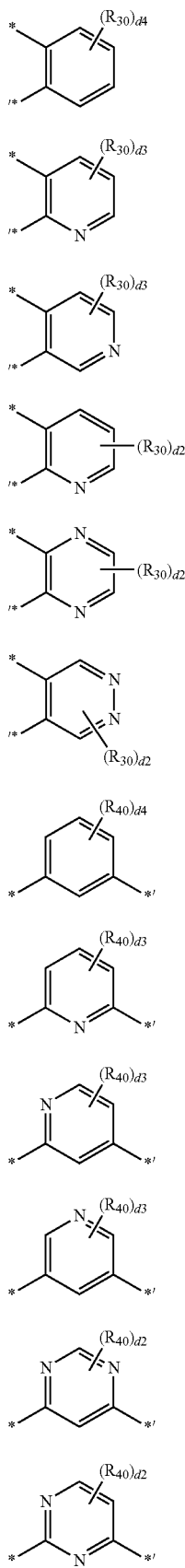
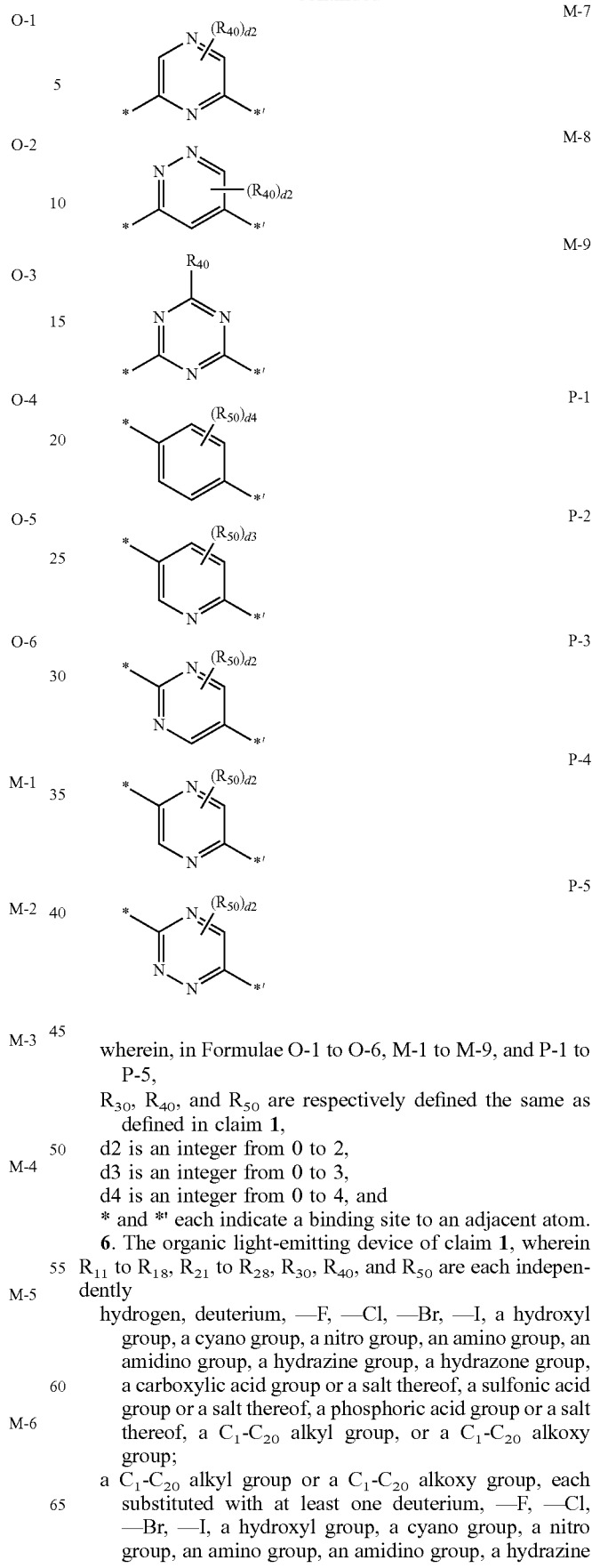

wherein, in Formulae O-1 to O-6, M-1 to M-9, and P-1 to P-5, $R_{30}$, $R_{40}$, and $R_{50}$ are respectively defined the same as defined in claim 1, d2 is an integer from 0 to 2, d3 is an integer from 0 to 3, d4 is an integer from 0 to 4, and

* and *' each indicate a binding site to an adjacent atom.

6. The organic light-emitting device of claim 1, wherein $R_{11}$ to $R_{18}$, $R_{21}$ to $R_{28}$, $R_{30}$, $R_{40}$, and $R_{50}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, or a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, or an imidazopyridinyl group; or a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, or an imidazopyridinyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, or a quinazolinyl group, and at least one of $R_{30}$, $R_{40}$, or $R_{50}$ is a cyano group.

7. The organic light-emitting device of claim 1, wherein $R_{11}$ to $R_{18}$, $R_{21}$ to $R_{28}$, $R_{30}$, $R_{40}$, and $R_{50}$ are each independently hydrogen, deuterium, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, a cyano group, a phenyl group, a biphenyl group, a terphenyl group, or a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, or a dibenzothiophenyl group; or a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, or a dibenzothiophenyl group, each substituted with at least one deuterium, a cyano group, a $C_1$-$C_{20}$ alkyl group, a $C_1$-$C_{20}$ alkoxy group, a phenyl group, a biphenyl group, a terphenyl group, or a naphthyl group, or at least one of $R_{30}$, $R_{40}$, or $R_{50}$ is a cyano group.

8. The organic light-emitting device of claim 1, wherein $R_{30}$, $R_{40}$, and $R_{50}$ are each independently hydrogen or a cyano group, and at least one of $R_{30}$, $R_{40}$, or $R_{50}$ is a cyano group.

9. The organic light-emitting device of claim 1, wherein the number of cyano groups comprised in the heterocyclic compound represented by Formula 1 is 1 to 4.

10. The organic light-emitting device of claim 1, wherein $R_{11}$ to $R_{18}$ and $R_{21}$ to $R_{28}$ are not each a cyano group, or one or two of $R_{11}$ to $R_{18}$ and $R_{21}$ to $R_{28}$ are each a cyano group; one, two, or three of $R_{30}$, $R_{40}$, and $R_{50}$ are each a cyano group; and the number of cyano groups comprised in the heterocyclic compound represented by Formula 1 is 1 to 4.

11. The organic light-emitting device of claim 1, wherein the heterocyclic compound represented by Formula 1 is represented by one of Formulae 10-1 to 10-6:

10-1

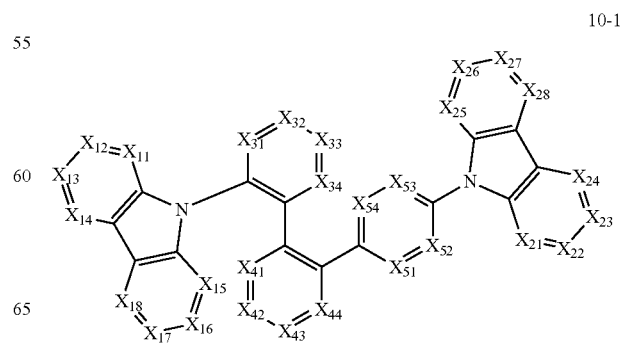

10-2

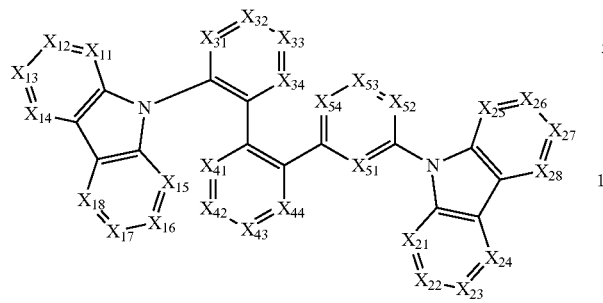

10-3

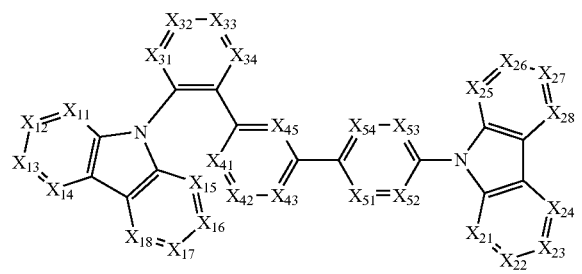

10-4

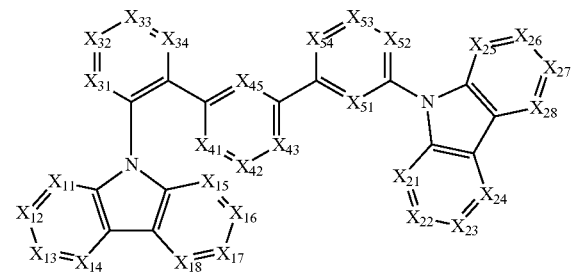

10-5

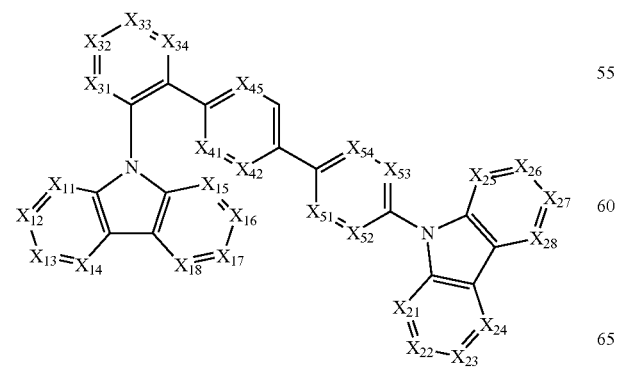

10-6

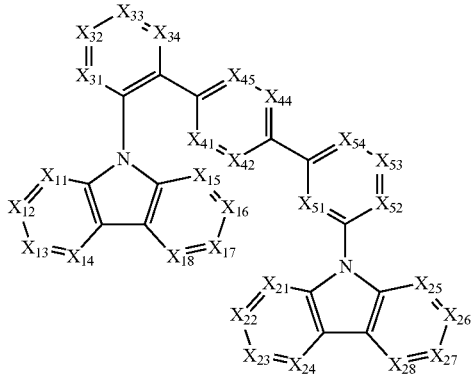

wherein, in Formulae 10-1 to 10-6, $X_{11}$ to $X_{18}$ and $X_{21}$ to $X_{28}$ are respectively defined the same as in claim 1, $X_{31}$ is N or $C(R_{31})$, $X_{32}$ is N or $C(R_{32})$, $X_{33}$ is N or $C(R_{33})$, $X_{34}$ is N or $C(R_{34})$, $X_{41}$ is N or $C(R_{41})$, $X_{42}$ is N or $C(R_{42})$, $X_{43}$ is N or $C(R_{43})$, $X_{44}$ is N or $C(R_{44})$, $X_{45}$ is N or $C(R_{45})$, $X_{51}$ is N or $C(R_{51})$, $X_{52}$ is N or $C(R_{52})$, $X_{53}$ is N or $C(R_{53})$, $X_{54}$ is N or $C(R_{54})$, $R_{31}$ to $R_{34}$ are each defined the same as $R_{30}$ in claim 1, $R_{41}$ to $R_{45}$ are each defined the same as $R_{40}$ in claim 1, $R_{51}$ to $R_{54}$ are each defined the same as $R_{50}$ in claim 1, and at least one of $R_{31}$ to $R_{34}$, $R_{41}$ to $R_{45}$, or $R_{51}$ to $R_{54}$ is a cyano group.

12. The organic light-emitting device of claim 1, wherein the heterocyclic compound represented by Formula 1 is of Compounds 152, 224, 404, 582, 670, 813, 857, 2168, and 2451:

152

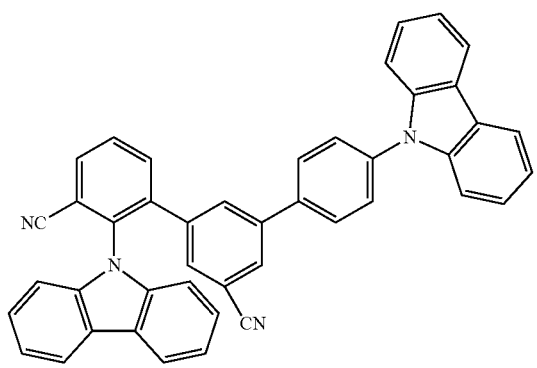 [SMILES: N#Cc1cc(-c2ccc(-n3c4ccccc4c4ccccc43)cc2)cc(-c2cccc(C#N)c2-n2c3ccccc3c3ccccc32)c1]

-continued

224
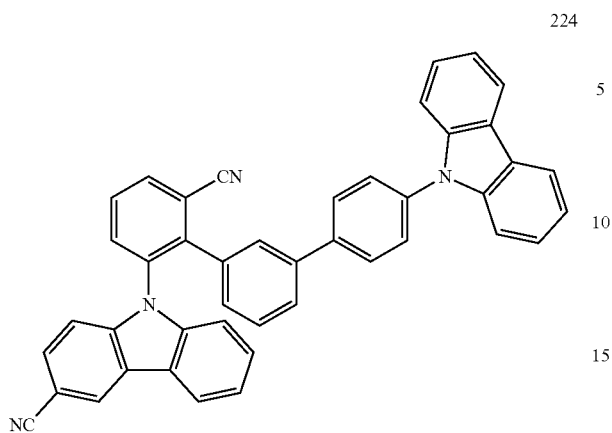

404
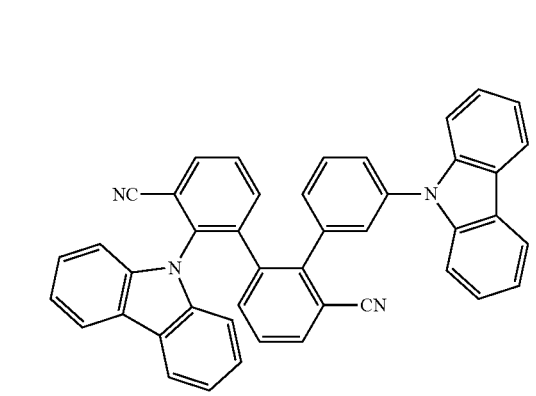 [SMILES: N#Cc1cccc(-c2cccc(C#N)c2-n2c3ccccc3c3ccccc32)c1-c1cccc(-n2c3ccccc3c3ccccc32)c1]

582
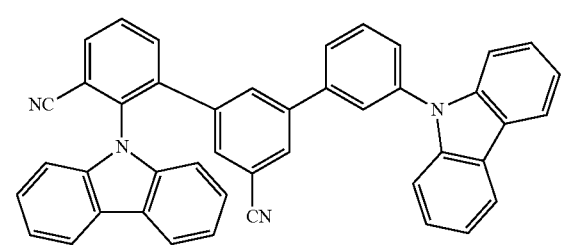

670
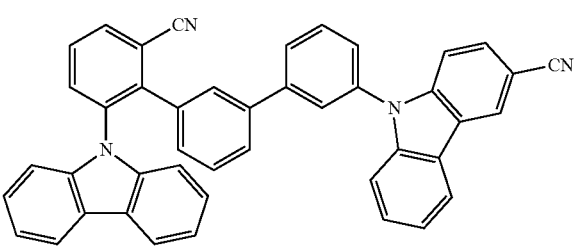

-continued

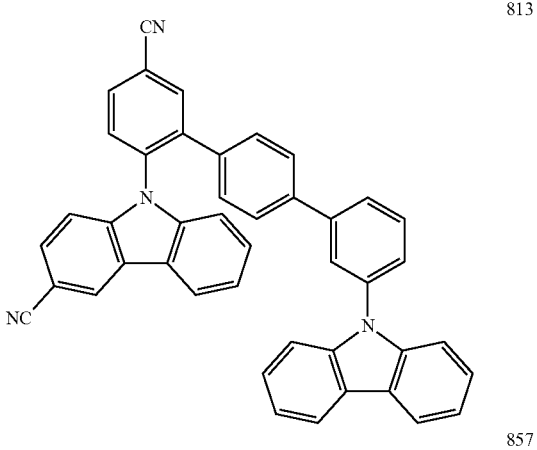

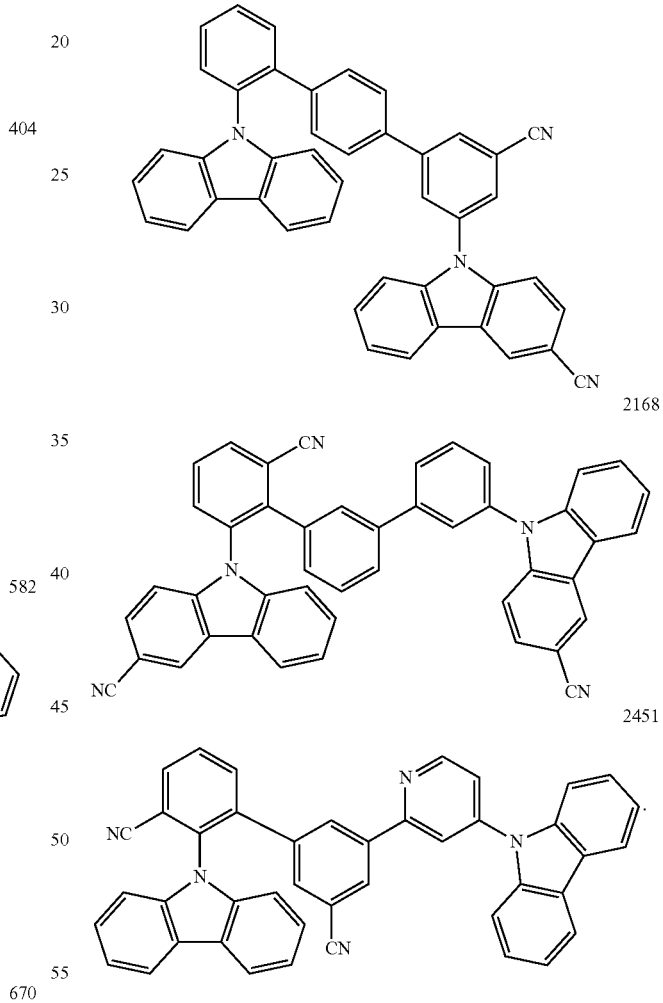

13. The organic light-emitting device of claim 1, wherein the first electrode is an anode, the second electrode is a cathode, the organic layer comprises a hole transport region between the first electrode and the emission layer and an electron transport region between the emission layer and the second electrode, the hole transport region comprises at least one of a hole injection layer, a hole transport layer, or an electron blocking layer, and the electron transport region comprises at least one of a hole blocking layer, an electron transport layer, or an electron injection layer.

14. The organic light-emitting device of claim 13, wherein the emission layer emits blue light having a maximum emission wavelength in a range of about 410 nanometers (nm) to 490 nm.

15. The organic light-emitting device of claim 13, wherein the hole transport region comprises the heterocyclic compound represented by Formula 1.

16. The organic light-emitting device of claim 13, wherein the electron transport region comprises the heterocyclic compound represented by Formula 1.

17. The organic light-emitting device of claim 13, wherein the electron transport region comprises a hole blocking layer, the hole blocking layer is in direct contact with the emission layer, and the hole blocking layer comprises the heterocyclic compound represented by Formula 1.

* * * * *